US008445692B2

(12) United States Patent
Karanewsky et al.

(10) Patent No.: US 8,445,692 B2
(45) Date of Patent: May 21, 2013

(54) COMPOUNDS THAT INHIBIT (BLOCK) BITTER TASTE IN COMPOSITION AND USE THEREOF

(75) Inventors: Donald S Karanewsky, Escondido, CA (US); Joseph R. Fotsing, San Diego, CA (US); Catherine Tachdjian, San Diego, CA (US); Melissa Arellano, San Diego, CA (US)

(73) Assignee: Senomyx Inc., San Diego, CA (US)

( * ) Notice: Subject to any disclaimer, the term of this patent is extended or adjusted under 35 U.S.C. 154(b) by 0 days.

(21) Appl. No.: 13/289,821

(22) Filed: Nov. 4, 2011

(65) Prior Publication Data
US 2012/0088796 A1 Apr. 12, 2012

Related U.S. Application Data

(60) Division of application No. 12/656,936, filed on Feb. 19, 2010, now Pat. No. 8,076,491, which is a continuation-in-part of application No. 12/222,918, filed on Aug. 19, 2008, now Pat. No. 7,939,671.

(60) Provisional application No. 60/957,129, filed on Aug. 21, 2007, provisional application No. 61/047,187, filed on Apr. 23, 2008.

(51) Int. Cl.
*C07D 261/06* (2006.01)
*C07D 413/14* (2006.01)
*A61K 31/422* (2006.01)
*A61K 31/42* (2006.01)

(52) U.S. Cl.
USPC ......... 548/247; 546/272.1; 514/378; 514/341

(58) Field of Classification Search .................. None
See application file for complete search history.

(56) References Cited

U.S. PATENT DOCUMENTS

| | | | |
|---|---|---|---|
| 2,805,250 | A | 9/1957 | Werner et al. |
| 3,557,111 | A | 1/1971 | Shetty |
| 3,954,994 | A | 5/1976 | Holland et al. |
| 4,029,787 | A | 6/1977 | Sturm et al. |
| 6,096,895 | A | 8/2000 | Brown et al. |
| 6,774,241 | B2 | 8/2004 | Clark et al. |
| 6,903,086 | B2 | 6/2005 | Lopez-Tapia et al. |
| 7,338,771 | B2 | 3/2008 | Pronin et al. |
| 2002/0052349 | A1 | 5/2002 | Krauss et al. |
| 2004/0167183 | A1 | 8/2004 | Klopfenstein et al. |
| 2005/0065133 | A1 | 3/2005 | Lee et al. |
| 2005/0203086 | A1 | 9/2005 | Constan et al. |
| 2005/0288340 | A1 | 12/2005 | Hamanaka |
| 2006/0122181 | A1 | 6/2006 | Ikemoto et al. |
| 2006/0135773 | A1 | 6/2006 | Semple et al. |
| 2006/0263411 | A1 | 11/2006 | Tachdjian et al. |
| 2007/0037212 | A1 | 2/2007 | Li et al. |
| 2009/0274632 | A1 | 11/2009 | Li et al. |
| 2010/0254916 | A1 | 10/2010 | Karanewsky et al. |

FOREIGN PATENT DOCUMENTS

| | | |
|---|---|---|
| CA | 1 000 736 | 11/1976 |
| WO | WO 90/11695 | 10/1990 |
| WO | WO 96/34851 | 11/1996 |
| WO | WO 00/42003 | 7/2000 |
| WO | WO 00/71537 | 11/2000 |
| WO | WO 2006003495 | 1/2006 |
| WO | WO 2006009876 | 1/2006 |
| WO | WO 2006/043839 | 4/2006 |

OTHER PUBLICATIONS

Berry et al. (2005) *Journal of Organic Chemistry* 70(10): 4038-4042.
Caturla et al. (2004) *Journal of Medicinal Chemistry* 47(15): 3874-3886.
Harada et al. (1987) *Chem. Pharm. Bull.* 35(8): 3195-3214.
Holmes et al. (2005) *Bioorganic & Medicinal Chemistry Letters* 15(19): 4336-4341.
Sabbioni et al. (2000) *Chem. Res. Toxicol.* 13: 82-89.
Vippagunta et al.(2001) *Advanced Drug Delivery Reviews* 48:3-26.
Database Reaxys [Online] (1952) Accession No. 3465353 (Abstract Only).
Database Registry [Online] (2006) Accession No. 889802-83-9 (Abstract Only).
Database Registry [Online] (2006) Accession No. 873790-10-4 (Abstract Only).
Database Registry [Online] (2005) Accession No. 846575-85-7 (Abstract Only).
Database Registry [Online] (2004) Accession No. 751424-69-8 (Abstract Only).
Database Registry [Online] (2004) Accession No. 685088-92-0 (Abstract Only).
Database Registry [Online] (2003) Accession No. 483978-17-2 (Abstract Only).
Database Registry [Online] (2003) Accession No. 483978-13-8 (Abstract Only).
Database Registry [Online] (2002) Accession No. 460338-64-1 (Abstract Only).
Extended European Search Report for European Application No. 08795436.8, mailed Sep. 19, 2011.
International Search Report for International Application No. PCT/US2011/0021302, mailed Jun. 13, 2011.
Written Opinion for International Application No. PCT/US2011/0021302, mailed Jun. 13, 2011.
International Search Report for International Application No. PCT/US08/09864, mailed Mar. 18, 2009.
Written Opinion for International Application No. PCT/US08/09864, mailed Mar. 18, 2009.
Raju et al., *Tetrahedron Letters*, "Quinone Methide Initiated Cyclization Reaction: Synthesis of 4-aryl-1,2,3,4-Tetrahydroiosoquinolines", vol. 45, #40, (2004), pp. 7487-7489.

*Primary Examiner* — Kamal Saeed
*Assistant Examiner* — Nyeemah A Grazier
(74) *Attorney, Agent, or Firm* — Hunton & Williams LLP

(57) ABSTRACT

The present invention relates to the discovery that specific human taste receptors in the T2R taste receptor family respond to particular bitter compounds present in, e.g., coffee. Also, the invention relates to the discovery of specific compounds and compositions containing that function as bitter taste blockers and the use thereof as bitter taste blockers or flavor modulators in, e.g., coffee and coffee flavored foods, beverages and medicaments. Also, the present invention relates to the discovery of a compound that antagonizes numerous different human T2Rs and the use thereof in assays and as a bitter taste blocker in compositions for ingestion by humans and animals.

10 Claims, 3 Drawing Sheets

*Fig. 1 The bitter coffee fraction activated hT2R8 and hT2R14*
*[Coffee fraction] = 1 mg/mL*
*Blue dye = 1.9 mM FD&C 1*
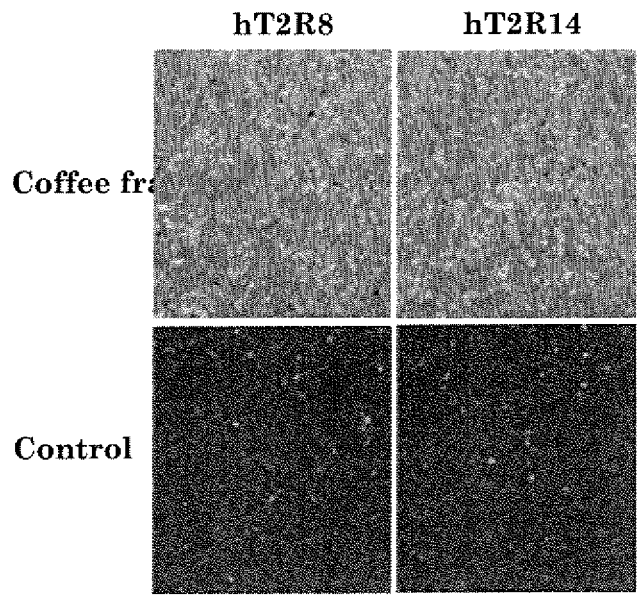
*Fig. 2 Dose-dependent response of hT2R8 and hT2R14 to the coffee fraction*
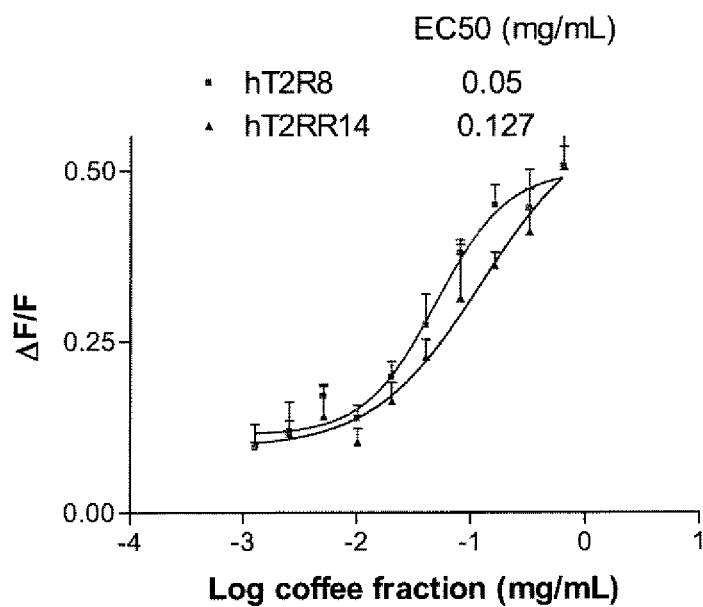

*Fig. 3 Dose-dependent inhibition curves for compound A and B on hT2R8 stable cell line*
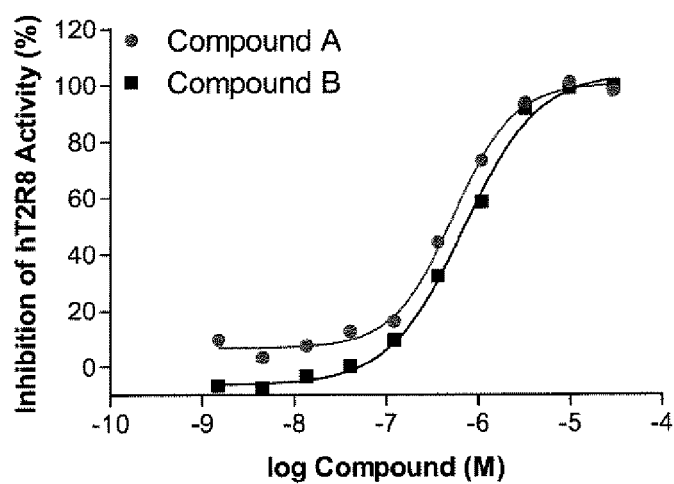
*Fig. 4 Dose-dependent inhibition curves for compound C on hT2R14 stable cell line*
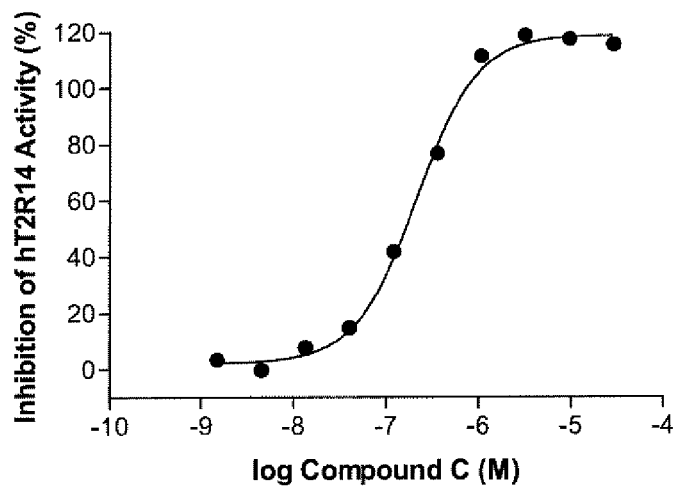

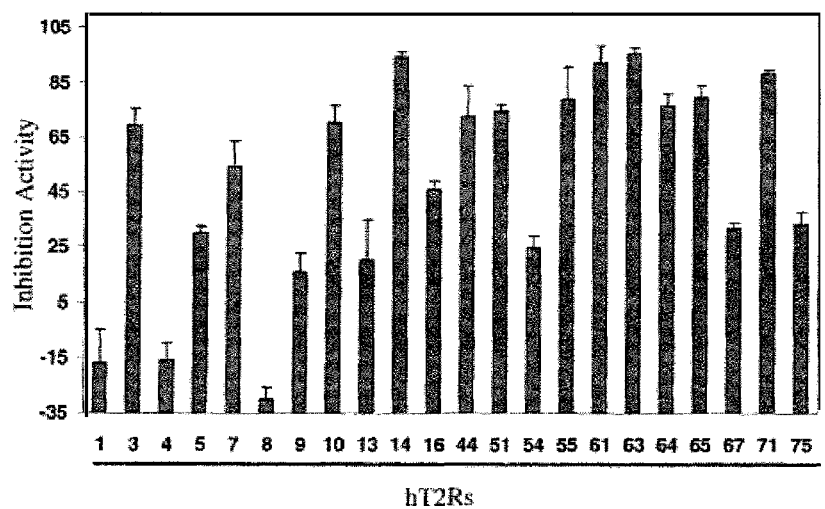
Figure 5 Inhibition activity of S5105 on 22 hT2Rs
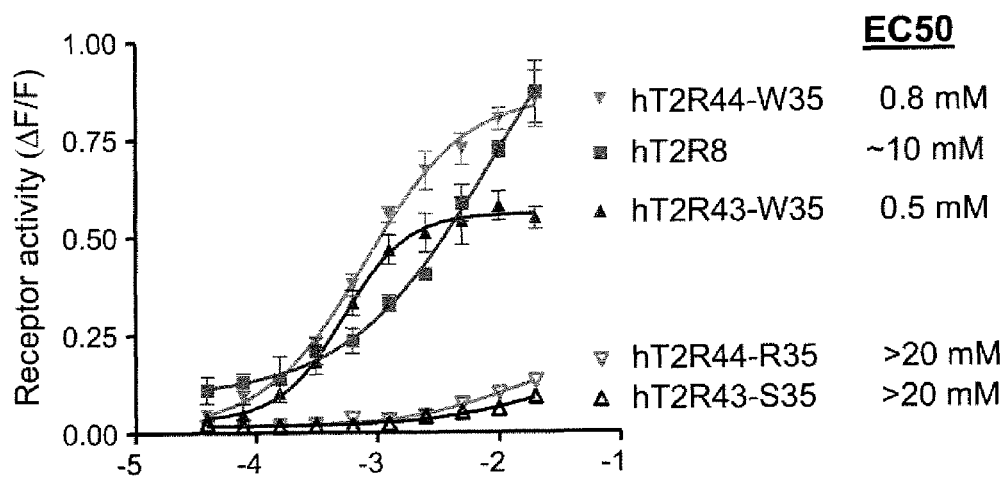
FIG. 6

COMPOUNDS THAT INHIBIT (BLOCK) BITTER TASTE IN COMPOSITION AND USE THEREOF

RELATED APPLICATIONS

This application is a Division of U.S. application Ser. No. 12/656,936, filed Feb. 19, 2010, which is a continuation-in-part of U.S. application Ser. No. 12/222,918, filed Aug. 19, 2008, which claims the benefit of U.S. Provisional Application Ser. No. 60/957,129 filed on Aug. 21, 2007 and U.S. Provisional Application Ser. No 61/047,187, filed on Apr. 23, 2008 and relates to U.S. application Ser. No. 11/766,974, which is a continuation-in-part U.S. application Ser. No. 11/555,617 filed on Nov. 1, 2006, which is in turn a continuation-in-part of U.S. application Ser. No. 10/191,058 filed Jul. 10, 2002 now U.S. Pat. No. 7,338,771 and is also a continuation-in-part of U.S. application Ser. No. 10/742,209 filed on Dec. 1, 2003, which is a divisional of U.S. application Ser. No. 09/825,882 filed on Apr. 5, 2001, now U.S. Pat. No. 7,105,650, all of which applications are incorporated by reference in their entireties herein.

FIELD OF THE INVENTION

This application relates to the identification of human type 2 taste receptors (hT2Rs) and the use thereof in assays for the identification of ligands that activate specific T2Rs. These ligands are useful for modulating taste perception, particularly bitter taste. In our previous patent applications, we described functional expression of human bitter taste receptors, including hT2R8 and hT2R14. In this patent application, we report that hT2R8 and hT2R14 are activated by a bitter-enriched fraction of coffee, we also report the identification of antagonists for hT2R8 and hT2R14 using a high throughput screening assay, and that combinations of the antagonists can reduce the bitter taste of coffee and coffee fractions. This invention provides a method to modify and improve the taste of coffee drinks.

Specifically, the present invention relates to the use of hT2R8 and/or hT2T14 in screening assays and taste tests to identify compounds that inhibit (block) the bitter taste of coffee and other foods and beverages.

Also, this invention relates to the discovery of a ligand that has broad bitter antagonistic properties, i.e., it appreciably blocks or inhibits the activation of many (13) different bitter receptors by a diverse set of bitter ligands and blocks or inhibits the activation of six other bitter taste receptors as well as inhibiting bitterness elicited by some bitter compounds for which the bitter receptor(s) that they interact with has not as yet been elucidated.

More specifically, this invention relates to the discovery of a ligand referred to herein as compound C that has broad bitter antagonistic properties, i.e., it appreciably blocks or inhibits the activation of hT2R3, 7, 10, 14, 16, 44, 51, 55, 61, 63, 64, 65 and 71 bitter taste receptors by a diverse set of bitter ligands and blocks or inhibits the activation of six other bitter taste receptors, i.e., hT2R5, 9, 13, 54, 67 and 75 as well as inhibiting bitterness elicited by some bitter compounds for which the bitter receptor(s) that they interact with has not as yet been elucidated.

Also more specifically the invention provides the discovery that this antagonist compound reduces the bitter taste of salicin, an hT2R16 antagonist, and phenylthiourea a hT2R51 agonist.

Also more specifically this invention provides the discovery that this same antagonist compound blocks the bitter taste elicited by bitter compounds that activate multiple bitter taste receptors, including omeprazole that activates hT2R10, 14 and 75; Rebaudioside A, a natural sweetener that activates at least 7 bitter taste receptors; and that this same antagonist further also inhibits bitter taste elicited by bitter compounds wherein the bitter receptor(s) with which they interact is unknown including dextromethorphan and diphenhydramine.

Based thereon, the invention relates to the use of this compound in foods, beverages, medicaments and other ingestibles in order to alleviate the bitter taste thereof, including bitter taste elicited by unidentified bitter ligands or compounds wherein bitterness involves the activation of multiple bitter receptors or for bitter compounds wherein the receptor specificity thereof is undetermined.

Also, based thereon the invention relates to the use of this antagonist in order to elucidate a conserved motif present in different human T2Rs that is involved in ligand binding and T2R activation and the design of chimeric and mutated G protein-coupled receptors (GPCRs) which are engineered to contain this motif.

Further, the invention relates to any of the compounds identified using these screening assays and the use thereof in foods beverages and medicaments including coffee and coffee flavored foods and beverages and medicaments.

DESCRIPTION OF THE RELATED ART

One of the basic taste modalities that humans can recognize is bitter. The physiology of bitter taste until quite recently was very poorly understood. Recent studies have started to shed light on the biology of taste (Lindemann, Nature (2001)). It is now known that many bitter compounds produce bitter taste by interacting with cell surface receptors. These receptors belong to the family of seven transmembrane domain receptors that interact with intracellular G proteins. A novel family of GPCRs, termed T2Rs, has been identified in humans and rodents (Adler et al., Cell 100(6):693-702 (2000); Chandrashekar et al., Cell 100(6): 703-711 (2000); Matsunami H, Montmayeur J P, Buck L B. Nature 404(6778): 601-4 (2000)). Several lines of evidence prior to the subject invention suggested that T2Rs mediate responses to bitter compounds. First, T2R genes are specifically expressed in subset of taste receptor cells of the tongue and palate epithelia. Second, the gene for one of the human T2Rs (hT2R1) is located in a chromosomal locus that is linked to sensitivity to bitter compound 6-n-propyl-2-thiouracil in humans (Adler et al., (Id.) (2000)). Third, one of the mouse T2Rs (mT2R5) is located in a chromosomal locus that is linked to sensitivity to bitter compound cycloheximide in mice. It was also shown that mT2R5 can activate gustducin, G protein specifically expressed in taste cells and linked to bitter stimuli transduction (Wong et al., Nature 381:796-800 (1996)). Gustducin activation by mT2R5 occurs only in response to cycloheximide (Chandrashekar et al., (Id.) (2000). Thus, it has been proposed that mT2R family mediates bitter taste response in mice, whereas hT2R family mediates bitter taste response in humans. Only one human T2R was suggested as having identified bitter ligand-hT2R4 was shown as being activated by denatonium (Chandrashekar et al., (Id.) 2000). However, effective denatonium concentrations used in the study (1.5 mM) were unusually high, i.e., were $10^5$-fold higher than the reported bitter threshold for denatonium to humans (Saroli, Naturwissenschaften 71:428-429 (1984)). Thus, no specific bitter ligand was convincingly matched to any hT2R. It has been also suggested that each hT2R is able to bind multiple bitter ligands. This hypothesis is based on the fact that hT2R family consists of only 25 identified members, whereas humans can recognize hundreds of different compounds as bitter. Sequences of hT2Rs have been previously reported and are discloses in published PCT applications by Zuker et al. (WO 01/18050 A2, (2001)) and Adler et al. (WO 01/77676 A1 (2001)) both of which are incorporated by reference in their entirety herein.

One of the difficulties of studying T2R function is that these receptors are not readily expressed in cultured mammalian cell lines. To improve T2R expression an N-terminal sequence from well-expressed GPCR, rhodopsin, was attached to T2R sequences (Chandrashekar et al., (Id.) 2000). This N-terminal tag also allowed easy monitoring of protein expression due to available antibody. In addition, SSTR3 tag (Bufe et al., Nat. Genet. 32:397-400 (2002)), a different N-terminal tag has been used to improve T2R expression. Whereas the incorporation of the rhodopsin tag improved expression of some T2Rs in mammalian cell lines, many of them still were not expressed well enough for functional studies. In a different approach mT2R5 was successfully expressed in insect Sf9 cells and used for functional studies using biochemical GTPγS binding assay (Chandrashekar et al., (Id.) 2000).

In Applicants' earlier patent application, U.S. application Ser. No. 09/825,882 now U.S. Pat. No. 7,105,650, Applicants identified and provided the nucleic acid sequences and polypeptide sequences for a number of then-novel human taste receptors including hT2R51, hT2R54, hT2R55, hT2R61, hT2R63, hT2R64, hT2R65, hT2R67, hT2R71, and hT2R75. Additionally in U.S. application Ser. Nos. 11/182,942 and 10/628,464, the entireties of which are incorporated by reference herein, Applicants provided the polypeptide and DNA sequence for another identified novel human taste receptor named therein hT2R76.

Also, in U.S. application Ser. No. 10/191,058 incorporated by reference herein in its entirety, Applicants discovered ligands that specifically activate three different human T2Rs. Additionally, Applicants recently filed U.S. application Ser. No. 11/455,693, the entirety of which is incorporated by reference herein, which further identified bitter ligands that specifically bind to other human T2Rs, and provided related assays.

Also, relating to practical utilities of the invention it has been reported that both T2Rs and T1Rs taste receptors are expressed in the gastrointestinal system. For example, Wu et al., Proc, Natl. Acad. Sci, USA 99(4):2392-7 (2002) report that T2Rs are expressed in enterendocrine cells (STC1 cells) as well as gustducin and transducin subunits and that these cells likely respond to bitter ligands in the gastrointestinal tract. Also, it has been reported by Chen et al., AM J. Physiol. Cell Phyisol. 291(4):C726-39 (2006) that bitter taste stimuli induce Ca++ signaling and cholecystokinin (CCK) release in enterendocrine STC-1 cells. Also, Rozengurt, A J Physiol Gastrointes Liver Physiol 291(2):G171-7 (2006) report that taste receptors in the gut likely play a role in molecular sensing the control of digestive functions, and hormonal and/or neuronal pathways and that they may play a role in the detection of harmful drugs and survival responses. Further, Stermini Am J Physiol Gastrointest Liver Physiol. 292(2): G457-61 (2007) report that taste receptors in the gut may be involved in gastrointestinal functions such as molecular sensing, nutrient absorption, protection from harmful substances, and further suggest that an understanding of these mechanisms may be relevant to disease states and conditions such as feeding disorders, and inflammation. Further, it has been recently suggested by Mace et al., J. Physiol. 2007 (Epub) that T2Rs and T1Rs activate phospholipase C beta 2, PLC beta2, and that there is likely a molecular intestinal sensing system in the gut similar to that present in lingual cells and that gastrointestinal cells such as brush cells or solitary chemosensory cells expressing taste receptors may result in GLUT2 increase and may play a role in nutrient sensing, and nutrition in the treatment of obesity and diabetes. Also, Cui et al, Curr Pharm Des. 12(35):4591-600 (2006) suggest that T1Rs expressed in the gut may be used in assays for compounds in treating obesity and diabetes as well as artificial sweeteners.

However, notwithstanding what has been reported and the understanding that T2R members regulate bitter taste, and their possible role in gastrointestinal functions there exists a need for the identification of specific ligands which activate human bitter T2R taste receptors. A greater understanding of the binding properties of different T2Rs, particularly human T2Rs, would be highly beneficial as it will greater facilitate the use thereof in selecting compounds having desired taste modulatory properties, i.e., which block or inhibit the taste of specific bitter compounds. Also, it will provide for the identification of compounds for treating and modulating gastrointestinal functions and related diseases such as obesity, diabetes, food absorption, food sensing, eating disorders, and in the regulation of related hormones and peptides such as GLUT2, cholecystokin et al.

SUMMARY OF THE INVENTION

Toward that end, the present invention relates to the discovery that hT2R8 and hT2R14 are activated by a bitter-enriched fraction of coffee.

Also, the present invention relates to the use thereof for the identification of antagonists for hT2R8 and hT2R14 that inhibit or block the bitter taste of coffee and coffee related foods, beverages and medicaments Further the invention relates to specific antagonist (bitter blocker) compounds that inhibit the bitter taste of coffee and other coffee flavored foods, beverages and medicaments.

Also, this invention relates to the discovery of a ligand that has broad bitter antagonistic properties, i.e., it appreciably blocks or inhibits the activation of many (13) different bitter receptors by a diverse set of bitter ligands and blocks or inhibits the activation of six other bitter taste receptors as well as inhibiting bitterness elicited by some bitter compounds for which the bitter receptor(s) that they interact with has not as yet been elucidated.

More specifically, this invention relates to the discovery of a ligand referred to herein as compound C that has broad bitter antagonistic properties, i.e., it appreciably blocks or inhibits the activation of hT2R3, 7, 10, 14, 16, 44, 51, 55, 61, 63, 64, 65 and 71 bitter taste receptors by a diverse set of bitter ligands and blocks or inhibits the activation of six other bitter taste receptors, i.e., hT2R5, 9, 13, 54, 67 and 75 as well as inhibiting bitterness elicited by some bitter compounds for which the bitter receptor(s) that they interact with has not as yet been elucidated.

Also more specifically the invention provides the discovery that this antagonist compound reduces the bitter taste of salicin an hT2R16 antagonist and phenylthiourea a hT2R51 agonist.

Also more specifically this invention provides the discovery that this same antagonist compound blocks the bitter taste elicited by bitter compounds that activate multiple bitter taste receptors, including omeprazole, a compound that activates hT2R10, 14 and 75; Rebaudioside A, a natural sweetener that activates at least 7 bitter taste receptors; and that this same antagonist compound further also inhibits bitter taste elicited by bitter compounds wherein the bitter receptor(s) with which they interact is unknown including dextromethorphan and diphenhydramin.

Based thereon, the invention relates to the use of this and related compounds according to the invention in foods, beverages, medicaments and other ingestibles in order to alleviate the bitter taste thereof, including bitter taste elicited by unidentified bitter ligands or compounds wherein bitterness involves the activation of multiple bitter receptors or bitter compounds wherein the receptor specificity thereof is undetermined.

Also, the present invention relates to foods, beverages and medicaments that contain an amount of at least one of the identified bitter antagonist compounds sufficient to inhibit or block the bitter taste thereof.

The inventive discoveries were made using cell-based assays that measured the activity of T2Rs using cells that express a particular T2R in the presence and absence of specific bitter ligands. In particular, as described in greater detail infra, HEK cell lines expressing the above-identified specific T2Rs on their surface and which further expressed a chimeric G protein that functionally couple to said T2Rs were used in cell-based assays that detected changes in intracellular calcium concentrations, and were found to be specifically activated by specific bitter compounds whereas other hT2Rs were not activated under similar conditions.

Therefore, the invention embraces the use of these human taste receptors in assays, preferably high-throughput assays, to identify other compounds that modulate, preferably block, the activation of these receptors by these and other bitter compounds present in coffee and related foods and beverages Also, the invention relates to the use of these receptors to identify compounds particularly those present in coffee and coffee flavored foods, beverages and medicaments that elicit a bitter taste.

Also, the invention relates to the use of an antagonist compound possessing broad ranging antagonist properties for use in vitro assays and in vivo taste tests to identify bitter compound(s) or bitter fractions for which this compound inhibits the bitter taste elicited thereby and/or inhibits the activation of one or more bitter taste receptors by the bitter compound or a fraction containing this bitter compound.

Further the invention specifically relates to the use of this broad acting antagonist in foods, beverages, medicaments and other consumed products for ingestion by humans or animals wherein bitter taste is desirably alleviated.

The invention also embraces assays which include an additional step which evaluates the effect of the identified modulating compounds in human or other taste tests, and particularly evaluates the effect of the identified compounds on bitter taste especially bitter taste elicited by coffee and fractions derived from coffee containing one or more compounds that elicit a bitter taste perception.

Further, the invention embraces the production of coffee and coffee flavored foods, beverages and medicinals which have been treated to remove compounds that specifically activate these bitter taste receptors, e.g., foods and beverages that have been processed to remove or reduce the amount of bitter compounds comprised therein.

In some aspects, the invention also relates to the structural classes of compounds represented by the two scaffolds given below. Scaffold 1 shows a representative urazole scaffold and scaffold 2 shows a representative hydantoin scaffold.

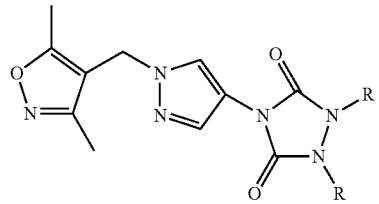

Scaffold 1

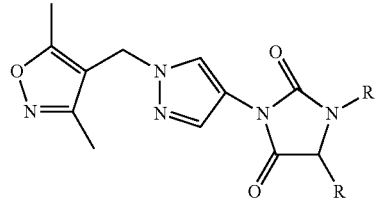

Scaffold 2

It is another specific object of the invention to use the compounds shown supra and analogs of scaffold 1, and scaffold 2 as bitter blockers to reduce bitterness in food/pharmaceutical applications that are mediated by T2R8 receptors, especially coffee and coffee flavored foods, beverages and medicaments.

It is another object of the invention to confirm that the identified compounds modulate, preferably inhibit or block, bitter taste, e.g. that elicited by coffee and coffee flavored foods, beverages and medicaments in human or animal taste tests, preferably human taste tests. Example 1 shows representative sensory data for one of these compounds. The data clearly demonstrates a significant decrease in bitterness for a specific T2R8 agonist and a significant increase in potency over a known T2R8 bitter blocker.

It is another object of the invention to utilize compounds described herein as additives or flavor modulators in compositions in order to inhibit or block the bitter taste elicited by compounds that specifically activate these taste receptors. A preferred object of the invention is to use a compound that inhibits activation of T2R8 receptors in order to block the bitter taste of compounds present in coffee and coffee flavored foods, beverages and medicinals.

Compounds identified according to the invention may be added to foods, beverages, cosmetics or medicinal compositions to modulate, preferably block bitter taste triggered by activation of hT2R8 by bitter compounds present in coffee and related foods, beverages and medicaments or structurally related compounds or other bitter compounds, e.g., compounds found in foods and beverages or medicinals or cosmetics that elicit a bitter taste perception.

OBJECTS OF THE INVENTION

It is an object of the invention to provide assays that use hT2R8 and/or hT2R14 and chimeras and variants thereof which identify compounds and compositions containing which elicit or block the bitter taste associated with coffee and coffee flavored foods, beverages and medicaments.

It is a specific object of the invention to provide assays that identify compounds which activate or which block or modulate the activation and/or binding of hT2R8 to compounds or compositions containing responsible for coffee's bitter taste.

It is also a specific object of the invention to provide assays that identify compounds which activate or which block or modulate the activation and/or binding of hT2R14 to compounds or compositions containing responsible for coffee's bitter taste.

It is another specific object of the invention to provide the specific compounds identified using the inventive assays and compositions containing especially coffee and coffee flavored foods, beverages and medicaments.

It is a specific object of the invention to provide the compounds shown below which are T2R8 and T2R14 antagonists that have been shown to block bitterness of coffee.

Compound A

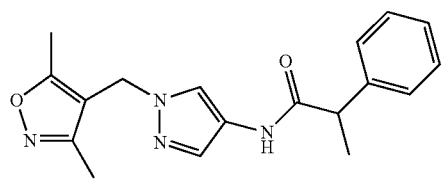

IC$_{50}$ = 0.3 uM (hT2R08)

Compound B

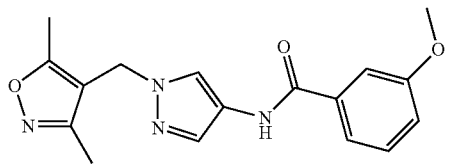

IC$_{50}$ = 0.4 uM (hT2R08)

Compound C

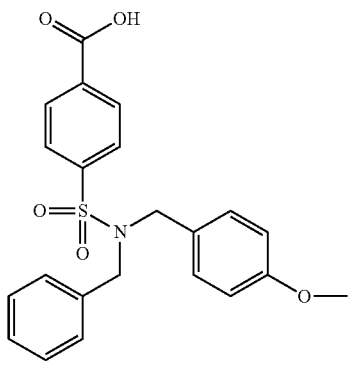

IC$_{50}$ = 0.2 uM(hT2R14)

It is another specific object of the invention to use the compounds shown supra and analogs of Compound A, Compound B and Compound C as bitter blockers to reduce bitterness in food/pharmaceutical application that is mediated by T2R8 and/or T2R14 receptors, especially coffee and coffee flavored foods, beverages and medicaments.

It is another specific object of the invention to use Compound C and analogs thereof as broadly acting bitter blockers to reduce bitterness in food/pharmaceutical application that is mediated by any of human T2R3, 7, 10, 14, 16, 44, 51, 55, 61, 63, 64, 65, or 71 and/or human T2R5, 9, 13, 54, 67 or 75, especially in foods, beverages and medicaments containing multiple bitter compounds, bitter compounds that interact with multiple bitter taste receptors or compositions containing unknown bitter compounds or bitter compounds wherein their receptor specificity is unknown.

It is another specific object of the invention to provide the compounds which can be represented by the following formulae.

In a first aspect, a compound of structural Formula (I) is provided:

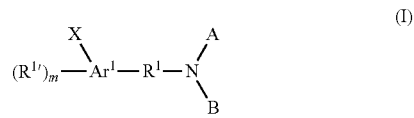

or a salt, hydrate, solvate or N-oxide thereof wherein:

Ar$^1$ a five or six membered aryl, heteroaryl or cycloalkyl ring;

m is 0, 1, 2 or 3;

R$^1$ is SO$_2$; C=O; C=S; or C=NOR$^4$;

X is selected from the group consisting of hydrogen, halogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, CN, NO$_2$, OR$^6$, S(O)$_b$R$^6$, NR$^6$R$^7$, CONR$^6$R$^7$, CO$_2$R$^6$, NR$^6$CO$_2$R$^7$, NR$^6$CONR$^7$R$^8$, NR$^6$CSNR$^7$R$^8$, NR$^6$C(=NH)NR$^7$R$^8$, SO$_2$NR$^5$R$^6$, NR$^5$SO$_2$R$^6$, NR$^5$SO$_2$NR$^6$R$^7$, B(OR$^5$)(OR$^6$), P(O)(OR$^5$)(OR$^6$), and P(O)(R$^5$)(OR$^6$);

each R$^{1\prime}$ is independently selected from the group consisting of hydrogen, halogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, CN, NO$_2$, OR$^6$, S(O)$_b$R$^6$, NR$^6$R$^7$, CONR$^6$R$^7$, CO$_2$R$^6$, NR$^6$CO$_2$R$^7$, NR$^6$CONR$^7$R$^8$, NR$^6$CSNR$^7$R$^8$, NR$^6$C(=NH) NR$^7$R$^8$, SO$_2$NR$^5$R$^6$, NR$^5$SO$_2$R$^6$, NR$^5$SO$_2$NR$^6$R$^7$, B(OR$^5$) (OR$^6$), P(O)(OR$^5$)(OR$^6$), and P(O)(R$^5$)(OR$^6$);

or alternatively, X and/or at least one R$^{1\prime}$ together with the atoms to which they are bonded form an aryl, substituted aryl, heteroaryl, substituted heteroaryl, cycloalkyl, substituted cycloalkyl, cycloheteroalkyl or substituted cycloheteroalkyl ring where the ring is optionally fused to another aryl, substituted aryl, heteroaryl, substituted heteroaryl, cycloalkyl, substituted cycloalkyl, cycloheteroalkyl or substituted cycloheteroalkyl ring;

R$^4$-R$^8$ are independently selected from the group consisting of hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl and substituted heteroarylalkyl or alternatively, R$^5$ and R$^6$, R$^6$ and R$^7$, R$^7$ and R$^8$, together with the atoms to which they are bonded form a cycloheteroalkyl or substituted cycloheteroalkyl ring;

A and B are independently selected from the group consisting of hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl; and b is 0, 1, or 2.

In some embodiments, A and B, together with the nitrogen atom to which they are attached, form a ring that can be fused with additional substituted or unsubstituted rings and can comprise at least one double bond. A non-limiting example of such a ring includes a group having the formula:

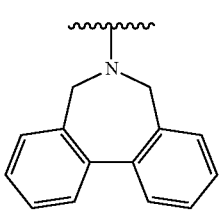 [SMILES: *N1Cc2ccccc2-c2ccccc2C1]

In a second aspect the invention provides compounds of structural Formula (II) shown below:

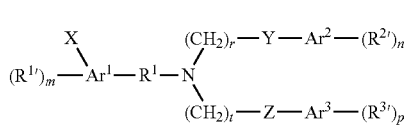

or a salt, hydrate, solvate or N-oxide thereof wherein:

$Ar^1$, $Ar^2$ and $Ar^3$ are independently a five or six membered aryl, heteroaryl, or cyclolalkyl ring;

m is 0, 1, 2 or 3;

n and p are independently 0, 1, 2, 3 or 4;

r and t are independently 0, 1 or 2;

Y and Z are independently selected from the group consisting of $CR^6R^7$, C=O, C=S, $C=NOR^6$, O, $NR^6$, and $S(O)_b$;

$R^1$ is selected from the group consisting of $SO_2$, C=O, C=S, and $C=NOR^4$;

X may be selected from the group consisting of hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, CN, $NO_2$, $-OR^6$, $S(O)_bR^6$, $NR^6R^7$, $CONR^6R^7$, $CO_2R^6$, $NR^6CO_2R^7$, $NR^6CONR^7R^8$, $NR^6CSNR^7R^8$, $NR^6C(=NH)NR^7R^8$, $SO_2NR^5R^6$, $NR^5SO_2R^6$, $NR^5SO_2NR^6R^7$, $B(OR^5)(OR^6)$, $P(O)(OR^5)(OR^6)$, and $P(O)(R^5)(OR^6)$.

X is preferably selected from the group consisting of hydrogen, heteroalkyl, substituted heteroalkyl, heteroaryl, substituted heteroaryl, heteroarylalkyl, substituted heteroarylalkyl, CN, $S(O)_bR^6$, $CONR^6R^7$, $-CO_2R^6$, $SO_2NR^5R^6$, $NR^5SO_2R^6$, $NR^5SO_2NR^6R^7$, $B(OR^5)(OR^6)$, $P(O)(OR^5)(OR^6)$, and $P(O)(R^5)(OR^6)$.

each $R^{1'}$ is independently selected from the group consisting of hydrogen, halogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, CN, $NO_2$, $OR^6$, $S(O)_bR^6$, $NR^6R^7$, $CONR^6R^7$, $CO_2R^6$, $NR^6CO_2R^7$, $NR^6CONR^7R^8$, $NR^6CSNR^7R^8$, $NR^6C(=NH)NR^7R^8$, $SO_2NR^5R^6$, $NR^5SO_2R^6$, $NR^5SO_2NR^6R^7$, $B(OR^5)(OR^6)$, $P(O)(OR^5)(OR^6)$, and $P(O)(R^5)(OR^6)$;

each $R^{2'}$ is independently selected from the group consisting of hydrogen, halogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, CN, $NO_2$, $OR^6$, $S(O)_bR^6$, $NR^6R^7$, $CONR^6R^7$, $CO_2R^6$, $NR^6CO_2R^7$, $NR^6CONR^7R^8$, $NR^6CSNR^7R^8$, $NR^6C(=NH)NR^7R^8$, $SO_2NR^5R^6$, $NR^5SO_2R^6$, $NR^5SO_2NR^6R^7$, $B(OR^5)(OR^6)$, and $P(O)(OR^5)(OR^6)$;

each $R^{3'}$ is independently selected from the group consisting of hydrogen, halogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, CN, $NO_2$, $OR^6$, $S(O)_bR^6$, $NR^6R^7$, $CONR^6R^7$, $CO_2R^6$, $NR^6CO_2R^7$, $NR^6CONR^7R^8$, $NR^6CSNR^7R^8$, $NR^6C(=NH)NR^7R^8$, $SO_2NR^5R^6$, $NR^5SO_2R^6$, $NR^5SO_2NR^6R^7$, $B(OR^5)(OR^6)$, $P(O)(OR^5)(OR^6)$, and $P(O)(R^5)(OR^6)$;

or alternatively, X and/or at least one of $R^{1'}$ together with the atoms to which they are bonded form an aryl, substituted aryl, heteroaryl, substituted heteroaryl, cycloalkyl, substituted cycloalkyl, cycloheteroalkyl or substituted cycloheteroalkyl ring where the ring is optionally fused to another aryl, substituted aryl, heteroaryl, substituted heteroaryl, cycloalkyl, substituted cycloalkyl, cycloheteroalkyl or substituted cycloheteroalkyl ring;

$R^4$-$R^8$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl or alternatively, $R^5$ and $R^6$, $R^6$ and $R^7$, $R^7$ and $R^8$, together with the atoms to which they are bonded form a cycloheteroalkyl or substituted cycloheteroalkyl ring;

b is 0, 1, or 2.

In another aspect the invention provides compounds having structural Formula (III) shown below:

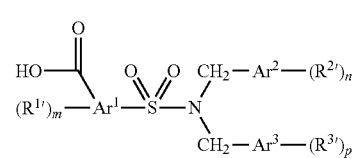

or a salt, hydrate, solvate or N-oxide thereof wherein:

$Ar^1$, $Ar^2$ and $Ar^3$ are independently a five or six membered aryl, heteroaryl, or cyclolalkyl ring, and $Ar^2$ and $Ar^3$ may optionally be omitted;

m is 0, 1, 2 or 3;

n and p are independently 0, 1, 2, 3 or 4;

each $R^{1'}$ is independently selected from the group consisting of hydrogen, halogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, CN, $NO_2$, $OR^6$, $S(O)_bR^6$, $NR^6R^7$, $CONR^6R^7$, $CO_2R^6$, $NR^6CO_2R^7$, $NR^6CONR^7R^8$, $NR^6CSNR^7R^8$, $NR^6C(=NH)NR^7R^8$, $SO_2NR^5R^6$, $NR^5SO_2R^6$, $NR^5SO_2NR^6R^7$, $B(OR^5)(OR^6)$, $P(O)(OR^5)(OR^6)$, and $P(O)(R^5)(OR^6)$;

each $R^{2'}$ is independently selected from the group consisting of hydrogen, halogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, CN, $NO_2$, $OR^6$, $S(O)_bR^6$, $NR^6R^7$, $CONR^6R^7$, $CO_2R^6$, $NR^6CO_2R^7$, $NR^6CONR^7R^8$, $NR^6CSNR^7R^8$, $NR^6C(=NH)NR^7R^8$, $SO_2NR^5R^6$, $NR^5SO_2R^6$, $NR^5SO_2NR^6R^7$, $B(OR^5)(OR^6)$, $P(O)(OR^5)(OR^6)$, and $P(O)(R^5)(OR^6)$;

each $R^{3'}$ is independently selected from the group consisting of hydrogen, halogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, CN, $NO_2$, $OR^6$, $S(O)_bR^6$, $NR^6R^7$, $CONR^6R^7$, $CO_2R^6$, $NR^6CO_2R^7$, $NR^6CONR^7R^8$, $NR^6CSNR^7R^8$, $NR^6C(=NH)NR^7R^8$, $SO_2NR^5R^6$, $NR^5SO_2R^6$, $NR^5SO_2NR^6R^7$, $B(OR^5)(OR^6)$, $P(O)(OR^5)(OR^6)$, and $P(O)(R^5)(OR^6)$;

$R^5$-$R^8$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl or alternatively, $R^5$ and $R^6$, $R^6$ and $R^7$, $R^7$ and $R^8$, together with the atoms to which they are bonded form a cycloheteroalkyl or substituted cycloheteroalkyl ring;

b is 0, 1, or 2.

In yet another aspect the invention provides a compound having the structure below:

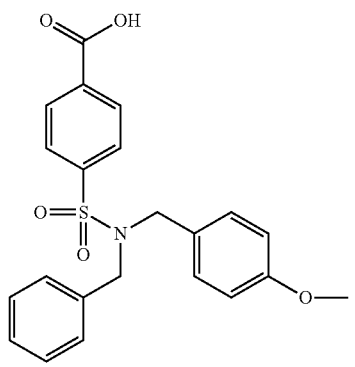 [SMILES: COc1ccc(CN(Cc2ccccc2)S(=O)(=O)c2ccc(C(=O)O)cc2)cc1]

or a salt, hydrate, solvate or N-oxide thereof.

In yet another aspect the invention provides compounds having the structure below:

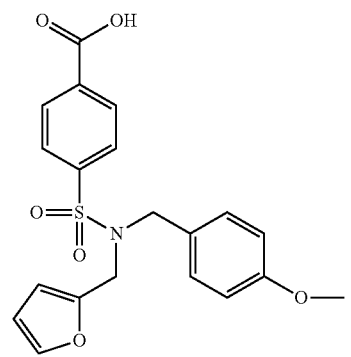

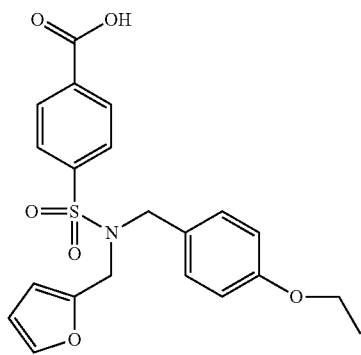

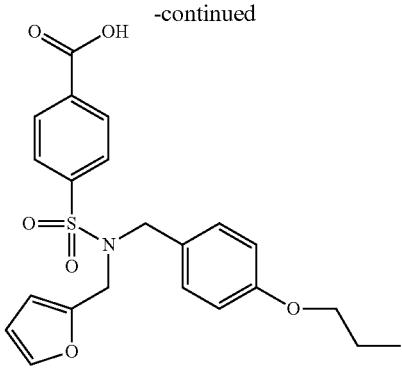

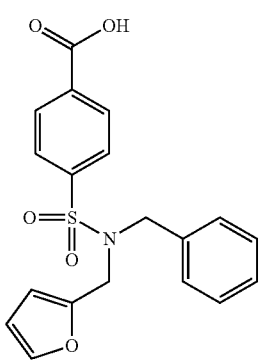

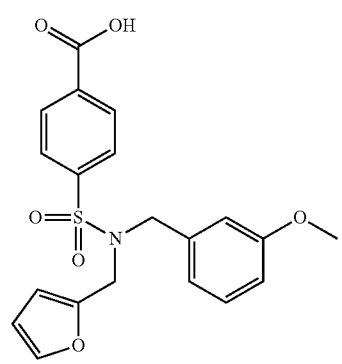

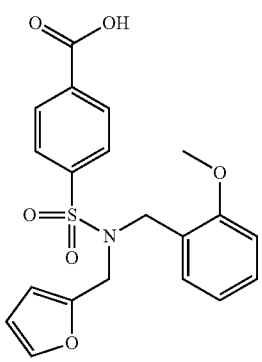

or a salt, hydrate, solvate or N-oxide thereof.

In still other embodiments, the invention provides compounds having the structure below:

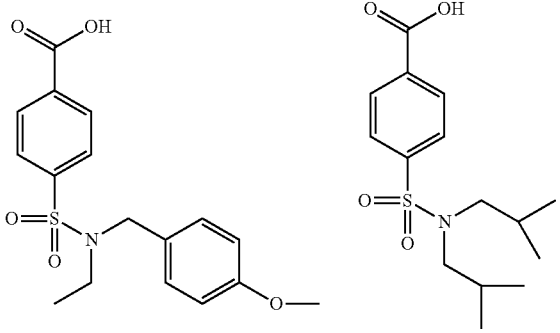 [SMILES: CCN(Cc1ccc(OC)cc1)S(=O)(=O)c1ccc(C(=O)O)cc1 ; CC(C)CN(CC(C)C)S(=O)(=O)c1ccc(C(=O)O)cc1]

or a salt, hydrate, solvate or N-oxide thereof.

In a related aspect, a compound of structural Formula (IV) is provided:

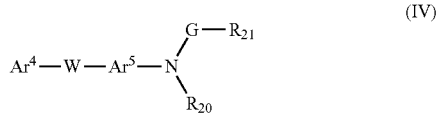
(IV)

or a salt, hydrate, solvate or N-oxide thereof wherein:

$Ar^4$ and $Ar^5$ are independently a five or six membered aryl or heteroaryl ring;

W is selected from the group consisting of $CR^6R^7$, C=O, C=S; C=NOR$^6$; O, NR$^6$, S, SO, SO$_2$, and (CH$_2$)$_n$;

n is 0, 1, 2, or 3;

G is selected from the group consisting of $CR^6R^7$, C=O, C=S, C=NOR$^6$, and S(O)$_b$;

$R^{20}$ is selected from the group consisting of hydrogen, arylalkenyl, heteroarylalkenyl, arylalkyl, heteroarylalkyl, aryl, heteroaryl, alkyl, alkoxy-alkyl, alkenyl, cycloalkyl, cycloalkenyl, and substituted derivatives;

$R^{21}$ is selected from the group consisting of an arylalkenyl, heteroarylalkenyl, arylalkyl, heteroarylalkyl, aryl, heteroaryl, alkyl, alkoxy-alkyl, alkenyl, cycloalkyl, cycloalkenyl, and substituted derivatives;

$R^6$ and $R^7$ are independently selected from the group consisting of hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl or alternatively, $R^6$ and $R^7$, together with the atoms to which they are bonded form a cycloheteroalkyl or substituted cycloheteroalkyl ring; and b is 0, 1, or 2.

In another related aspect a compound of structural Formula (V) is provided:

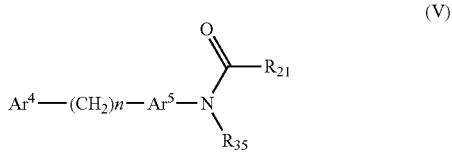
(V)

or a salt, hydrate, solvate or N-oxide thereof wherein:

$Ar^4$ and $Ar^5$ are independently a five or six membered aryl or heteroaryl ring;

n is 0, 1, 2, or 3;

$R^{21}$ is selected from the group consisting of an arylalkenyl, heteroarylalkenyl, arylalkyl, hereoarylalky, aryl, heteroaryl, alkyl, alkoxy-alkyl, alkenyl, cycloalkyl, cycloalkenyl, and substituted derivatives;

$R^{35}$ is selected from the group consisting of hydrogen, alkyl, and substituted alkyl.

In still additional embodiments the invention a compound of structural Formula (VI) is provided

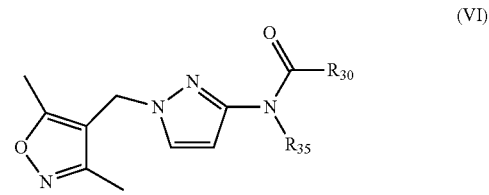
(VI)

or a salt, hydrate, solvate or N-oxide thereof wherein:

$R^{30}$ is selected from the group consisting of an arylalkenyl, heteroarylalkenyl, arylalkyl, hereoarylalky, aryl, heteroaryl, alkyl, alkoxy-alkyl, alkenyl, cycloalkyl, cycloalkenyl, and substituted derivatives;

$R^{35}$ is selected from the group consisting of hydrogen, alkyl, and substituted alkyl.

In still additional embodiments the invention provides compounds having the structure below:

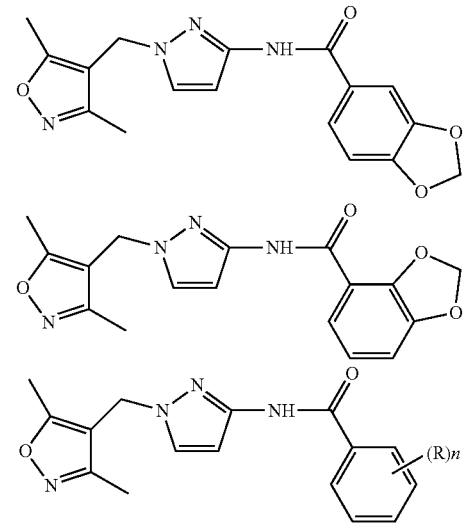

or a salt, hydrate, solvate or N-oxide thereof, wherein each R is independently Cl, MeO, CN, EtO, OH, Me, —SO$_2$Me, F, or H, and n is 0, 1, 2, 3 or 4.

In still other embodiments, the invention provides compounds having the structure below:

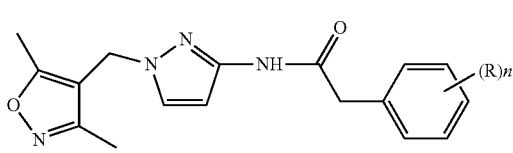

or a salt, hydrate, solvate or N-oxide thereof,
wherein each R is independently MeO or OH and
n is 0, 1, 2, 3 or 4.
In still other embodiments, the invention provides compounds having the structure below:
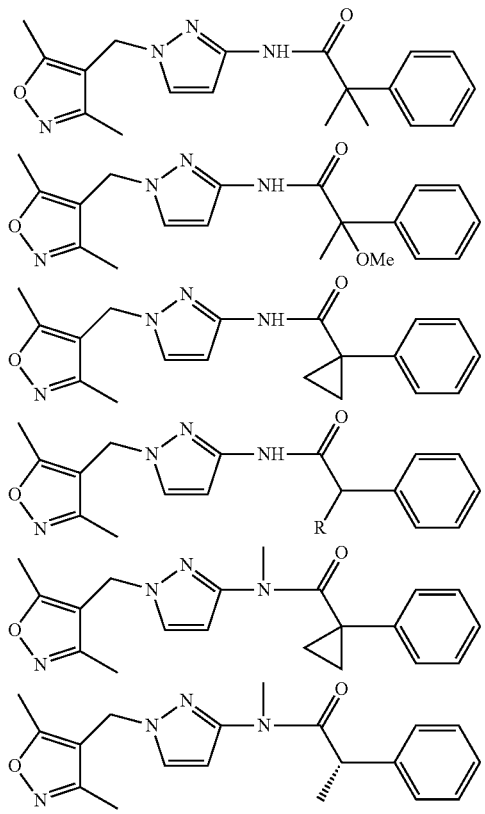
or a salt, hydrate, solvate or N-oxide thereof,
wherein R is H, Me, Et, OCOMe, CH₂OH, OMe, or Ph.
In still other embodiments, the invention provides compounds having the structure below:
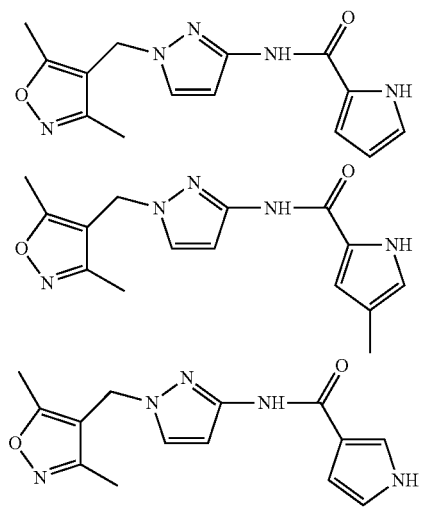
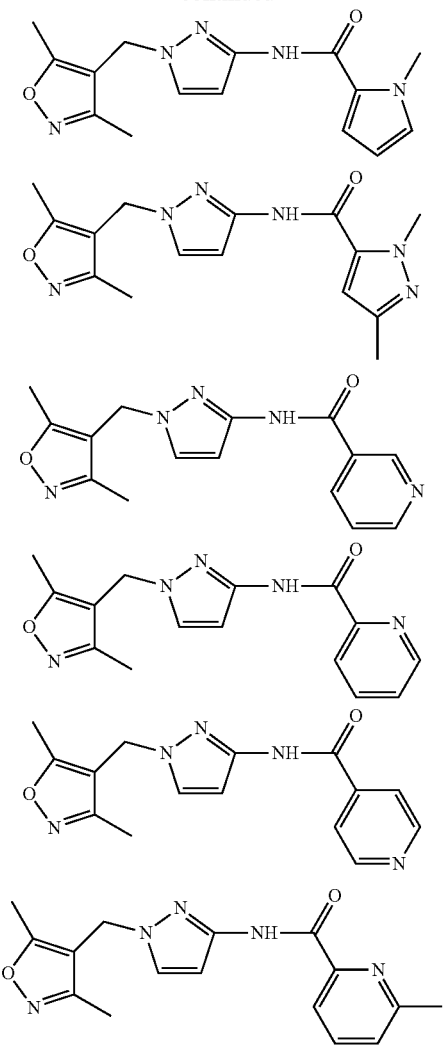
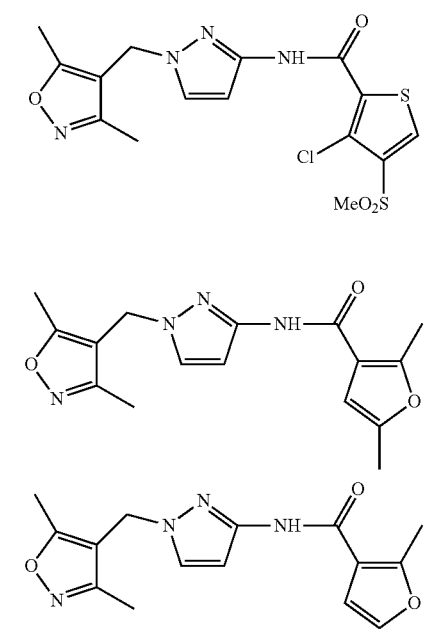

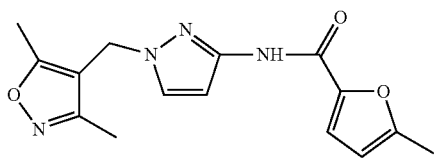

or a salt, hydrate, solvate or N-oxide thereof.

In still other embodiments, the invention provides compounds having the structure below:

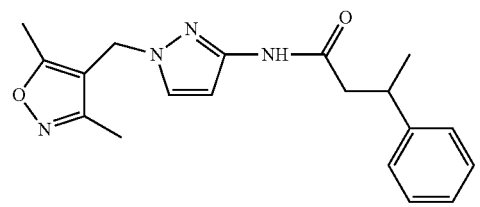

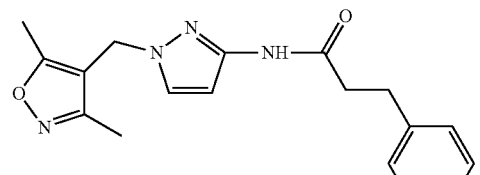

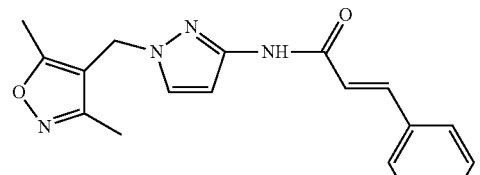

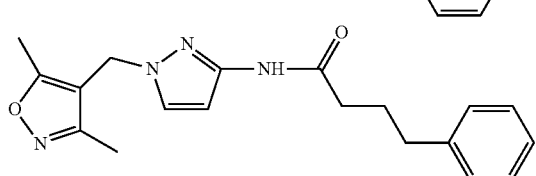

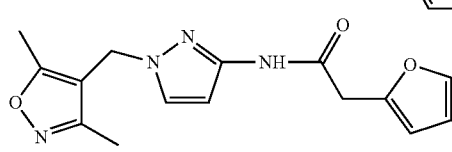

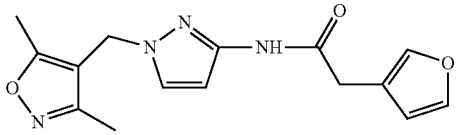

or a salt, hydrate, solvate or N-oxide thereof.

In still other embodiments, the invention provides compounds having the structure below:

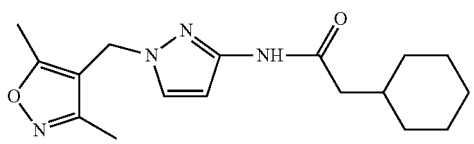

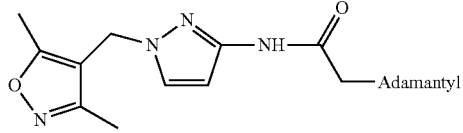

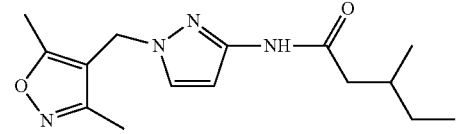

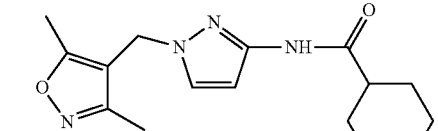

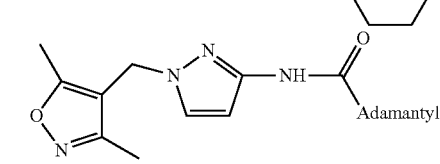

or a salt, hydrate, solvate or N-oxide thereof.

In still other embodiments, the invention provides compounds having the structure below:

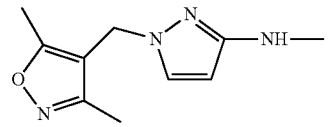

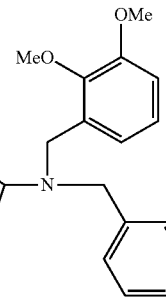

or a salt, hydrate, solvate or N-oxide thereof.

In one aspect, the invention relates to a compound of the formula:

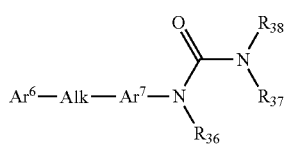

or a salt, hydrate, solvate, N-oxide or prodrug thereof,
wherein $Ar^6$ and $Ar^7$ are, the same or different independently one from the other, a five- or six-membered aryl group or a five- or six-membered heteroaryl group;
Alk is an alkyl group, optionally interrupted by a heteroatom;
$R_{36}$ and $R_{37}$ are, the same or different independently one from the other, H, alkyl, or, $R_{36}$ and $R_{37}$, together with the atoms to which they are attached, form an optionally substituted five- or six-membered heterocycle; and $R_{38}$ is H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted heteroarylamidoalkyl, substituted or unsubstituted arylalkyl, substituted or unsubstituted arylalkoxy, substituted or unsubstituted heteroaryl, substituted or unsubstituted heteroarylalkyl, or haloalkyl.

In one aspect the compounds of the invention contain a five-membered heterocycle. In one embodiment, the five-membered heterocycle is a hydantoin or a substituted or unsubstituted cyclic urea.

In one embodiment, the hydantoin is a hydantoin of the formula:

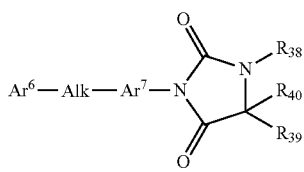

or a salt, hydrate, solvate, N-oxide or prodrug thereof, wherein $Ar^6$ and $Ar^7$ are, the same or different independently one from the other, a five- or six-membered aryl group or a five- or six-membered heteroaryl group;

Alk is an alkyl group, optionally interrupted by a heteroatom;

$R_{38}$ is H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted heteroarylamidoalkyl, substituted or unsubstituted arylalkyl, substituted or unsubstituted arylalkoxy, substituted or unsubstituted heteroaryl, substituted or unsubstituted heteroarylalkyl, or haloalkyl; and $R_{39}$ and $R_{40}$ are, the same or different independently one from the other, H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted arylalkylamidoalkyl, substituted or unsubstituted heteroarylamidoalkyl, substituted or unsubstituted heteroarylalkylamidoalkyl, substituted or unsubstituted arylalkyl, substituted or unsubstituted arylalkoxy, substituted or unsubstituted heteroaryl, substituted or unsubstituted heteroarylalkyl, haloalkyl, or $R_{39}$ and $R_{40}$, together with the carbon atom to which they are attached, form a C=O group or a substituted or unsubstituted alkenyl group.

In another aspect the compounds of the invention contain a five-membered heterocycle which is a urazole. In one embodiment, the urazole is a urazole of the formula:

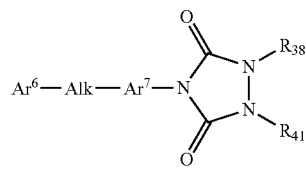

or a salt, hydrate, solvate, N-oxide or prodrug thereof, wherein $Ar^6$ and $Ar^7$ are, the same or different independently one from the other, a five- or six-membered aryl group or a five- or six-membered heteroaryl group;

Alk is an alkyl group, optionally interrupted by a heteroatom;

$R_{38}$ is H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted heteroarylamidoalkyl, substituted or unsubstituted arylalkyl, substituted or unsubstituted arylalkoxy, substituted or unsubstituted heteroaryl, substituted or unsubstituted heteroarylalkyl, or haloalkyl; and $R_{41}$ is H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted arylalkylamidoalkyl, substituted or unsubstituted heteroarylamidoalkyl, substituted or unsubstituted heteroarylalkylamidoalkyl, substituted or unsubstituted arylalkyl, substituted or unsubstituted arylalkoxy, substituted or unsubstituted heteroaryl, substituted or unsubstituted heteroarylalkyl, or haloalkyl.

In another aspect the compounds of the invention contain a six-membered heterocycle.

In one embodiment, the six-membered heterocycle is a six-membered heterocycle of the formula:

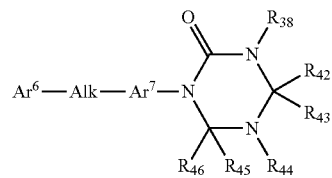

or a salt, hydrate, solvate, N-oxide or prodrug thereof, wherein $R_{38}$ is H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted heteroarylamidoalkyl, substituted or unsubstituted arylalkyl, substituted or unsubstituted arylalkoxy, substituted or unsubstituted heteroaryl, substituted or unsubstituted heteroarylalkyl, or haloalkyl; and $R_{42}$, $R_{43}$, $R_{44}$, $R_{45}$, and $R_{46}$ are, the same or different independently one from the other, H, substituted or unsubstituted alkyl, substituted or unsubstituted cycloalkyl alkyl, substituted or unsubstituted arylalkyl, substituted or unsubstituted arylalkoxy, substituted or unsubstituted heteroaryl, substituted or unsubstituted heteroarylalkyl, or $R_{42}$ and $R_{43}$, or $R_{45}$ and $R_{46}$, together with the carbon atoms to which each are attached, form a C=O group.

In another aspect, the invention relates to a compound of the formula:

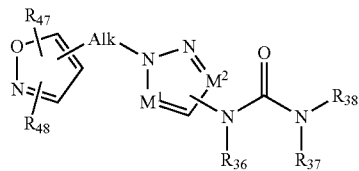

or a salt, hydrate, solvate, N-oxide or prodrug thereof,
wherein Alk is an alkyl group, optionally interrupted by a heteroatom;
$M^1$ is N or $CR_{49}$, wherein $R_{49}$ is H or substituted or unsubstituted alkyl;
$M^2$ is N or $CR_{50}$, wherein $R_{50}$ is H or substituted or unsubstituted alkyl;
$R_{36}$ and $R_{37}$ are, the same or different independently one from the other, H, alkyl, or, $R_{36}$ and $R_{37}$, together with the atoms to which they are attached, form an optionally substituted five- or six-membered heterocycle; and
$R_{38}$ is H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted heteroarylamidoalkyl, substituted or unsubstituted arylalkyl, substituted or unsubstituted arylalkoxy, substituted or unsubstituted heteroaryl, substituted or unsubstituted heteroarylalkyl, or haloalkyl;
$R_{47}$ is H, substituted or unsubstituted alkyl, substituted or unsubstituted alkoxy, substituted or unsubstituted aryl, substituted or unsubstituted arylalkyl, or halo; and
$R_{48}$ is H, substituted or unsubstituted alkyl, substituted or unsubstituted alkoxy, substituted or unsubstituted aryl, substituted or unsubstituted arylalkyl, or halo.

In still another aspect, the invention relates to a compound of the formula:

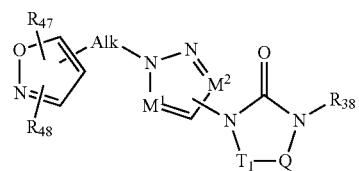

or a salt, hydrate, solvate, N-oxide or prodrug thereof,
wherein Alk is an alkyl group, optionally interrupted by a heteroatom;
$T_1$ is C=O and Q is $CR_{51}R_{52}$ or $NR_{51}$, wherein $R_{51}$ and $R_{52}$ are, the same or different independently one from the other, H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted arylalkylamidoalkyl, substituted or unsubstituted heteroarylamidoalkyl, substituted or unsubstituted heteroarylalkylamidoalkyl, substituted or unsubstituted arylalkyl, substituted or unsubstituted arylalkoxy, substituted or unsubstituted heteroaryl, substituted or unsubstituted heteroarylalkyl, haloalkyl, or $R_{51}$ and $R_{52}$, together with the carbon atom to which they are attached, form a C=O group or a substituted or unsubstituted alkenyl group;
$M^1$ is N or $CR_{49}$, wherein $R_{49}$ is H or substituted or unsubstituted alkyl;
$M^2$ is N or $CR_{50}$, wherein $R_{50}$ is H or substituted or unsubstituted alkyl;
$R_{38}$ is H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted heteroarylamidoalkyl, substituted or unsubstituted arylalkyl, substituted or unsubstituted arylalkoxy, substituted or unsubstituted heteroaryl, substituted or unsubstituted heteroarylalkyl, or haloalkyl;
$R_{47}$ is H, substituted or unsubstituted alkyl, substituted or unsubstituted alkoxy, substituted or unsubstituted aryl, substituted or unsubstituted arylalkyl, or halo; and
$R_{48}$ is H, substituted or unsubstituted alkyl, substituted or unsubstituted alkoxy, substituted or unsubstituted aryl, substituted or unsubstituted arylalkyl, or halo.

In another embodiment, the invention relates to a compound of the formula:

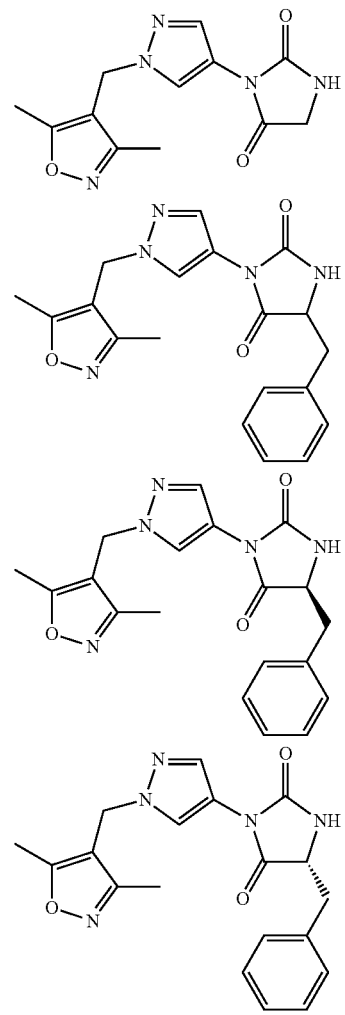

-continued
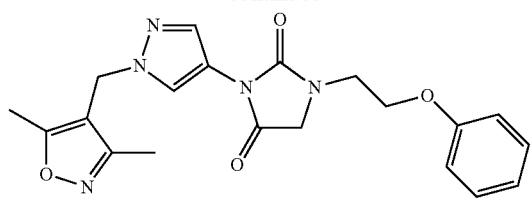
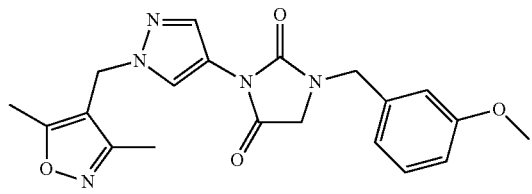
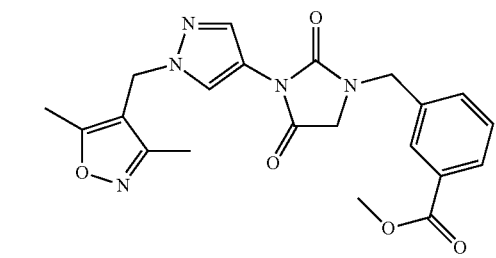
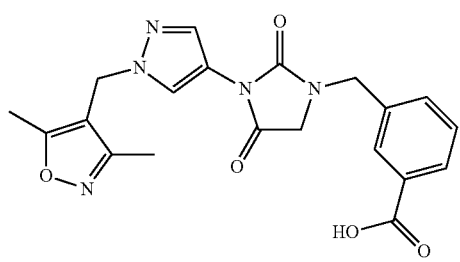
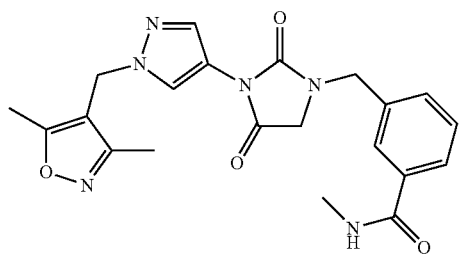
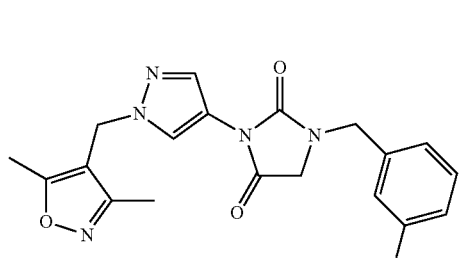
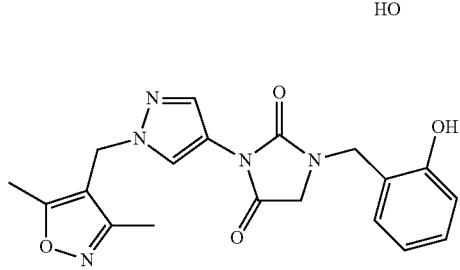
-continued
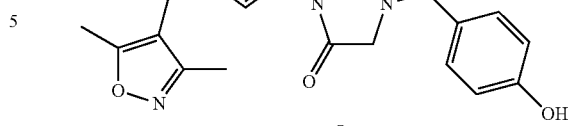
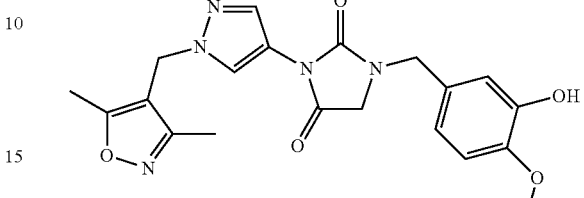
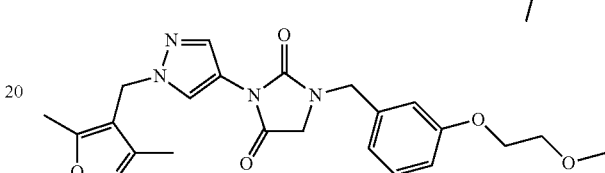
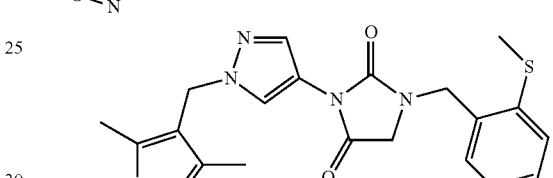
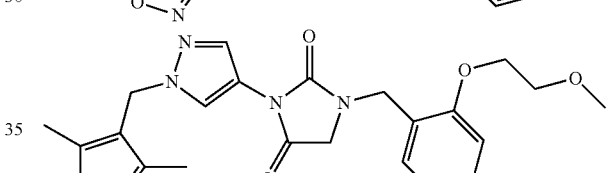
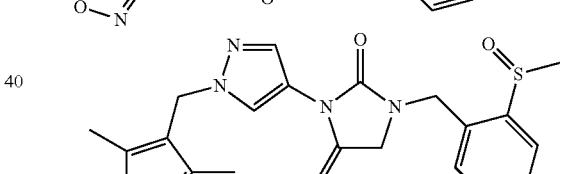
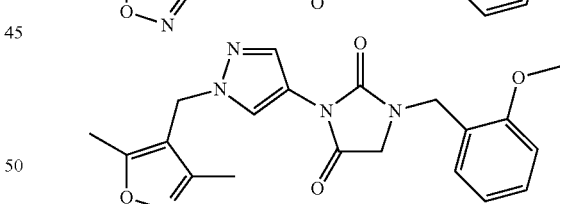
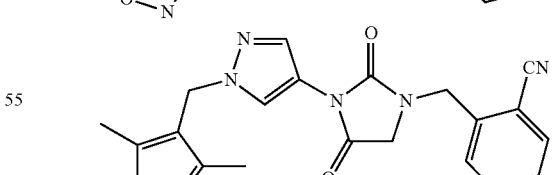
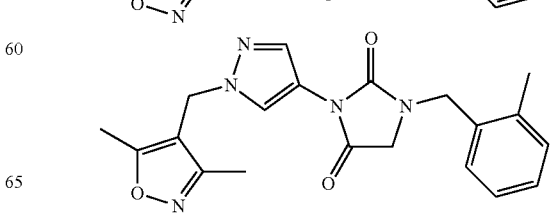

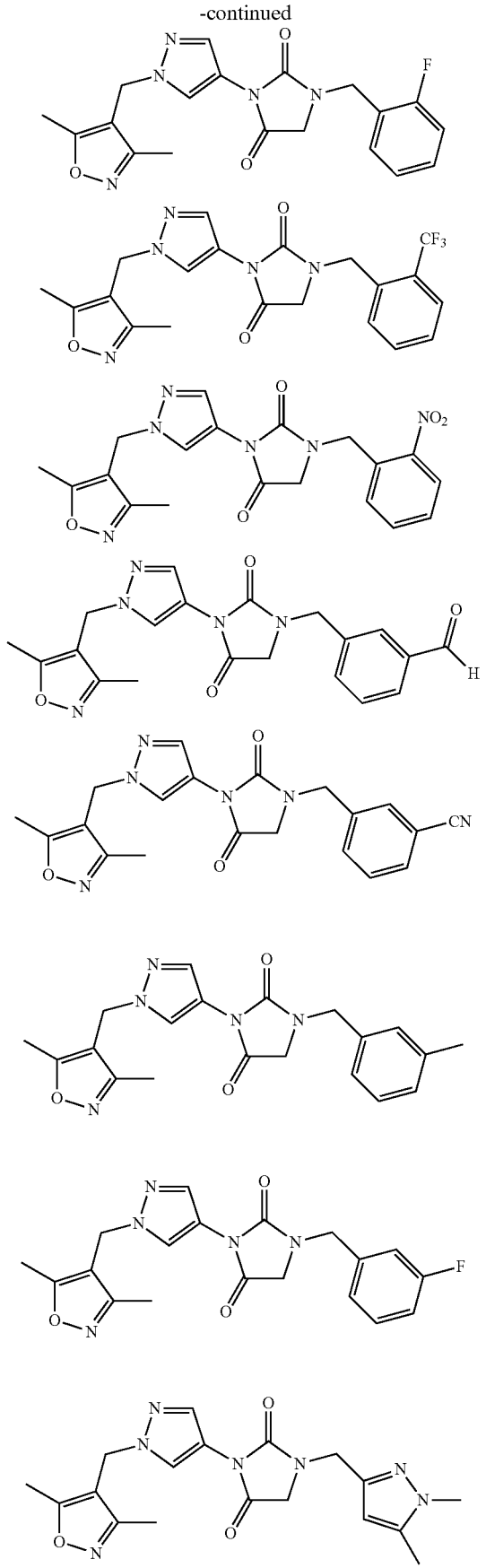
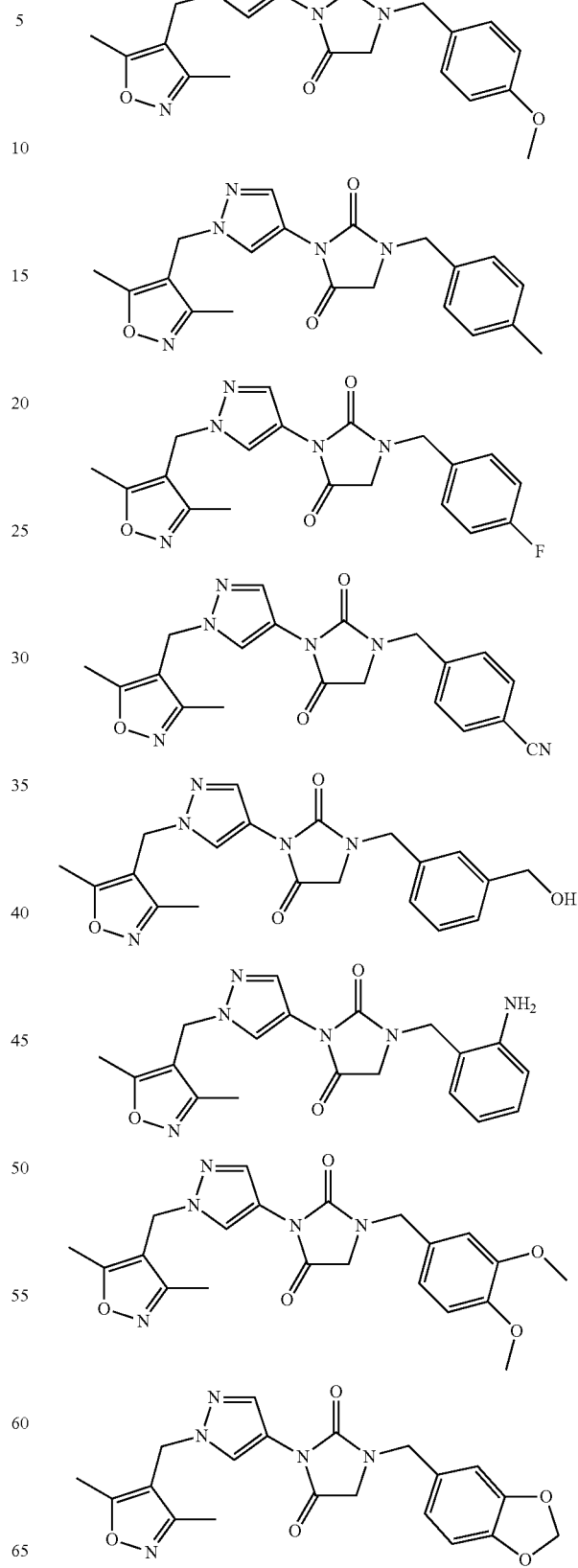

27
-continued
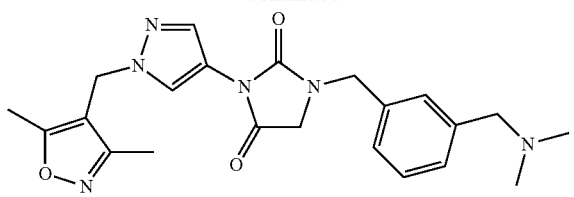
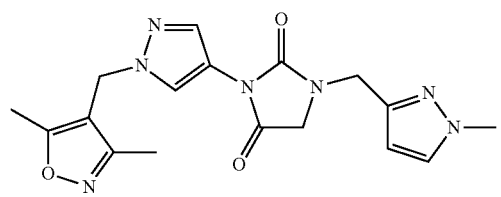
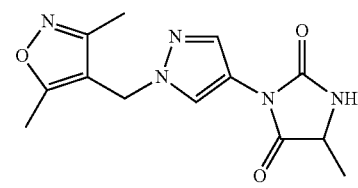
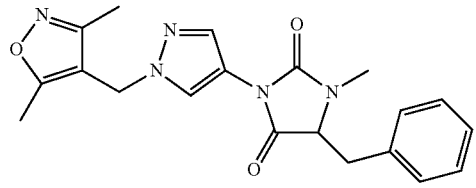
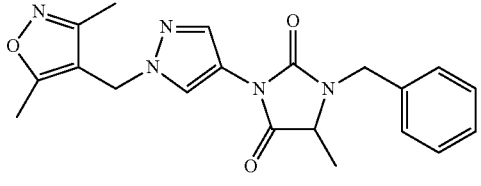
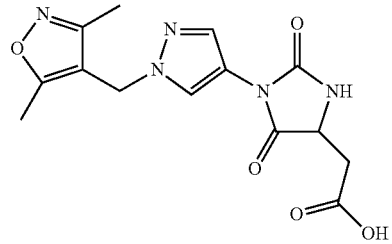
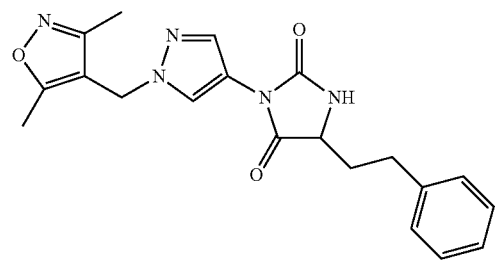
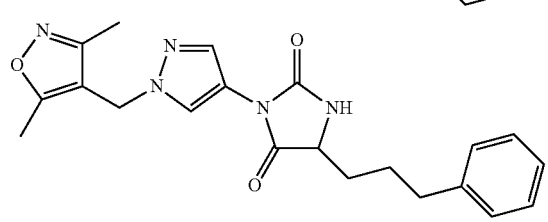
28
-continued
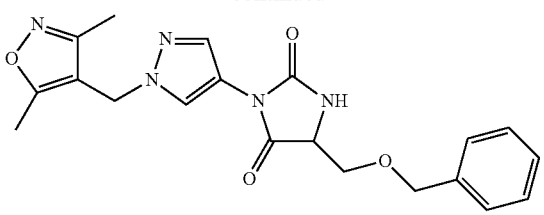
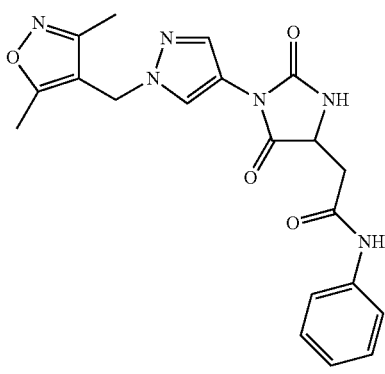
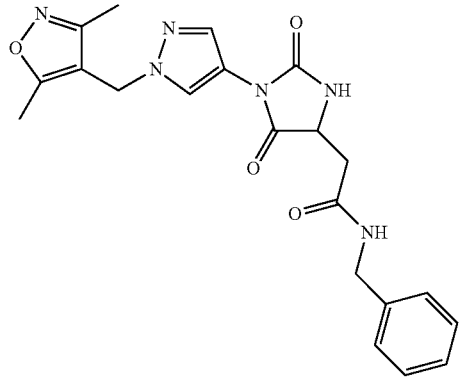
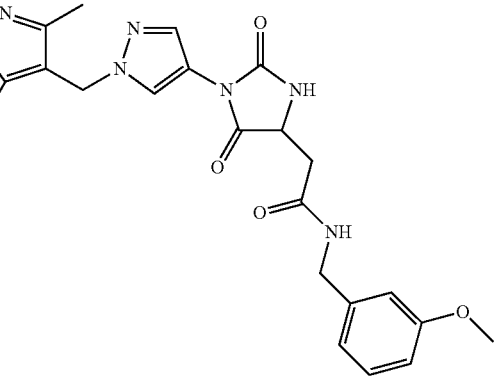
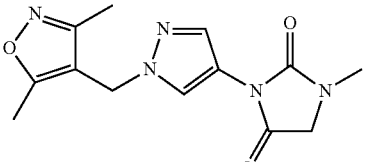
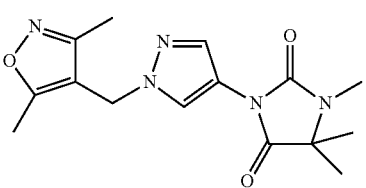

29
-continued
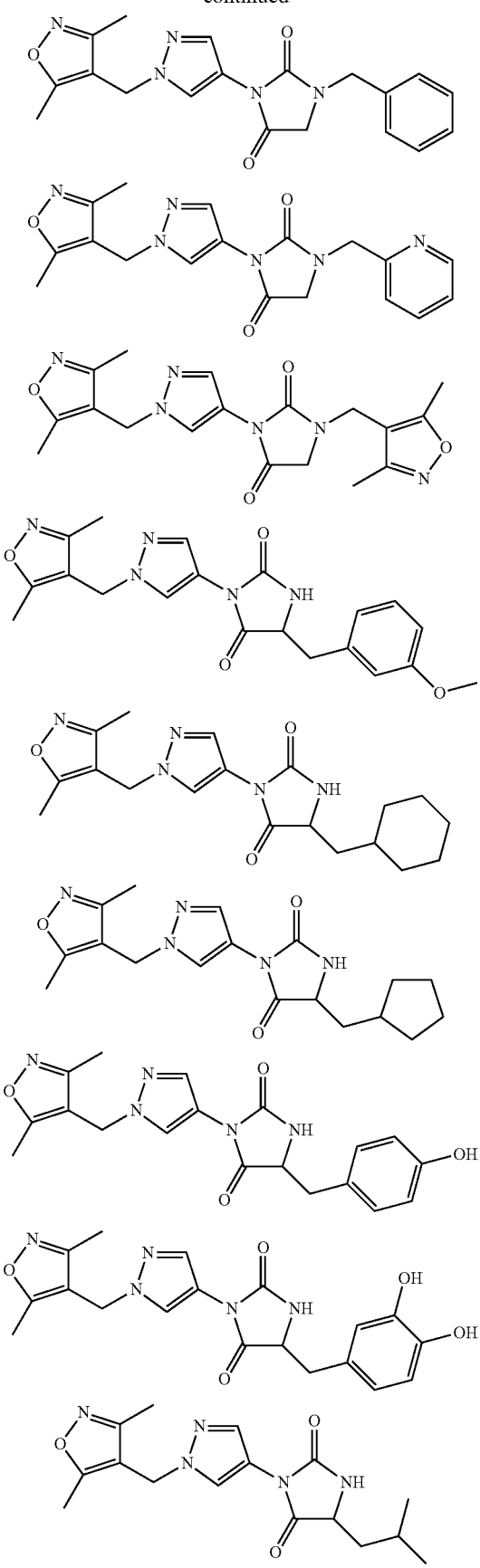
30
-continued
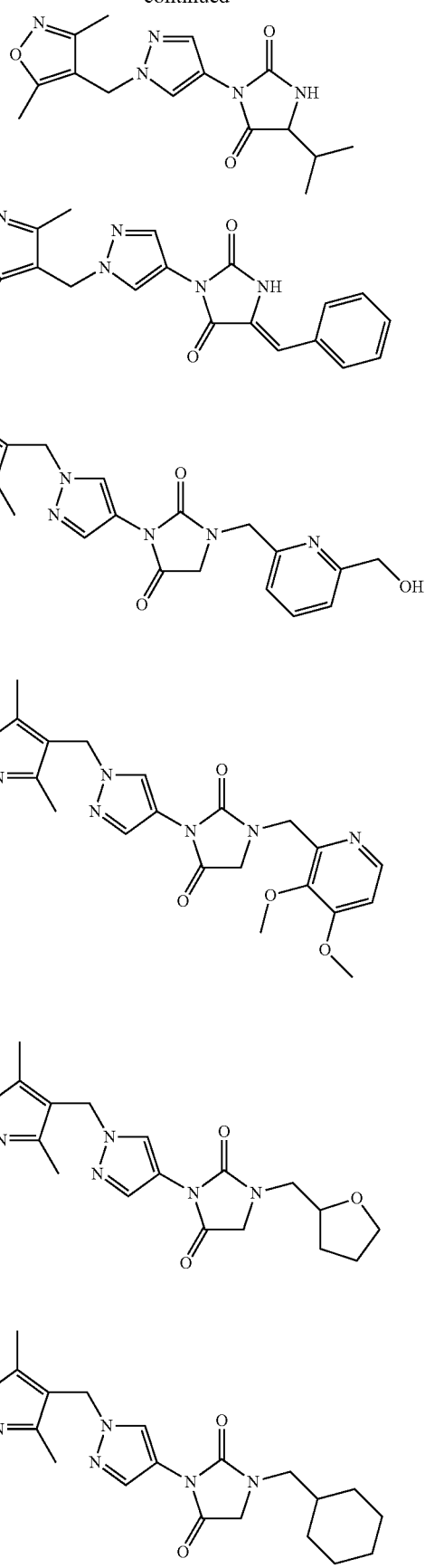

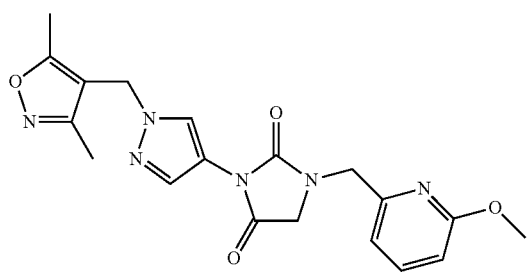
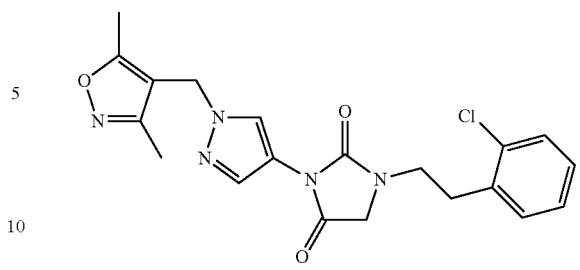
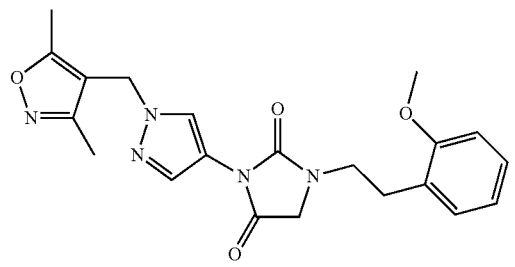
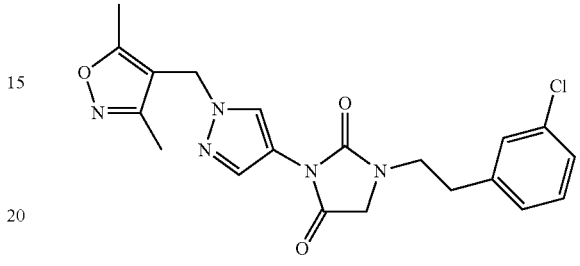
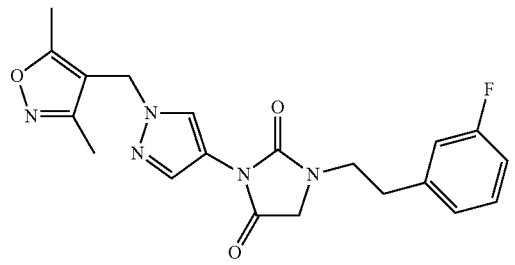
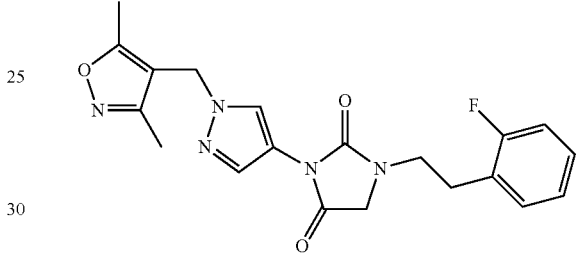
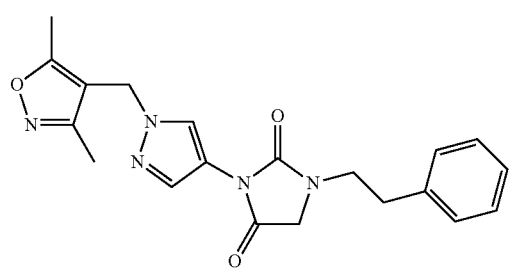
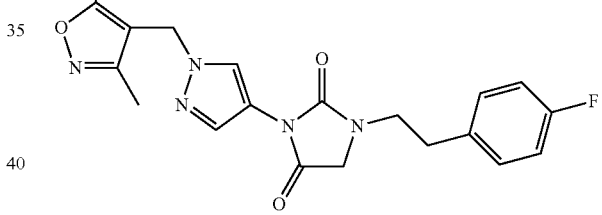
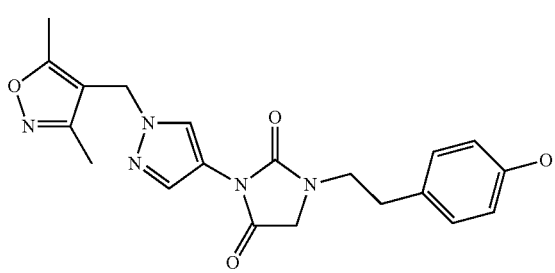
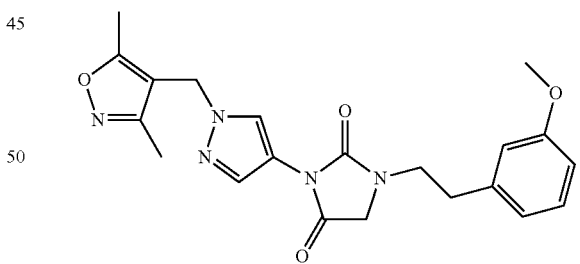
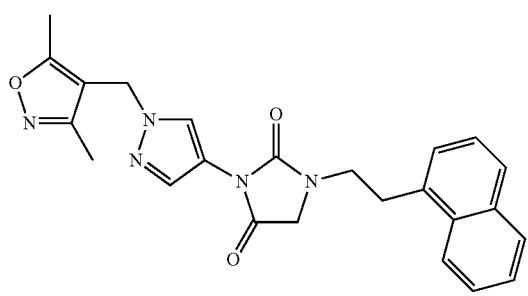
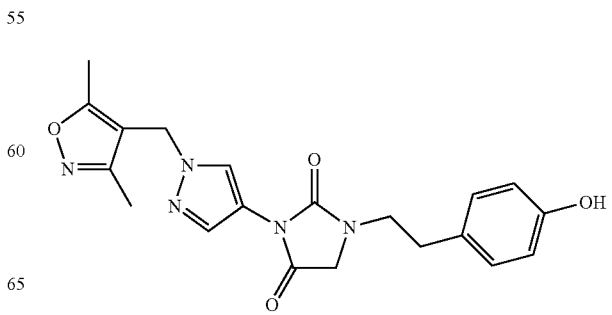

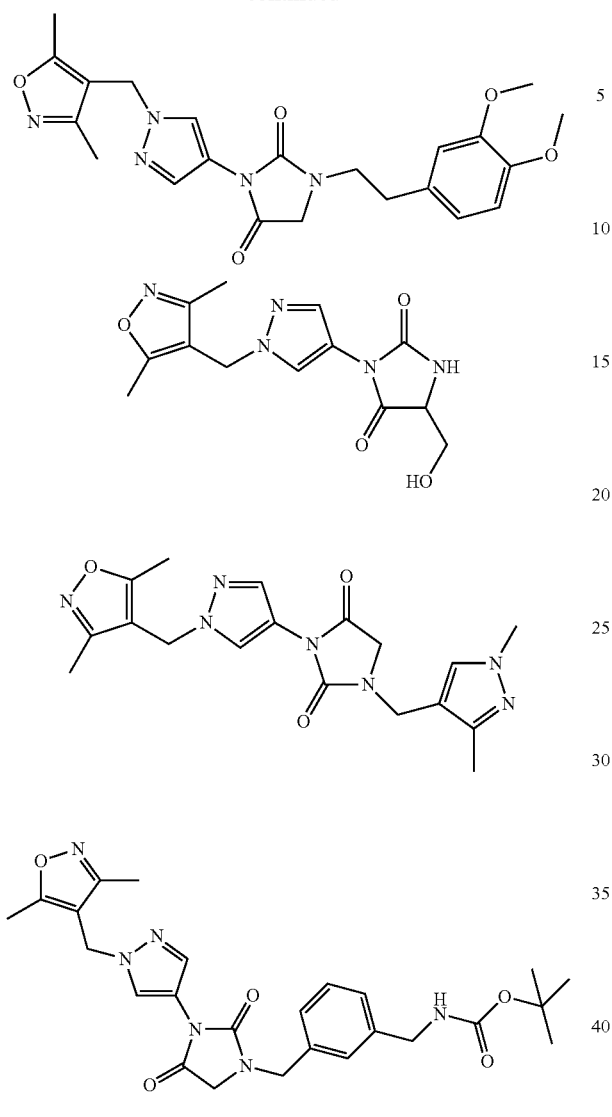
or a salt, hydrate, solvate, N-oxide or prodrug thereof.
In another aspect, the invention relates to a compound of the formula:
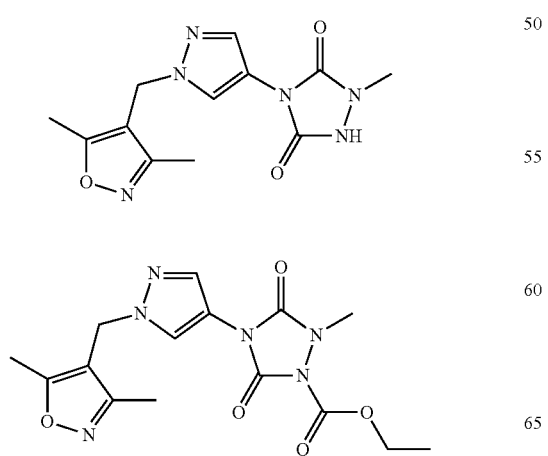
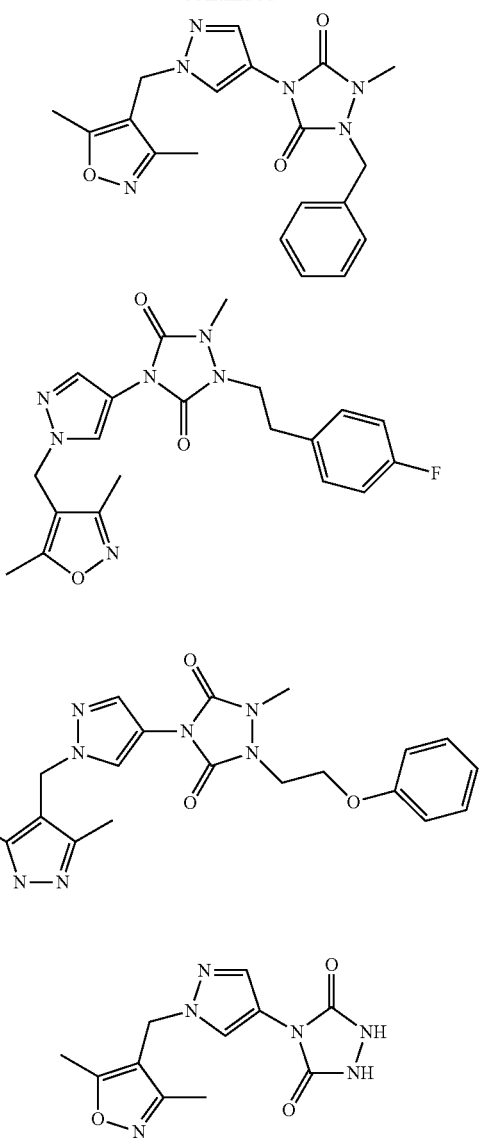
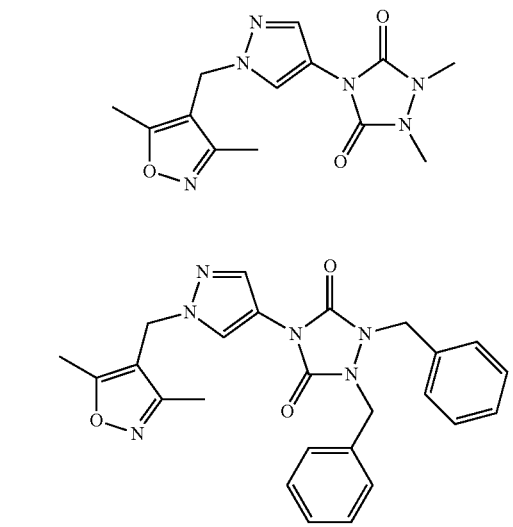

-continued

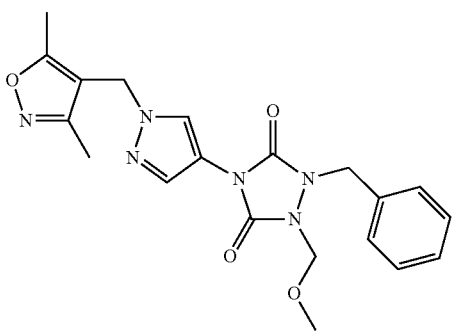
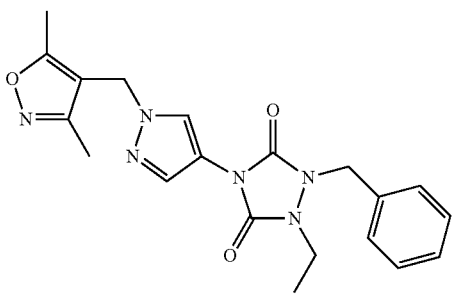
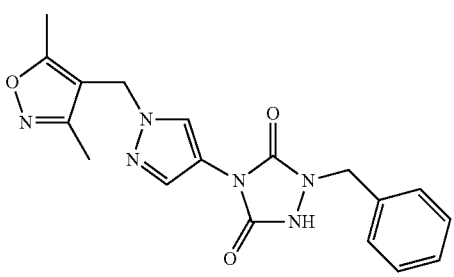
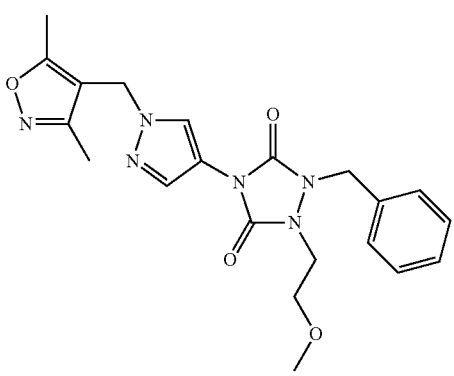
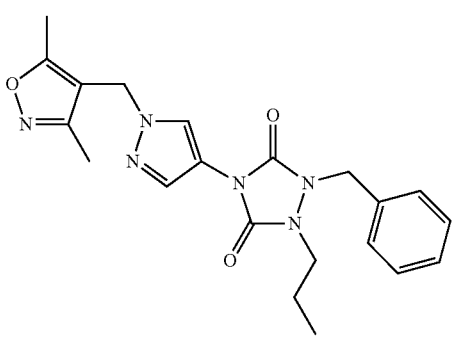

-continued

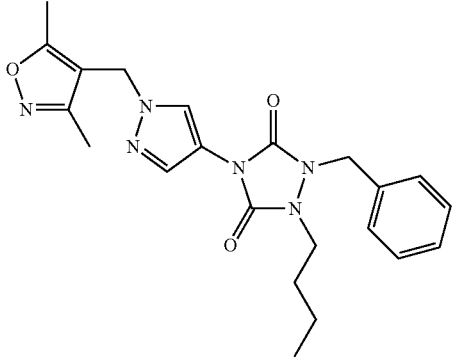

or a salt, hydrate, solvate, N-oxide or prodrug thereof.

In still another aspect, the invention relates to a method of making a compound of the formula:

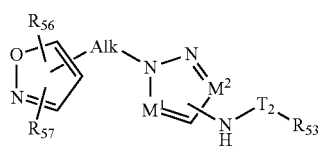

or a salt, hydrate, solvate, N-oxide or prodrug thereof, wherein Alk is an alkyl group, optionally interrupted by a heteroatom;

$T_2$ is C=S, C=O, or $S(O)_2$;

$R_{53}$ is substituted or unsubstituted alkyl, substituted or unsubstituted cycloalkyl, substituted or unsubstituted heteroaryl, substituted or unsubstituted aryl, or substituted or unsubstituted arylalkyl;

$M^1$ is N or $CR_{54}$, wherein $R_{54}$ is H or substituted or unsubstituted alkyl;

$M^2$ is N or $CR_{55}$, wherein $R_{55}$ is H or substituted or unsubstituted alkyl;

$R_{56}$ is H, substituted or unsubstituted alkyl, substituted or unsubstituted alkoxy, substituted or unsubstituted aryl, substituted or unsubstituted arylalkyl, or halo; and $R_{57}$ is H, substituted or unsubstituted alkyl, substituted or unsubstituted alkoxy, substituted or unsubstituted aryl, substituted or unsubstituted arylalkyl, or halo;

wherein the method comprises reacting a compound of the formula:

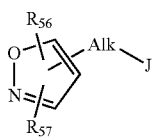

wherein $R_{56}$, $R_{57}$, and Alk are defined above and J is a leaving group; with a compound of the formula:

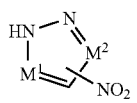

wherein $M^1$ and $M^2$ are defined above to give a compound of the formula

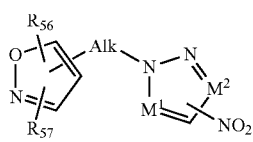

having an NO$_2$ group;
reducing the NO$_2$ group to give a compound having an NH$_2$ group; and reacting the compound having an NH$_2$ group with a compound of the formula

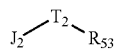

wherein J$_2$ is a leaving group and T$_2$ and R$_{53}$ are defined above.

In still another aspect, the invention relates to a method of making a compound of the formula:

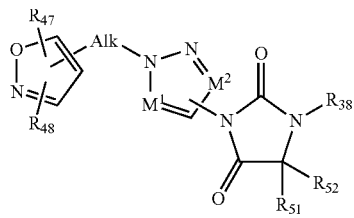

or a salt, hydrate, solvate, N-oxide or prodrug thereof,
wherein Alk is an alkyl group, optionally interrupted by a heteroatom;
R$_{51}$ and R$_{52}$ are, the same or different independently one from the other, H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted arylalkylamidoalkyl, substituted or unsubstituted heteroarylamidoalkyl, substituted or unsubstituted heteroarylalkylamidoalkyl, substituted or unsubstituted arylalkyl, substituted or unsubstituted arylalkoxy, substituted or unsubstituted heteroaryl, substituted or unsubstituted heteroarylalkyl, haloalkyl, or R$_{51}$ and R$_{52}$, together with the carbon atom to which they are attached, form a substituted or unsubstituted alkenyl group;
M$^1$ is N or CR$_{49}$, wherein R$_{49}$ is H or substituted or unsubstituted alkyl;
M$^2$ is N or CR$_{50}$, wherein R$_{50}$ is H or substituted or unsubstituted alkyl;
R$_{38}$ is H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted heteroarylamidoalkyl, substituted or unsubstituted arylalkyl, substituted or unsubstituted arylalkoxy, substituted or unsubstituted heteroaryl, substituted or unsubstituted heteroarylalkyl, or haloalkyl;
R$_{47}$ is H, substituted or unsubstituted alkyl, substituted or unsubstituted alkoxy, substituted or unsubstituted aryl, substituted or unsubstituted arylalkyl, or halo; and R$_{48}$ is H, substituted or unsubstituted alkyl, substituted or unsubstituted alkoxy, substituted or unsubstituted aryl, substituted or unsubstituted arylalkyl, or halo;
wherein the method comprises heating a compound of the formula:

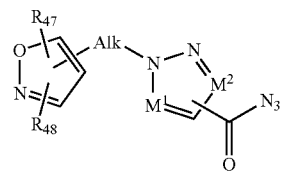

wherein R$_{47}$, R$_{48}$, Alk, M$^1$ and M$^2$ are defined above;
to convert the —CON$_3$ group to a —N=C=O group, and then reacting with a compound of the formula:

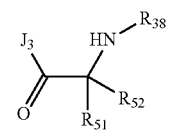

wherein J$_3$ is a leaving group and R$_{38}$, R$_{51}$, and R$_{52}$ are defined above.

In still another aspect, the invention relates to a method of making a compound of the formula:

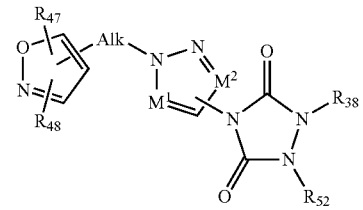

or a salt, hydrate, solvate, N-oxide or prodrug thereof,
wherein Alk is an alkyl group, optionally interrupted by a heteroatom;
R$_{52}$ is H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted arylalkylamidoalkyl, substituted or unsubstituted heteroarylamidoalkyl, substituted or unsubstituted heteroarylalkylamidoalkyl, substituted or unsubstituted arylalkyl, substituted or unsubstituted arylalkoxy, substituted or unsubstituted heteroaryl, substituted or unsubstituted heteroarylalkyl, haloalkyl;
M$^1$ is N or CR$_{49}$, wherein R$_{49}$ is H or substituted or unsubstituted alkyl;
M$^2$ is N or CR$_{50}$, wherein R$_{50}$ is H or substituted or unsubstituted alkyl;
R$_{38}$ is H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted heteroarylamidoalkyl, substituted or unsubstituted arylalkyl, substituted or unsubstituted arylalkoxy, substituted or unsubstituted heteroaryl, substituted or unsubstituted heteroarylalkyl, or haloalkyl;

$R_{47}$ is H, substituted or unsubstituted alkyl, substituted or unsubstituted alkoxy, substituted or unsubstituted aryl, substituted or unsubstituted arylalkyl, or halo; and $R_{48}$ is H, substituted or unsubstituted alkyl, substituted or unsubstituted alkoxy, substituted or unsubstituted aryl, substituted or unsubstituted arylalkyl, or halo;

wherein the method comprises heating a compound of the formula:

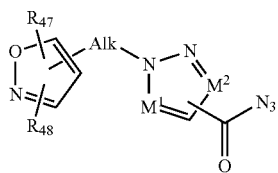

wherein $R_{47}$, $R_{48}$, Alk, $M^1$ and $M^2$ are defined above;

to convert the —$CON_3$ group to a —N=C=O group, and then reacting with a hydrazine of the formula:

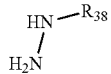

wherein $R_{38}$ is defined above.

In still another aspect, the invention relates to a method of making a compound of the formula:

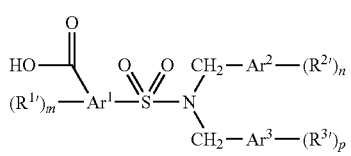

or a salt, hydrate, solvate or N-oxide thereof wherein:

$Ar^1$, $Ar^2$ and $Ar^3$ are independently a five or six membered aryl, heteroaryl, or cycloalkyl ring, and $Ar^2$ and $Ar^3$ may optionally be omitted;

m is 0, 1, 2 or 3;

n and p are independently 0, 1, 2, 3 or 4;

each $R^{1'}$ is independently selected from the group consisting of hydrogen, halogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, CN, $NO_2$, $OR^6$, $S(O)_bR^6$, $NR^6R^7$, $CONR^6R^7$, $CO_2R^6$, $NR^6CO_2R^7$, $NR^6CONR^7R^8$, $NR^6CSNR^7R^8$, $NR^6C(=NH)NR^7R^8$, $SO_2NR^5R^6$, $NR^5SO_2R^6$, $NR^5SO_2NR^6R^7$, $B(OR^5)(OR^6)$, $P(O)(OR^5)(OR^6)$, and $P(O)(R^5)(OR^6)$;

each $R^{2'}$ is independently selected from the group consisting of hydrogen, halogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, CN, $NO_2$, $OR^6$, $S(O)_bR^6$, $NR^6R^7$, $CONR^6R^7$, $CO_2R^6$, $NR^6CO_2R^7$, $NR^6CONR^7R^8$, $NR^6CSNR^7R^8$, $NR^6C(=NH)NR^7R^8$, $SO_2NR^5R^6$, $NR^5SO_2R^6$, $NR^5SO_2NR^6R^7$, $B(OR^5)(OR^6)$, $P(O)(OR^5)(OR^6)$, and $P(O)(R^5)(OR^6)$;

each $R^{3'}$ is independently selected from the group consisting of hydrogen, halogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, CN, $NO_2$, $OR^6$, $S(O)_bR^6$, $NR^6R^7$, $CONR^6R^7$, $CO_2R^6$, $NR^6CO_2R^7$, $NR^6CONR^7R^8$, $NR^6CSNR^7R^8$, $NR^6C(=NH)NR^7R^8$, $SO_2NR^5R^6$, $NR^5SO_2R^6$, $NR^5SO_2NR^6R^7$, $B(OR^5)(OR^6)$, $P(O)(OR^5)(OR^6)$, and $P(O)(R^5)(OR^6)$;

$R^5$-$R^8$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl or alternatively, $R^6$ and $R^7$, $R^7$ and $R^8$, together with the atoms to which they are bonded form a cycloheteroalkyl or substituted cycloheteroalkyl ring;

b is 0, 1, or 2;

wherein the method comprises reacting a compound of the formula:

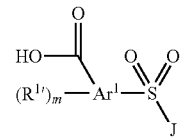

wherein J is a leaving group;

with a compound of the formula:

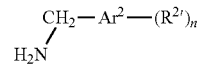

to give a product; and reacting the product with a compound of the formula:

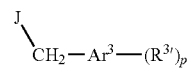

wherein J is a leaving group.

In still another aspect, the invention relates to a compound of the formula:

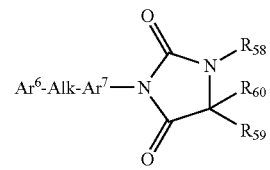

or a salt, hydrate, solvate or N-oxide thereof, wherein $Ar^6$ and $Ar^7$ are, the same or different independently one from the other, a five- or six-membered aryl group or a five- or six-membered heteroaryl group;

Alk is an alkyl group, optionally interrupted by a heteroatom;

$R_{58}$ is H, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl;

$R_{59}$ and $R_{60}$ are the same or different independently one from the other, H, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl, with the proviso that when one of $R_{59}$ or $R_{60}$ is H, then the other of $R_{59}$ or $R_{60}$ is not H; or $R_{59}$ and $R_{60}$, together with the atom to which they are attached form a cycloalkyl, a substituted cycloalkyl, a cycloheteroalkyl or substituted cycloheteroalkyl ring; or $R_{58}$ and $R_{60}$, together with the atoms to which they are attached, form a five- or six-membered cycloheteroalkyl or substituted cycloheteroalkyl ring.

In another aspect, the invention relates to a compound of the formula:

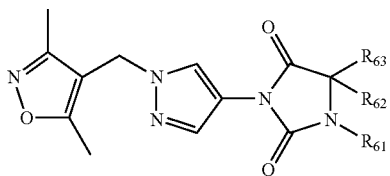

a salt, hydrate, solvate or N-oxide thereof,
wherein:

$R_{61}$ is H, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl;

$R_{62}$ and $R_{63}$ are the same or different independently one from the other, H, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl, with the proviso that when one of $R_{62}$ or $R_{63}$ is H, then the other of $R_{62}$ or $R_{63}$ is not H;

or $R_{62}$ and $R_{63}$, together with the atoms to which they are attached form a cycloalkyl, a substituted cycloalkyl, a cycloheteroalkyl or substituted cycloheteroalkyl ring; or $R_{61}$ and $R_{62}$, together with the atoms to which they are attached, form a five- or six-membered cycloheteroalkyl or substituted cycloheteroalkyl ring.

In yet another aspect, the invention relates to a compound of the formula:

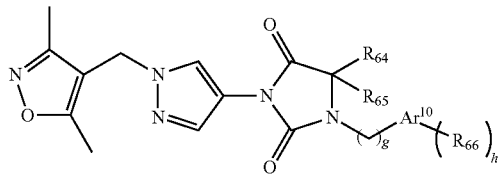

a salt, hydrate, solvate or N-oxide thereof,
wherein:

$R_{64}$ and $R_{65}$ are the same or different independently one from the other, H, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl, with the proviso that when one of $R_{64}$ or $R_{65}$ is H, then the other of $R_{64}$ or $R_{65}$ is not H;

or $R_{64}$ and $R_{65}$, together with the atoms to which they are attached, form a cycloalkyl, a substituted cycloalkyl, a cycloheteroalkyl or substituted cycloheteroalkyl ring;

each $R_{66}$ is independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, F, Cl, —CN, —NO$_2$, —OR$_{67}$, —S(O)$_i$R$_{67}$, —NR$_{67}$R$_{68}$, —CONR$_{67}$R$_{68}$, —CO$_2$R$_{67}$, —NR$_{67}$CO$_2$R$_{68}$, —NR$_{67}$CONR$_{68}$R$_{69}$, —NR$_{67}$CSNR$_{68}$R$_{69}$ or —NR$_{67}$C(=NH)NR$_{68}$R$_{69}$, —SO$_2$NR$_{67}$R$_{68}$, —NR$_{67}$SO$_2$R$_{68}$, —NR$_{67}$SO$_2$NR$_{68}$R$_{69}$, —B(OR$_{67}$)(OR$_{68}$), —P(O)(OR$_{67}$)(OR$_{68}$), or —P(O)(R$_{67}$)(OR$_{68}$), wherein $R_{67}$, $R_{68}$, and $R_{69}$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl or alternatively, $R_{67}$ and $R_{68}$ or $R_{68}$ and $R_{69}$, together with the atoms to which they are attached form a cycloheteroalkyl or substituted cycloheteroalkyl ring;

Ar$^{10}$ is an aryl or heteroaryl ring;
g is 0, 1, 2, 3 or 4;
h is 0, 1, 2, 3 or 4; and
i is 0, 1 or 2.

In another aspect, the invention relates to a A compound of the formula:

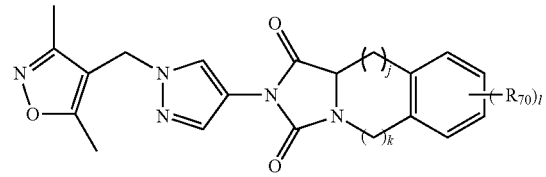

a salt, hydrate, solvate or N-oxide thereof,
wherein:

each $R_{70}$ is independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, F, Cl, —CN, —NO$_2$, —OR$_{67}$, —S(O)$_i$R$_{67}$, —NR$_{67}$R$_{68}$, —CONR$_{67}$R$_{68}$, —CO$_2$R$_{67}$, —NR$_{67}$CO$_2$R$_{68}$, —NR$_{67}$CONR$_{68}$R$_{69}$, —NR$_{67}$CSNR$_{68}$R$_{69}$ or —NR$_{67}$C(=NH)NR$_{68}$R$_{69}$, —SO$_2$NR$_{67}$R$_{68}$, —NR$_{67}$SO$_2$R$_{68}$, —NR$_{67}$SO$_2$NR$_{68}$R$_{69}$, —B(OR$_{67}$)(OR$_{68}$), —P(O)(OR$_{67}$)(OR$_{68}$), or —P(O)(R$_{67}$)(OR$_{68}$), wherein $R_{67}$, $R_{68}$, and $R_{69}$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl or alternatively, $R_{67}$ and $R_{68}$ or $R_{68}$ and $R_{69}$, together with the atoms to which they are attached form a cycloheteroalkyl or substituted cycloheteroalkyl ring;

j is 0, 1 or 2;
k is 0, 1 or 2; and
l is 0, 1 or 2;
with the proviso that j and k are not simultaneously both 0.

It is another object of the invention to utilize compounds identified in the assays described herein as additives or flavor modulators in compositions in order to inhibit or block the bitter taste elicited by compounds that specifically activate these taste receptors. A preferred object of the invention is to use a compound that inhibits activation of at least one of the above-identified human T2R receptors in order to block the bitter taste of compounds present in coffee and coffee flavored foods, beverages and medicinals.

It is another object of the invention to utilize compounds of the present invention as broadly acting bitter blockers in order to inhibit or block the bitter taste elicited by compounds that specifically activate hT2R8 taste receptors, ligands that activate multiple bitter taste receptors, bitter compounds having unknown recetor specificity or compositions containing unknown or multiple bitter compounds. In one embodiment, the compounds of the invention are utilized to inhibit activation of at least one of the above-identified human T2R receptors thereby blocking the bitter taste of compounds present in coffee and coffee flavored foods, beverages and medicinals. It is another object of the invention to confirm that the identified compounds modulate, preferably inhibit or block, bitter taste, e.g. that elicited by coffee and coffee flavored foods, beverages and medicaments in human or animal taste tests, preferably human taste tests.

It is another object of the invention to utilize compounds identified in the assays described herein as additives or flavor modulators in compositions in order to inhibit or block the bitter taste elicited by compounds that specifically activate these taste receptors. A preferred object of the invention is to use a compound that inhibits activation of at least one of the above-identified human T2R receptors in order to block the bitter taste of compounds present in coffee and coffee flavored foods, beverages and medicinals.

In an especially preferred embodiment Compound C and analogs thereof are used as broadly acting bitter blockers in order to inhibit or block the bitter taste elicited by compounds that specifically activate hT2R3, 7, 10, 14, 16, 44, 51, 55, 61, 63, 64, 65, 71 and/or hT2R5, 9, 13, 54, 67 and 75 taste receptors, ligands that activate multiple bitter taste receptors, bitter compounds having unknown recetor specificity or compositions containing unknown or multiple bitter compounds. Given Compound C's broad antagonistic properties it should substantially alleviate bitter taste of most bitter compounds and compositions containing A preferred object of the invention is to use a compound that inhibits activation of at least one of the above-identified human T2R receptors such as Compound C or an analog in order to block the bitter taste of compounds present in coffee and coffee flavored foods, beverages and medicinals.

DETAILED DESCRIPTION OF THE FIGURES

FIG. 1 relates to experiments wherein a partially purified bitter fraction from coffee is used to screen the 25 human T2Rs in transiently transfected HEK cells as described in Applicant's previous patent applications incorporated by reference herein. As shown in FIG. 1, the coffee fraction activated HEK293 cells transiently transfected with hT2R8 and hT2R14 in calcium imaging assay. A blue dye FD&C was used to reduce the fluorescence level of the coffee fraction, which would interfere with the assay.

FIG. 2 is a plot of ΔF/F vs. log coffee fraction showing the dose-dependent response of hT2R8 and hT2R14 to a bitter tasting fraction derived from coffee. The assay was carried out using hT2R8 and hT2R14 stable cell lines and automated fluorescence detector FLIPR.

FIG. 3 is a plot of percent inhibition of hT2R8 activity vs. log of the concentration of a compound and shows the dose-dependent inhibition for compounds A and B on a stable hT2R8 expressing cell line.

FIG. 4 is a plot of percent inhibition of hT2R14 activity vs. log of the concentration of compound C and shows the dose inhibition for compound C on a stable hT2R8 expressing cell line.

FIG. 5 shows the inhibitory activity of Compound C against different (2) human bitter taste receptors.

FIG. 6 is a plot of receptor activity as a function of log of the saccharin concentration. FIG. 6 shows the dose-response relationships and the effects of saccharin on receptor activities in transfected cells expressing variants of hT2R43, hT2R44 and hT2R8. hT2R8 is less responsive to saccharin in the in vitro assay than the "taster" hT2R43-W35 and hT2R44-W35 alleles, but responds better than the "non-taster" hT2R43-S35 and hT2R44-R35 alleles.

DETAILED DESCRIPTION OF THE INVENTION

According to the present invention, the compounds of the present invention can be used alleviate or reduce the bitter taste of compositions, e.g., an ingestible composition. As used herein, an "ingestible composition" includes any substance intended for oral consumption either alone or together with another substance. The ingestible composition includes both "food or beverage products" and "non-edible products". By "food or beverage products", it is meant any edible product intended for consumption by humans or animals, including solids, semi-solids, or liquids (e.g., beverages). The term "non-edible products" or "noncomestible composition" includes supplements, nutraceuticals, functional food products (e.g., any fresh or processed food claimed to have a health-promoting and/or disease-preventing properties beyond the basic nutritional function of supplying nutrients), pharmaceutical and over the counter medications, oral care products such as dentifrices and mouthwashes, cosmetic products such as lip balms and other personal care products.

The ingestible composition also includes pharmaceutical, medicinal or comestible composition, or alternatively in a formulation, e.g., a pharmaceutical or medicinal formulation or a food or beverage product or formulation.

The compounds of the present invention can also be provided, individually or in combination, with any ingestible composition known or later discovered. For example, the ingestible composition can be a comestible composition or noncomestible composition. By "comestible composition", it is meant any composition that can be consumed as food by humans or animals, including solids, gel, paste, foamy material, semi-solids, liquids, or mixtures thereof. By "noncomestible composition", it is meant any composition that is intended to be consumed or used by humans or animals not as food, including solids, gel, paste, foamy material, semi-solids, liquids, or mixtures thereof. The noncomestible composition includes, but is not limited to medical composition, which refers to a noncomestible composition intended to be used by humans or animals for therapeutic purposes. By "animal", it includes any non-human animal, such as, for example, farm animals and pets.

In one embodiment, the compounds of the invention can be added to a noncomestible composition or non-edible product, such as supplements, nutraceuticals, functional food products (e.g., any fresh or processed food claimed to have a health-promoting and/or disease-preventing properties beyond the basic nutritional function of supplying nutrients), pharmaceutical and over the counter medications, oral care products such as dentifrices and mouthwashes, cosmetic products such as lip balms and other personal care products.

In general, over the counter (OTC) product and oral hygiene product generally refer to product for household and/or personal use which may be sold without a prescription and/or without a visit to a medical professional. Examples of the OTC products include, but are not limited to Vitamins and dietary supplements; Topical analgesics and/or anaesthetic; oral analgesics (e.g., acetaminophen, ibuprofen, and aspirin); Cough, cold and allergy remedies; Antihistamines and/or allergy remedies (e.g., loratadine, diphenhydramine, fexofenadine, and cetirizine); digestive remedies (e.g., omeprazole, loperamide, calcium carbonate, and psyllium seed husks) and combinations thereof. Vitamins and dietary supplements include, but are not limited to vitamins, dietary supplements, tonics/bottled nutritive drinks, child-specific vitamins, dietary supplements, any other products of or relating to or providing nutrition, and combinations thereof. Topical analgesics and/or anaesthetic include any topical creams/ointments/gels used to alleviate superficial or deep-seated aches and pains, e.g. muscle pain; teething gel; patches with analgesic ingredient; and combinations thereof. Cough, cold and allergy remedies include, but are not limited to decongestants, cough remedies, pharyngeal preparations, medicated confectionery (e.g., any candy confectionery product in any oral format that contains added menthol, pectin, vitamins, herbs and/or plant extracts, including products for one or more of the following uses: nasal cooling, cough suppression, breath freshening, sinus relief, dry mouth relief, mouth moistening, throat soothing, and immunity boosting; the confectionery may be in the form of, e.g., cough drops and throat drops), antihistamines and child-specific cough, cold and allergy remedies; and combination products. Antihistamines and/or allergy remedies include, but are not limited to any systemic treatments for hay fever, nasal allergies, insect bites and stings. Examples of oral hygiene products include, but are not limited to mouth cleaning strips, toothpaste, toothbrushes, mouthwashes/dental rinses, denture care, mouth fresheners at-home teeth whiteners and dental floss.

In another embodiment, the compounds of the present invention can be added to food or beverage products or formulations. Examples of food and beverage products or formulations include, but are not limited to coatings, frostings, or glazes for comestible products or any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionary category, the Dairy Product category, the Ice Cream category, the Meal Replacement category, the Pasta and Noodle category, and the Sauces, Dressings, Condiments category, the Baby Food category, and/or the Spreads category.

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready to serve, semi condensed or condensed and may be served hot or cold, as a first course or as the main course of a meal or as a between meal snack (sipped like a beverage). Soup may be used as an ingredient for preparing other meal components and may range from broths (consomme) to sauces (cream or cheese based soups).

"Dehydrated and Culinary Food Category" usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready to cook soups, dehydrated or ambient preparations of ready made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

The Beverage category usually means beverages, beverage mixes and concentrates, including but not limited to, carbonated and non carbonated beverages, alcoholic and non alcoholic beverages, ready to drink beverages, liquid concentrate formulations for preparing beverages such as sodas, and dry powdered beverage precursor mixes. The Beverage category also include the alcoholic drinks, the soft drinks, sports drinks, isotonic beverages, and hot drinks. The alcoholic drinks include, but are not limited to beer, cider/perry, FABs, wine, absinthe-containing drinks, and spirits. The soft drinks include, but are not limited to carbonates, such as colas and non-cola carbonates; fruit juice, such as juice, nectars, juice drinks and fruit flavoured drinks; bottled water, which includes sparkling water, spring water and purified/table water; functional drinks, which can be carbonated or still and include sport, energy or elixir drinks; concentrates, such as liquid and powder concentrates in ready to drink measure. The hot drinks include, but are not limited to coffee, such as fresh (e.g., brewed), instant, combined coffee, liquid, ready-to-drink, soluble and dry coffee beverages, coffee beverage mixes and concentrates (syrups, pure, formulated, or in powder form; example of a "powder form" is a product comprising coffee, sweetener, and whitener all in powder form); tea, such as black, green, white, oolong, and flavored tea; and other hot drinks including flavour-, malt- or plant-based powders, granules, blocks or tablets mixed with milk or water.

The Snack Food category generally refers to any food that can be a light informal meal including, but not limited to Sweet and savoury snacks and snack bars. Examples of snack food include, but are not limited to fruit snacks, chips/crisps, extruded snacks, tortilla/corn chips, popcorn, pretzels, nuts and other sweet and savoury snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, buns, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream; take-home ice cream; frozen yoghurt and artisanal ice cream; soy, oat, bean (e.g., red bean and mung bean), and rice-based ice creams.

The Confectionary category generally refers to edible product that is sweet to the taste. Examples of confectionary include, but are not limited to candies, gelatins, chocolate confectionery, sugar confectionery, gum, and the likes and any combination products.

The Meal Replacement category generally refers to any food intended to replace the normal meals, particularly for people having health or fitness concerns. Examples of meal replacement include, but are not limited to slimming products and convalescence products.

The Ready Meal category generally refers to any food that can be served as meal without extensive preparation or processing. The read meal include products that have had recipe "skills" added to them by the manufacturer, resulting in a high degree of readiness, completion and convenience. Examples of ready meal include, but are not limited to canned/preserved, frozen, dried, chilled ready meals; dinner mixes; frozen pizza; chilled pizza; and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, dessert mixes, dried ready meals, dehydrated soup, instant soup, dried pasta, plain noodles, and instant noodles.

The Chill Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, bouillon/stock cubes, herbs and spices, monosodium glutamate (MSG), table sauces, soy based sauces, pasta sauces, wet/cooking sauces, dry sauces/powder mixes, ketchup, mayonnaise, mustard, salad dressings, vinaigrettes, dips, pickled products, and other sauces, dressings and condiments.

The Baby Food category includes, but is note limited to milk- or soybean-based formula; and prepared, dried and other baby food.

The Spreads category includes, but is not limited to jams and preserves, honey, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

Additional examples for comestible composition, particularly food and beverage products or formulations, are provided as follows. Exemplary comestible compositions include one or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, gum, chewing gum, sugarized gum, sugar free gum, functional gum, bubble gum, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other cereals, children's breakfast cereals, hot cereals, ice cream, impulse ice cream, single portion dairy ice cream, single portion water ice cream, multi pack dairy ice cream, multi pack water ice cream, take home ice cream, take home dairy ice cream, ice cream desserts, bulk ice cream, take home water ice cream, frozen yoghurt, artisanal ice cream, dairy products, milk, fresh/pasteurized milk, full fat fresh/pasteurized milk, semi skimmed fresh/pasteurized milk, long life/uht milk, full fat long life/uht milk, semi skimmed long life/uht milk, fat free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners (e.g., dairy and non-dairy based creamers or whiteners for coffee beverages), powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf stable desserts, dairy based desserts, soy based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, hot soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow on milk formula, toddler milk formula, hypoallergenic milk formula, prepared baby food, dried baby food, other baby food, spreads, jams and preserves, honey, chocolate spreads, nut based spreads, and yeast based spreads. Exemplary comestible compositions also include confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads or a mixture thereof. Exemplary comestible compositions also include breakfast cereals, sweet beverages or solid or liquid concentrate compositions for preparing beverages. Exemplary comestible compositions also include coffee flavored food (e.g., coffee flavored ice cream).

In some embodiments, the compounds of the present invention can be added to a comestible composition, particularly food and beverage products or formulations, including, without limitation, cereal products, rice products, tapioca products, sago products, baker's products, biscuit products, pastry products, bread products, confectionery products, desert products, gums, chewing gums, chocolates, ices, honey products, treacle products, yeast products (e.g., yeast extract, tortula yeast, and brewers yeast and other savory enhancer ingredients), baking-powder, salt and spice products, savory products, mustard products, vinegar products, sauces (condiments), tobacco products, cigars, cigarettes, processed foods, cooked fruits and vegetable products, meat and meat products, jellies, jams, fruit sauces, egg products, milk and dairy products, yoghurts, cheese products, butter and butter substitute products, milk substitute products, soy products, edible oils and fat products, medicaments, beverages, carbonated beverages, alcoholic drinks, beers, soft drinks, mineral and aerated waters and other non-alcoholic drinks (e.g., beverages functioning as dietary supplements and/or an added source of protein), fruit drinks, fruit juices, coffee, artificial coffee, tea, cocoa, including forms requiring reconstitution, food extracts, plant extracts, meat extracts, condiments, sweeteners, nutraceuticals, gelatins, pharmaceutical and non-pharmaceutical gums, tablets, lozenges, drops, emulsions, elixirs, syrups and other preparations for making beverages, and combinations thereof. Other comestible compositions include, without limitation, any comestible composition comprising caffeine and other methylxanthines (e.g., theophylline; theobromine; and nicotine, which can be contained in, for example, chewing gum to help to quit smoking).

In other embodiments, the compounds of the present invention can be added to a comestible composition, particularly food and beverage products or formulations, including, without limitation, water-based compositions including, without limitation, the following: aqueous drink, enhanced/slightly sweetened water drink, carbonated beverage, non-carbonated beverage, soft drink, non-alcoholic drink, alcoholic drink, fruit drink, juice, fruit juice, vegetable juice, coffee (iced or hot), tea, black tea (iced or hot and extracts thereof), green tea (iced or hot and extracts thereof), oolong tea (iced or hot), herbal tea (iced or hot), mate tea (iced or hot), cocoa (water-based), cocoa (milk-based), cocoa (soy-based), tea-based drink, coffee-based drink, cocoa-based drink, syrup, frozen fruit, frozen fruit juice, water-based ice, dairy ice, fruit ice, sorbet, and beverages formed from botanical materials (whole or ground) by brewing, soaking or otherwise extracting, and beverages formed by dissolving instant powders or concentrates (coffee beans, ground coffee, instant coffee, cocoa beans, cocoa powder, instant cocoa, tea leaves, instant tea powder), and the above-mentioned concentrates.

In still other embodiments, the compounds of the present invention can be added to a comestible composition, particularly food and beverage products or formulations, including, without limitation, solid dry compositions including, without limitation, cereals, baked food products, biscuits, bread, breakfast cereal, cereal bar, energy bars/nutritional bars, granola, cakes, cookies, crackers, donuts, muffins, pastries, confectioneries, chewing gum, chocolate, fondant, hard candy, marshmallow, pressed tablets, snack foods, and botanical materials (whole or ground), and instant powders for reconstitution as mentioned herein above.

In yet other embodiments, the compounds of the present invention can be added to a comestible composition, particularly food and beverage products or formulations, including, without limitation, dairy products, dairy-derived products and dairy-alternative products, including, without limitation, milk, fluid milk, cultured milk product, cultured and noncultured dairy-based drinks, cultured milk product cultured with lactobacillus, yoghurt, yoghurt-based beverage, smoothy, lassi, milk shake, acidified milk, acidified milk beverage, butter milk, kefir, milk-based beverage, milk/juice blend, fermented milk beverage, ice cream, dessert, frozen yoghurt, soy milk, rice milk, soy drink, rice milk drink. Milk includes, but is not limited to, whole milk, skim milk, condensed milk, evaporated milk, reduced fat milk, low fat milk, nonfat milk, and milk solids (which may be fat or nonfat).

In other embodiments, the compounds of the present invention can be added to a comestible composition, particularly food and beverage products or formulations, including, without limitation, compositions comprising one or more ingredient selected from the group consisting of one or more vitamins provided as an additive; one or more B-vitamins (e.g., choline, inositol, riboflavin, thiamin) provided as an additive; one or more amino acids; coffee or an extract thereof (*Coffea* spec.): cocoa or an extract thereof (*Theobroma* spec.); guarana or an extract thereof (*Paullinia cupana, P. crysan*, or *P. sorbilis*); black tea or an extract thereof, green tea or an extract thereof, verba mate or an extract thereof (*Camellia* spec. extracts), Yaupon/Cassina extracts (*Ilex vomitoria*); taurine; ginseng or an extract thereof; kola or an extract thereof (*Cola acuminata*); carob or an extract thereof (*Ceratonia siliqua*); maltodextrin; inositol; carnitine; creatine; glucuronolactone; *ginkgo biloba* extract; golden seal or an extract thereof; and dandelion or an extract thereof.

In other embodiments, the compounds of the present invention can be added to a comestible composition, particularly food and beverage products or formulations, including, without limitation, compositions comprising trilobtain extracted from a botanical source, optionally selected from parts or leaves of *Lithocarpus polystachyus* (Chinese sweet tea) and parts or leaves of an apple species, said apple species optionally being selected from *Malus trilobata*.

In other embodiments, the compounds of the present invention can be added to a comestible composition, particularly food and beverage products or formulations, including, without limitation, compositions comprising vegetable and/or non-vegetable proteins. As used herein, the term "non-vegetable protein(s)" means any protein(s), with the exception of vegetable proteins. Examples of non-vegetable proteins include, but are not limited to proteins derived from milk (e.g., whey proteins, isolates and other dairy hydrolysates such as milk casein hydrolysates). As used herein, the term "vegetable proteins" means any plant and vegetable protein(s) including, without limitation, proteins from grains (e.g., wheat, corn, barley, oats, rye, millet, and buckwheat);

proteins from nuts (e.g., walnuts, cashews, almonds, pecans); soy protein(s) (hydrolyzed and unhydrolyzed); proteins from seeds (e.g., sunflower, pumpkin, hemp, and flax); proteins from legumes (e.g., beans, lentils, and garbanzos (chickpeas)); and proteins from rice and pea isolates.

In other embodiments, the compounds of the present invention can be added to a comestible composition, particularly food and beverage products or formulations, including, without limitation, compositions comprising menthol, goji berry juice (or an extract thereof), pomegranate extract, grapeseed extract, rhodiola (or an extract thereof), black cohosh (or an extract thereof; also known as *Actaea racemosa* and *Cimicifuga racemosa*). artificial sweeteners (e.g. aspartame, saccharin, sucralose, and acesulfame-K), cooling agents (e.g., menthane carboxamide), spirulina, verba mate (or extracts thereof), spirulina (or extracts thereof), chicory (or extracts thereof), and natural sweeteners (e.g. Luo Han Guo, monatin, and stevia), including sweeteners comprising stevioside, steviol glycosides, rebaudioside A, rebaudioside C, and/or dulcoside A.

In other embodiments, the compounds of the present invention can be added to a comestible composition, particularly food and beverage products or formulations, including, without limitation, hot or cold chocolate and/or malt-based flavored drinks including, without limitation, in powdered, granulated or in a block/tablet form, or in ready to drink form.

In other embodiments, the compounds of the present invention can be added to a comestible composition, particularly food and beverage products or formulations, including, without limitation, compositions comprising isoflavones, citrus oils (e.g., orange extract, lemon extract, lime extract, and combinations thereof).savory ingredients (e.g., hydrolyzed vegetable proteins), potassium chloride, various leavening agents (e.g., beer, buttermilk, ginger beer, kefir, sourdough starter, yeast, yogurt, baking powder, baking soda (sodium bicarbonate), monocalcium phosphate, sodium aluminum phosphate, sodium acid pyrophosphate, other phosphates, ammonium bicarbonate (hartshorn, horn salt, bakers ammonia), potassium bicarbonate (potash), potassium bitartrate (cream of tartar), potassium carbonate (pearlash), and hydrogen peroxide) or chocolate liquor.

Typically an amount sufficient to alleviate or reduce the bitter taste associated with a composition, e.g., an ingestible composition, is added to the composition to alleviate or reduce the bitter taste associated with the composition as compared to compositions that are prepared without the compounds of the present invention, as judged by human beings or animals. Or, in the case of formulations testing, as judged by a majority of a panel of, e.g., eight human taste testers, via procedures commonly known in the field.

The concentration of the compounds of the present invention effective to alleviate or reduce the bitter taste associated with a composition will of course depend on many variables, including the specific type of comestible composition and its various other ingredients, the natural genetic variability and individual preferences and health conditions of various human beings tasting the compositions, and the subjective effect of the particular compound on the taste of such chemosensory compounds. In some embodiments, concentration of the compounds of the present invention effective to alleviate or reduce the bitter taste associated with a composition is from about 0.001 ppm to about 100 ppm, e.g., from about 0.1 ppm to about 100 ppm, from about 1 ppm to about 25 ppm, from about 1 ppm to about 10 ppm, from about 0.1 ppm to about 10 ppm, from about 0.01 ppm to about 30 ppm, from about 0.05 ppm to about 10 ppm, from about 0.01 ppm to about 5 ppm, from about 0.02 ppm to about 2 ppm, or from about 0.01 ppm to about 1 ppm.

It is contemplated that in some embodiments of the present invention, a mixture of one or more compounds of the present invention will be used to alleviate or reduce the bitter taste associated with a composition. The concentration of the one or more compounds may be the same or the concentration of each compound may be different.

Prior to further describing the invention, the following definitions are provided.

The term "T2R" family includes polymorphic variants, alleles, mutants, and homologs that: (1) have about 30-40% amino acid sequence identity, more specifically about 40, 50, 60, 70, 75, 80, 85, 90, 95, 96, 97, 98, or 99% amino acid sequence identity to the T2Rs disclosed infra, and in the Zuker (Id) (2001) and Adler (Id.) (2001) applications incorporated, by reference herein over a window of about 25 amino acids, optimally 50-100 amino acids; (2) specifically bind to antibodies raised against an immunogen comprising an amino acid sequence selected from the group consisting of the T2R sequences disclosed infra, and conservatively modified variants thereof; (3) specifically hybridize (with a size of at least about 100, optionally at least about 500-1000 nucleotides) under stringent hybridization conditions to a sequence selected from the group consisting of the T2R DNA sequences disclosed infra, and conservatively modified variants thereof; (4) comprise a sequence at least about 40% identical to an amino acid sequence selected from the group consisting of the T2R amino acid sequences disclosed infra or (5) are amplified by primers that specifically hybridize under stringent hybridization conditions to the described T2R sequences.

In particular, these "T2R's" include taste receptor GPCRs referred to herein as hT2R8 and hT2R14 having the nucleic acid sequences and amino acid sequences provided in this application, and variants, alleles, mutants, orthologs and chimeras thereof which specifically bind to bitter ligands which are identified herein and other structurally related compounds and bitter compounds.

While T2R genes exhibit substantial sequence divergence at both the protein and DNA level, all T2Rs isolated to date have been found to contain certain consensus sequences in particular regions that are identical or which possess or at least 70-75% sequence identity to the T2R consensus sequence identified previously in the Adler et al (WO 01/77676 A1 (2001) and Zuker et al. WO 01/18050 A2, both incorporated by reference in their entirety herein.

Topologically, certain chemosensory GPCRs have an "N-terminal domain;" "extracellular domains," a "transmembrane domain" comprising seven transmembrane regions, and corresponding cytoplasmic and extracellular loops, "cytoplasmic regions," and a "C-terminal region" (see, e.g., Hoon et al, Cell, 96:541-51 (1999); Buck & Axel, Cell, 65:175-87 (1991)). These regions can be structurally identified using methods known to those of skill in the art, such as sequence analysis programs that identify hydrophobic and hydrophilic domains (see, e.g., Stryer, Biochemistry, (3rd ed. 1988); see also any of a number of Internet based sequence analysis programs, such as those found at dot.imgen.bcm.tmc.edu). These regions are useful for making chimeric proteins and for in vitro assays of the invention, e.g., ligand binding assays. For example chimeric T2Rs can be made by combining the extracellular region of one T2R and the transmembrane region of another T2R of the same or different species.

"Extracellular domains" therefore refers to the domains of T2R polypeptides that protrude from the cellular membrane and are exposed to the extracellular face of the cell. Such regions would include the "N-terminal domain" that is exposed to the extracellular face of the cell, as well as the extracellular loops of the transmembrane domain that are exposed to the extracellular face of the cell, i.e., the extracellular loops between transmembrane regions 2 and 3, transmembrane regions 4 and 5, and transmembrane regions 6 and 7. The "N-terminal domain" starts at the N-terminus and extends to a region close to the start of the transmembrane region. These extracellular regions are useful for in vitro ligand binding assays, both soluble and solid phase. In addition, transmembrane regions, described below, can also be involved in ligand binding, either in combination with the extracellular region or alone, and are therefore also useful for in vitro ligand binding assays.

"T2R Expressing Cell" herein encompasses recombinant cells which express a human T2R sequence according to the invention as well as endogenous T2R expressing cells. Such cells are comprised in the lingual and gastrointestinal system and include cells in the oral cavity such as taste buds expressed on the tongue as well as cells in the gastrointestinal system and associated organs such as brush cells in the gastrointestinal tract, enteroendocrine cells such as STC-1 cells. These cells may also express a G protein such as gustducin, transducin, $G_{\alpha 15}$ or $G_{\alpha 16}$. Cells which express specific T2Rs can be identified and isolated by known methods such as by FACS cell separation and/or magnetic bead cell isolation procedures.

"Transmembrane domain," which comprises the seven transmembrane "regions," refers to the domain of T2R polypeptides that lies within the plasma membrane, and may also include the corresponding cytoplasmic (intracellular) and extracellular loops, also referred to as transmembrane "regions." The seven transmembrane regions and extracellular and cytoplasmic loops can be identified using standard methods, as described in Kyte & Doolittle, J. Mol. Biol., 157:105-32 (1982)), or in Stryer, supra.

"Cytoplasmic domains" refers to the domains of T2R proteins that face the inside of the cell, e.g., the "C-terminal domain" and the intracellular loops of the transmembrane domain, e.g., the intracellular loops between transmembrane regions 1 and 2, transmembrane regions 3 and 4, and transmembrane regions 5 and 6. "C-terminal domain" refers to the region that spans from the end of the last transmembrane region to the C-terminus of the protein, and which is normally located within the cytoplasm.

The term "7-transmembrane receptor" means a polypeptide belonging to a superfamily of transmembrane proteins that have seven regions that span the plasma membrane seven times (thus, the seven regions are called "transmembrane" or "TM" domains TM I to TM VII). The families of olfactory and certain taste receptors each belong to this super-family. 7-transmembrane receptor polypeptides have similar and characteristic primary, secondary and tertiary structures, as discussed in further detail below.

The term "ligand-binding region" refers to sequences derived from a chemosensory or taste receptor that substantially incorporates transmembrane domains II to VII (TM II to VII). The region may be capable of binding a ligand, and more particularly, a taste eliciting compound.

The term "plasma membrane translocation domain" or simply "translocation domain" means a polypeptide domain which when incorporated into the amino terminus of a polypeptide coding sequence, can with great efficiency "chaperone" or "translocate" the hybrid ("fusion") protein to the cell plasma membrane. For example a particular "translocation domain" initially derived from the amino terminus of the human rhodopsin receptor polypeptide, a 7-transmembrane receptor can be used. Another translocation domain has been derived from the bovine rhodopsin sequence and is also useful for facilitating translocation. Rhodopsin derived sequences are particularly efficient in translocating 7-transmembrane fusion proteins to the plasma membrane.

"Functional equivalency" means the domain's ability and efficiency in translocating newly translated proteins to the plasma membrane as efficiently as an exemplary translocation domain such as one derived from rhodopsin under similar conditions; relative efficiencies can be measured (in quantitative terms) and compared, as described herein. Domains falling within the scope of the invention can be determined by routine screening for their efficiency in translocating newly synthesized polypeptides to the plasma membrane in a cell (mammalian, Xenopus, and the like) with the same efficiency as the twenty amino acid long translocation domain SEQ ID NO:1.

The phrase "functional effects" in the context of assays for testing compounds that modulate T2R family member mediated taste transduction includes the determination of any parameter that is indirectly or directly under the influence of the receptor, e.g., functional, physical and chemical effects. It includes ligand binding, changes in ion flux, membrane potential, current flow, transcription, G protein binding, GPCR phosphorylation or dephosphorylation, signal transduction, receptor-ligand interactions, second messenger concentrations (e.g., cAMP, cGMP, IP3, or intracellular $Ca^{2+}$), in vitro, in vivo, and ex vivo and also includes other physiologic effects such increases or decreases of neurotransmitter or hormone release.

By "determining the functional effect" is meant assays for a compound that increases or decreases a parameter that is indirectly or directly under the influence of a T2R family member, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, oocyte T2R gene expression; tissue culture cell T2R expression; transcriptional activation of T2R genes; ligand binding assays; voltage, membrane potential and conductance changes; ion flux assays; changes in intracellular second messengers such as cAMP, cGMP, and inositol triphosphate (IP3); changes in intracellular calcium levels; neurotransmitter release, and the like.

"Inhibitors," "activators," and "modulators" of T2R proteins receptors are used interchangeably to refer to inhibitory, activating, or modulating molecules identified using in vitro and in vivo assays for taste transduction, e.g., ligands, agonists, antagonists, and their homologs and mimetics. Inhibitors are compounds that, e.g., bind to, partially or totally block stimulation, decrease, prevent, delay activation, inactivate, desensitize, or down regulate taste transduction, e.g., antagonists. Activators are compounds that, e.g., bind to, stimulate, increase, open, activate, facilitate, enhance activation, sensitize, or up regulate taste transduction, e.g., agonists. Modulators include compounds that, e.g., alter the interaction of a receptor with extracellular proteins that bind activators or inhibitor (e.g., ebnerin and other members of the hydrophobic carrier family); G Proteins; kinases (e.g., homologs of rhodopsin kinase and beta adrenergic receptor kinases that are involved in deactivation and desensitization of a receptor); and arrestins, which also deactivate and desensitize receptors. Modulators include genetically modified versions of T2R family members, e.g., with altered activity, as well as naturally occurring and synthetic ligands, antagonists, agonists, small chemical molecules and the like.

Such assays for inhibitors and activators include, e.g., expressing T2R family members in cells or cell membranes, applying putative modulator compounds in the presence or absence of compounds that modulate, e.g., bitter compounds, and then determining the functional effects on taste transduction, as described above. Samples or assays comprising T2R family members that are treated with a potential activator, inhibitor, or modulator are compared to control samples without the inhibitor, activator, or modulator to examine the extent of modulation. Control samples (untreated with modulators) are assigned a relative T2R activity value of 100%. Inhibition of a T2R is achieved when the T2R activity value relative to the control is about 80%, optionally 50% or 25-0%. Activation of a T2R is achieved when the T2R activity value relative to the control is 110%, optionally 150%, optionally 200-500%, or 1000-3000% higher.

The terms "purified," "substantially purified," and "isolated" as used herein refer to the state of being free of other, dissimilar compounds with which the compound of the invention is normally associated in its natural state. Preferably, "purified," "substantially purified," and "isolated" means that the composition comprises at least 0.5%, 1%, 5%, 10%, or 20%, and most preferably at least 50% or 75% of the mass, by weight, of a given sample. In one preferred embodiment, these terms refer to the compound of the invention comprising at least 95% of the mass, by weight, of a given sample. As used herein, the terms "purified," "substantially purified," and "isolated", when referring to a nucleic acid or protein, of nucleic acids or proteins, also refers to a state of purification or concentration different than that which occurs naturally in the mammalian, especially human, body. Any degree of purification or concentration greater than that which occurs naturally in the mammalian, especially human, body, including (1) the purification from other associated structures or compounds or (2) the association with structures or compounds to which it is not normally associated in the mammalian, especially human, body, are within the meaning of "isolated." The nucleic acid or protein or classes of nucleic acids or proteins, described herein, may be isolated, or otherwise associated with structures or compounds to which they are not normally associated in nature, according to a variety of methods and processes known to those of skill in the art.

As used herein, the term "isolated," when referring to a nucleic acid or polypeptide refers to a state of purification or concentration different than that which occurs naturally in the mammalian, especially human, body. Any degree of purification or concentration greater than that which occurs naturally in the body, including (1) the purification from other naturally-occurring associated structures or compounds, or (2) the association with structures or compounds to which it is not normally associated in the body are within the meaning of "isolated" as used herein. The nucleic acids or polypeptides described herein may be isolated or otherwise associated with structures or compounds to which they are not normally associated in nature, according to a variety of methods and processed known to those of skill in the art.

As used herein, the terms "amplifying" and "amplification" refer to the use of any suitable amplification methodology for generating or detecting recombinant or naturally expressed nucleic acid, as described in detail, below. For example, the invention provides methods and reagents (e.g., specific oligonucleotide primer pairs) for amplifying (e.g., by polymerase chain reaction, PCR) naturally expressed (e.g., genomic or mRNA) or recombinant (e.g., cDNA) nucleic acids of the invention (e.g., taste eliciting compound-binding sequences of the invention) in vivo or in vitro.

The term "expression vector" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression "cassettes which contain only the minimum elements needed for transcription of the recombinant nucleic acid.

The term "library" means a preparation that is a mixture of different nucleic acid or poly-peptide molecules, such as the library of recombinant generated sensory, particularly taste receptor ligand-binding regions generated by amplification of nucleic acid with degenerate primer pairs, or an isolated collection of vectors that incorporate the amplified ligand-binding regions, or a mixture of cells each randomly transfected with at least one vector encoding an taste receptor.

The term "nucleic acid" or "nucleic acid sequence" refers to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating, e.g., sequences in which the third position of one or more selected codons is substituted with mixed-base and/or deoxyinosine residues (Batzer et al., Nucleic Acid Res., 19:5081 (1991); Ohtsuka et al., J. Biol. Chem., 260:2605-08 (1985); Rossolini et al., Mol. Cell. Probes, 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. Preferred alkyl groups have 1-4 carbons. "Alkenyl" and other like terms include carbon chains containing at least one unsaturated carbon-carbon bond. "Alkynyl" and other like terms include carbon chains containing at least one carbon-carbon triple bond.

The term "cycloalkyl" means carbocycles containing no heteroatoms, and includes mono-, bi- and tricyclic saturated carbocycles, as well as fused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphthalene and the like.

The term "aryl" means an aromatic substituent that is a single ring or multiple rings fused together. Exemplary aryl groups include, without limitation, phenyl, naphthyl, anthracenyl, pyridinyl, pyrazinyl, pyrimidinyl, triazinyl, thiophenyl, furanyl, pyrrolyl, oxazolyl, pyrazolyl, imidazolyl, triazyolyl, and tetrazolyl groups. Aryl groups that contain one or more heteroatoms (e.g., pyridinyl) are often referred to as "heteroaryl groups." When formed of multiple rings, at least one of the constituent rings is aromatic. In some embodiments, at least one of the multiple rings comprise a heteroatom, thereby forming heteroatom-containing aryl groups. Heteroatom-containing aryl groups include, without limitation, benzoxazolyl, benzimidazolyl, quinoxalinyl, benzofuranyl, and 1H-benzo[d][1,2,3]triazolyl groups. Heteroatom-containing aryl groups also include, without limitation, 2,3-dihydrobenzo[b][1,4]dioxinyl and benzo[d][1,3]dioxolyl groups. Heteroatom-containing aryl groups also include aromatic rings fused to a heterocyclic ring comprising at least one heteroatom and at least one carbonyl group. Such groups include, without limitation, dioxo tetrahydroquinoxalinyl and dioxo tetrahydroquinazolinyl groups.

The term "acyl" means a R—C(O)— group.

The term "arylalkoxy" means an aryl group bonded to an alkoxy group.

The term "arylamidoalkyl" means an aryl-C(O)NR-alkyl or aryl-NRC(O)-alkyl.

The term "arylalkylamidoalkyl" means an aryl-alkyl-C(O)NR-alkyl or aryl-alkyl-NRC(O)-alkyl, wherein R is anyl suitable group listed below.

The term "arylalkyl" refers to an aryl group bonded to an alkyl group.

The term "halogen" or "halo" refers to chlorine, bromine, fluorine or iodine.

The term "leaving group" refers to a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "haloalkyl" means an alkyl group having one or more halogen atoms (e.g., $CF_3$).

The term "heteroalkyl" refers to an alkyl moiety which comprises a heteroatom such as N, O, P, B, S, or Si. The heteroatom may be connected to the rest of the heteroalkyl moiety by a saturated or unsaturated bond. Thus, an alkyl substituted with a group, such as heterocycloalkyl, substituted heterocycloalkyl, heteroaryl, substituted heteroaryl, alkoxy, aryloxy, boryl, phosphino, amino, silyl, thio, or seleno, is within the scope of the term heteroalkyl. Examples of heteroalkyls include, but are not limited to, cyano, benzoyl, 2-pyridyl and 2-furyl.

The term "heteroarylalkyl" means a heteroaryl group to which an alkyl group is attached.

The term "heterocycle" means a monocyclic or polycyclic ring comprising carbon and hydrogen atoms, optionally having 1 or 2 multiple bonds, and the ring atoms contain at least one heteroatom, specifically 1 to 4 heteroatoms, independently selected from nitrogen, oxygen, and sulfur. Heterocycle ring structures include, but are not limited to, mono-, bi-, and tri-cyclic compounds. Specific heterocycles are monocyclic or bicyclic. Representative heterocycles include cyclic ureas, morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrazolyl, and urazolyl. A heterocyclic ring may be unsubstituted or substituted. Preferred heterocycles are 5- and 6-membered heterocycles, particularly hydantoinyl and urazolyl.

The term "heterocycloalkyl" or "cycloheteroalkyl" refers to a cycloalkyl group in which at least one of the carbon atoms in the ring is replaced by a heteroatom (e.g., O, S or N). In some embodiments, the heterocycloalkyl group may have one or more unsaturated bonds. In another embodiment, the heterocycloalkyl group is fused with another cycloalkyl, heterocycloalkyl, aryl or heteroaryl group.

The term "heterocycloalkylalkyl" means a heterocycloalkyl group to which the an alkyl group is attached.

The term "substituted" specifically envisions and allows for one or more substitutions that are common in the art. However, it is generally understood by those skilled in the art that the substituents should be selected so as to not adversely affect the useful characteristics of the compound or adversely interfere with its function. Suitable substituents may include, for example, halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, amino groups, alkyl- and dialkylamino groups, carbamoyl groups, alkylcarbonyl groups, carboxyl groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups, cycloalkyl groups, cyano groups, $C_1$-$C_6$ alkylthio groups, arylthio groups, nitro groups, keto groups, acyl groups, boronate or boronyl groups, phosphate or phosphonyl groups, sulfamyl groups, sulfonyl groups, sulfinyl groups, and combinations thereof. In the case of substituted combinations, such as "substituted arylalkyl," either the aryl or the alkyl group may be substituted, or both the aryl and the alkyl groups may be substituted with one or more substituents. Additionally, in some cases, suitable substituents may combine to form one or more rings as known to those of skill in the art.

Compounds described herein contain one or more double bonds and may thus give rise to cis/trans isomers as well as other conformational isomers. The present invention includes all such possible isomers as well as mixtures of such isomers.

Compounds described herein, and particularly the substituents described above, may contain one or more asymmetric centers and may thus give rise to diastereomers and optical isomers. The present invention includes all such possible diastereomers as well as their racemic mixtures, their substantially pure resolved enantiomers, all possible geometric isomers, and acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6th ed. (Donald J. Abraham ed., 2001, Wiley) and *Design and Application of Prodrugs* (H. Bundgaard ed., 1985, Harwood Academic Publishers Gmfh).

As used herein, and unless otherwise indicated, the terms "biohydrolyzable amide," "biohydrolyzable ester," "biohydrolyzable carbamate," "biohydrolyzable carbonate," "biohydrolyzable ureido," "biohydrolyzable phosphate" mean an amide, ester, carbamate, carbonate, ureido, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters. Examples of biohydrolyzable amides include, but are not limited to, lower alkyl amides, .alpha.-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, the term "analog thereof" in the context of the compounds disclosed herein includes diastereomers, hydrates, solvates, salts, prodrugs, and N-oxides of the compounds.

The "translocation domain," "ligand-binding region", and chimeric receptors compositions described herein also include "analogs," or "conservative variants" and "mimetics" ("peptidomimetics") with structures and activity that substantially correspond to the exemplary sequences. Thus, the terms "conservative variant" or "analog" or "mimetic" refer to a polypeptide which has a modified amino acid sequence, such that the change(s) do not substantially alter the polypeptide's (the conservative variant's) structure and/or activity, as defined herein. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity.

More particularly, "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein.

For instance, the codons GCA, GCC, GCG and GCU all encode the amino acid alanine. Thus, at every position where an alanine is specified by a codon, the codon can be altered to any of the corresponding codons described without altering the encoded polypeptide.

Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gln; ile/leu or val; leu/ile or val; lys/arg or gln or glu; met/leu or tyr or ile; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (I); 5) Isoleucine (I), Leucine (L), Methionine (M), Valine (V); and 6) Phenylalanine (F), Tyrosine (Y), Tryptophan (W); (see also, e.g., Creighton, Proteins, W. H. Freeman and Company (1984); Schultz and Schimer, Principles of Protein Structure, Springer-Verlag (1979)). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations."

The terms "mimetic" and "peptidomimetic" refer to a synthetic chemical compound that has substantially the same structural and/or functional characteristics of the polypeptides, e.g., translocation domains, ligand-binding regions, or chimeric receptors of the invention. The mimetic can be either entirely composed of synthetic, non-natural analogs of amino acids, or may be a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity.

As with polypeptides of the invention which are conservative variants, routine experimentation will determine whether a mimetic is within the scope of the invention, i.e., that its structure and/or function is not substantially altered. Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(.=O)—CH$_2$ for —C(.=O)—NH—), aminomethylene (CH$_2$NH), ethylene, olefin (CH.dbd.CH), ether (CH$_2$O), thioether (CH$_2$—S), tetrazole (CN$_4$), thiazole, retroamide, thioamide, or ester (see, e.g., Spatola, Chemistry and Biochemistry of Amino Acids, Peptides and Proteins, Vol. 7, 267-357, Marcell Dekker, Peptide Backbone Modifications, NY (1983)). A polypeptide can also be characterized as a mimetic by containing all or some non-natural residues in place of naturally occurring amino acid residues; non-natural residues are well described in the scientific and patent literature.

A "label" or a "detectable moiety" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are optionally directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant means" also encompass the ligation of nucleic acids having various coding regions or domains or promoter sequences from different sources into an expression cassette or vector for expression of, e.g., inducible or constitutive expression of a fusion protein comprising a translocation domain of the invention and a nucleic acid sequence amplified using a primer of the invention.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Such hybridizations and wash steps can be carried out for, e.g., 1, 2, 5, 10, 15, 30, 60; or more minutes.

Nucleic acids that do not hybridize to each other under stringent conditions are still substantially related if the polypeptides which they encode are substantially related. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such hybridizations and wash steps can be carried out for, e.g., 1, 2, 5, 10, 15, 30, 60, or more minutes. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-T2R" antibody is an antibody or antibody fragment that specifically binds a polypeptide encoded by a T2R gene, cDNA, or a subsequence thereof.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or, "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein.

For example, polyclonal antibodies raised to a T2R family member from specific species such as rat, mouse, or human can be selected to obtain only those polyclonal antibodies that are specifically immunoreactive with the T2R polypeptide or an immunogenic portion thereof and not with other proteins, except for orthologs or polymorphic variants and alleles of the T2R polypeptide. This selection may be achieved by subtracting out antibodies that cross-react with T2R molecules from other species or other T2R molecules. Antibodies can also be selected that recognize only T2R GPCR family members but not GPCRs from other families. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual, (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

The term "expression vector" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression "cassettes which contain only the minimum elements needed for transcription of the recombinant nucleic acid.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa, HEK-293, and the like, e.g., cultured cells, explants, and cells in vivo.

Based on the foregoing, the present invention provides assays for identifying compounds that modulate, preferably block, the specific activation of the previously identified human bitter taste receptor by bitter compounds, e.g., bitter compounds present in coffee and extracts derived therefrom and structurally related and other bitter compounds. Particularly, the invention provides cell-based assays for identifying compounds that modulate (e.g., block) the activation of hT2R8 and hT2R14. These compounds will modulate bitter taste associated with these taste receptors in human subjects. This will be confirmed in taste tests.

Also, the invention identifies and provides an antagonist with broad ranging antagonist properties that can be used in foods, beverages, medicaments and other materials for human or animal ingestion containing known and unknown bitter compounds wherein bitter taste is desirably minimized or eliminated.

That the above taste receptors specifically respond to bitter compound(s) present in coffee and to specific bitter compounds that interact with one, multiple, or unknown bitter taste receptors was determined essentially using the HEK293 expression system and calcium imaging methods reported in other publications as well as patent applications filed by the present Assignee, e.g., U.S. Ser. Nos. 10/191,058 and 09/825,882, both incorporated by reference in their entireties herein. More particularly, the present inventors transfected HEK293 cells with a particular hT2R tagged with a rhodopsin 35 amino acid tag (SEQ ID NO:1) together with a chimeric G protein (G16gust44) which comprises the $G_{\alpha 16}$ G protein sequence modified by the replacement of carboxy-44 amino acid residues with those of gustducin, and recorded responses of these cells to specific bitter ligands by calcium imaging methods.

Specifically, the inventors used a mammalian cell-based assay to monitor hT2R activities. For calcium imaging assays, cells were seeded into 48-well tissue culture plates. 24 hours later the cells were transiently transfected with an expression plasmid (pEAK10) containing an hT2R nucleic acid sequence, and a plasmid (pEAK10) containing a chimeric G protein (G16gust44). Another 24 hours later the cells were incubated with a fluorescent dye specific for calcium (Fluo-4; Molecular Probes). The loaded cells are exposed to different bitter molecules, and the activation of an hT2R leads to activation of G16gust44, which in turn leads to calcium mobilization inside within the cells. This increase in calcium concentration changes the fluorescence properties of the calcium dye inside the cells. These changes are monitored using fluorescence microscopy.

The inventors also used the automated fluorimetric aiming system FLIPR using a slightly different protocol. A HEK293 cell line stably expressing G16gust44 was transfected with a hT2R expression plasmid, 24 hours later, the cells are loaded and analyzed on FLIPR.

After a ligand is identified for a particular hT2R, a HEK293 cell line stably expressing both the hT2R and G16gust44 are generated, facilitating future screening assays to identify other ligands that activate the particular hT2R or which modulate (block or enhance) the activation of this hT2R by another bitter ligand such as a bitter compound contained in coffee. This avoids the need for transient transfection.

As shown in the Figures, such experiments revealed that hT2R8 and hT2R14 respond to bitter compounds present in coffee and identified compounds that inhibit or block the bitter taste of coffee. Also, the experiments in FIG. 5 and Example 3 infra reveal the broad antagonistic properties of Compound C in particular.

These results indicate that cells which identified hT2R taste receptors may be used in assays to identify ligands that modulate bitter taste associated with at least one of said particular hT2Rs, as well as assays to detect compounds responsible for bitter taste.

Preferably, these assays will utilize a test cell that expresses a DNA encoding an hT2R having one of the amino acid sequences identified infra. However, it is anticipated that fragments, orthologs, variants or chimeras of these receptor polypeptides which retain the functional properties of these bitter taste receptors, i.e., respond to some bitter compounds, will also be useful in these assays. Examples of such variants include splice variants, single nucleotide polymorphisms, allelic variants, and mutations produced by recombinant or chemical means, or naturally occurring. Means for isolation and expression of T2Rs, which are used in the assays of the present invention and assays which are contemplated for use in the present invention to identify compounds that inhibit activation of these receptors, are set forth below.

Isolation and Expression of T2Rs

Isolation and expression of the T2Rs, or fragments or variants thereof, of the invention can be effected by well-established cloning procedures using probes or primers constructed based on the T2R nucleic acids sequences disclosed in the application. Related T2R sequences may also be identified from human or other species genomic databases using the sequences disclosed herein and known computer-based search technologies, e.g., BLAST sequence searching. In a particular embodiment, the pseudogenes disclosed herein can be used to identify functional alleles or related genes.

Expression vectors can then be used to infect or transfect host cells for the functional expression of these sequences. These genes and vectors can be made and expressed in vitro or in vivo. One of skill will recognize that desired phenotypes for altering and controlling nucleic acid expression can be obtained by modulating the expression or activity of the genes and nucleic acids (e.g., promoters, enhancers and the like) within the vectors of the invention. Any of the known methods described for increasing or decreasing expression or activity can be used. The invention can be practiced in conjunction with any method or protocol known in the art, which are well described in the scientific and patent literature.

Alternatively, these nucleic acids can be synthesized in vitro by well-known chemical synthesis techniques, as described in, e.g., Carruthers, Cold Spring Harbor Symp. Quant. Biol. 47:411-18 (1982); Adams, Am. Chem. Soc., 105:661 (1983); Belousov, Nucleic Acids Res. 25:3440-3444 (1997); Frenkel, Free Radic. Biol. Med. 19:373-380 (1995); Blommers, Biochemistry 33:7886-7896 (1994); Narang, Meth. Enzymol. 68:90 (1979); Brown, Meth. Enzymol. 68:109 (1979); Beaucage, Tetra. Lett. 22:1859 (1981); U.S. Pat. No. 4,458,066. Double-stranded DNA fragments may then be obtained either by synthesizing the complementary strand and annealing the strands together under appropriate conditions, or by adding the complementary strand using DNA polymerase with an appropriate primer sequence.

Techniques for the manipulation of nucleic acids, such as, for example, for generating mutations in sequences, subcloning, labeling probes, sequencing, hybridization and the like are well described in the scientific and patent literature. See, e.g., Sambrook, ed., Molecular Cloning: A Laboratory Manual (2nd ed.), Vols. 1-3, Cold Spring Harbor Laboratory (1989); Ausubel, ed., Current Protocols in Molecular Biology, John Wiley & Sons, Inc., New York (1997); Tijssen, ed., Laboratory Techniques in Biochemistry and Molecular Biology: Hybridization With Nucleic Acid Probes, Part I, Theory and Nucleic Acid Preparation, Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g., fluid or gel precipitin reactions, immunodiffusion, immunoelectrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

Oligonucleotide primers may be used to amplify nucleic acids encoding a T2R ligand-binding region. The nucleic acids described herein can also be cloned or measured quantitatively using amplification techniques. Amplification methods are also well known in the art, and include, e.g., polymerase chain reaction (PCR) (Innis ed., PCR Protocols, a Guide to Methods and Applications, Academic Press, N.Y. (1990); Innis ed., PCR Strategies, Academic Press, Inc., N.Y. (1995)); ligase chain reaction (LCR) (Wu, Genomics, 4:560 (1989); Landegren, Science, 241:1077 (1988); Barringer, Gene, 89:117 (1990)); transcription amplification (Kwoh, PNAS, 86:1173 (1989)); self-sustained sequence replication (Guatelli, PNAS, 87:1874 (1990)); Q Beta replicase amplification (Smith, J. Clin. Microbiol., 35:1477-91 (1997)); automated Q-beta replicase amplification assay (Burg, Mol. Cell. Probes, 10:257-71 (1996)); and other RNA polymerase mediated techniques (e.g., NASBA, Cangene, Mississauga, Ontario). See also, Berger, Methods Enzymol., 152:307-16 (1987); Sambrook; Ausubel; U.S. Pat. Nos. 4,683,195 and 4,683,202; Sooknanan, Biotechnology, 13:563-64 (1995).

Once amplified, the nucleic acids, either individually or as libraries, may be cloned according to methods known in the art, if desired, into any of a variety of vectors using routine molecular biological methods; methods for cloning in vitro amplified nucleic acids are described, e.g., U.S. Pat. No. 5,426,039. To facilitate cloning of amplified sequences, restriction enzyme sites can be "built into" the PCR primer pair. For example, Pst I and Bsp E1 sites were designed into the exemplary primer pairs of the invention. These particular restriction sites have a sequence that, when ligated, are "in-frame" with respect to the 7-membrane receptor "donor" coding sequence into which they are spliced (the ligand-binding region coding sequence is internal to the 7-membrane polypeptide, thus, if it is desired that the construct be translated downstream of a restriction enzyme splice site, out of frame results should be avoided; this may not be necessary if the inserted ligand-binding region comprises substantially most of the transmembrane VII region). The primers can be designed to retain the original sequence of the "donor" 7-membrane receptor. Alternatively, the primers can encode amino acid residues that are conservative substitutions (e.g., hydrophobic for hydrophobic residue, see above discussion) or functionally benign substitutions (e.g., do not prevent plasma membrane insertion, cause cleavage by peptidase, cause abnormal folding of receptor, and the like).

The primer pairs may be designed to selectively amplify ligand-binding regions of T2R proteins. These binding regions may vary for different ligands; thus, what may be a minimal binding region for one ligand, may be too limiting for a second potential ligand. Thus, binding regions of different sizes comprising different domain structures may be amplified; for example, transmembrane (TM) domains II through VII, III through VII, III through VI or II through VI, or variations thereof (e.g., only a subsequence of a particular domain, mixing the order of the domains, and the like), of a 7-transmembrane T2R.

As domain structures and sequence of many 7-membrane T2R proteins are known, the skilled artisan can readily select domain-flanking and internal domain sequences as model sequences to design degenerate amplification primer pairs. For example, a nucleic acid sequence encoding domain regions II through VII can be generated by PCR amplification using a primer pair. To amplify a nucleic acid comprising transmembrane domain I (TM I) sequence, a degenerate primer can be designed from a nucleic acid that encodes the amino acid sequence of the T2R family consensus sequence 1 described above. Such a degenerate primer can be used to generate a binding region incorporating TM I through TM III, TM I through TM IV, TM I through TM V, TM I through TM VI or TM I through TM VII). Other degenerate primers can be designed based on the other T2R family consensus sequences provided herein. Such a degenerate primer can be used to generate a binding region incorporating TM III through TM IV, TM III through TM V, TM III through TM VI or TM III through TM VII.

Paradigms to design degenerate primer pairs are well known in the art. For example, a COnsensus-DEgenerate Hybrid Oligonucleotide Primer (CODEHOP) strategy computer program is accessible as http://blocks.fhcrc.org/codehop.html, and is directly linked from the BlockMaker multiple sequence alignment site for hybrid primer prediction beginning with a set of related protein sequences, as known taste receptor ligand-binding regions (see, e.g., Rose, Nucleic Acids Res., 26:1628-35 (1998); Singh, Biotechniques, 24:318-19 (1998)).

Means to synthesize oligonucleotide primer pairs are well known in the art. "Natural" base pairs or synthetic base pairs can be used. For example, use of artificial nucleobases offers a versatile approach to manipulate primer sequence and generate a more complex mixture of amplification products. Various families of artificial nucleobases are capable of assuming multiple hydrogen bonding orientations through internal bond rotations to provide a means for degenerate molecular recognition. Incorporation of these analogs into a single position of a PCR primer allows for generation of a complex library of amplification products. See, e.g., Hoops, Nucleic Acids Res., 25:4866-71 (1997). Nonpolar molecules can also be used to mimic the shape of natural DNA bases. A non-hydrogen-bonding shape mimic for adenine can replicate efficiently and selectively against a nonpolar shape mimic for thymine (see, e.g., Morales, Nat. Struct. Biol., 5:950-54 (1998)). For example, two degenerate bases can be the pyrimidine base 6H, 8H-3,4-dihydropyrimido[4,5-c][1,2]oxazin-7-one or the purine base N6-methoxy-2,6-diaminopurine (see, e.g., Hill, PNAS, 95:4258-63 (1998)). Exemplary degenerate primers of the invention incorporate the nucleobase analog 5'-Dimethoxytrityl-N-benzoyl-2'-deoxy-Cytidine,3'-[(2-cyanoethyl)-(N,N-diisopropyl)]-phosphoramidite (the term "P" in the sequences, see above). This pyrimidine analog hydrogen bonds with purines, including A and G residues.

Polymorphic variants, alleles, and interspecies homologs that are substantially identical to a taste receptor disclosed herein can be isolated using the nucleic acid probes described above. Alternatively, expression libraries can be used to clone T2R polypeptides and polymorphic variants, alleles, and interspecies homologs thereof, by detecting expressed homologs immunologically with antisera or purified antibodies made against a T2R polypeptide, which also recognize and selectively bind to the T2R homolog.

Nucleic acids that encode ligand-binding regions of taste receptors may be generated by amplification (e.g., PCR) of appropriate nucleic acid sequences using appropriate (perfect or degenerate) primer pairs. The amplified nucleic acid can be genomic DNA from any cell or tissue or mRNA or cDNA derived from taste receptor-expressing cells.

In one embodiment, hybrid protein-coding sequences comprising nucleic acids encoding T2Rs fused to a translocation sequences may be constructed. Also provided are hybrid T2Rs comprising the translocation motifs and taste eliciting compound-binding regions of other families of chemosensory receptors, particularly taste receptors. These nucleic acid sequences can be operably linked to transcriptional or translational control elements, e.g., transcription and translation initiation sequences, promoters and enhancers, transcription and translation terminators, polyadenylation sequences, and other sequences useful for transcribing DNA into RNA. In construction of recombinant expression cassettes, vectors, and transgenics, a promoter fragment can be employed to direct expression of the desired nucleic acid in all desired cells or tissues.

In another embodiment, fusion proteins may include C-terminal or N-terminal translocation sequences. Further, fusion proteins can comprise additional elements, e.g., for protein detection, purification, or other applications. Detection and purification facilitating domains include, e.g., metal chelating peptides such as polyhistidine tracts, histidine-tryptophan modules, or other domains that allow purification on immobilized metals; maltose binding protein; protein A domains that allow purification on immobilized immunoglobulin; or the domain utilized in the FLAGS extension/affinity purification system (Immunex Corp, Seattle Wash.).

The inclusion of a cleavable linker sequences such as Factor Xa (see, e.g., Ottavi, Biochimie, 80:289-93 (1998)), subtilisin protease recognition motif (see, e.g., Polyak, Protein Eng., 10:615-19 (1997)); enterokinase (Invitrogen, San Diego, Calif.), and the like, between the translocation domain (for efficient plasma membrane expression) and the rest of the newly translated polypeptide may be useful to facilitate purification. For example, one construct can include a polypeptide encoding a nucleic acid sequence linked to six histidine residues followed by a thioredoxin, an enterokinase cleavage site (see, e.g., Williams, Biochemistry, 34:1787-97 (1995)), and an C-terminal translocation domain. The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the scientific and patent literature (see, e.g., Kroll, DNA Cell. Biol,. 12:441-53 (1993)).

Expression vectors, either as individual expression vectors or as libraries of expression vectors, comprising the ligand-binding region encoding sequences may be introduced into a genome or into the cytoplasm or a nucleus of a cell and expressed by a variety of conventional techniques, well described in the scientific and patent literature. See, e.g., Roberts, Nature, 328:731 (1987); Berger supra; Schneider, Protein Exper. Purif., 6435:10 (1995); Sambrook; Tijssen; Ausubel. Product information from manufacturers of biological reagents and experimental equipment also provide information regarding known biological methods. The vectors can be isolated from natural sources, obtained from such sources as ATCC or GenBank libraries, or prepared by synthetic or recombinant methods.

The nucleic acids can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required. For example, the marker may encode antibiotic resistance (e.g., chloramphenicol, kanamycin, G418, bleomycin, hygromycin) or herbicide resistance (e.g., chlorosulfurone or Basta) to permit selection of those cells transformed with the desired DNA sequences (see, e.g., Blondelet-Rouault, Gene, 190:315-17 (1997); Aubrecht, J. Pharmacol. Exp. Ther., 281:992-97 (1997)). Because selectable marker genes conferring resistance to substrates like neomycin or hygromycin can only be utilized in tissue culture, chemoresistance genes are also used as selectable markers in vitro and in vivo.

A chimeric nucleic acid sequence may encode a T2R ligand-binding region within any 7-transmembrane polypeptide. Because 7-transmembrane receptor polypeptides have similar primary sequences and secondary and tertiary structures, structural domains (e.g., extracellular domain, TM domains, cytoplasmic domain, etc.) can be readily identified by sequence analysis. For example, homology modeling, Fourier analysis and helical periodicity detection can identify and characterize the seven domains with a 7-transmembrane receptor sequence. Fast Fourier Transform (FFT) algorithms can be used to assess the dominant periods that characterize profiles of the hydrophobicity and variability of analyzed sequences. Periodicity detection enhancement and alpha helical periodicity index can be done as by, e.g., Donnelly, Protein Sci., 2:55-70 (1993). Other alignment and modeling algorithms are well known in the art (see, e.g., Peitsch, Receptors Channels, 4:161-64 (1996); Kyte & Doolittle, J. Md. Biol., 157:105-32 (1982); and Cronet, Protein Eng., 6:59-64 (1993).

The present invention also includes not only the nucleic acid molecules and polypeptides having the specified nucleic and amino acid sequences, but also fragments thereof, particularly fragments of, e.g., 40, 60, 80, 100, 150, 200, or 250 nucleotides, or more, as well as polypeptide fragments of, e.g., 10, 20, 30, 50, 70, 100, or 150 amino acids, or more. Optionally, the nucleic acid fragments can encode an antigenic polypeptide that is capable of binding to an antibody raised against a T2R family member. Further, a protein fragment of the invention can optionally be an antigenic fragment that is capable of binding to an antibody raised against a T2R family member.

Also contemplated are chimeric proteins, comprising at least 10, 20, 30, 50, 70, 100, or 150 amino acids, or more, of one of at least one of the T2R polypeptides described herein, coupled to additional amino acids representing all or part of another GPCR, preferably a member of the 7 transmembrane superfamily. These chimeras can be made from the instant receptors and another GPCR, or they can be made by combining two or more of the present receptors. In one embodiment, one portion of the chimera corresponds to, or is derived from the transmembrane domain of a T2R polypeptide of the invention. In another embodiment, one portion of the chimera corresponds to, or is derived from the one or more of the transmembrane regions of a T2R polypeptide described herein, and the remaining portion or portions can come from another GPCR. Chimeric receptors are well known in the art, and the techniques for creating them and the selection and boundaries of domains or fragments of G Protein-Coupled Receptors for incorporation therein are also well known. Thus, this knowledge of those skilled in the art can readily be used to create such chimeric receptors. The use of such chimeric receptors can provide, for example, a taste selectivity characteristic of one of the receptors specifically disclosed herein, coupled with the signal transduction characteristics of another receptor, such as a well known receptor used in prior art assay systems.

For example, a region such as a ligand-binding region, an extracellular domain, a transmembrane domain, a transmembrane domain, a cytoplasmic domain, an N-terminal domain, a C-terminal domain, or any combination thereof, can be covalently linked to a heterologous protein. For instance, a T2R transmembrane region can be linked to a heterologous GPCR transmembrane domain, or a heterologous GPCR extracellular domain can be linked to a T2R transmembrane region. Other heterologous proteins of choice can include, e.g., green fluorescent protein, .beta.-galactosidase polypeptides, glutamate receptor, and the rhodopsin polypeptides, e.g., N-terminal fragments of rhodopsin e.g., bovine rhodopsin.

It is also within the scope of the invention to use different host cells for expressing the T2Rs, fragments, or variants of the invention. To obtain high levels of expression of a cloned gene or nucleic acid, such as cDNAs encoding the T2Rs, fragments, or variants of the invention, one of skill typically subclones the nucleic acid sequence of interest into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. Preferably, eukaryotic expression systems are used to express the subject hT2R receptor.

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al.) It is only necessary that the particular genetic engineering procedure used be capable of successfully introducing at lest one nucleic acid molecule into the host cell capable of expressing the T2R, fragment, or variant of interest.

After the expression vector is introduced into the cells, the transfected cells are cultured under conditions favoring expression of the receptor, fragment, or variant of interest, which is then recovered from the culture using standard techniques. Examples of such techniques are well known in the art. See, e.g., WO 00/06593, which is incorporated by reference in a manner consistent with this disclosure.

Assays for Detection of Compounds that Modulate the Activity of a hT2R According to the Invention Methods and compositions for determining whether a test compound specifically binds to a T2R polypeptide of the invention, both in vitro and in vivo are described below. Many aspects of cell physiology can be monitored to assess the effect of ligand-binding to a naturally occurring or chimeric T2Rs. These assays may be performed on intact cells expressing a T2R polypeptide, on permeabilized cells, or on membrane fractions produced by standard methods.

Taste receptors bind taste eliciting compounds and initiate the transduction of chemical stimuli into electrical signals. An activated or inhibited G protein will in turn alter the properties of target enzymes, channels, and other effector proteins. Some examples are the activation of cGMP phosphodiesterase by transducin in the visual system, adenylate cyclase by the stimulatory G protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

The subject hT2R proteins or polypeptides of the assay will typically be selected from a polypeptide having a sequence contained in the sequence listing preceding the claims herein or fragments or conservatively modified variants thereof.

Alternatively, the T2R proteins or polypeptides of the assay can be derived from a eukaryotic host cell, and can include an amino acid sequence having a certain percentage amino acid sequence identity to these hT2R polypeptides or conservatively modified variants thereof. Generally, the amino acid sequence identity will be at least 30% preferably 30-40%, more specifically 50-60, 70%, 75%, 80%, 85%, 90%, 95%, 96%, 97%, 98%, or 99%. Optionally, the T2R proteins or polypeptides of the assays can comprise a region of a T2R polypeptide, such as an extracellular domain, transmembrane region, cytoplasmic domain, ligand-binding domain, and the like. Optionally, as exemplified herein the T2R polypeptide, or a portion thereof, can be covalently linked to a heterologous protein to create a chimeric protein used in the assays described herein.

Modulators of T2R activity may be tested using T2R proteins or polypeptides as described above, either recombinant or naturally occurring. The T2R proteins or polypeptides can be isolated, expressed in a cell, expressed in a membrane derived from a cell, expressed in tissue or in an animal, either recombinant or naturally occurring. For example, tongue slices, dissociated cells from a tongue, transformed cells, or membranes can be used. Modulation can be tested using one of the in vitro or in vivo assays described herein.

Detection of Modulators

Compositions and methods for determining whether a test compound specifically binds to a T2R receptor of the invention, both in vitro and in vivo, are described below. Many aspects of cell physiology can be monitored to assess the effect of ligand binding to a T2R polypeptide of the invention. These assays may be performed on intact cells expressing a chemosensory receptor, on permeabilized cells, or on membrane fractions produced by standard methods or in vitro using de novo synthesized proteins.

In vivo, taste receptors bind to taste modulatory compounds and initiate the transduction of chemical stimuli into electrical signals. An activated or inhibited G protein will in turn alter the properties of target enzymes, channels, and other effector proteins. Some examples are the activation of cGMP phosphodiesterase by transducin in the visual system, adenylate cyclase by the stimulatory G protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

Alternatively, the T2R proteins or polypeptides of the assay can be derived from a eukaryotic host cell and can include an amino acid subsequence having amino acid sequence identity to the T2R polypeptides disclosed herein, or fragments or conservatively modified variants thereof. Generally, the amino acid sequence identity will be at least 35 to 50%, or optionally 75%, 85%, 90%, 95%, 96%, 97%, 98%, or 99%. Optionally, the T2R proteins or polypeptides of the assays can comprise a domain of a T2R protein, such as an extracellular domain, transmembrane region, transmembrane domain, cytoplasmic domain, ligand-binding domain, and the like. Further, as described above, the T2R protein or a domain thereof can be covalently linked to a heterologous protein to create a chimeric protein used in the assays described herein.

Modulators of T2R receptor activity are tested using T2R proteins or polypeptides as described above, either recombinant or naturally occurring. The T2R proteins or polypeptides can be isolated, expressed in a cell, expressed in a membrane derived from a cell, expressed in tissue or in an animal, either recombinant or naturally occurring. For example, tongue slices, dissociated cells from a tongue, transformed cells, or membranes can be used. Modulation can be tested using one of the in vitro or in vivo assays described herein.

In vitro Binding Assays

Taste transduction can also be examined in vitro with soluble or solid state reactions, using the T2R polypeptides of the invention. In a particular embodiment, T2R ligand-binding domains can be used in vitro in soluble or solid state reactions to assay for ligand binding.

It is possible that the ligand-binding domain may be formed by the N-terminal domain together with additional portions of the extracellular domain, such as the extracellular loops of the transmembrane domain.

In vitro binding assays have been used with other GPCRs, such as the metabotropic glutamate receptors (see, e.g., Han and Hampson, J. Biol. Chem. 274:10008-10013 (1999)). These assays might involve displacing a radioactively or fluorescently labeled ligand, measuring changes in intrinsic fluorescence or changes in proteolytic susceptibility, etc.

Ligand binding to a T2R polypeptide according to the invention can be tested in solution, in a bilayer membrane, optionally attached to a solid phase, in a lipid monolayer, or in vesicles. Binding of a modulator can be tested using, e.g., changes in spectroscopic characteristics (e.g., fluorescence, absorbance, refractive index) hydrodynamic (e.g., shape), chromatographic, or solubility properties.

In a preferred embodiment of the invention, a [35S]GTPγS binding assay is used. As described above, upon activation of a GPCR, the Gα subunit of the G protein complex is stimulated to exchange bound GDP for GTP. Ligand-mediated stimulation of G protein exchange activity can be measured in a biochemical assay measuring the binding of added radioactively labeled $[^{35}S]$GTPγS to the G protein in the presence of a putative ligand. Typically, membranes containing the chemosensory receptor of interest are mixed with a G protein. Potential inhibitors and/or activators and $[^{35}S]$GTPγS are added to the assay, and binding of $[^{35}S]$GTPγS to the G protein is measured. Binding can be measured by liquid scintillation counting or by any other means known in the art, including scintillation proximity assays (SPA). In other assays formats, fluorescently labeled GTPγS can be utilized.

Fluorescence Polarization Assays

In another embodiment, Fluorescence Polarization ("FP") based assays may be used to detect and monitor ligand binding. Fluorescence polarization is a versatile laboratory technique for measuring equilibrium binding, nucleic acid hybridization, and enzymatic activity. Fluorescence polarization assays are homogeneous in that they do not require a separation step such as centrifugation, filtration, chromatography, precipitation, or electrophoresis. These assays are done in real time, directly in solution and do not require an immobilized phase. Polarization values can be measured repeatedly and after the addition of reagents since measuring the polarization is rapid and does not destroy the sample. Generally, this technique can be used to measure polarization values of fluorophores from low picomolar to micromolar levels. This section describes how fluorescence polarization can be used in a simple and quantitative way to measure the binding of ligands to the T2R polypeptides of the invention.

When a fluorescently labeled molecule is excited with plane polarized light, it emits light that has a degree of polarization that is inversely proportional to its molecular rotation. Large fluorescently labeled molecules remain relatively stationary during the excited state (4 nanoseconds in the case of fluorescein) and the polarization of the light remains relatively constant between excitation and emission. Small fluorescently labeled molecules rotate rapidly during the excited state and the polarization changes significantly between excitation and emission. Therefore, small molecules have low polarization values and large molecules have high polarization values. For example, a single-stranded fluorescein-labeled oligonucleotide has a relatively low polarization value but when it is hybridized to a complementary strand, it has a higher polarization value. When using FP to detect and monitor taste eliciting compound-binding which may activate or inhibit the chemosensory receptors of the invention, fluorescence-labeled taste eliciting compounds or auto-fluorescent taste eliciting compounds may be used.

Fluorescence polarization (P) is defined as:

$$P = \frac{[Int_{par} - Int_{perp}]}{[Int_{par} + Int_{perp}]}$$

Where $Int_{par}$ is the intensity of the emission light parallel to the excitation light plane and $Int_{perp}$ is the intensity of the emission light perpendicular to the excitation light plane. P, being a ratio of light intensities, is a dimensionless number. For example, the Beacon™ and Beacon 2000™. System may be used in connection with these assays. Such systems typically express polarization in millipolarization units (1 Polarization Unit=1000 mP Units).

The relationship between molecular rotation and size is described by the Perrin equation and the reader is referred to Jolley, M. E. (1991) in Journal of Analytical Toxicology, pp. 236-240 incorporated by reference, which gives a thorough explanation of this equation. Summarily, the Perrin equation states that polarization is directly proportional to the rotational relaxation time, the time that it takes a molecule to rotate through an angle of approximately 68.5°. Rotational relaxation time is related to viscosity (eta.), absolute temperature (T), molecular volume (V), and the gas constant (R) by the following equation: 2(Rotational Relaxation Time)=3 V RT The rotational relaxation time is small (~nanosecond) for small molecules (e.g. fluorescein) and large (~100 nanoseconds) for large molecules (e.g. immunoglobulins). If viscosity and temperature are held constant, rotational relaxation time, and therefore polarization, is directly related to the molecular volume. Changes in molecular volume may be due to interactions with other molecules, dissociation, polymerization, degradation, hybridization, or conformational changes of the fluorescently labeled molecule. For example, fluorescence polarization has been used to measure enzymatic cleavage of large fluorescein labeled polymers by proteases, DNases, and RNases. It also has been used to measure equilibrium binding for protein/protein interactions, antibody/antigen binding, and protein/DNA binding.

Solid State and Soluble High Throughput Assays

In yet another embodiment, the invention provides soluble assays using a T2R polypeptide; or a cell or tissue expressing a T2R polypeptide. In another embodiment, the invention provides solid phase based in vitro assays in a high throughput format, where the T2R polypeptide, or cell or tissue expressing the T2R polypeptide is attached to a solid phase substrate or a taste stimulating compound and contacted with a T2R receptor, and binding detected using an appropriate tag or antibody raised against the T2R receptor.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 1000 to about 1500 different compounds. It is also possible to assay multiple compounds in each plate well. It is possible to assay several different plates per day; assay screens for up to about 6,000-20,000 different compounds is possible using the integrated systems of the invention. More recently, microfluidic approaches to reagent manipulation have been developed.

The molecule of interest can be bound to the solid state component, directly or indirectly, via covalent or non-covalent linkage, e.g., via a tag. The tag can be any of a variety of components. In general, a molecule which binds the tag (a tag binder) is fixed to a solid support, and the tagged molecule of interest (e.g., the taste transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, The Adhesion Molecule Facts Book I (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, J. Am. Chem. Soc., 85:2149-2154 (1963) (describing solid phase synthesis of, e.g., peptides); Geysen et al., J. Immun. Meth., 102:259-274 (1987) (describing synthesis of solid phase components on pins); Frank & Doring, Tetrahedron, 44:60316040 (1988) (describing synthesis of various peptide sequences on cellulose disks); Fodor et al., Science, 251:767-777 (1991); Sheldon et al., Clinical Chemistry, 39(4):718-719 (1993); and Kozal et al., Nature Medicine, 2(7):753759 (1996) (all describing arrays of biopolymers fixed to solid substrates). Non-chemical approaches for fixing tag binders to substrates include other common methods, such as heat, cross-linking by UV radiation, and the like.

Cell-based Assays

In one preferred embodiment, a T2R protein is expressed in a eukaryotic cell either in unmodified forms or as chimeric, variant or truncated receptors with or preferably without a heterologous, chaperone sequence that facilitates its maturation and targeting through the secretory pathway. Such T2R polypeptides can be expressed in any eukaryotic cell, such as HEK-293 cells. Preferably, the cells comprise a functional G protein, e.g., G.α15, or a chimeric G.α16, gustducin or transducin or a chimeric G protein such as G16gust44 that is capable of coupling the chimeric receptor to an intracellular signaling pathway or to a signaling protein such as phospholipase C. Activation of T2R receptors in such cells can be detected using any standard method, such as by detecting changes in intracellular calcium by detecting FURA-2 dependent fluorescence in the cell. Such an assay is the basis of the experimental findings presented in this application.

Activated GPCR receptors often are substrates for kinases that phosphorylate the C-terminal tail of the receptor (and possibly other sites as well). Thus, activators will promote the transfer of 32P from radiolabeled ATP to the receptor, which can be assayed with a scintillation counter. The phosphorylation of the C-terminal tail will promote the binding of arrestin-like proteins and will interfere with the binding of G proteins. For a general review of GPCR signal transduction and methods of assaying signal transduction, see, e.g., Methods in Enzymology, vols. 237 and 238 (1994) and volume 96

(1983); Bourne et al., Nature, 10:349:117-27 (1991); Bourne et al., Nature, 348:125-32 (1990); Pitcher et al., Annu. Rev. Biochem., 67:653-92 (1998).

T2R modulation may be assayed by comparing the response of T2R polypeptides treated with a putative T2R modulator to the response of an untreated control sample or a sample containing a known "positive" control. Such putative T2R modulators can include molecules that either inhibit or activate T2R polypeptide activity. In one embodiment, control samples treated with a compound that activates the T2R are assigned a relative T2R activity value of 100. Inhibition of a T2R polypeptide is achieved when the T2R activity value relative to the control sample is about 90%, optionally 50%, optionally 25-0%. Activation of a T2R polypeptide is achieved when the T2R activity value relative to the control is 110%, optionally 150%, 200-500%, or 1000-2000%.

Changes in ion flux may be assessed by determining changes in ionic polarization (i.e., electrical potential) of the cell or membrane expressing a T2R polypeptide. One means to determine changes in cellular polarization is by measuring changes in current (thereby measuring changes in polarization) with voltage-clamp and patch-clamp techniques (see, e.g., the "cell-attached" mode, the "inside-out" mode, and the "whole cell" mode, e.g., Ackerman et al., New Engl. J. Med., 336:1575-1595 (1997)). Whole cell currents are conveniently determined using the standard. Other known assays include: radiolabeled ion flux assays and fluorescence assays using voltage-sensitive dyes (see, e.g., Vestergarrd-Bogind et al., J. Membrane Biol., 88:67-75 (1988); Gonzales & Tsien, Chem. Biol., 4:269-277 (1997); Daniel et al., J. Pharmacol. Meth., 25:185-193 (1991); Holevinsky et al., J. Membrane Biology, 137:59-70 (1994)).

The effects of the test compounds upon the function of the polypeptides can be measured by examining any of the parameters described above. Any suitable physiological change that affects GPCR activity can be used to assess the influence of a test compound on the polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as Ca2+, IP3, cGMP, or cAMP.

Preferred assays for GPCRs include cells that are loaded with ion or voltage sensitive dyes to report receptor activity. Assays for determining activity of such receptors can also use known agonists and antagonists for other G protein-coupled receptors as controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog. For G protein-coupled receptors, promiscuous G proteins such as Gα15 and Gα16 can be used in the assay of choice (Wilkie et al., Proc. Nat'l Acad. Sci., 88:10049-10053 (1991)). Alternatively, other G proteins such as gustducin, transducin and chimeric G proteins such as Gα16gust44 or Galpha16t25 may be used.

Receptor activation initiates subsequent intracellular events, e.g., increases in second messengers. Activation of some G protein-coupled receptors stimulates the formation of inositol triphosphate (IP3) through phospholipase C-mediated hydrolysis of phosphatidylinositol (Berridge & Irvine, Nature, 312:315-21 (1984)). IP3 in turn stimulates the release of intracellular calcium ion stores. Thus, a change in cytoplasmic calcium ion levels, or a change in second messenger levels such as IP3 can be used to assess G protein-coupled receptor function. Cells expressing such G protein-coupled receptors may exhibit increased cytoplasmic calcium levels as a result of contribution from both calcium release from intracellular stores and extracellular calcium entry via plasma membrane ion channels.

In a preferred embodiment, T2R polypeptide activity is measured by expressing T2R gene in a heterologous cell with a promiscuous G protein that links the receptor to a phospholipase C signal transduction pathway (see Offermanns & Simon, J. Biol. Chem., 270:15175-15180 (1995)). Preferably, the cell line is HEK-293 (which does not normally express T2R genes) and the promiscuous G protein is Gα15 (Offermanns & Simon, supra) or a chimeric G protein such as Gα16gust44. Modulation of taste transduction is assayed by measuring changes in intracellular Ca2+ levels, which change in response to modulation of the T2R signal transduction pathway via administration of a molecule that associates with the T2R polypeptide. Changes in Ca2+ levels are optionally measured using fluorescent Ca2+ indicator dyes and fluorimetric imaging.

In another embodiment, phosphatidyl inositol (PI) hydrolysis can be analyzed according to U.S. Pat. No. 5,436,128, herein incorporated by reference. Briefly, the assay involves labeling of cells with 3H-myoinositol for 48 or more hrs. The labeled cells are treated with a test compound for one hour. The treated cells are lysed and extracted in chloroform-methanol-water after which the inositol phosphates were separated by ion exchange chromatography and quantified by scintillation counting. Fold stimulation is determined by calculating the ratio of cpm in the presence of agonist, to cpm in the presence of buffer control. Likewise, fold inhibition is determined by calculating the ratio of cpm in the presence of antagonist, to cpm in the presence of buffer control (which may or may not contain an agonist).

Other receptor assays can involve determining the level of intracellular cyclic nucleotides, e.g., cAMP or cGMP. In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. In one embodiment, the changes in intracellular cAMP or cGMP can be measured using immunoassays. The method described in Offermanns & Simon, J. Bio. Chem., 270:15175-15180 (1995), may be used to determine the level of cAMP. Also, the method described in Felley-Bosco et al., Am. J. Resp. Cell and Mol. Biol., 11:159-164 (1994), may be used to determine the level of cGMP. Further, an assay kit for measuring cAMP and/or cGMP is described in U.S. Pat. No. 4,115,538, herein incorporated by reference.

In another embodiment, transcription levels can be measured to assess the effects of a test compound on signal transduction. A host cell containing T2R polypeptide of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays.

Alternatively, transcription based assays using a reporter gene may be used as described in U.S. Pat. No. 5,436,128, herein incorporated by reference. The reporter genes can be, e.g., chloramphenicol acetyltransferase, luciferase, beta-galactosidase, beta-lactamase and alkaline phosphataste. Furthermore, the protein of interest can be used as an indirect reporter via attachment to a second reporter such as green fluorescent protein (see, e.g., Mistili & Spector, Nature Biotechnology, 15:961-964 (1997)).

The amount of transcription is then compared to the amount of transcription in either the same cell in the absence of the test compound, or it may be compared with the amount of transcription in a substantially identical cell that lacks the T2R polypeptide(s) of interest. A substantially identical cell may be derived from the same cells from which the recombinant cell was prepared but which had not been modified by introduction of heterologous DNA. Any difference in the amount of transcription indicates that the test compound has in some manner altered the activity of the T2R polypeptide of interest.

Transgenic Non-human Animals Expressing Chemosensory Receptors

Non-human animals expressing one or more taste receptor sequences of the invention can also be used for receptor assays. Such expression can be used to determine whether a test compound specifically binds to a mammalian taste transmembrane receptor complex in vivo by contacting a non-human animal stably or transiently transfected with nucleic acids encoding chemosensory receptors or ligand-binding regions thereof with a test compound and determining whether the animal reacts to the test compound by specifically binding to the receptor polypeptide complex.

Animals transfected or infected with the vectors of the invention are particularly useful for assays to identify and characterize taste stimuli that can bind to a specific or sets of receptors. Such vector-infected animals expressing human taste receptor sequences can be used for in vivo screening of taste stimuli and their effect on, e.g., cell physiology (e.g., on taste neurons), on the CNS, or behavior.

Means to infect/express the nucleic acids and vectors, either individually or as libraries, are well known in the art. A variety of individual cell, organ, or whole animal parameters can be measured by a variety of means. The T2R sequences of the invention can be for example expressed in animal taste tissues by delivery with an infecting agent, e.g., adenovirus expression vector.

The endogenous taste receptor genes can remain functional and wild-type (native) activity can still be present. In other situations, where it is desirable that all taste receptor activity is by the introduced exogenous hybrid receptor, use of a knockout line is preferred. Methods for the construction of non-human transgenic animals, particularly transgenic mice, and the selection and preparation of recombinant constructs for generating transformed cells are well known in the art.

Construction of a "knockout" cell and animal is based on the premise that the level of expression of a particular gene in a mammalian cell can be decreased or completely abrogated by introducing into the genome a new DNA sequence that serves to interrupt some portion of the DNA sequence of the gene to be suppressed. Also, "gene trap insertion" can be used to disrupt a host gene, and mouse embryonic stem (ES) cells can be used to produce knockout transgenic animals (see, e.g., Holzschu, Transgenic Res 6:97-106 (1997)). The insertion of the exogenous is typically by homologous recombination between complementary nucleic acid sequences. The exogenous sequence is some portion of the target gene to be modified, such as exonic, intronic or transcriptional regulatory sequences, or any genomic sequence which is able to affect the level of the target gene's expression; or a combination thereof. Gene targeting via homologous recombination in pluripotential embryonic stem cells allows one to modify precisely the genomic sequence of interest. Any technique can be used to create, screen for, propagate, a knockout animal, e.g., see Bijvoet, Hum. Mol. Genet. 7:53-62 (1998); Moreadith, J. Mol. Med. 75:208-216 (1997); Tojo, Cytotechnology 19:161-165 (1995); Mudgett, Methods Mol. Biol. 48:167-184 (1995); Longo, Transgenic Res. 6:321-328 (1997); U.S. Pat. Nos. 5,616,491; 5,464,764; 5,631,153; 5,487,992; 5,627,059; 5,272,071; WO 91/09955; WO 93/09222; WO 96/29411; WO 95/31560; WO 91/12650.

The nucleic acids of the invention can also be used as reagents to produce "knockout" human cells and their progeny. Likewise, the nucleic acids of the invention can also be used as reagents to produce "knock-ins" in mice. The human or rat T2R gene sequences can replace the orthologs T2R in the mouse genome. In this way, a mouse expressing a human or rat T2R is produced. This mouse can then be used to analyze the function of human or rat T2Rs, and to identify ligands for such T2Rs.

Modulators

The compounds tested as modulators of a T2R family member can be any small chemical compound, or a biological entity, such as a protein, sugar, nucleic acid or lipid. Alternatively, modulators can be genetically altered versions of a T2R family member. Typically, test compounds may be small chemical molecules and peptides. Essentially any chemical compound can be used as a potential modulator or ligand in the assays of the invention, although most often compounds can be dissolved in aqueous or organic (especially DMSO-based) solutions are used. The assays may be designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In one embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual consumer products.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res., 37:487-93 (1991) and Houghton et al., Nature, 354:84-88 (1991)). Other chemistries for generating chemical diversity libraries can also be used. Such chemistries include, but are not limited to: peptoids (e.g., WO 91/19735), encoded peptides (e.g., WO 93/20242), random bio-oligomers (e.g., WO 92/00091), benzodiazepines (e.g., U.S. Pat. No. 5,288,514), diversomers such as hydantoins, benzodiazepines and dipeptides (Hobbs et al., PNAS., 90:6909-13 (1993)), vinylogous polypeptides (Hagihara et al., J. Amer. Chem. Soc., 114:6568 (1992)), nonpeptidal peptidomimetics with glucose scaffolding (Hirschmann et al., J. Amer. Chem. Soc., 114:9217-18 (1992)), analogous organic syntheses of small compound libraries (Chen et al., J. Amer. Chem. Soc., 116:2661 (1994)), oligocarbamates (Cho et al., Science, 261:1303 (1993)), peptidyl phosphonates (Campbell et al., J. Org. Chem., 59:658 (1994)), nucleic acid libraries (Ausubel, Berger, and Sambrook, all supra), peptide nucleic acid libraries (U.S. Pat. No. 5,539,083), antibody libraries (Vaughn et al., Nature Biotechnology, 14(3):309-14 (1996) and PCT/US96/10287), carbohydrate libraries (Liang et al., Science, 274:1520-22 (1996) and U.S. Pat. No. 5,593, 853), small organic molecule libraries (benzodiazepines, Baum, C&EN, Jan 18, page 33 (1993); thiazolidinones and metathiazanones, U.S. Pat. No. 5,549,974; pynrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS (Advanced Chem Tech, Louisville Ky.), Symphony (Rainin, Woburn, Mass.), 433A (Applied Biosystems, Foster City, Calif.), 9050 Plus (Millipore, Bedford, Mass.)). In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences; Columbia, Md.; etc.).

In one aspect of the invention, the T2R modulators can be used in any food product, confectionery, pharmaceutical composition, or ingredient thereof to thereby modulate the taste of the product, composition, or ingredient in a desired manner. For instance, T2R modulators that enhance bitter taste sensation can be added to provide a bitter taste to a product or composition, while T2R modulators which block bitter taste sensations can be added to block the bitter taste of a product or composition. Also, the invention provides means of identifying bitter compounds found in foods, beverages, cosmetics and medicinals and producing taste improved foods, beverages and medicinals lacking or having a reduced quantity thereof.

Use of Compounds Identified by the Invention

Compounds identified according to the invention may be added to foods, beverages, cosmetics or medicinal compositions to modulate, preferably block bitter taste triggered by activation at least one of one of hT2R8 and/or hT2R14 by bitter compounds present in coffee and related foods, beverages and medicaments or structurally related compounds or other bitter compounds, e.g., compounds found in foods and beverages or medicinals or cosmetics that elicit a bitter taste perception.

In particular Compound C, and its analogs, based on its broad ranging antagonist properties may be used as an additive in any food, beverage, medicament or material for consumption by humans or animals wherein bitter taste is desirably alleviated. Given Compound C's properties, these materials may contain bitter ligands known to interact with specific bitter ligands such as hT2R3, 7, 10, 14, 16, 44, 51, 55, 61, 63, 64, 65, or 71 and/or with hT2R5, 9, 13, 54, 67 and 75, or a combination thereof or which contain bitter compounds for which their bitter receptor selectivity is undetermined. Especially preferred applications are compositions containing compounds that activate multiple bitter taste receptors.

In addition, the subject compounds including Compound C may be used in competitive binding and functional assays as well as taste tests to identify bitter compounds for which Compound C blocks or inhibits bitter taste.

As noted previously, preferably, the taste modulatory properties, preferably bitter taste blocking properties of compounds identified in the subject T2R cell-based assays will be confirmed in human or animal taste tests, preferably human taste tests.

Kits

T2R genes and their homologs are useful tools for identifying taste receptor cells, for forensics and paternity determinations, and for examining taste transduction. T2R family member-specific reagents that specifically hybridize to T2R nucleic acids, such as T2R probes and primers, and T2R specific reagents that specifically bind to a T2R protein, e.g., T2R antibodies are used to examine taste cell expression and taste transduction regulation.

Nucleic acid assays for the presence of DNA and RNA for a T2R family member in a sample include numerous techniques are known to those skilled in the art, such as southern analysis, northern analysis, dot blots, RNase protection, S1 analysis, amplification techniques such as PCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., Biotechniques, 4:230250 (1986); Haase et al., Methods in Virology, vol. VII, 189-226 (1984); and Names et al., eds., Nucleic Acid Hybridization: A Practical Approach (1987). In addition, a T2R protein can be detected with the various immunoassay techniques described above. The test sample is typically compared to both a positive control (e.g., a sample expressing a recombinant T2R protein) and a negative control.

The present invention also provides for kits for screening for modulators of T2R family members. Such kits can be prepared from readily available materials and reagents. For example, such kits can comprise any one or more of the following materials: T2R nucleic acids or proteins, reaction tubes, and instructions for testing T2R activity. Optionally, the kit contains a functional T2R polypeptide. A wide variety of kits and components can be prepared according to the present invention, depending upon the intended user of the kit and the particular needs of the user.

Having now generally described the invention, the same will be more readily understood by reference to the following examples, which are provided by way of illustration and are not intended as limiting. It is understood that various modifications and changes can be made to the herein disclosed exemplary embodiments without departing from the spirit and scope of the invention.

EXAMPLES

Example 1 hT2R8 and hT2R14 are Activated by Bitter Coffee Fraction

A partially purified bitter fraction from coffee was used to screen the 25 human T2Rs in transiently transfected HEK cells as described in previous patent applications. In brief (as discussed in more detail in U.S Patent Publication No. 2003/

0170608, incorporated herein by reference), human embryonic kidney cells that stably express large T-cell antigen and G15 protein (HEK-G15) were transiently tranfected with an hT2R expression plasmid (e.g., by use of $Ca^{2+}$ phosphate or by use of lipid-based systems). Additionally, other HEK-G15 cell lines were transiently transfected with other human T2Rs. Thereafter, a fluorescent-based assay was used to detect changes in calcium concentration in the transiently transfected cells. Interaction of the test compound(s) with the transfected cells elicits a signaling cascade leading to the activation of PLC and a subsequent increase in intracellular calcium concentration resulting in an increase of fluorescence which was detected using a calcium-sensitive fluorescent dye. These changes were monitored e.g., using fluorescence microscopic and appropriately designed software (such as Imaging Workstation, Axon).

The coffee fraction has high level of fluorescence, which interfered with the assay. To overcome the interference, a number of blue dyes were tested for ability to block the fluorescence from the coffee fraction. As shown in FIG. 1, the coffee fraction activated hT2R8 and hT2R14 in calcium imaging assay using transiently transfected cells. The blue dye used in the experiment of FIG. 1 is FD&C 1 at 1.9 mM. Several other hT2Rs also appeared to be activated by this coffee fraction. With different blue dyes, different combinations of hT2Rs are activated (Table 1). However, hT2R8 and hT2R14 are consistently picked up as responsive to the coffee fraction, and the activities of these two receptors are coffee fraction dose-dependent (FIG. 2) The blue dye used in the experiment of FIG. 2 was tryptan blue.

TABLE 1 hT2Rs activated by the coffee fraction with different blue dyes

| Blue Dye | hT2R Receptors Identified | |
|---|---|---|
| | Activate | Weakly activate |
| FD&C 1 | 8, 14 | — |
| Trypan | 1, 8, 14 | 10, 75 |
| Coomassie | 14 | — |

Using this assay, it was found that the addition of the bitter fraction from coffee to cells that express hT2R8 and hT2R14 activated intracellular G proteins. By contrast, using the same assay, the bitter fraction from coffee did not specifically activate HEK-G15 cells that were transiently transfected with other hT2Rs. This experiment supports the conclusion that taste receptors hT2R8 and hT2R14 specifically respond to bitter compound(s) present in coffee.

Example 2

Identification of Antagonists of hT2R8 and hT2R14

To identify antagonists, cell lines stably expressing hT2R8 and hT2R14, respectively, together with the promiscuous chimeric G16g44 protein were generated as described in previous patent applications. A high-throughput assay was established using the stable cell lines and FLIPR (Fluorescent Imaging Plate Reader). An agonist of hT2R8 or hT2R14 was used to activate the receptors up to 70-80% of their respective maximal activity. For hT2R8, the agonist used was andrographolide (200 μM); for hT2R14, it was aristolochic acid (3 μM). To identify antagonists, compounds with diverse chemical structures were added together with the agonist. Compounds that cause statistically significant reduction of the receptor activity are pooled together, and reconfirmed with dose-dependent inhibition curves. Compound A and Compound B were identified as hT2R8 antagonists (FIG. 3). Compound C was identified as an hT2R14 antagonist (FIG. 4).

Example 2a

Combinations hT2R8 and hT2R14 Antagonists Reduce Bitter Taste of Coffee

Taste tests were performed with combinations of hT2R8 and hT2R14 antagonists in the coffee fraction and two types of instant coffee (medium roast and medium-dark roast), using a 2-alternative forced choice method with a taste panel of 4-5 panelists. Coffee samples with the antagonists were given to the taste panelists together with the same sample without antagonists, the panelists were asked to identify the bitterer sample within the pair. As shown in Table 2, the panelists consistently identified the coffee fraction samples without antagonists as being bitterer than the ones with antagonists, indicating that the antagonists reduced the bitter taste of the coffee fraction. Similarly, as shown in Table 3, the antagonists reduced the bitter taste of both types of instant coffee.

As demonstrated by the taste tests of this example, the perception of bitterness in compositions (e.g., foods, beverages and/or medicaments) which exhibit bitter taste may be reduced or eliminated by incorporation of antagonists of hT2R8 and/or hT2R14 into such compositions.

To determine the contribution of an individual antagonist, taste tests were performed with medium roast instant coffee with Compound C. As shown in Table 4, the hT2R14 antagonist (Compound C) is sufficient by itself to reduce the bitter taste in the coffee of this example.

TABLE 2

Taste test results with coffee fraction and 2 different combinations of antagonists

| Test | Antagonist | | Concentration (μM) | Selected as bitterer | | P value |
|---|---|---|---|---|---|---|
| | hT2R8 | hT2R14 | | Without antagonists | With antagonists | |
| 1 | Cmp A | Cmp C | 30 | 32 | 0 | <0.001 |
| 2 | Cmp B | Cmp C | 30 | 15 | 1 | 0.001 |
| 3 | Cmp A | Cmp C | 10 | 16 | 0 | <0.001 |

TABLE 3

Taste test results with 2 types of instant coffee

| Instant Coffee | Antagonists | | Concentration (μM) | Selected as bitterer | | P value |
|---|---|---|---|---|---|---|
| | hT2R8 | hT2R14 | | Without antagonists | Plus antagonists | |
| Medium | Cmp A | Cmp C | 30 | 16 | 0 | <0.001 |
| Medium-dark | Cmp A | Cmp C | 30 | 13 | 3 | 0.021 |

TABLE 4

Taste test results with medium roast coffee and individual antagonist

| Taste Test | Antagonist | Concentration (µM) | Selected as bitterer Without antagonist | Selected as bitterer With Antagonist | P value |
|---|---|---|---|---|---|
| 1 | Compound C | 50 | 18 | 2 | <0.001 |
| 2 | Compound C | 25 | 19 | 1 | <0.001 |

Example 3

Compound C is a Broadly Acting Bitter Receptor Antagonist

Example 2 above teaches that compound C is a human T2R antagonist identified by high throughput screening assays using hT2R14. Additional experiments reveal that Compound C is a broadly tuned antagonist for 13 human T2Rs and to a lesser extent antagonizes six other human T2Rs. Moreover, this compound in taste tests blocks the bitter taste intensity elicited by a number of diverse bitter substances.

Specifically, in order to evaluate the inhibitory selectivity of the Compound C compound, this compound was tested against 22 human T2Rs which were deorphaned by Senomyx. These receptors and the bitter ligands that activate these human T2Rs are reported in earlier patent applications which are incorporated by reference herein. These 22 human T2Rs are hT2R1, 3, 4, 5, 7, 8, 9, 10, 13, 14, 16, 44, 51, 54, 55, 61, 63, 64, 65, 67, 71 and 75. The amino acid and nucleic acid sequences of all of these T2Rs may be found in these earlier patent applications. These human T2Rs were each individually transiently transfected into HEK293 cells that stably express the promiscuous G protein G16g44 and functional assays were effected using these receptors as disclosed in these same patent applications. In these experiments each receptor was activated by one of its ligands selected from bitter molecules previously demonstrated to activate the particular T2R. The ligands were used at EC80 concentration levels. The list of bitter ligands utilized and the tested ligand concentrations are contained in Table 5 of this example.

Furthermore, in order to confirm the in vitro activity of this compound in the receptor assay, the inventors performed paired comparison taste test to determine the effect of the compound in vivo. The taste panelists were asked to taste bitter substances with and without Compound C, and to identify which sample tastes more bitter. Multiple pairs were tasted by each panelist to increase the sample size, and the results were analyzed using appropriate statistical methods. The order of samples with and without Compound C were randomized and counter balanced.

In order to establish the broad antagonistic properties of this compound, it was tested for its ability to block bitter taste elicited by a variety of bitter ligands as well bitter taste elicited by bitter ligands known to activate multiple bitter taste receptors and bitter ligands which have not yet been demonstrated to activate a specific hT2R. Several bitter molecules known to activate bitter receptors were tested for which activation is inhibited by Compound C. Specifically, salicin is a bitter molecule that activates hT2R16, and taste test results showed that Compound C at 40 µM can reduce its bitter taste. Phenylthiourea is a bitter molecule that activates hT2R51, and Compound C reduced its bitter taste at 25 µM.

Several bitter molecules that can activate multiple T2Rs were similarly tested with Compound C. The activation of bitter receptors for some of these molecules were partially inhibited by Compound C. Omeprazole is a bitter molecule that activates hT2R10, 14 and 75. Notwithstanding that its bitter taste may involve multiple bitter receptors, its bitter taste was also appreciably reduced by Compound C. Rebaudioside A is a natural sweetener with strong bitter taste, which activates at least 7 human T2Rs. Its bitter taste is also reduced by Compound C.

In addition, Compound C inhibited bitter taste for some compounds wherein the receptor(s) with which they interact is unknown, such as dextromethorphan and diphenhydramin. The effect of Compound C on these compounds was tested and it was discovered that their bitter taste was also reduced.

Relating to the foregoing, FIG. 5 contains experimental results wherein Compound C was tested with different agonist compounds. The inhibition activity is represented by the reduction of receptor activity in the presence of Compound C. FIG. 5 reveals that 13 different hT2Rs were significantly (greater than 30%) inhibited by Compound C. These 13 hT2Rs are hT2R3, 7, 10, 14, 16, 44, 51, 55, 61, 63, 64, 65, and 71. Six other receptors, including hT2R5, 9, 13, 54, 67 and 75 were also inhibited, although to a lesser extent.

TABLE 5

List of ligands and concentrations used for each tested T2R.

| hT2Rs | Agonist | Concentration |
|---|---|---|
| 1 | Picric Acid | 0.05 mM |
| 3 | Chloroquine pH 6.5 | 50 µM |
| 4 | Chloroquine pH 6.5 | 5 mM |
| 5 | Picoline | 10 mM |
| 7 | Chloroquine pH 6.5 | 10 mM |
| 8 | Andrographolide | 0.5 mM |
| 9 | Ofloxacin | 1 mM |
| 10 | Strychnine | 50 µM |
| 13 | Oxyphenonium | 1 mM |
| 14 | Aristolochic Acid | 2 µM |
| 16 | Salicin | 1 mM |
| 44 | Denatonium | 0.5 µM |
| 51 | Prop | 2.5 µM |
| 54 | Ranitidine | 5 mM |
| 55 | Cinchonine | 150 µM |
| 61 | Aristolochic Acid | 25 nM |
| 63 | Caffeine | 1 mM |
| 63 | Andrographolide | 100 µM |
| 64 | Aristolochic Acid | 1 µM |
| 65 | Oleuropein | 1 mM |
| 67 | Andrographolide | 5 µM |
| 71 | Picric Acid | 10 µM |
| 75 | Strychnine | 1 µM |

Example 4 hT2R8 Antagonists: Making the Compounds of the Invention
Exemplary compounds according to the invention are synthesized as follows.

Example 4-1

N-(1-((3,5-dimethylisoxazol-4-yl)methyl)-1H-pyrazol-4-yl)picolinamide

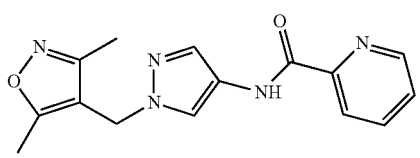

1-((3,5-dimethylisoxazol-4-yl)methyl)-1H-pyrazol-4-amine hydrochloride (example 4-1a) (400 mg, 2.1 mmol), picolinic acid (256 mg, 2.1 mmol), and HOBt (388 mg, 2.50 mmol) were mixed in DCM (7 mL). The reaction was treated with triethylamine (670 mL, 4.8 mmol) and stirred for 15 minutes at room temperature under a nitrogen atmosphere. EDC (598 mg, 3.1 mmol) was added and the reaction was stirred for an additional 4 hours. The reaction was then diluted with dichloromethane (5 mL) and washed with aqueous saturated NaHCO$_3$ solution (5 mL, 2×) and then with aqueous saturated NaCl solution (5 mL). The organic layer was collected, dried, and filtered. Solvents were removed under vacuum. The crude product was re-suspended in EtOH (5 mL) and purified by reversed phase HPLC (5%-95% ACN in H$_2$O: 25 minute gradient). The pure fractions were combined and concentrated to afford N-(1-((3,5-dimethylisoxazol-4-yl)methyl)-1H-pyrazol-4-yl)picolinamide (372 mg, 60%) as a white solid. $^1$H NMR (CDCl$_3$, 400 MHz): δ 2.21 (s, 3H), 2.44 (s, 3H), 5.05 (s, 2H), 7.49-7.47 (m, 1H), 7.59 (s, 1H), 7.93-7.88 (dt, J=14, 2 Hz, 1H), 8.07 (s, 1H), 8.24-8.21 (d, J=8 Hz, 1H), 8.61-8.56 (m, 1H), 9.83 (bs, 1H). LC/MS; [M+H] calculated for C, 15; H, 15; N, 5; O, 2; expected 297.1; found 298.3. Melting point: 135-137° C.

The compound had an IC$_{50}$ on hT2R8 bitter receptor of 0.57 μM

Example 4-1a 1-((3,5-dimethylisoxazol-4-yl)methyl)-1H-pyrazol-4-amine hydrochloride Tert-butyl 1-((3,5-dimethylisoxazol-4-yl)methyl)-1H-pyrazol-4-ylcarbamate (Example 4-1b) (592 mg, 2 mmol) was stirred in a solution of 4N HCl in dioxane (20 mL) at ambient temperature for 2 hours. The solvent was removed under reduced pressure and the residue was taken up in a 1/1 mixture of ethyl acetate/hexanes (30 mL) and concentrated (twice). The solid was triturated with hexanes and collected by filtration providing 1-((3,5-dimethylisoxazol-4-yl)methyl)-1H-pyrazol-4-amine hydrochloride (500 mg, 99%) as a white solid. $^1$H NMR (DMSO-d$_6$, 400 MHz): δ 2.11 (s, 3H), 2.38 (s, 3H), 5.16 (s, 2H), 7.51 (s, 1H), 8.03 (s, 1H), 10.27 (bs, 3H).

Example 4-1b tert-butyl 1-((3,5-dimethylisoxazol-4-yl)methyl)-1H-pyrazol-4-ylcarbamate 3,5-dimethyl-4-((4-nitro-1H-pyrazol-1-yl)methyl)isoxazole (Example 4-1c) (14.6 g, 66 mmol), Boc anhydride, and 10% Pd/C (3.8 g) was stirred in MeOH (400 mL) under 1 atmosphere of H$_2$ for 16 hours at ambient temperature. The mixture was filtered and the solution was removed under reduced pressure. The residue was purified by silica gel chromatography (20% ethyl acetate in hexanes) to afford tert-butyl 1-((3,5-dimethylisoxazol-4-yl)methyl)-1H-pyrazol-4-ylcarbamate (12.7 g, 66%) as a light pink solid. $^1$H NMR (CDCl$_3$, 400 MHz): δ 1.41 (s, 9H), 2.10 (s, 3H), 2.32 (s, 3H), 4.90 (s, 2H), 6.19 (bs, 1H), 7.19 (s, 1H), 7.50 (s, 1H). MS 293 (MH$^+$).

Example 4-1c 3,5-dimethyl-4-((4-nitro-1H-pyrazol-1-yl)methyl)isoxazole

To 4-nitro-1H-pyrazole (Example 4-id) (3.8 g, 34 mmol) in DMF (80 mL) cooled to 0° C., via an ice/water bath, was added t-BuOK (4.2 g, 38 mmol). After addition of the base the ice bath was removed and the mixture was stirred for 30 minutes followed by the addition of 4-(chloromethyl)-3,5-dimethylisoxazole (5 g, 34 mmol). The reaction was refluxed for 16 hours then cooled to ambient temperature. H$_2$O was added to the reaction mixture and the precipitate formed was collected by filtration. The precipitate was washed with additional H$_2$O then dried under high vacuum to afford 3,5-dimethyl-4-((4-nitro-1H-pyrazol-1-yl)methyl)isoxazole (5.8 g, 78%) as a light yellow solid. $^1$H NMR (CDCl$_3$, 400 MHz): δ 2.23 (s, 3H), 2.46 (s, 3H), 5.08 (s, 2H), 8.02 (s, 1H), 8.08 (s, 1H).

Example 4-1d 4-nitro-1H-pyrazole

Pyrazole (10 g, 147 mmol), was added to concentrated sulfuric acid (100 mL), in portions, while maintaining the internal reaction temperature below 50° C. via an ice water bath. Concentrated nitric acid (10 mL) was then added, dropwise, maintaining the internal reaction temperature below 50° C. via an ice water bath. The ice water bath was removed and the reaction was heated to 60° C. and stirred for 4 hours. The reaction was cooled via an ice water bath and made basic, to ~pH 8, with 18 N aqueous NaOH solution (150 mL). The product, which precipitated as a white solid, was collected by filtration, washed with H$_2$O, and dried under high vacuum to afford 4-nitro-1H-pyrazole (7 g, 42%) as a white solid. $^{13}$C NMR (100 MHz, CDCl$_3$): δ 126.4, 137.0.

Example 4-2

3-chloro-N-(1-((3,5-dimethylisoxazol-4-yl)methyl)-1H-pyrazol-4-yl)-4-(methylsulfonyl)thiophene-2-carboxamide

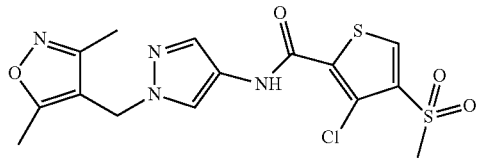

4-2

To a stirring mixture of ((3,5-dimethylisoxazol-4-yl)methyl)-1H-pyrazol-4-amine hydrochloride (Example 4-1a) (500 mg, 2 mmol) in DCM (20 mL), cooled to 0° C. via an ice water bath, was added triethylamine (600 mg, 6 mmol). The mixture was stirred until all solids were in solution (~10 minutes). 3-Chloro-4-(methylsulfonyl)thiophene-2-carbonyl chloride (543 mg, 2.1 mmol), in 2 mL CH$_3$CN, was added via syringe to the free amine at 0° C. The ice bath was removed and the mixture was stirred for 2 hours. The reaction was diluted with dichloromethane (100 mL) and the organic phase was washed with H$_2$O (200 mL). The organic layer was dried over sodium sulfate, filtered and concentrated under reduced pressure. The solid was triturated with ethyl acetate/hexanes (1/5) to afford 3-chloro-N-(1-((3,5-dimethylisoxazol-4-yl)methyl)-1H-pyrazol-4-yl)-4 (methylsulfonyl)thiophene-2-carboxamide (375 mg, 45%) as a white solid. $^1$H NMR (CDCl$_3$, 400 MHz): δ 2.20 (s, 3H), 2.43 (s, 4H), 3.22 (s, 3H), 5.05 (s, 2H), 7.57 (s, 1H), 7.94 (s, 1H), 8.41 (s, 1H), 8.59 (bs, 1H). LC/MS; [M+H] 415.5. Melting point: 202-204° C.

The compound had an IC$_{50}$ on hT2R8 bitter receptor of 2.09 µM

Example 4-3

(S)-N-(1-((3,5-dimethylisoxazol-4-yl)methyl)-1H-pyrazol-4-yl)-2-phenylpropanamide

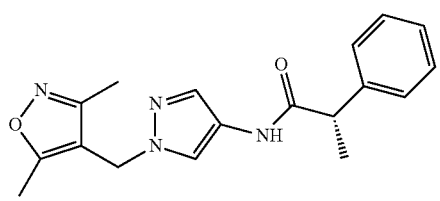

4-3

1-((3,5-dimethylisoxazol-4-yl)methyl)-1H-pyrazol-4-amine hydrochloride (Example 4-1a) (200 mg, 1 mmol), (S)-2-phenyl propionic acid (156 mg, 1 mmol), and PyBop (650 mg, 1.3 mmol) were added to DMF (4 mL) followed by triethylamine (0.3 mL, 2.1 mmol). The reaction stirred for 4 hours at room temperature under a nitrogen atmosphere then diluted with ethyl acetate (20 mL), washed with aqueous saturated NaHCO$_3$ solution (2×15 mL) followed by aqueous saturated NaCl solution (15 mL). The organic phase was dried, filtered and concentrated on the rotovap. The crude product was re-suspended in methanol (3 mL) and purified by reversed phase HPLC (5%-95% ACN in H$_2$O: 25 minute gradient). The fractions containing the pure product were concentrated to afford (S)-N-(1-((3,5-dimethylisoxazol-4-yl) methyl)-1H-pyrazol-4-yl)-2-phenylpropanamide (200 mg, 60%) as a white solid. $^1$H NMR (400 MHz, DMSO-d$_6$) δ 1.36 (d, J=7.2, Hz, 3H), 2.09 (s, 3H), 2.36 (s, 3H), 3.71-3.66 (m, 1H), 5.05 (s, 2H), 7.33-7.17 (m, 5H), 7.37 (s, 1H), 7.90 (s, 1H), 10.05 (s, 1H). MS 325 (M+H). Melting point 108° C.-110° C.

The compound had an IC$_{50}$ on hT2R8 bitter receptor of 0.41 µM

Example 4-4

N-(1-((3,5-dimethylisoxazol-4-yl)methyl)-1H-pyrazol-4-yl)-2-(4-hydroxy-3,5-dimethoxyphenyl)acetamide

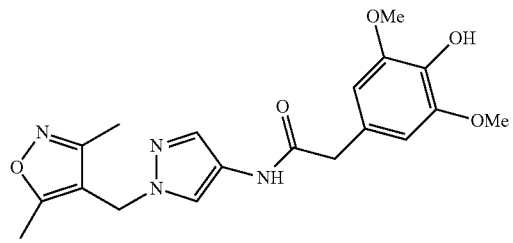

4-4

1-((3,5-dimethylisoxazol-4-yl)methyl)-1H-pyrazol-4-amine hydrochloride (Example 4-1a) (376 mg, 1.7 mmol), 2-(4-hydroxy-3,5-dimethoxyphenyl)acetic acid (350 mg, 1.7 mmol), PyBop (1 g, 2 mmol) and triethylamine (605 mg, 6 mmol) were stirred together in DMF (10 mL) at room temperature for 2 hours. The reaction mixture was diluted with aqueous 1N HCl (100 mL) and extracted with DCM (3×, 75 mL). The combined organic extracts were dried over sodium sulfate, filtered and concentrated on the rotovap. The residue was purified by silica gel chromatography (30% ethyl acetate in hexanes) to afford N-(1-((3,5-dimethylisoxazol-4-yl)methyl)-1H-pyrazol-4-yl)-2-(4-hydroxy-3,5-dimethoxyphenyl) acetamide (189 mg, 29%) as a white solid. $^1$H NMR (CDCl$_3$, 400 MHz) δ 2.10 (s, 3H), 2.36 (s, 3H), 3.40 (s, 2H), 3.70 (s, 6H), 5.07 (s, 2H), 6.53 (s, 2H), 7.39 (s, 1H), 7.92 (s, 1H), 8.18 (s, 1H), 10.03 (s, 1H). LC/MS; [M+H] calculated for C, 19; H, 22; N, 4; O, 5; expected 387.16; found 387.6. Melting point: 187-188° C.

The compound had an $IC_{50}$ on hT2R8 bitter receptor of 0.46 µM

Example 4-5

N-(1-((3,5-dimethylisoxazol-4-yl)methyl)-1H-pyrazol-4-yl)-2-phenylpropanamide

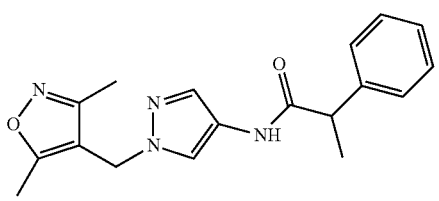

4-5

1-((3,5-dimethylisoxazol-4-yl)methyl)-1H-pyrazol-4-amine hydrochloride (Example 4-1a) (300 mg, 1.3 mmol), 2-phenylpropanoic acid (225 mg, 1.5 mmol), triethylamine (300 mg, 3 mmol), DMAP (61 mg, 0.5 mmol), and EDC (386 mg, 2 mmol) were stirred together in DCM (10 mL) at room temperature for 4 hours. The reaction mixture was diluted with aqueous 1N HCl (100 mL) and extracted with DCM (3×, 75 mL). The combined organic extracts were dried over sodium sulfate, filtered and concentrated on the rotovap. The residue was purified by silica gel chromatography (30% ethyl acetate in hexanes) to afford N-(1-((3,5-dimethylisoxazol-4-yl)methyl)-1H-pyrazol-4-yl)-2-phenylpropanamide (272 mg, 81%) as a white solid. $^1$H NMR (CDCl$_3$, 400 MHz) δ 1.36 (d, 3H, J=7.2 Hz), 2.10 (s, 3H), 2.37 (s, 3H), 3.70 (m, 1H, J=6.8 Hz), 5.06 (s, 2H), 7.20 (t, 1H, J=8.4 Hz), 7.31-7.28 (m, 4H), 7.38 (s, 1H), 7.91 (s, 1H), 10.10 (s, 1H). LC/MS; [M+H] calculated for C, 18; H, 20; N, 4; O, 2; expected 325.16; found 325.5. Melting point: 129-130° C.

The compound had an $IC_{50}$ on hT2R8 bitter receptor of 0.32 µM

Example 4-6

N-(1-((3,5-dimethylisoxazol-4-yl)methyl)-1H-pyrazol-4-yl)-2-phenylacetamide

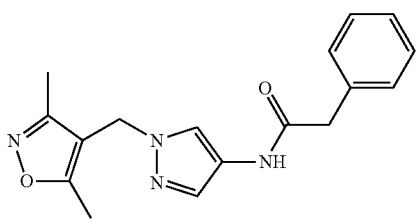

4-6

1-((3,5-dimethylisoxazol-4-yl)methyl)-1H-pyrazol-4-amine hydrochloride salt (Example 4-1a) (230 mg, 1 mmol) and triethylamine (300 mg, 3 mmol) were stirred in DCM (10 mL) cooled to 0° C. via an ice/water bath. 2-Phenylacetyl chloride (184 mg, 1.3 mmol) was added dropwise to the stirring reaction mixture. When the addition was complete the ice bath was removed and the reaction was stirred for 1 hour. The mixture was diluted with DCM (50 mL), washed with 1N aqueous HCl (100 mL), followed by 1N aqueous NaOH (100 mL) and then H$_2$O (100 mL). The combined organic extracts were dried over sodium sulfate, filtered and the solvent was removed on the rotovap. The resulting residue was purified by silica gel chromatography (50% ethyl acetate in hexanes) to afford 210 mg of solid product which was triturated in ethyl acetate/hexanes (1/9) to afford N-(1-((3,5-dimethylisoxazol-4-yl)methyl)-1H-pyrazol-4-yl)-2-phenylacetamide (188 mg, 68%) as a white solid. $^1$H NMR (CDCl$_3$, 400 MHz): δ 2.15 (s, 3H), 2.38 (s, 3H), 3.69 (s, 2H), 4.97 (s, 2H), 7.15 b(s, 1H), 7.40-7.27 (m, 6H), 7.84 (s, 1H). LC/MS; [M+H] calculated for C, 17; H, 18; N, 4; O, 2; expected 311.14; found 311.40. Melting point: 106-108° C.

The compound had an $IC_{50}$ on hT2R8 bitter receptor of 0.53 µM

Example 4-7

N-(1-((3,5-dimethylisoxazol-4-yl)methyl)-1H-pyrazol-4-yl)-3-methoxybenzamide

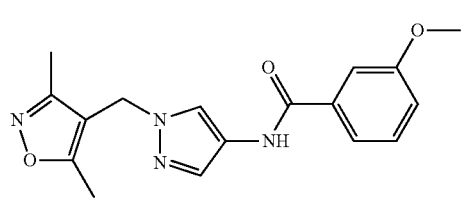

4-7

1-((3,5-dimethylisoxazol-4-yl)methyl)-1H-pyrazol-4-amine hydrochloride (Example 4-1a) (300 mg, 1.3 mmol), 3-methoxybenzoic acid (172 mg, 1.3 mmol), EDC (386 mg, 2 mmol), and triethyl amine (303 mg, 3 mmol) were stirred in DCM (5 mL) at ambient temperature for 6 hours. The reaction was diluted with DCM (50 mL) and the organic phase was washed with aqueous 0.1 N HCL (150 mL) followed by aqueous 1N NaOH (150 mL). The organic layer was dried over sodium sulfate, filtered and concentrated on the rotovap. The crude product was purified by silica gel chromatography (40% ethyl acetate in hexanes) to afford 225 mg of an off white solid. The solid was triturated with ethyl acetate/hexanes (1/9) and the white solid was collect by filtration. The pure product was dissolved in absolute ethanol and concentrated on the rotovap (4×, 25 mL) to afford N-(1-((3,5-dimethylisoxazol-4-yl)methyl)-1H-pyrazol-4-yl)-3-methoxybenzamide (185 mg, 43%) as a white solid. $^1$H NMR (CDCl$_3$, 400 MHz): δ 2.20 (s, 3H), 2.42 (s, 3H), 3.85 (s, 3H), 5.03 (s, 2H), 7.09-7.06 (m, 1H), 7.37-7.35 (m, 2H), 7.41 (m, 1H), 7.51 (s, 1H), 7.93 (bs, 1H), 8.03 (s, 1H). LC/MS; [M+H] calculated for C, 17; H, 18; N, 4; O, 3; expected 327.14; found 327.30. Melting point: 127-129° C.

The compound had an $IC_{50}$ on hT2R8 bitter receptor of 0.39 μM

Example 4-8

N-(1-((3,5-dimethylisoxazol-4-yl)methyl)-1H-pyrazol-4-yl)benzo[d][1,3]dioxole-5-carboxamide

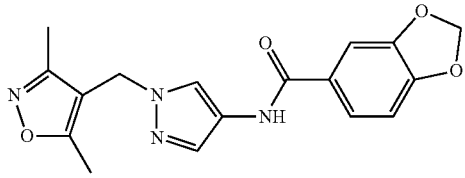

4-8

1-((3,5-dimethylisoxazol-4-yl)methyl)-1H-pyrazol-4-amine hydrochloride (example 1a) (8 mg, 35 μmol) and benzo[d][1,3]dioxole-5-carboxylic acid (7 mg, 42 μmol) were each dissolved in 200 uL dimethylformamide. Si-Carbodiimide resin (70 mg, 70 μmol) was loaded into a 1.2 mL 96 well Greiner plate, followed by the addition of amine and acid. Hydroxybenzotriazole (6 mg, 42 μmol) was dissolved in 100 uL dimethylformamide and was added into the reaction well. The reaction was shaken overnight at room temperature. To remove excess carboxylic acid and hydroxybenzotriazole, PS-Trisamine resin (35 mg, 70 μmol) was added into the reaction mixture and was allowed to shake overnight at room temperature. 200 uL of Acetonitrile was added into the reaction well and shaken for 1 minute. The top clear solution was transferred into a new plate. The extraction process was repeated two more times. The solution was evaporated under vacuum and gave the desired product. Yield 6%. MS M+H calculated 341.1, found 341.2.

The compound had an $IC_{50}$ on hT2R8 bitter receptor of 0.2 μM

Example 4-9

N-(1-((3,5-dimethylisoxazol-4-yl)methyl)-1H-pyrazol-4-yl)-2,5-dimethoxybenzamide

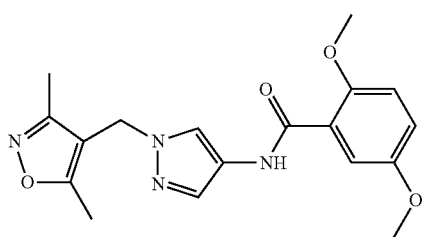

4-9

Prepared as in Example 4-8 from 2,5-dimethoxybenzoic acid and 1-((3,5-dimethylisoxazol-4-yl)methyl)-1H-pyrazol-4-amine hydrochloride (Example 4-1a). Yield 13%. MS M+H calculated 357.5, found 357.3.

The compound had an $IC_{50}$ on hT2R8 bitter receptor of 0.17 μM

Example 4-10

3-cyano-N-(1-((3,5-dimethylisoxazol-4-yl)methyl)-1H-pyrazol-4-yl)benzamide

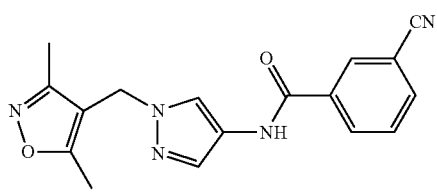

4-10

Prepared as in Example 4-8 from 3-cyanobenzoic acid and 1-((3,5-dimethylisoxazol-4-yl)methyl)-1H-pyrazol-4-amine hydrochloride (Example 4-1a). Yield 15%. MS M+H calculated 322.6, found 322.3.

The compound had an $IC_{50}$ on hT2R8 bitter receptor of 0.2 μM

Example 4-11

N-(1-((3,5-dimethylisoxazol-4-yl)methyl)-1H-pyrazol-4-yl)-1-phenylcyclopropanecarboxamide

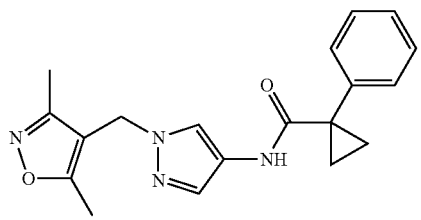

4-11

Prepared as in Example 4-8 from 1-phenylcyclopropanecarboxylic acid and 1-((3,5-dimethylisoxazol-4-yl)methyl)-1H-pyrazol-4-amine hydrochloride (Example 4-1a). Yield 6%. MS M+H calculated 337.6, found 337.5.

The compound had an $IC_{50}$ on hT2R8 bitter receptor of 0.25 μM

Example 4-12

N-(1-((3,5-dimethylisoxazol-4-yl)methyl)-1H-pyrazol-4-yl)-3-phenylbutanamide

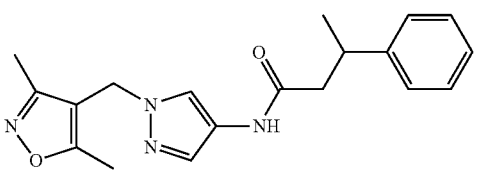

4-12

Prepared as in Example 4-8 from 3-phenylbutanoic acid and 1-((3,5-dimethylisoxazol-4-yl)methyl)-1H-pyrazol-4-amine hydrochloride (Example 4-1a). Yield 6%. MS M+H calculated 339.6, found 339.5.

The compound had an $IC_{50}$ on hT2R8 bitter receptor of 0.28 μM

Example 4-13

N-(1-((3,5-dimethylisoxazol-4-yl)methyl)-1H-pyrazol-4-yl)-1H-pyrrole-2-carboxamide

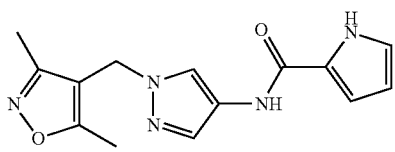

4-13

Prepared as in Example 4-8 from 1H-pyrrole-2-carboxylic acid and 1-((3,5-dimethylisoxazol-4-yl)methyl)-1H-pyrazol-4-amine hydrochloride (Example 4-1a). Yield 18%. MS M+H calculated 286.6, found 286.3.

The compound had an $IC_{50}$ on hT2R8 bitter receptor of 0.57 μM

Example 4-14

2-cyclohexyl-N-(1-((3,5-dimethylisoxazol-4-yl)methyl)-1H-pyrazol-4-yl)acetamide

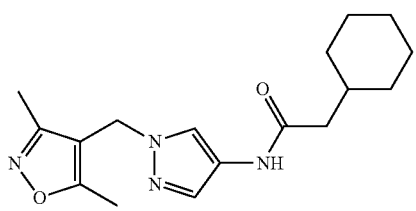

4-14

Prepared as in Example 4-8 from 2-cyclohexylacetic acid and 1-((3,5-dimethylisoxazol-4-yl)methyl)-1H-pyrazol-4-amine hydrochloride (Example 4-1a). Yield 17%. MS M+H calculated 317.6, found 317.4.

The compound had an $IC_{50}$ on hT2R8 bitter receptor of 0.73 μM

Example 4-15

N-(1-((3,5-dimethylisoxazol-4-yl)methyl)-1H-pyrazol-4-yl)cinnamamide

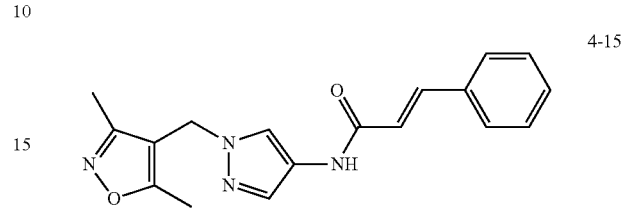

4-15

Prepared as in Example 4-8 from cinnamic acid and 1-((3,5-dimethylisoxazol-4-yl)methyl)-1H-pyrazol-4-amine hydrochloride (Example 4-1a). Yield 4%. MS M+H calculated 322.6, found 322.4.

The compound had an $IC_{50}$ on hT2R8 bitter receptor of 0.7 μM

Example 4-16

N-(1-((3,5-dimethylisoxazol-4-yl)methyl)-1H-pyrazol-4-yl)adamantane

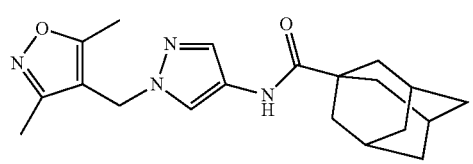

4-16

1-((3,5-dimethylisoxazol-4-yl)methyl)-1H-pyrazol-4-amine hydrochloride (300 mg, 1.56 mmol), adamantane-1-carboxylic acid (281 mg, 1.56 mmol), PyBop (972 mg, 1.87 mmol), and triethylamine (0.438 mL, 3.12 mmol) were mixed in DMF (5 mL). The reaction stirred at room temperature for 4 hours under a nitrogen atmosphere. The reaction was diluted with ethyl acetate (4 mL) and washed with saturated $NaHCO_3$ solution (2×, 3 mL) and then with saturated NaCl solution (3 mL). The organic layer was extracted, dried, and filtered. Solvents were removed under vacuum. The crude product was re-suspended in methanol (4 mL) and purified by HPLC. The pure product was re-dissolved in ethanol and concentrated under vacuum (3×3 mL) to afford N-(1-((3,5-dimethylisoxazol-4-yl)methyl)-1H-pyrazol-4-yl)adamantane as a white solid in 60% yield. $^1$H NMR (400 MHz, $CDCl_3$): δ 1.79-1.70 (m, 6H), 1.93-1.92 (m, 6H), 2.08 (bs, 3H), 2.18 (s, 3H), 2.41 (s, 3H), 4.98 (s, 2H), 7.37 (s, 1H), 7.38 (s, 1H), 7.92 (s, 1H). MS 355 (M+H). Melting point 167-169° C.

The compound had an $IC_{50}$ on hT2R8 bitter receptor of 0.88 μM

Additional compounds were synthesized following similar procedures as described in examples 4-1 to 4-16 and experimentally tested and found to have a relatively high level of effectiveness as inhibitors of hT2R8 bitter receptor. The results of that testing are shown below in Table A.

TABLE A

| Compound No. | Compound | hT2R8 IC$_{50}$ (μM) |
|---|---|---|
| 4-17 | 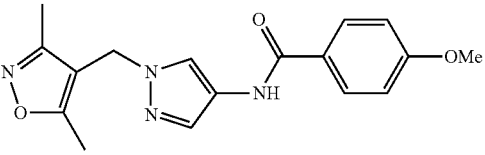 [SMILES: COc1ccc(C(=O)Nc2cnn(Cc3c(C)noc3C)c2)cc1]<br>N-(1-((3,5-dimethylisoxazol-4-yl)methyl)-1H-pyrazol-4-yl)-4-methoxybenzamide | 0.26 |
| 4-18 | 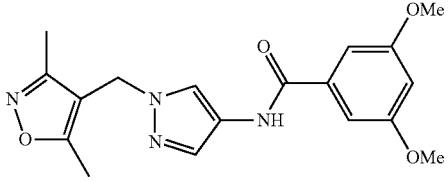 [SMILES: COc1cc(OC)cc(C(=O)Nc2cnn(Cc3c(C)noc3C)c2)c1]<br>N-(1-((3,5-dimethylisoxazol-4-yl)methyl)-1H-pyrazol-4-yl)-3,5-dimethoxybenzamide | 0.28 |
| 4-19 | 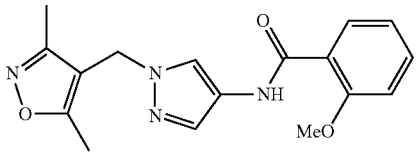 [SMILES: COc1ccccc1C(=O)Nc1cnn(Cc2c(C)noc2C)c1]<br>N-(1-((3,5-dimethylisoxazol-4-yl)methyl)-1H-pyrazol-4-yl)-2-methoxybenzamide | 0.39 |
| 4-20 | 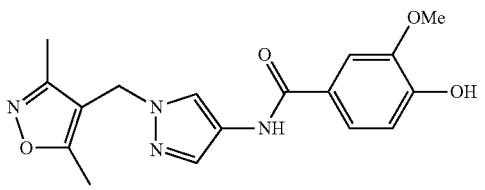 [SMILES: COc1cc(C(=O)Nc2cnn(Cc3c(C)noc3C)c2)ccc1O]<br>N-(1-((3,5-dimethylisoxazol-4-yl)methyl)-1H-pyrazol-4-yl)-4-hydroxy-3-methoxybenzamide | 0.48 |
| 4-21 | 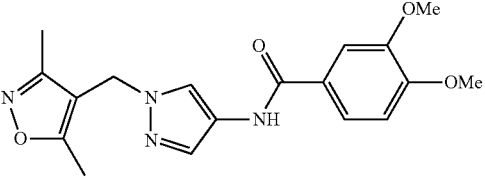 [SMILES: COc1ccc(C(=O)Nc2cnn(Cc3c(C)noc3C)c2)cc1OC]<br>N-(1-((3,5-dimethylisoxazol-4-yl)methyl)-1H-pyrazol-4-yl)-3,4-dimethoxybenzamide | 0.56 |
| 4-23 | 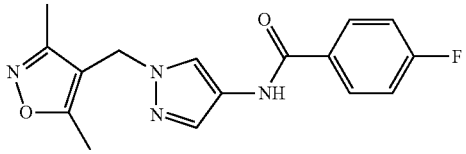 [SMILES: Cc1noc(C)c1Cn1cc(NC(=O)c2ccc(F)cc2)cn1]<br>N-(1-((3,5-dimethylisoxazol-4-yl)methyl)-1H-pyrazol-4-yl)-4-fluorobenzamide | 1.56 |

TABLE A-continued

| Compound No. | Compound | hT2R8 IC$_{50}$ (μM) |
|---|---|---|
| 4-24 | 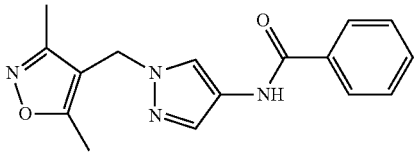 [SMILES: Cc1noc(C)c1Cn1cc(NC(=O)c2ccccc2)cn1]<br>N-(1-((3,5-dimethylisoxazol-4-yl)methyl)-1H-pyrazol-4-yl)benzamide | 2.62 |
| 4-25 | 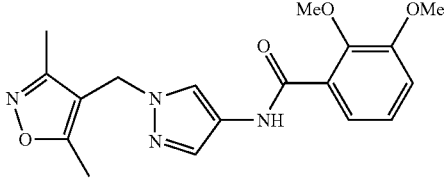 [SMILES: COc1cccc(C(=O)Nc2cnn(Cc3c(C)noc3C)c2)c1OC]<br>N-(1-((3,5-dimethylisoxazol-4-yl)methyl)-1H-pyrazol-4-yl)-2,3-dimethoxybenzamide | 0.61 |
| 4-26 | 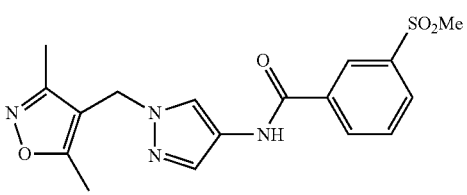 [SMILES: Cc1noc(C)c1Cn1cc(NC(=O)c2cccc(S(C)(=O)=O)c2)cn1]<br>N-(1-((3,5-dimethylisoxazol-4-yl)methyl)-1H-pyrazol-4-yl)-3-(methylsulfonyl)benzamide | 0.72 |
| 4-27 | 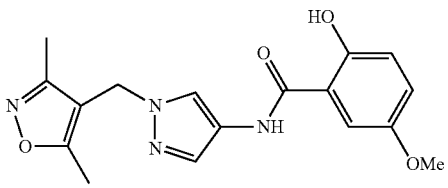 [SMILES: COc1ccc(O)c(C(=O)Nc2cnn(Cc3c(C)noc3C)c2)c1]<br>N-(1-((3,5-dimethylisoxazol-4-yl)methyl)-1H-pyrazol-4-yl)-2-hydroxy-5-methoxybenzamide | 0.98 |
| 4-28 | 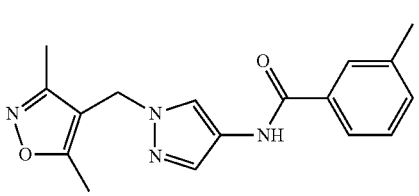 [SMILES: Cc1cccc(C(=O)Nc2cnn(Cc3c(C)noc3C)c2)c1]<br>N-(1-((3,5-dimethylisoxazol-4-yl)methyl)-1H-pyrazol-4-yl)-3-methylbenzamide | 0.57 |
| 4-29 | 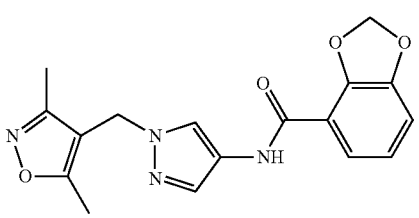 [SMILES: Cc1noc(C)c1Cn1cc(NC(=O)c2cccc3c2OCO3)cn1]<br>N-(1-((3,5-dimethylisoxazol-4- | 0.30 |

TABLE A-continued

| Compound No. | Compound | hT2R8 IC$_{50}$ (μM) |
|---|---|---|
| | yl)methyl)-1H-pyrazol-4-yl)-2-methoxybenzamide | |
| 4-30 | N-(1-((3,5-dimethylisoxazol-4-yl)methyl)-1H-pyrazol-4-yl)-2-methoxybenzamide | 0.39 |
| 4-31 | 2-(2,3-dimethoxyphenyl)-N-(1-((3,5-dimethylisoxazol-4-yl)methyl)-1H-pyrazol-4-yl)acetamide | 0.80 |
| 4-32 | 2-(3,5-dimethoxyphenyl)-N-(1-((3,5-dimethylisoxazol-4-yl)methyl)-1H-pyrazol-4-yl)acetamide | 0.96 |
| 4-33 | N-(1-((3,5-dimethylisoxazol-4-yl)methyl)-1H-pyrazol-4-yl)-2-(4-methoxyphenyl)acetamide | 0.99 |

TABLE A-continued

| Compound No. | Compound | hT2R8 IC$_{50}$ (μM) |
|---|---|---|
| 4-34 | N-(1-((3,5-dimethylisoxazol-4-yl)methyl)-1H-pyrazol-4-yl)-2-methoxybenzamide | 1.11 |
| 4-35 | N-(1-((3,5-dimethylisoxazol-4-yl)methyl)-1H-pyrazol-4-yl)-2-(2-methoxyphenyl)acetamide | 1.16 |
| 4-36 | N-(1-((3,5-dimethylisoxazol-4-yl)methyl)-1H-pyrazol-4-yl)-2-methoxybenzamide | 1.85 |
| 4-37 | N-(1-((3,5-dimethylisoxazol-4-yl)methyl)-1H-pyrazol-4-yl)-2-phenylbutanamide | 0.50 |
| 4-38 | N-(1-((3,5-dimethylisoxazol-4-yl)methyl)-1H-pyrazol-4-yl)-2-methoxybenzamide | 0.53 |

TABLE A-continued

| Compound No. | Compound | hT2R8 IC$_{50}$ (μM) |
|---|---|---|
| 4-39 | 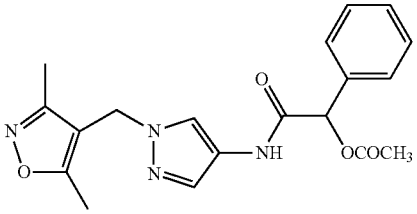<br>2-(1-((3,5-dimethylisoxazol-4-yl)methyl)-1H-pyrazol-4-ylamino)-2-oxo-1-phenylethyl acetate | 0.83 |
| 4-40 | 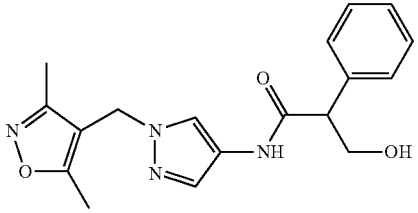 [SMILES: Cc1noc(C)c1Cn1cc(NC(=O)C(CO)c2ccccc2)cn1]<br>N-(1-((3,5-dimethylisoxazol-4-yl)methyl)-1H-pyrazol-4-yl)-3-hydroxy-2-phenylpropanamide | 0.96 |
| 4-41 | 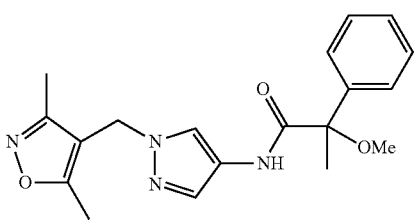 [SMILES: COC(C)(C(=O)Nc1cnn(Cc2c(C)noc2C)c1)c1ccccc1]<br>N-(1-((3,5-dimethylisoxazol-4-yl)methyl)-1H-pyrazol-4-yl)-2-methoxybenzamide | 2.10 |
| 4-42 | 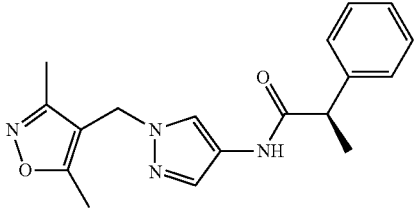 [SMILES: Cc1noc(C)c1Cn1cc(NC(=O)[C@H](C)c2ccccc2)cn1]<br>(R)-N-(1-((3,5-dimethylisoxazol-4-yl)methyl)-1H-pyrazol-4-yl)-2-phenylpropanamide | 3.72 |
| 4-43 | 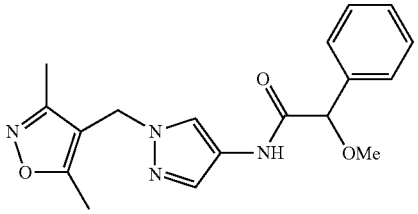 [SMILES: COC(C(=O)Nc1cnn(Cc2c(C)noc2C)c1)c1ccccc1]<br>N-(1-((3,5-dimethylisoxazol-4-yl)methyl)-1H-pyrazol-4-yl)-2-methoxy-2-phenylacetamide | 3.43 |

TABLE A-continued

| Compound No. | Compound | hT2R8 IC$_{50}$ (μM) |
|---|---|---|
| 4-44 | 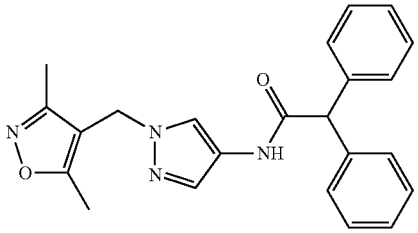 [SMILES: Cc1noc(C)c1Cn1cc(NC(=O)C(c2ccccc2)c2ccccc2)cn1]<br>N-(1-((3,5-dimethylisoxazol-4-yl)methyl)-1H-pyrazol-4-yl)-2,2-diphenylacetamide | 5.19 |
| 4-45 | 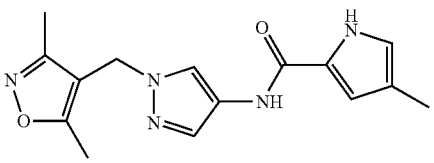 [SMILES: Cc1c[nH]c(C(=O)Nc2cnn(Cc3c(C)noc3C)c2)c1]<br>N-(1-((3,5-dimethylisoxazol-4-yl)methyl)-1H-pyrazol-4-yl)-4-methyl-1H-pyrrole-2-carboxamide | 0.72 |
| 4-46 | 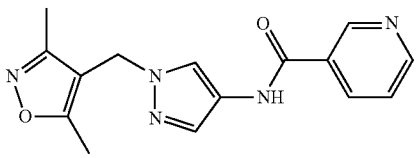 [SMILES: Cc1noc(C)c1Cn1cc(NC(=O)c2cccnc2)cn1]<br>N-(1-((3,5-dimethylisoxazol-4-yl)methyl)-1H-pyrazol-4-yl)nicotinamide | 1.05 |
| 4-47 | 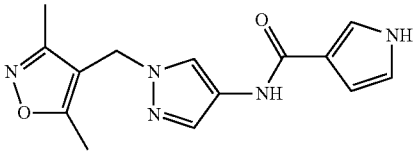 [SMILES: Cc1noc(C)c1Cn1cc(NC(=O)c2cc[nH]c2)cn1]<br>N-(1-((3,5-dimethylisoxazol-4-yl)methyl)-1H-pyrazol-4-yl)-2-methoxybenzamide | 1.35 |
| 4-48 | 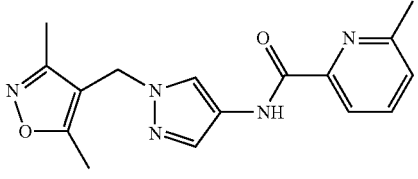 [SMILES: Cc1cccc(C(=O)Nc2cnn(Cc3c(C)noc3C)c2)n1]<br>N-(1-((3,5-dimethylisoxazol-4-yl)methyl)-1H-pyrazol-4-yl)-6-methylpicolinamide | 1.95 |
| 4-49 | 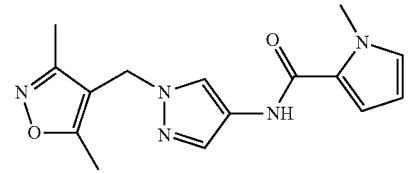 [SMILES: Cc1noc(C)c1Cn1cc(NC(=O)c2cccn2C)cn1]<br>N-(1-((3,5-dimethylisoxazol-4-yl)methyl)-1H-pyrazol-4-yl)-1-methyl-1H-pyrrole-2-carboxamide | 3.40 |

TABLE A-continued

| Compound No. | Compound | hT2R8 IC$_{50}$ (μM) |
|---|---|---|
| 4-50 | 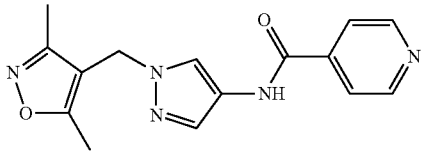 [SMILES: Cc1noc(C)c1Cn1cc(NC(=O)c2ccncc2)cn1]<br>N-(1-((3,5-dimethylisoxazol-4-yl)methyl)-1H-pyrazol-4-yl)isonicotinamide | 4.59 |
| 4-51 | 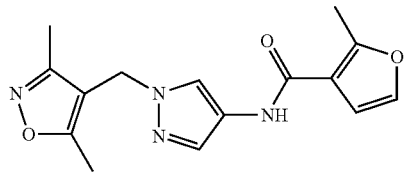 [SMILES: Cc1noc(C)c1Cn1cc(NC(=O)c2ccoc2C)cn1]<br>N-(1-((3,5-dimethylisoxazol-4-yl)methyl)-1H-pyrazol-4-yl)-2-methylfuran-3-carboxamide | 7.87 |
| 4-52 | 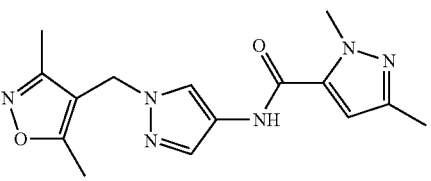 [SMILES: Cc1cc(C(=O)Nc2cnn(Cc3c(C)noc3C)c2)n(C)n1]<br>N-(1-((3,5-dimethylisoxazol-4-yl)methyl)-1H-pyrazol-4-yl)-1,3-dimethyl-1H-pyrazole-5-carboxamide | 18.05 |
| 4-53 | 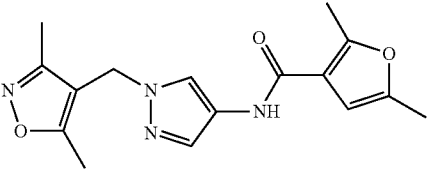 [SMILES: Cc1cc(C(=O)Nc2cnn(Cc3c(C)noc3C)c2)c(C)o1]<br>N-(1-((3,5-dimethylisoxazol-4-yl)methyl)-1H-pyrazol-4-yl)-2,5-dimethylfuran-3-carboxamide | 3.03 |
| 4-54 | 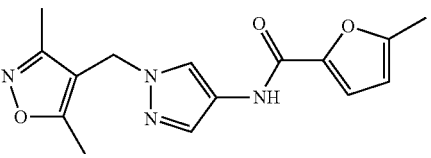 [SMILES: Cc1ccc(C(=O)Nc2cnn(Cc3c(C)noc3C)c2)o1]<br>N-(1-((3,5-dimethylisoxazol-4-yl)methyl)-1H-pyrazol-4-yl)-5-methylfuran-2-carboxamide | 3.19 |
| 4-55 | 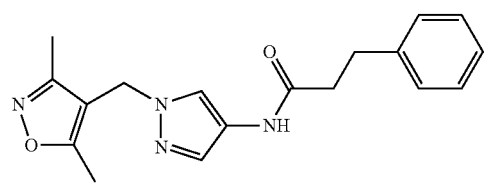 [SMILES: Cc1noc(C)c1Cn1cc(NC(=O)CCc2ccccc2)cn1]<br>N-(1-((3,5-dimethylisoxazol-4-yl)methyl)-1H-pyrazol-4-yl)-3-phenylpropanamide | 0.49 |

TABLE A-continued

| Compound No. | Compound | hT2R8 IC$_{50}$ (μM) |
|---|---|---|
| 4-56 | 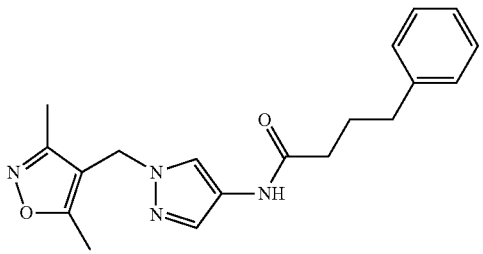 [SMILES: Cc1noc(C)c1Cn1cc(NC(=O)CCCc2ccccc2)cn1]<br>N-(1-((3,5-dimethylisoxazol-4-yl)methyl)-1H-pyrazol-4-yl)-4-phenylbutanamide | 0.83 |
| 4-57 | 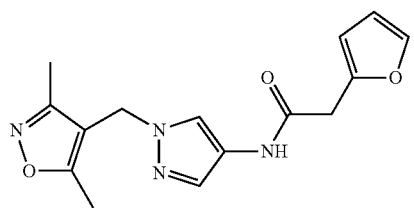 [SMILES: Cc1noc(C)c1Cn1cc(NC(=O)Cc2ccco2)cn1]<br>N-(1-((3,5-dimethylisoxazol-4-yl)methyl)-1H-pyrazol-4-yl)-2-methoxybenzamide | 4.16 |
| 4-58 | 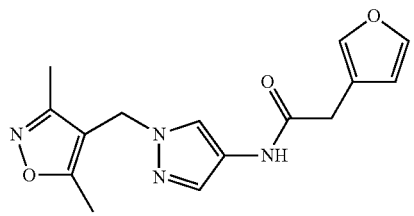 [SMILES: Cc1noc(C)c1Cn1cc(NC(=O)Cc2ccoc2)cn1]<br>N-(1-((3,5-dimethylisoxazol-4-yl)methyl)-1H-pyrazol-4-yl)-2-(furan-3-yl)acetamide | 8.66 |
| 4-59 | 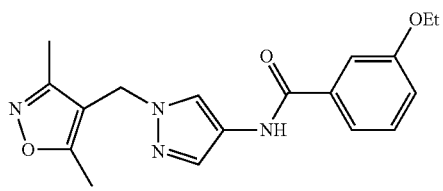 [SMILES: CCOc1cccc(C(=O)Nc2cnn(Cc3c(C)noc3C)c2)c1]<br>N-(1-((3,5-dimethylisoxazol-4-yl)methyl)-1H-pyrazol-4-yl)-3-ethoxybenzamide | 0.22 |
| 4-60 | 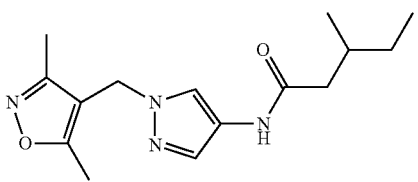 [SMILES: CCC(C)CC(=O)Nc1cnn(Cc2c(C)noc2C)c1]<br>N-(1-((3,5-dimethylisoxazol-4-yl)methyl)-1H-pyrazol-4-yl)-3-methylpentanamide | 1.94 |

TABLE A-continued

| Compound No. | Compound | hT2R8 IC$_{50}$ (μM) |
|---|---|---|
| 4-61 | 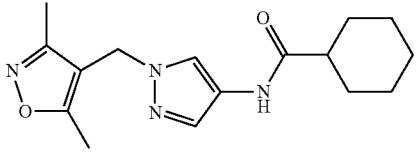 [SMILES: Cc1noc(C)c1Cn1cc(NC(=O)C2CCCCC2)cn1]<br>N-(1-((3,5-dimethylisoxazol-4-yl)methyl)-1H-pyrazol-4-yl)cyclohexanecarboxamide | 2.20 |
| 4-62 | 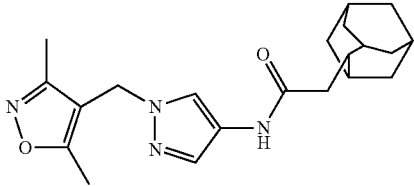 [SMILES: Cc1noc(C)c1Cn1cc(NC(=O)CC2C3CC4CC(C3)CC2C4)cn1]<br>N-(1-((3,5-dimethylisoxazol-4-yl)methyl)-1H-pyrazol-4-yl)-2-(adamanth-1-yl)acetamide | 3.77 |
| 4-63 | 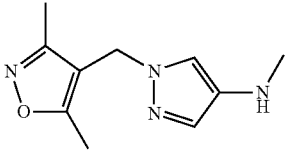<br>1-((3,5-dimethylisoxazol-4-yl)methyl)-N-methyl-1H-pyrazol-4-amine | 8.76 |
| 4-64 | 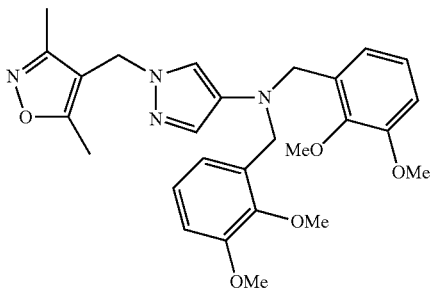 [SMILES: COc1cccc(CN(Cc2cccc(OC)c2OC)c2cnn(Cc3c(C)noc3C)c2)c1OC]<br>N,N-bis(2,3-dimethoxybenzyl)-1-((3,5-dimethylisoxazol-4-yl)methyl)-1H-pyrazol-4-amine | 12.60 |
| 4-65 | 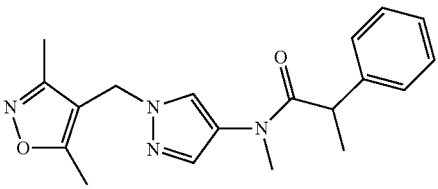 [SMILES: Cc1noc(C)c1Cn1cc(N(C)C(=O)C(C)c2ccccc2)cn1]<br>N-(1-((3,5-dimethylisoxazol-4-yl)methyl)-1H-pyrazol-4-yl)-N-methyl-2-phenylpropanamide | 2.81 |

TABLE A-continued

| Compound No. | Compound | hT2R8 IC$_{50}$ (μM) |
|---|---|---|
| 4-66 | N-(1-((3,5-dimethylisoxazol-4-yl)methyl)-1H-pyrazol-4-yl)-N-methyl-1-phenylcyclopropanecarboxamide | 8.23 |
| 4-67 | (S)-N-(1-((3,5-dimethylisoxazol-4-yl)methyl)-1H-pyrazol-4-yl)-2-methoxy-2-phenylacetamide | 8.6 |
| 4-68 | (R)-N-(1-((3,5-dimethylisoxazol-4-yl)methyl)-1H-pyrazol-4-yl)-2-methoxy-2-phenylacetamide | 5.0 |
| 4-69 | N-(1-((3,5-dimethylisoxazol-4-yl)methyl)-1H-pyrazol-4-yl)-2-(4-hydroxy-3-methoxyphenyl)acetamide | 4.7 |
| 4-70 | | 3.1 |

TABLE A-continued

| Compound No. | Compound | hT2R8 IC$_{50}$ (μM) |
|---|---|---|
| | N-(1-((3,5-dimethylisoxazol-4-yl)methyl)-1H-pyrazol-4-yl)-2-(3-hydroxy-4-methoxyphenyl)acetamide | |
| 4-71 | 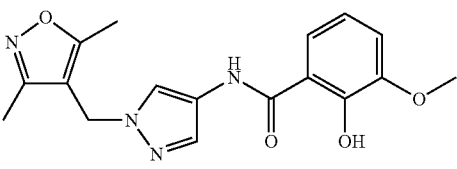<br>N-(1-((3,5-dimethylisoxazol-4-yl)methyl)-1H-pyrazol-4-yl)-2-hydroxy-3-methoxybenzamide | 2.9 |
| 4-72 | 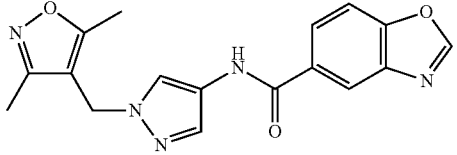 [SMILES: Cc1noc(C)c1Cn1cc(NC(=O)c2ccc3ocnc3c2)cn1]<br>N-(1-((3,5-dimethylisoxazol-4-yl)methyl)-1H-pyrazol-4-yl)benzo[d]oxazole-5-carboxamide | 2.6 |
| 4-73 | 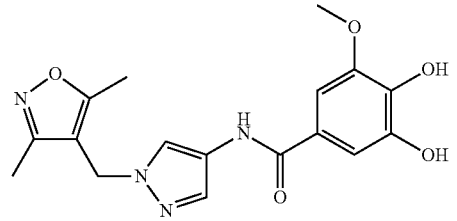 [SMILES: COc1cc(C(=O)Nc2cnn(Cc3c(C)noc3C)c2)cc(O)c1O]<br>N-(1-((3,5-dimethylisoxazol-4-yl)methyl)-1H-pyrazol-4-yl)-3,4-dihydroxy-5-methoxybenzamide | 2.2 |
| 4-74 | 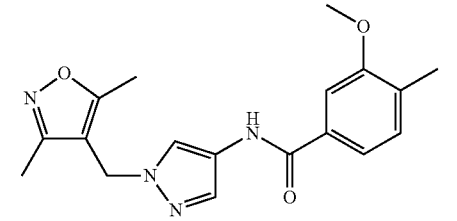<br>N-(1-((3,5-dimethylisoxazol-4-yl)methyl)-1H-pyrazol-4-yl)-3-methoxy-4-methylbenzamide | 2.2 |
| 4-75 | 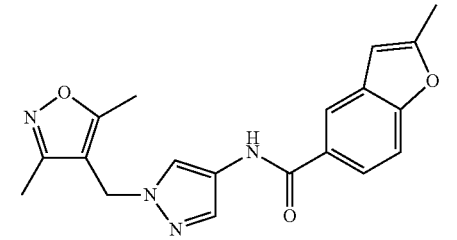<br>N-(1-((3,5-dimethylisoxazol-4-yl)methyl)-1H-pyrazol-4-yl)-2-methylbenzofuran-5-carboxamide | 2.1 |

TABLE A-continued

| Compound No. | Compound | hT2R8 IC$_{50}$ (μM) |
|---|---|---|
| 4-76 | 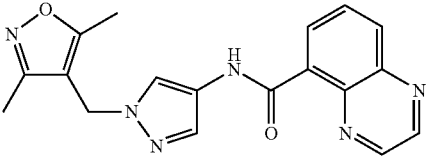 [SMILES: Cc1noc(C)c1Cn1cc(NC(=O)c2cccc3nccnc23)cn1]<br>N-(1-((3,5-dimethylisoxazol-4-yl)methyl)-1H-pyrazol-4-yl)quinoxaline-5-carboxamide | 1.7 |
| 4-77 | 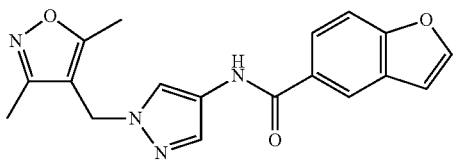 [SMILES: Cc1noc(C)c1Cn1cc(NC(=O)c2ccc3occc3c2)cn1]<br>N-(1-((3,5-dimethylisoxazol-4-yl)methyl)-1H-pyrazol-4-yl)benzofuran-5-carboxamide | 1.4 |
| 4-78 | 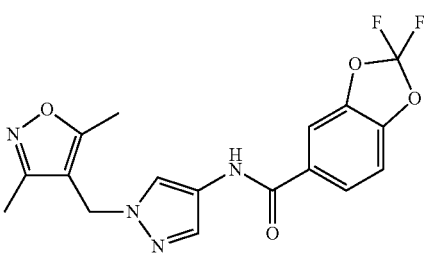 [SMILES: Cc1noc(C)c1Cn1cc(NC(=O)c2ccc3c(c2)OC(F)(F)O3)cn1]<br>N-(1-((3,5-dimethylisoxazol-4-yl)methyl)-1H-pyrazol-4-yl)-2,2-difluorobenzo[d][1,3]dioxole-5-carboxamide | 1.3 |
| 4-79 | 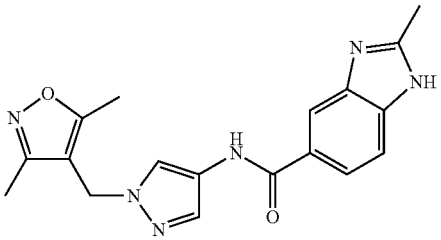<br>N-(1-((3,5-dimethylisoxazol-4-yl)methyl)-1H-pyrazol-4-yl)-2-methyl-1H-benzo[d]imidazole-5-carboxamide | 1.0 |
| 4-80 | 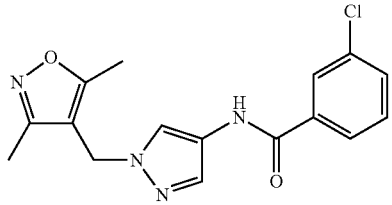 [SMILES: Cc1noc(C)c1Cn1cc(NC(=O)c2cccc(Cl)c2)cn1]<br>3-chloro-N-(1-((3,5-dimethylisoxazol-4-yl)methyl)-1H-pyrazol-4-yl)benzamide | 0.9 |

TABLE A-continued

| Compound No. | Compound | hT2R8 IC$_{50}$ (μM) |
|---|---|---|
| 4-81 | 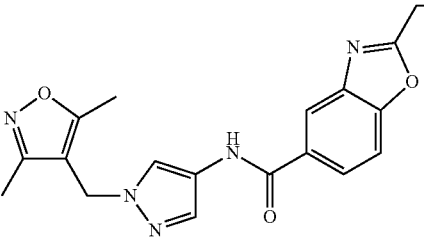<br>N-(1-((3,5-dimethylisoxazol-4-yl)methyl)-1H-pyrazol-4-yl)-2-ethylbenzo[d]oxazole-5-carboxamide | 0.8 |
| 4-82 | 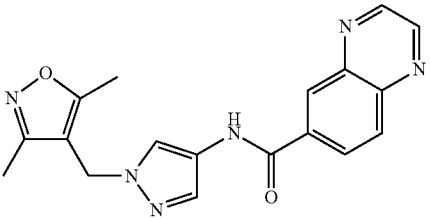 [SMILES: Cc1noc(C)c1Cn1cc(NC(=O)c2ccc3nccnc3c2)cn1]<br>N-(1-((3,5-dimethylisoxazol-4-yl)methyl)-1H-pyrazol-4-yl)quinoxaline-6-carboxamide | 0.8 |
| 4-83 | 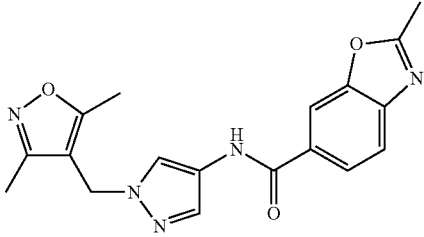<br>N-(1-((3,5-dimethylisoxazol-4-yl)methyl)-1H-pyrazol-4-yl)-2-methylbenzo[d]oxazole-6-carboxamide | 0.7 |
| 4-85 | 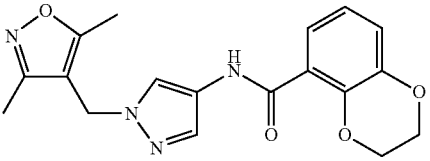 [SMILES: Cc1noc(C)c1Cn1cc(NC(=O)c2cccc3c2OCCO3)cn1]<br>N-(1-((3,5-dimethylisoxazol-4-yl)methyl)-1H-pyrazol-4-yl)-1H-benzo[d]imidazole-5-carboxamide | 0.6 |
| 4-86 | 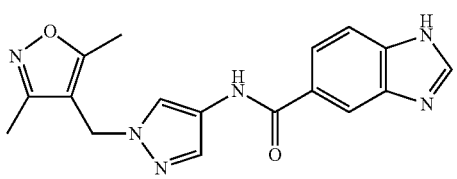 [SMILES: Cc1noc(C)c1Cn1cc(NC(=O)c2ccc3[nH]cnc3c2)cn1]<br>2-(1H-benzo[d]imidazol-6-yl)-N-(1-((3,5-dimethylisoxazol-4-yl)methyl)-1H-pyrazol-4-yl)acetamide | 0.6 |

TABLE A-continued

| Compound No. | Compound | hT2R8 IC$_{50}$ (μM) |
|---|---|---|
| 4-87 | 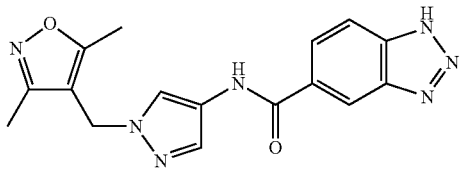 [SMILES: Cc1noc(C)c1Cn1cc(NC(=O)c2ccc3[nH]nnc3c2)cn1]<br>N-(1-((3,5-dimethylisoxazol-4-yl)methyl)-1H-pyrazol-4-yl)-1H-benzo[d][1,2,3]triazole-5-carboxamide | 0.6 |
| 4-88 | 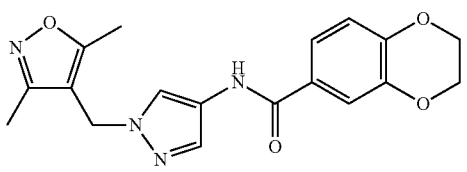 [SMILES: Cc1noc(C)c1Cn1cc(NC(=O)c2ccc3c(c2)OCCO3)cn1]<br>N-(1-((3,5-dimethylisoxazol-4-yl)methyl)-1H-pyrazol-4-yl)-2,3-dihydrobenzo[b][1,4]dioxine-6-carboxamide | 0.4 |
| 4-89 | 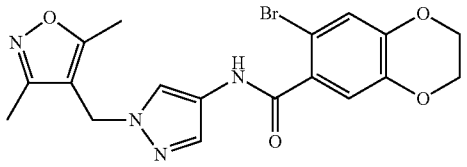<br>7-bromo-N-(1-((3,5-dimethylisoxazol-4-yl)methyl)-1H-pyrazol-4-yl)-2,3-dihydrobenzo[b][1,4]dioxine-6-carboxamide | 0.3 |
| 4-90 | 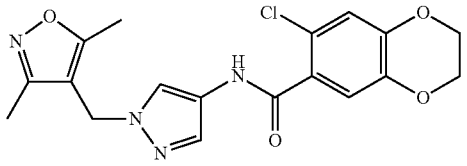 [SMILES: Cc1noc(C)c1Cn1cc(NC(=O)c2cc3c(cc2Cl)OCCO3)cn1]<br>7-chloro-N-(1-((3,5-dimethylisoxazol-4-yl)methyl)-1H-pyrazol-4-yl)-2,3-dihydrobenzo[b][1,4]dioxine-6-carboxamide | 0.1 |
| 4-91 | 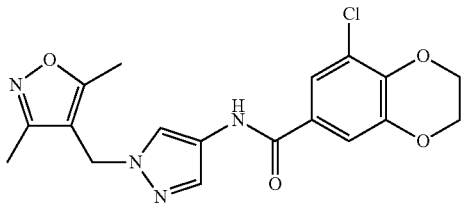 [SMILES: Cc1noc(C)c1Cn1cc(NC(=O)c2cc(Cl)c3c(c2)OCCO3)cn1]<br>8-chloro-N-(1-((3,5-dimethylisoxazol-4-yl)methyl)-1H-pyrazol-4-yl)-2,3-dihydrobenzo[b][1,4]dioxine-6-carboxamide | 0.1 |
| 4-96 | 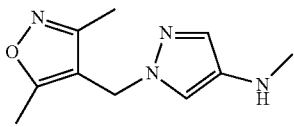 | 8.764 |

TABLE A-continued

| Compound No. | Compound | hT2R8 IC$_{50}$ (μM) |
|---|---|---|
| | 1-((3,5-dimethylisoxazol-4-yl)methyl)-N-methyl-1H-pyrazol-4-amine | |
| 4-97 | N-(1-((3,5-dimethylisoxazol-4-yl)methyl)-1H-pyrazol-4-yl)-N-methyl-2-phenylpropanamide | 2.126 |
| 4-98 | (S)-N-(1-((3,5-dimethylisoxazol-4-yl)methyl)-1H-pyrazol-4-yl)-N-methyl-2-phenylpropanamide | 2.811 |
| 4-99 | 2-cyano-N-(1-((3,5-dimethylisoxazol-4-yl)methyl)-1H-pyrazol-4-yl)benzenesulfonamide | 1.358 |
| 4-100 | N-(1-((3,5-dimethylisoxazol-4-yl)methyl)-1H-pyrazol-4-yl)-2-fluorobenzenesulfonamide | 8.510 |
| 4-101 | N-(1-((3,5-dimethylisoxazol-4-yl)methyl)-1H-pyrazol-4-yl)-2,5-dimethoxybenzenesulfonamide | 1.631 |

TABLE A-continued

| Compound No. | Compound | hT2R8 IC$_{50}$ (μM) |
|---|---|---|
| 4-102 | 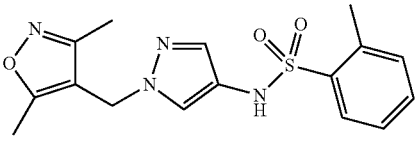 [SMILES: Cc1ccccc1S(=O)(=O)Nc1cnn(Cc2c(C)noc2C)c1]<br>N-(1-((3,5-dimethylisoxazol-4-yl)methyl)-1H-pyrazol-4-yl)-2-methylbenzenesulfonamide | 2.153 |
| 4-103 | 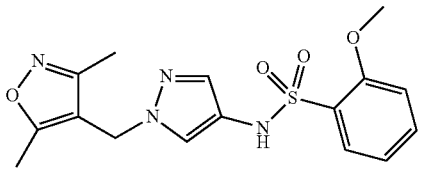 [SMILES: COc1ccccc1S(=O)(=O)Nc1cnn(Cc2c(C)noc2C)c1]<br>N-(1-((3,5-dimethylisoxazol-4-yl)methyl)-1H-pyrazol-4-yl)-2-methoxybenzenesulfonamide | 3.801 |
| 4-104 | 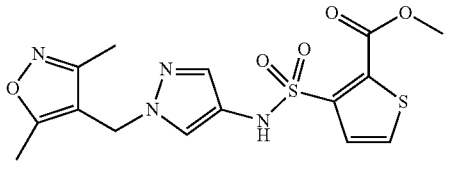 [SMILES: COC(=O)c1sccc1S(=O)(=O)Nc1cnn(Cc2c(C)noc2C)c1]<br>methyl 3-(N-(1-((3,5-dimethylisoxazol-4-yl)methyl)-1H-pyrazol-4-yl)sulfamoyl)thiophene-2-carboxylate | 1.252 |
| 4-105 | 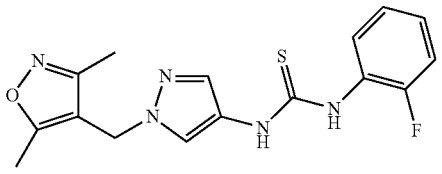<br>1-(1-((3,5-dimethylisoxazol-4-yl)methyl)-1H-pyrazol-4-yl)-3-(2-fluorophenyl)thiourea | 1.629 |
| 4-106 | 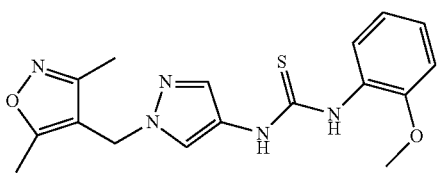 [SMILES: COc1ccccc1NC(=S)Nc1cnn(Cc2c(C)noc2C)c1]<br>1-(1-((3,5-dimethylisoxazol-4-yl)methyl)-1H-pyrazol-4-yl)-3-(2-methoxyphenyl)thiourea | 2.607 |
| 4-107 | 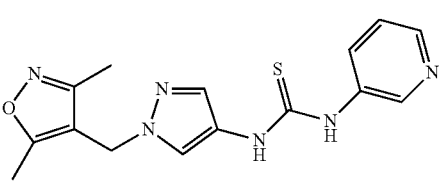 [SMILES: Cc1noc(C)c1Cn1cc(NC(=S)Nc2cccnc2)cn1]<br>1-(1-((3,5-dimethylisoxazol-4-yl)methyl)-1H-pyrazol-4-yl)-3-(pyridin-3-yl)thiourea | 2.999 |

TABLE A-continued

| Compound No. | Compound | hT2R8 IC$_{50}$ (μM) |
|---|---|---|
| 4-108 | 1-(1-((3,5-dimethylisoxazol-4-yl)methyl)-1H-pyrazol-4-yl)-3-o-tolylthiourea | 3.013 |
| 4-109 | 1-(3-cyanophenyl)-3-(1-((3,5-dimethylisoxazol-4-yl)methyl)-1H-pyrazol-4-yl)thiourea | 0.783 |
| 4-110 | 1-benzyl-3-(1-((3,5-dimethylisoxazol-4-yl)methyl)-1H-pyrazol-4-yl)thiourea | 1.097 |
| 4-111 | 1-(2-cyanophenyl)-3-(1-((3,5-dimethylisoxazol-4-yl)methyl)-1H-pyrazol-4-yl)thiourea | 2.347 |
| 4-112 | 1-(1-((3,5-dimethylisoxazol-4-yl)methyl)-1H-pyrazol-4-yl)-3-phenylthiourea | 2.492 |
| 4-113 | | 5.240 |

TABLE A-continued

| Compound No. | Compound | hT2R8 IC$_{50}$ (μM) |
|---|---|---|
| 4-114 | ![structure] 1-(2,5-dimethoxyphenyl)-3-(1-((3,5-dimethylisoxazol-4-yl)methyl)-1H-pyrazol-4-yl)thiourea | 1.866 |
| 4-115 | ![structure] N-(2-((3,5-dimethylisoxazol-4-yl)methyl)-2H-tetrazol-5-yl)-3-methoxybenzamide | 9.248 |
| 4-116 | ![structure] N-(1-((3,5-dimethylisoxazol-4-yl)methyl)-3-methyl-1H-pyrazol-4-yl)-3-methoxybenzamide | 2.279 |
|  | ![structure] 3-((3,5-dimethylisoxazol-4-yl)methyl)-2-oxo-N-(thiophen-2-ylmethyl)-2,3-dihydrothiazole-5-carboxamide |  |

Examples 4-67 to 4-91

Prepared as in example 4-73 from 1-((3,5-dimethylisoxazol-4-yl)methyl)-1H-pyrazol-4-amine hydrochloride (example 4-1a) and their corresponding functionalized carboxylic acids. Characterization was done by LCMS where the desired masses were found.

Example 4-73

N-(1-((3,5-dimethylisoxazol-4-yl)methyl)-1H-pyrazol-4-yl)-3,4-dihydroxy-5-methoxybenzamide

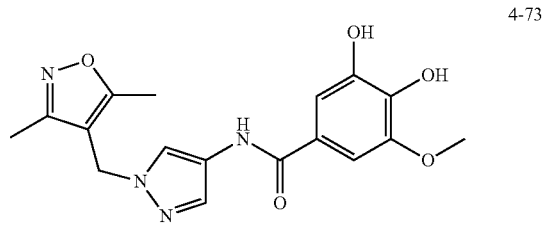

4-73

1-((3,5-dimethylisoxazol-4-yl)methyl)-1H-pyrazol-4-amine hydrochloride (example 4-1a) (228 mg, 1 mmol), 3,4-dihydroxy-5-methoxybenzoic acid (184 mg, 1 mmol), HOBt (135 mg, 1 mmol), and EDC (191 mg, 1 mmol) were dissolved in 2 mL DMF in a microwave vial followed by the addition of triethylamine (101 mg, 1 mmol). The reaction was placed in a microwave reactor at 165° C. for 5 minutes. The crude product was purified directly using Varian HPLC (10%-95% ACN in H$_2$O: 25 minute gradient). The pure fractions were combined and concentrated to afford N-(1-((3,5-dimethylisoxazol-4-yl)methyl)-1H-pyrazol-4-yl)-3,4-dihydroxy-5-methoxybenzamide. (280 mg, 70%). LC/MS; [M+H] calculated for C, 17; H, 18; N, 4; O, 5; expected 359.1; found 359.1.

The compound had an IC$_{50}$ on hT2R8 bitter receptor of 2.2 μM

Example 4-92

N-(1-((3,5-dimethylisoxazol-4-yl)methyl)-1H-pyrazol-4-yl)-7-methoxybenzo[d][1,3]dioxole-5-carboxamide

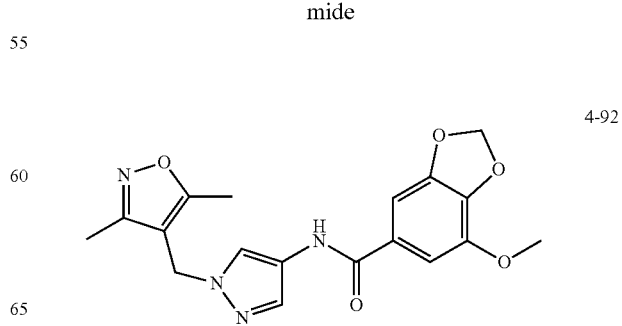

4-92

N-(1-((3,5-dimethylisoxazol-4-yl)methyl)-1H-pyrazol-4-yl)-3,4-dihydroxy-5-methoxybenzamide (example 73) (50 mg, 0.14 mmol) and Cesium Carbonate (113 mg, 2.5 mmol) were dissolved in 1 mL acetone followed by the addition of dibromomethane (239 mg, 1.4 mmol). The reaction was placed in a microwave reactor at 120° C. for 20 minutes. The clear solution from the reaction was removed and evaporated under vacuum. The crude product was dissolved in 1 mL ethanol and purified by varian HPLC (10%-95% ACN in $H_2O$: 25 minute gradient). The pure fractions were combined and concentrated to afford N-(1-((3,5-dimethylisoxazol-4-yl)methyl)-1H-pyrazol-4-yl)-2-(7-methoxybenzo[d][1,3]dioxol-5-yl)acetamide. (12 mg, 23%). LC/MS; [M+H] calculated for C, 18; H, 18; N, 4; O, 5; expected 371.1; found 371.1.

The compound had an $IC_{50}$ on hT2R8 bitter receptor of 0.7 μM

Example 4-93

N-(1-((3,5-dimethylisoxazol-4-yl)methyl)-1H-pyrazol-4-yl)-8-methoxy-2,3-dihydrobenzo[b][1,4]dioxine-6-carboxamide

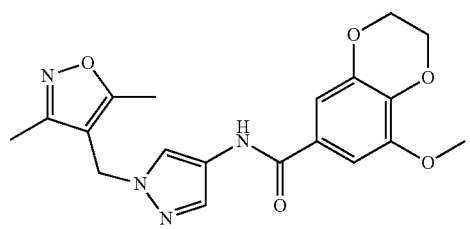

4-93

Prepared as in Example 4-92 from N-(1-((3,5-dimethylisoxazol-4-yl)methyl)-1H-pyrazol-4-yl)-3,4-dihydroxy-5-methoxybenzamide (Example 4-73), cesium carbonate and dibromoethane. Yield 20%. MS M+H calculated 385.1, found 385.1.

The compound had an $IC_{50}$ on hT2R8 bitter receptor of 0.7 μM

Example 4-94

N-(1-((3,5-dimethylisoxazol-4-yl)methyl)-1H-pyrazol-4-yl)-7-methoxy-2-methylbenzo[d][1,3]dioxole-5-carboxamide

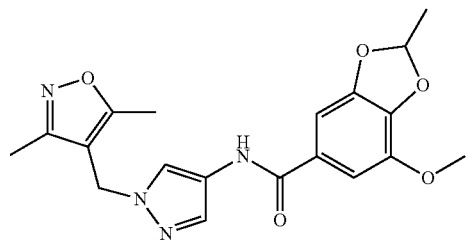

4-94

Prepared as in Example 4-92 from N-(1-((3,5-dimethylisoxazol-4-yl)methyl)-1H-pyrazol-4-yl)-3,4-dihydroxy-5-methoxybenzamide (Example 4-73), cesium carbonate and 1,1-dibromoethane. Yield 25%. MS M+H calculated 385.1, found 385.1.

The compound had an $IC_{50}$ on hT2R8 bitter receptor of 0.7 μM.

Example 4-95

N-(1-((3,5-dimethylisoxazol-4-yl)methyl)-1H-pyrazol-4-yl)-7-methoxy-2,3-dihydrobenzo[b][1,4]dioxine-6-carboxamide

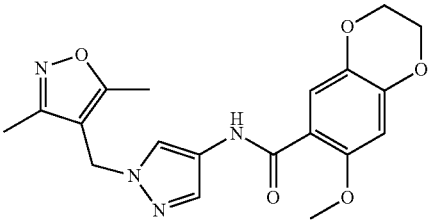

4-95

Prepared as in Example 4-73 from 1-((3,5-dimethylisoxazol-4-yl)methyl)-1H-pyrazol-4-amine hydrochloride (example 4-1a) and 7-methoxy-2,3-dihydrobenzo[b][1,4]dioxine-6-carboxylic acid (example 4-95a). Yield 50%. MS M+H calculated 385.1, found 385.1. $^1$H NMR (400 MHz, DMSO): 2.136 (s,3H), 2.410 (s, 3H), 3.851 (s, 3H), 4.214 (bs, 2H), 4.296 (bs, 2H), 5.120 (s, 2H), 6.688 (s, 1H), 7.290 (s, 1H), 7.6006 (s, 1H), 8.069 (s, 1H), 9.856 (s, 1H).

The compound had an $IC_{50}$ on hT2R8 bitter receptor of 0.7 μM

Example 4-95a

7-Methoxy-2,3-dihydrobenzo[b][1,4]dioxine-6-carboxylic acid

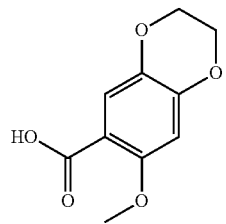

4-95a

In a 2 mL microwave vial, methyl 7-bromo-2,3-dihydrobenzo[b][1,4]dioxine-6-carboxylate (273 mg, 1 mmol) and CuBr (14.3 mg, 0.1 mmol) were dissolved in dry DMF and was placed in ice bath. Sodium methoxide (540 mg, 10 mmol) was added into the reaction mixture dropwise while stirring at 0° C. The reaction was warmed to room temperature and stirred for 45 minutes. The reaction was then placed in a microwave reactor for 5 minutes at 135° C. The reaction mixture was dissolved in water and washed with ethyl acetate. The water layer was collected and acidified to pH 4 with 1M HCl. The product was extracted using ethyl acetate then dried over sodium sulfate. The solvent was evaporated under vacuum to give the desired intermediate of 7-methoxy-2,3-dihydrobenzo[b][1,4]dioxine-6-carboxylic acid which was used directly without further purification. Yield 57%. MS M+H calculated 211.1, found 211.1.

Example 5 hT2R14 Antagonists: Making the Compounds of the Invention

The following Examples are given to illustrate a variety of exemplary embodiments of the invention and are not intended to be limiting in any matter.

Example 5-1

4-(N-benzyl-N-(4-methoxybenzyl)sulfamoyl)benzoic acid

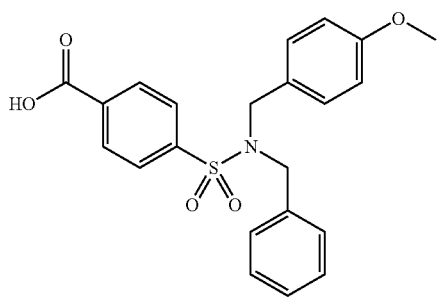

5-1

Benzyl 4-(N-benzyl-N-(4-methoxybenzyl)sulfamoyl) benzoate (Example 5-1a) (517 mg, 1 mmol) was stirred a 10/1/2 solution of 6N NaOH (aq)/THF/MeOH (27 mL) at ambient temperature for 6 hours. The solution was acidified with 3N HCl (aq) to a pH of ~3 (ca. 50 mL), and the aqueous phase was extracted with ethyl acetate (3×, 75 mL). The combined organic extracts were dried over sodium sulfate and concentrated on the rotovap. The residue was taken up in MeOH (15 mL) and purified by reverse phased HPLC (5-95% acetonitrile in $H_2O$ gradient: 25 minutes) in three 5 mL aliquots. The pure fractions were combined and concentrated to a white solid. The product was dissolved in 15 mL of absolute ethanol and evaporated on the rotovap (4×) to provide pure 4-(N-benzyl-N-(4-methoxybenzyl)sulfamoyl)benzoic acid (174 mg, 42%) as a white solid. M.p 161-163° C. $^1$H NMR ($CDCl_3$, 400 MHz): δ 3.78 (s, 3H), 4.32 (s, 2H), 4.36 (s, 2H), 6.78 (d, J=8.4 Hz, 2H), 6.99 (d, J=8.8 Hz, 2H), 709-7.07 (m, 2H), 7.27-7.24 (m, 3H), 7.93 (d, J=8.8 Hz, 2H), 8.24 (d, J=8 Hz, 2H). MS 412 (MH$^+$).

The compound had an $IC_{50}$ on hT2R14 bitter receptor of 0.22 μM

Example 5-1a

Benzyl 4-(N-benzyl-N-(4-methoxybenzyl)sulfamoyl)benzoate 4-(N-(4-methoxybenzyl)sulfamoyl)benzoic acid (Example 5-1b) (450, mg, 1.4 mmol), benzyl bromide (770 mg, 4.5 mmol), and cesium carbonate (1.5 g, 4.5 mmol) in DMF (10 mL) were stirred at 80° C. for 2 hours. The solution was cooled to room temperature, diluted with $H_2O$ (200 mL) and extract with ethyl acetate (3×, 100 mL). The combined organic layers were dried over sodium sulfate, filtered and concentrated under vacuum. The residue was purified by silica gel chromotography (10% ethyl acetate in hexanes) to afford benzyl 4-(N-benzyl-N-(4-methoxybenzyl)sulfamoyl) benzoate (517 mg, 73%) as a white solid. $^1$H NMR (400 MHz, $CDCl_3$) δ 3.76 (s, 3H), 4.28 (s, 2H), 4.32 (s, 2H0, 5.40 (s, 2H), 6.79 (d, J=8 Hz, 2H), 6.96 (d, J=8 Hz, 2H), 7.04-7.07 (m, 2H), 7.21-7.23 (m, 3H), 7.35-7.47 (m, 5H), 7.85 (d, J=8 Hz, 2H), 8.17 (d, J=8.4 Hz, 2H).

Example 5-1b 4-(N-(4-methoxybenzyl)sulfamoyl)benzoic acid 4-(Chlorosulfonyl)benzoic acid (5 g, 22.7 mmol) was added, in three portions as a solid, to a stirring solution of 4-methoxy benzylamine (6.1 g, 45 mmol) and triethylamine (2.3 g, 22.7 mmol) in acetone (100 mL) cooled to 0° C. via an ice water bath over a 10 minute period. The ice bath was removed and the reaction was stirred for an additional 4 hours. The reaction mixture was diluted with a solution of 5% acetic acid in $H_2O$ (150 mL) and extracted with ethyl acetate (3×, 100 mL). The combined organic extracts were dried over sodium sulfate, filtered, and concentrated on the rotovap. The resulting white solid was triturated with hexanes/ethyl acetate (9/1) to afford 4-(N-(4-methoxybenzyl)sulfamoyl)benzoic acid (5.1 g, 70%) as a white solid. $^1$H NMR (400 MHz, DMSO d$_6$) δ 3.68 (s, 3H), 3.91 (s, 2H), 6.79 (d, J=8.4 Hz, 2H), 7.10 (d, J=8.8 Hz, 2H), 7.80 (d, J=8.8 Hz, 2H), 8.02 (d, J=8.4 Hz, 2H).

Example 5-2

4-(N-(furan-2-ylmethyl)-N-(4-methoxybenzyl)sulfamoyl)benzoic acid

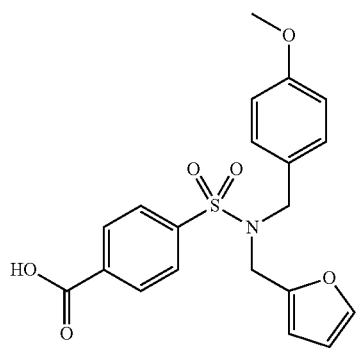

5-2

4-Methoxybenzyl 4-(N-(furan-2-ylmethyl)-N-(4-methoxybenzyl)sulfamoyl)benzoate (Example 5-2a) (750 mg, 1.4 mmol) was stirred a 2/2/1 mixture of aqueous 2N LiOH/THF/MeOH (45 mL) at ambient temperature for 3 hours. The solution was acidified with aqueous 1N aq HCl to a pH of ~3 (ca. 100 mL) and extracted with ethyl acetate (3×, 100 mL). The combined organic extracts were dried over sodium sulfate and concentrated on the rotovap. The residue was taken up in MeOH (9 mL) and purified by reverse phased HPLC (5-95% ACN in $H_2O$ gradient: 40 minutes) in three-3 mL aliquots. The pure fractions were combined and concentrated to a white solid. The product was dissolved in absolute ethanol and evaporated (4×, 20 mL) to provide pure 4-(N-(furan-2-ylmethyl)-N-(4-methoxybenzyl)sulfamoyl)benzoic acid (205 mg, 36%) as a white solid. M.p. 151-152° C. $^1$H NMR (DMSO-d$_6$, 400 MHz): δ 3.71 (s, 3H), 4.24 (s, 2H), 4.27 (s, 2H), 6.14 (d, 1H, J=3.2 Hz), 6.26 (m, 1H), 6.87 (d, 2H, J=9.2 Hz), 7.14 (d, 2H, J=8.8 Hz), 7.41 (s, 1H), 7.89 (d, 2H, J=8 Hz), 8.06 (d, 2H, J=8.4 Hz), 13.48 (bs, 1H). MS 400 (M−H).

The compound had an $IC_{50}$ on hT2R14 bitter receptor of 0.59 μM

Example 5-2a 4-methoxybenzyl 4-(N-(furan-2-ylmethyl)-N-(4-methoxybenzyl)sulfamoyl)benzoate 4-(N-(furan-2-ylmethyl)sulfamoyl)benzoic acid (Example 5-2b) (500 mg, 1.8 mmol), p-methoxy benzyl chloride (624 mg, 4.0 mmol), and cesium carbonate (1.3 g, 4.0 mmol) were dissolved in DMF (10 mL) and stirred at 80° C. for 1 hour. The mixture was cooled to ambient temperature, diluted with $H_2O$ (200 mL), and extracted with ethyl acetate (3×100 mL). The combined organics were dried over sodium sulfate and concentrated on the rotovap. The product was purified by silica gel chromatography (15% ethyl acetate in hexanes) to provide the 4-methoxybenzyl 4-(N-(furan-2-ylmethyl)-N-(4-methoxybenzyl)sulfamoyl)benzoate (753 mg, 80%) as a clear oil. $^1$H NMR (DMSO-$d_6$, 400 MHz): δ 3.70 (s, 3H), 3.75 (s, 3H), 4.22 (s, 2H), 4.26 (s, 2H), 5.39 (s, 2H), 6.14 (d, 1H, J=3.2 Hz), 6.25 (m, 1H), 6.87 (d, 2H, J=8.8 Hz), 6.97 (d, 2H, J=8.8 Hz), 7.13 (d, 2H, J=8.4 Hz), 7.39 (m, 1H), 7.43 (d, 2H, J=8.4 Hz), 7.91 (d, 2H, J=8.4 Hz), 8.07 (d, 2H, J=8.4 Hz).

Example 5-2b 4-(N-(furan-2-ylmethyl)sulfamoyl)benzoic acid 4-(Chlorosulfonyl)benzoic acid (5.0 g, 22.7 mmol) was added in three portions over a 10 minute period to a stirring solution of furfuryl amine (6.6 g, 68 mmol) in acetone (200 mL) cooled to 0° C. via an ice water bath. After addition of the sulfonyl chloride was complete the ice bath was removed and the solution was stirred for 1 hour at ambient temperature. The mixture was concentrated and subjected to silica gel chromatography (90% ethyl acetate, 8% hexanes and 2% acetic acid) to afford 4.4 of 4-(N-(furan-2-ylmethyl)sulfamoyl)benzoic acid (4.4 g, 68%) as a white solid. $^1$H NMR (DMSO-$d_6$, 400 MHz): δ 4.04 (d, 2H, J=6 Hz), 6.13 (d, 1H, J=3.2 Hz), 6.25 (m, 1H), 7.43 (m, 1H), 7.83 (d, 2H, J=8.4 Hz), 8.05 (d, 2H, J=8.4 Hz), 8.36 (t, 1H, J=6 Hz), 13.4 (bs, 1H).

Example 5-3

4-(N-(4-ethoxybenzyl)-N-(furan-2-ylmethyl)sulfamoyl)benzoic acid 5-3

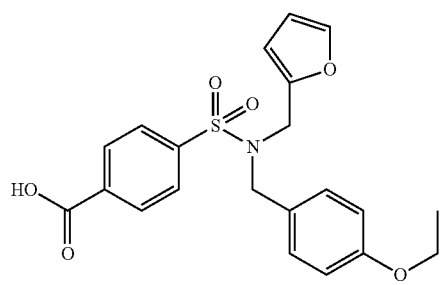

4-cyano-N-(4-ethoxybenzyl)-N-(furan-2-ylmethyl)benzenesulfonamide (Example 5-3a) (300 mg, 0.8 mmol) was stirred in a 1/1 mixture of dioxane/1.5 N aqueous NaOH (100 mL) at 80° C. for 16 hours. The mixture was cooled, acidified with 1N aqueous HCl (100 mL), and extracted with ethyl acetate (3×, 75 mL). The combined organic extracts were dried over sodium sulfate, filtered, and concentrated on the rotovap. The solid was triturated with ethyl acetate/hexanes (~1/9) and collected by filtration to afford 4-(N-(4-ethoxybenzyl)-N-(furan-2-ylmethyl)sulfamoyl)benzoic acid (250 mg, 69%) as a white solid. NMR (DMSO-$d_6$, 400 MHz): δ 1.29 (t, J=6.8 Hz, 3H), 3.97 (q, J=6.4 Hz, 2H), 4.23 (s, 2H), 4.27 (s, 2H), 6.15 (d, J=3.2 Hz, 1H), 6.27 (m, 1H), 6.84 (d, J=8.8 Hz, 2H), 7.11 (d, J=8.8 Hz, 2H), 7.39 (m, 1H), 7.87 (d, J=8.4 Hz, 2H), 8.00 (d, J=8.4 Hz, 2H).

The compound had an $IC_{50}$ on hT2R14 bitter receptor of 3.0 μM

Example 5-3a 4-cyano-N-(4-ethoxybenzyl)-N-(furan-2-ylmethyl)benzenesulfonamide 4-cyanobenzene-1-sulfonyl chloride (600 mg, 2.9 mmol) was added to a stirring solution of N-(4-ethoxybenzyl)-1-(furan-2-yl)methanamine (Example 5-3b) (685 mg, 2.9 mmol) and triethylamine (455 mg, 4.5 mmol) in DCM (100 mL) and the reaction was stirred for 2 hours. The reaction was diluted with $H_2O$ (200 mL) and extracted with DCM (3×, 75 mL). The combined organic extracts were dried over sodium sulfate, filtered and concentrated on the rotovap. The residue was purified by silica gel chromatography (10% ethyl acetate in hexanes) to afford 4-cyano-N-(4-ethoxybenzyl)-N-(furan-2-ylmethyl)benzenesulfonamide (665 mg, 68%) as an off white solid. NMR (DMSO-$d_6$, 400 MHz): δ 1.29 (t, J=7.2 Hz, 3H), 3.97 (q, J=6.8 Hz, 2H), 4.23 (s, 2H), 4.27 (s, 2H), 6.15 (d, J=3.2 Hz, 1H), 6.27 (m, 1H), 6.84 (d, J=8.8 Hz, 2H), 7.11 (d, J=8.8 Hz, 2H), 7.39 (m, 1H), 7.92 (d, J=8.4 Hz, 2H), 8.03 (d, J=8.4 Hz, 2H).

Example 5-3b

4 N-(4-ethoxybenzyl)-1-(furan-2-yl)methanamine

4-Ethoxy benzaldehyde (5 g, 33 mmol) and furfuryl amine (4.2 g, 43 mmol.) in a mixture of methanol (50 mL), trimethylorthoformate (10 mL) and AcOH (1 mL) were stirred at room temperature, under an atmosphere of nitrogen for 16 hours. Sodium borohydride (1.4 g, 35 mmol) was added, in 4 portions, over a period of 30 minutes (exothermic reaction). The reaction was stirred for an additional 2 hours at room temperature. The solvent was removed under vacuum and the residue taken up in ethyl acetate (150 mL). The organic phase was washed with $H_2O$ (200 mL) and aqueous phase was back extracted with ethyl acetate (2×, 100 mL). The combined organic layers were concentrated and the residue was purified on silica gel (70% ethyl acetate in hexanes with ~0.5% triethylamine) to afford N-(4-ethoxybenzyl)-1-(furan-2-yl)methanamine (6.1 g, 80%) as a clear oil. NMR (CDCl$_3$, 400 MHz): δ 1.40 (t, J=7.2 Hz, 3H), 3.71 (s, 2H), 3.76 (s, 2H), 4.02

(q, J=7.2 Hz, 2H), 6.17 (d, J=4 Hz, 1H), 6.31 (m, 1H), 6.84 (d, J=8.8 Hz, 2H), 7.23 (d, J=8.8 Hz, 2H), 7.36 (m, 1H).

Example 5-4

4-(N-ethyl-N-(4-methoxybenzyl)sulfamoyl)benzoic acid

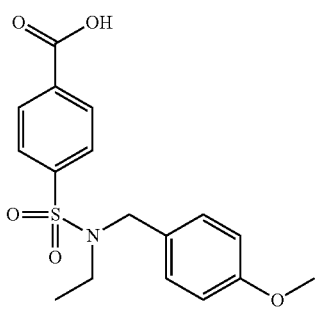

5-4

4-(N-(4-methoxybenzyl)sulfamoyl)benzoic acid (Example 5-1b) (160 mg, 0.5 mmol) and Cesium Carbonate (325 mg, 1 mmol) were placed in a microwave vial and dissolved in 2 mL DMF. Ethyl iodide (155 mg, 1 mmol) was added into the reaction mixture. The reaction was placed in a microwave reactor and heated at 165° C. for 5 minutes. The reaction mixture was dissolved in Ethyl Acetate and washed with water. The organic layer was dried over sodium sulfate and evaporated under vacuum. The crude product was dissolved in 4/1 solution of 6N NaOH (aq)/tetrahydrofuran (3 mL) and stirred at ambient temperature for 6 hours. The solution was acidified with 3N HCl (aq) to a pH of ~3 and the product was extracted with ethyl acetate (3×, 75 mL). The combined organic extracts were dried over sodium sulfate and concentrated under vacuum. The residue was taken up in methanol (3 mL) and purified by reverse phased HPLC (5-95% acetonitrile in $H_2O$ gradient: 25 minutes). The compound was known to inhibit the hT2R14 with $IC_{50}$ of 20 μM. Yield 35%. MS M+H calculated 350.11, found 350.0.

The compound had an $IC_{50}$ on hT2R14 bitter receptor of 10 μM.

Example 5-5

4-(N-benzyl-N-(furan-2-ylmethyl)sulfamoyl)benzoic acid

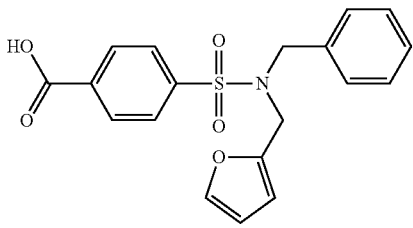

5-5

4-(N-(furan-2-ylmethyl)sulfamoyl)benzoic acid (Example 5-2b) (140 mg, 0.5 mmol) and Cesium Carbonate (325 mg, 1 mmol) were placed in a microwave vial and dissolved in 2 mL DMF. (Bromomethyl)benzene (170 mg, 1 mmol) was added into the reaction mixture. The reaction was placed in a microwave reactor and heated at 165° C. for 5 minutes. The reaction mixture was dissolved in Ethyl Acetate and washed with water. The organic layer was dried over sodium sulfate and evaporated under vacuum. The crude product was dissolved in 4/1 solution of 6N NaOH (aq)/tetrahydrofuran (3 mL) and stirred at ambient temperature for 6 hours. The solution was acidified with 3N HCl (aq) to a pH of ~3 and the product was extracted with ethyl acetate (3×, 75 mL). The combined organic extracts were dried over sodium sulfate and concentrated under vacuum. The residue was taken up in methanol (3 mL) and purified by reverse phased HPLC (5-95% acetonitrile in $H_2O$ gradient: 25 minutes). Yield 35%. MS M+H calculated 372.4, found 372.0.

The compound had an $IC_{50}$ on hT2R14 bitter receptor of 4.6 μM

Example 5-6

4-(N-(furan-2-ylmethyl)-N-(3-methoxybenzyl)sulfamoyl)benzoic acid

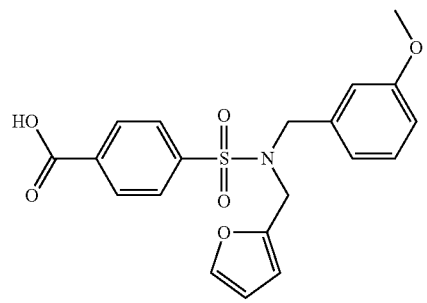

5-6

Prepared as in Example 5-5 from 1-(bromomethyl)-3-methoxybenzene and 4-(N-(furan-2-ylmethyl)sulfamoyl)benzoic acid (Example 5-2b). Yield 35%. MS M+H calculated 402.3, found 402.0.

The compound had an $IC_{50}$ on hT2R14 bitter receptor of 10 μM

Example 5-7

4-(N-(furan-2-ylmethyl)-N-(2-methoxybenzyl)sulfamoyl)benzoic acid

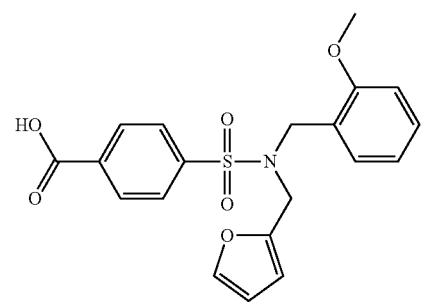

5-7

Prepared as in Example 5-5 from 1-(bromomethyl)-2-methoxybenzene and 4-(N-(furan-2-ylmethyl)sulfamoyl)benzoic acid (Example 5-2b). Yield 35%. MS M+H calculated 402.3, found 402.0.

The compound had an IC$_{50}$ on hT2R14 bitter receptor of 12 µM

Example 5-8

4-(N-(4-propoxybenzyl)-N-(furan-2-ylmethyl)sulfamoyl)benzoic acid

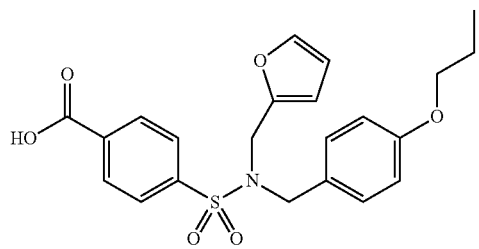

5-8

4-cyano-N-(4-propoxybenzyl)-N-(furan-2-ylmethyl)benzenesulfonamide (Example 5-8a) (300 mg, 0.8 mmol) was stirred in a 1/1 mixture of dioxane/1.5 N aqueous NaOH (100 mL) at 80° C. for 16 hours. The mixture was cooled, acidified with 1N aqueous HCl (100 mL), and extracted with ethyl acetate (3×, 75 mL). The combined organic extracts were dried over sodium sulfate, filtered, and concentrated on the rotovap. The solid was triturated with ethyl acetate/hexanes (~1/9) and collected by filtration to afford 4-(N-(4-propoxybenzyl)-N-(furan-2-ylmethyl)sulfamoyl)benzoic acid (165 mg, 63%) as a white solid. NMR (DMSO-d$_6$, 400 MHz): δ 0.94 (t, J=7.6 Hz, 3H), 1.70 (m, J=6.8 Hz, 2H), 3.87 (t, J=6.4 Hz, 2H), 4.23 (s, 2H), 4.27 (s, 2H), 6.13 (d, J=2.8 Hz, 1H), 6.27 (m, 1H), 6.84 (d, J=6.8 Hz, 2H), 7.11 (d, J=8.8 Hz, 2H), 7.39 (m, 1H), 7.87 (d, J=6.8 Hz, 2H), 8.05 (d, J=6.8 Hz, 2H), 13.45 (bs, 1H).

The compound had an IC$_{50}$ on hT2R14 bitter receptor of 2.5 µM

Example 5-8a 4-cyano-N-(4-propoxybenzyl)-N-(furan-2-ylmethyl) benzenesulfonamide 4-cyanobenzene-1-sulfonyl chloride (600 mg, 2.9 mmol) was added to a stirring solution of N-(4-propoxybenzyl)-1-(furan-2-yl)methanamine (Example 5-8b) (685 mg, 2.9 mmol) and triethylamine (455 mg, 4.5 mmol) in DCM (100 mL) and the reaction was stirred for 2 hours. The reaction was diluted with H$_2$O (200 mL) and extracted with DCM (3×, 75 mL). The combined organic extracts were dried over sodium sulfate, filtered and concentrated on the rotovap. The residue was purified by silica gel chromatography (10% ethyl acetate in hexanes) to afford 4-cyano-N-(4-propoxybenzyl)-N-(furan-2-ylmethyl)benzenesulfonamide (500 mg, 50%) as an off white solid. NMR (DMSO-d$_6$, 400 MHz): δ 0.95 (t, J=7.2 Hz, 3H), 1.70 (m, J=6.4 Hz, 2H), 3.88 (t, J=6.4 Hz, 2H), 4.25 (s, 2H), 4.28 (s, 2H), 6.15 (d, J=3.2 Hz, 1H), 6.27 (m, 1H), 6.84 (d, J=6.8 Hz, 2H), 7.11 (d, J=8.8 Hz, 2H), 7.39 (m, 1H), 7.93 (d, J=6.4 Hz, 2H), 8.01 (d, J=6.4 Hz, 2H).

Example 5-8b

4 N-(4-propoxybenzyl)-1-(furan-2-yl)methanamine

4-Propoxy benzaldehyde (5 g, 31 mmol) and furfuryl amine (3.9 g, 40 mmol) in a mixture of methanol (50 mL), trimethylorthoformate (10 mL) and AcOH (~1 mL) were stirred at room temperature, under an atmosphere of nitrogen for 16 hours. Sodium borohydride (1.4 g, 35 mmol) was added in 4 portions, over a period of 30 minutes (exothermic reaction). The reaction was stirred for an additional 2 hours at room temperature. The solvent was removed on the rotovap and the residue taken up in ethyl acetate (150 mL). The organic phase was washed with H$_2$O (200 mL) and aqueous phase was back extracted with ethyl acetate (2×, 100 mL). The combined organic layers were concentrated and the residue was purified on silica gel (70% ethyl acetate in hexanes with ~2% triethylamine) to afford N-(4-propoxybenzyl)-1-(furan-2-yl)methanamine (5.3 g, 75%) as a yellow oil. NMR (CDCl$_3$, 400 MHz): δ 1.03 (t, J=7.2 Hz, 3H), 1.79 (m, J=6.4 Hz, 2H), 3.71 (s, 2H), 3.76 (s, 2H), 3.90 (t, J=6.8 Hz, 2H), 6.17 (d, J=3.2 Hz, 1H), 6.32 (m, 1H), 6.85 (d, J=8.4 Hz, 2H), 7.22 (d, J=8.8 Hz, 2H), 7.37 (m, 1H).

Additional compounds were experimentally tested and found to have a relatively high level of effectiveness as inhibitors of hT2R14 bitter receptor. The results of that testing are shown below in Table B.

TABLE B

| Compound No. | Compound | hT2R14 IC$_{50}$ (µM) |
|---|---|---|
| 5-9 | 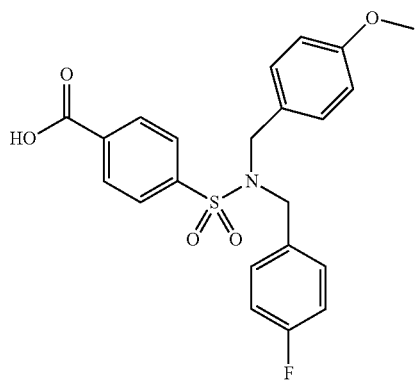 [SMILES: COc1ccc(CN(Cc2ccc(F)cc2)S(=O)(=O)c2ccc(C(=O)O)cc2)cc1]<br>4-(N,N-diisobutylsulfamoyl)benzoic acid | 15 |

Example 5-10

4-(N-(4-fluorobenzyl)-N-(4-methoxybenzyl)sulfamoyl)benzoic acid

Methyl 4-(N-(4-fluorobenzyl)-N-(4-methoxybenzyl)sulfamoyl)benzoate (Example 5-10a) (3.7 g, 8.3 mmol) was dissolved in MeOH/THF (1:1.5, 30 mL) and treated with aqueous NaOH (3 N, 15 mL). The mixture was stirred at ambient temperature overnight, then MeOH and THF were removed in vacuo. The resulting aqueous solution was acidified with 6 N aq HCl to a pH of ~3 and extracted with EtOAc (3×40 mL). The combined organic layers were washed with water and brine, dried over Na$_2$SO$_4$ and concentrated. The crude product was purified by recrystallization from EtOH to afford pure 4-(N-(4-fluorobenzyl)-N-(4-methoxybenzyl)sulfamoyl)benzoic acid as a white crystalline solid (2.1 g, 58.6%). MS (M−H, 428.1); $^1$H NMR (400 MHz, DMSO-d6): δ, ppm: 3.66 (s, 3H), 4.23 (s, 2H), 4.26 (s, 2H), 6.72 (d, 2H, J=8 Hz), 6.95 (m, 6H), 7.92 (d, 2H J=8 Hz), 8.07(d, 2H, J=8 Hz). The compound had an IC$_{50}$ on hT2R14 bitter receptor of 1.97 μM.

Example 5-10a

Methy 4-(N-(4-fluorobenzyl)-N-(4-methoxybenzyl)sulfamoyl)-benzoate

Methyl 4-(N-(4-methoxybenzyl)sulfamoyl)benzoate (Example 5-10b) (4.3 g, 12.8 mmol) was dissolved in acetone (70 mL). Cesium carbonate (8.57 g, 25.6 mmol) and (4-fluorobenzyl bromide (1.76 mL, 14.08 mmol) were added and the mixture was stirred at room temperature overnight. The inorganic salts were filtered off and acetone was removed in vacuo. The residue was re-dissolved in ethyl acetate, washed with water and brine, then the organic layer was dried over magnesium sulfate and concentrated. The crude product was purified by re-crystallization with ethyl acetate/hexanes to afford pure Methyl 4-(N-(4-fluorobenzyl)-N-(4-methoxybenzyl)sulfamoyl)benzoate (3.7 g, 65%) as a white solid. $^1$H NMR (400 MHz, CDCl$_3$): δ, ppm: 3.77 (s, 3H), 3.98 (s, 3H), 4.27 (s, 2H), 4.28(s, 2H), 6.74 (d, 2H, J=8 Hz), 6.92 (m, 4H), 7.03(m, 2H), 7.88 (d, 2H J=8 Hz), 8.16(d, 2H, J=8 Hz).

Example 5-10b

Methyl 4-(N-(4-methoxybenzyl)sulfamoyl)benzoate

To a solution of methyl 4-(chlorosulfonyl)benzoate (Example 5-10c) (4 g, 17.09 mmol) in dichloromethane (40 mL) at 0° C. in an ice bath, was added (4-methoxyphenyl)methanamine (2.56 mL, 19.65 mmol) and triethylamine (2.38 mL, 17.1 mmol). The ice bath was then removed and the mixture was allowed to warm to ambient temperature with stirring for an additional 2 hours. Upon completion (monitored by TLC 40% ethyl acetate/hexanes), the solvent was removed in vacuo. The residue was re-dissolved in ethyl acetate (200 mL), washed with 1N HCl (aq, 20 mL), water (20 mL) and brine (20 mL) then dried over magnesium sulfate. The solution was concentrated and the product purified by re-crystallization with hot ethyl acetate/hexanes to afford pure methyl 4-(N-(4-methoxybenzyl)sulfamoyl)benzoate (4.3 g, 74.8%) as a white solid. $^1$H NMR (400 MHz, DMSO-d6): δ, ppm: 3.67 (s, 3H), 3.78 (s, 3H), 3.93 (s, 2H), 6.78 (m, 2H), 7.09 (m, 2H), 7.87(m, 2H), 8.08 (m, 2H), 8.25(br, s, 1H).

Example 5-10c

Methyl 4-(chlorosulfonyl)benzoate

4-Chlorosulfonyl benzoic acid (5 g, 23 mmol) and thionyl chloride (20 mL) in dichloroethane (10 mL) was heated to 80° C. for 2 hr. The reaction mixture was concentrated via rotary evaporation to give a brownish solid. The solid was chilled on ice for 5 minutes and ice-cold methanol (40 mL) was added with stirring for 5 minutes. The reaction mixture was allowed to warm to ambient temperature and stirred an additional 10 min. The addition of ice-cold water (40 mL), produced a white solid that was collected by filtration and dried under vacuum to afford pure methyl 4-(chlorosulfonyl)benzoate (4.5 g, 84%). $^1$H NMR (400 MHz, DMSO-d6): δ, ppm: 3.84 (s, 3H), 7.70 (d, 2H, J=8.4 Hz), 7.93 (d, 2H, J=8.4 Hz).

Example 5-11

4-((N-benzyl-4-methylphenylsulfonamido)methyl)cyclohexane-carboxylic acid

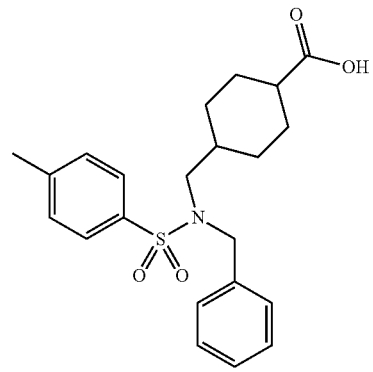 [SMILES: Cc1ccc(S(=O)(=O)N(Cc2ccccc2)CC2CCC(C(=O)O)CC2)cc1]

To the suspension of 4-(aminomethyl)cyclohexanecarboxylic acid (1.57 g, 10 mmol) in 100 ml of 2,2-dimethoxypropane, was added HCl (10 ml, 36% aq). The mixture was stirred at ambient temperature for 18 h and then concentrated. The residue was dissolved in a minimum volume of MeOH and Diethyl ether was added to precipitate the HCl salt, of methyl 4-(aminomethyl)cyclohexanecarboxylate as an off-white solid. This material was used without further purification or characterization.

To the mixture of the HCl salt of methyl 4-(aminomethyl)cyclohexanecarboxylate (208 mg, 1 mmol) in 5 mL of dichloromethane, at 0° C. in an ice bath, were added triethylamine (360 uL, 2.58 mmol) and 4-methylbenzene-1-sulfonyl chloride (190 mg, 1 mmol). The ice bath was allowed to warm slowly to ambient temperature and stirred overnight. The solvent was removed in vacuo. The residue was re-dissolved in ethyl acetate (20 mL), washed with 1N HCl (5 mL), water (5 mL) and brine (5 mL), then dried over magnesium sulfate and concentrated. This crude product (162 mg, 0.5 mmol) was redissolved in acetone (5 mL) and treated with potassium carbonate (110 mg, 0.79 mmol) and (4-fluorophenyl)methanamine (1.76 mL, 14.08 mmol). The mixture was stirred in a pressure vessel at 80° C. overnight, then cooled and the inorganic salts were filtered off. Acetone was removed in vacuo and the residue was re-dissolved in ethyl acetate and washed with water followed by brine. The organic layer was dried over magnesium sulfate and concentrated. The crude product (162 mg, 0.4 mmol) was dissolved in MeOH/THF (1:1.5, 10 mL) and treated with aqueous NaOH (10N, 400 uL). The mixture was stirred at 100° C. for 20 min in a microwave, and then MeOH and THF were removed in vacuo. The residue was acidified with 6 N aq HCl to a pH of ~3 and extracted with EtOAc; the combined organic layers were washed with water and brine, dried over Na$_2$SO$_4$ and concentrated. The crude product was purified by recrystallization from EtOH to afford pure 4-((N-benzyl-4-methylphenylsulfonamido)methyl)cyclohexanecarboxylic acid as a white solid (120 mg, 74%). MS (M+H, 402); $^1$H NMR (400 MHz, DMSO-d6): δ, ppm: 0.68 (m, 2H)), 0.91 (m, 2H), 1.06 (br, s, 1H), 1.50 (d, 2H), 1.72(d, 2H), 2.0(1H), 2.41 (s, 3H), 2.86 (m, 2H), 4.21(s, 2H), 7.30(m, 5H), 7.43(m, 2H), 7.73(m, 2H), 11.97(br, s, 1H).

The compound had an $IC_{50}$ on hT2R14 bitter receptor of 0.014 µM.

Example 5-12

4-(N-(3-fluorobenzyl)-N-(4-methoxybenzyl)sulfamoyl)benzoic acid

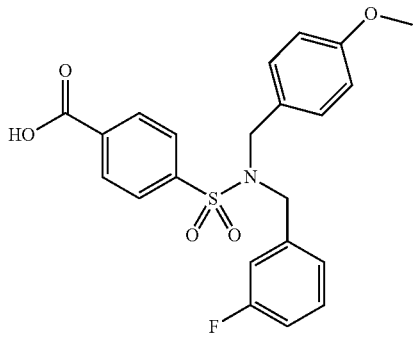 [SMILES: COc1ccc(CN(Cc2cccc(F)c2)S(=O)(=O)c2ccc(C(=O)O)cc2)cc1]

Methyl 4-(N-(4-methoxybenzyl)sulfamoyl)benzoate (Example 5-10b) (500 mg, 1.49 mmol), 3-fluorobenzyl bromide (280 mg, 2.98 mmol), and cesium carbonate (971 mg, 2.98 mmol) were placed in DMF (12 mL) and stirred at 90° C. for 4 hours. The solution was cooled to ambient temperature, diluted with $H_2O$ (200 mL) and extracted with ethyl acetate (3×, 100 mL). The combined organic layers were dried over $MgSO_4$, filtered and concentrated under vacuum. The residue was purified by silica gel chromatography (10-20% ethyl acetate in hexane) to afford methyl 4-(N-(3-fluorobenzyl)-N-(4-methoxybenzyl)sulfamoyl)benzoate (528 mg, 80%) as a white solid.

Methyl 4-(N-(3-fluorobenzyl)-N-(4-methoxybenzyl)sulfamoyl)benzoate (500 mg, 1.12 mmol) was dissolved in MeOH/THF (1:1, 40 mL) and treated with a solution of aqueous NaOH (10 N, 8 ml). The mixture was stirred at ambient temperature overnight, then MeOH and THF were removed by rotary evaporation. The resulting aqueous solution was washed with EtOAc (10 mL) and acidified with 6 N aq HCl (~15 mL) to pH~4. The aqueous solution was extracted with EtOAc (3×, 40 mL) and the combined organic layers were washed with water, brine, dried over $MgSO_4$ and concentrated. The crude product was purified by recrystallization from EtOH to afford the title compound 4-(N-(3-fluorobenzyl)-N-(4-methoxybenzyl)sulfamoyl)benzoic acid as a white crystalline solid (150 mg) in 30% yield.

MS (M–H, 428.1); $^1$H NMR (400 MHz, DMSO-d6): δ, ppm: 3.65 (s, 3H), 4.27 (s, 2H), 4.29 (s, 2H), 6.75-7.00 (m, 7H), 7.20 (m, 1H), 7.95 (d, 2H, J=8 Hz); 8.10 (d, 2H, J=8 Hz).

Example 5-13

4-(N-benzyl-N-(2,4-dimethoxybenzyl)sulfamoyl)benzoic acid

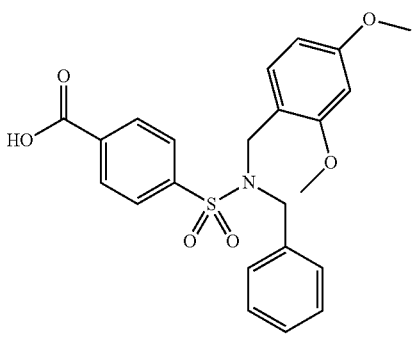 [SMILES: COc1ccc(CN(Cc2ccccc2)S(=O)(=O)c2ccc(C(=O)O)cc2)c(OC)c1]

Prepared as in example 5-10 from (2,4-dimethoxyphenyl)methanamine, methyl 4-(chlorosulfonyl)benzoate (Example 5-10c) and benzyl bromide. MS (M–H, 440.10); $^1$H NMR (400 MHz, DMSO-d6): δ, ppm: 3.50(s, 63H), 3.66(s, 3H), 4.20(s, 2H), 4.34(s, 2H), 6.29(s, 1H), 6.33(d, J=8.0 Hz, 1H), 6.91(d, J=8.8 Hz, 1H), 7.12-7.23 (m, 5H), 7.80(d, J=8.0 Hz, 2H), 8.01 (d, J=8.4 Hz, 2H), 13.49(s, 1H).

Example 5-14

4-(N-(3-chlorobenzyl)-N-(4-methoxybenzyl)sulfamoyl)benzoic acid

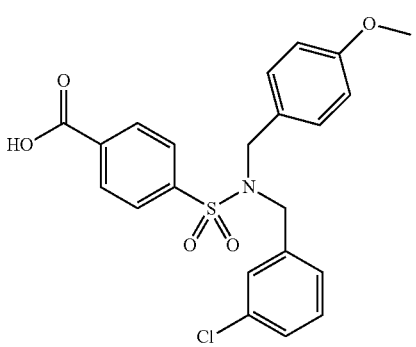 [SMILES: COc1ccc(CN(Cc2cccc(Cl)c2)S(=O)(=O)c2ccc(C(=O)O)cc2)cc1]

Prepared as in example 5-10 from Methyl 4-(N-(4-methoxybenzyl)sulfamoyl)benzoate (Example 5-10b) and 1-(bromomethyl)-3-chlorobenzene. MS (M–H, 444.1); $^1$H NMR (400 MHz, DMSO-d6): δ, ppm: 3.69 (s, 3H), 4.30 (m, 4H), 6.76-7.24 (m, 8H), 7.99 (m, 2H), 8.13 (m, 2H).

The compound had an IC$_{50}$ on hT2R14 bitter receptor of 1.88 µM.

Example 5-15

4-(N-benzyl-N-(2,4,6-trimethoxybenzyl)sulfamoyl)benzoic acid

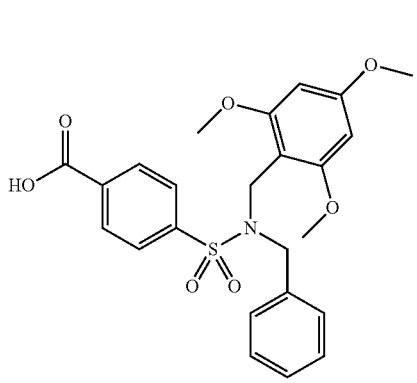 [SMILES: COc1cc(OC)c(CN(Cc2ccccc2)S(=O)(=O)c2ccc(C(=O)O)cc2)c(OC)c1]

Prepared as in example 5-10 from (2,4,6-trimethoxyphenyl)methanamine, methyl 4-(chlorosulfonyl)benzoate (Example 5-10c) and benzyl bromide. MS (M–H, 470.10); $^1$H NMR (400 MHz, DMSO-d6): δ, ppm: 3.45(s, 6H), 3.69(s, 3H), 4.26(s, 2H), 4.28(s, 2H), 5.98(s, 2H), 7.11-7.26(m, 5H), 7.82(d, J=8.0 Hz, 2H), 8.07(d, J=8 Hz, 2H), 13.49(s, 1H). Elemental analysis (found, %): C, 61.05; H, 5.49; N, 2.98; (calculated, %): C, 61.13; H, 5.34 and N, 2.97.

The compound had an IC$_{50}$ on hT2R14 bitter receptor of 10.76 µM.

Example 5-16

4-((N-benzyl-N-(4-methoxybenzyl)sulfamoyl)methyl)benzoic acid

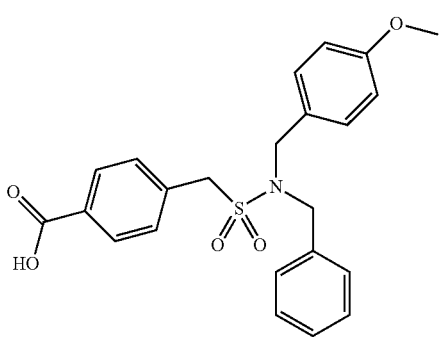 [SMILES: COc1ccc(CN(Cc2ccccc2)S(=O)(=O)Cc2ccc(C(=O)O)cc2)cc1]

Prepared as in example 5-10 from Methyl 4-(N-(4-methoxybenzyl)sulfamoyl)benzoate (Example 5-10b) and benzyl bromide. MS (M–H, 424.1); $^1$H NMR (400 MHz, DMSO-d6): δ, ppm: 3.72 (s, 3H), 4.18 (d, 2H), 4.55 (s, 2H), 6.83 (m, 2H), 7.12 (m, 2H), 7.21 (m, 2H), 7.28 (m, 3H), 7.43 (m, 2H), 7.93 (m, 2H).

Example 5-17

4-(N-(4-methoxybenzyl)-N-propylsulfamoyl)benzoic acid

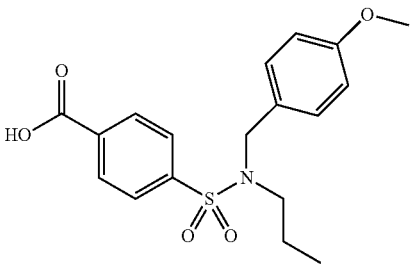 [SMILES: CCCN(Cc1ccc(OC)cc1)S(=O)(=O)c1ccc(C(=O)O)cc1]

Prepared as in example 5-10 from Methyl 4-(N-(4-methoxybenzyl)sulfamoyl)benzoate (Example 5-10b) and n-propyl bromide. MS (M–H, 362.1); $^1$H NMR (400 MHz, CDCl$_3$): δ, ppm: 0.70 (m, 3H), 1.35 (m, 3H), 3.08 (m, 2H), 3.73 (s, 3H), 4.31 (s, 2H), 6.83 (m, 2H), 7.17 (m, 2H), 7.93 (m, 2H), 8.23 (m, 2H).

The compound had an IC$_{50}$ on hT2R14 bitter receptor of 3.75 µM.

Example 5-18

4-(N-(4-methoxybenzyl)-N-phenylsulfamoyl)benzoic acid

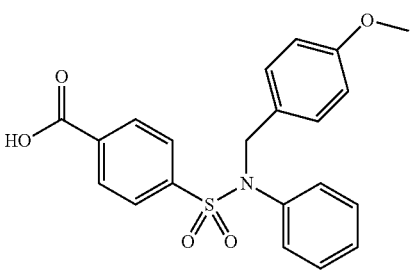 [SMILES: COc1ccc(CN(c2ccccc2)S(=O)(=O)c2ccc(C(=O)O)cc2)cc1]

Prepared as in example 5-10 from aniline, methyl 4-(chlorosulfonyl)benzoate (Example 5-10c) and 1-(chloromethyl)-4-methoxybenzene. MS (M–H, 396.1); $^1$H NMR (400 MHz, DMSO-d6): δ, ppm: 3.66(s, 3H), 4.73(s, 2H), 6.78(d, J=8.4

Hz, 2H), 7.00(d, J=7.6 Hz, 2H), 7.12(d, J=8.0 Hz, 2H), 7.24 (d, J=8.0 Hz, 2H), 8.11(d, J=8.4 Hz, 2H), 13.49(s, 1H).

Example 5-19

4-(N-(4-methoxybenzyl)-N-phenethylsulfamoyl)benzoic acid

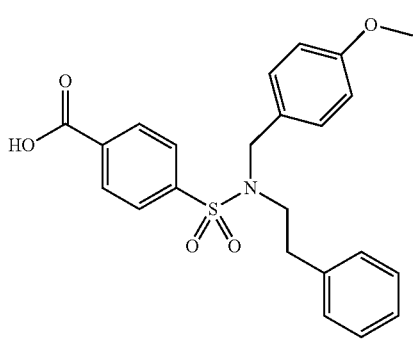 [SMILES: COc1ccc(CN(CCc2ccccc2)S(=O)(=O)c2ccc(C(=O)O)cc2)cc1]

Prepared as in example 5-10 from 2-phenylethanamine, methyl 4-(chlorosulfonyl)-benzoate (Example 5-10c) and 1-(chloromethyl)-4-methoxybenzene. MS (M−H, 424.1); $^1$H NMR (400 MHz, DMSO-d6): δ, ppm: 2.51 (m, 2H), 3.23 (m, 2H), 3.74 (s, 3H), 4.31 (s, 2H), 4.31 (s, 2H), 6.92 (m, 2H), 6.98 (m, 2H), 7.20-7.27 (m, 5H), 7.85 (m, 2H), 8.06 (m, 2H).

The compound had an IC$_{50}$ on hT2R14 bitter receptor of 4.58 μM.

Example 5-20

4-((N-(4-fluorobenzyl)-4-methylphenylsulfonamido)methyl)-cyclohexanecarboxylic acid

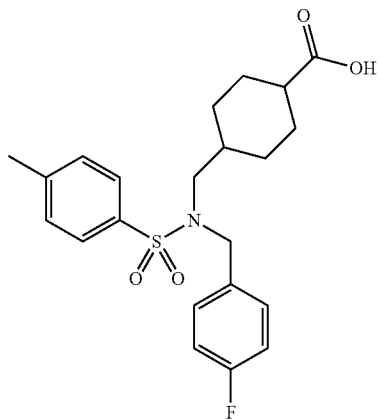 [SMILES: Cc1ccc(S(=O)(=O)N(Cc2ccc(F)cc2)CC2CCC(C(=O)O)CC2)cc1]

Prepared as in example 5-11 from 1-(bromomethyl)-4-fluorobenzene, 4-(aminomethyl)cyclohexanecarboxylic acid and 4-methylbenzene-1-sulfonylchloride. MS (M+H, 420); $^1$H NMR (400 MHz, DMSO-d6): δ, ppm: 0.71 (m, 2H)), 0.95 (m, 2H), 1.15 (br, s, 1H), 1.51 (d, 2H), 1.76(d, 2H), 2.0(1H), 2.40 (s, 3H), 2.85 (m, 2H), 4.22(s, 2H), 7.14(m, 2H), 7.32(m, 2H), 7.40(m, 2H), 7.69(m, 2H), 11.93(br, s, 1H).

The compound had an IC$_{50}$ on hT2R14 bitter receptor of 0.083 μM.

Example 5-21

4-((4-acetamido-N-benzylphenylsulfonamido)methyl)-cyclohexanecarboxylic acid

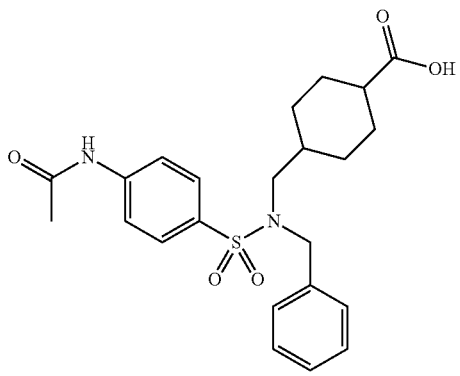 [SMILES: CC(=O)Nc1ccc(S(=O)(=O)N(Cc2ccccc2)CC2CCC(C(=O)O)CC2)cc1]

Prepared as in example 5-11 from acetamidobenzene-1-sulfonyl chloride, 4-(aminomethyl)cyclohexanecarboxylic acid and benzyl bromide. MS (M+H, 445.2); $^1$H NMR (400 MHz, DMSO-d6): δ, ppm: 0.65 (m, 2H), 0.68 (m, 2H), 1.05 (m, 1H), 1.48 (m, 2H), 1.70 (m, 2H), 1.92 (m, 1H), 2.00 (s, 3H), 2.82 (s, 2H), 4.21 (s, 2H), 7.27 (m, 5H), 7.76(m, 4H), 7.62(m, 2H), 10.1(s, 1H), 11.93(br, s, 1H).

The compound had an IC$_{50}$ on hT2R14 bitter receptor of 1.619 μM.

Example 5-22

4-((N-(4-fluorobenzyl)phenylsulfonamido)methyl)-cyclohexanecarboxylic acid

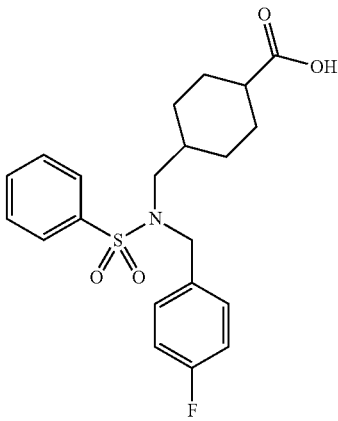 [SMILES: O=C(O)C1CCC(CN(Cc2ccc(F)cc2)S(=O)(=O)c2ccccc2)CC1]

Prepared as in example 5-11 from benzenesulfonyl chloride, 4-(aminomethyl)-cyclohexanecarboxylic acid and 1-(bromomethyl)-4-fluorobenzene. MS (M+H, 406); $^1$H NMR (400 MHz, DMSO-d6): δ, ppm: 0.77 (m, 2H), 0.94 (m, 2H), 0.98 (m, 2H), 1.50 (m, 2H0, 1.75 (m, 2H), 1.77 (m, 1H), 2.80 (d, 2H), 4.28 (s, 2H), 7.20 (m, 2H), 7.38(m, 2H), 7.62(m, 2H), 7.70(m, 1H), 7.88(m, 2H), 11.93(br, s, 1H).

The compound had an IC$_{50}$ on hT2R14 bitter receptor of 0.240 μM.

Example 5-23

4-(N-(cyclohexylmethyl)-N-(4-methoxybenzyl)sulfamoyl)-benzoic acid

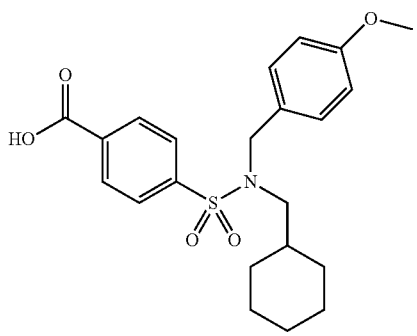 [SMILES: COc1ccc(CN(CC2CCCCC2)S(=O)(=O)c2ccc(C(=O)O)cc2)cc1]

Prepared as in example 5-10 from Methyl 4-(N-(4-methoxybenzyl)sulfamoyl)benzoate (Example 5-10b) and cyclohexylmethanamine. MS (M–H, 416.1); $^1$H NMR (400 MHz, DMSO-d6): δ, ppm: 0.63 (m, 2H), 0.87 (m, 3H), 0.94 (m, 1H), 1.25-1.52 (m, 5H), 1.70 (m, 2H), 2.86 (m, 2H), 3.70 (s, 3H), 4.22 (s, 2H), 6.84 (m, 2H), 7.16 (m, 2H), 7.91(m, 2H), 7.62(m, 2H), 8.09(m, 2H).

The compound had an IC$_{50}$ on hT2R14 bitter receptor of 3.47 μM.

Example 5-24

4-((N-(4-fluorobenzyl)-1-phenylmethylsulfonamido)methyl)-cyclohexanecarboxylic acid

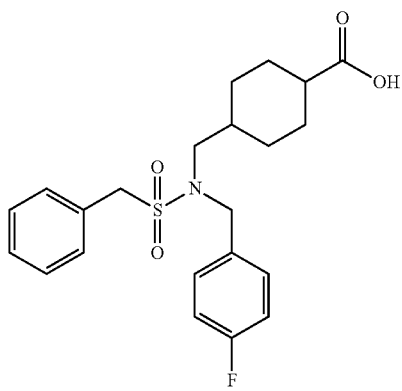 [SMILES: O=C(O)C1CCC(CN(Cc2ccc(F)cc2)S(=O)(=O)Cc2ccccc2)CC1]

Prepared as in example 5-10 from phenylmethanesulfonyl chloride and methyl 4-(aminomethyl)cyclohexanecarboxylate and 1-(bromomethyl)-4-fluorobenzene. MS (M–H, 418); $^1$H NMR (400 MHz, DMSO-d6): δ, ppm: 0.639 (m, 2H), 0.897 (m, 2H), 1.034 (m, 1H), 1.467 (d, broad, 2H, J=11.2 Hz), 1.709 (d, broad, 2H, J=11.2 Hz), 1.961 (m, 1H), 2.828 (d, 2H, J=7.6 Hz), 4.207(s, 2H), 4.449 (s, 2H), 7.155 (t, 2H, J=9.2 Hz), 7.377 (m, 7H), 12 (s, broad, 1H)

The compound had an IC$_{50}$ on hT2R14 bitter receptor of 9.57 μM.

Example 5-25

4-(N-(2-cyanobenzyl)-N-(4-methoxybenzyl)sulfamoyl)benzoic acid

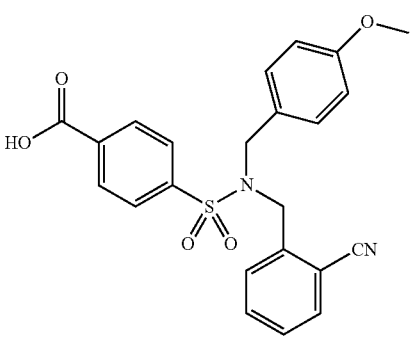 [SMILES: COc1ccc(CN(Cc2ccccc2C#N)S(=O)(=O)c2ccc(C(=O)O)cc2)cc1]

Prepared as in example 5-10 from Methyl 4-(N-(4-methoxybenzyl)sulfamoyl)-benzoate (Example 5-10b) and alpha-bromo-o-tolunitrile. MS(M–H, 435.1); $^1$H NMR (400 MHz, DMSO-d6): δ, ppm: 3.664 (s, 2H), 4.348 (s, 2H), 4.498 (s, 2H), 6.728 (d, 2H, J=8.4 Hz), 7.036 (d, 2H, j=8.4 Hz), 7.352 (t, 2H, J=9.2 Hz), 7.548 (t, 1H, J=7.6 Hz), 7.640 (d, 1H, J=7.6 Hz), 8.003 (d, 2H, J=8 Hz), 8.139 (d, 2H, J=8.4 Hz), 13.559 (s, broad, 1H).

The compound had an IC$_{50}$ on hT2R14 bitter receptor of 4.61 μM.

Example 5-26

4-(N-(4-acetamidobenzyl)-N-(4-methoxybenzyl)sulfamoyl)benzoic acid

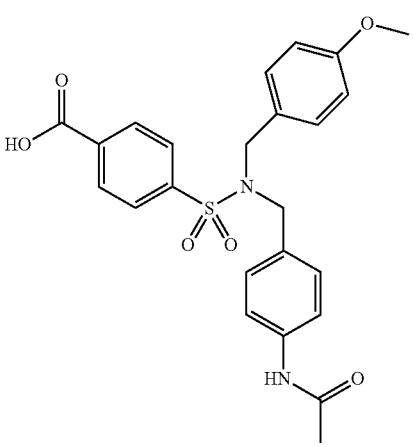 [SMILES: COc1ccc(CN(Cc2ccc(NC(C)=O)cc2)S(=O)(=O)c2ccc(C(=O)O)cc2)cc1]

Prepared as in example 5-10 from Methyl 4-(N-(4-methoxybenzyl)sulfamoyl)benzoate (Example 5-10b) and N-(4-(chloromethyl)phenyl)acetamide. MS (M–H, 467.1); $^1$H NMR (400 MHz, DMSO-d6): δ, ppm: 2.0(s, 3H), 3.69s, 3H), 4.23(s, 4H), 6.78(d, 2H, J=7.6 Hz), 6.98(m, 4H), 7.41(d, 2H, J=8 Hz), 7.94(d, 2H, J=8 Hz), 8.09(d, 2H, J=8 Hz), 9.90(s, 1H).

Example 5-27

4-(N-(furan-3-ylmethyl)-N-(4-methoxybenzyl)sulfamoyl)benzoic acid

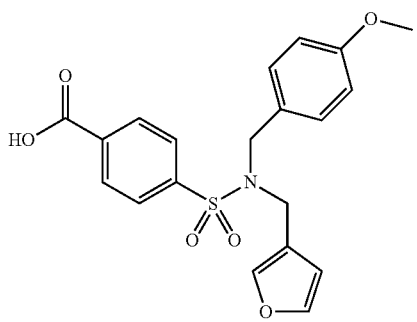 [SMILES: COc1ccc(CN(Cc2ccoc2)S(=O)(=O)c2ccc(C(=O)O)cc2)cc1]

110 mg of 1-(furan-3-yl)-N-(4-methoxybenzyl)methanamine (example 5-27a) was mixed with methyl 4-(chlorosulfonyl)benzoate (example 5-10c) (117 mg, 0.5 mmol) and triethyl amine (100 uL) in DCM (5 mL). The mixture was stirred overnight at ambient temperature and concentrated. The residue was re-dissolved in ethyl acetate (20 mL), washed with 1N HCl (aq., 2 mL), followed by water (5 mL) and brine (5 mL) then dried over magnesium sulfate. The crude product was purified by preparative TLC (40% Ethyl Acetate/hexanes) to give methyl 4-(N-(furan-3-ylmethyl)-N-(4-methoxybenzyl)sulfamoyl)benzoate as a white solid. Saponification as in example 5-10 gave 4-(N-(furan-3-ylmethyl)-N-(4-methoxybenzyl)sulfamoyl)benzoic acid as a white crystalline solid (68 mg, 64% yield). MS (M–H, 400.1); $^1$H NMR (400 MHz, DMSO-d6): δ, ppm: 3.72(s, 3H), 4.13(s, 2H), 4.26(s, 2H), 5.99 (s, 1H), 6.87(m, 4H), 6.87 (d, 2H, J=8.8 Hz), 7.13 (d, 2H, J=8.8 Hz), 7.39 (s, 1H), 7.49 (s, 1H), 7.95 (d, 2H, J=8.4 Hz), 8.09 (d, 2H, J=8.8 Hz).

Example 5-27a 1-(furan-3-yl)-N-(4-methoxybenzyl)methanamine

A mixture of 3-Furaldehyde (5 mmol, 437 μL) and (4-methoxyphenyl)methanamine in MeOH (20 mL) was stirred at ambient temperature overnight then sodium borohydride (300 mg, 7.89 mmol) was slowly added. The resulting mixture was stirred at room temperature for 15 minutes and quenched with NaOH (1 N, aq). Methanol was removed in vacuo and the resulting slurry was redissolved in ethyl acetate then, washed with water, brine, dried over sodium sulfate and concentrated. Purification by silica gel chromatography (Ethyl acetate:Hexanes 7:3) gave 1-(furan-3-yl)-N-(4-methoxybenzyl)methanamine as an oil. MS (M+H, 218.10); $^1$H NMR (400 MHz, CDCl3): δ, ppm: 3.64(s, 2H), 3.74(s, 2H), 3.80(s, 3H), 6.39(m, 1H), 6.86(m, 1H), 6.88(m, 1H), 7.23(m, 1H), 7.25(m, 1H), 7.35(m, 1H), 7.38(m, 1H).

Example 5-28

4-(N,N-dibenzylsulfamoyl)benzoic acid

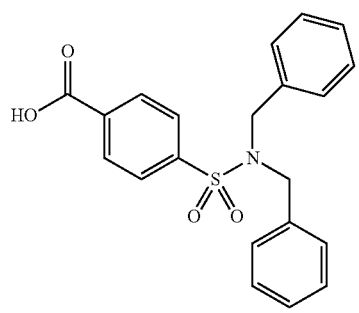 [SMILES: O=C(O)c1ccc(S(=O)(=O)N(Cc2ccccc2)Cc2ccccc2)cc1]

Prepared as in example 5-27 from dibenzylamine and methyl 4-(chlorosulfonyl)-benzoate (Example 5-10c). MS (M–H, 380.1); $^1$H NMR (400 MHz, DMSO-d6): δ, ppm: 4.52 (s, 4H), 7.10 (m, 4H), 7.25 (m, 6H), 8.00 (d, 2H, J=8.4 Hz), 8.15 (d, 2H J=8.4 Hz), 13.5(s, broad, 1H).

The compound had an IC$_{50}$ on hT2R14 bitter receptor of 7.74 μM.

Example 5-29

4-(N-(4-methoxybenzyl)-N-methylsulfamoyl)benzoic acid

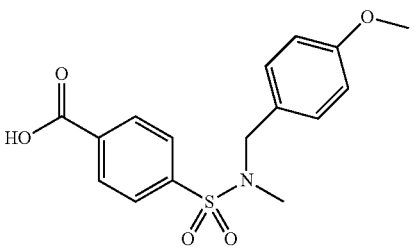 [SMILES: COc1ccc(CN(C)S(=O)(=O)c2ccc(C(=O)O)cc2)cc1]

Prepared as in example 5-27 from 1-(4-methoxyphenyl)-N-methylmethanamine and methyl 4-(chlorosulfonyl)-benzoate (Example 5-10c). MS (M–H, 335.1); $^1$H NMR (400 MHz, DMSO-d6): δ, ppm: 2.51 (s, 3H), 3.71 (s, 3H), 4.05 (s, 2H), 6.88 (d, 2H), 7.18 (d, 2H), 7.91 (d, 2H); 8.13 (d, 2H).

Elemental analysis: (found): C, 57.47%, H, 4.77% and N, 4.31%; (theoretical): C, 57.30%, H, 5.11% and N, 4.18%

Example 5-30

4-(N,N-bis(4-methoxybenzyl)sulfamoyl)benzoic acid

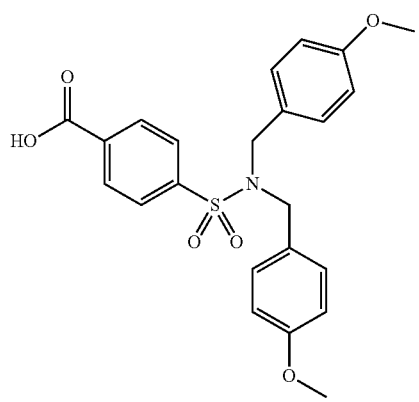 [SMILES: COc1ccc(CN(Cc2ccc(OC)cc2)S(=O)(=O)c2ccc(C(=O)O)cc2)cc1]

Prepared as in example 5-27 from bis(4-methoxybenzyl) amine and methyl 4-(chlorosulfonyl)-benzoate (Example 5-10c). MS (M–H, 440.1); $^1$H NMR (400 MHz, DMSO-d6): δ, ppm: 3.68 (s, 6H), 4.20 (s, 4H), 6.77 (d, 4H, J=10 Hz), 6.98 (d, 4H, J=10 Hz), 7.92 (dd, 2H J=8 Hz), 8.06(dd, 2H, J=8 Hz). Elemental analysis: (found): C, 62.45%, H, 5.19% and N, 3.06%; (theoretical): C, 62.57%, H, 5.25% and N, 3.17%

The compound had an IC$_{50}$ on hT2R14 bitter receptor of 4.14 μM.

Example 5-31

4-(N-(2-fluorobenzyl)-N-(4-methoxybenzyl)sulfamoyl)benzoic acid

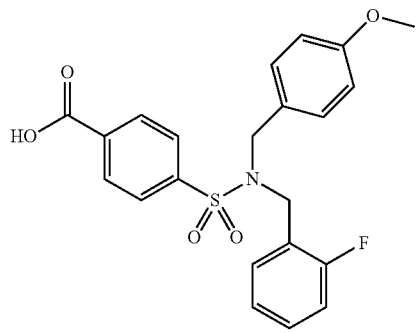 [SMILES: COc1ccc(CN(Cc2ccccc2F)S(=O)(=O)c2ccc(C(=O)O)cc2)cc1]

Prepared as in example 5-10 from Methyl 4-(N-(4-methoxybenzyl)sulfamoyl)-benzoate (Example 5-10b) and 1-(bromomethyl)-2-fluorobenzene. $^1$H NMR (400 MHz, DMSO-d6): δ, ppm: 3.66(s, 3H), 4.29 (s, 2H), 4.37(s, 2H), 6.72 (d, 2H, J=8 Hz), 7.01-7.03 (m, 6H), 7.93 (d, 2H, J=8 Hz), 8.08 (d, 2H, J=8 Hz).

Example 5-32

4-(N-(2,5-difluorobenzyl)-N-(4-methoxybenzyl)sulfamoyl)-benzoic acid

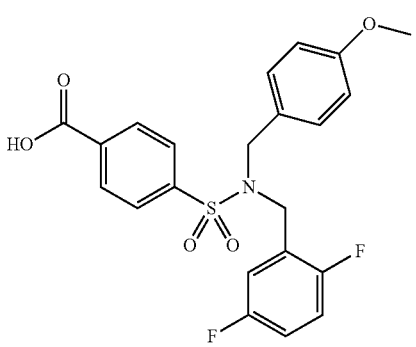 [SMILES: COc1ccc(CN(Cc2cc(F)ccc2F)S(=O)(=O)c2ccc(C(=O)O)cc2)cc1]

Prepared as in example 5-10 from Methyl 4-(N-(4-methoxybenzyl)sulfamoyl)-benzoate (Example 5-10b) and 2-(bromomethyl)-1,4-difluorobenzene. $^1$H NMR (400 MHz, DMSO-d6): δ, ppm: 3.66 (s, 3H), 4.31 (s, 2H), 4.33 (s, 2H), 6.74-7.06 (m, 7H), 7.95 (d, 2H, J=8 Hz), 8.09 (d, 2H, J=8 Hz).

Example 5-33

4-(N-(2,3-difluorobenzyl)-N-(4-methoxybenzyl)sulfamoyl)benzoic acid

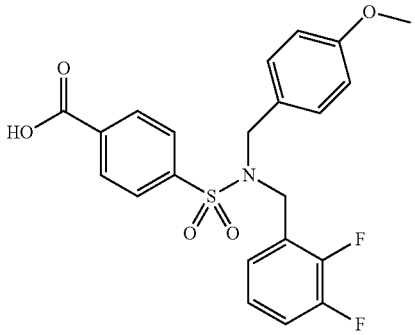 [SMILES: COc1ccc(CN(Cc2cccc(F)c2F)S(=O)(=O)c2ccc(C(=O)O)cc2)cc1]

Prepared as in example 5-10 from Methyl 4-(N-(4-methoxybenzyl)sulfamoyl)-benzoate (Example 5-10b) and 1-(bromomethyl)-2,3-difluorobenzene. $^1$H NMR (400 MHz, DMSO-d6): δ, ppm: 3.30 (s, 3H), 4.29 (s, 2H), 4.32(s, 2H), 6.87 (d, 2H, J=8 Hz), 7.02-7.20 (m, 5H), 7.95 (d, 2H, J=8 Hz). 8.05 (d, 2H, J=8 Hz).

Example 5-34

4-(N-(3-methoxybenzyl)-N-(4-methoxybenzyl)sulfamoyl)-benzoic acid

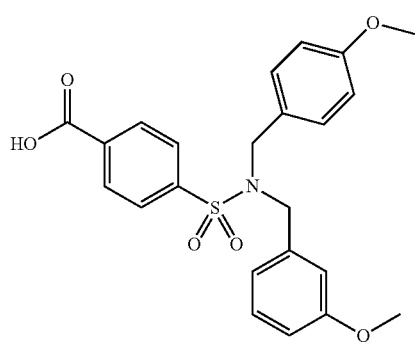 [SMILES: COc1ccc(CN(Cc2cccc(OC)c2)S(=O)(=O)c2ccc(C(=O)O)cc2)cc1]

Prepared as in example 5-10 from Methyl 4-(N-(4-methoxybenzyl)sulfamoyl)benzoate (Example 5-10b) and 3-methoxybenzyl bromide. MS (M−H, 440.50); $^1$H NMR (400 MHz, DMSO-d6): δ, ppm: 3.58(s, 3H), 3.68(s, 3H), 4.24(s, 2H), 4.25(s, 2H), 6.50(s, 1H), 6.64(d, J=4 Hz, 1H), 6.73(m, 1H), 6.77(d, J=8 Hz, 2H), 7.00(d, J=8 Hz, 2H), 7.12 (t, J=8 Hz, 1H), 7.94(d, J=8 Hz, 2H), 8.09(d, J=8 Hz, 2H), 13.49(s, 1H).

The compound had an $IC_{50}$ on hT2R14 bitter receptor of 2.46 μM.

Example 5-35

4-(N-benzyl-N-(4-methoxyphenyl)sulfamoyl)benzoic acid

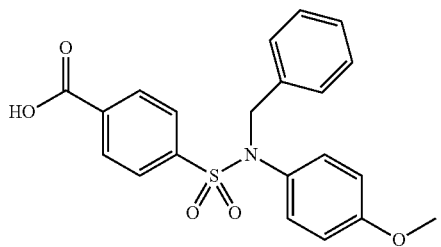 [SMILES: COc1ccc(N(Cc2ccccc2)S(=O)(=O)c2ccc(C(=O)O)cc2)cc1]

Prepared as in example 5-10 from Methyl 4-(N-(4-methoxyphenyl)sulfamoyl)-benzoate (example 5-35a) and benzyl bromide MS (M−H, 396); $^1$H NMR (400 MHz, DMSO-d6): δ, ppm: 3.66(s, 3H), 4.75(s, 2H), 6.76(d, J=8 Hz, 2H), 6.90(d, J=8 Hz, 2H), 7.23(m, 5H), 7.74(d, J=8 Hz, 2H), 8.11(d, J=8 Hz, 2H), 13.51(s, 1H).

Example 5-35a

Methyl 4-(N-(4-methoxyphenyl)sulfamoyl)benzoate

To 4-methoxybenzenamine (580 mg, 4.71 mmol) and triethylamine (1.48 mL, 10.7 mmol) in dichloromethane (10 mL) was added methyl 4-(chlorosulfonyl)benzoate (1.00 g, 4.28 mmol). This mixture was stirred for 16 hours at room temperature. The reaction was diluted with dichloromethane (50 mL) and washed consecutively with water, 10% citric acid, and brine. The organics were dried over sodium sulfate and concentrated via rotovap. The resulting crude material was chromatographed on silica gel using 100% dichloromethane as eluent affording Methyl 4-(N-(4-methoxyphenyl)sulfamoyl)benzoate as a white crystalline solid (400 mg, 30% yield)

Example 5-36

4-(N-(3,4-difluorobenzyl)-N-(4-methoxybenzyl) sulfamoyl)benzoic acid

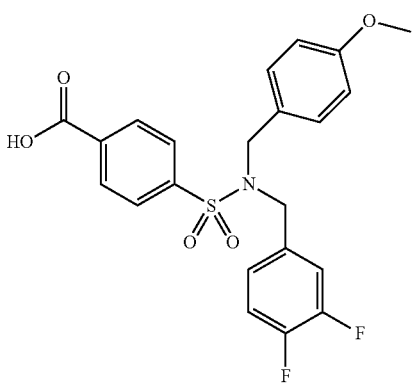 [SMILES: COc1ccc(CN(Cc2ccc(F)c(F)c2)S(=O)(=O)c2ccc(C(=O)O)cc2)cc1]

Prepared as in example 5-10 from N-(3,4-difluorobenzyl)(4-methoxyphenyl)-methanamine (example 5-36a) and methyl 4-(chlorosulfonyl)benzoate (example 5-10c). MS (M−H, 446); $^1$H NMR (400 MHz, DMSO-d6): δ ppm: 3.69 (s, 3H), 4.20 (s, 4H), 6.73 (d, J=8.8 Hz, 2H), 6.93 (m, 2H), 6.98 (d, J=8.8 Hz, 2H), 7.22 (m, 1H), 7.74(d, J=8.4 Hz, 2H), 7.99 (d, J=8.4 Hz, 2H).

Example 5-36a

N-(3,4-difluorobenzyl)(4-methoxyphenyl)methanamine

To (4-methoxyphenyl)methanamine (1.77 mL, 13.6 mmol) and acetic acid (2.7 mL, 45 mmol) in dichloromethane (15 mL) was added 3,4-difluorobenzaldehyde (1.0 m, 9.08 mmol). This mixture was heated in the microwave at 100° C. for 15 min. The reaction was cooled to room temperature and macroporous cyanoborohydride resin (9.8 g, 22.7 mmol) was added in portions. This mixture was stirred at room temperature for 16 hours. The resin was filtered off and rinsed with dichloromethane and the organics were washed with saturated sodium bicarbonate until bubbling ceased. The organics were dried over sodium sulfate and concentrated via rotovap. The resulting crude material was purified by silica gel chromatography using methanol dichloromethane gradient as eluent to afford N-(3,4-difluorobenzyl)(4-methoxyphenyl) methanamine as a yellowish oil (1.9 g, 80% yield). MS (M+H, 264); $^1$H NMR (400 MHz, DMSO-d6): δ, ppm: 2.63

(br s, 1H), 3.56 (s, 2H), 3.61 (s, 2H), 3.71 (s, 3H), 6.84 (d, J=8.8 Hz, 2H), 7.14 (m, 1H), 7.21 (d, J=8.4 Hz, 2H), 7.34 (m, 2H).

Example 5-37

4-((N-(4-fluorobenzyl)-4-methylphenylsulfonamido)methyl)benzoic acid

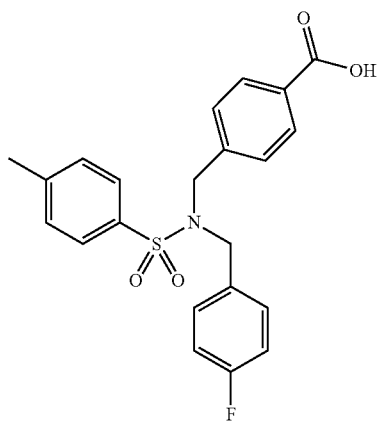 [SMILES: Cc1ccc(S(=O)(=O)N(Cc2ccc(F)cc2)Cc2ccc(C(=O)O)cc2)cc1]

Prepared as in example 5-11 from 4-(aminomethyl)phenylcarboxylic acid, 4-methylbenzene-1-sulfonylchloride and 4-fluorobenzyl bromide. $^1$H NMR (400 MHz, DMSO-d6): δ, ppm: 3.11 (s, 3H), 4.21 (s, 2H), 4.24(s, 2H), 6.94-7.08 (m, 6H), 7.40-7.42 (d, 2H, J=8 Hz), 7.63 (d, 2H, J=8 Hz), 7.73 (d, 2H, J=8 Hz)

The compound had an $IC_{50}$ on hT2R14 bitter receptor of 0.054 μM.

Example 5-38

4-((4-carboxy-N-(4-methoxybenzyl)phenylsulfonamido)methyl)-benzoic acid

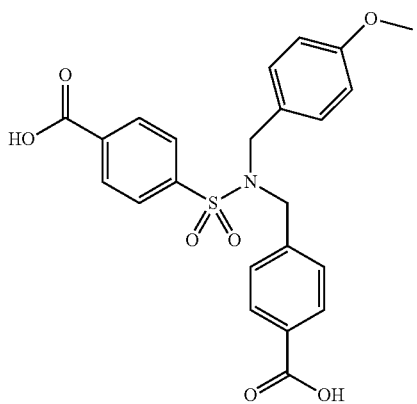 [SMILES: COc1ccc(CN(Cc2ccc(C(=O)O)cc2)S(=O)(=O)c2ccc(C(=O)O)cc2)cc1]

Prepared as in example 5-10 from methyl 4-(bromomethyl)benzoate and Methyl 4-(N-(4-methoxybenzyl)sulfamoyl)benzoate (example 5-10b). $^1$H NMR (400 MHz, DMSO-d6): δ, ppm: 3.65 (s, 3H), 4.24 (s, 2H), 4.33(s, 2H), 6.71 (d, 2H, J=8 Hz), 6.95 (d, 2H, J=8 Hz), 7.14 (d, 2H, J=8 Hz). 7.73 (d, 2H, J=8 Hz), 7.89(d, 2H, J=8 Hz), 8.06(d, 2H, J=8 Hz).

Example 5-39

4-(N-benzyl-N-(3,4-dimethoxybenzyl)sulfamoyl)benzoic acid

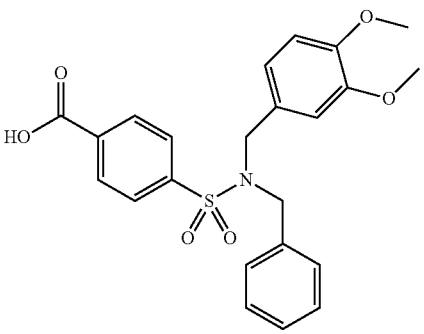 [SMILES: COc1ccc(CN(Cc2ccccc2)S(=O)(=O)c2ccc(C(=O)O)cc2)cc1OC]

Prepared as in example 5-10 from (3,4-dimethoxyphenyl)methanamine, methyl 4-(chlorosulfonyl)benzoate (Example 5-10c) and benzyl chloride. MS (M–H, 440.10); $^1$H NMR (400 MHz, CD$_3$OD): δ, ppm: 3.59 (s, 3H), 3.76 (s, 3H), 4.30 (s, 2H), 4.36 (s, 2H), 6.51 (d, 1H, J=1.7 Hz), 6.60 (m, 1H), 6.76 (d, 1H, J=8.2 Hz), 7.12 (m, 2H), 7.21 (m, 3H), 7.95 (d, 2H, J=8.6 Hz), 8.18 (d, 2H, J=8.6 Hz).

The compound had an $IC_{50}$ on hT2R14 bitter receptor of 0.678 μM.

Example 5-40

4-(N-(3,4-dimethoxybenzyl)-N-(4-methoxybenzyl)sulfamoyl)benzoic acid

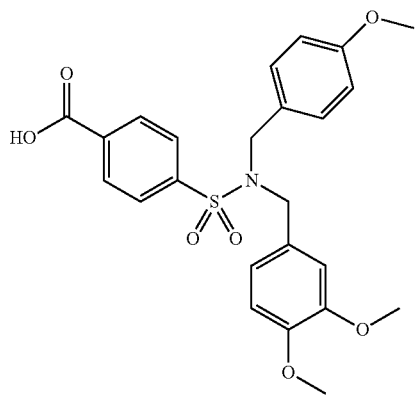 [SMILES: COc1ccc(CN(Cc2ccc(OC)c(OC)c2)S(=O)(=O)c2ccc(C(=O)O)cc2)cc1]

Prepared as in example 5-10 from (3,4-dimethoxyphenyl)methanamine, methyl 4-(chlorosulfonyl)benzoate (Example 5-10c) and 4-methoxybenzylbromide. MS (M–H, 470.10); $^1$H NMR (400 MHz, DMSO-d6): δ, ppm: 3.49 (s, 3H), 3.67 (s, 3H), 3.68 (s, 3H), 4.20 (s, 2H), 4.22 (s, 2H), 6.41 (d, 1H, J=1.4 Hz), 6.58 (dd, 1H, J1=8.2 Hz, J2=1.4 Hz), 6.78 (m, 3H), 7.02 (d, 2H, J=8.6 Hz), 7.94 (d, 2H, J=8.4 Hz), 8.09 (d, 2H, J=8.4 Hz).

The compound had an IC$_{50}$ on hT2R14 bitter receptor of 1.47 µM.

Example 5-41

4-(N-(3-fluoro-4-methoxybenzyl)-N-(4-methoxybenzyl)sulfamoyl)-benzoic acid

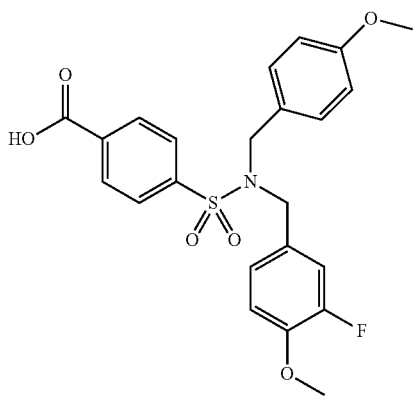 [SMILES: COc1ccc(CN(Cc2ccc(OC)c(F)c2)S(=O)(=O)c2ccc(C(=O)O)cc2)cc1]

Prepared as in example 5-10 from 4-(bromomethyl)-2-fluoro-1-methoxybenzene and methyl 4-(N-(4-methoxybenzyl)sulfamoyl)benzoate (example 5-10b). MS (M−H, 458.10); $^1$H NMR (400 MHz, CD$_3$OD): δ, ppm: 3.73 (s, 3H), 3.80 (s, 3H), 4.24 (s, 2H), 4.28 (s, 2H), 6.75 (m, 4H), 6.88 (m, 1H), 6.97 (d, 2H, J=8.6 Hz), 7.88 (d, 2H, J=8.3 Hz), 8.14 (d, 2H, J=8.3 Hz).

The compound had an IC$_{50}$ on hT2R14 bitter receptor of 1.11 µM.

Example 5-42

4-((4-hydroxy-N-(2-methoxybenzyl)phenylsulfonamido)methyl)-benzoic acid

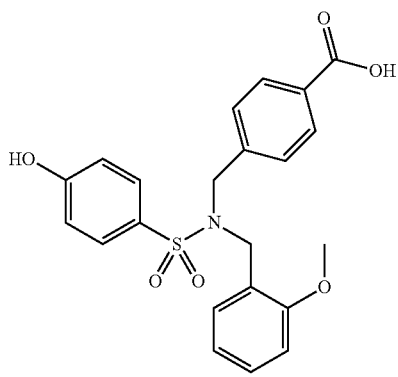 [SMILES: COc1ccccc1CN(Cc1ccc(C(=O)O)cc1)S(=O)(=O)c1ccc(O)cc1]

4-(N-(2-methoxybenzyl)sulfamoyl)phenyl acetate (example 5-42a) (50 mg, 0.15 mmol) was dissolved in acetone (1.0 mL) followed by the addition of cesium carbonate (97 mg, 0.30 mmol) and methyl 4-(bromomethyl)benzoate (38 mg, 0.17 mmol). The mixture was stirred at room temperature overnight and then the inorganic salts were filtered off. Acetone was removed in vacuo and the residue was re-dissolved in ethyl acetate and washed with water followed by brine. The organic layer was dried over magnesium sulfate and concentrated. The crude product was purified by column chromatography with ethyl acetate/hexanes as the eluent to afford methyl 4-((4-acetoxy-N-(2-methoxybenzyl)phenylsulfonamido)methyl)benzoate.

Methyl 4-((4-acetoxy-N-(2-methoxybenzyl)phenylsulfonamido)methyl)benzoate (crude) was dissolved in THF (1.0 mL) and treated with aqueous NaOH (1N, 2.0. mL, 2.0 mmol). The mixture was refluxed for an hour. Upon completion the THF was removed in vacuo and the resulting aqueous solution was acidified with 6 N aq HCl to a pH of ~3. The aqueous phase was extracted with EtOAc (2×15 mL) and the combined organic layers were washed with water, brine, dried over Na$_2$SO$_4$ and concentrated. The crude product was purified by reverse phase HPLC to afford 10.8 mg of the title compound (15% yield over two steps). MS (M−H, 426.1); $^1$H NMR (400 MHz, acetone-d6): δ, ppm: 3.65 (s, 3H), 4.37 (s, 2H), 4.43 (s, 2H), 6.79 (m, 2H), 7.01 (d, 2H, J=8.0 Hz), 7.17 (m, 2H), 7.28 (d, 2H, J=7.9 Hz), 7.73 (d, 2H, J=8.0 Hz), 7.87 (d, 2H, J=7.9 Hz).

The compound had an IC$_{50}$ on hT2R14 bitter receptor of 2.56 µM.

Example 5-42a 4-(N-(2-methoxybenzyl)sulfamoyl)phenyl acetate

A solution of 4-(chlorosulfonyl)phenyl acetate (example 5-42b) (531 mg, 2.265 mmol) in 5.0 mL of dichloromethane, was cooled to 0° C. in an ice bath. (2-methoxyphenyl)methanamine (325 µL, 2.492 mmol) and triethylamine (347 µL, 2.492 mmol) were added. The ice bath was then removed and the mixture warmed to ambient temperature and stirred for 2 hours. The reaction mixture was concentrated and the crude product was purified by column chromatography (hexanes/ethyl acetate=90/10 to 30/70) to afford pure 4-(N-(2-methoxybenzyl)sulfamoyl)phenyl acetate (743 mg, 89%) as a white solid. MS (M+H, 336.1) $^1$H NMR (400 MHz, CDCl$_3$): δ, ppm: 2.32 (s, 3H), 3.71 (s, 3H), 4.18 (d, 2H, J=5.8 Hz), 5.15 (t, 1H, J=5.8 Hz), 6.71 (d, 1H, J=8.2 Hz), 6.82 (br t, 1H, J=7.4 Hz), 7.07(br d, 1H, J=7.4 Hz), 7.10 (d, 2H, J=8.7 Hz), 7.19 (br t, 1H, J=7.8 Hz), 7.74 (d, 2H, J=8.7 Hz).

Example 5-42b 4-(chlorosulfonyl)phenyl acetate 6.285 g (36.08 mmol) of 4-hydroxybenzenesulfonic acid was dissolved in a mixture of 30 mL of acetic anhydride and 15 mL of acetic acid and refluxed for 6 hours. The volatiles were evaporated and placed under high vacuum overnight. The resulting crude product was dissolved in 100 mL of DCM and treated with 4.72 mL of oxalyl chloride (54.12 mmol) and 139 µL of DMF (1.804 mmol) at 0° C. Stirring was continued until gas evolution ceased then the reaction was concentrated and re-dissolved in EtOAc. The organic layer was washed twice with 2 N H$_2$SO$_4$, and dried with brine and MgSO$_4$. concentration gave 7.067 g of 4-(chlorosulfonyl)phenyl acetate as a dark thick oil that eventually solidified (83% yield over two steps).

$^1$H-NMR (400 MHz, CDCl$_3$): δ, ppm: 2.35 (s, 3H), 7.37 (d, 2H, J=8.9 Hz), 8.06 (d, 2 H, J=8.9 Hz). $^{13}$C-NMR (100 MHz, CDCl$_3$): δ, ppm: 21.13, 123.05, 128.91, 141.15, 155.80, 168.29.

Example 5-43

4-((4-hydroxy-N-(3-methoxybenzyl)phenylsulfonamido)methyl)-benzoic acid

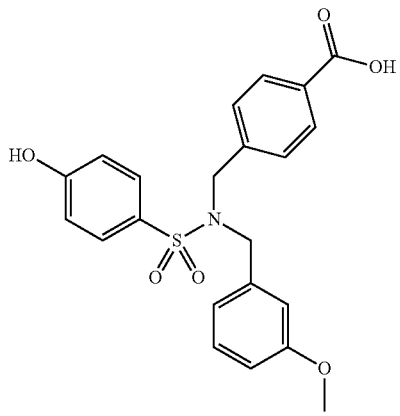 [SMILES: COc1cccc(CN(Cc2ccc(C(=O)O)cc2)S(=O)(=O)c2ccc(O)cc2)c1]

Prepared as in example 5-42 from (3-methoxyphenyl)methanamine and methyl 4-(bromomethyl)benzoate. MS (M−H, 426.10); $^1$H NMR (400 MHz, acetone-d6): δ, ppm: 3.66 (s, 3H), 4.32 (s, 2H), 4.40 (s, 2H), 6.65 (br s, 1H), 6.73 (m, 2H), 7.05 (d, 2H, J=8.5 Hz), 7.12 (t, 1H, J=8.0 Hz), 7.27 (d, 2H, J=8.0 Hz), 7.82 (d, 2H, J=8.5 Hz), 7.88 (d, 2H, J=8.0 Hz).

The compound had an IC$_{50}$ on hT2R14 bitter receptor of 0.188 μM.

Example 5-44

4-((4-hydroxy-N-(4-methoxybenzyl)phenylsulfonamido)methyl)-benzoic acid

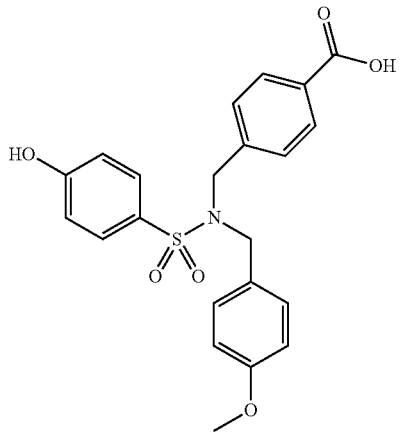 [SMILES: COc1ccc(CN(Cc2ccc(C(=O)O)cc2)S(=O)(=O)c2ccc(O)cc2)cc1]

Prepared as in example 5-42 from (4-methoxyphenyl)methanamine and methyl 4-(bromomethyl)benzoate. MS (M−H, 426.10); $^1$H NMR (400 MHz, acetone-d6): δ, ppm: 3.73 (s, 3H), 4.27 (s, 2H), 4.35 (s, 2H), 6.76 (d, 2H, J=8.0 Hz), 7.04 (d, 4H), 7.24 (d, 2H, J=7.8 Hz), 7.79 (d, 2H, J=8.2 Hz), 7.88 (d, 2H, J=7.8 Hz).

The compound had an IC$_{50}$ on hT2R14 bitter receptor of 3.43 μM.

Example 5-45

4-((N-(3-fluorobenzyl)-4-hydroxyphenylsulfonamido)methyl)benzoic acid

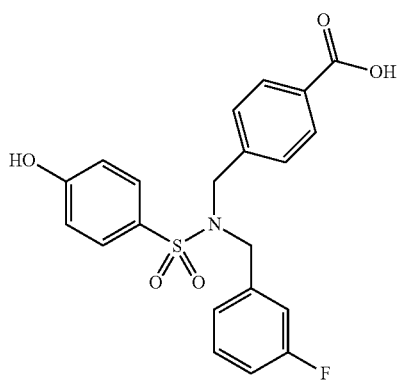 [SMILES: O=C(O)c1ccc(CN(Cc2cccc(F)c2)S(=O)(=O)c2ccc(O)cc2)cc1]

Prepared as in example 5-42 from (3-fluorophenyl)methanamine and methyl 4-(bromomethyl)benzoate. MS (M−H, 414.1), $^1$H NMR (400 MHz, acetone-d6): δ, ppm: 4.37 (s, 2H), 4.42 (s, 2H), 6.94 (m, 3H), 7.06 (d, 2H, J=8.3 Hz), 7.21 (m, 1H), 7.28 (d, 2H, J=7.6 Hz), 7.81 (d, 2H, J=8.3 Hz), 7.87 (d, 2H, J=7.6 Hz).

The compound had an IC$_{50}$ on hT2R14 bitter receptor of 0.459 μM.

Example 5-46

N-benzyl-N-(4-methoxybenzyl)-4-(1H-tetrazol-5-yl)benzene-sulfonamide

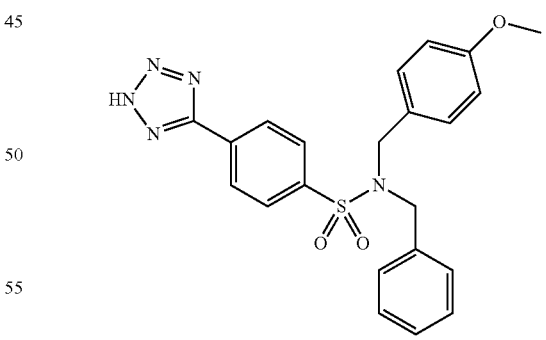

N-benzyl-4-cyano-N-(4-methoxybenzyl)benzenesulfonamide (example 5-46a, 400 mg, 1 mmol) and trimethyltin azide (400 mg, 2 mmol) were dissolved in toluene (10 mL) and microwaved at 150° C. for 3 hours. An additional 2 equivalents of trimethyltin azide were added and the reaction was microwaved at 150° C. for another 3 hr. The mixture was cooled and filtered to give crude tin tetrazole which was hydrolyzed in MeOH/conc HCl (50 mL:20 mL). Water was added and the resulting precipitate was collected by filtration.

The product was recrystallized with absolute ethanol and water to provide N-benzyl-N-(4-methoxybenzyl)-4-(1H-tetrazol-5-yl)benzene-sulfonamide as a white solid. MS (M+H, 436.10); ¹H NMR (400 MHz, DMSO-d6): δ, ppm: 3.65(s, 3H), 4.27(s, 2H), 4.30(s, 2H), 6.75(d, J=8.4 Hz, 2H), 6.98(d, J=8.4 Hz, 2H), 7.08(m, 2H), 7.20(m, 3H), 8.05(d, J=8.4 Hz, 2H), 8.22(d, J=9.2 Hz, 2H).

The compound had an $IC_{50}$ on hT2R14 bitter receptor of 3.67 μM.

Example 5-46a

N-benzyl-4-cyano-N-(4-methoxybenzyl)benzene-sulfonamide 4-cyanobenzene-1-sulfonyl chloride (600 mg, 3 mmol) was added to a solution of N-benzyl-1-(4-methoxyphenyl)methanamine (example 5-46b, 750 mg, 3.3 mmol) and triethylamine (500 mg, 3.6 mmol) in dichloromethane (15 mL). The reaction was stirred at ambient temperature for 4 hours then concentrated on the rotovap. The crude was purified on silica gel to afford N-benzyl-4-cyano-N-(4-methoxybenzyl)benzene-sulfonamide as a white solid. ¹H NMR (400 MHz, DMSO-d6): δ, ppm: 3.68(s, 3H), 4.26(s, 2H), 4.31(s, 2H), 6.75(d, J=8.4 Hz, 2H), 6.97(d, J=9.2 Hz, 2H), 7.07(m, 2H), 7.21(m, 3H), 7.98(d, J=8.4 Hz, 2H), 8.04(d, J=8.8 Hz, 2H).

Example 5-46b

N-benzyl-1-(4-methoxyphenyl)methanamine 4-methoxybenzaldehyde (5 g, 35 mmol) and benzylamine (3.8 g, 35 mmol) were added to sodium triacetoxyborohydride (10.4 g, 49 mmol) in dichloroethane (125 mL). The reaction was stirred at ambient temperature 2 hours, then concentrated. The mixture was diluted with dichloromethane (200 mL), washed with saturated aqueous sodium hydrogen carbonate (200 mL), brine (200 mL) and dried over magnesium sulfate. The crude amine was concentrated and purified by silica gel chromatography (70% ethyl acetate in hexanes) To afford N-benzyl-1-(4-methoxyphenyl)methanamine as an oil. ¹H NMR (400 MHz, DMSO-d6): δ, ppm: 3.59(s, 2H), 3.64(s, 2H), 3.71(s, 3H), 6.86(d, J=8.8 Hz, 2H), 7.28(m, 7H).

Example 5-47

2-(4-(N-benzyl-N-(4-methoxybenzyl)sulfamoyl)phenyl)acetic acid

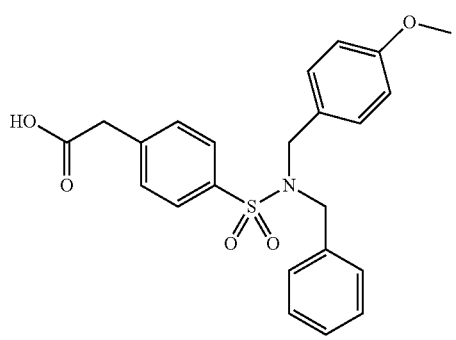 [SMILES: COc1ccc(CN(Cc2ccccc2)S(=O)(=O)c2ccc(CC(=O)O)cc2)cc1]

Prepared as in example 5-27 from Methyl 2-(4-(chlorosulfonyl)phenyl)acetate (example 5-47a), 4-methoxybenzaldehyde and benzylamine. MS (M−H, 424.10); ¹H NMR (400 MHz, DMSO-d6): δ, ppm: 3.66(s, 3H), 3.72(s, 2H), 4.18(s, 2H), 4.22(s, 2H), 6.73(d, J=8.4 Hz, 2H), 6.91(d, J=8.4 Hz, 2H), 7.02(m, 2H), 7.19(m, 3H), 7.49(d, J=8.4 Hz, 2H), 7.80 (d, J=8 Hz, 2H).

Example 5-47a

Methyl 2-(4-(chlorosulfonyl)phenyl)acetate 2-(4-(chlorosulfonyl)phenyl)acetic acid (600 mg, 2.6 mmol) was added to thionyl chloride (3 mL) and heated at 80° C. for 1 hour. The reaction mixture was concentrated, cooled to 0° C. in an ice bath and ice cold methanol was added dropwise. The mixture was stirred for 30 minutes and concentrated to afford Methyl 2-(4-(chlorosulfonyl)phenyl)-acetate as an oil. ¹H NMR (400 MHz, DMSO-d6): δ, ppm: 3.57(s, 3H), 3.65(s, 2H), 7.21(d, J=8 Hz, 2H), 7.55(d, J=8 Hz, 2H).

Example 5-48

4-((N-benzyl-4-carboxyphenylsulfonamido)methyl)benzoic acid

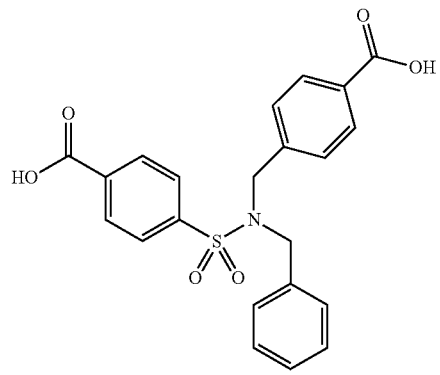 [SMILES: O=C(O)c1ccc(CN(Cc2ccccc2)S(=O)(=O)c2ccc(C(=O)O)cc2)cc1]

Prepared as in example 5-10 from methyl-4-(chlorosulfonyl)benzoate (example 5-10c), benzyl amine and methyl 4-(bromomethyl)benzoate MS (M+H, 426.10); ¹H NMR (400 MHz, DMSO-d6): δ, ppm: 4.29(s, 2H), 4.34(s, 2H), 7.03(m, 2H), 7.12(m, 2H), 7.68(d, J=8 Hz, 2H), 7.94(d, J=8.8 Hz, 2H), 8.06(d, J=8.8 Hz, 2H), 13.03(s, 2H).

Example 5-49

4-(benzyl(4-methoxybenzyl)carbamoyl)benzoic acid

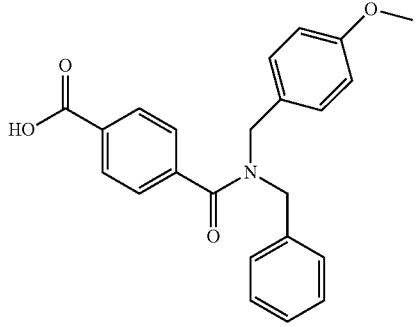 [SMILES: COc1ccc(CN(Cc2ccccc2)C(=O)c2ccc(C(=O)O)cc2)cc1]

Prepared as in example 5-27 from 4-(chlorocarbonyl)benzoate and N-benzyl-1-(4-methoxyphenyl)methanamine. ¹H NMR (400 MHz, DMSO-d6): δ, ppm: 3.72(d, J=7.6 Hz, 3H), 4.26(s, 1H), 4.30(s, 1H), 4.50(s, 1H), 4.55(s, 1H), 6.89(m, 2H), 7.02(m, 1H), 7.10(m, 1H), 7.10(m, 1H), 7.20(m, 1H), 7.28(m, 4H), 7.55(m, 2H), 7.96(m, 2H), 13.13(s, 1H).

Example 5-50

4-(N-(4-fluoro-3-methoxybenzyl)-N-(4-methoxybenzyl)sulfamoyl)-benzoic acid

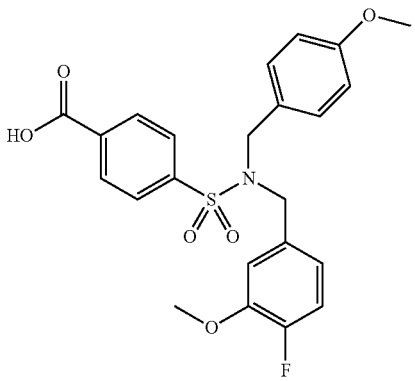 [SMILES: COc1ccc(CN(Cc2ccc(F)c(OC)c2)S(=O)(=O)c2ccc(C(=O)O)cc2)cc1]

Prepared as in example 5-10 from 4-(bromomethyl)-4-fluoro-3-methoxybenzene and methyl 4-(N-(4-methoxybenzyl)sulfamoyl)benzoate (example 5-10b). MS (M−H, 458.10); ¹H NMR (400 MHz, DMSO-d6): δ, ppm: 3.59(s, 3H), 3.67(s, 3H), 4.25(s, 2H), 4.25(s, 2H), 6.62(m, 2H), 6.77 (d, J=8.4 Hz, 2H), 7.02(m, 3H), 7.97(d, J=8 Hz, 2H), 8.01(d, J=8.8 Hz, 2H), 13.49(s, 1H).

The compound had an IC$_{50}$ on hT2R14 bitter receptor of 1.65 μM.

Additional compounds were experimentally tested and found to have a relatively high level of effectiveness as inhibitors of hT2R14 bitter receptor. The results of that testing are shown below in Table C.

TABLE C

| Compound No. | Compound | hT2R14 IC$_{50}$ (μM) |
|---|---|---|
| 5-51 | 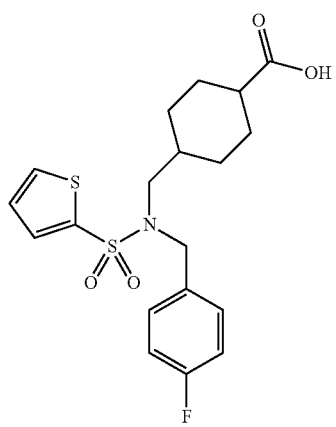 [SMILES: O=C(O)C1CCC(CN(Cc2ccc(F)cc2)S(=O)(=O)c2cccs2)CC1]<br>4-((N-(4-fluorobenzyl)thiophene-2-sulfonamido)methyl)cyclohexanecarboxylic acid | 0.342 |

TABLE C-continued
5-52 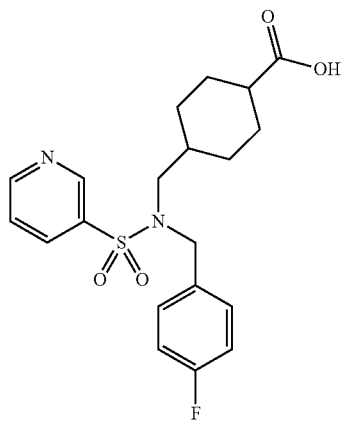 [SMILES: O=C(O)C1CCC(CN(Cc2ccc(F)cc2)S(=O)(=O)c2cccnc2)CC1] 8.434
4-((N-(4-fluorobenzyl)pyridine-3-sulfonamido)methyl)cyclohexanecarboxylic acid
5-53 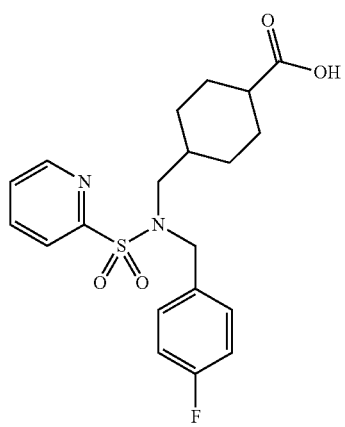 [SMILES: O=C(O)C1CCC(CN(Cc2ccc(F)cc2)S(=O)(=O)c2ccccn2)CC1]
4-((N-(4-fluorobenzyl)pyridine-2-sulfonamido)methyl)cyclohexanecarboxylic acid
5-54 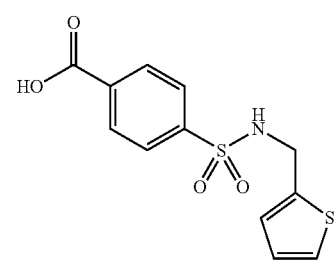 [SMILES: O=C(O)c1ccc(S(=O)(=O)NCc2cccs2)cc1]
4-(N-(furan-2-ylmethyl)sulfamoyl)benzoic acid
5-55 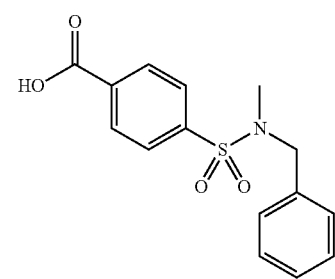 [SMILES: CN(Cc1ccccc1)S(=O)(=O)c1ccc(C(=O)O)cc1]
4-(N-benzyl-N-methylsulfamoyl)benzoic

TABLE C-continued
acid
5-56
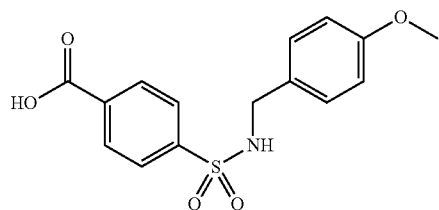 [SMILES: COc1ccc(CNS(=O)(=O)c2ccc(C(=O)O)cc2)cc1]
4-(N-(4-methoxybenzyl)sulfamoyl)benzoic
acid
5-57
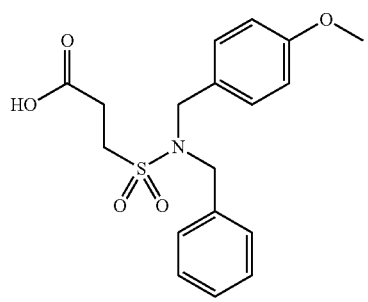 [SMILES: COc1ccc(CN(Cc2ccccc2)S(=O)(=O)CCC(=O)O)cc1]
3-(N-benzyl-N-(4-
methoxybenzyl)sulfamoyl)propanoic acid
5-58
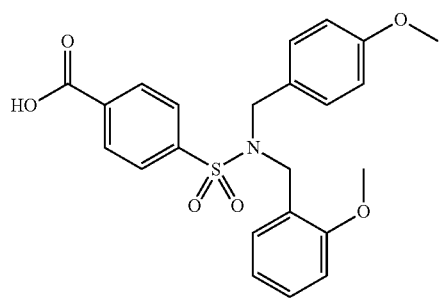 [SMILES: COc1ccc(CN(Cc2ccccc2OC)S(=O)(=O)c2ccc(C(=O)O)cc2)cc1]
2.943
4-(N-(2-methoxybenzyl)-N-(4-
methoxybenzyl)sulfamoyl)benzoic acid
5-59
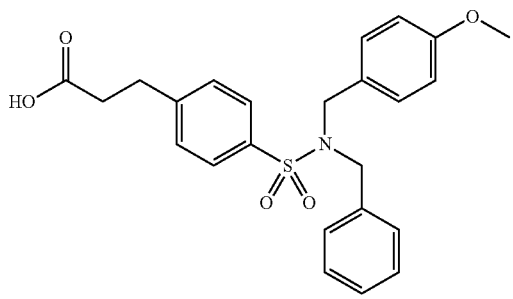 [SMILES: COc1ccc(CN(Cc2ccccc2)S(=O)(=O)c2ccc(CCC(=O)O)cc2)cc1]
3-(4-(N-benzyl-N-(4-
methoxybenzyl)sulfamoyl)phenyl)propanoic
acid TABLE C-continued
5-60
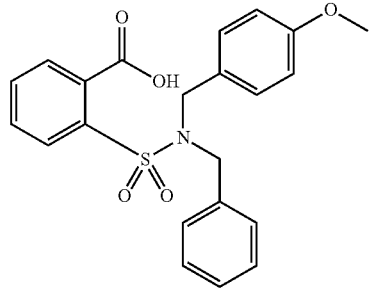 [SMILES: COc1ccc(CN(Cc2ccccc2)S(=O)(=O)c2ccccc2C(=O)O)cc1]
2-(N-benzyl-N-(4-methoxybenzyl)sulfamoyl)benzoic acid
5-61
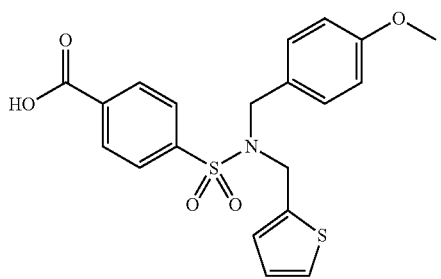 [SMILES: COc1ccc(CN(Cc2cccs2)S(=O)(=O)c2ccc(C(=O)O)cc2)cc1]
4-(N-(4-methoxybenzyl)-N-(thiophen-2-ylmethyl)sulfamoyl)benzoic acid
5-62
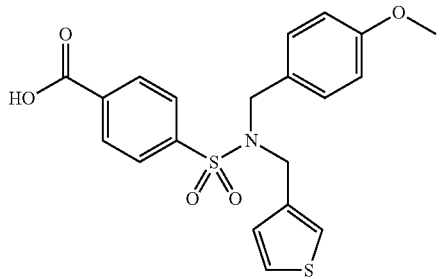 [SMILES: COc1ccc(CN(Cc2ccsc2)S(=O)(=O)c2ccc(C(=O)O)cc2)cc1]
4-(N-(4-methoxybenzyl)-N-(thiophen-3-ylmethyl)sulfamoyl)benzoic acid
5-63
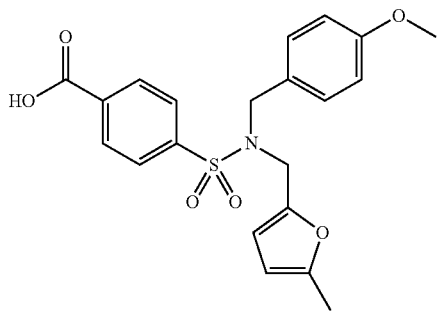 [SMILES: COc1ccc(CN(Cc2ccc(C)o2)S(=O)(=O)c2ccc(C(=O)O)cc2)cc1]
4-(N-(4-methoxybenzyl)-N-((5-methylfuran-2-yl)methyl)sulfamoyl)benzoic acid

| | | |
|---|---|---|
| 5-64 | 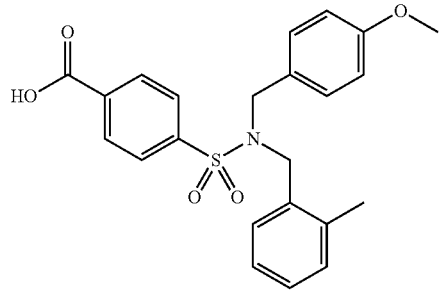 [SMILES: COc1ccc(CN(Cc2ccccc2C)S(=O)(=O)c2ccc(C(=O)O)cc2)cc1]<br>4-(N-(4-methoxybenzyl)-N-(2-methylbenzyl)sulfamoyl)benzoic acid | |
| 5-65 | 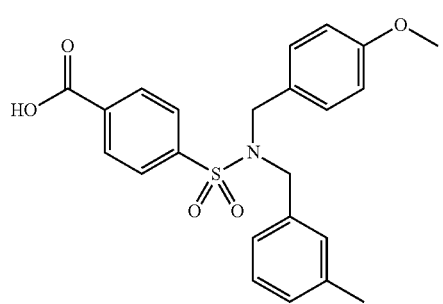 [SMILES: COc1ccc(CN(Cc2cccc(C)c2)S(=O)(=O)c2ccc(C(=O)O)cc2)cc1]<br>4-(N-(4-methoxybenzyl)-N-(3-methylbenzyl)sulfamoyl)benzoic acid | |
| 5-66 | 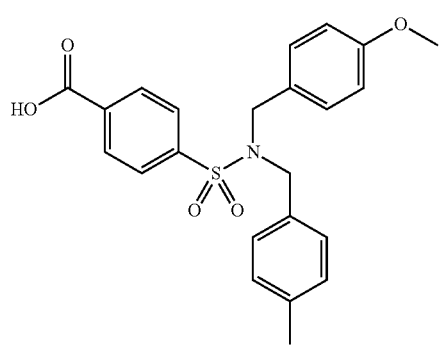 [SMILES: COc1ccc(CN(Cc2ccc(C)cc2)S(=O)(=O)c2ccc(C(=O)O)cc2)cc1]<br>4-(N-(4-methoxybenzyl)-N-(4-methylbenzyl)sulfamoyl)benzoic acid | |
| 5-67 | 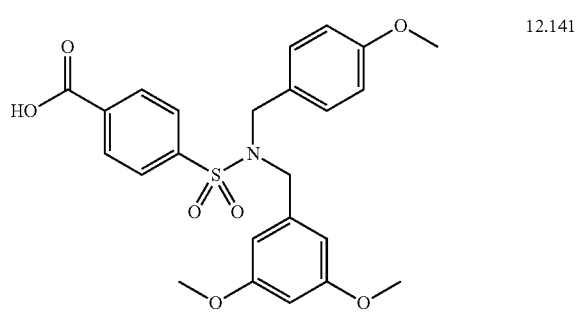<br>4-(N-(3,5-dimethoxybenzyl)-N-(4-methoxybenzyl)sulfamoyl)benzoic acid | 12.141 |

TABLE C-continued
| | | |
|---|---|---|
| 5-68 | 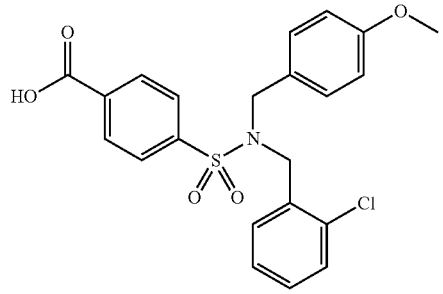 [SMILES: COc1ccc(CN(Cc2ccccc2Cl)S(=O)(=O)c2ccc(C(=O)O)cc2)cc1]<br>4-(N-(2-chlorobenzyl)-N-(4-methoxybenzyl)sulfamoyl)benzoic acid | 7.044 |
| 5-69 | 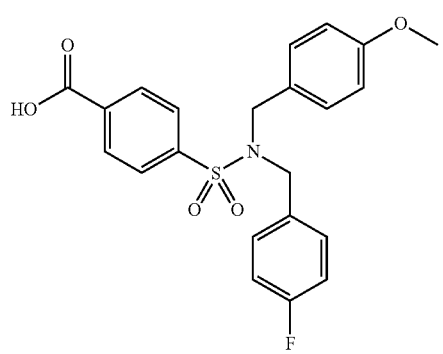 [SMILES: COc1ccc(CN(Cc2ccc(F)cc2)S(=O)(=O)c2ccc(C(=O)O)cc2)cc1]<br>4-(N-(4-fluorobenzyl)-N-(4-methoxybenzyl)sulfamoyl)benzoic acid | 8.283 |
| 5-70 | 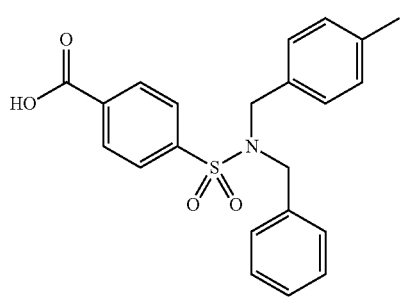 [SMILES: Cc1ccc(CN(Cc2ccccc2)S(=O)(=O)c2ccc(C(=O)O)cc2)cc1]<br>4-(N-benzyl-N-(4-methylbenzyl)sulfamoyl)benzoic acid | 5.394 |
| 5-71 | 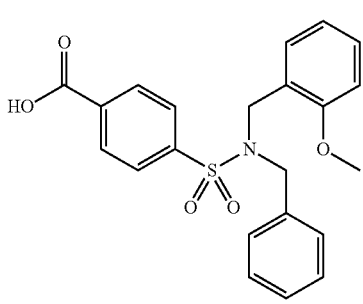 [SMILES: COc1ccccc1CN(Cc1ccccc1)S(=O)(=O)c1ccc(C(=O)O)cc1]<br>4-(N-benzyl-N-(2-methoxybenzyl)sulfamoyl)benzoic acid | 5.061 |

TABLE C-continued
5-72 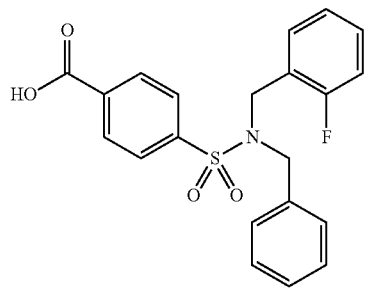 [SMILES: O=C(O)c1ccc(S(=O)(=O)N(Cc2ccccc2)Cc2ccccc2F)cc1] 6.164
4-(N-benzyl-N-(2-fluorobenzyl)sulfamoyl)benzoic acid
5-73 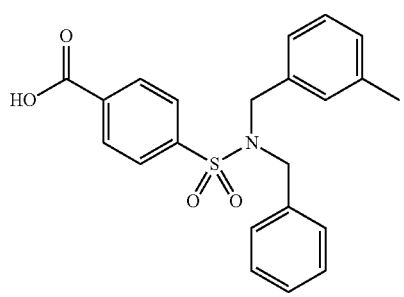 [SMILES: Cc1cccc(CN(Cc2ccccc2)S(=O)(=O)c2ccc(C(=O)O)cc2)c1] 2.290
4-(N-benzyl-N-(3-methylbenzyl)sulfamoyl)benzoic acid
5-74 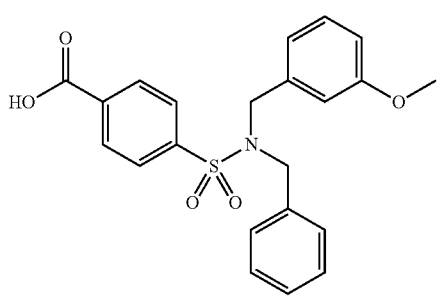 [SMILES: COc1cccc(CN(Cc2ccccc2)S(=O)(=O)c2ccc(C(=O)O)cc2)c1] 5.991
4-(N-benzyl-N-(3-methoxybenzyl)sulfamoyl)benzoic acid
5-75 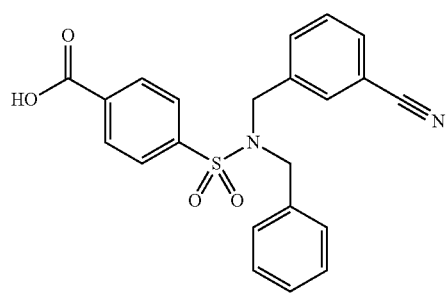 [SMILES: N#Cc1cccc(CN(Cc2ccccc2)S(=O)(=O)c2ccc(C(=O)O)cc2)c1]
4-(N-benzyl-N-(3-cyanobenzyl)sulfamoyl)benzoic acid TABLE C-continued
| | | |
|---|---|---|
| 5-76 | 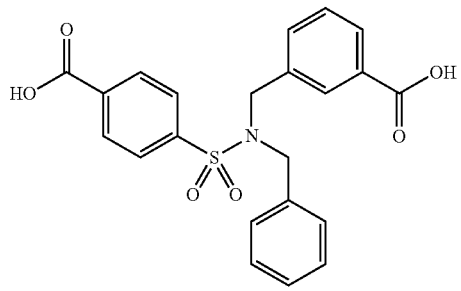 [SMILES: O=C(O)c1ccc(S(=O)(=O)N(Cc2ccccc2)Cc2cccc(C(=O)O)c2)cc1]
3-((N-benzyl-4-carboxyphenylsulfonamido)methyl)benzoic acid | |
| 5-77 | 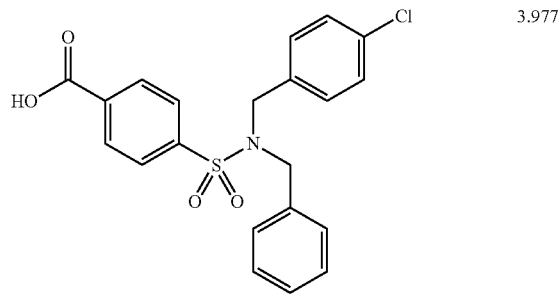
4-(N-benzyl-N-(4-chlorobenzyl)sulfamoyl)benzoic acid | 3.977 |
| 5-78 | 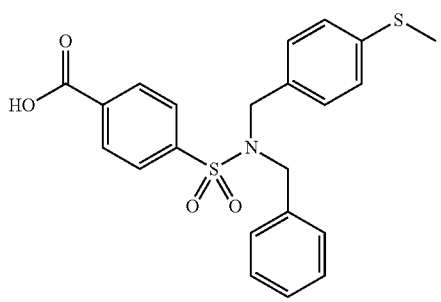 [SMILES: CSc1ccc(CN(Cc2ccccc2)S(=O)(=O)c2ccc(C(=O)O)cc2)cc1]
4-(N-benzyl-N-(4-(methylthio)benzyl)sulfamoyl)benzoic acid | 2.458 |
| 5-79 | 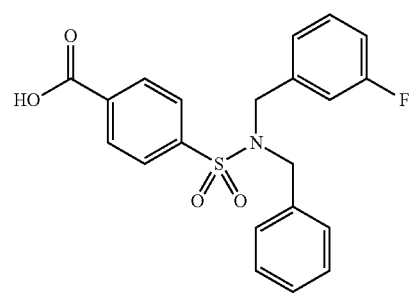
4-(N-benzyl-N-(3-fluorobenzyl)sulfamoyl)benzoic acid | 2.310 |

TABLE C-continued
| 5-80 | 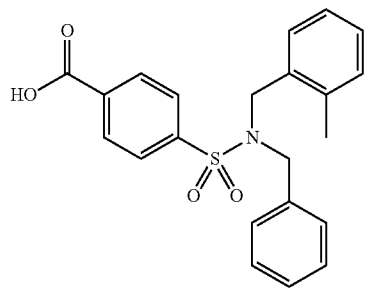 [SMILES: Cc1ccccc1CN(Cc1ccccc1)S(=O)(=O)c1ccc(C(=O)O)cc1] 4-(N-benzyl-N-(2-methylbenzyl)sulfamoyl)benzoic acid | 2.926 |
| 5-81 | 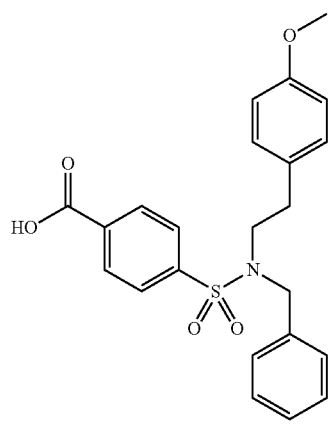 [SMILES: COc1ccc(CCN(Cc2ccccc2)S(=O)(=O)c2ccc(C(=O)O)cc2)cc1] 4-(N-benzyl-N-(4-methoxyphenethyl)sulfamoyl)benzoic acid | |
| 5-82 | 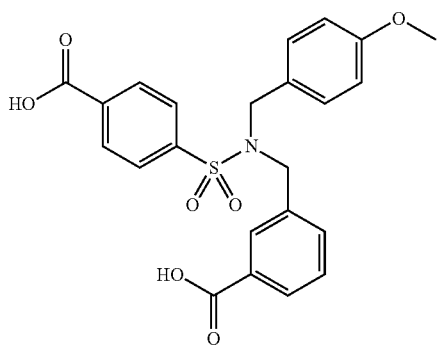 [SMILES: COc1ccc(CN(Cc2cccc(C(=O)O)c2)S(=O)(=O)c2ccc(C(=O)O)cc2)cc1] 3-((4-carboxy-N-(4-methoxybenzyl)phenylsulfonamido)methyl)benzoic acid | |
| 5-83 | 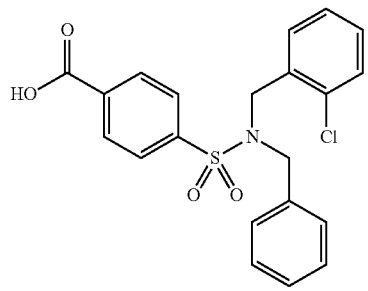 [SMILES: O=C(O)c1ccc(S(=O)(=O)N(Cc2ccccc2)Cc2ccccc2Cl)cc1] 4-(N-benzyl-N-(2-chlorobenzyl)sulfamoyl)benzoic acid | 4.486 |

TABLE C-continued
| | | |
|---|---|---|
| 5-84 | 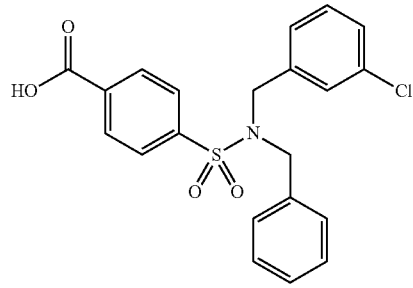 [SMILES: O=C(O)c1ccc(S(=O)(=O)N(Cc2ccccc2)Cc2cccc(Cl)c2)cc1]<br>4-(N-benzyl-N-(3-chlorobenzyl)sulfamoyl)benzoic acid | 4.286 |
| 5-85 | 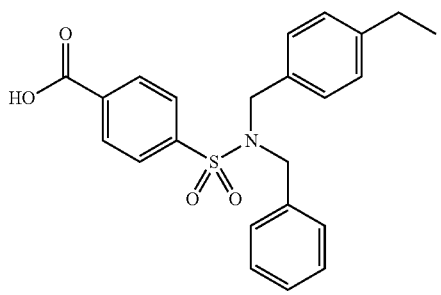 [SMILES: CCc1ccc(CN(Cc2ccccc2)S(=O)(=O)c2ccc(C(=O)O)cc2)cc1]<br>4-(N-benzyl-N-(4-ethylbenzyl)sulfamoyl)benzoic acid | 8.580 |
| 5-86 | 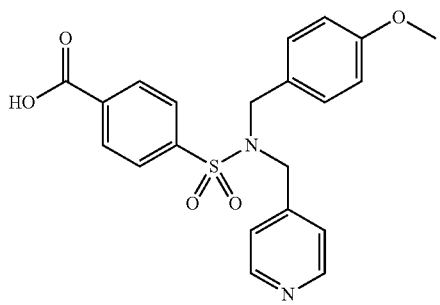 [SMILES: COc1ccc(CN(Cc2ccncc2)S(=O)(=O)c2ccc(C(=O)O)cc2)cc1]<br>4-(N-(4-methoxybenzyl)-N-(pyridin-4-ylmethyl)sulfamoyl)benzoic acid | |
| 5-87 | 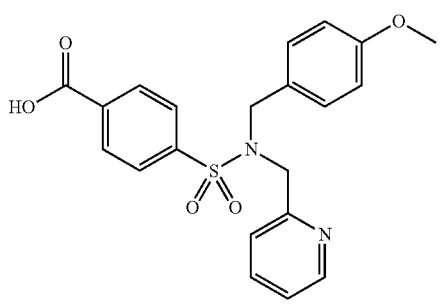 [SMILES: COc1ccc(CN(Cc2ccccn2)S(=O)(=O)c2ccc(C(=O)O)cc2)cc1]<br>4-(N-(4-methoxybenzyl)-N-(pyridin-2-ylmethyl)sulfamoyl)benzoic acid | |

TABLE C-continued
5-88
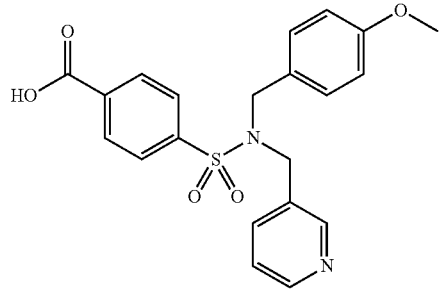 [SMILES: COc1ccc(CN(Cc2cccnc2)S(=O)(=O)c2ccc(C(=O)O)cc2)cc1]
4-(N-(4-methoxybenzyl)-N-(pyridin-3-ylmethyl)sulfamoyl)benzoic acid
5-89
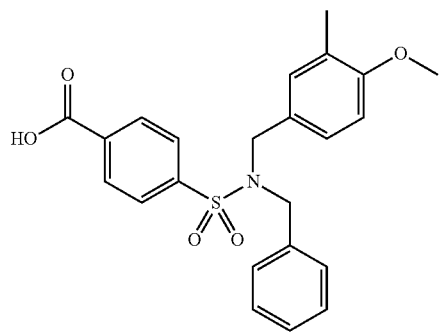 [SMILES: COc1ccc(CN(Cc2ccccc2)S(=O)(=O)c2ccc(C(=O)O)cc2)cc1C]
4-(N-benzyl-N-(4-methoxy-3-methylbenzyl)sulfamoyl)benzoic acid
1.995
5-90
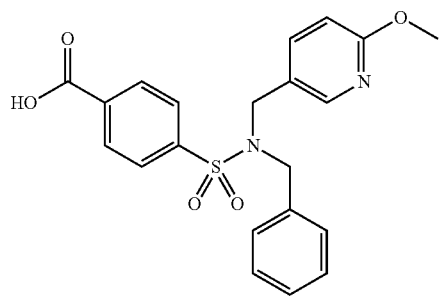 [SMILES: COc1ccc(CN(Cc2ccccc2)S(=O)(=O)c2ccc(C(=O)O)cc2)cn1]
4-(N-benzyl-N-((6-methoxypyridin-3-yl)methyl)sulfamoyl)benzoic acid
3.258
5-91
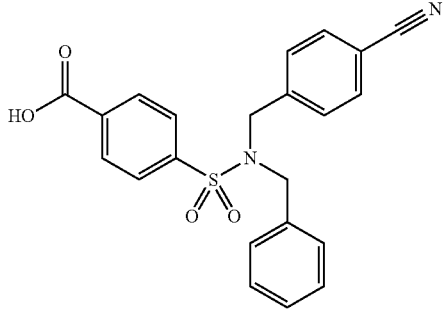 [SMILES: N#Cc1ccc(CN(Cc2ccccc2)S(=O)(=O)c2ccc(C(=O)O)cc2)cc1]
4-(N-benzyl-N-(4-cyanobenzyl)sulfamoyl)benzoic acid
1.848

| | | |
|---|---|---|
| 5-92 | 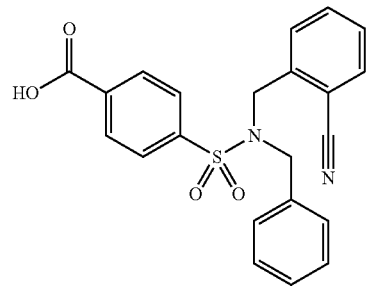 [SMILES: N#Cc1ccccc1CN(Cc1ccccc1)S(=O)(=O)c1ccc(C(=O)O)cc1]<br>4-(N-benzyl-N-(2-cyanobenzyl)sulfamoyl)benzoic acid | 4.627 |
| 5-93 | 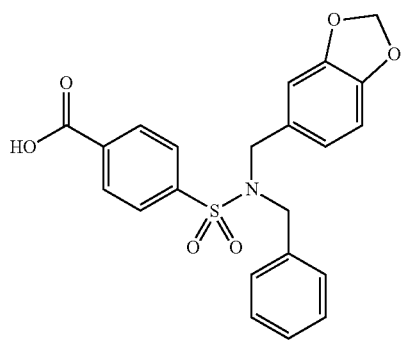 [SMILES: O=C(O)c1ccc(S(=O)(=O)N(Cc2ccccc2)Cc2ccc3c(c2)OCO3)cc1]<br>4-(N-(benzo[d][1,3]dioxol-5-ylmethyl)-N-benzylsulfamoyl)benzoic acid | 2.167 |
| 5-94 | 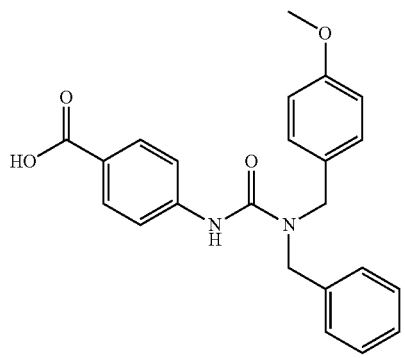 [SMILES: COc1ccc(CN(Cc2ccccc2)C(=O)Nc2ccc(C(=O)O)cc2)cc1]<br>4-(3-benzyl-3-(4-methoxybenzyl)ureido)benzoic acid | |
| 5-95 | 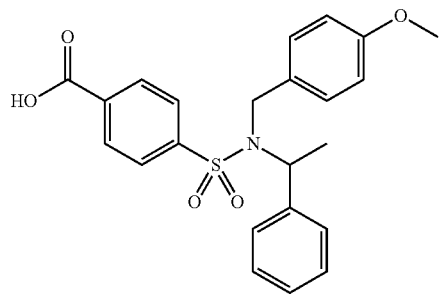 [SMILES: COc1ccc(CN(C(C)c2ccccc2)S(=O)(=O)c2ccc(C(=O)O)cc2)cc1]<br>4-(N-(4-methoxybenzyl)-N-(1-phenylethyl)sulfamoyl)benzoic acid | 1.397 |

TABLE C-continued
| | | |
|---|---|---|
| 5-96 | 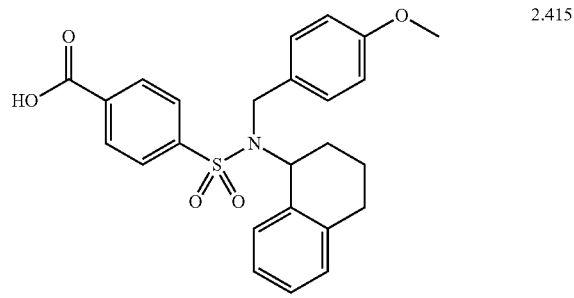<br>4-(N-(4-methoxybenzyl)-N-(1,2,3,4-tetrahydronaphthalen-1-yl)sulfamoyl)benzoic acid | 2.415 |
| 5-97 | 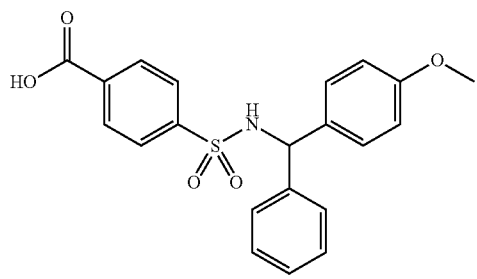 [SMILES: COc1ccc(C(NS(=O)(=O)c2ccc(C(=O)O)cc2)c2ccccc2)cc1]<br>4-(N-((4-methoxyphenyl)(phenyl)methyl)sulfamoyl)benzoic acid | |
| 5-98 | 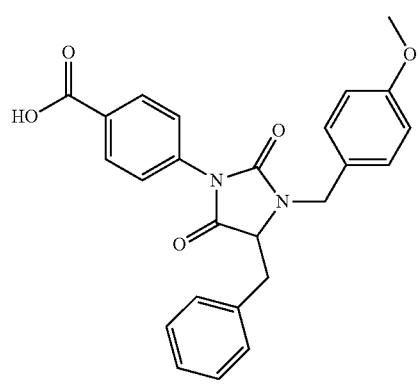 [SMILES: COc1ccc(CN2C(=O)N(c3ccc(C(=O)O)cc3)C(=O)C2Cc2ccccc2)cc1]<br>4-(4-benzyl-3-(4-methoxybenzyl)-2,5-dioxoimidazolidin-1-yl)benzoic acid | |
| 5-99 | 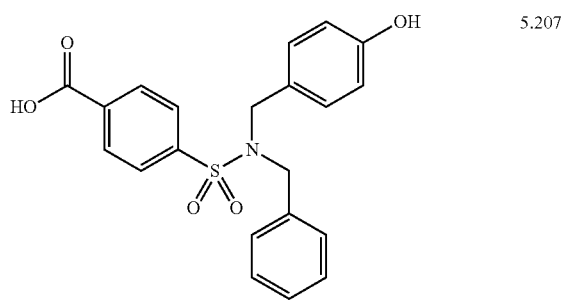<br>4-(N-benzyl-N-(4-hydroxybenzyl)sulfamoyl)benzoic acid | 5.207 |

TABLE C-continued
| | | | |
|---|---|---|---|
| 5-100 | 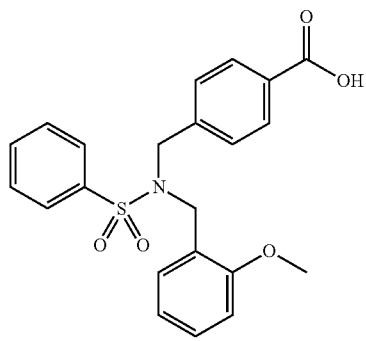 [SMILES: COc1ccccc1CN(Cc1ccc(C(=O)O)cc1)S(=O)(=O)c1ccccc1] 4-((N-(2-methoxybenzyl)phenylsulfonamido)methyl)benzoic acid | 1.294 | |
| 5-101 | 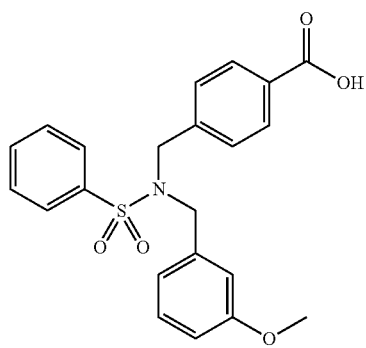 [SMILES: COc1cccc(CN(Cc2ccc(C(=O)O)cc2)S(=O)(=O)c2ccccc2)c1] 4-((N-(3-methoxybenzyl)phenylsulfonamido)methyl)benzoic acid | 0.345 | |
| 5-102 | 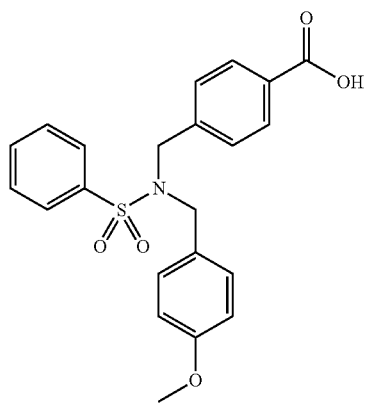 [SMILES: COc1ccc(CN(Cc2ccc(C(=O)O)cc2)S(=O)(=O)c2ccccc2)cc1] 4-((N-(4-methoxybenzyl)phenylsulfonamido)methyl)benzoic acid | 2.219 | |

TABLE C-continued
| 5-103 | 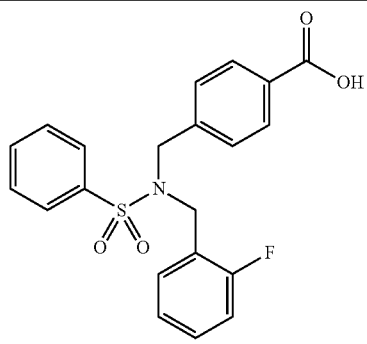 4-((N-(2-fluorobenzyl)phenylsulfonamido)methyl)-benzoic acid | 0.429 |
| --- | --- | --- |
| 5-104 | 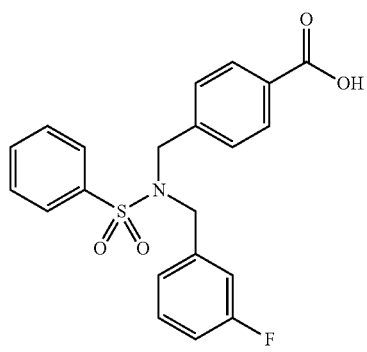 [SMILES: O=C(O)c1ccc(CN(Cc2cccc(F)c2)S(=O)(=O)c2ccccc2)cc1] 4-((N-(3-fluorobenzyl)phenylsulfonamido)methyl)-benzoic acid | 0.406 |
| 5-105 | 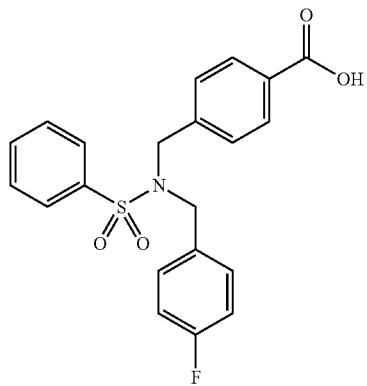 [SMILES: O=C(O)c1ccc(CN(Cc2ccc(F)cc2)S(=O)(=O)c2ccccc2)cc1] 4-((N-(4-fluorobenzyl)phenylsulfonamido)methyl)-benzoic acid | 0.935 |
| 5-106 | 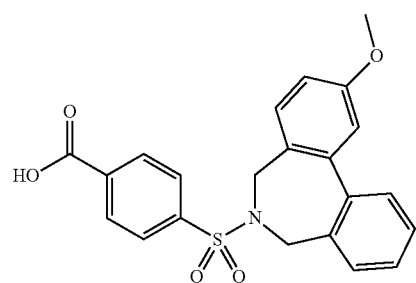 [SMILES: COc1ccc2c(c1)-c1ccccc1CN(S(=O)(=O)c1ccc(C(=O)O)cc1)C2] 4-(2-methoxy-5H-dibenzo[c,e]azepin- | |

TABLE C-continued
| | | |
|---|---|---|
| 5-107 | 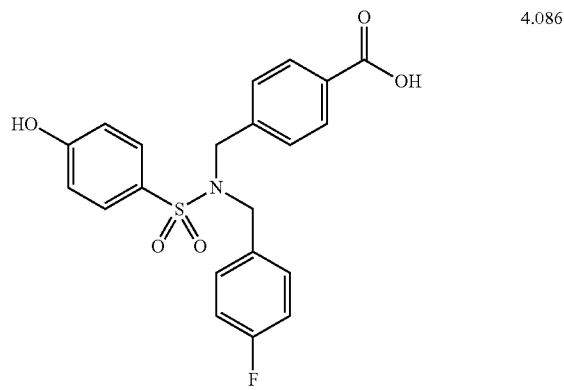<br>4-((N-(4-fluorobenzyl)-4-hydroxyphenylsulfonamido)methyl)benzoic acid | 4.086 |
| 5-108 | 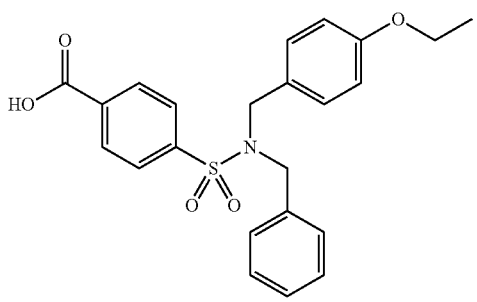 [SMILES: CCOc1ccc(CN(Cc2ccccc2)S(=O)(=O)c2ccc(C(=O)O)cc2)cc1]<br>4-(N-benzyl-N-(4-ethoxybenzyl)sulfamoyl)benzoic acid | |
| 5-109 | 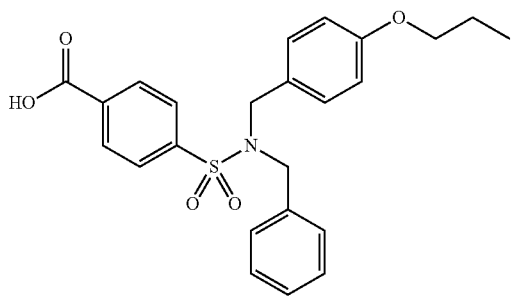 [SMILES: CCCOc1ccc(CN(Cc2ccccc2)S(=O)(=O)c2ccc(C(=O)O)cc2)cc1]<br>4-(N-benzyl-N-(4-propoxybenzyl)sulfamoyl)benzoic acid | |
| 5-110 | 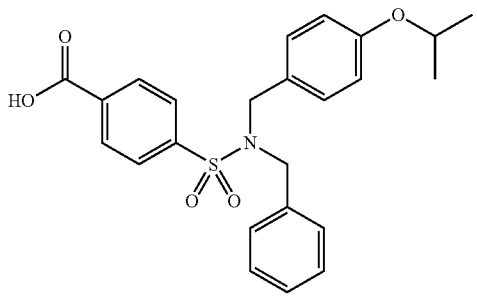 [SMILES: CC(C)Oc1ccc(CN(Cc2ccccc2)S(=O)(=O)c2ccc(C(=O)O)cc2)cc1]<br>4-(N-benzyl-N-(4-isopropoxybenzyl)sulfamoyl)benzoic acid | |

TABLE C-continued
| | | |
|---|---|---|
| 5-111 | 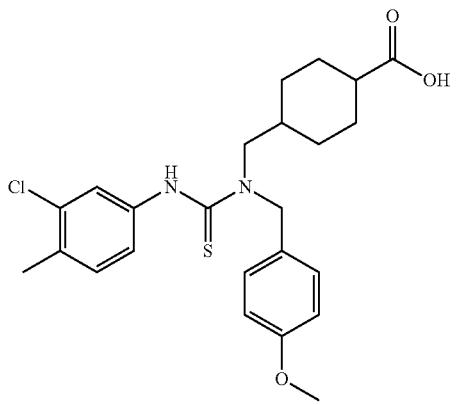 [SMILES: COc1ccc(CN(CC2CCC(C(=O)O)CC2)C(=S)Nc2ccc(C)c(Cl)c2)cc1]<br>4-((3-(3-chloro-4-methylphenyl)-1-(4-methoxybenzyl)thioureido)methyl)cyclo-hexanecarboxylic acid | 6.136 |
| 5-112 | 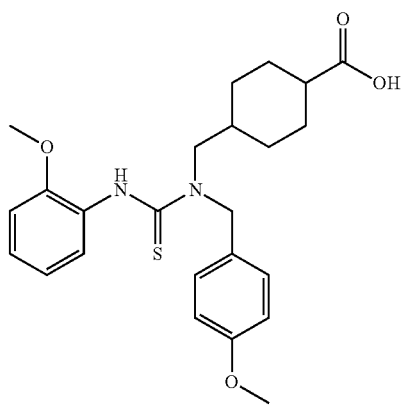 [SMILES: COc1ccc(CN(CC2CCC(C(=O)O)CC2)C(=S)Nc2ccccc2OC)cc1]<br>4-((1-(4-methoxybenzyl)-3-(2-methoxyphenyl)thioureido)methyl)cyclo-hexanecarboxylic acid | 8.852 |
| 5-113 | 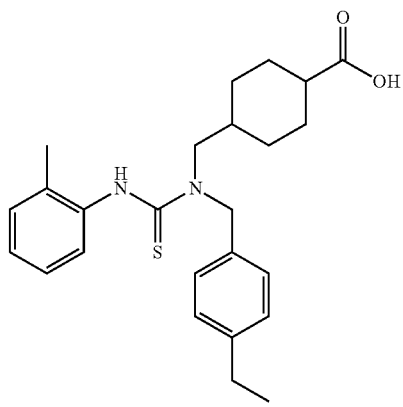 [SMILES: CCc1ccc(CN(CC2CCC(C(=O)O)CC2)C(=S)Nc2ccccc2C)cc1]<br>4-((1-(4-ethylbenzyl)-3-o-tolylthioureido)methyl)cyclohexanecarboxylic acid | 5.018 |

TABLE C-continued
| | | |
|---|---|---|
| 5-114 | 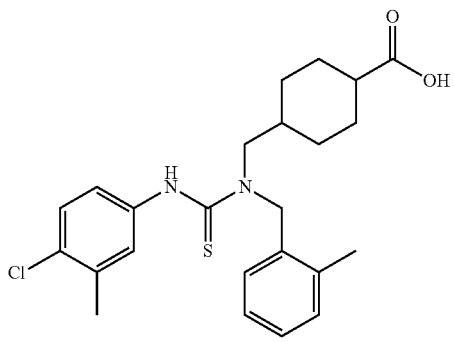 [SMILES: Cc1cc(NC(=S)N(Cc2ccccc2C)CC2CCC(C(=O)O)CC2)ccc1Cl]
4-((3-(4-chloro-3-methylphenyl)-1-(2-methylbenzyl)thioureido)methyl)cyclo-hexanecarboxylic acid | 4.872 |
| 5-115 | 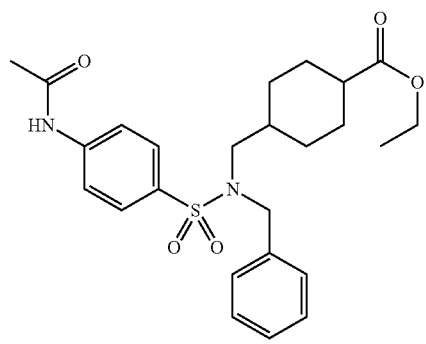 [SMILES: CCOC(=O)C1CCC(CN(Cc2ccccc2)S(=O)(=O)c2ccc(NC(C)=O)cc2)CC1]
ethyl 4-((4-acetamido-N-benzylphenylsulfonamido)methyl)cyclo-hexanecarboxylate | 0.334 |
| 5-116 | 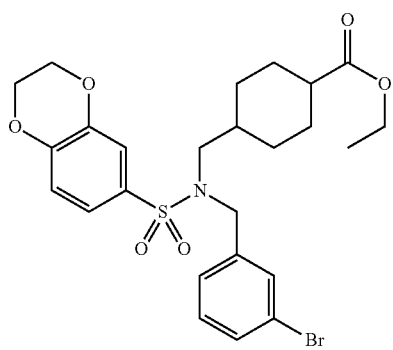 [SMILES: CCOC(=O)C1CCC(CN(Cc2cccc(Br)c2)S(=O)(=O)c2ccc3c(c2)OCCO3)CC1]
ethyl 4-((N-(3-bromobenzyl)-2,3-dihydrobenzo[b][1,4]dioxine-6-sulfonamido)methyl)cyclohexanecarboxylate | 2.567 |
| 5-117 | 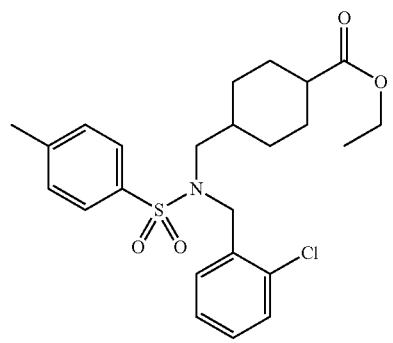 [SMILES: CCOC(=O)C1CCC(CN(Cc2ccccc2Cl)S(=O)(=O)c2ccc(C)cc2)CC1] | 2.816 |

TABLE C-continued
| | | |
|---|---|---|
| | ethyl 4-((N-(2-chlorobenzyl)-4-methylphenylsulfonamido)methyl)cyclohexanecarboxylate | |
| 5-118 | 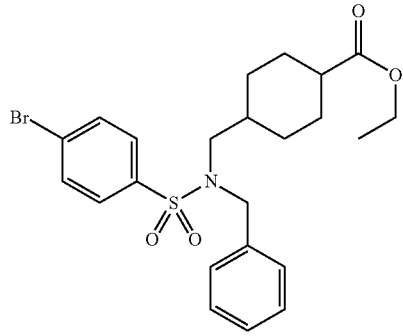 | 2.344 |
| | ethyl 4-((N-benzyl-4-bromophenylsulfonamido)methyl)cyclohexanecarboxylate | |
| 5-119 | 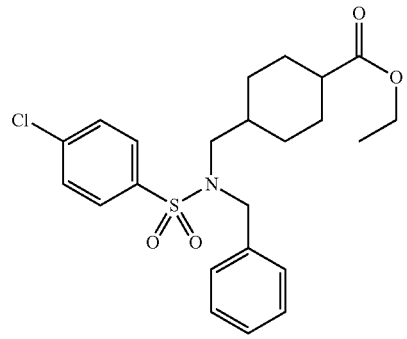 [SMILES: CCOC(=O)C1CCC(CN(Cc2ccccc2)S(=O)(=O)c2ccc(Cl)cc2)CC1] | 0.672 |
| | ethyl 4-((N-benzyl-4-chlorophenylsulfonamido)methyl)cyclohexanecarboxylate | |
| 5-120 | 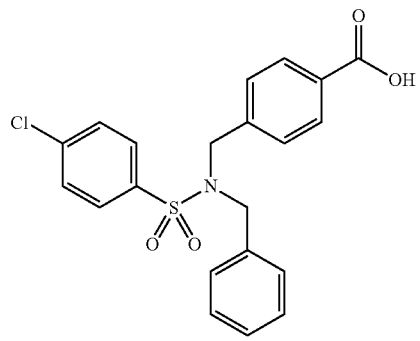 [SMILES: O=C(O)c1ccc(CN(Cc2ccccc2)S(=O)(=O)c2ccc(Cl)cc2)cc1] | 0.394 |
| | 4-((N-benzyl-4-chlorophenylsulfonamido)methyl)benzoic acid | |
| 5-121 | 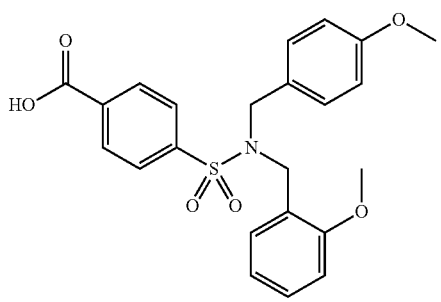 [SMILES: COc1ccc(CN(Cc2ccccc2OC)S(=O)(=O)c2ccc(C(=O)O)cc2)cc1] | 2.943 |

TABLE C-continued
| | | |
|---|---|---|
| 5-122 | 4-(N-(2-methoxybenzyl)-N-(4-methoxybenzyl)sulfamoyl)benzoic acid | 2.219 |
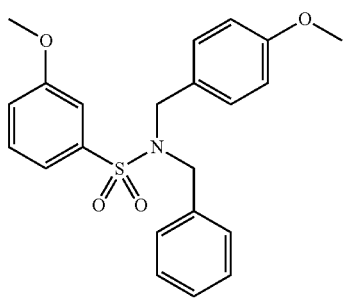 [SMILES: COc1ccc(CN(Cc2ccccc2)S(=O)(=O)c2cccc(OC)c2)cc1]
N-benzyl-3-methoxy-N-(4-methoxybenzyl)benzenesulfonamide
| | | |
|---|---|---|
| 5-123 | | 0.092 |
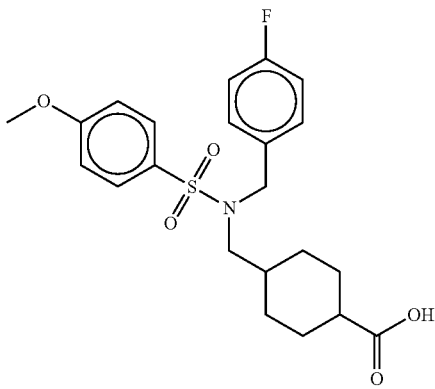
4-((N-(4-fluorobenzyl)-4-methoxyphenylsulfonamido)methyl)cyclohexanecarboxylic acid
| | | |
|---|---|---|
| 5-124 | | 0.842 |
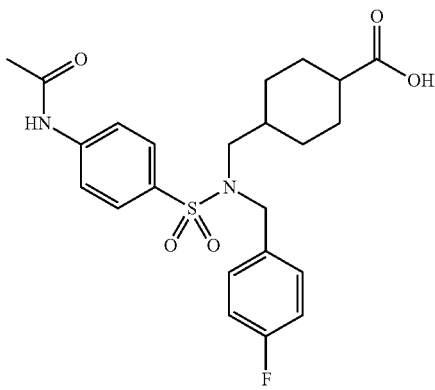 [SMILES: CC(=O)Nc1ccc(S(=O)(=O)N(Cc2ccc(F)cc2)CC2CCC(C(=O)O)CC2)cc1]
4-((4-acetamido-N-(4-fluorobenzyl)phenylsulfonamido)methyl)cyclohexanecarboxylic acid

| | | |
|---|---|---|
| 5-125 | 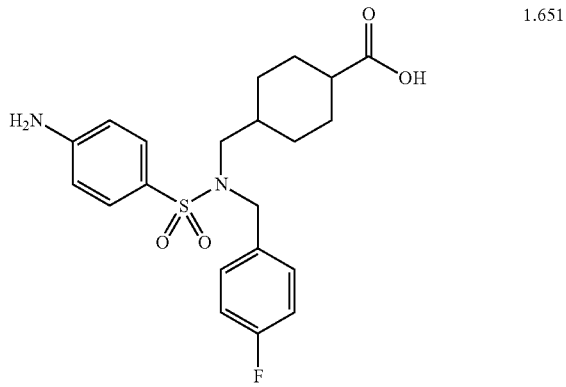<br>4-((4-amino-N-(4-fluorobenzyl)phenylsulfonamido)methyl)cyclohexanecarboxylic acid | 1.651 |
| 5-126 | 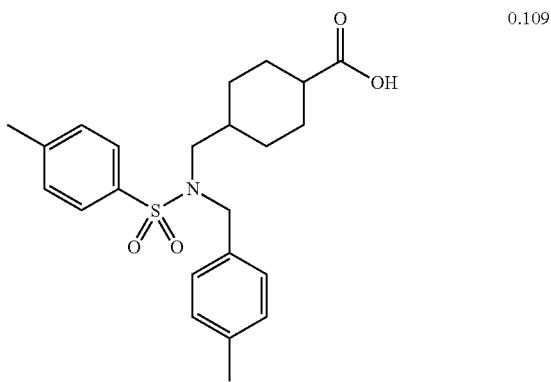<br>4-((4-methyl-N-(4-methylbenzyl)phenylsulfonamido)methyl)cyclohexanecarboxylic acid | 0.109 |
| 5-127 | 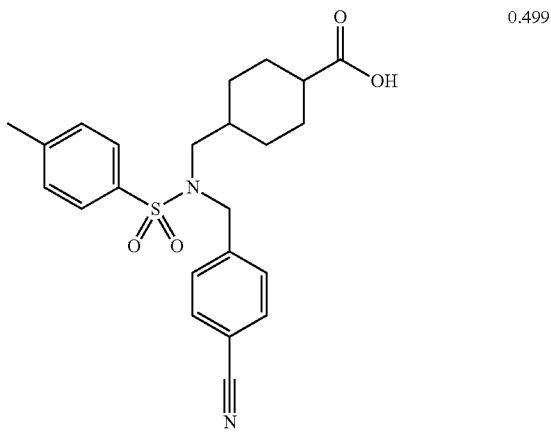<br>4-((N-(4-cyanobenzyl)-4-methylphenylsulfonamido)methyl)cyclohexanecarboxylic acid | 0.499 |

TABLE C-continued
| 5-128 | 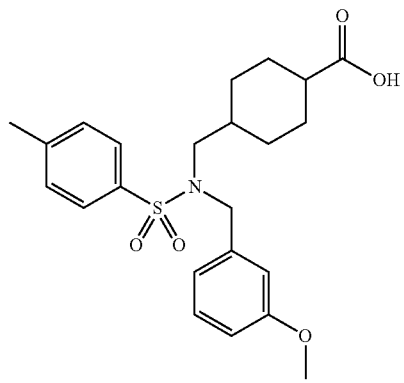 [SMILES: COc1cccc(CN(CC2CCC(C(=O)O)CC2)S(=O)(=O)c2ccc(C)cc2)c1] | 0.036 |
4-((N-(3-methoxybenzyl)-4-methylphenylsulfonamido)methyl)cyclohexanecarboxylic acid
| 5-129 | 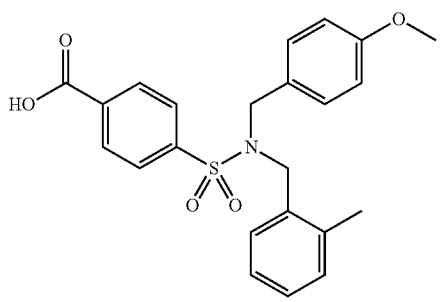 [SMILES: COc1ccc(CN(Cc2ccccc2C)S(=O)(=O)c2ccc(C(=O)O)cc2)cc1] | 5.316 |
4-(N-(4-methoxybenzyl)-N-(2-methylbenzyl)sulfamoyl)benzoic acid
| Compound No. | Compound | hT2R14 IC50 (µM) |
|---|---|---|
| 5-130 | 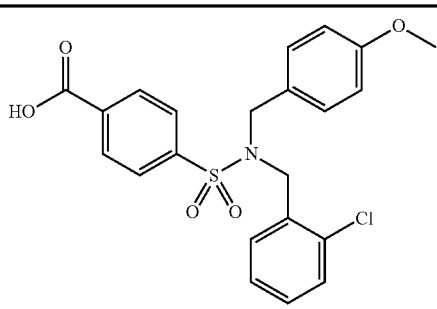 | 7.044 |
4-(N-(2-chlorobenzyl)-N-(4-methoxybenzyl)sulfamoyl)benzoic acid
| Compound No. | Compound | hT2R14 IC$_{50}$ (µM) |
|---|---|---|
| 5-131 | 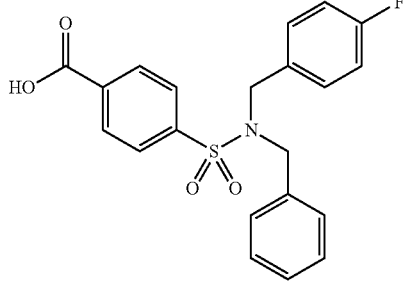 | 8.283 |

| Compound No. | Compound | hT2R14 IC50 (μM) |
|---|---|---|
| 5-132 | 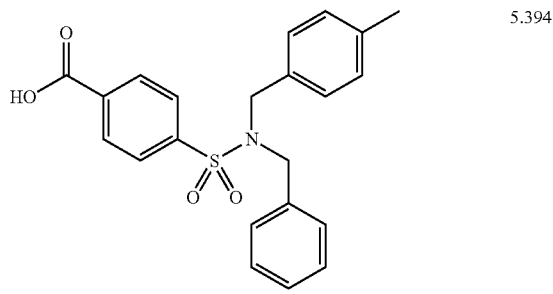 4-(N-benzyl-N-(4-methylbenzyl)sulfamoyl)benzoic acid | 5.394 |
| 5-133 | 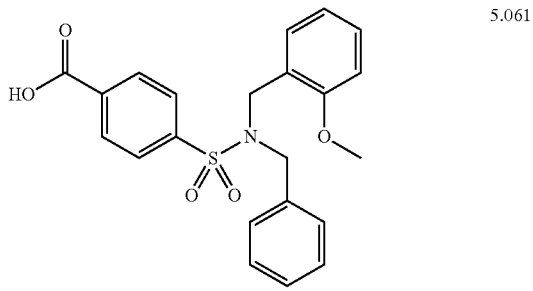 4-(N-benzyl-N-(2-methoxybenzyl)sulfamoyl)benzoic acid | 5.061 |
| Compound No. | Compound | hT2R14 IC$_{50}$ (μM) |
|---|---|---|
| 5-134 | 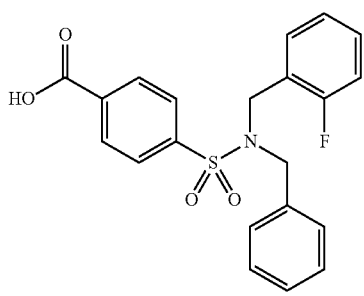 4-(N-benzyl-N-(2-fluorobenzyl)sulfamoyl)benzoic acid | 6.164 |
| Compound No. | Compound | hT2R14 IC$_{50}$ (μM) |
|---|---|---|
| 5-135 | 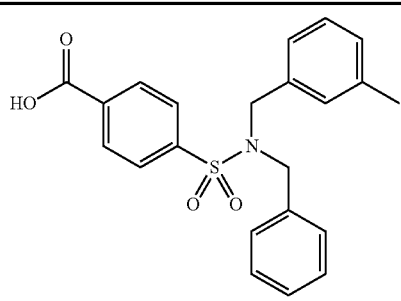 4-(N-benzyl-N-(3-methylbenzyl)sulfamoyl)benzoic acid | 2.290 |

TABLE C-continued
| | | |
|---|---|---|
| 5-136 | 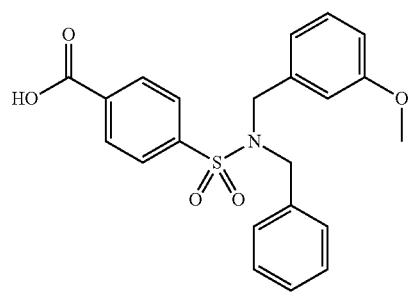 [SMILES: COc1cccc(CN(Cc2ccccc2)S(=O)(=O)c2ccc(C(=O)O)cc2)c1] 4-(N-benzyl-N-(3-methoxybenzyl)sulfamoyl)benzoic acid | 5.991 |
| 5-137 | 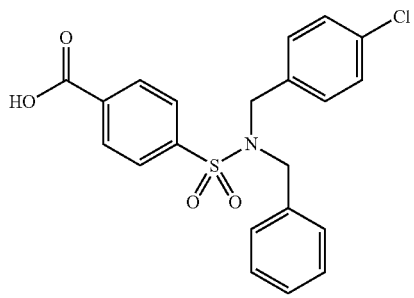 [SMILES: O=C(O)c1ccc(S(=O)(=O)N(Cc2ccccc2)Cc2ccc(Cl)cc2)cc1] 4-(N-benzyl-N-(4-chlorobenzyl)sulfamoyl)benzoic acid | 3.977 |
| Compound No. | Compound | hT2R14 IC50 (μM) |
|---|---|---|
| 5-138 | 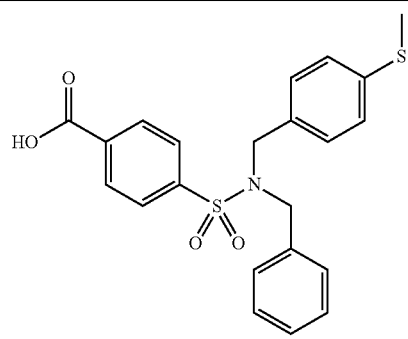 4-(N-benzyl-N-(4-(methylthio)benzyl)sulfamoyl)benzoic acid | 2.458 |
| Compound No. | Compound | hT2R14 IC$_{50}$ (μM) |
|---|---|---|
| 5-139 | 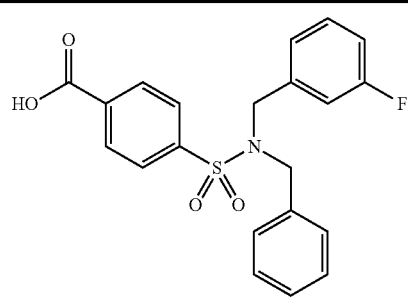 4-(N-benzyl-N-(3-fluorobenzyl)sulfamoyl)benzoic acid | 2.310 |

TABLE C-continued
| 5-140 | 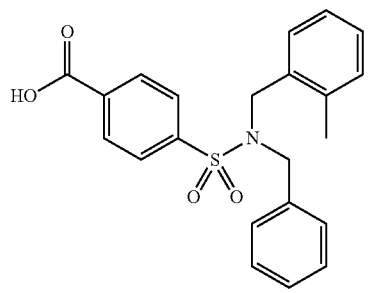 [SMILES: Cc1ccccc1CN(Cc1ccccc1)S(=O)(=O)c1ccc(C(=O)O)cc1] 4-(N-benzyl-N-(2-methylbenzyl)sulfamoyl)benzoic acid | 2.926 |
|---|---|---|
| 5-141 | 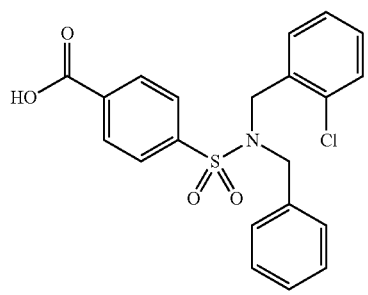 [SMILES: O=C(O)c1ccc(S(=O)(=O)N(Cc2ccccc2)Cc2ccccc2Cl)cc1] 4-(N-benzyl-N-(2-chlorobenzyl)sulfamoyl)benzoic acid | 4.486 |
| Compound No. | Compound | hT2R14 IC50 (μM) |
|---|---|---|
| 5-142 | 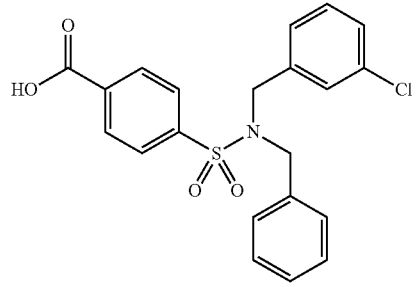 [SMILES: O=C(O)c1ccc(S(=O)(=O)N(Cc2ccccc2)Cc2cccc(Cl)c2)cc1] 4-(N-benzyl-N-(3-chlorobenzyl)sulfamoyl)benzoic acid | 4.286 |
| Compound No. | Compound | hT2R14 IC$_{50}$ (μM) |
|---|---|---|
| 5-143 | 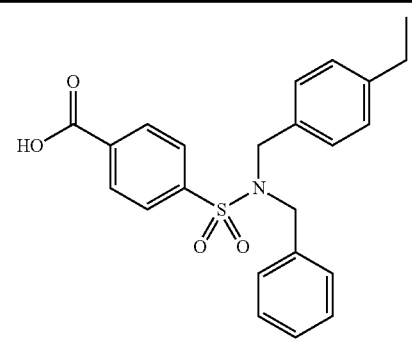 4-(N-benzyl-N-(4-ethylbenzyl)sulfamoyl)benzoic acid | 8.580 |

TABLE C-continued
| Compound No. | Compound | hT2R14 IC50 (μM) |
|---|---|---|
| 5-144 | 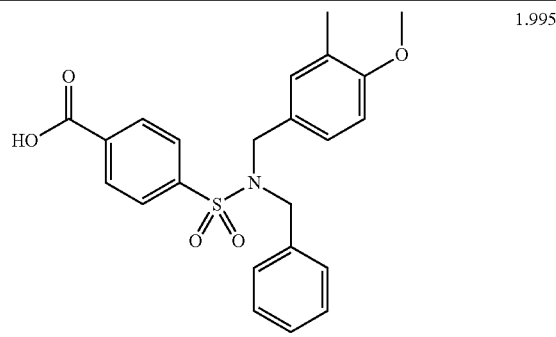<br>4-(N-benzyl-N-(4-methoxy-3-methylbenzyl)sulfamoyl)benzoic acid | 1.995 |
| 5-145 | 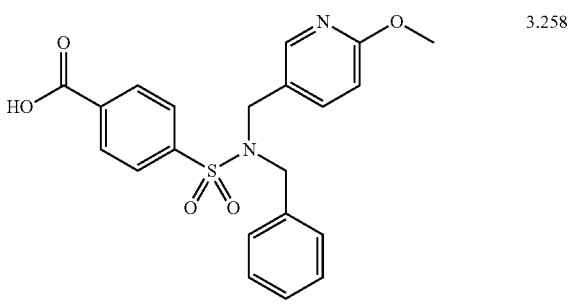<br>4-(N-benzyl-N-((6-methoxypyridin-3-yl)methyl)sulfamoyl)benzoic acid | 3.258 |
| Compound No. | Compound | hT2R14 IC50 (μM) |
|---|---|---|
| 5-146 | 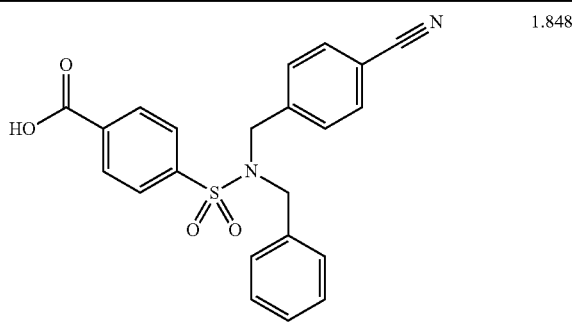<br>4-(N-benzyl-N-(4-cyanobenzyl)sulfamoyl)benzoic acid | 1.848 |
| Compound No. | Compound | hT2R14 IC$_{50}$ (μM) |
|---|---|---|
| 5-147 | 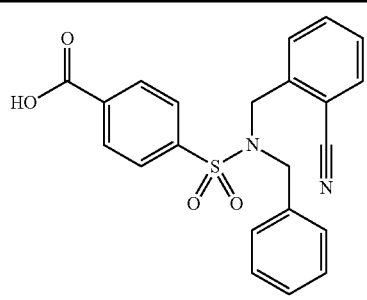<br>4-(N-benzyl-N-(2-cyanobenzyl)sulfamoyl)benzoic acid | 4.627 |

TABLE C-continued
| | | |
|---|---|---|
| 5-148 | 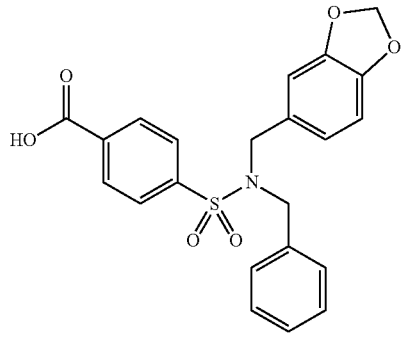 [SMILES: O=C(O)c1ccc(S(=O)(=O)N(Cc2ccccc2)Cc2ccc3c(c2)OCO3)cc1]<br>4-(N-(benzo[d][1,3]dioxol-5-ylmethyl)-N-benzylsulfamoyl)benzoic acid | 2.167 |
| 5-149 | 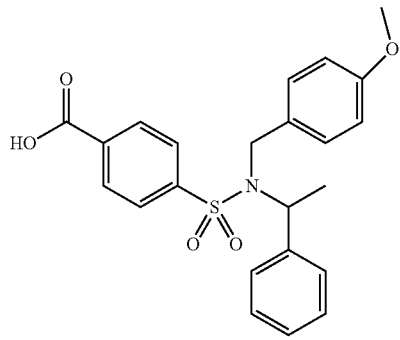 [SMILES: COc1ccc(CN(C(C)c2ccccc2)S(=O)(=O)c2ccc(C(=O)O)cc2)cc1]<br>4-(N-(4-methoxybenzyl)-N-(1-phenylethyl)sulfamoyl)benzoic acid | 1.397 |
| Compound No. | Compound | hT2R14 IC50 (μM) |
|---|---|---|
| 5-150 | 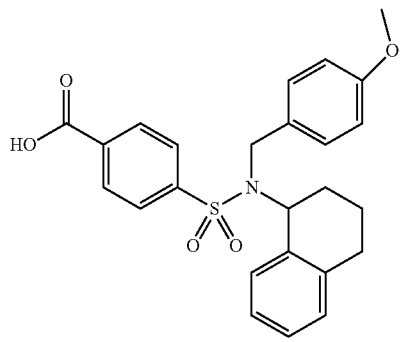 [SMILES: COc1ccc(CN(C2CCCc3ccccc32)S(=O)(=O)c2ccc(C(=O)O)cc2)cc1]<br>4-(N-(4-methoxybenzyl)-N-(1,2,3,4-tetrahydronaphthalen-1-yl)sulfamoyl)benzoic acid | 2.415 |
| Compound No. | Compound | hT2R14 IC$_{50}$ (μM) |
|---|---|---|
| 5-151 | 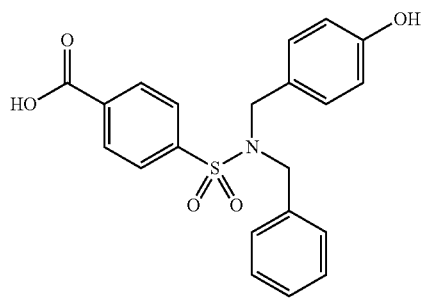 [SMILES: O=C(O)c1ccc(S(=O)(=O)N(Cc2ccccc2)Cc2ccc(O)cc2)cc1] | 5.207 |

TABLE C-continued
4-(N-benzyl-N-(4-hydroxybenzyl)sulfamoyl)benzoic acid
| 5-152 | 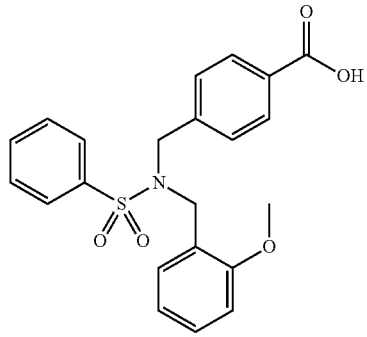 [SMILES: COc1ccccc1CN(Cc1ccc(C(=O)O)cc1)S(=O)(=O)c1ccccc1] | 1.294 |
4-((N-(2-methoxybenzyl)phenylsulfonamido)methyl)benzoic acid
| Compound No. | Compound | hT2R14 IC50 (µM) |
| 5-153 | 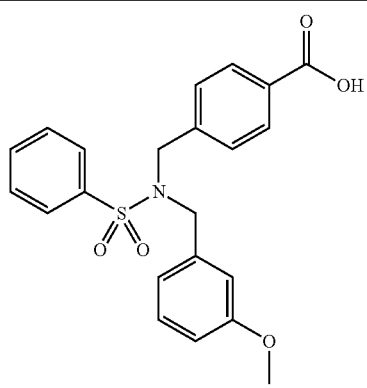 | 0.345 |
4-((N-(3-methoxybenzyl)phenylsulfonamido)methyl)benzoic acid
| Compound No. | Compound | hT2R14 $IC_{50}$ (µM) |
| 5-154 | 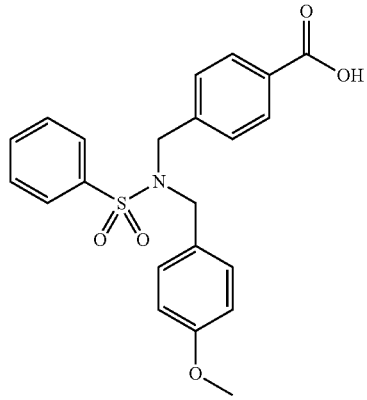 [SMILES: COc1ccc(CN(Cc2ccc(C(=O)O)cc2)S(=O)(=O)c2ccccc2)cc1] | 2.219 |
4-((N-(4-methoxybenzyl)phenylsulfonamido)methyl)benzoic acid TABLE C-continued
| 5-155 | 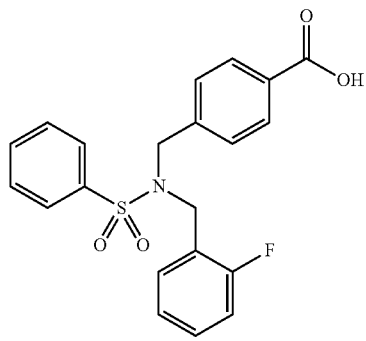 [SMILES: O=C(O)c1ccc(CN(Cc2ccccc2F)S(=O)(=O)c2ccccc2)cc1] 4-((N-(2-fluorobenzyl)phenylsulfonamido)methyl)benzoic acid | 0.429 |
| Compound No. | Compound | hT2R14 IC50 (μM) |
|---|---|---|
| 5-156 | 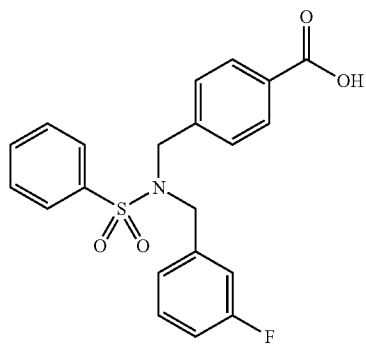 [SMILES: O=C(O)c1ccc(CN(Cc2cccc(F)c2)S(=O)(=O)c2ccccc2)cc1] 4-((N-(3-fluorobenzyl)phenylsulfonamido)methyl)benzoic acid | 0.406 |
| Compound No. | Compound | hT2R14 IC$_{50}$ (μM) |
|---|---|---|
| 5-157 | 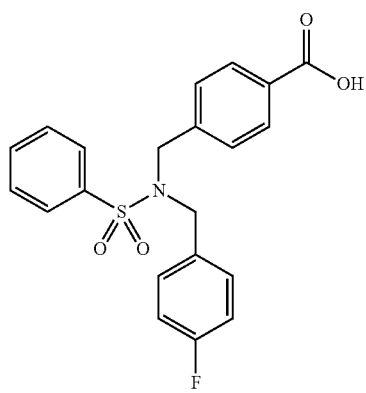 [SMILES: O=C(O)c1ccc(CN(Cc2ccc(F)cc2)S(=O)(=O)c2ccccc2)cc1] 4-((N-(4-fluorobenzyl)phenylsulfonamido)methyl)benzoic acid | 0.935 |

TABLE C-continued
| 5-158 | 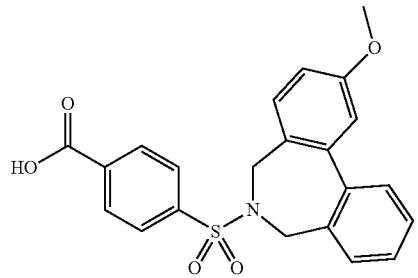 [SMILES: COc1ccc2c(c1)-c1ccccc1CN(S(=O)(=O)c1ccc(C(=O)O)cc1)C2] | 3.571 |
|---|---|---|
| | 4-(2-methoxy-5H-dibenzo[c,e]azepin-6(7H)-ylsulfonyl)benzoic acid | |
| Compound No. | Compound | hT2R14 IC50 (μM) |
|---|---|---|
| 5-159 | 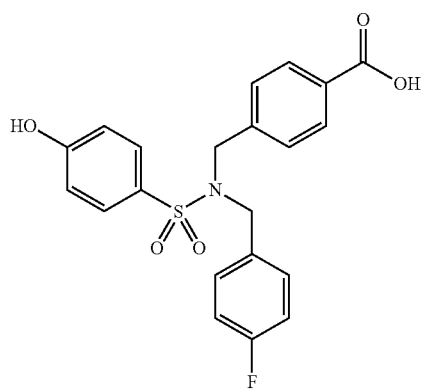 [SMILES: O=C(O)c1ccc(CN(Cc2ccc(F)cc2)S(=O)(=O)c2ccc(O)cc2)cc1] | 4.086 |
| | 4-((N-(4-fluorobenzyl)-4-hydroxyphenylsulfonamido)methyl)benzoic acid | |
| 5-160 | 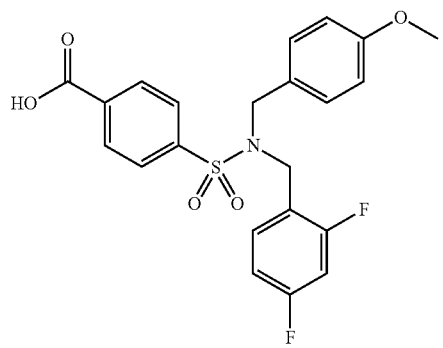 [SMILES: COc1ccc(CN(Cc2ccc(F)cc2F)S(=O)(=O)c2ccc(C(=O)O)cc2)cc1] | 1.255 |
| | 4-(N-(2,4-difluorobenzyl)-N-(4-methoxybenzyl)sulfamoyl)benzoic acid | |

TABLE C-continued
| Compound No. | Compound | hT2R14 IC$_{50}$ (μM) |
|---|---|---|
| 5-161 | 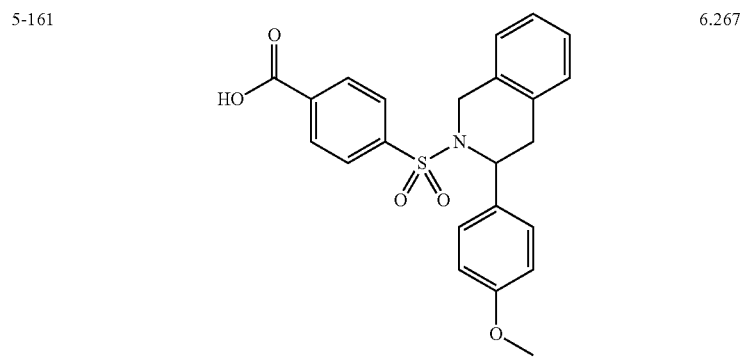<br>4-(3-(4-methoxyphenyl)-3,4-dihydroisoquinolin-2(1H)-ylsulfonyl)benzoic acid | 6.267 |
| Compound No. | Compound | hT2R14 IC50 (μM) |
|---|---|---|
| 5-162 | 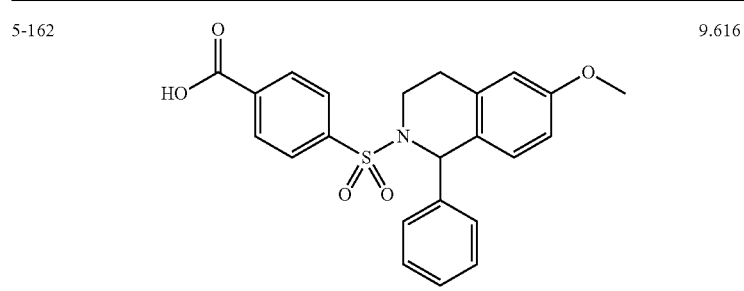<br>4-(6-methoxy-1-phenyl-3,4-dihydroisoquinolin-2(1H)-ylsulfonyl)benzoic acid | 9.616 |
| 5-163 | 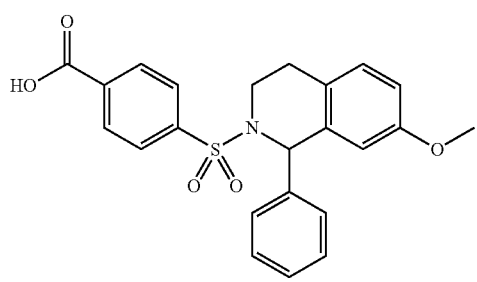 [SMILES: COc1ccc2c(c1)C(c1ccccc1)N(S(=O)(=O)c1ccc(C(=O)O)cc1)CC2]<br>4-(7-methoxy-1-phenyl-3,4-dihydroisoquinolin-2(1H)-ylsulfonyl)benzoic acid | 2.879 |

Example 6-1

(Z)-3-(5-(2,5-dimethoxybenzylidene)-4-oxo-2-thioxothiazolidin-3-yl)propanoic acid

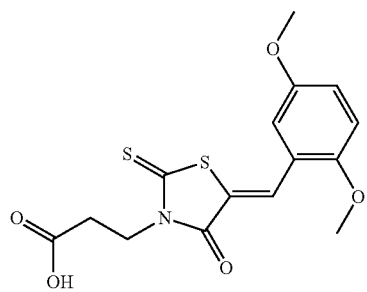 [SMILES: COc1ccc(OC)c(/C=C2\SC(=S)N(CCC(=O)O)C2=O)c1]

3-(4-oxo-2-thioxothiazolidin-3-yl)propanoic acid (200 mg, 1 mmol), 2,5-dimethoxybenzaldehyde (168 mg, 1 mmol) and piperidine (0.3 mL) were combined in ethanol (3 mL) and irradiated in the microwave at 100° C. for 10 minutes. The reaction was cooled, the solid was collected by filtration, washed with ethyl acetate/hexanes (1/1) and recrystallized from ethanol to afford 85% yield of the title compound (309 mg, brown-orange solid). MS (M+H, 284); $^1$H NMR (400 MHz, DMSO-d6): δ, ppm: 2.57 (t, 2H)), 3.74 (s, J=6.8 Hz, 3H), 3.84 (s, 3H), 4.19 (t, 2H), 6.90 (s, 1H), 7.10 (s, 2H), 7.86 (s, 1H).

The compound had an IC$_{50}$ on hT2R14 bitter receptor of 2.75 μM.

Example 6-2

(E)-2-cyano-3-(furan-2-yl)-N-(5-phenyl-1,3,4-thiadiazol-2-yl)acrylamide

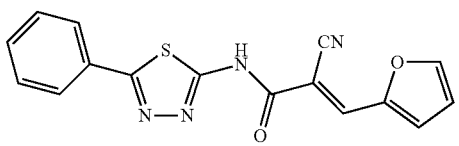 [SMILES: N#C/C(=C\c1ccco1)C(=O)Nc1nnc(-c2ccccc2)s1]

5-phenyl-1,3,4-thiadiazol-2-amine (600 mg, 3.3 mmol), cyano acetic acid (300 mg, 3.6 mmol), and EDC-HCl (861 mg, 4.5 mmol) were stirred in acetonitrile (15 mL) at room temperature for 2 hours. The mixture was diluted with aqueous 1N HCl and the aqueous phase was extracted with ethyl acetate. The combined organic extracts were dried over sodium sulfate, filtered and concentrated in vacuo. The residue was triturated with ethyl acetate/hexanes (1/9) to afford 2-cyano-N-(5-phenyl-1,3,4-thiadiazol-2-yl)acetamide as a white solid which was used without further purification.

312 mg of 2-cyano-N-(5-phenyl-1,3,4-thiadiazol-2-yl)acetamide and 150 uL of furan-2-carbaldehyde were mixed in 2.5 mL of DMF and heated in a microwave at 150° C. for 15 min. 5 ml of H$_2$O was added and the resulting precipitate was collected and washed with water (4×) to give the crude product. Recrystallization from ethanol gave 180 mg of pure product as a brown solid. MS (M+H, 323); $^1$H NMR (400 MHz, DMSO-d6): δ, ppm: 6.82 (m, 1H)), 7.43 (d, 1H), 7.49 (m, 4H), 7.87 (m, 2H), 8.15 (s, 1H), 8.22 (br, s, 1H).

The compound had an IC$_{50}$ on hT2R14 bitter receptor of 0.499 μM.

Example 6-3

N-(2,3-dihydrobenzo[b][1,4]dioxin-6-yl)-1,4-dimethyl-2,3-dioxo-1,2,3,4-tetrahydroquinoxaline-6-sulfonamide

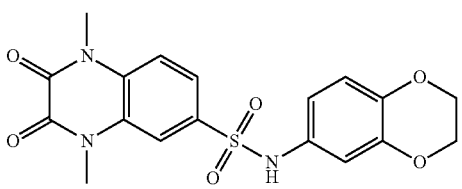 [SMILES: Cn1c(=O)c(=O)n(C)c2cc(S(=O)(=O)Nc3ccc4c(c3)OCCO4)ccc21]

1,4-dimethyl-2,3-dioxo-1,2,3,4-tetrahydroquinoxaline-6-sulfonyl chloride (example 6-3a, 450 mg, 1.6 mmol) was added to a stirred solution of the 2,3-dihydrobenzo[b][1,4]dioxin-6-amine (215 mg, 1.4 mmol) and triethylamine (170 mg, 1.7 mmol) in dichloromethane (10 mL). The reaction was stirred at ambient temperature overnight then concentrated. The crude product was purified by silica gel chromatography (0-30% ethyl acetate in hexanes) to provide N-(2,3-dihydrobenzo[b][1,4]dioxin-6-yl)-1,4-dimethyl-2,3-dioxo-1,2,3,4-tetrahydroquinoxaline-6-sulfonamide as a white solid. MS (M+H, 404.10); $^1$H NMR (400 MHz, DMSO-d6): δ, ppm: 3.47(s, 3H), 3.49(s, 3H), 4.12(m, 4H), 6.55(m, 1H), 6.61(d, J=2.4 Hz, 1H), 6.69(d, J=8.4 Hz, 1H), 7.53(m, 1H), 7.59(d, J=2 Hz, 1H), 10.00(s, 1H).

The compound had an IC$_{50}$ on hT2R14 bitter receptor of 7.71 μM.

Example 6-3a 1,4-dimethyl-2,3-dioxo-1,2,3,4-tetrahydroquinoxaline-6-sulfonyl chloride Chlorosulfonic acid (3 mL) was heated to 65° C. and 1,4-dimethylquinoxaline-2,3 (1H,4H)-dione (example 6-3b, 1 g, 5.5 mmol) was added in portions over 0.5 hour. The reaction mixture was stirred for 4 hours then cooled to ambient temperature and poured slowly onto ice. The resulting precipitate was filtered and washed with water to give 1,4-dimethyl-2,3-dioxo-1,2,3,4-tetrahydroquinoxaline-6-sulfonyl chloride as a white solid. $^1$H NMR (400 MHz, DMSO-d6): δ, ppm: 3.50(s, 6H), 7.25(m, 2H), 7.38(m, 4H).

Example 6-3b 1,4-dimethylquinoxaline-2,3(1H,4H)-dione

To a solution of NaH (2.5 g) in DMF (200 mL) was added quinoxaline-2,3(1H,4H)-dione (5 g) in portions, followed by the slow addition of methyl iodide (3.8 mL). The reaction mixture was stirred at ambient temperature for 4 hours, then water was added (200 mL). The resulting precipitate was collected by filtration and washed with water to afford 1,4-dimethylquinoxaline-2,3(1H,4H)-dione as a white solid in 95% yield. $^1$H NMR (400 MHz, DMSO-d6): δ, ppm: 3.50(s, 6H), 7.25(m, 2H), 7.38(m, 4H).

Example 6-4

1,4-dimethyl-2,3-dioxo-N-(4-(pyridin-2-ylmethyl)phenyl)-1,2,3,4-tetrahydroquinoxaline-6-sulfonamide

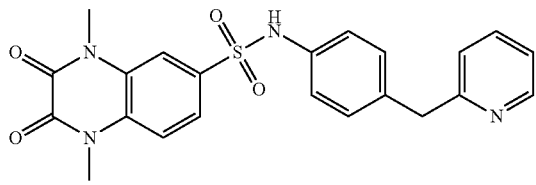 [SMILES: Cn1c(=O)c(=O)n(C)c2cc(S(=O)(=O)Nc3ccc(Cc4ccccn4)cc3)ccc21]

The compound is commercially available and was purchased through Ryan Scientific.

The compound had an $IC_{50}$ on hT2R14 bitter receptor of 6.14 μM.

Additional compounds were experimentally tested and found to have a relatively high level of effectiveness as inhibitors of hT2R14 bitter receptor. The results of that testing are shown below in Table D.

TABLE D

| Compound No. | Compound | hT2R14 $IC_{50}$ (μM) |
|---|---|---|
| 6-5 | N-(benzo[d][1,3]dioxol-5-yl)-1,3-dimethyl-2,4-dioxo-1,2,3,4-tetrahydroquinazoline-6-sulfonamide | 0.264 |
| 6-6 | N-(2,3-dihydrobenzo[b][1,4]dioxin-6-yl)-1,3-dimethyl-2,4-dioxo-1,2,3,4-tetrahydroquinazoline-6-sulfonamide | 0.706 |
| 6-7 | N-(3-fluoro-2-methylphenyl)-1,3-dimethyl-2,4-dioxo-1,2,3,4-tetrahydroquinazoline-6-sulfonamide | 0.935 |
| 6-8 | N-(2,6-dimethylphenyl)-1,3-dimethyl-2,4-dioxo-1,2,3,4-tetrahydroquinazoline-6-sulfonamide | |

TABLE D-continued

| Compound No. | Compound | hT2R14 IC$_{50}$ (μM) |
|---|---|---|
| 6-9 | 1,3-dimethyl-2,4-dioxo-N-o-tolyl-1,2,3,4-tetrahydroquinazoline-6-sulfonamide | 1.726 |
| 6-10 | N-(4-fluorophenyl)-1,4,7-trimethyl-2,3-dioxo-1,2,3,4-tetrahydroquinoxaline-6-sulfonamide | 12.623 |
| 6-11 | N-ethyl-N-m-tolyl-2-(N,1,4-trimethyl-2,3-dioxo-1,2,3,4-tetrahydroquinoxaline-6-sulfonamido)acetamide | 14.926 |
| 6-12 | (Z)-3-(4-oxo-2-thioxo-5-(2,4,6-trimethoxybenzylidene)thiazolidin-3-yl)propanoic acid | 9.371 |
| 6-13 | (Z)-3-(5-(3,5-dimethoxybenzylidene)-4-oxo-2-thioxothiazolidin-3-yl)propanoic acid | 5.378 |

TABLE D-continued
| Compound No. | Compound | hT2R14 IC$_{50}$ (μM) |
|---|---|---|
| 6-14 | 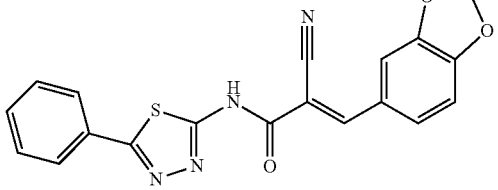<br>(E)-3-(benzo[d][1,3]dioxol-5-yl)-2-cyano-N-(5-phenyl-1,3,4-thiadiazol-2-yl)acrylamide | 2.906 |
| 6-15 | 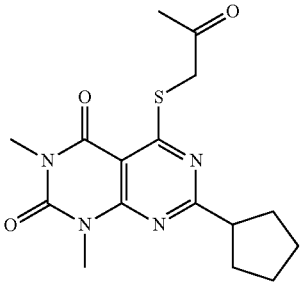 [SMILES: CC(=O)CSc1nc(C2CCCC2)nc2c1c(=O)n(C)c(=O)n2C]<br>7-cyclopentyl-1,3-dimethyl-5-(2-oxopropylthio)pyrimido[4,5-d]pyrimidine-2,4(1H,3H)-dione | 5.428 |
| 6-16 | 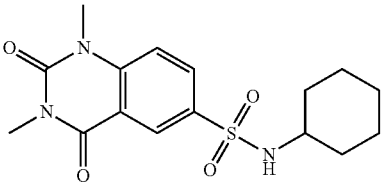 [SMILES: Cn1c(=O)c2cc(S(=O)(=O)NC3CCCCC3)ccc2n(C)c1=O]<br>N-cyclohexyl-1,3-dimethyl-2,4-dioxo-1,2,3,4-tetrahydroquinazoline-6-sulfonamide | 7.239 |
| 6-17 | 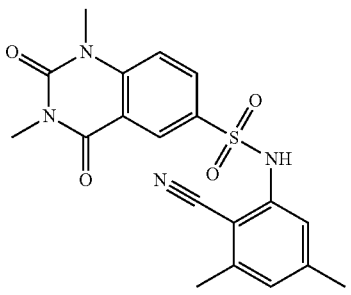 [SMILES: Cc1cc(C)c(C#N)c(NS(=O)(=O)c2ccc3c(c2)c(=O)n(C)c(=O)n3C)c1]<br>N-(2-cyano-3,5-dimethylphenyl)-1,3-dimethyl-2,4-dioxo-1,2,3,4-tetrahydroquinazoline-6-sulfonamide | 1.946 |

TABLE D-continued
| Compound No. | Compound | hT2R14 IC$_{50}$ (μM) |
|---|---|---|
| 6-18 | 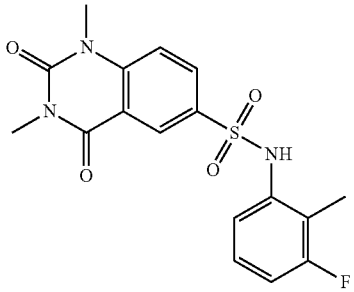 [SMILES: Cc1c(F)cccc1NS(=O)(=O)c1ccc2c(c1)c(=O)n(C)c(=O)n2C]<br>N-(3-fluoro-2-methylphenyl)-1,3-dimethyl-2,4-dioxo-1,2,3,4-tetrahydroquinazoline-6-sulfonamide | 0.935 |
| 6-19 | 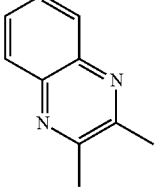<br>N-(2,3-dimethylquinoxalin-6-yl)-1,4-dimethyl-2,3-dioxo-1,2,3,4-tetrahydroquinoxaline-6-sulfonamide | 6.332 |
| 6-20 | 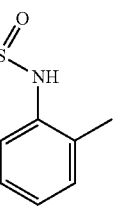<br>1,3-dimethyl-2,4-dioxo-N-o-tolyl-1,2,3,4-tetrahydroquinazoline-6-sulfonamide | 1.726 |
| 6-22 | 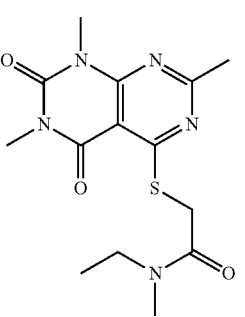 [SMILES: CCN(C)C(=O)CSc1nc(C)nc2c1c(=O)n(C)c(=O)n2C] | 0.861 |

TABLE D-continued

| Compound No. | Compound | hT2R14 IC$_{50}$ (μM) |
|---|---|---|
| | N-ethyl-N-methyl-2-(2,6,8-trimethyl-5,7-dioxo-5,6,7,8-tetrahydropyrimido[4,5-d]pyrimidin-4-ylthio)acetamide | |
| 6-23 | N-(4-chloro-2-fluorophenyl)-1,3-dimethyl-2,4-dioxo-1,2,3,4-tetrahydroquinazoline-6-sulfonamide | 9.703 |
| 6-24 | 1,3,7-trimethyl-5-(2-oxo-2-(piperidin-1-yl)ethylthio)pyrimido[4,5-d]pyrimidine-2,4(1H,3H)-dione | 0.292 |
| 6-25 | 1,3,7-trimethyl-5-(2-morpholino-2-oxoethylthio)pyrimido[4,5-d]pyrimidine-2,4(1H,3H)-dione | 1.006 |
| 6-26 | | 0.721 |

TABLE D-continued

| Compound No. | Compound | hT2R14 IC$_{50}$ (μM) |
|---|---|---|
| | 7-ethyl-1,3-dimethyl-5-(2-(4-methylpiperidin-1-yl)-2-oxoethylthio)pyrimido[4,5-d]pyrimidine-2,4(1H,3H)-dione | |
| 6-27 | 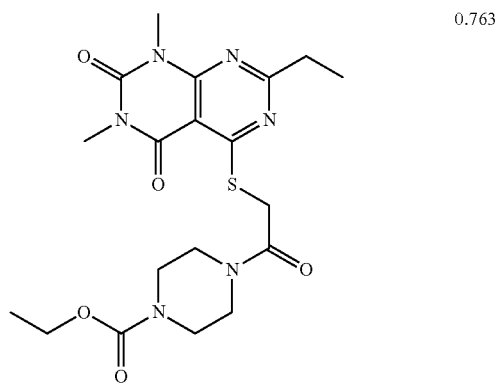<br>ethyl 4-(2-(2-ethyl-6,8-dimethyl-5,7-dioxo-5,6,7,8-tetrahydropyrimido[4,5-d]pyrimidin-4-ylthio)acetyl)piperazine-1-carboxylate | 0.763 |
| 6-28 | 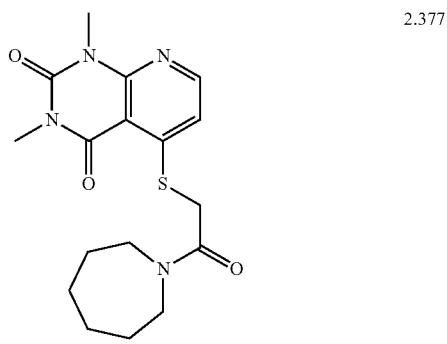<br>5-(2-(azepan-1-yl)-2-oxoethylthio)-1,3-dimethylpyrido[2,3-d]pyrimidine-2,4(1H,3H)-dione | 2.377 |
| 6-29 | 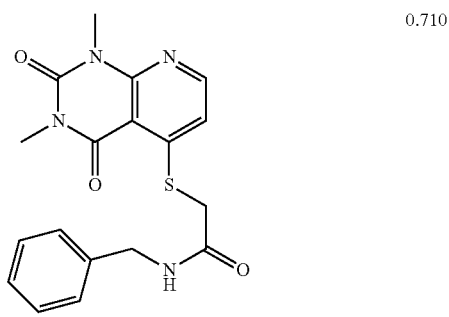<br>N-benzyl-2-(1,3-dimethyl-2,4-dioxo-1,2,3,4-tetrahydropyrido[2,3-d]pyrimidin-5-ylthio)acetamide | 0.710 |

TABLE D-continued

| Compound No. | Compound | hT2R14 IC$_{50}$ (μM) |
|---|---|---|
| 6-30 | 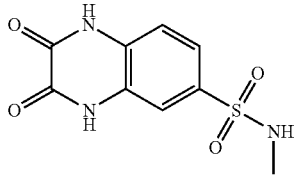 [SMILES: CNS(=O)(=O)c1ccc2[nH]c(=O)c(=O)[nH]c2c1]<br>N-methyl-2,3-dioxo-1,2,3,4-tetrahydroquinoxaline-6-sulfonamide | 6.234 |

TABLE 7

Representative screening results against 23 bitter receptors.

| | Example | | | | | | | | | | | | |
|---|---|---|---|---|---|---|---|---|---|---|---|---|---|
| | 1 | 3 | 4 | 5 | 7 | 8 | 9 | 10 | 13 | 14 | 16 | 44 | 51 |
| 5-51 | | ++ | + | | + | | | + | | ++++ | + | ++ | |
| 5-25 | | | + | | | | | | | +++ | | | |
| 5-53 | | | + | | + | | | | | ++ | | | |
| 5-22 | | ++ | ++ | | + | | | + | | ++++ | + | ++ | |
| 5-11 | | +++ | +++ | + | ++ | | + | ++ | | ++++ | ++ | +++ | |
| 5-24 | | | + | | + | | | | | | | + | |
| 5-37 | | | +++ | + | + | | | | | ++++ | + | + | |
| 5-30 | + | ++ | 275 | + | + | | + | ++ | + | ++++ | + | +++ | |
| 5-60 | | | | | | | | | | | | | |
| 5-46 | | + | | | + | | | | | ++++ | + | ++ | |
| 5-59 | | | | | | | | | | | | | |
| 5-47 | | + | | | | | | | | | | + | |
| 5-28 | | | | | | | | | + | ++++ | + | + | ++ |
| 5-1 | | +++ | | ++ | ++ | | + | +++ | + | ++++ | +++ | +++ | +++ |
| 5-54 | | + | | | | | | | | | | | |
| 5-5 | | ++ | | + | ++ | | | + | + | ++++ | ++ | ++ | + |
| 5-56 | | + | | | | | | | | | | | |
| 5-49 | | + | | | | | | | | | | + | |
| 5-20 | | ++++ | | + | + | | + | ++ | + | ++++ | ++ | +++ | |
| 5-21 | | + | + | | | | | | | ++++ | + | ++ | |
| 5-3 | | ++ | +++ | | | | + | ++ | | ++++ | + | ++ | + |
| 5-8 | | + | ++ | | | | | ++ | | ++++ | + | ++ | ++ |
| 5-4 | | | + | | | | | ++ | | ++ | | | |
| 5-29 | | | | | | | | | | | | | |
| 5-2 | | ++ | + | + | ++ | | | +++ | | ++++ | +++ | +++ | ++ |
| 5-7 | | + | + | | + | | | + | | ++ | | ++ | |
| 5-6 | | + | + | | + | | | ++ | | ++++ | + | ++ | ++ |
| 5-35 | | + | | + | + | | | | | + | + | + | |
| 5-81 | | + | | | + | | | + | | ++++ | + | ++ | + |
| 5-55 | | + | | + | | | | | | ++++ | | | |
| 5-61 | | | | + | | | | | | | | | |
| 5-63 | | + | | + | | | | | | | | | |
| 5-62 | | + | | + | + | + | | | | | | | |
| 5-76 | | + | | + | | | + | | | | | | |
| 5-77 | | ++ | | + | + | + | | + | | ++++ | + | + | ++ |
| 5-78 | | + | | + | | | | + | | ++++ | + | + | + |
| 5-80 | | ++ | | + | + | | + | + | | ++++ | + | + | ++ |
| 5-79 | | ++ | | + | | | | + | | ++++ | + | ++ | ++++ |
| 5-69 | | + | | + | | + | | + | | ++++ | | + | ++ |
| 5-70 | | ++ | | ++ | + | + | | ++ | | +++ | ++ | + | ++ |
| 5-48 | | | | | | | | | | | | | |
| 5-75 | | | | + | | | | | | | | | + |
| 5-72 | | + | | ++ | | | + | + | | ++++ | + | + | + |
| 5-71 | | + | | + | + | | | + | | ++++ | + | | ++ |
| 5-73 | | ++ | | + | + | | | ++ | | ++++ | + | | ++++ |
| 5-74 | | + | | + | + | | | ++ | | ++++ | | + | ++ |
| 5-1 | | +++ | | ++ | ++ | | | +++ | + | ++++ | ++ | ++ | +++ |
| 5-1 | | +++ | | ++ | ++ | + | + | +++ | + | ++++ | ++ | ++ | ++++ |
| 5-65 | | + | | | | | | | | | | | |
| 5-68 | | + | | ++ | + | | | + | | ++++ | + | ++ | + |
| 5-64 | | + | | + | | + | + | | | | | + | |
| 5-34 | | ++ | 734 | ++ | + | | + | ++ | | ++++ | + | ++ | + |
| 5-67 | | ++ | | + | | | + | ++ | | +++ | + | ++ | |
| 5-31 | | + | | | | | + | | | | | + | |

TABLE 7-continued

Representative screening results against 23 bitter receptors.

| ID | C1 | C2 | C3 | C4 | C5 | C6 | C7 | C8 | C9 | C10 | C11 | C12 |
|---|---|---|---|---|---|---|---|---|---|---|---|---|
| 5-66 | | + | | | | + | + | | | | + | |
| 5-14 | + | ++++ | | +++ | +++ | + | ++ | ++++ | + | ++++ | ++ | +++ | +++ |
| 5-23 | | +++ | | + | ++ | | + | ++++ | + | ++++ | ++ | +++ | +++ |
| 5-18 | | | | | | | | +++ | | | ++ | +++ | |
| 5-19 | | | | | | | | + | | ++++ | | ++ | |
| 5-25 | | +++ | | ++ | ++ | | + | +++ | | ++++ | ++ | +++ | + |
| 5-38 | + | | | | | | | | | | | | |
| 5-82 | | | | | | | | | | | | | |
| 5-10 | | +++ | 477 | | ++ | | ++ | ++++ | ++ | ++++ | ++++ | ++ | ++++ |
| 5-12 | | +++ | 371 | ++ | ++ | | ++ | ++++ | + | ++++ | +++ | +++ | ++++ |
| 5-1 | | +++ | 201 | ++ | ++ | | + | +++ | + | ++++ | +++ | + | ++++ |
| 5-83 | | ++ | | + | + | | | ++ | | ++++ | ++ | + | + |
| 5-84 | | ++ | | + | | | | + | | ++++ | + | + | +++ |
| 5-85 | | ++ | | + | + | | | ++ | + | ++++ | ++ | | + |
| 5-87 | | | | | | | | | | | | | |
| 5-88 | | + | 345 | | | | | | | + | | + | |
| 5-89 | | ++ | | + | ++ | | + | +++ | + | ++++ | + | +++ | ++++ |
| 5-90 | | ++ | | + | +++ | | | ++ | | ++++ | + | +++ | |
| 5-86 | | | | | | | | | | + | | + | |
| 5-58 | | +++ | | + | +++ | | | +++ | | ++++ | + | +++ | + |
| 5-17 | | + | | | + | | | +++ | | ++++ | + | +++ | |
| 5-37 | | + | | | | | | | | ++++ | | +++ | |
| 5-1 | | ++++ | | + | ++ | | + | ++++ | + | ++++ | ++ | +++ | +++ |
| 5-16 | | ++ | | + | | | | + | | + | | +++ | |
| 5-92 | | + | | + | + | | | + | | ++++ | + | ++++ | |
| 5-91 | | +++ | | + | | | | ++ | | ++++ | + | +++ | |
| 5-1 | | +++ | + | ++ | ++ | | ++ | +++ | + | ++++ | ++ | +++ | +++ |
| 5-13 | | ++ | | + | + | | + | + | | ++++ | + | +++ | + |
| 5-15 | | + | | + | + | | + | ++ | | +++ | + | +++ | |
| 5-19 | | + | | + | | | | + | | ++++ | + | ++ | |
| 5-16 | | +++ | + | | + | | + | + | | + | + | +++ | |
| 5-1 | | +++ | ++ | + | ++ | | ++ | +++ | + | ++++ | ++ | +++ | +++ |
| 5-17 | | + | + | | | | | + | | +++ | | | |
| 5-1 | | ++ | | ++ | ++ | | | ++ | + | ++++ | +++ | +++ | ++++ |
| 5-30 | | ++ | 396 | + | + | | | ++ | + | ++++ | ++ | +++ | ++ |
| 5-96 | | + | + | | | | | | + | ++++ | + | +++ | |
| 5-95 | | ++ | | + | + | | | + | | ++++ | ++ | +++ | + |
| 5-97 | | | | | | | | | | + | +++ | + | |
| 5-50 | | ++ | 565 | + | + | | | + | + | ++++ | ++ | +++ | + |
| 5-98 | | + | ++ | | | | | | | | | +++ | |
| 5-1 | | +++ | | + | ++ | | + | +++ | + | ++++ | ++ | +++ | +++ |
| 5-48 | | ++ | 410 | + | | | | +++ | | ++++ | + | +++ | |
| 5-57 | | + | | | | | | + | | | | | |
| 5-1 | | +++ | | + | + | | + | +++ | + | ++++ | ++ | +++ | +++ |
| 5-94 | | + | | | | | | | | | | ++ | |
| 5-107 | | | | | | | | | | +++ | | + | |
| 5-45 | | ++ | | | | | | | | ++++ | + | ++ | |
| 5-44 | | + | | | | | | | | ++++ | | ++ | |
| 5-43 | | + | + | | | | | | | ++++ | + | + | |
| 5-42 | | + | | | | | | | | ++++ | + | ++ | |
| 5-40 | | + | + | + | | | | ++ | | ++++ | + | +++ | + |
| 5-41 | | ++ | 332 | + | | | | ++ | + | ++++ | + | +++ | |
| 5-1 | + | ++ | | ++ | ++ | | + | +++ | + | ++++ | ++ | ++++ | +++ |
| 5-33 | | ++ | ++ | ++ | + | | + | +++ | + | ++++ | ++ | +++ | ++ |
| 5-23 | | +++ | ++ | ++ | ++ | | ++ | ++++ | + | ++++ | +++ | ++++ | ++ |
| 5-27 | | ++ | | ++ | + | | | +++ | + | ++++ | + | +++ | ++ |
| 5-26 | | | ++ | | + | | | | | | | + | |
| 5-93 | | + | ++ | + | + | | | ++ | | ++++ | ++ | +++ | ++ |
| 5-99 | | | 310 | | + | | | | | ++++ | + | +++ | |
| 5-105 | | + | + | + | + | | | + | | ++++ | ++ | ++ | |
| 5-104 | | ++ | ++ | ++ | ++ | | + | ++ | | ++++ | + | +++ | + |
| 5-1 | | ++ | | ++ | ++ | | + | +++ | | ++++ | ++ | +++ | +++ |
| 5-103 | | ++ | ++ | + | + | | | + | | ++++ | + | +++ | + |
| 5-102 | | ++ | ++ | + | ++ | | | + | | ++++ | + | +++ | + |
| 5-101 | | +++ | ++ | ++ | +++ | | + | +++ | | ++++ | + | +++ | ++ |
| 5-100 | | + | ++ | + | + | | + | + | | ++ | + | +++ | |
| 5-1 | | ++ | + | + | ++ | | + | +++ | | ++++ | ++ | +++ | +++ |
| 5-93 | | +++ | ++++ | + | ++ | | +++ | + | ++++ | ++ | +++ | ++ |
| 5-36 | | ++ | | | + | | | + | | ++++ | + | ++ | |
| 5-106 | | | | | | | | | | ++++ | + | ++ | |
| 5-108 | | ++ | +++ | + | + | | | ++ | | ++++ | + | +++ | ++ |
| 5-109 | | ++ | ++ | | + | | | ++ | + | ++++ | | ++ | ++ |
| 5-110 | | ++ | +++ | + | ++ | + | + | ++ | + | ++++ | + | +++ | ++ |
| 6-2 | | | 331 | | | | | | | ++++ | | | |
| 6-9 | | | | ++ | | | | | | ++++ | | + | |
| 6-3 | | | | | | | | | + | ++++ | | + | |
| 6-8 | | | | | | | | | | + | | | |
| 6-7 | | | | | + | | | | | ++ | | | |

TABLE 7-continued

Representative screening results against 23 bitter receptors.

| | | | | | | | | | | |
|---|---|---|---|---|---|---|---|---|---|---|
| 6-11 | | | + | + | | | ++ | + | | |
| 6-10 | | + | + | + | | | ++ | ++ | | + |
| 6-4 | | | | + | | + | ++++ | ++++ | | + |
| 6-5 | | | 717 | | | | | ++++ | | ++ |
| 6-1 | | + | 3866 | | 932 | ++++ | | ++++ | + | ++ |
| 6-6 | | | 895 | | | | | ++++ | | |

| | Example | | | | | | | | |
|---|---|---|---|---|---|---|---|---|---|
| | 54 | 55 | 61 | 63 | 64 | 65 | 67 | 71 | 75 |
| 5-51 | | +++ | ++++ | +++ | ++ | + | | ++ | + |
| 5-25 | | | ++ | + | ++ | | | + | |
| 5-53 | | | | ++ | ++ | | | + | |
| 5-22 | | +++ | ++++ | +++ | ++ | | | ++ | + |
| 5-11 | | ++++ | ++++ | +++ | ++ | + | + | +++ | ++ |
| 5-24 | | ++ | ++++ | + | +++ | | | + | |
| 5-37 | | ++++ | + | + | +++ | | | + | |
| 5-30 | + | ++++ | ++ | ++++ | ++++ | + | + | +++ | + |
| 5-60 | | | | | + | | | | |
| 5-46 | | + | ++++ | +++ | | ++ | ++ | +++ | |
| 5-59 | | | ++ | + | | | | | + |
| 5-47 | | | +++ | + | | | | + | |
| 5-28 | + | ++++ | ++ | ++++ | ++++ | | + | ++ | + |
| 5-1 | + | +++ | ++++ | ++++ | +++ | +++ | ++ | +++ | + |
| 5-54 | | | | | | + | | | |
| 5-5 | + | ++++ | ++++ | ++++ | +++ | + | + | +++ | + |
| 5-56 | | | | | + | | | | |
| 5-49 | | ++++ | +++ | + | ++ | | | + | |
| 5-20 | | ++++ | ++++ | ++ | +++ | + | | ++ | ++ |
| 5-21 | | + | +++ | +++ | + | | | + | |
| 5-3 | ++ | ++++ | ++ | +++ | ++++ | + | | + | |
| 5-8 | + | ++++ | +++ | ++ | ++++ | ++ | | ++ | + |
| 5-4 | | ++++ | + | +++ | ++++ | | | | + |
| 5-29 | | | | +++ | ++ | | | | |
| 5-2 | + | ++++ | ++++ | ++++ | +++ | + | + | +++ | + |
| 5-7 | | ++++ | ++++ | ++++ | ++++ | | + | ++ | + |
| 5-6 | + | ++++ | ++++ | ++++ | ++++ | + | | ++ | + |
| 5-35 | + | +++ | ++++ | +++ | + | | | ++ | |
| 5-81 | | +++ | +++ | +++ | ++ | + | + | + | |
| 5-55 | | ++ | + | ++++ | ++ | | | | |
| 5-61 | | + | ++ | ++++ | + | | | + | |
| 5-63 | | +++ | | +++ | ++ | | + | + | |
| 5-62 | | +++ | ++ | ++++ | ++ | | + | + | |
| 5-76 | | | ++ | ++ | | | + | + | |
| 5-77 | ++ | ++ | +++ | +++ | ++ | ++ | + | ++ | |
| 5-78 | + | +++ | ++++ | +++ | ++ | +++ | + | ++ | + |
| 5-80 | + | +++ | +++ | ++++ | +++ | ++ | + | +++ | + |
| 5-79 | + | +++ | ++++ | ++++ | +++ | ++ | + | +++ | |
| 5-69 | | +++ | +++ | ++++ | ++ | | | + | + |
| 5-70 | ++ | +++ | ++ | ++++ | + | ++ | + | ++ | + |
| 5-48 | | ++++ | +++ | | | | | | |
| 5-75 | | | + | + | | | | | + |
| 5-72 | + | ++ | +++ | ++++ | + | + | + | + | ++ |
| 5-71 | +++ | ++ | ++++ | ++++ | + | ++ | + | ++ | + |
| 5-73 | +++ | ++ | +++ | ++++ | + | ++ | + | ++ | + |
| 5-74 | ++ | +++ | ++++ | ++++ | + | ++ | + | +++ | |
| 5-1 | ++ | +++ | ++++ | ++++ | + | +++ | + | +++ | + |
| 5-1 | + | ++++ | ++++ | ++++ | +++ | +++ | ++ | +++ | + |
| 5-65 | | | | | | | | | |
| 5-68 | + | ++++ | +++ | ++++ | +++ | + | + | +++ | + |
| 5-64 | + | | | + | + | | | | |
| 5-34 | +++ | ++++ | ++++ | ++++ | +++ | ++ | + | +++ | |
| 5-67 | ++ | ++++ | ++ | ++++ | +++ | + | + | ++ | |
| 5-31 | | | | | | | | | |
| 5-66 | | | | | | | | | |
| 5-14 | ++++ | ++++ | ++++ | ++++ | +++ | ++++ | ++ | ++++ | ++ |
| 5-23 | ++ | ++++ | ++++ | ++++ | ++++ | ++++ | ++ | +++ | ++ |
| 5-18 | ++ | ++++ | +++ | +++ | ++++ | + | | ++ | |
| 5-19 | + | ++++ | + | +++ | ++++ | + | | + | |
| 5-25 | +++ | +++ | ++++ | ++++ | ++++ | ++++ | ++ | ++++ | |
| 5-38 | | | ++++ | ++++ | + | | | + | |
| 5-82 | | | ++++ | ++++ | + | | | + | |
| 5-10 | ++++ | +++ | ++++ | ++++ | +++ | ++++ | +++ | +++ | + |
| 5-12 | ++++ | ++++ | ++++ | ++++ | +++ | ++++ | +++ | ++++ | + |
| 5-1 | +++ | +++ | ++++ | ++++ | + | ++++ | ++ | + | + |
| 5-83 | ++ | +++ | ++++ | +++ | + | +++ | ++ | + | ++ |
| 5-84 | ++ | +++ | ++++ | +++ | + | +++ | + | + | + |

TABLE 7-continued

Representative screening results against 23 bitter receptors.

| Compound | | | | | | | | | |
|---|---|---|---|---|---|---|---|---|---|
| 5-85 | +++ | +++ | ++++ | +++ | | +++ | ++ | + | + |
| 5-87 | | | ++ | + | + | | + | | |
| 5-88 | | | ++ | +++ | + | | + | + | |
| 5-89 | + | ++++ | ++++ | ++++ | +++ | ++++ | + | +++ | + |
| 5-90 | | +++ | ++++ | ++++ | +++ | ++ | | +++ | |
| 5-86 | | | +++ | +++ | | | | | |
| 5-58 | +++ | +++ | ++++ | ++++ | +++ | ++++ | + | ++++ | + |
| 5-17 | ++ | ++++ | ++++ | ++++ | ++++ | ++ | | ++ | + |
| 5-37 | | ++++ | +++ | + | +++ | ++ | | +++ | |
| 5-1 | ++ | ++++ | ++++ | ++++ | +++ | ++ | + | ++++ | ++ |
| 5-16 | | ++++ | +++ | ++ | ++++ | | | ++ | + |
| 5-92 | | ++++ | ++++ | ++++ | ++++ | | | ++ | |
| 5-91 | + | ++++ | ++++ | ++++ | ++++ | | + | +++ | |
| 5-1 | ++ | ++++ | ++++ | ++++ | ++ | +++ | + | +++ | + |
| 5-13 | +++ | ++++ | ++++ | ++++ | +++ | + | | ++ | |
| 5-15 | | ++++ | ++++ | +++ | +++ | | | ++ | |
| 5-19 | + | ++++ | +++ | ++ | +++ | | | ++ | |
| 5-16 | | ++++ | ++++ | +++ | +++ | + | | ++ | |
| 5-1 | ++ | ++++ | ++++ | ++++ | +++ | +++ | ++ | +++ | ++ |
| 5-17 | ++ | ++++ | ++++ | ++ | ++ | | | + | + |
| 5-1 | ++ | ++++ | ++++ | ++++ | +++ | +++ | ++ | +++ | + |
| 5-30 | +++ | ++++ | ++++ | ++++ | ++++ | +++ | ++ | +++ | |
| 5-96 | | ++++ | ++++ | ++++ | +++ | ++++ | + | ++ | |
| 5-95 | | ++++ | ++++ | ++++ | +++ | +++ | + | ++ | + |
| 5-97 | | | + | +++ | + | | | | |
| 5-50 | | ++++ | ++++ | ++++ | +++ | ++ | ++ | +++ | |
| 5-98 | | ++++ | ++++ | | +++ | | | | |
| 5-1 | ++ | ++++ | ++++ | ++++ | +++ | +++ | ++ | +++ | + |
| 5-48 | ++ | ++++ | ++++ | ++++ | +++ | ++ | + | +++ | |
| 5-57 | | +++ | ++++ | | ++ | | | | |
| 5-1 | ++ | ++++ | ++++ | ++++ | +++ | +++ | + | ++++ | + |
| 5-94 | | | + | | +++ | | | + | |
| 5-107 | | + | ++++ | +++ | +++ | | | + | |
| 5-45 | | ++ | ++++ | ++++ | +++ | + | | +++ | |
| 5-44 | | + | ++++ | ++++ | ++ | | | ++ | |
| 5-43 | | + | ++++ | ++++ | +++ | | | ++ | |
| 5-42 | | | ++++ | ++ | ++ | | | ++ | + |
| 5-40 | + | ++++ | ++++ | ++++ | +++ | | | ++ | |
| 5-41 | + | +++ | ++++ | ++++ | +++ | | | ++ | |
| 5-1 | ++ | ++++ | ++++ | +++ | +++ | +++ | ++ | +++ | + |
| 5-33 | +++ | ++++ | ++++ | +++ | +++ | +++ | ++ | +++ | |
| 5-23 | +++ | ++++ | ++++ | +++ | +++ | ++++ | ++ | ++++ | |
| 5-27 | ++ | ++++ | ++++ | +++ | +++ | ++ | ++ | +++ | + |
| 5-26 | | | + | +++ | +++ | | | + | |
| 5-93 | +++ | ++++ | ++++ | ++++ | ++++ | ++++ | ++ | +++ | |
| 5-99 | | + | ++++ | ++++ | +++ | ++ | ++ | +++ | |
| 5-105 | + | ++++ | ++++ | ++ | ++++ | +++ | ++ | +++ | + |
| 5-104 | + | +++ | ++++ | ++ | ++++ | +++ | ++ | +++ | ++ |
| 5-1 | ++ | ++++ | ++++ | ++++ | ++++ | +++ | ++ | +++ | |
| 5-103 | ++ | ++++ | ++++ | ++ | ++++ | ++ | + | ++++ | + |
| 5-102 | + | ++++ | ++++ | + | +++ | ++ | + | +++ | + |
| 5-101 | ++ | +++ | ++++ | +++ | ++++ | +++ | ++ | +++ | ++ |
| 5-100 | + | ++++ | +++ | + | ++++ | ++ | | +++ | + |
| 5-1 | ++ | +++ | ++++ | ++++ | ++++ | +++ | ++ | +++ | + |
| 5-93 | +++ | ++++ | ++++ | ++++ | ++++ | +++ | ++ | +++ | |
| 5-36 | + | ++++ | ++++ | +++ | ++++ | ++ | | +++ | |
| 5-106 | ++ | ++++ | ++ | ++++ | +++ | | + | + | |
| 5-108 | + | ++++ | ++++ | +++ | ++++ | ++ | + | +++ | |
| 5-109 | + | ++++ | +++ | ++ | ++++ | +++ | + | +++ | |
| 5-110 | + | ++++ | ++++ | +++ | +++ | +++ | + | +++ | |
| 6-2 | | | | ++ | + | + | | | |
| 6-9 | | | + | + | | | | | |
| 6-3 | | | | + | | | | + | |
| 6-8 | | | | | | | | | |
| 6-7 | | | | + | | | | | |
| 6-11 | | | + | | | | | + | |
| 6-10 | | | + | | + | | | | |
| 6-4 | | | + | + | | | | | |
| 6-5 | | | + | ++++ | 278 | ++ | | +++ | |

TABLE 7-continued

Representative screening results against 23 bitter receptors.

| | | | | | | | | | |
|---|---|---|---|---|---|---|---|---|---|
| 6-1 | | | + | ++ | + | +++ | + | + | + |
| 6-6 | | + | 210 | | | 447 | | | |

Compounds from examples 5 and 6 above were screened against a panel of 23 bitter receptors. The bitter receptors were activated to EC80 with the corresponding agonist then treated with the above compounds at a concentration of 25 µM. The data is summarized in the table below.
80% or greater inhibition = ++++
60% to 80% inhibition = +++
40% to 60% inhibition = ++
20% to 40% inhibition = +
*

Example 7

Sensory data for Example 10-10

To determine the effectiveness of an individual antagonist, taste tests were performed with a T2R8 specific agonist, the compound of interest and a reference bitter blocker. We have previously described a good hT2R8 antagonist that was proven to have taste effect, Example 4-8 from U.S. Provisional Appl. Ser. No. 60/957,129, filed Aug. 21, 2007: N-(1-((3,5-dimethylisoxazol-4-yl)methyl)-1H-pyrazol-4-yl)benzo[d][1,3]dioxole-5-carboxamide. It was shown to reduce bitterness of coffee by itself and in combination with a Broad spectrum bitter blocker). As shown in Table 6, when compared to our control antagonist (Example 10-8) the hT2R8 antagonist of example 10-10 shows a greater ability to block perceived bitterness.

TABLE 6

Taste test results comparing a control bitter blocker and a more potent bitter blocker 10-10.

| Example Number | HTS assay IC$_{50}$ µM | Selected as more bitter | | p value | Antagonist conc. M |
|---|---|---|---|---|---|
| | | 10-8 | +other | | |
| 10-10 | 0.02-0.04 | 14 | 2 | 0.004 | 1 |

As demonstrated by the taste tests of this example, the perception of bitterness may be reduced or eliminated by incorporation of antagonists of hT2R8 and the antagonist of Example 10-10 appears to be a more potent analog when compared to known bitter antagonists like N-(1-((3,5-dimethylisoxazol-4-yl)methyl)-1H-pyrazol-4-yl)benzo[d][1,3]dioxole-5-carboxamide (7767). It follows that the perception of bitterness may be reduced or eliminated by incorporation of antagonists of hT2R8 in compositions such as foods, beverages and/or medicaments where bitter taste is elicited by T2R8 agonists.

Example 8

Identification of Antagonists of hT2R8

To identify antagonists, cell lines stably expressing hT2R8 together with the promiscuous chimeric G16g44 protein were generated as described in previous patent applications. A high-throughput assay was established using the stable cell lines and FLIPR (Fluorescent Imaging Plate Reader). An agonist of hT2R8 was used to activate the receptors up to 70-80% of their respective maximal activity. For hT2R8, the agonist used was andrographolide (200 µM). To identify antagonists, compounds with diverse chemical structures were added together with the agonist. Compounds that cause statistically significant reduction of the receptor activity are pooled together, and reconfirmed with dose-dependent inhibition curves. scaffold A and scaffold B were identified as hT2R8 antagonists (FIG. 1). Specific examples are presented in Table 1.

Example 9 hT2R8 Antagonists

Example 9-1

2-(1-((3,5-dimethylisoxazol-4-yl)methyl)-1H-pyrazol-4-yl)isoindoline-1,3-dione

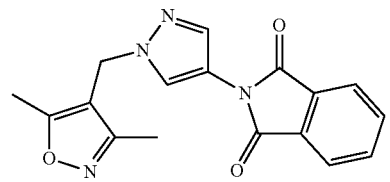 [SMILES: Cc1noc(C)c1Cn1cc(N2C(=O)c3ccccc3C2=O)cn1]

2-(1H-pyrazol-4-yl)isoindoline-1,3-dione (example 9-1a) (1.5 g, 7 mmol), 4-(chloromethyl)-3,5-dimethylisoxazole (1.5 g, 10 mmol), and cesium carbonate (3.3 g, 10 mmol) were stirred in DMF (20 mL) at 80° C. for 3 hours. The reaction was cooled, diluted with H$_2$O (150 mL), and extracted with ethyl acetate (3×, 75 mL). The combined organic extracts were dried over sodium sulfate, filtered and concentrated on the rotovap. The solid product was triturated with ethyl acetate/hexanes (1/9) and re-crystallized from refluxing absolute ethanol (30 mL) to afford 2-(1-((3,5-dimethylisoxazol-4-yl)methyl)-1H-pyrazol-4-yl)isoindoline-1,3-dione (900 mg, 38%) as a bright, light yellow solid. $^1$H NMR (DMSO-d$_6$, 400 MHz) 1.36 (d, 3H,δ J2.16 (s, 3H), 2.41 (s, 3H),=7.2 Hz), 5.22 (s, 2H), 7.81 (s, 1H), 7.91-7.83 (m, 4H), 8.21(s, 1H). MS M+H calculated 323.11; found 323.1.

Melting point: 170-171° C. The title compound was shown to inhibit hT2R08 bitter receptor and had an IC$_{50}$ of 0.18 μM.

Example 9-1a 1-tosyl-1H-pyrazol-4-amine

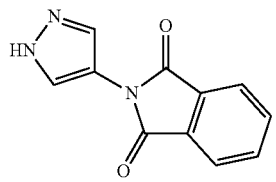 [SMILES: O=C1c2ccccc2C(=O)N1c1cn[nH]c1]

1-tosyl-1H-pyrazol-4-amine (example 9-1b) (3 g, 12.7 mmol) and isobenzofuran-1,3-dione (1.9 g, 13 mmol) were stirred in DMF/Acetonitrile (1/1) (20 mL) at 100° C. for 1 hour. The mixture was cooled and diluted with H$_2$O. The precipitate was collected by filtration, washed with additional water followed by ethyl acetate and hexanes. The solid product was dried under high vacuum to afford 2-(1H-pyrazol-4-yl)isoindoline-1,3-dione (2.5 g, 92%) as a yellow solid. MS M+H calculated 214.1; found 214.1. $^1$H NMR (CDCl$_3$, 400 MHz) δ 7.93-8.10 (m, 6H), 13.03 (bs, 1H).

Example 9-1b 1-tosyl-1H-pyrazol-4-amine

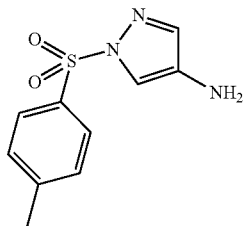 [SMILES: Cc1ccc(S(=O)(=O)n2cc(N)cn2)cc1]

4-nitro-1-tosyl-1H-pyrazole (example 9-1c) (3 g, 11.2 mmol) and 10% palladium on carbon (800 mg) in MeOH (150 mL) were stirred under 2 atmospheres of hydrogen on the Parr hydrogenator for 3 hours. The mixture was filtered through celite, concentrated and purified by silica gel chromotography (80% ethyl acetate in hexanes) to afford 1-tosyl-1H-pyrazol-4-amine (1.9 g, 71%) as a pink solid. $^1$H NMR (CDCl$_3$, 400 MHz) δ 2.40 (s, 3H), 3.01 (bs, 2H), 7.29 (d, 2H, J=8 Hz), 7.41 (d, 1H, J=1.2 Hz), 7.53 (d, 1H, J=1.2 Hz), 7.81 (d, 2H, J=8 Hz).

Example 9-1c 4-nitro-1-tosyl-1H-pyrazole

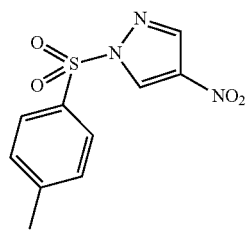 [SMILES: Cc1ccc(S(=O)(=O)n2cc([N+](=O)[O-])cn2)cc1]

4-nitro-1H-pyrazole (500 mg, 4.4 mmol), 4-methylbenzene-1-sulfonyl chloride (840 mg, 4.4 mmol), and triethylamine (510 mg, 5 mmol) were stirred in DMF (25 mL) at 80° C. for 1 hour. The reaction was cooled, diluted with H$_2$O (200 mL) and extracted with ethyl acetate (3×, 100 ml). The organic phase was washed with aqueous 1N HCl (200 mL) and H$_2$O (200 mL), dried over sodium sulfate, filtered and concentrated on the rotovap. The solid was triturated with hexanes to afford 4-nitro-1-tosyl-1H-pyrazole (600 mg, 50%) as an off white solid. $^1$H NMR (DMSO-d$_6$, 400 MHz) δ 2.40 (s, 3H), 7.52 (d, 2H, J=8.4 Hz), 7.98 (d, 2H, J=8.8 Hz), 8.57 (s, 1H), 9.58 (s, 1H).

Example 9-2

2-((1-((3,5-dimethylisoxazol-4-yl)methyl)-1H-pyrazol-4-ylamino)methyl)benzonitrile

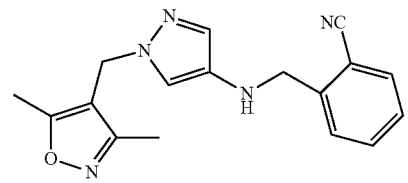 [SMILES: Cc1noc(C)c1Cn1cc(NCc2ccccc2C#N)cn1]

1-((3,5-dimethylisoxazol-4-yl)methyl)-1H-pyrazol-4-amine-hydrochloride (100 mg, 0.44 mmol), 2-(bromomethyl)benzonitrile (115 mg, 0.6 mmol), and triethylamine (0.5 mL, 3.5 mmol) in DMF (3 mL) were irradiated and stirred in the microwave reactor at 80° C. for 10 minutes. The reaction was cooled, diluted with H$_2$O (50 mL) and extracted with ethyl acetate (3×, 30 mL). The combined organic extracts were dried over sodium sulfate and concentrated on the rotovap. The residue was dissolved in ethanol (70 mL), H$_2$O (3 mL) and acetic acid (1 mL) and the mixture was refluxed for 2 hours. The solution was concentrated on the rotovap, taken up in methanol (3 mL) and purified by reversed phase HPLC in 3-1 mL aliquots (5 to 95% acetonitrile in H$_2$O: 16 minute gradient). The pure fractions were combined and concentrated on the rotovap. The residue was triturated with ethyl acetate/hexanes (1/9) to afford 2-(1-((3,5-dimethylisoxazol-4-yl)methyl)-1H-pyrazol-4-yl)isoindolin-1-one (85 mg, 61%) as a pure white solid. $^1$H NMR (DMSO-d$_6$, 400 MHz): δ2.18 (s, 3H), 2.43 (s, 3H), 4.97 (s, 2H), 5.18 (s, 2H), 7.58-

7.68 (m, 3H), 7.77 (s, 1H), 8.10 (d, J=8 Hz, 1H), 8.27 (s, 1H), 9.19 (bs, 1H). The title compound was shown to inhibit hT2R08 bitter receptor and had an IC$_{50}$ value greater than 30 µM.

Example 9-3

2-(1-((3,5-dimethylisoxazol-4-yl)methyl)-1H-pyrazol-4-yl)isoindolin-1-one

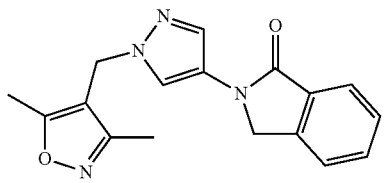 [SMILES: Cc1noc(C)c1Cn1cc(N2Cc3ccccc3C2=O)cn1]

2-((1-((3,5-dimethylisoxazol-4-yl)methyl)-1H-pyrazol-4-ylamino)methyl)benzonitrile (example 9-2) (30 mg, 0.14 mmol) was stirred in a mixture of MeOH/2N aqueous NaOH (5 mL) at 100° C. for 30 minutes in the microwave reactor. The reaction was acidified with 1N aqueous HCl (100 mL) and extracted with ethyl acetate (3×, 70 mL). The combined organic extracts were dried over sodium sulfate and concentrated. The residue was dissolved in MeOH (3 mL) and purified by reversed phase HPLC in 2-1.5 mL aliquots (5 to 95% acetonitrile in H$_2$O: 16 minute gradient). The pure fractions were combined and concentrated to afford 2-(1-((3,5-dimethylisoxazol-4-yl)methyl)-1H-pyrazol-4-yl)isoindolin-1-one (21 mg, 50%) as a pure white solid. $^1$H NMR (DMSO-d$_6$, 400 MHz): δ 2.15 (s, 3H), 2.41 (s, 3H), 4.81 (s, 2H), 5.17 (s, 2H), 7.48-7.50 (m, 1H), 7.51-7.52 (m, 2H), 7.72 (d, J=7.2 Hz, 1H), 7.75 (s, 1H), 8.20 (s, 1H). The title compound was shown to inhibit hT2R08 bitter receptor and had an IC$_{50}$ of 11 µM.

Example 9-4

3-(1-((3,5-dimethylisoxazol-4-yl)methyl)-1H-pyrazol-4-yl)quinazoline-2,4(1H,3H)-dione

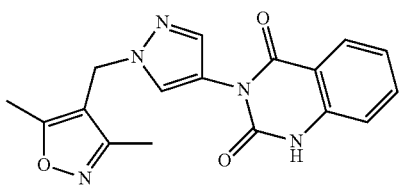 [SMILES: Cc1noc(C)c1Cn1cc(-n2c(=O)[nH]c3ccccc3c2=O)cn1]

1-((3,5-dimethylisoxazol-4-yl)methyl)-1H-pyrazol-4-amine hydrochloride (75 mg, 0.33 mmol), methyl 2-isocyanatobenzoate, and triethylamine (200 mg, 2 mmol) in acetonitrile (3 mL) were irradiated in the microwave reactor at 100° C. for 30 minutes. The reaction was cooled, diluted with H$_2$O (75 mL), and extracted with ethyl acetate (3×, 50 mL). The combined organic extracts were dried over sodium sulfate, filtered and concentrated on the rotovap. The residue was purified by silica gel chromatography (75% ethyl acetate in hexanes) to afford 3-(1-((3,5-dimethylisoxazol-4-yl)methyl)-1H-pyrazol-4-yl)quinazoline-2,4(1H,3H)-dione (20 mg, 18%) as a light pink solid. $^1$H NMR (DMSO-d$_6$, 400 MHz): δ 2.16 (s, 3H), 2.40 (s, 3H), 5.17 (s, 2H), 7.17-7.22 (m, 2H), 7.50 (s, 1H), 7.66 (dt, J=8, 1.2 Hz, 1H), 7.92 (d, J=6.8 Hz, 1H), 7.95 (s, 1H), 11.52 (bs, 1H). The title compound was shown to inhibit hT2R08 bitter receptor and had an IC$_{50}$ of 1.5 µM.

Example 9-5

1-benzyl-3-(1-((3,5-dimethylisoxazol-4-yl)methyl)-1H-pyrazol-4-yl)tetrahydropyrimidin-2(1H)-one

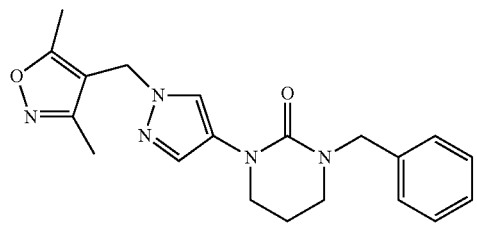 [SMILES: Cc1noc(C)c1Cn1cc(N2CCCN(Cc3ccccc3)C2=O)cn1]

1-(1-((3,5-dimethylisoxazol-4-yl)methyl)-1H-pyrazol-4-yl)tetrahydropyrimidin-2(1H)-one (example 9-5a) (50 mg, 0.18 mmol) and 60% sodium hydride (8 mg, 0.20 mmol) in DMF (3 mL) were stirred at room temperature for 15 minutes then cooled to 0° C. Benzyl bromide (31 mg, 0.18 mmol) was added to the mixture and allowed to warm up at room temperature then stirred for 2 hours. The reaction was quenched with methanol and concentrated. The reaction was diluted with brine (50 mL) and extracted with dichloromethane (2×, 50 mL). The combined organic extracts were dried over magnesium sulfate, filtered and concentrated on the rotovap. The residue was taken up in dichloromethane (5 mL) and purified by silica column chromatography (100% to 90% dichloromethane in methanol: 30 minute gradient) to afford 1-benzyl-3-(1-((3,5-dimethylisoxazol-4-yl)methyl)-1H-pyrazol-4-yl)tetrahydropyrimidin-2(1H)-one (20 mg, 30%) as a white solid. $^1$H NMR (DMSO-d$_6$, 400 MHz): δ 85-1.91 (m, 2H), 2.10 (s, 3H), 2.37 (s, 3H), 3.12 (m, 2H), 3.55 (t, J=5.8 Hz, 2H), 4.48 (s, 2H), 5.05 (s, 2H), 7.22-7.31 (m, 5H), 7.49 (s, 1H), 7.84 (s, 1H). LC/MS; [M+H] calculated for C$_{20}$H$_{23}$N$_5$O$_2$; expected 366.19; found 366.15. The title compound was shown to inhibit hT2R08 bitter receptor and had an IC$_{50}$ of 1.65 µM.

Example 9-5a 1-(1-((3,5-dimethylisoxazol-4-yl)methyl)-1H-pyrazol-4-yl)tetrahydropyrimidin-2(1H)-one

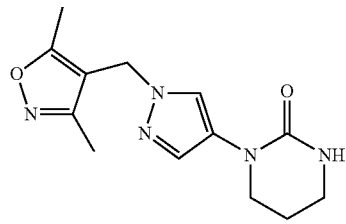 [SMILES: Cc1noc(C)c1Cn1cc(N2CCCNC2=O)cn1]

1-(3-chloropropyl)-3-(1-((3,5-dimethylisoxazol-4-yl)methyl)1H-pyrazol-4-yl)urea (example 9-5b) (200 mg, 0.64 mmol) and 60% sodium hydride (28 mg, 0.71 mmol) in DMF (2 mL) were stirred at 0° C. for 15 minutes then allowed to warm up to room temperature and stir for 2 hours. The reaction was quenched with methanol and concentrated. The reaction was diluted with brine (50 mL) and extracted with dichloromethane (2×, 50 mL). The combined organic extracts were dried over magnesium sulfate, filtered and concentrated. The residue was taken up in dichloromethane (5 mL) and purified by silica column chromatography (100% to 90% dichloromethane in methanol: 30 minute gradient) to afford 1-(1-((3,5-dimethylisoxazol-4-yl)methyl)-1H-pyrazol-4-yl)tetrahydropyrimidin-2(1H)-one (84 mg, 48%) as a white solid. $^{1}$H NMR (DMSO-$d_6$, 400 MHz): δ1.85-1.91 (m, 2H), 2.10 (s, 3H), 2.37 (s, 3H), 3.12 (m, 2H), 3.48 (t, J=6.0 Hz, 2H), 5.05 (s, 2H), 6.57 (s, 1H), 7.46 (s, 1H), 7.80 (s, 1H). LC/MS; [M+H] calculated for $C_{13}H_{17}N_5O_2$; expected 276.14; found 276.10.

Example 9-5b 1-(3-chloropropyl)-3-(1-((3,5-dimethylisoxazol-4-yl)methyl)-1H-pyrazol-4-yl)urea

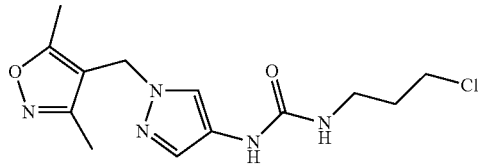 [SMILES: Cc1noc(C)c1Cn1cc(NC(=O)NCCCCl)cn1]

1-((3,5-dimethylisoxazol-4-yl)methyl)-1H-pyrazol-4-amine (342 mg, 1.78 mmol) and 2-chloropropyl isocyanate (213 mg, 1.78 mmol) in acetonitrile (5 mL) were heated at 65° C. for 16 hours. The reaction was cooled down to room temperature, concentrated and the residue was dissolved in dichloromethane (5 mL) and purified by silica column chromotography (100% to 90% dichloromethane in methanol: 30 minute gradient). The pure fractions were combined and concentrated, then triturated with ethyl acetate/hexanes (1/9) to afford (1-(3-chloropropyl)-3-(1-((3,5-dimethylisoxazol-4-yl)methyl)1H-pyrazol-4-yl)urea (218 mg, 39%) as white solid. LC/MS; [M+H] calculated for $C_{12}H_{16}ClN_5O_2$; expected 298.10; found 298.10.

Example 9-6

1-benzyl-3-(1-((3,5-dimethylisoxazol-4-yl)methyl)-1H-pyrazol-4-yl)-1,3,5-triazinan-2-one

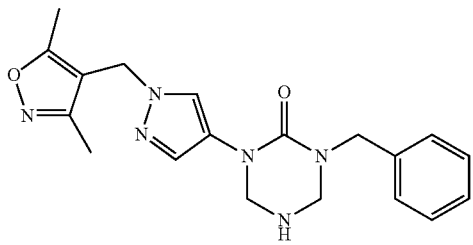 [SMILES: Cc1noc(C)c1Cn1cc(N2CNCN(Cc3ccccc3)C2=O)cn1]

1-benzyl-5-(2,4-dimethoxybenzyl)-3-(1-((3,5-dimethylisoxazol-4-yl)methyl)-1H-pyrazol-4-yl)-1,3,5-triazinan-2-one (example 9-6a) (44 mg, 0.09 mmol), anisole (9 mg, 0.09 mmol), and 50% trifluoroacetic acid/dichloromethane solution (1 mL) in dichloromethane (1 mL) were stirred at room temperature for 2 hours. The reaction was concentrated, quenched with saturated sodium bicarbonate (50 mL), extracted with ethyl acetate (2×, 50 mL) and washed with brine (50 mL). The combined organic extracts were dried over magnesium sulfate, filtered and, concentrated. Purification by silica column chromatography (100% to 90% dichloromethane in methanol: 30 minute gradient) afforded 1-benzyl-3-(1-((3,5-dimethylisoxazol-4-yl)methyl)-1H-pyrazol-4-yl)-1,3,5-triazinan-2-one (19 mg, 62%) as a white solid. LC/MS; [M+H] calculated for $C_{19}H_{22}N_6O_2$; expected 367.18; found 367.20. The title compound was shown to inhibit hT2R08 bitter receptor and had an $IC_{50}$ of 5.84 μM.

Example 9-6a 1-benzyl-5-(2,4-dimethoxybenzyl)-3-(1-((3,5-dimethylisoxazol-4-yl)methyl)-1H-pyrazol-4-yl)-1,3,5-triazinan-2-one

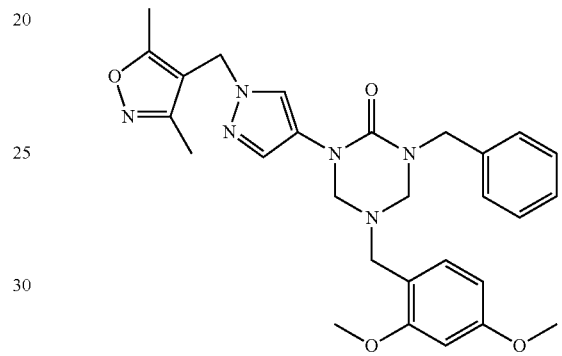

1-benzyl-3-(1-((3,5-dimethylisoxazol-4-yl)methyl)-1H-pyrazol-4-yl)urea (example 9-6b) (50 mg, 0.15 mmol), 2,4-methoxy benzyl amine (26 mg, 0.15 mmol), and formaldehyde (37% wt. in water) (25 mg, 0.31 mmol) were heated at 100° C. for 16 hours. The reaction was cooled to room temperature, diluted with brine (50 mL) and extracted with dichloromethane (2×, 50 mL). The combined organic extracts were dried over magnesium sulfate, filtered and concentrated. The residue was purified by silica column chromatography (100% to 90% dichloromethane in methanol: 30 minute gradient) to afford 1-benzyl-5-(2,4-dimethoxybenzyl)-3-(1-((3,5-dimethylisoxazol-4-yl)methyl)-1H-pyrazol-4-yl)-1,3,5-triazinan-2-one (44 mg, 56%) as an oil. LC/MS; [M+H] calculated for $C_{28}H_{32}N_6O_4$; expected 517.25; found 517.20.

Example 9-6b 1-benzyl-3-(1-((3,5-dimethylisoxazol-4-yl)methyl)-1H-pyrazol-4-yl)urea

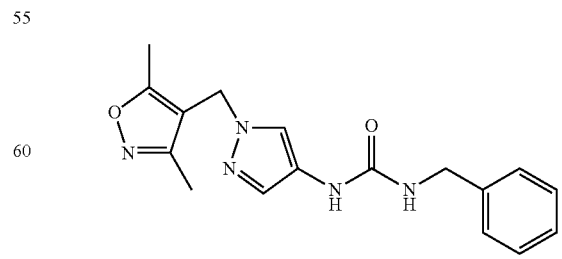

1-((3,5-dimethylisoxazol-4-yl)methyl)-1H-pyrazol-4-amine (287 mg, 1.49 mmol) and benzyl isocyanate (199 mg, 1.49 mmol) in acetonitrile (5 mL) were heated at 65° C. for 16 hours. The reaction was cooled down to room temperature and concentrated. The residue was purified by silica column chromatography (100% to 90% dichloromethane in methanol: 30 minute gradient) and triturated with ethyl acetate/hexanes (1/9) to afford 1-benzyl-3-(1-((3,5-dimethylisoxazol-4-yl)methyl)-1H-pyrazol-4-yl)urea (246 mg, 51%) as a white solid. LC/MS; [M+H] calculated for $C_{17}H_{19}N_5O_2$; expected 326.15; found 326.10.

Example 9-7

5-benzyl-1-(1-((3,5-dimethylisoxazol-4-yl)methyl)-1H-pyrazol-4-yl)-3-phenethyl-1,3,5-triazinan-2-one

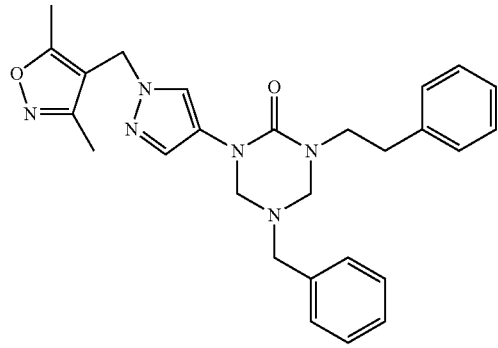 [SMILES: Cc1noc(C)c1Cn1cc(N2CN(Cc3ccccc3)CN(CCc3ccccc3)C2=O)cn1]

Prepared as in example 9-6a from 1-(1-((3,5-dimethylisoxazol-4-yl)methyl)-1H-pyrazol-4-yl)-3-phenethylurea (example 9-7a), formaldehyde, and benzyl amine. Yield: 15%. $^1$H NMR (DMSO-$d_6$, 400 MHz): δ2.11 (s, 3H), 2.37 (s, 3H), 2.69 (t, J=7.6 Hz, 2H), 3.39 (t, J=7.8 Hz, 2H), 3.81 (s, 2H), 4.16 (s, 2H), 4.42 (s, 2H), 5.05 (s, 2H), 7.17-7.32 (m, 10H), 7.42 (s, 1H), 7.78 (s, 1H). LC/MS; [M+H] calculated for $C_{27}H_{30}N_6O_2$; expected 471.24; found 471.15. The title compound was shown to inhibit hT2R08 bitter receptor and had an $IC_{50}$ of 2.64 μM.

Example 9-7a 1-(1-((3,5-dimethylisoxazol-4-yl)methyl)-1H-pyrazol-4-yl)-3-phenethylurea

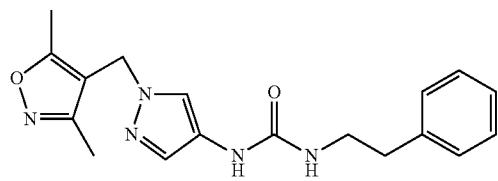 [SMILES: Cc1noc(C)c1Cn1cc(NC(=O)NCCc2ccccc2)cn1]

Prepared as in example 9-6b from 1-((3,5-dimethylisoxazol-4-yl)methyl)-1H-pyrazol-4-amine and phenethyl isocyanate. Yield: 29%. $^1$H NMR (DMSO-$d_6$, 400 MHz): δ2.10 (s, 3H), 2.36 (s, 3H), 2.69 (t, J=7.2 Hz, 2H), 3.25 (q, J=7.4 Hz, 2H), 5.02 (s, 2H), 6.00 (t, J=5.8 Hz, 1H), 7.16-7.30 (m, 6H), 7.68 (s, 1H), 8.13 (s, 1H). LC/MS; [M+H] calculated for $C_{18}H_{21}N_5O_2$; expected 340.17; found 340.20.

Example 9-8

1-(1-((3,5-dimethylisoxazol-4-yl)methyl)-1H-pyrazol-4-yl)-3-phenethyl-1,3,5-triazinane-2,4,6-trione

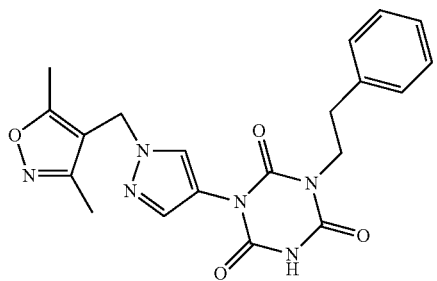 [SMILES: Cc1noc(C)c1Cn1cc(-n2c(=O)[nH]c(=O)n(CCc3ccccc3)c2=O)cn1]

1-(1-((3,5-dimethylisoxazol-4-yl)methyl)-1H-pyrazol-4-yl)-3-phenethylurea (example 9-7a) (100 mg, 0.29 mmol) in THF (2 mL) was cooled to 0° C. and n-chlorocarbonyl isocyanate (93 mg, 0.88 mmol) was slowly added. After addition, the reaction was allowed to warm to room temperature and stirred for 1 hour. The reaction was concentrated and the residue was purified by silica column chromotography (100% to 90% dichloromethane in methanol: 30 minute gradient) to afford (1-(1-((3,5-dimethylisoxazol-4-yl)methyl)-1H-pyrazol-4-yl)-3-phenethyl-1,3,5-triazinane-2,4,6-trione (100 mg, 83%) as a white solid. $^1$H NMR (DMSO-$d_6$, 400 MHz): δ2.13 (s, 3H), 2.39(s, 3H), 2.82 (t, J=5.8 Hz, 2H), 3.88 (t, J=8.0 Hz, 2H), 5.17 (s, 2H), 7.19-7.31 (m, 5H), 7.44 (s, 1H), 7.89 (s, 1H), 11.84 (s, 1H). LC/MS; [M+H] calculated for $C_{20}H_{20}N_6O_4$; expected 409.15; found 409.20. The title compound was shown to inhibit hT2R08 bitter receptor and had an $IC_{50}$ of 3.03 μM.

Example 9-9

1-benzyl-3-(1-((3,5-dimethylisoxazol-4-yl)methyl)-1H-pyrazol-4-yl)-1,3,5-triazinane-2,4,6-trione

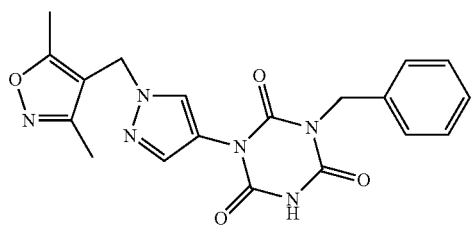 [SMILES: Cc1noc(C)c1Cn1cc(-n2c(=O)[nH]c(=O)n(Cc3ccccc3)c2=O)cn1]

1-benzyl-3-(1-((3,5-dimethylisoxazol-4-yl)methyl)-1H-pyrazol-4-yl)urea (example 95b) (100 mg, 0.31 mmol) in THF (2 mL) was cooled to 0° C. and n-chlorocarbonyl isocyanate (97 mg, 0.92 mmol) was slowly added. After addition, the reaction was allowed to warm up to room temperature and stirred for 1 hour. The reaction was concentrated and the residue was purified by silica column chromotography (100% to 90% dichloromethane in methanol: 30 minute gradient) to afford 1-benzyl-3-(1-((3,5-dimethylisoxazol-4-yl)methyl)-1H-pyrazol-4-yl)-1,3,5-triazinane-2,4,6-trione (112 mg, 93%) as a white solid. ¹H NMR (DMSO-d₆, 400 MHz): δ2.12 (s, 3H), 2.38(s, 3H), 4.87 (s, 2H), 5.16 (s, 2H), 7.23-7.34 (m, 5H), 7.45 (s, 1H), 7.90 (s, 1H), 11.93 (s, 1H). LC/MS; [M+H] calculated for $C_{19}H_{18}N_6O_4$; expected 395.14; found 395.15. The title compound was shown to inhibit hT2R08 bitter receptor and had an $IC_{50}$ of 1.14 μM.

Example 10 hT2R8 Antagonists: Making the Compounds of the Invention

Example 10-1

3-(1-((3,5-dimethylisoxazol-4-yl)methyl)-1H-pyrazol-4-yl)imidazolidine-2,4-dione

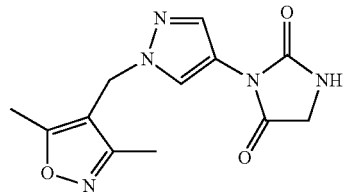 [SMILES: Cc1noc(C)c1Cn1cc(N2C(=O)CNC2=O)cn1]

1-((3,5-dimethylisoxazol-4-yl)methyl)-1H-pyrazole-4-carbonyl azide (example 10-1a) (6 g, 25.5 mmol) in toluene (100 mL) was refluxed for 1 hour and cooled to ambient temperature under an atmosphere of nitrogen. Glycine methyl ester-hydrochloride (3.1 g, 26 mmol) and triethylamine (3.2 g, 32 mmol) was added the mixture was refluxed for 16 hours. The reaction was cooled and the solvent removed on the rotovap. The solid was redissolved in ethyl acetate (100 mL) and the organic phase was washed with 1N HCl solution (2×, 150 mL). The aqueous phase was back extracted with ethyl acetate (2×, 75 mL) and the combined organic extracts were dried over sodium sulfate and concentrated. The resulting solid was triturated with ethyl acetate/hexanes (1/9) and dried under high vacuum to afford 3-(1-((3,5-dimethylisoxazol-4-yl)methyl)-1H-pyrazol-4-yl)imidazolidine-2,4-dione (5.2 g, 74%) as a white solid. ¹H NMR (DMSO-d₆, 400 MHz): δ 2.19 (s, 3H), 2.42 (s, 3H), 4.09 (s, 2H), 5.06 (s, 2H), 5.68 (bs, 1H), 7.90 (s, 1H), 8.05 (1H). The title compound was shown to inhibit hT2R08 bitter receptor and had an $IC_{50}$ of 1.7 μM.

Example 10-1a 1-((3,5-dimethylisoxazol-4-yl)methyl)-1H-pyrazole-4-carbonyl azide

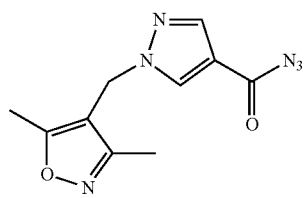 [SMILES: Cc1noc(C)c1Cn1cc(C(=O)N=[N+]=[N-])cn1]

Sodium nitrite (450 mg, 6.5 mmol, in H₂O) (10 mL) was added dropwise, over 10 minutes, to a suspension of 1-((3,5-dimethylisoxazol-4-yl)methyl)-1H-pyrazole-4-carbohydrazide (example 10-1b) (1 g, 4.3 mmol) in 10% aqueous acetic acid (50 mL) and cooled to 0° C. via an ice water bath. The reaction was stirred for an additional 15 minutes then extracted with ethyl acetate (3×, 75 mL). The combined organic extracts were washed with aqueous saturated sodium carbonate (100 mL) followed by H₂O (100 mL). The combined organic extracts were dried over sodium sulfate, filtered and concentrated. The solid product was triturated with ethyl acetate/hexanes (1/9) and dried en vacuo to afford 1-((3,5-dimethylisoxazol-4-yl)methyl)-1H-pyrazole-4-carbonyl azide (1 g, 93%) as a white solid. ¹H NMR (CDCl₃, 400 MHz): δ2.20 (s, 3H), 2.44 (s, 3H), 5.07 (s, 2H), 7.81 (s, 1H), 7.93 (s, 1H).

Example 10-1b 1-((3,5-dimethylisoxazol-4-yl)methyl)-1H-pyrazole-4-carbohydrazide

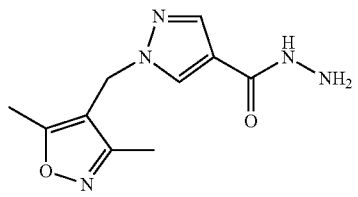 [SMILES: Cc1noc(C)c1Cn1cc(C(=O)NN)cn1]

Ethyl 1-((3,5-dimethylisoxazol-4-yl)methyl)-1H-pyrazole-4-carboxylate (example 10-1c) (6 g, 24 mmol) and hydrazine (7.5 g, 240 mmol) were stirred in EtOH (100 mL) at reflux for 12 hours. The solution was concentrated on the rotovap and the solid product was triturated with ethyl acetate/hexanes (1/9) and dried under high vacuum to afford 1-((3,5-dimethylisoxazol-4-yl)methyl)-1H-pyrazole-4-carbohydrazide (5.5 g, 97%) as a pure white solid. ¹H NMR (DMSO-d₆, 400 MHz): δ2.11 (s, 3H), 2.39 (s, 3H), 5.15 (s, 2H), 7.81 (s, 1H), 8.17 (s, 1H), 9.31 (bs, 1H).

Example 10-1c 1-((3,5-dimethylisoxazol-4-yl)methyl)-1H-pyrazole-4-carboxylate

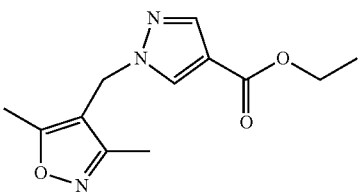 [SMILES: CCOC(=O)c1cnn(Cc2c(C)noc2C)c1]

Ethyl 1H-pyrazole-4-carboxylate (4.2 g, 30 mmol), 4-(chloromethyl)-3,5-dimethylisoxazole (5.1 g, 35 mmol), and cesium carbonate (9.8 g, 30 mmol), in DMF (50 mL), were stirred at 80° C. for 12 hours. The reaction was cooled to ambient temperature, diluted with 0.1 N HCl (150 mL) and extracted with ethyl acetate (3×, 75 mL). The combined organic extracts were dried over sodium sulfate and concentrated on the rotovap. The solid product was triturated with ethyl acetate/hexanes(1/9) and collected by filtration to afford ethyl 1-((3,5-dimethylisoxazol-4-yl)methyl)-1H-pyrazole-4-carboxylate (6g, 80%) as a white solid. ¹H NMR (CDCl₃, 400

MHz): δ1.34 (t, J=7.2 Hz, 3H), 2.19 (s, 3H), 2.43 (s, 3H), 4.29 (q, J=7.2 Hz, 2H), 5.06 (s, 2H), 7.77 (s, 1H), 7.91 (s, 1H).

Example 10-2

3-(1-((3,5-dimethylisoxazol-4-yl)methyl)-1H-pyrazol-4-yl)imidazolidine-2,4-dione

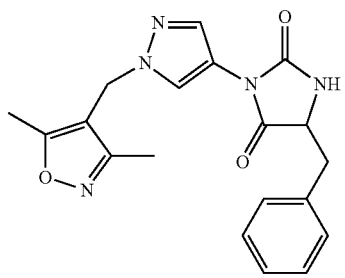 [SMILES: Cc1noc(C)c1Cn1cc(N2C(=O)NC(Cc3ccccc3)C2=O)cn1]

Prepared as in example 10-1 from (+/−)-phenylalanine methyl ester hydrochloride and 1-((3,5-dimethylisoxazol-4-yl)methyl)-1H-pyrazole-4-carbonyl azide. Yield: 58%. $^1$H NMR (Acetone-$d_6$, 400 MHz): δ2.17 (s, 3H), 2.43 (s, 3H), 3.07 (dd, J=14.4, 6.4 Hz, 1H), 3.20 (dd, J=14, 4.4 Hz, 1H), 4.53 (t, J=4.8 Hz, 1H), 5.18 (s, 2H), 7.27-7.19 (m, 5H), 7.46 (bs, 1H), 7.79 (s, 1H), 7.99 (s, 1H). MS M+H calculated 366.15; found 366.1. Melting point: 169-171° C. The title compound was shown to inhibit hT2R08 bitter receptor and had an $IC_{50}$ of 0.18 μM.

Example 10-3

(S)-5-benzyl-3-(1-((3,5-dimethylisoxazol-4-yl)methyl)-1H-pyrazol-4-yl)imidazolidine-2,4-dione

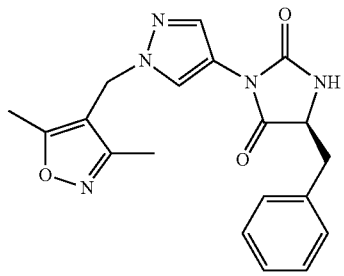 [SMILES: Cc1noc(C)c1Cn1cc(N2C(=O)N[C@@H](Cc3ccccc3)C2=O)cn1]

Prepared as in example 10-1 from (S)-phenylalanine methyl ester hydrochloride and 1-((3,5-dimethylisoxazol-4-yl)methyl)-1H-pyrazole-4-carbonyl azide (example 6a). Yield: 13% isolated from chiral chromotography $^1$H NMR (CDCl$_3$, 400 MHz): δ2.19 (s, 3H), 2.42 (s, 3H), 2.88 (dd, J=13.6, 9.2 Hz, 1H), 3.35 (dd, J=13.6, 3.6 Hz, 1H), 4.31-4.35 (m, 1H) 5.06 (s, 2H), 5.53 (bs, 1H), 7.21-7.36 (m, 5H), 7.85 (s, 1H), 8.01 (s, 1H). LC/MS; [M+H] calculated for $C_{19}H_{19}N_5O_3$; expected 366.15; found 366.1. [α]$_D$=(−)−136, c=0.1, ethanol. The title compound was shown to inhibit hT2R08 bitter receptor and had an $IC_{50}$ of 0.12 μM.

Example 10-4

(R)-5-benzyl-3-(1-((3,5-dimethylisoxazol-4-yl)methyl)-1H-pyrazol-4-yl)imidazolidine-2,4-dione

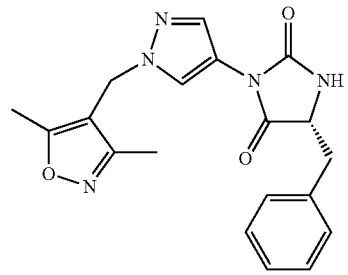 [SMILES: Cc1noc(C)c1Cn1cc(N2C(=O)N[C@H](Cc3ccccc3)C2=O)cn1]

Prepared as in example 10-1 from (R)-phenylalanine methyl ester hydrochloride and 1-((3,5-dimethylisoxazol-4-yl)methyl)-1H-pyrazole-4-carbonyl azide. Yield: 9% isolated from chiral chromotography $^1$H NMR (CDCl$_3$, 400 MHz): δ2.19 (s, 3H), 2.42 (s, 3H), 2.88 (dd, J=13.6, 9.2 Hz, 1H), 3.35 (dd, J=13.6, 3.6 Hz, 1H), 4.31-4.35 (m, 1H) 5.06 (s, 2H), 5.53 (bs, 1H), 7.21-7.36 (m, 5H), 7.85 (s, 1H), 8.01 (s, 1H). MS M+H calculated 366.15; found 366.1. [α]$_D$=(+)−124, c=0.2, ethanol. The title compound was shown to inhibit hT2R08 bitter receptor and had an $IC_{50}$ of 0.11 μM.

Example 10-5

3-(1-((3,5-dimethylisoxazol-4-yl)methyl)-1H-pyrazol-4-yl)-1-(2-phenoxyethyl)imidazolidine-2,4-dione

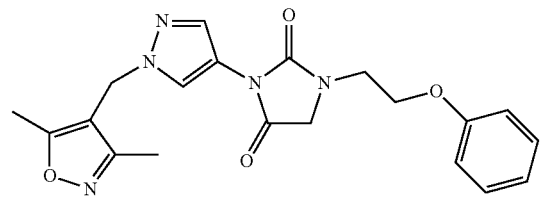 [SMILES: Cc1noc(C)c1Cn1cc(N2C(=O)CN(CCOc3ccccc3)C2=O)cn1]

3-(1-((3,5-dimethylisoxazol-4-yl)methyl)-1H-pyrazol-4-yl)imidazolidine-2,4-dione (example 10-1) (200 mg, 0.7 mmol), (2-bromoethoxy)benzene (200 mg, 1 mmol), and cesium carbonate (325 mg, 1 mmol) were irradiated in the microwave reactor at 85° C. for 20 minutes. The reaction was cooled to room temperature, diluted with aqueous 1N HCl (100 mL) and extracted with ethyl acetate (3×, 75 mL). The combined organic extracts were dried over sodium sulfate, filtered and concentrated. The residue was taken up in methanol (10 mL) and purified by reversed phase HPLC (5 to 95% acetonitrile in H$_2$O: 25 minute gradient). The pure fractions were pooled, concentrated then re-dissolved in absolute ethanol and concentrated on the rotovap (4×) to afford 3-(1-((3, 5-dimethylisoxazol-4-yl)methyl)-1H-pyrazol-4-yl)-1-(2-phenoxyethyl)imidazolidine-2,4-dione (150 mg, 54%) as a white solid. $^1$H NMR (CDCl$_3$ 2.18, 400 MHz): δ (s, 3H), 2.41 (s, 3H), 3.86 (t, J=5.2 Hz, 2H), 4.19 (t, J=4.4 Hz, 2H), 4.25 (s, 2H), 5.05 (s, 2H), 6.88 (dd, J=9.2, 1.2 Hz, 2H), 7.00 (dt, J=7.6, 1.2 Hz, 1H), 7.27-7.32 (m, 2H), 7.89 (s, 1H), 8.05 (s, 1H). MS M+H calculated 396.17; found 396.1. Melting point: 117-118° C. The title compound was shown to inhibit hT2R08 bitter receptor and had an IC$_{50}$ of 0.06 µM.

Example 10-6

3-(1-((3,5-dimethylisoxazol-4-yl)methyl)-1H-pyrazol-4-yl)-1-(3-methoxybenzyl)imidazolidine-2,4-dione

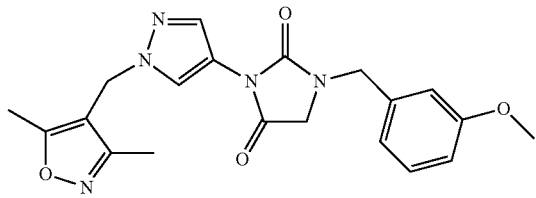

Prepared as in example 10-5 from 3-(1-((3,5-dimethylisoxazol-4-yl)methyl)-1H-pyrazol-4-yl)imidazolidine-2,4-dione (example 6) and 3-methoxy-benzyl bromide. Yield: 55%. $^1$H NMR (CDCl$_3$, 400 MHz): δ2.19 (s, 3H), 2.42 (s, 3H), 3.81 (s, 3H), 3.85 (s, 2H), 4.58 (s, 2H), 5.06 (s, 2H), 6.81-6.88 (m, 3H), 7.26-7.31 (m, 1H), 7.92 (s, 1H), 8.08 (s, 1H). The title compound was shown to inhibit hT2R08 bitter receptor and had an IC$_{50}$ of 0.07 µM.

Example 10-7

Methyl 3-((3-(1-((3,5-dimethylisoxazol-4-yl)methyl)-1H-pyrazol-4-yl)-2,4-dioxoimidazolidin-1-yl)methyl)benzoate

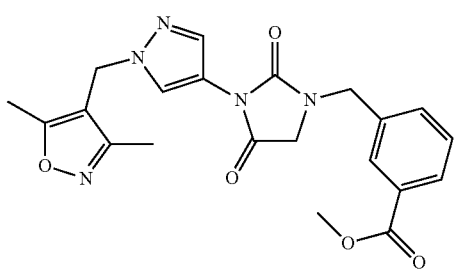 [SMILES: COC(=O)c1cccc(CN2CC(=O)N(c3cnn(Cc4c(C)noc4C)c3)C2=O)c1]

Prepared as in example 10-5 from 3-(1-((3,5-dimethylisoxazol-4-yl)methyl)-1H-pyrazol-4-yl)imidazolidine-2,4-dione and 3-methoxy-benzyl bromide. Yield: 83%. $^1$H NMR (CDCl$_3$, 400 MHz): δ2.20 (s, 3H), 2.43 (s, 3H), 3.86 (s, 2H), 3.93 (s, 3H), 4.67 (s, 2H), 5.07 (s, 2H), 7.45-7.52 (m, 2H), 7.93 (s, 1H), 7.95 (s, 1H), 8.03 (dd, J=7.2, 1.6 Hz, 1H), 8.08 (s, 1H). The title compound was shown to inhibit hT2R08 bitter receptor and had an IC$_{50}$ of 0.09 µM.

Example 10-8

3-((3-(1-((3,5-dimethylisoxazol-4-yl)methyl)-1H-pyrazol-4-yl)-2,4-dioxoimidazolidin-1-yl)methyl)benzoic acid

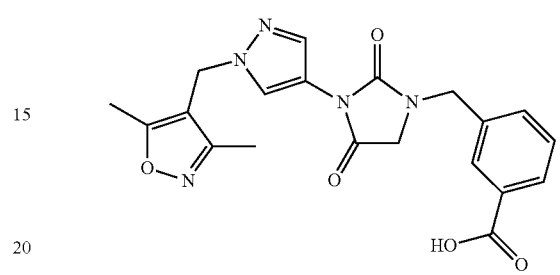

3-(1-((3,5-dimethylisoxazol-4-yl)methyl)-1H-pyrazol-4-yl)imidazolidine-2,4-dione (500 mg, 1.8 mmol) (example 10-5), methyl 3-(bromomethyl)benzoate (456 mg, 2 mmol), and cesium carbonate (650 mg, 2 mmol) were stirred in DMF (4 mL) in the microwave reactor at 85° C. for 20 minutes. The reaction was cooled, diluted with 1N aqueous HCl (100 mL) and extracted with ethyl acetate (3×, 75 mL). The combined organic extracts were dried over sodium sulfate, filtered and concentrated. The crude ester was dissolved in methanol (5 mL) and aqueous NaOH (50 mL, 10% by wt) was added and the mixture was stirred at ambient temperature for 2 hours. The reaction was acidified with 1N HCl (150 mL) and extracted with ethyl acetate (3×, 75 mL). The combined organic extracts were dried over sodium sulfate, filtered, and concentrated on the rotovap. The free acid was triturated with ethyl acetate/hexanes (1/9) and dried under vacuum to afford 3-((3-(1-((3,5-dimethylisoxazol-4-yl)methyl)-1H-pyrazol-4-yl)-2,4-dioxoimidazolidin-1-yl)methyl)benzoic acid (610.mg, 83%) as a white solid. $^1$H NMR (DMSO-d$_6$, 400 2.13 (s, 3H), 2.29 (s, 3H), 4.00 (s, 2H), 4.59 (s, 2H), 5.18 (s, 2H),MHz): δ 7.46-7.59 (m, 2H), 7.78 (s, 1H), 7.85-7.88 (m, 2H), 8.18 (s, 1H). The title compound was shown to inhibit hT2R08 bitter receptor and had an IC$_{50}$ of 1.8 µM.

Example 10-9

3-((3-(1-((3,5-dimethylisoxazol-4-yl)methyl)-1H-pyrazol-4-yl)-2,4-dioxoimidazolidin-1-yl)methyl)-N-methylbenzamide

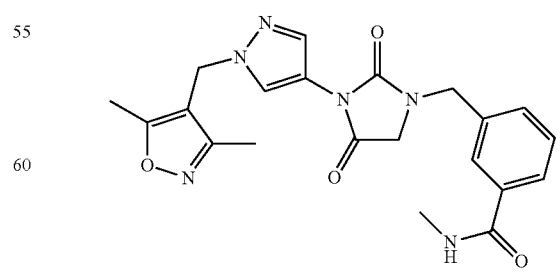

3-((3-(1-((3,5-dimethylisoxazol-4-yl)methyl)-1H-pyrazol-4-yl)-2,4-dioxoimidazolidin-1-yl)methyl)benzoic acid (100 mg, 0.24 mmol) (example 10-8), methylamaine hydrochloride (67 mg, 1 mmol), triethylamine (155 mg, 1.5 mmol), and EDC (57 mg, 0.3 mmol) in acetonitrile (3 mL) were irradiated in the microwave reactor at 80° C. for 10 minutes. The reaction was cooled, diluted with aqueous 1N HCl (100 mL) and extracted with ethyl acetate (3×, 75 mL). The combined organic extracts were dried over sodium sulfate, filtered and concentrated. The crude product was dissolved in MeOH (3 mL) and purified by reversed phase HPLC (5 to 95% acetonitrile in H2O: 25 minute gradient) to afford 3-((3-(1-((3,5-dimethylisoxazol-4-yl)methyl)-1H-pyrazol-4-yl)-2,4-dioxoimidazolidin-1-yl)methyl)-N-methylbenzamide (25 mg, 25%) as white solid. MS M+H calculated 423.17; found 423.2. The title compound was shown to inhibit hT2R08 bitter receptor and had an IC$_{50}$ of 0.14 µM.

Example 10-10

3-(1-((3,5-dimethylisoxazol-4-yl)methyl)-1H-pyrazol-4-yl)-1-(3-hydroxybenzyl)imidazolidine-2,4-dione

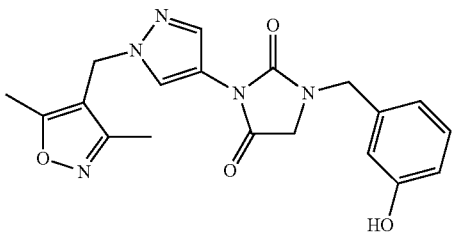 [SMILES: Cc1noc(C)c1Cn1cc(N2C(=O)CN(Cc3cccc(O)c3)C2=O)cn1]

Prepared as in example 10-1 from 1-((3,5-dimethylisoxazol-4-yl)methyl)-1H-pyrazole-4-carbonyl azide (example 10-1a) and methyl 2-(3-hydroxybenzylamino)acetate (example 10-10a). Yield: 24%. $^1$H NMR (DMSO, 400 MHz): δ2.15 (s, 3H), 2.41 (s, 3H), 3.99 (s, 2H), 4.45 (s, 2H), 5.21 (s, 2H), 6.70 (m, 3H), 7.15 (m, H), 7.80 (s, 1H), 8.19 (s, H), 9.44 (s, H). LC/MS; [M+H] expected 382.1; found 382.1. Melting point: 35-136° C. The title compound was shown to inhibit hT2R08 bitter receptor and had an IC$_{50}$ of 0.035 uM.

Example 10-10a methyl 2-(3-hydroxybenzylamino)acetate

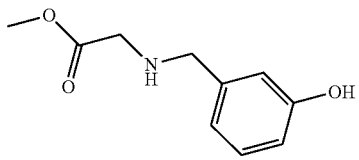

Glycine methyl ester (500 mg, 4 mmol) and 3-hydroxybenzaldehyde (480 mg, 4 mmol) were dissolved in 5 mL THF/Methanol (1:1). Acetic acid (240 mg, 4 mmol), and 1M sodium cyanoborohydride in THF (4.8 mL, 4.8 mmol) were slowly added into the reaction. The reaction was irradiated in the microwave reactor at 85° C. for 15 minutes, cooled to room temperature and the salts were removed by filtration. The clear solution was concentrated and the residue was purified by reversed phase HPLC (10 to 95% Acetonitrile in H2O:25 minute gradient) to give the title compound as a clear gel. Yield 45%. MS M+H calculated 196.1; found 196.1.

Alternatively 3-(1-((3,5-dimethylisoxazol-4-yl)methyl)-1H-pyrazol-4-yl)-1-(3-hydroxybenzyl)imidazolidine-2,4-dione can be prepared in large scale as in Example 12-1 from 1-(3-(tert-butyldimethylsilyloxy)benzyl)-3-(1-((3,5-dimethylisoxazol-4-yl)methyl)-1H-pyrazol-4-yl)imidazolidine-2,4-dione (Example 10-10b, below):

1-(3-(tert-butyldimethylsilyloxy)benzyl)-3-(1-((3,5-dimethylisoxazol-4-yl)methyl)-1H-pyrazol-4-yl)imidazolidine-2,4-dione (Example 10-10b) (6.00 g, 12.11 mmol) was dissolved in methanol (100 mL) and treated with HCl (2.0 M solution in diethyl ether, 5 equivalents). The solution was refluxed for 2. The mixture was allowed to cool down to room temperature and the solvent was removed. The residue was triturated in toluene, filtered and recrystallized from ethanol at 4° C. to give 3-(1-((3,5-dimethylisoxazol-4-yl)methyl)-1H-pyrazol-4-yl)-1-(3-hydroxybenzyl)imidazolidine-2,4-dione (4.50 g, 11.80 mmol, 97%) as a white solid. $^1$H NMR (DMSO, 400 MHz): δ 2.15 (s, 3H), 2.39 (s, 3H), 3.97 (s, 2H), 4.43 (s, 2H), 5.18 (s, 2H), 6.68 (m, 3H), 7.12 (m, 1H), 7.80 (s, 1H), 8.17 (s, H), 9.41 (s, H). MS 382 (MH$^+$).

Example 10-10b 1-(3-(tert-butyldimethylsilyloxy)benzyl)-3-(1-((3,5-dimethylisoxazol-4-yl)methyl)-1H-pyrazol-4-yl)imidazolidine-2,4-dione

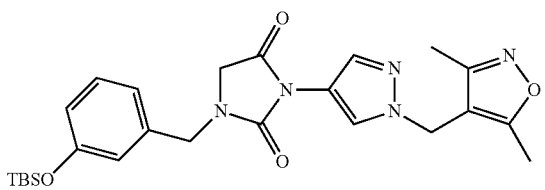 [SMILES: Cc1noc(C)c1Cn1cc(N2C(=O)CN(Cc3cccc(O[Si](C)(C)C(C)(C)C)c3)C2=O)cn1]

1-((3,5-dimethylisoxazol-4-yl)methyl)-1H-pyrazole-4-carbonyl azide (Example 10-1a) (3.00 g, 12.20 mmol) along with molecular sieves are stirred at reflux in dry toluene (300 mL) under nitrogen gas until no emission of nitrogen was observed, which indicates complete conversion of 1-((3,5-dimethylisoxazol-4-yl)methyl)-1H-pyrazole-4-carbonyl azide into 4-((4-isocyanato-1H-pyrazol-1-yl)methyl)-3,5-dimethylisoxazole. A solution of methyl 2-(3-(tert-butyldimethylsilyloxy)benzylamino)acetate (Example 10-10c) (3.78 g, 12.20 mmol) in dry toluene (50 mL) was prepared and added in one portion at 50° C. to the reaction mixture. The reaction was refluxed over the weekend, then cooled down to room temperature and filtered over a pad of celite. The filtrate was concentrated and to give 1-(3-(tert-butyldimethylsilyloxy)benzyl)-3-(1-((3,5-dimethylisoxazol-4-yl)methyl)-1H-pyrazol-4-yl)imidazolidine-2,4-dione as a yellowish oily used in the next step without further purification. MS 496 (MH$^+$). $^1$H NMR (CDCl$_3$, 400 MHz): δ 0.19 (s, 6H), 0.97 (s, 9H), 2.19 (s, 3H), 2.42 (s, 3H), 3.83 (s, 2H), 4.55 (s, 2H), 5.06 (s, 2H), 6.75 (m, 1H), 6.80 (m, 1H), 6.86 (m, 1H), 7.23 (t, J=8.0 Hz, 1H).

Example 10-10c methyl 2-(3-(tert-butyldimethylsilyloxy)benzylamino)acetate

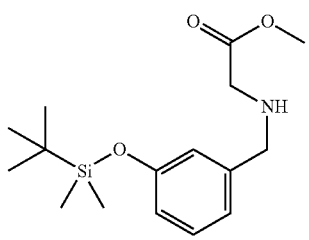 [SMILES: COC(=O)CNCc1cccc(O[Si](C)(C)C(C)(C)C)c1]

3-Hydroxybenzaldehyde (10 g, 81.88 mmol) was dissolved in anhydrous THF (200 mL) and N-ethyl-N-isopropylpropan-2-amine (Huenig's base, 31.8 mL, ~3 equivalent) was added. Upon addition of Huenig's base, the solution changed to yellow and was cooled down to 0° C. A solution of tert-butylchlorodimethylsilane (13.6 g, 1.1 equiv.) in THF (100 mL) was added dropwise. After stirring for 60 hours at room temperature, methyl 2-aminoacetate hydrochloride (21 g, 16.73 mmol, ~2 equiv.) was added and the mixture was stirred for 6 hours at room temperature. The reaction mixture was cooled down to about 10° C. using ice water and while stirring vigorously, it was treated rapidly with NaBH(OAc)$_3$ (35 g, 16.51, ~2 equiv.). After addition was completed, the cooling was immediately removed and the reaction mixture was stirred overnight under nitrogen. The mixture was quenched with saturated aqueous NaHCO$_3$ solution and the layers were separated. The aqueous phase was further extracted with DCM (2×300 mL). The combined organic extract was washed with water (50 mL), brine (100 mL) and dried over MgSO$_4$. The solvent was removed under vacuum and the residue purified over silica gel using 25% ethyl acetate in hexanes. After evaporation of solvent from clean fractions methyl 2-(3-(tert-butyldimethylsilyloxy)benzylamino)acetate (19.9 g, 64.30 mmol, 78%) was obtained as a colorless liquid. $^1$H NMR (DMSO-d$_6$, 400 MHz): δ 0.17 (s, 6H), 0.94 (s, 9H), 2.47 (br s, 1H), 3.28 (s, 2H), 3.61 (s, 3H), 3.65 (s, 2H), 6.70 (ddd, J=0.8, 1.2, 8.0 Hz, 1H), 6.81 (m, 1H), 6.89 (br dt, J=0.8, 7.6 Hz, 1H), 7.17 (pseudo t, J=7.6, 8.0 Hz, 1H).

Example 10-11

3-(1-((3,5-dimethylisoxazol-4-yl)methyl)-1H-pyrazol-4-yl)-1-(2-hydroxybenzyl)imidazolidine-2,4-dione

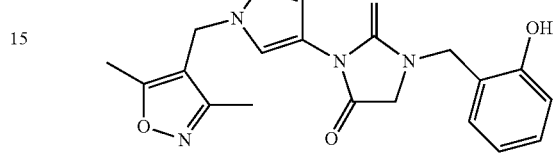

Prepared as in example 10-1 from 1-((3,5-dimethylisoxazol-4-yl)methyl)-1H-pyrazole-4-carbonyl azide (example 10-1a) and methyl 2-(2-hydroxybenzylamino)acetate (example 10-11a). Yield: 28%. $^1$H NMR (DMSO, 400 MHz): δ2.12 (s, 3H), 2.38 (s, 3H), 4.00 (s, 2H), 4.45 (s, 2H), 5.17 (s, 2H), 6.83 (m, 2H), 7.10 (m, 2H), 7.78 (s, 1H), 8.16 (s, H), 9.66 (s, H). LC/MS; [M+H] expected 382.1; found 382.2. The title compound was shown to inhibit hT2R08 bitter receptor and had an IC$_{50}$ of 0.07 uM.

Example 10-11a methyl 2-(2-hydroxybenzylamino)acetate

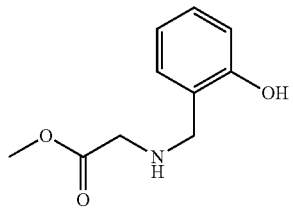

Prepared as in example 10-10a from glycine methyl ester and 2-hydroxybenzaldehyde. Yield 40%. MS M+H calculated 196.1; found 196.1

Example 10-12

3-(1-((3,5-dimethylisoxazol-4-yl)methyl)-1H-pyrazol-4-yl)-1-(4-hydroxybenzyl)imidazolidine-2,4-dione

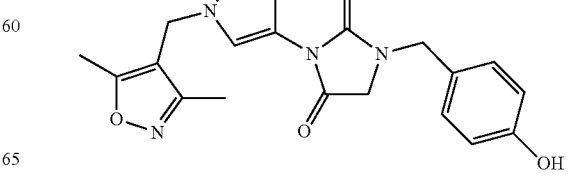

Prepared as in example 10-1 from 1-((3,5-dimethylisoxazol-4-yl)methyl)-1H-pyrazole-4-carbonyl azide and methyl 2-(4-hydroxybenzylamino)acetate (example 10-12a). Yield 9%. ¹H NMR (DMSO, 400 MHz): δ2.117 (s, 3H), 2.383 (s, 3H), 3.918 (s, 2H), 4.387 (s, 2H), 5.174 (s, 2H), 6.719 (J=8.8, d, 2H), 7.108 (J=8.8, m, 2H), 7.761 (s, 1H), 8.154 (s, H), 9.399 (s, H). LC/MS; [M+H] expected 382.1; found 382.2. The title compound was shown to inhibit hT2R08 bitter receptor and had an IC$_{50}$ of 0.06 uM.

Example 10-12a methyl 2-(4-hydroxybenzylamino)acetate

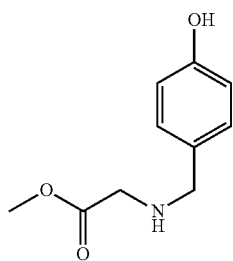

Prepared as in example 10-10a from glycine methyl ester and 4-hydroxybenzaldehyde. Yield 40%. MS M+H calculated 196.1; found 196.1

Example 10-13

3-(1-((3,5-dimethylisoxazol-4-yl)methyl)-1H-pyrazol-4-yl)-1-(3-hydroxy-4-methoxybenzyl)imidazolidine-2,4-dione

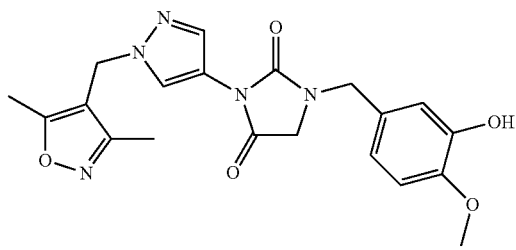 [SMILES: COc1ccc(CN2CC(=O)N(c3cnn(Cc4c(C)noc4C)c3)C2=O)cc1O]

Prepared as in example 10-1 from 1-((3,5-dimethylisoxazol-4-yl)methyl)-1H-pyrazole-4-carbonyl azide (example 10-1a) and methyl 2-(3-hydroxy-4-methoxybenzylamino)acetate (example 10-13a). Yield 22%. ¹H NMR (DMSO, 400 MHz): δ2.119 (s, 3H), 2.383 (s, 3H), 3.716 (s, 3H), 3.923 (s, 2H), 4.361 (s, 2H), 5.117 (s, 2H), 6.667 (m, 2H), 6.863 (J=8.4, d, 1H), 7.766 (s, H), 8.159 (s, H). MS M+H calculated 412.1; found 412.1. The title compound was shown to inhibit hT2R08 bitter receptor and had an IC$_{50}$ of 0.1 uM.

Example 10-13a methyl 2-(3-hydroxy-4-methoxybenzylamino)acetate

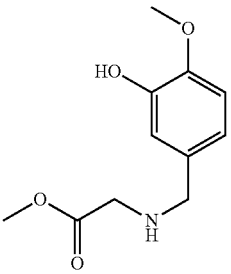 [SMILES: COC(=O)CNCc1ccc(OC)c(O)c1]

Prepared as in example 10-10a from glycine methyl ester and 3-hydroxy-4-methoxybenzaldehyde. Yield 47%. MS M+H calculated 226.1; found 226.1

Example 10-14

3-(1-((3,5-dimethylisoxazol-4-yl)methyl)-1H-pyrazol-4-yl)-1-(3-(2-methoxyethoxy)benzyl)imidazolidine-2,4-dione

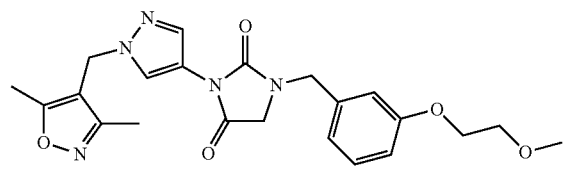

Prepared as in example 10-1 from 1-((3,5-dimethylisoxazol-4-yl)methyl)-1H-pyrazole-4-carbonyl azide (example 10-1a) and methyl 2-(3-(2-methoxyethoxy)benzylamino)acetate (example 10-14a). Yield 27%. ¹H NMR (DMSO, 400 MHz): δ2.12 (s, 3H), 2.38 (s, 3H), 3.26 (s, 3H), 3.62 (t, J=4.4, 2H), 3.98 (s, 2H), 4.06 (t, J=4.4, 2H), 4.48 (s, 2H), 5.18 (s, 2H), 6.86 (m, 3H), 7.24 (t, J=8, 1H), 7.78 (s, 1H), 8.17 (s, 1H). MS M+H calculated 440.2; found 440.2. The title compound was shown to inhibit hT2R08 bitter receptor and had an IC$_{50}$ of 0.07 uM.

Example 10-14a methyl 2-(3-(2-methoxyethoxy)benzylamino)acetate

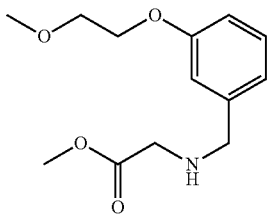 [SMILES: COCCOc1cccc(CNCC(=O)OC)c1]

Prepared as in example 10-10a from glycine methyl ester and 3-(2-methoxyethoxy)benzaldehyde. Yield 55%. MS M+H calculated 254.1; found 254.1

Example 10-15

3-(1-((3,5-dimethylisoxazol-4-yl)methyl)-1H-pyrazol-4-yl)-1-(2-(methylthio)benzyl)imidazolidine-2,4-dione

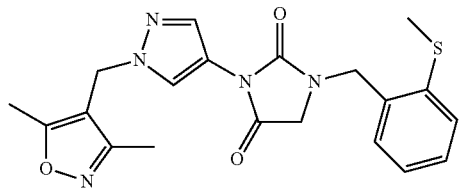 [SMILES: CSc1ccccc1CN1CC(=O)N(c2cnn(Cc3c(C)noc3C)c2)C1=O]

Prepared as in example 10-1 from 1-((3,5-dimethylisoxazol-4-yl)methyl)-1H-pyrazole-4-carbonyl azide (example 10-1a) and methyl 2-(2-(methylthio)benzylamino)acetate (example 10-15a). Yield 67%. $^1$H NMR (DMSO, 400 MHz): δ2.12 (s, 3H), 2.39 (s, 3H), 2.48 (s, 3H), 3.98 (s, 2H), 4.54 (s, 2H), 5.19 (s, 2H), 7.18 (m, 1H), 7.30 (m, 3H), 7.79 (s, 1H), 8.18 (s, 1H). LC/MS; [M+H] expected 412.1; found 412.1. The title compound was shown to inhibit hT2R08 bitter receptor and had an $IC_{50}$ of 0.03 uM.

Example 10-15a methyl 2-(2-(methylthio)benzylamino)acetate

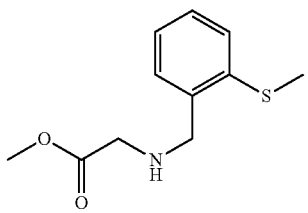

Prepared as in example 10-10a from glycine methyl ester and 2-(methylthio)benzaldehyde. Yield 50%. MS M+H calculated 226.1; found 226.1

Example 10-16

3-(1-((3,5-dimethylisoxazol-4-yl)methyl)-1H-pyrazol-4-yl)-1-(2-(2-methoxyethoxy)benzyl)imidazolidine-2,4-dione

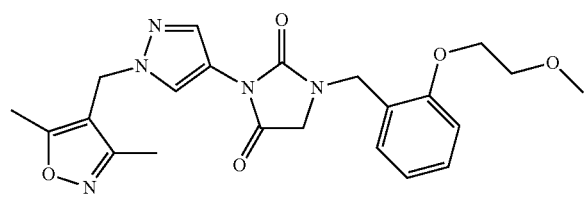

Prepared as in example 10-5 from 3-(1-((3,5-dimethylisoxazol-4-yl)methyl)-1H-pyrazol-4-yl)-1-(2-hydroxybenzyl)imidazolidine-2,4-dione (example 10-11) and 2-bromoethyl methyl ether. Yield 19%. $^1$H NMR (DMSO, 400 MHz): δ2.11 (s, 3H), 2.08 (s, 3H), 3.25 (s, 3H), 3.64 (t, J=3.6, 2H), 4.00 (s, 2H), 4.11 (t, J=3.2, 2H), 4.27 (s, 2H), 5.17 (s, 2H), 6.90 (m, 1H), 7.00 (m, 1H), 7.26 (m, 2H), 7.76 (s, 1H), 8.15 (s, 1H). The title compound was shown to inhibit hT2R08 bitter receptor and had an $IC_{50}$ of 0.1 uM.

Example 10-17

33-(1-((3,5-dimethylisoxazol-4-yl)methyl)-1H-pyrazol-4-yl)-1-(2-(methylsulfinyl)benzyl)imidazolidine-2,4-dione

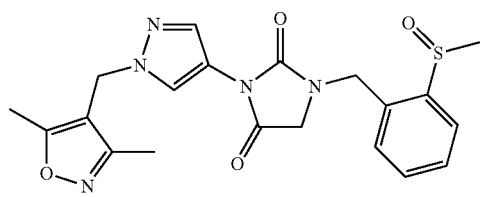

In a 20 mL microwave vial, 3-(1-((3,5-dimethylisoxazol-4-yl)methyl)-1H-pyrazol-4-yl)-1-(2-(methylthio)benzyl)imidazolidine-2,4-dione (example 10-15) (70 mg, 0.17 mmol) and m-CPBA (58 mg, 0.34 mmol) were dissolved in dichloromethane at 0° C. The reaction was stirred at 0° C. and allowed to warm up to room temperature for 4 hours. Solvent of the reaction was removed under vacuum, and the crude product was dissolved in 1 mL ethanol and was purified by varian HPLC (10 to 95% Acetonitrile/water; 25 minutes). The purified fraction was evaporated under vacuum to give the title compound. MS M+H calculated 428.1; found 428.1. The title compound was shown to inhibit hT2R08 bitter receptor and had an $IC_{50}$ of 0.4 uM. Yield: 12 mg, 17%.

Example 10-18

3-(1-((3,5-dimethylisoxazol-4-yl)methyl)-1H-pyrazol-4-yl)-1-(2-methoxybenzyl)imidazolidine-2,4-dione

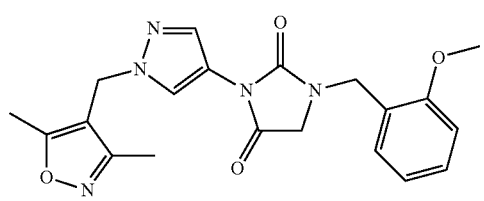

Prepared as in example 10-5 from 3-(1-((3,5-dimethylisoxazol-4-yl)methyl)-1H-pyrazol-4-yl)imidazolidine-2,4-dione (example 10-1) and 1-(bromomethyl)-2-methoxybenzene (199 mg, 1 mmol). Yield: 33%. MS M+H calculated

Example 10-19

2-((3-(1-((3,5-dimethylisoxazol-4-yl)methyl)-1H-pyrazol-4-yl)-2,4-dioxoimidazolidin-1-yl)methyl)benzonitrile

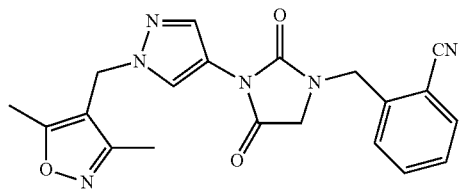 [SMILES: Cc1noc(C)c1Cn1cc(N2C(=O)CN(Cc3ccccc3C#N)C2=O)cn1]

Prepared as in example 10-5 from 3-(1-((3,5-dimethylisoxazol-4-yl)methyl)-1H-pyrazol-4-yl)imidazolidine-2,4-dione (example 10-1) and 2-(bromomethyl)benzonitrile. Yield: 27%. MS M+H calculated 391.1; found 391.1. The title compound was shown to inhibit hT2R08 bitter receptor and had an $IC_{50}$ of 0.5 μM.

Example 10-20

3-(1-((3,5-dimethylisoxazol-4-yl)methyl)-1H-pyrazol-4-yl)-1-(2-methylbenzyl)imidazolidine-2,4-dione

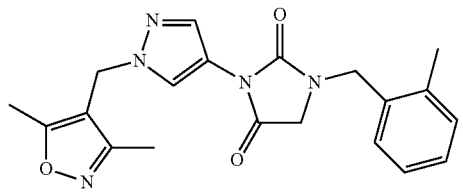 [SMILES: Cc1ccccc1CN1CC(=O)N(c2cnn(Cc3c(C)noc3C)c2)C1=O]

Prepared as in example 10-5 from 3-(1-((3,5-dimethylisoxazol-4-yl)methyl)-1H-pyrazol-4-yl)imidazolidine-2,4-dione (example 10-1) and 1-(bromomethyl)-2-methylbenzene. Yield: 21%. MS M+H calculated 380.1;. found 380.1. The title compound was shown to inhibit hT2R08 bitter receptor and had an $IC_{50}$ of 0.1 uM.

Example 10-21

3-(1-((3,5-dimethylisoxazol-4-yl)methyl)-1H-pyrazol-4-yl)-1-(2-fluorobenzyl)imidazolidine-2,4-dione

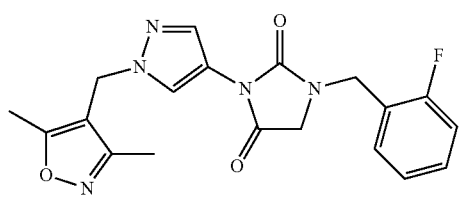 [SMILES: Cc1noc(C)c1Cn1cc(N2C(=O)CN(Cc3ccccc3F)C2=O)cn1]

Prepared as in example 10-5 from 3-(1-((3,5-dimethylisoxazol-4-yl)methyl)-1H-pyrazol-4-yl)imidazolidine-2,4-dione (example 10-1) and 1-(bromomethyl)-2-fluorobenzene. Yield 42%. MS M+H calculated 384.1; found 384.1. The title compound was shown to inhibit hT2R08 bitter receptor and had an $IC_{50}$ of 0.08 uM.

Example 10-22

3-(1-((3,5-dimethylisoxazol-4-yl)methyl)-1H-pyrazol-4-yl)-1-(2-(trifluoromethyl)benzyl)imidazolidine-2,4-dione

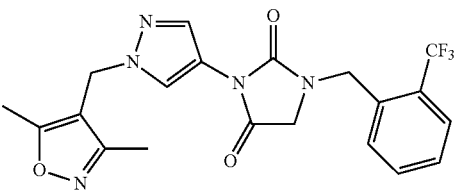 [SMILES: Cc1noc(C)c1Cn1cc(N2C(=O)CN(Cc3ccccc3C(F)(F)F)C2=O)cn1]

Prepared as in example 10-5 from 3-(1-((3,5-dimethylisoxazol-4-yl)methyl)-1H-pyrazol-4-yl)imidazolidine-2,4-dione (example 10-1) and 1-(bromomethyl)-2-(trifluoromethyl)benzene. Yield: 37%. MS M+H calculated 434.1; found 434.1. The title compound was shown to inhibit hT2R08 bitter receptor and had an $IC_{50}$ of 0.2 uM.

Example 10-23

3-(1-((3,5-dimethylisoxazol-4-yl)methyl)-1H-pyrazol-4-yl)-1-(2-nitrobenzyl)imidazolidine-2,4-dione

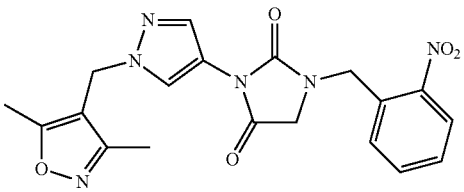

Prepared as in example 10-5 from 3-(1-((3,5-dimethylisoxazol-4-yl)methyl)-1H-pyrazol-4-yl)imidazolidine-2,4-dione (example 10-1) and 1-(bromomethyl)-2-nitrobenzene. Yield 22%. MS M+H calculated 411.1; found 411.1. The title compound was shown to inhibit hT2R08 bitter receptor and had an $IC_{50}$ of 0.07 uM.

Example 10-24

3-((3-(1-((3,5-dimethylisoxazol-4-yl)methyl)-1H-pyrazol-4-yl)-2,4-dioxoimidazolidin-1-yl)methyl)benzaldehyde

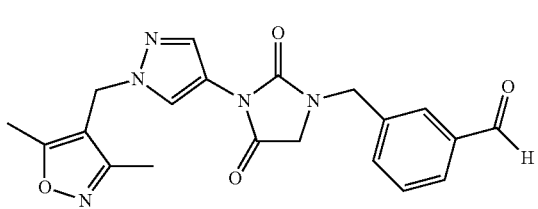 [SMILES: Cc1noc(C)c1Cn1cc(N2C(=O)CN(Cc3cccc(C=O)c3)C2=O)cn1]

Prepared as in example 10-5 from 3-(1-((3,5-dimethyl-isoxazol-4-yl)methyl)-1H-pyrazol-4-yl)imidazolidine-2,4-dione (example 10-1) and 3-(bromomethyl)benzaldehyde. Yield: 35%. ¹H NMR (DMSO, 400 MHz): δ2.123 (s, 3H), 2.388 (s, 3H), 4.035 (s, 2H), 4.631 (s, 2H), 5.186 (s, 2H), 7.581 (m, 1H), 7.643 (m, 1H), 7.787 (m, 3H), 8.178 (s, H), 9.997 (s, H). The title compound was shown to inhibit hT2R08 bitter receptor and had an $IC_{50}$ of 0.2 uM.

Example 10-25

3-((3-(1-((3,5-dimethylisoxazol-4-yl)methyl)-1H-pyrazol-4-yl)-2,4-dioxoimidazolidin-1-yl)methyl)benzonitrile

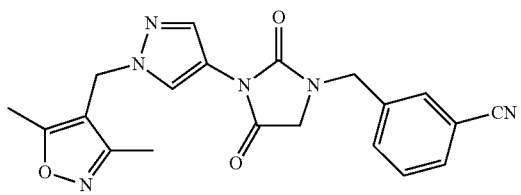 [SMILES: Cc1noc(C)c1Cn1cc(N2C(=O)CN(Cc3cccc(C#N)c3)C2=O)cn1]

Prepared as in example 10-5 from 3-(1-((3,5-dimethyl-isoxazol-4-yl)methyl)-1H-pyrazol-4-yl)imidazolidine-2,4-dione (example 10-1) and 3-(bromomethyl)benzonitrile. Yield 21%. MS M+H calculated 411.1; found 411.1. The title compound was shown to inhibit hT2R08 bitter receptor and had an $IC_{50}$ of 1 uM.

Example 10-26

3-(1-((3,5-dimethylisoxazol-4-yl)methyl)-1H-pyrazol-4-yl)-1-(3-methylbenzyl)imidazolidine-2,4-dione

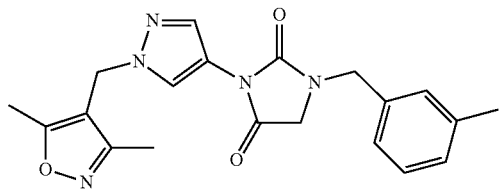

Prepared as in example 10-5 from 3-(1-((3,5-dimethyl-isoxazol-4-yl)methyl)-1H-pyrazol-4-yl)imidazolidine-2,4-dione (example 10-1) and 1-(bromomethyl)-3-methylbenzene. Yield 25%. MS M+H calculated 380.1; found 380.1.

The title compound was shown to inhibit hT2R08 bitter receptor and had an $IC_{50}$ of 0.02 uM.

Example 10-27

3-(1-((3,5-dimethylisoxazol-4-yl)methyl)-1H-pyrazol-4-yl)-1-(3-fluorobenzyl)imidazolidine-2,4-dione

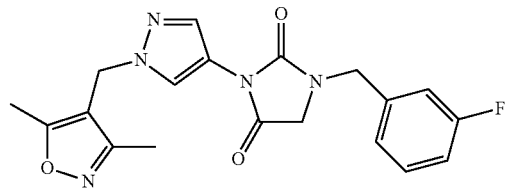 [SMILES: Cc1noc(C)c1Cn1cc(N2C(=O)CN(Cc3cccc(F)c3)C2=O)cn1]

Prepared as in example 10-5 from 3-(1-((3,5-dimethyl-isoxazol-4-yl)methyl)-1H-pyrazol-4-yl)imidazolidine-2,4-dione (example 10-1) and 1-(bromomethyl)-3-fluorobenzene. Yield 27%. MS M+H calculated 384.1; found 384.1. The title compound was shown to inhibit hT2R08 bitter receptor and had an $IC_{50}$ of 0.06 uM.

Example 10-28

1-((1,5-dimethyl-1H-pyrazol-3-yl)methyl)-3-(1-((3,5-dimethylisoxazol-4-yl)methyl)-1H-pyrazol-4-yl)imidazolidine-2,4-dione

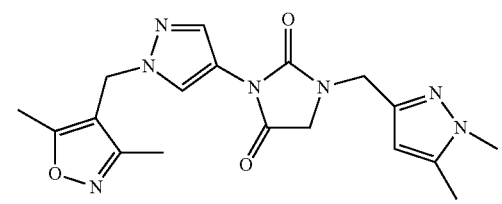

Prepared as in example 10-5 from 3-(1-((3,5-dimethyl-isoxazol-4-yl)methyl)-1H-pyrazol-4-yl)imidazolidine-2,4-dione (example 10-1) and 3-(bromomethyl)-1,5-dimethyl-1H-pyrazole. Yield: 22%. MS M+H calculated 384.1; found 384.1. The title compound was shown to inhibit hT2R08 bitter receptor and had an IC$_{50}$ of 0.3 uM

Example 10-29

3-(1-((3,5-dimethylisoxazol-4-yl)methyl)-1H-pyrazol-4-yl)-1-(4-methoxybenzyl)imidazolidine-2,4-dione

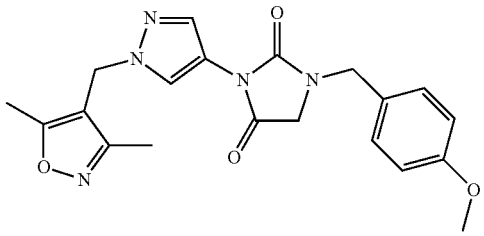 [SMILES: COc1ccc(CN2CC(=O)N(c3cnn(Cc4c(C)noc4C)c3)C2=O)cc1]

Prepared as in example 10-5 from 3-(1-((3,5-dimethylisoxazol-4-yl)methyl)-1H-pyrazol-4-yl)imidazolidine-2,4-dione (example 10-1) and 1-(bromomethyl)-4-methoxybenzene. Yield 19%. MS M+H calculated 396.1; found 396.1. The title compound was shown to inhibit hT2R08 bitter receptor and had an IC$_{50}$ of 0.07 uM.

Example 10-30

3-(1-((3,5-dimethylisoxazol-4-yl)methyl)-1H-pyrazol-4-yl)-1-(4-methylbenzyl)imidazolidine-2,4-dione

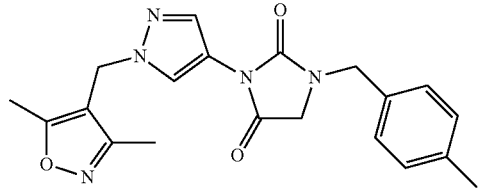

Prepared as in example 10-5 from 3-(1-((3,5-dimethylisoxazol-4-yl)methyl)-1H-pyrazol-4-yl)imidazolidine-2,4-dione (example 10-1) and 1-(bromomethyl)-4-methylbenzene. Yields 25%. MS M+H calculated 380.1; found 380.1. The title compound was shown to inhibit hT2R08 bitter receptor and had an IC$_{50}$ of 0.06 uM.

Example 10-31

3-(1-((3,5-dimethylisoxazol-4-yl)methyl)-1H-pyrazol-4-yl)-1-(4-fluorobenzyl)imidazolidine-2,4-dione

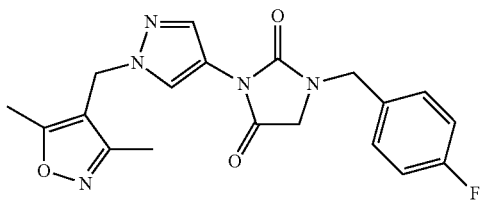 [SMILES: Cc1noc(C)c1Cn1cc(N2C(=O)CN(Cc3ccc(F)cc3)C2=O)cn1]

Prepared as in example 10-5 from 3-(1-((3,5-dimethylisoxazol-4-yl)methyl)-1H-pyrazol-4-yl)imidazolidine-2,4-dione (example 10-1) and 1-(bromomethyl)-4-fluorobenzene. Yield 33%. MS M+H calculated 384.1; found 384.1. The title compound was shown to inhibit hT2R08 bitter receptor and had an I IC$_{50}$ of 0.05 uM.

Example 10-32

4-((3-(1-((3,5-dimethylisoxazol-4-yl)methyl)-1H-pyrazol-4-yl)-2,4-dioxoimidazolidin-1-yl)methyl)benzonitrile

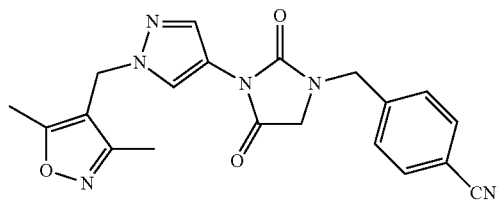 [SMILES: Cc1noc(C)c1Cn1cc(N2C(=O)CN(Cc3ccc(C#N)cc3)C2=O)cn1]

Prepared as in example 10-5 from 3-(1-((3,5-dimethylisoxazol-4-yl)methyl)-1H-pyrazol-4-yl)imidazolidine-2,4-dione (example 10-1) and 4-(bromomethyl)benzonitrile. Yield 21%. MS M+H calculated 391.1; found 391.2. The title compound was shown to inhibit hT2R08 bitter receptor and had an IC$_{50}$ of 0.05 uM.

Example 10-33

3-(1-((3,5-dimethylisoxazol-4-yl)methyl)-1H-pyrazol-4-yl)-1-(3-(hydroxymethyl)benzyl)imidazolidine-2,4-dione

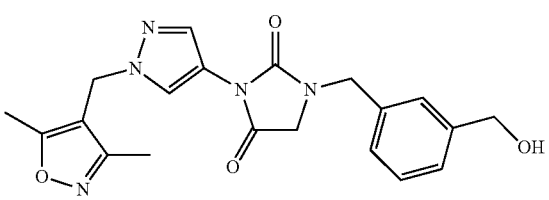 [SMILES: Cc1noc(C)c1Cn1cc(N2C(=O)CN(Cc3cccc(CO)c3)C2=O)cn1]

3-((3-(1-((3,5-dimethylisoxazol-4-yl)methyl)-1H-pyrazol-4-yl)-2,4-dioxoimidazolidin-1-yl)methyl)benzaldehyde (example 10-24) (131 mg, 0.3 mmol) was dissolved in 2 mL ethanol. The solution was passed through the H-Cube instrument at room temperature using 10% Pd/C catalyst at a flow rate of 1 ml/minute. The collected fraction was concentrated, redissolved in 2 mL ethanol and purified by HPLC (10-95% Acetonitrile/Water, 25 minutes). The purified fractions were combined and concentrated to give the title compound. $^1$H NMR (DMSO, 400 MHz): δ2.123 (s, 3H), 2.388 (s, 3H), 3.978 (s, 2H), 4.516 (s, 2H), 5.182 (s, 2H), 7.242 (m, 4H), 7.779 (s, 1H), 8.172 (s, 1H), 8.505 (s, 1H). MS M+H calculated 396.1; found 396.1. The title compound was shown to inhibit hT2R08 bitter receptor and had an IC$_{50}$ of 0.3 uM. Yield: 24 mg, 18%.

Example 10-34

1-(2-aminobenzyl)-3-(1-((3,5-dimethylisoxazol-4-yl)methyl)-1H-pyrazol-4-yl)imidazolidine-2,4-dione

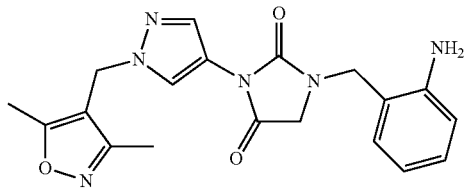 [SMILES: Cc1noc(C)c1Cn1cc(N2C(=O)CN(Cc3ccccc3N)C2=O)cn1]

3-(1-((3,5-dimethylisoxazol-4-yl)methyl)-1H-pyrazol-4-yl)-1-(2-nitrobenzyl)imidazolidine-2,4-dione (example 10-23) (126 mg, 0.3 mmol) was dissolved in 2 mL ethanol. The solution was passed through the H-Cube instrument at room temperature using 10% Pd/C catalyst at a flow rate of 1 ml/minute. The collected fraction was concentrated, redissolved in 2 mL ethanol and purified by HPLC (10-95% Acetonitrile/Water, 25 minutes). The purified fractions were combined and concentrated to afford the title compound. Yield 26%. MS M+H calculated 381.1; found 381.1. The title compound was shown to inhibit hT2R08 bitter receptor and had an IC$_{50}$ of 0.02 uM.

Example 10-35

1-(3,4-dimethoxybenzyl)-3-(1-((3,5-dimethylisoxazol-4-yl)methyl)-1H-pyrazol-4-yl)imidazolidine-2,4-dione

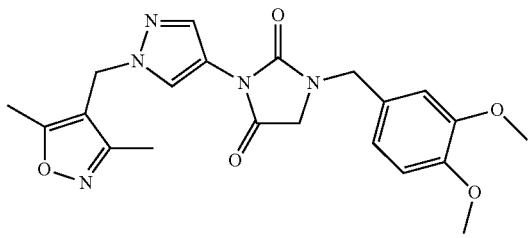

3-(1-((3,5-dimethylisoxazol-4-yl)methyl)-1H-pyrazol-4-yl)imidazolidine-2,4-dione (example 10-1) (275 mg, 1 mmol), (3,4-dimethoxyphenyl)methanol (201 mg, 1.2 mmol), N,N,N,N-tetramethylazodicarboxamide (344 mg, 2 mmol) were dissolved in 2 mL anhydrous THF. Tributylphosphine (404 mg, 2 mmol) was added and the reaction mixture was placed in a microwave reactor for 5 minutes at 90° C. The reaction was filtered, concentrated and purified by HPLC (10-95% Acetonitrile/Water, 25 minutes) to afford the title compound. Yield: 25 mg, 6%. $^1$H NMR (DMSO, 400 MHz): δ2.119 (s, 3H), 2.385 (s, 3H), 3.724 (J=6.4 d, 6H), 3.946 (s, 2H), 4.435 (s, 2H), 5.178 (s, 2H), 6.885 (m, 3H), 7.776 (s, 1H), 8.166 (s, 1H). MS M+H calculated 426.1; found 426.1. The title compound was shown to inhibit hT2R08 bitter receptor and had an IC$_{50}$ of 0.06 uM.

Example 10-36

1-(benzo[d][1,3]dioxol-5-ylmethyl)-3-(1-((3,5-dimethylisoxazol-4-yl)methyl)-1H-pyrazol-4-yl)imidazolidine-2,4-dione

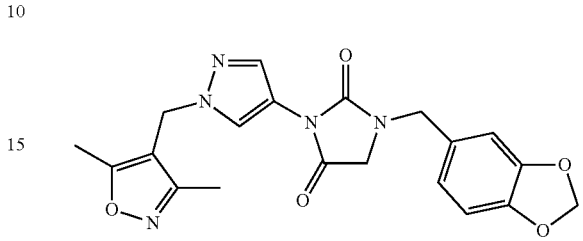

Prepared as in example 10-35 from 3-(1-((3,5-dimethylisoxazol-4-yl)methyl)-1H-pyrazol-4-yl)imidazolidine-2,4-dione (example 10-1) and benzo[d][1,3]dioxol-5-ylmethanol. Yield: 19%. $^1$H NMR (DMSO, 400 MHz): δ2.143 (s, 3H), 2.408 (s, 3H), 3.977 (s, 2H), 4.440 (s, 2H), 5.202 (s, 2H), 6.003 (s, 2H), 6.897 (m, 3H), 7.788 (s, 1H), 8.181 (s, 1H). MS M+H calculated 410.1; found 410.1. The title compound was shown to inhibit hT2R08 bitter receptor and had an IC$_{50}$ of 0.07 uM.

Example 10-37

1-(3-((dimethylamino)methyl)benzyl)-3-(1-((3,5-dimethylisoxazol-4-yl)methyl)-1H-pyrazol-4-yl)imidazolidine-2,4-dione

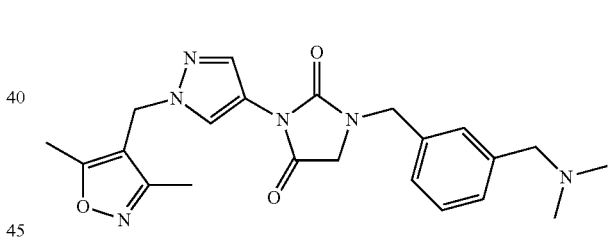

3-(1-((3,5-dimethylisoxazol-4-yl)methyl)-1H-pyrazol-4-yl)imidazolidine-2,4-dione (example 10-1) (275 mg, 1 mmol) 1,3-bis(bromomethyl)benzene (263 mg, 1 mmol), and cesium carbonate (325 mg, 1 mmol) were dissolved in 2 mL DMF and irradiated in the microwave reactor at 165° C. for 5 minutes. The reaction was cooled to room temperature, and salt precipitate was removed by filtration. The clear solution containing crude product was concentrated and redissolved in ethyl acetate. The organic solution was washed with water twice followed by brine. The organic layer was dried over sodium sulfate and evaporated to give the crude product which was carried forward to the next step without further purification or characterization. 1-(3-(bromomethyl)benzyl)-3-(1-((3,5-dimethylisoxazol-4-yl)methyl)-1H-pyrazol-4-yl) imidazolidine-2,4-dione (example 42a) (152 mg, 0.3 mmol), dimethylamine (2 M solution in THF) (1.5 mL, 3 mmol), and sodium hydride (9 mg, 0.36 mmol) were dissolved in 1 mL anhydrous THF. The reaction was placed in a microwave reactor for 5 minutes at 120° C. The crude product was redissolved in 2 mL ethanol and was purified by HPLC (10-95% Acetonitrile/Water, 25 minutes) to afford 1-(3-((dimethylamino)methyl)benzyl)-3-(1-((3,5-dimethylisoxazol-4-yl) methyl)-1H-pyrazol-4-yl)imidazolidine-2,4-dione (16 mg, 13%). MS M+H calculated 423.1; found 423.1. The title compound was shown to inhibit hT2R08 bitter receptor and had an IC$_{50}$ of 1.2 uM.

Example 10-38

3-(1-((3,5-dimethylisoxazol-4-yl)methyl)-1H-pyrazol-4-yl)-1-((1-methyl-1H-pyrazol-3-yl)methyl)imidazolidine-2,4-dione

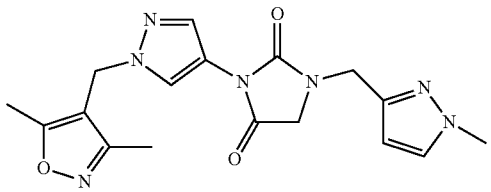

Prepared as in example 10-5 from 3-(1-((3,5-dimethylisoxazol-4-yl)methyl)-1H-pyrazol-4-yl)imidazolidine-2,4-dione (example 10-1) and 3-(bromomethyl)-1-methyl-1H-pyrazole. Yield 19%. MS M+H calculated 370.1; found 370. The title compound was shown to inhibit hT2R08 bitter receptor and had an IC$_{50}$ of 0.4 uM.

Example 10-39

N-(2-((3,5-dimethylisoxazol-4-yl)methyl)-2H-tetrazol-5-yl)-3-methoxybenzamide

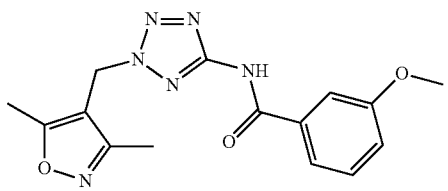

2-((3,5-dimethylisoxazol-4-yl)methyl)-2H-tetrazol-5-amine (Example 10-39a) (102 mg, 0.528 mmol), 3-methoxybenzoyl chloride (0.065 mL, 0.528 mmol) and pyridine (0.043 mL, 0.528 mmol) in acetonitrile (3 mL) were stirred at 100° C. for one hour. The reaction was diluted with dichloromethane (30 mL) and washed with brine (30 mL). The organics were dried over sodium sulfate, concentrated and purified by reverse phase HPLC (Solvent system: acetonitrile/water 10% to 100% gradient), 25 minute run) affording N-(2-((3,5-dimethylisoxazol-4-yl)methyl)-2H-tetrazol-5-yl)-3-methoxybenzamide as a white crystalline solid (60 mg, 35% yield) MS M+H calculated 329.1; found 329. $^1$H NMR (400 MHz, DMSO-d6): δ 2.02 (s, 3H), 2.46 (s, 3H), 3.81 (s, 3H), 5.78 (s, 2H), 7.16 (m, 1H), 7.42 (t, J=8 Hz, 2H), 7.54 (m, 1H), 11.3 (s, 1H). The compound had an IC$_{50}$ on hT2R8 bitter receptor of 1.87 μM.

Example 10-39a 2-((3,5-dimethylisoxazol-4-yl)methyl)-2H-tetrazol-5-amine 2H-tetrazol-5-amine (1.29 g, 12.5 mmol), 4-(chloromethyl)-3,5-dimethylisoxazole (1.56 mL, 12.5 mmol) and potassium carbonate (1.73 g, 15.5 mmol) in DMF (20 mL) were heated to 80° C. with stirring for 16 hours. The reaction was cooled to room temperature, diluted with dichloromethane (100 mL) and washed consecutively with brine and water. The organics were dried over sodium sulfate and concentrated with rotary evaporation. The crude product was purified by silica gel chromatography (0-10% gradient ethyl acetate/dichloromethane) affording 2-((3,5-dimethylisoxazol-4-yl)methyl)-2H-tetrazol-5-amine as a white crystalline solid (970 mg, 40% yield) MS M+H calculated 195.1, found 195.

Example 10-40

N-(1-((3,5-dimethylisoxazol-4-yl)methyl)-1H-imidazol-4-yl)benzo[d][1,3]dioxole-5-carboxamide 1-((3,5-dimethylisoxazol-4-yl)methyl)-1H-imidazol-4-amine (example 10-40a) (110 mg, 0.57 mmol), benzo[d][1,3]dioxole-5-carbonyl chloride (105 mg, 0.57 mmol), and triethylamine (90 μL, 0.69 mmol) in dichloromethane was stirred for 16 hours. The reaction was diluted with dichloromethane (30 mL) and washed consecutively with brine and water. The organics were dried over sodium sulfate and concentrated by rotary evaporation. The crude product was purified by reverse phase HPLC (Solvent system: acetonitrile/water, 10% to 100% gradient, 25 minute run) to afford N-(1-((3,5-dimethylisoxazol-4-yl)methyl)-1H-imidazol-4-yl)benzo[d][1,3]dioxole-5-carboxamide as a white crystalline solid (32 mg, 15% yield). MS M+H calculated 341.3, found 341.3. $^1$H NMR (400 MHz, DMSO-d6): δ 2.08 (s, 3H), 2.41 (s, 3H), 5.02 (s, 2H), 6.07 (s, 2H), 6.95 (d, J=8.4 Hz, 1H), 7.27 (d, J=1.6 Hz, 1H), 7.54 (m, 3H), 10.6 (s, 1H). The compound had an IC$_{50}$ on hT2R8 bitter receptor of 12.1 μM.

Example 10-40a

1-((3,5-dimethylisoxazol-4-yl)methyl)-1H-imidazol-4-amine 3,5-dimethyl-4-((4-nitro-1H-imidazol-1-yl)methyl)isoxazole (example 10-40b) (1.0 g, 4.5 mmol) and 10% palladium on charcoal (200 mg) in methanol (40 mL) was shaken on a Parr shaker under a pressure of 2.5 bar hydrogen for 2 hours. Filtration through a plug of celite followed by rotary evaporation afforded 1-((3,5-dimethylisoxazol-4-yl)methyl)-1H-imidazol-4-amine as a yellowish-red solid (800 mg, 93% yield). MS M+H calculated 193, found 193.

Example 10-40b

3,5-dimethyl-4-((4-nitro-1H-imidazol-1-yl)methyl)isoxazole 3,5-dimethyl-4-((4-nitro-1H-imidazol-1-yl)methyl)isoxazole was prepared in a similar manner to example 10-41c by alkylation of 4-nitro-1H-imidazole affording 3,5-dimethyl-4-((4-nitro-1H-imidazol-1-yl)methyl)isoxazole as a white crystalline solid (5.0 g, 80% yield). MS M+H calculated 223, found 223. $^1$H NMR (400 MHz, DMSO-d6): δ, ppm: 2.09 (s, 3H), 2.43 (s, 3H), 5.15 (s, 2H), 7.90 (d, J=1.6 Hz, 1H), 8.35 (d, J=1.9 Hz, 1H).

Example 10-41

3-(1-((3,5-dimethylisoxazol-4-yl)methyl)-1H-pyrazol-4-yl)-5-methylimidazolidine-2,4-dione

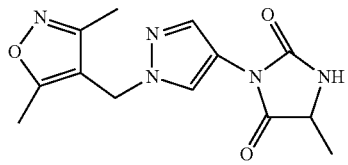 [SMILES: Cc1noc(C)c1Cn1cc(N2C(=O)NC(C)C2=O)cn1]

1-((3,5-dimethylisoxazol-4-yl)methyl)-1H-pyrazol-4-amine hydrochloride (example 10-41a) (1.0 g, 5.20 mmol), ethyl-2-isocynatepropionate (0.745 g, 5.20 mmol) and triethylamine (1.5 mL, 10.4 mmol) were mixed in EtOH (20 mL). The reaction was refluxed for 12 hours and then allowed to cool to room temperature. Solvent was removed under vacuum and crystals formed upon standing. The crystals were collected and washed with hexanes to afford the 3-(1-((3,5-dimethylisoxazol-4-yl)methyl)-1H-pyrazol-4-yl)-5-methylimidazolidine-2,4-dione in 80% yield as a white solid. $^1$H NMR (DMSO-d$_6$, 400 MHz): δ 1.53-1.51 (d, 3H), 2.19 (s, 3H), 2.42 (s, 3H), 4.21-4.19 (m, 1H), 5.06 (s, 2H), 6.00 (bs, 1H), 7.90 (s, 1H), 8.05 (s, 1H). The title compound was shown to inhibit hT2R08 bitter receptor and had an IC$_{50}$ of 1.3 μM.

Example 10-41a

1-((3,5-dimethylisoxazol-4-yl)methyl)-1H-pyrazol-4-amine hydrochloride

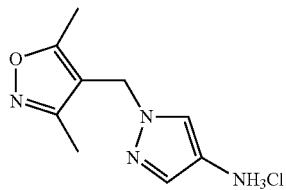

Tert-butyl 1-((3,5-dimethylisoxazol-4-yl)methyl)-1H-pyrazol-4-ylcarbamate (example 10-41b) (592 mg, 2 mmol) was stirred in a solution of 4N HCl in dioxane (20 mL) at ambient temperature for 2 hours. The solvent was removed and the residue was dissolved in a 1/1 mixture of ethyl acetate/hexanes (30 mL) and concentrated twice. The solid was triturated with hexanes and collected by filtration providing 1-((3,5-dimethylisoxazol-4-yl)methyl)-1H-pyrazol-4-amine hydrochloride (500 mg, 99%) as a white solid. $^1$H NMR (DMSO-d$_6$, 400 MHz); δ 2.11 (s, 3H), 2.38 (s, 3H), 5.16 (s, 2H), 7.51 (s, 1H), 8.03 (s, 1H), 10.27 (bs, 3H).

Example 10-41b tert-butyl 1-((3,5-dimethylisoxazol-4-yl)methyl)-1H-pyrazol-4-ylcarbamate

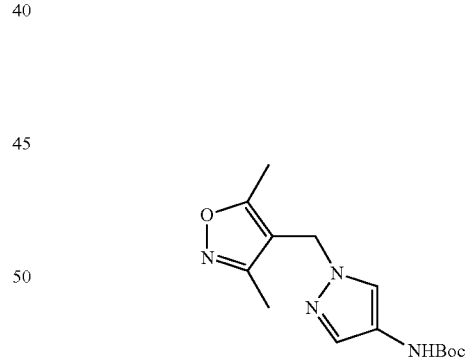

3,5-dimethyl-4-((4-nitro-1H-pyrazol-1-yl)methyl)isoxazole (example 10-41c) (12 g, 53.8 mmol) and BOC anhydride (12.8 g, 64 mmol) were dissolved in a 3/1/1 mixture of MeOH/EtOH/THF (300 mL) in a Parr reaction bottle, followed by the addition of 10% Pd/C (1.5 g). The mixture was shaken on the Parr hydrogenator under 2 atmospheres of hydrogen for 3 hours. The mixture was filtered through a 3 inch plug of celite and concentrated on the rotovap. The pink oil was purified by silica gel chromatography (25% ethyl acetate in hexanes) to afford tert-butyl 1-((3,5-dimethylisoxazol-4-yl)methyl)-1H-pyrazol-4-ylcarbamate (12.6 g, 80%) as a pink/red oil which solidified on standing to a light pink solid. ¹H NMR (CDCl₃, 400 MHz): δ 1.41 (s, 9H), 2.10 (s, 3H), 2.32 (s, 3H), 4.90 (s, 2H), 6.19 (bs, 1H), 7.19 (s, 1H), 7.50 (s, 1H).

Example 10-41c 3,5-dimethyl-4-((4-nitro-1H-pyrazol-1-yl)methyl) isoxazole

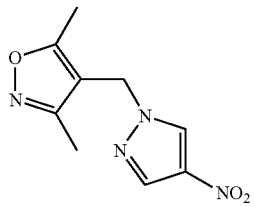 [SMILES: Cc1noc(C)c1Cn1cc([N+](=O)[O-])cn1]

1H-pyrazole (10 g, 147 mmol) was added in small portions to concentrated H₂SO₄ (100 mL), cooled to 0° C. via an ice/water bath, maintaining the internal reaction temperature below 40° C. Concentrated HNO₃ (10 mL) was carefully added, dropwise, to the reaction mixture maintaining the internal reaction temperature below 55° C. The reaction was then heated to 55° C. and stirred for 5 hours. The mixture was cooled to 0° C. and carefully made basic (pH~8) with aqueous NaOH solution (110 g NaOH in 150 mL H₂O) until a white precipitate formed, carefully ensuring the internal temperature of the solution remain below 40° C. The white solid was collected by filtration and washed with ethyl acetate/hexanes (1/3) then dried en vacuo to afford 4-nitro-1H-pyrazole (7 g, 42%, isolated yield). ¹³C NMR (DMSO-d₆, 137.0, 126.4. To 4-nitro-1H-pyrazole (9 g, 80 mmol) in DMF (100 mL)100 MHz) δ was added cesium carbonate (26 g, 80 mmol) followed by the addition of 4-(chloromethyl)-3,5-dimethylisoxazole (12.3 g, 85 mmol). The reaction mixture was stirred in DMF (100 mL) at 80° C. for 30 minutes, then cooled, diluted with H₂O (150 mL) and extracted with ethyl acetate (3×, 75 mL). The combined organic layers were dried over sodium sulfate, filtered and concentrated. The residue was taken up in ethyl acetate (200 mL) and washed with H₂O (2×, 100 mL). The organic layer was dried over sodium sulfate, filtered and concentrated. The solid product was triturated with ethyl acetate/hexanes(1/9) and collected by filtration. The product was dried under high vacuum to afford 3,5-dimethyl-4-((4-nitro-1H-pyrazol-1-yl)methyl)isoxazole (12 g, 67%) as a light yellow solid. ¹H NMR (CDCl₃, 400 MHz): δ 2.23 (s, 3H), 2.46 (s, 3H), 5.08 (s, 2H), 8.02 (s, 1H), 8.08 (s, 1H).

Example 10-42

5-benzyl-3-(1-((3,5-dimethylisoxazol-4-yl)methyl)-1H-pyrazol-4-yl)-1-methylimidazolidine-2,4-dione

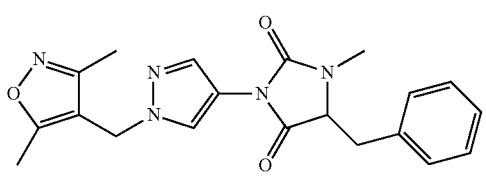 [SMILES: Cc1noc(C)c1Cn1cc(N2C(=O)C(Cc3ccccc3)N(C)C2=O)cn1]

Prepared as in example 10-5 from 5-benzyl-3-(1-((3,5-dimethylisoxazol-4-yl)methyl)-1H-pyrazol-4-yl)imidazolidine-2,4-dione (example 10-2) and iodomethane. Yield: 95%. ¹H NMR (CDCl₃, 400 MHz): δ 2.04 (s, 3H), 2.15 (s, 3H), 2.96 (s, 3H), 3.24-3.23 (m, 2 H, J=4.0 Hz), 4.23-4.21 (m, 1H), 5.00 (s, 2H), 7.24-7.23 (m, 5H, J=4.0 Hz), 7.70 (s, 1H), 7.87 (s, 1H).

The title compound was shown to inhibit hT2R08 bitter receptor and had an IC₅₀ of 0.15 μM.

Example 10-43

1-benzyl-3-(1-((3,5-dimethylisoxazol-4-yl)methyl)-1H-pyrazol-4-yl)-5-methylimidazolidine-2,4-dione

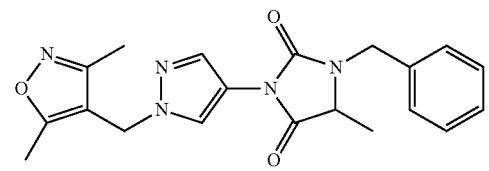 [SMILES: Cc1noc(C)c1Cn1cc(N2C(=O)C(C)N(Cc3ccccc3)C2=O)cn1]

Prepared as in example 10-5 from 3-(1-((3,5-dimethylisoxazol-4-yl)methyl)-1H-pyrazol-4-yl)-5-methylimidazolidine-2,4-dione (example 10-41) and benzyl bromide. Yield: 50%. ¹H NMR (CDCl₃, 400 MHz): δ 1.44 (s, 3H), 2.19 (s, 3H), 3.88 (s, 3H), 4.18 (d, J=8 Hz, 2H), 4.22 (t, 1H, J=4 Hz)), 5.06 (s, 2H), 7.39-7.29 (m, 5H), 7.94 (s, 1H), 8.10 (s, 1H). The title compound was shown to inhibit hT2R08 bitter receptor and had an IC₅₀ of 0.02 μM.

Example 10-44

2-(1-(1-((3,5-dimethylisoxazol-4-yl)methyl)-1H-pyrazol-4-yl)-2,5-dioxoimidazolidin-4-yl)acetic acid

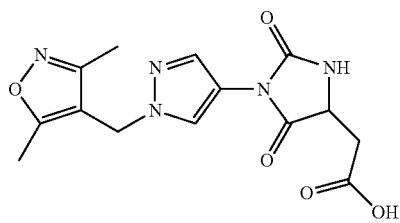 [SMILES: Cc1noc(C)c1Cn1cc(N2C(=O)NC(CC(=O)O)C2=O)cn1]

Prepared as in example 10-1 from 1-((3,5-dimethylisoxazol-4-yl)methyl)-1H-pyrazole-4-carbonyl azide (example 10-1a) and H-Asp-OMe. Yield: 85%. MS M+H calculated 334.1; found 334.1

Example 10-45

3-(1-((3,5-dimethylisoxazol-4-yl)methyl)-1H-pyrazol-4-yl)-5-phenethylimidazolidine-2,4-dione

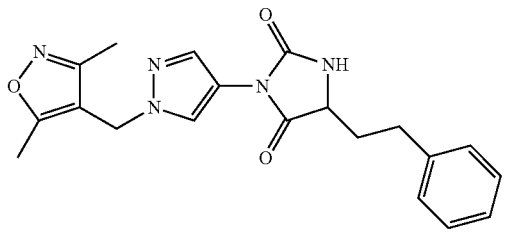 [SMILES: Cc1noc(C)c1Cn1cc(N2C(=O)NC(CCc3ccccc3)C2=O)cn1]

Prepared as in Example 10-1 from 1-((3,5-dimethylisoxazol-4-yl)methyl)-1H-pyrazole-4-carbonyl azide (example 10-1a) and methyl 2-amino-4-phenylbutanoate. Yield: 15%. $^1$H NMR (CDCl$_3$, 400 MHz): δ 2.09-2.02 (m, 2H), 2.19 (s, 3H), 2.41 (s, 3H), 2.83-2.78 (m, 2H), 4.13-4.09 (t, 1H, J=8 Hz), 5.05 (s, 2H), 5.95 (bs, 1H), 7.30-7.19 (m, 5H), 7.95 (s, 1H), 8.03 (s, 1H). The title compound was shown to inhibit hT2R08 bitter receptor and had an IC$_{50}$ of 0.22 μM.

Example 10-46

3-(1-((3,5-dimethylisoxazol-4-yl)methyl)-1H-pyrazol-4-yl)-5-(3-phenylpropyl)imidazolidine-2,4-dione

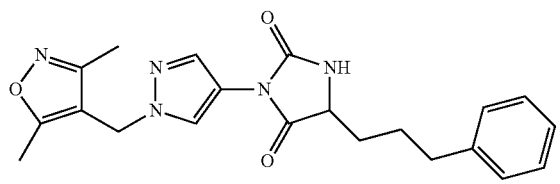 [SMILES: Cc1noc(C)c1Cn1cc(N2C(=O)NC(COCc3ccccc3)C2=O)cn1]

Prepared as in Example 10-1 from 1-((3,5-dimethylisoxazol-4-yl)methyl)-1H-pyrazole-4-carbonyl azide (example 10-1a) and methyl 2-amino-5-phenylpentanoate. Yield: 20%. $^1$H NMR (CDCl$_3$, 400 MHz): δ 1.72-1.68 (m, 1H), 1.85-1.78 (m, 2H), 1.99-1.91 (m, 1H), 2.19 (s, 3H), 2.41 (s, 3H), 2.69-2.63 (t, J=8 Hz, 2H), 4.13 (bs, 1H), 5.05 (s, 2H), 5.95 (bs, 1H), 7.30-7.19 (m, 5H), 7.95 (s, 1H), 8.03 (s, 1H). The title compound was shown to inhibit hT2R08 bitter receptor and had an IC$_{50}$ of 0.17 μM.

Example 10-47

5-(benzyloxymethyl)-3-(1-((3,5-dimethylisoxazol-4-yl)methyl)-1H-pyrazol-4-yl)imidazolidine-2,4-dione

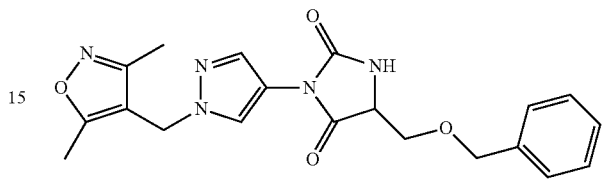

Prepared as in Example 10-1 from 1-((3,5-dimethylisoxazol-4-yl)methyl)-1H-pyrazole-4-carbonyl azide (example 10-1a) and methyl 2-amino-3-(benzyloxy)propanoate. Yield: 32%. $^1$H NMR (CDCl$_3$, 400 MHz): δ 2.19 (s, 3H), 2.43 (s, 3H), 3.70-3.67 (m, 1H), 3.89-3.86 (m, 1H), 4.31-4.30 (m,1H), 4.56-4.32 (d, J=1.6 Hz, 2H), 5.05 (s, 2H), 5.62 (bs, 1H), 7.35-7.29 (m, 5H), 7.88 (s, 1H), 8.04 (s, 1H). The title compound was shown to inhibit hT2R08 bitter receptor and had an IC$_{50}$ of 0.76 μM.

Example 10-48

2-(1-(1-((3,5-dimethylisoxazol-4-yl)methyl)-1H-pyrazol-4-yl)-2,5-dioxoimidazolidin-4-yl)-N-phenylacetamide

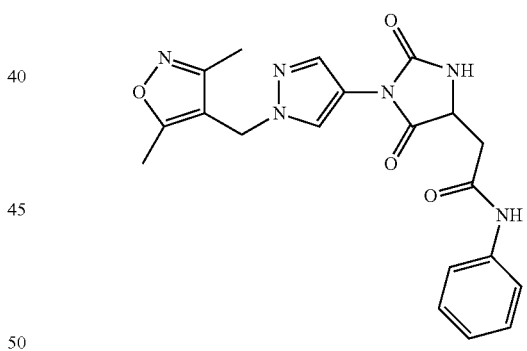

3-(1-(1-((3,5-dimethylisoxazol-4-yl)methyl)-1H-pyrazol-4-yl)-2,5-dioxoimidazolidin-4-yl)acetic acid (example 10-44) (100 mg, 0.3 mmol), aniline (33 mg, 0.36 mmol), Pybop (187 mg, 0.36 mmol) and triethyl ammine (0.05 mL, 0.36 mmol) were mixed in DMF (1 mL). The reaction stirred at 65° C. for 4 hours. The reaction was allowed to cool to room temperature and then diluted with ethyl aceate (2 mL). The organic phase was washed with saturated sodium bicarbonate solution (2×, 2 mL) and then with saturated NaCl solution (1 ml). The organic phase was extracted, dried over anhydrous Na$_2$SO$_4$, and filtered. The crude product was re-suspended in MeOH (1 mL) and purified by reversed phase HPLC (5-95% acetonitrile in H$_2$O; 16 minute gradient). The pure fractions were combined and solvent was removed on the rotovap to afford 2-(1-(1-((3,5-dimethylisoxazol-4-yl)methyl)-1H-pyrazol-4-yl)-2,5-dioxoimidazolidin-4-yl)-N-phenylacetamide as a white solid (50%). $^1$H NMR (CDCl$_3$, 400 MHz): δ 2.18 (s, 3H), 2.40 (s, 3H), 2.72 (m, 1 H), 3.14-3.13 (d, 1H, J=4 Hz), 4.54-4.51 (d, J=8 Hz 1H), 5.04 (s, 2H), 6.53 (bs, 1H), 7.15-7.13 (m, 1H), 7.33-7.22 (m, 2H), 7.47-7.45 (d, J=8 Hz, 2H), 7.78 (bs, 1H), 7.09 (s, 1H), 8.05 (s, 1H). The title compound was shown to inhibit hT2R08 bitter receptor and had an IC$_{50}$ of 0.75 µM.

Example 10-49

N-benzyl-2-(1-(1-((3,5-dimethylisoxazol-4-yl)methyl)-1H-pyrazol-4-yl)-2,5-dioxoimidazolidin-4-yl)acetamide

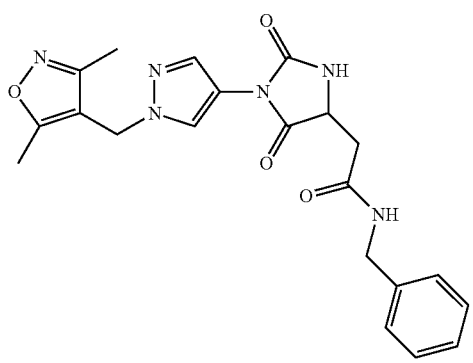 [SMILES: Cc1noc(C)c1Cn1cc(N2C(=O)NC(CC(=O)NCc3ccccc3)C2=O)cn1]

Prepared as in Example 10-48 from 3-(1-(1-((3,5-dimethylisoxazol-4-yl)methyl)-1H-pyrazol-4-yl)-2,5-dioxoimidazolidin-4-yl)acetic acid (example 10-44) and benzyl amine. Yield: 30%. $^1$H NMR (CDCl$_3$, 400 MHz): δ 2.18 (s, 3 H), 2.41 (s, 3 H), 2.56-2.52 (m, 1H, J=16 Hz), 2.56-2.52 (m, 1H), 3.00-2.96 (m, 1H), 4.45-4.44 (d, J=5.6 Hz, 2H), 5.04 (s, 2H), 5.96 (bs, 1H), 6.36 (bs, 1H), 7.36-7.25 (m, 5H), 7.90 (s, 1H, 8.05 (s, 1H). The title compound was shown to inhibit hT2R08 bitter receptor and had an IC$_{50}$ of 1.3 µM.

Example 10-50

2-(1-(1-((3,5-dimethylisoxazol-4-yl)methyl)-1H-pyrazol-4-yl)-2,5-dioxoimidazolidin-4-yl)-N-(3-methoxybenzyl)acetamide

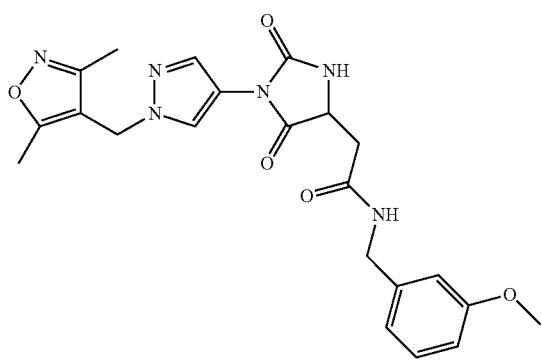 [SMILES: COc1cccc(CNC(=O)CC2NC(=O)N(c3cnn(Cc4c(C)noc4C)c3)C2=O)c1]

Prepared as in Example 10-48 from 3-(1-(1-((3,5-dimethylisoxazol-4-yl)methyl)-1H-pyrazol-4-yl)-2,5-dioxoimidazolidin-4-yl)acetic acid (example 10-44) and (3-methoxyphenyl)methanamine. Yield: 50%. LC/MS; expected 453; found 453.1 The title compound was shown to inhibit hT2R08 bitter receptor and had an IC$_{50}$ of 1.7 µM.

Example 10-51

3-(1-((3,5-dimethylisoxazol-4-yl)methyl)-1H-pyrazol-4-yl)-1-methylimidazolidine-2,4-dione

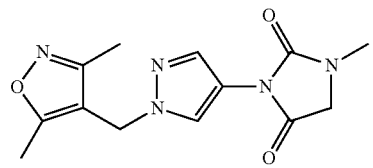 [SMILES: Cc1noc(C)c1Cn1cc(N2C(=O)CN(C)C2=O)cn1]

3-(1-((3,5-dimethylisoxazol-4-yl)methyl)-1H-pyrazol-4-yl)imidazolidine-2,4-dione (example 10-1) (50 mg, 0.182 mmol) and cesium carbonate (60 mg, 0.185 mmol) were mixed in DMF (1 mL) for 15 minutes under a nitrogen atmosphere at room temperature. Then, iodomethane (14 mg, 0.185 mmol) was added and the reaction continued to stir for an addition 2 hours. H$_2$O (2 mL) was added and the product was extracted with ethyl acetate (1 mL, 2×). The organic phase was collected and washed with saturated sodium bicarbonate solution (2 ml, 2×), dried, and filtered. Solvent was removed under a stream of nitrogen and then further dried under high vacuum to afford 3-(1-((3,5-dimethylisoxazol-4-yl)methyl)-1H-pyrazol-4-yl)-1-methylimidazolidine-2,4-dione as a white solid (42 mg, 80%). Yield: 80%. $^1$H NMR (CDCl$_3$, 400 MHz): δ 2.18 (s, 3H), 2.41 (s, 3H), 3.06 (s, 3H), 3.95 (s, 2H), 5.05 (s, 2H), 7.89 (s, 1H), 8.05 (s, 1H). The title compound was shown to inhibit hT2R08 bitter receptor and had an IC$_{50}$ of 0.58 µM.

Example 10-52

3-(1-((3,5-dimethylisoxazol-4-yl)methyl)-1H-pyrazol-4-yl)-1,5,5-trimethylimidazolidine-2,4-dione

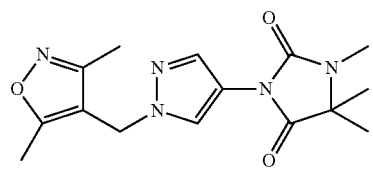 [SMILES: Cc1noc(C)c1Cn1cc(N2C(=O)N(C)C(C)(C)C2=O)cn1]

3-(1-((3,5-dimethylisoxazol-4-yl)methyl)-1H-pyrazol-4-yl)-5-methylimidazolidine-2,4-dione (example 10-41) (50 mg, 0.173 mmol) and 60% NaH (8 mg, 0.190 mmol) were mixed in DMF (1 mL) for 30 minutes. MeI (0.04 mL, 0.190 mmol) was added and the reaction was stirred an additional 4 hours. The reaction was acidified with 1N HCl and diluted with ethyl acetate (2 mL). The organic phase was dried, filtered and solvent was removed under a stream of nitrogen. The crude product was re-suspended in MeOH (1 mL) and purified by reversed phase HPLC (5 to 95% acetonitrile in H$_2$O: 16 minutes gradient). The pure fractions were combined and solvent removed under vacuum to afford 3-(1-((3,5-dimethylisoxazol-4-yl)methyl)-1H-pyrazol-4-yl)-1,5,5-trimethylimidazolidine-2,4-dione as a white solid (25 mg, 50%). $^1$H NMR (CDCl$_3$, (CDCl$_3$, 400 MHz): δ 1.45 (s, 6H), 2.19 (s, 3H), 2.42 (s, 3H), 2.94 (s, 3 H), 5.05 (s, 2 H), 7.92 (s, 1 H), 8.08 (s, 1H). The title compound was shown to inhibit hT2R08 bitter receptor and had an IC$_{50}$ of 0.80 μM.

Example 10-53

1-benzyl-3-(1-((3,5-dimethylisoxazol-4-yl)methyl)-1H-pyrazol-4-yl)imidazolidine-2,4-dione

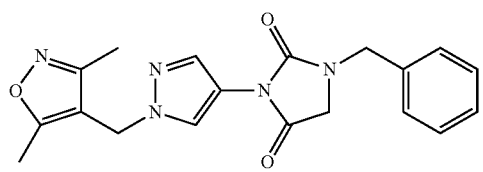 [SMILES: Cc1noc(C)c1Cn1cc(N2C(=O)CN(Cc3ccccc3)C2=O)cn1]

Prepared as in example 10-5 from 3-(1-((3,5-dimethylisoxazol-4-yl)methyl)-1H-pyrazol-4-yl)imidazolidine-2,4-dione (example 10-1) and benzyl bromide. Yield: 40%. $^1$H NMR (CDCl$_3$, 400 MHz): δ 2.18 (s, 3H), 2.42 (s, 3H), 3.84 (s, 2H), 4.61 (s, 2 H), 5.06 (s, 2H), 7.40-7.27 (m, 5H), 7.92 (s, 1 H), 8.08 (s, 1H). The title compound was shown to inhibit hT2R08 bitter receptor and had an IC$_{50}$ of 0.09 μM.

Example 10-54

3-(1-((3,5-dimethylisoxazol-4-yl)methyl)-1H-pyrazol-4-yl)-1-(pyridin-2-ylmethyl)imidazolidine-2,4-dione

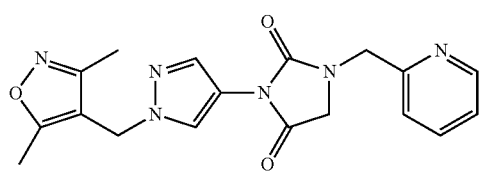 [SMILES: Cc1noc(C)c1Cn1cc(N2C(=O)CN(Cc3ccccn3)C2=O)cn1]

Prepared as in Example 10-5 from 3-(1-((3,5-dimethylisoxazol-4-yl)methyl)-1H-pyrazol-4-yl)imidazolidine-2,4-dione and 2-(bromomethyl)pyridine. Yield: 50%. $^1$H NMR (CDCl$_3$, 400 MHz): δ 2.19 (s, 3H), 2.41 (s, 3H), 4.12 (s, 2H), 4.71 (s, 2H), 5.05 (s, 2H), 7.72-7.23 (m, 4H), 7.92 (s, 1H) 8.08 (s, 1H). The title compound was shown to inhibit hT2R08 bitter receptor and had an IC$_{50}$ of 0.68 μM.

Example 10-55

1-((3,5-dimethylisoxazol-4-yl)methyl)-3-(1-((3,5-dimethylisoxazol-4-yl)methyl)-1H-pyrazol-4-yl)imidazolidine-2,4-dione

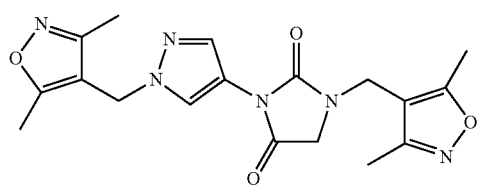 [SMILES: Cc1noc(C)c1CN1CC(=O)N(c2cnn(Cc3c(C)noc3C)c2)C1=O]

Prepared as in Example 10-5 from 3-(1-((3,5-dimethylisoxazol-4-yl)methyl)-1H-pyrazol-4-yl)imidazolidine-2,4-dione and 4-(chloromethyl)-3,5-dimethylisoxazole. Yield: 50%. $^1$H NMR (CDCl$_3$, 400 MHz): 2.19 (s, 3H), 2.27 (s, 3H), 2.43-2.42 (d, J=5.2 Hz, 6H), 3.82 (s, 2H), 4.40 (s, 2H), 5.05 (s, 2H), 7.92 (s, 1H), 8.05 (s, 1H). The title compound was shown to inhibit hT2R08 bitter receptor and had an IC$_{50}$ of 0.04 μM.

Example 10-56

3-(1-((3,5-dimethylisoxazol-4-yl)methyl)-1H-pyrazol-4-yl)-5-(3-methoxybenzyl)imidazolidine-2,4-dione

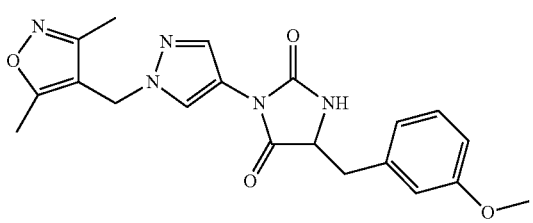 [SMILES: COc1cccc(CC2NC(=O)N(c3cnn(Cc4c(C)noc4C)c3)C2=O)c1]

1-((3,5-dimethylisoxazol-4-yl)methyl)-1H-pyrazol-4-amine hydrochloride (400 mg, 2.08 mmol), dipyridin-2-yl carbonate (450 mg, 2.08 mmol) and triethylamine (0.290 mL, 2.08 mmol) were stirred in dichloromethane (7 mL) for 12 hours at room temperature. The reaction was concentrated under vacuum to afford 4-((4-isocyanato-1H-pyrazol-1-yl)methyl)-3,5-dimethylisoxazole as an off-white solid in quantitative yield. Ethanol (1 mL) was added along with methyl 2-amino-3-(3-methoxyphenyl)propanoate (68 mg, 0.327 mmol) and triethylamine (0.064 mL, 0.461 mmol). The reaction was stirred at reflux for 12 hours, then allowed to cool to room temperature. The solvent was removed under a stream of nitrogen. The crude product was re-suspended in MeOH (1 mL) and purified by reversed phase HPLC (5 to 95% acetonitrile in H$_2$O: 16 minutes gradient). The pure fractions were combined and solvent removed under vacuum to afford 3-(1-((3,5-dimethylisoxazol-4-yl)methyl)-1H-pyrazol-4-yl)-5-(3-methoxybenzyl)imidazolidine-2,4-dione as a white solid yield: 50% $^1$H NMR (CDCl$_3$, 400 MHz): δ 2.19 (s, 3 H), 2.41 (s, 3H), 3.34-3.33 (d, J=3.2 Hz, 1H), 3.31-3.29 (d, J=8 Hz, 1H), 3.76 (s, 3H), 4.33-4.30 (m, 1H), 5.05 (s, 2H), 5.95 (bs, 1H), 7.25-7.21 (t, 1H), 6.82-6.78 (m, 3H), 7.85 (s, 1H), 7.99 (s, 1H). The title compound was shown to inhibit hT2R08 bitter receptor and had an IC$_{50}$ of 0.13 μM.

Example 10-57

5-(cyclohexylmethyl)-3-(1-((3,5-dimethylisoxazol-4-yl)methyl)-1H-pyrazol-4-yl)imidazolidine-2,4-dione

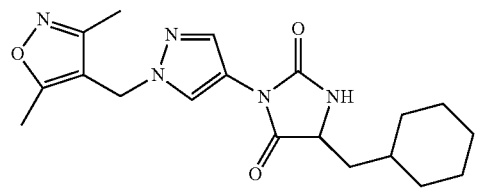 [SMILES: Cc1noc(C)c1Cn1cc(N2C(=O)NC(CC3CCCCC3)C2=O)cn1]

Prepared as in Example 10-56 from 1-((3,5-dimethylisoxazol-4-yl)methyl)-1H-pyrazol-4-amine hydrochloride (example 10-41a) and methyl 2-amino-3-cyclohexylpropanoate.

Yield: 30%. ¹H NMR (CDCl₃, 400 MHz): δ 1.06-0.95 (m, 2H), 1.29-1.15 (m,3H), 1.60-1.50 (1H) 1.77-1.67 (7 H), 1.91-1.85 (m, 1H), 2.19 (s, 3H), 2.41 (s, 3H), 4.19-4.15 (m, 1H), 5.05 (s, 2H), 6.01 (bs, 1H), 7.91 (s, 1H), 8.05 (s, 1H). The title compound was shown to inhibit hT2R08 bitter receptor and had an IC₅₀ of 0.96 μM.

Example 10-58

5-(cyclopentylmethyl)-3-(1-((3,5-dimethylisoxazol-4-yl)methyl)-1H-pyrazol-4-yl)imidazolidine-2,4-dione

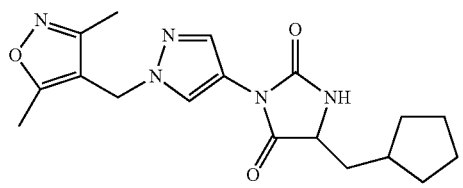 [SMILES: Cc1noc(C)c1Cn1cc(N2C(=O)NC(CC3CCCC3)C2=O)cn1]

Prepared as in Example 10-56 from 1-((3,5-dimethylisoxazol-4-yl)methyl)-1H-pyrazol-4-amine hydrochloride (example 10-41a) and methyl 2-amino-3-cyclopentylpropanoate. Yield: 50%. ¹H NMR (CDCl₃, 400 MHz): δ 1.20-1.14 (m, 3H), 1.68-1.55 (m, 6H), 2.04-1.92 (m, 2H), 2.19 (s, 3H), 2.42 (s, 3H), 4.14-4.11 (m, 1H), 5.05 (s, 2H), 5.52 (bs, 1H), 7.90 (s, 1H), 8.06 (s, 1H). The title compound was shown to inhibit hT2R08 bitter receptor and had an IC₅₀ of 0.31 μM.

Example 10-59

3-(1-((3,5-dimethylisoxazol-4-yl)methyl)-1H-pyrazol-4-yl)-5-(4-hydroxybenzyl)imidazolidine-2,4-dione

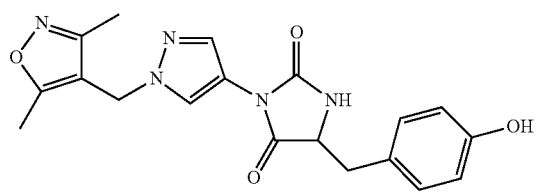 [SMILES: Cc1noc(C)c1Cn1cc(N2C(=O)NC(Cc3ccc(O)cc3)C2=O)cn1]

Prepared as in Example 10-56 from 1-((3,5-dimethylisoxazol-4-yl)methyl)-1H-pyrazol-4-amine hydrochloride (example 10-41a) and methyl 2-amino-3-(4-hydroxyphenyl)propanoate. Yield: 50%. ¹H NMR (CDCl₃, 400 MHz): δ 2.41 (s, 3H), 2.85 (s, 3H), 3.26-3.25 (d, 1H, J=4 Hz), 3.23-3.22 (d, J=4 Hz, 1H) 4.31-4.28 (m, 1H), 5.04 (s, 2H), 5.77-5.74 (bs, 1H), 7.07-7.04 (d, J=12 Hz, 2H), 6.75-6.73 (d, J=8 Hz, 2H), 7.06 (s, 1H), 7.97 (s,1H), 9.43 (bs, 1H). The title compound was shown to inhibit hT2R08 bitter receptor and had an IC₅₀ of 0.33 μM.

Example 10-60

5-(3,4-dihydroxybenzyl)-3-(1-((3,5-dimethylisoxazol-4-yl)methyl)-1H-pyrazol-4-yl)imidazolidine-2,4-dione

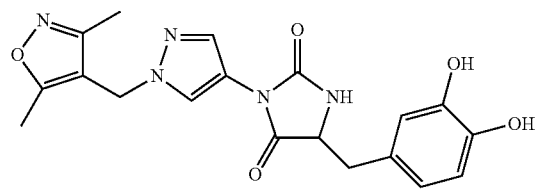 [SMILES: Cc1noc(C)c1Cn1cc(N2C(=O)NC(Cc3ccc(O)c(O)c3)C2=O)cn1]

Prepared as in Example 10-56 from 1-((3,5-dimethylisoxazol-4-yl)methyl)-1H-pyrazol-4-amine hydrochloride (example 10-41a) and methyl 2-amino-3-(3,4-dihydroxyphenyl)propanoate. Yield: 50%. MS M+H calculated 398.1; found 398.1. The title compound was shown to inhibit hT2R08 bitter receptor and had an IC₅₀ of 0.51 μM.

Example 10-61

3-(1-((3,5-dimethylisoxazol-4-yl)methyl)-1H-pyrazol-4-yl)-5-isobutylimidazolidine-2,4-dione

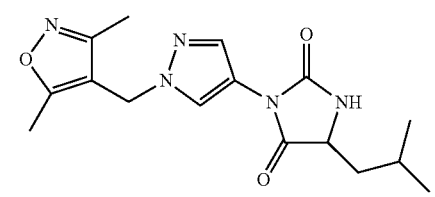 [SMILES: Cc1noc(C)c1Cn1cc(N2C(=O)NC(CC(C)C)C2=O)cn1]

Prepared as in Example 10-41 from 1-((3,5-dimethylisoxazol-4-yl)methyl)-1H-pyrazol-4-amine hydrochloride (example 10-41a) and ethyl 2-isocyanato-4-methylpentanoate. Yield: 50%. ¹H NMR (CDCl₃, 400 MHz): δ 1.01-0.98 (m, 8H), 1.87-1.82 (m, 1H), 2.19 (s, 3H), 2.41 (s, 3H), 4.13-4.12 (t, 1H), (5.05 (s, 2H), 5.70 (bs, 1H), 7.90 (s, 1H), 8.05 (s, 1H).

The title compound was shown to inhibit hT2R08 bitter receptor and had an IC$_{50}$ of 1.0 µM.

Example 10-62

3-(1-((3,5-dimethylisoxazol-4-yl)methyl)-1H-pyrazol-4-yl)-5-isopropylimidazolidine-2,4-dione

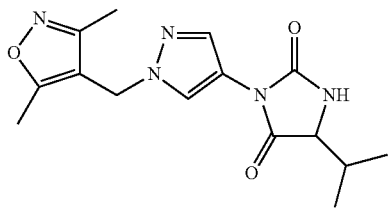 [SMILES: Cc1noc(C)c1Cn1cc(N2C(=O)NC(C(C)C)C2=O)cn1]

Prepared as in Example 10-41 from 1-((3,5-dimethylisoxazol-4-yl)methyl)-1H-pyrazol-4-amine hydrochloride (example 10-41a) and ethyl 2-isocyanato-3-methylbutanoate. Yield: 30%. $^1$H NMR (CDCl$_3$, 400 MHz): δ 0.96-0.94 (d, 3H, J=7.2 Hz), 1.09-1.07 (d, 3H, J=8 Hz), 2.19 (s, 3H), 2.26-2.22 (m, 1H), 2.40 (s, 3H), 4.02 (s, 1H), 5.05 (s, 2H), 5.53 (bs, 1H), 7.90 (s, 1H), 8.05 (s, 1H). The title compound was shown to inhibit hT2R08 bitter receptor and had an IC$_{50}$ of 1.1 µM.

Example 10-63

(Z)-5-benzylidene-3-(1-((3,5-dimethylisoxazol-4-yl)methyl)-1H-pyrazol-4-yl)imidazolidine-2,4-dione

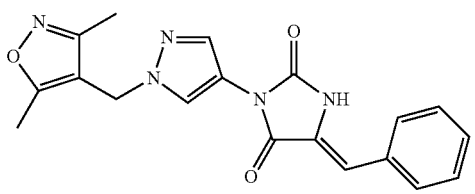 [SMILES: Cc1noc(C)c1Cn1cc(N2C(=O)N/C(=C\c3ccccc3)C2=O)cn1]

3-(1-((3,5-dimethylisoxazol-4-yl)methyl)-1H-pyrazol-4-yl)imidazolidine-2,4-dione (example 10-1) (275 mg, 1 mmol), benzaldehyde (140 mg, 1.3 mmol), and sodium acetate (205 mg, 2.5 mmol), in glacial acetic acid (3 mL) were irradiated in the microwave reactor for 7 hours at 185° C. Upon cooling the mixture was diluted with H$_2$O (100 mL) and extracted with ethyl acetate (3×, 50 mL). The combined organic extracts were washed with saturated aqueous sodium carbonate solution, dried over sodium sulfate, filtered and concentrated. the solid product was triturated with ethyl acetate/hexanes (1/1) and dried under high vacuum to afford (Z)-5-benzylidene-3-(1-((3,5-dimethylisoxazol-4-yl)methyl)-1H-pyrazol-4-yl)imidazolidine-2,4-dione (173 mg, 48%) as a light yellow solid. $^1$H NMR (DMSO-d$_6$, 400 MHz): δ 2.14 (s, 3H), 2.40 (s, 3H), 6.59 (s, 1H), 5.20 (s, 2H), 7.33-7.40 (m, 3H), 7.66 (s, 2H), 7.81 (s, 1H), 8.21 (s, 1H), 11.01 (bs, 1H). The title compound was shown to inhibit hT2R08 bitter receptor and had an IC$_{50}$ of 0.34 µM.

Example 10-64

4-(1-((3,5-dimethylisoxazol-4-yl)methyl)-1H-pyrazol-4-yl)-1-methyl-1,2,4-triazolidine-3,5-dione

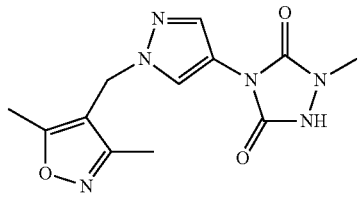

Ethyl 4-(1-((3,5-dimethylisoxazol-4-yl)methyl)-1H-pyrazol-4-yl)-2-methyl-3,5-dioxo-1,2,4-triazolidine-1-carboxylate (3.2 g, 8.8 mmol) was stirred in a (1/1) mixture of MeOH/1N aqueous NaOH (100 mL) at ambient temperature for 30 minutes. The mixture was acidified with aqueous 1N HCl (150 mL), extracted with ethyl acetate (3×, 100 mL), dried over sodium sulfate, filtered and concentrated to afford 4-(1-((3,5-dimethylisoxazol-4-yl)methyl)-1H-pyrazol-4-yl)-1-methyl-1,2,4-triazolidine-3,5-dione (2.3 g, 89%) as a yellow solid. $^1$H NMR (DMSO-d$_6$, 400 MHz): δ2.18 (s, 3H), 2.44 (s, 3H), 3.05 (s, 3H), 5.17 (s, 2H), 7.94 (s, 1H), 8.13 (s, 1H).

Example 10-64a

Ethyl 4-(1-((3,5-dimethylisoxazol-4-yl)methyl)-1H-pyrazol-4-yl)-2-methyl-3,5-dioxo-1,2,4-triazolidine-1-carboxylate

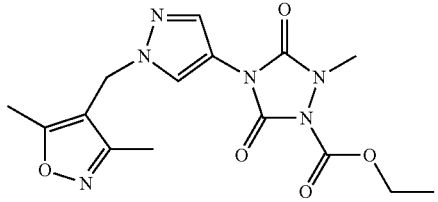 [SMILES: CCOC(=O)n1c(=O)n(-c2cnn(Cc3c(C)noc3C)c2)c(=O)n1C]

Ethyl chloroformate (1.3 g, 12 mmol) was added to a mixture of N-(1-((3,5-dimethylisoxazol-4-yl)methyl)-1H-pyrazol-4-yl)-1-methylhydrazinecarboxamide (example 10-64b) (2.5 g, 9 mmol) and triethylamine (1.2 g, 12 mmol) in acetonitrile (100 ml). The mixture was refluxed for 1 hour, cooled then diluted with 1N aqueous HCl (150 mL) and extracted with ethyl acetate (3×, 75 mL). The combined organic extracts were dried over sodium sulfate, filtered and concentrated on the rotovap. The solid was triturated with ethyl acetate/hexanes (1/3) and dried under high vacuum to afford ethyl 4-(1-((3,5-dimethylisoxazol-4-yl)methyl)-1H-pyrazol-4-yl)-2-methyl-3,5-dioxo-1,2,4-triazolidine-1-carboxylate (3.2 g, 94%) as a white solid. $^1$H NMR (DMSO-d$_6$, 400 MHz): δ1.28 (t, J=7.2 Hz, 3H), 2.13(s, 3H), 2.40 (s, 3H), 3.24 (s, 3H), 4.30 (t, J=7.2 Hz, 2H), 5.21 (s, 2H), 7.73 (m, 1H), 8.16 (s, 1H).

Example 10-64b

N-(1-((3,5-dimethylisoxazol-4-yl)methyl)-1H-pyrazol-4-yl)-1-methylhydrazinecarboxamide

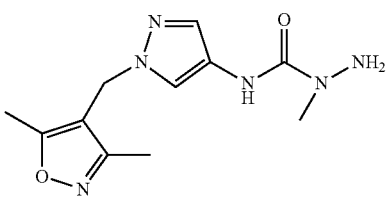 [SMILES: Cc1noc(C)c1Cn1cc(NC(=O)N(C)N)cn1]

1-((3,5-dimethylisoxazol-4-yl)methyl)-1H-pyrazole-4-carbonyl azide (example 10-1a) (1.25 g, 5.3 mmol) was stirred in toluene (30 mL) at reflux temperature for 40 minutes. The mixture was cooled to ambient temperature and methyl hydrazine (0.3 mL, 260 mg, 5.6 mmol) was added and the mixture was refluxed for 30 minutes. After cooling the reaction to room temperature the solvent was removed on the rotovap and the solid product was triturated with ethyl acetate/hexanes (2/5) and dried under high vacuum to afford N-(1-((3,5-dimethylisoxazol-4-yl)methyl)-1H-pyrazol-4-yl)-1-methylhydrazinecarboxamide (1.1 g, 79%) as a white solid. $^1$H NMR (DMSO-d$_6$, 400 MHz): δ2.09 (s, 3H), 2.36 (s, 3H), 2.98 (s, 3H), 4.61 (s, 2H), 5.02 (s, 2H), 7.42 (s, 1H), 7.72 (m, 1H), 8.78 (s, 1H).

Example 10-65

1-Benzyl-4-(1-((3,5-dimethylisoxazol-4-yl)methyl)-1H-pyrazol-4-yl)-2-methyl-1,2,4-triazolidine-3,5-dione

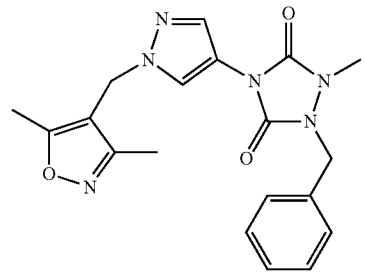

4-(1-((3,5-dimethylisoxazol-4-yl)methyl)-1H-pyrazol-4-yl)-1-methyl-1,2,4-triazolidine-3,5-dione (example 10-64) (785 mg, 2.7 mmol) was dissolved in acetonitrile (50 mL). Triethylamine (1 g, 10 mmol) and benzyl bromide (510 mg, 3 mmol) were added and the reaction was stirred at ambient temperature for 12 hours. The mixture was then concentrated on the rotovap, dissolved in methanol (5 mL) and purified by reversed phase HPLC (5-95% acetonitrile in H$_2$O: 25 minute gradient). The pure fractions were pooled and concentrated and the product was recrystallized form ethanol to afford 1-benzyl-4-(1-((3,5-dimethylisoxazol-4-yl)methyl)-1H-pyrazol-4-yl)-2-methyl-1,2,4-triazolidine-3,5-dione (210 mg, 20%) as a white solid. $^1$H NMR (DMSO-d$_6$, 400 MHz): δ2.13 (s, 3H), 2.39 (s, 3H), 3.09 (s, 3H), 4.81 (s, 2H), 5.18 (s, 2H), 7.30-7.35 (m, 5H), 7.76 (s, 1H), 8.18 (s, 1H). MS M+H calculated 381.1; found 381.1. Melting point: 124-126° C. The title compound was shown to inhibit hT2R08 bitter receptor and had an IC$_{50}$ of 0.02 μM.

Example 10-66

1-Benzyl-4-(1-((3,5-dimethylisoxazol-4-yl)methyl)-1H-pyrazol-4-yl)-2-methyl-1,2,4-triazolidine-3,5-dione

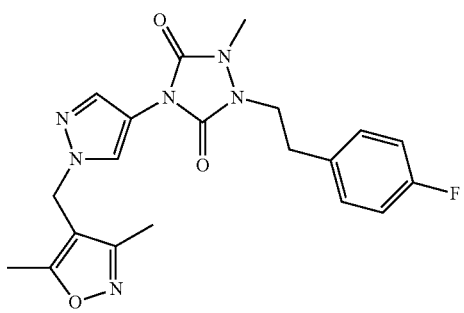 [SMILES: Cc1noc(C)c1Cn1cc(-n2c(=O)n(C)n(CCc3ccc(F)cc3)c2=O)cn1]

Prepared as in Example 10-65 from 4-(1-((3,5-dimethylisoxazol-4-yl)methyl)-1H-pyrazol-4-yl)-1-methyl-1,2,4-triazolidine-3,5-dione (example 10-64) and 1-(2-bromoethyl)-4-fluorobenzene. Yield: 14%. $^1$H NMR (CDCl$_3$, 400 MHz): δ2.18 (s, 3H), 2.40 (s, 3H), 2.87 (t, J=6.8 Hz, 2H), 3.14 (s, 3H), 3.83 (t, J=7.2 Hz, 2H), 5.03 (s, 2H), 6.95 (t, J=8.4 Hz, 2H), 7.14 (t, J=8 Hz, 2H), 7.77 (s, 1H), 7.95 (s, 1H). The title compound was shown to inhibit hT2R08 bitter receptor and had an IC$_{50}$ of 0.01 μM.

Example 10-67

4-(1-((3,5-dimethylisoxazol-4-yl)methyl)-1H-pyrazol-4-yl)-1-methyl-2-(2-phenoxyethyl)-1,2,4-triazolidine-3,5-dione

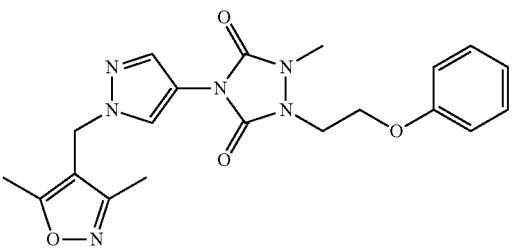 [SMILES: Cc1noc(C)c1Cn1cc(-n2c(=O)n(C)n(CCOc3ccccc3)c2=O)cn1]

Prepared as in Example 10-65 from 4-(1-((3,5-dimethylisoxazol-4-yl)methyl)-1H-pyrazol-4-yl)-1-methyl-1,2,4-triazolidine-3,5-dione (example 10-64) and (2-bromoethoxy)benzene. Yield: 20%. $^1$H NMR (DMSO-d$_6$, 400 MHz): δ2.13 (s, 3H), 2.40 (s, 3H), 3.15 (s, 3H), 3.99 (t, J=4.4 Hz, 2H), 4.13 (t, J=4.8 Hz, 2H), 5.20 (s, 2H), 6.80 (d, J=8 Hz, 2H), 6.90 (t, J=7.1 Hz, 1H), 7.22 (t, J=8 Hz, 2H), 7.75 (s, 1H), 8.17 (s, 1H).

The title compound was shown to inhibit hT2R08 bitter receptor and had an $IC_{50}$ of 0.031 µM.

Example 10-68

4-(1-((3,5-dimethylisoxazol-4-yl)methyl)-1H-pyrazol-4-yl)-1,2,4-triazolidine-3,5-dione

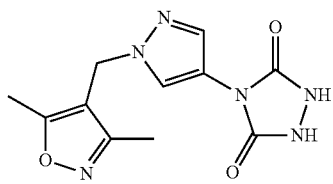 [SMILES: Cc1noc(C)c1Cn1cc(-n2c(=O)[nH][nH]c2=O)cn1]

1-((3,5-dimethylisoxazol-4-yl)methyl)-1H-pyrazole-4-carbonyl azide (example 10-1a) (1 g, 4.1 mmol) was refluxed in toluene (100 mL) for one hour. The reaction was cooled to room temperature and ethyl hydrazinecarboxylate (0.45 g, 43 mmol) was added. The reaction was heated to reflux and stirred for 1 hour, then cooled and concentrated on the rotovap. The residue was taken up in ethanol (100 ml) and potassium carbonate (100 mg) was added. The mixture was refluxed for 12 hours, then filtered, cooled to ambient temperature, and neutralized with acetic acid (ca. 7 drops). The solvent was removed on the rotovap and the resulting solid was triturated with ethyl acetate/hexanes (1/9) to afford 4-(1-((3,5-dimethylisoxazol-4-yl)methyl)-1H-pyrazol-4-yl)-1,2,4-triazolidine-3,5-dione (0.98 g, 85%) as an off white solid. $^1$H NMR (CDCl$_3$, 400 MHz): δ2.18 (s, 3H), 2.41 (s, 3H), 4.98 (s, 2H) 7.16 (s, 1H), 7.38 (s, 1H).

Example 10-69

4-(1-((3,5-dimethylisoxazol-4-yl)methyl)-1H-pyrazol-4-yl)-1,2-dimethyl-1,2,4-triazolidine-3,5-dione

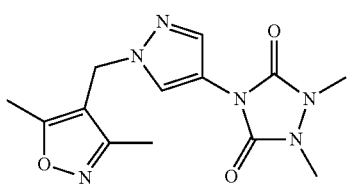

4-(1-((3,5-dimethylisoxazol-4-yl)methyl)-1H-pyrazol-4-yl)-1,2,4-triazolidine-3,5-dione (example 10-68) (100 mg, 0.36 mmol), methyl iodide (141 mg, 1 mmol), and cesium carbonate (325 mg, 1 mmol) were stirred in a 2/1 mixture of acetonitrile/DMF (5 mL) at ambient temperature for 2 hours. The mixture was diluted with aqueous 1N HCl (100 mL) and extracted with ethyl acetate (3×, 50 mL). The combined organic extracts were dried over sodium sulfate, concentrated and the crude residue taken up in MeOH and purified by reversed phase HPLC (5 to 95% acetonitrile in H$_2$O: 25 minute gradient). The pure fractions were pooled and concentrated to afford 4-(1-((3,5-dimethylisoxazol-4-yl)methyl)-1H-pyrazol-4-yl)-1,2-dimethyl-1,2,4-triazolidine-3,5-dione (89 mg, 80%) as a clear semi-solid. $^1$H NMR (CDCl$_3$, 400 MHz): δ2.18 (s, 3H), 2.41 (s, 3H), 3.22 (s, 6H), 5.04 (s, 2H), 7.88 (s, 1H), 8.03 (s, 1H). The title compound was shown to inhibit hT2R08 bitter receptor and had an $IC_{50}$ of 0.6 µM.

Example 10-70

1,2-dibenzyl-4-(1-((3,5-dimethylisoxazol-4-yl)methyl)-1H-pyrazol-4-yl)-1,2,4-triazolidine-3,5-dione

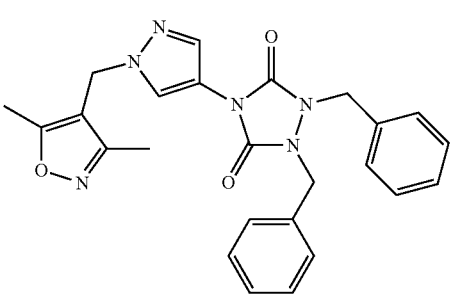 [SMILES: Cc1noc(C)c1Cn1cc(-n2c(=O)n(Cc3ccccc3)n(Cc3ccccc3)c2=O)cn1]

Prepared as in Example 10-65 from 4-(1-((3,5-dimethylisoxazol-4-yl)methyl)-1H-pyrazol-4-yl)-1,2-dimethyl-1,2,4-triazolidine-3,5-dione (example 10-69) and benzyl bromide. Yield: 69%. $^1$H NMR (CDCl$_3$, 400 MHz): δ2.14 (s, 3H), 2.36 (s, 3H), 4.65 (s, 4H), 4.99 (s, 2H), 7.06-7.08 (m, 4H), 7.19-7.25 (m, 6H), 7.86 (s, 1H), 8.02 (s, 1H). The title compound was shown to inhibit hT2R08 bitter receptor and had an $IC_{50}$ of 0.8 µM.

Example 10-71

3-(1-((3,5-dimethylisoxazol-4-yl)methyl)-1H-pyrazol-4-yl)-1-((6-(hydroxymethyl)pyridin-2-yl)methyl)imidazolidine-2,4-dione

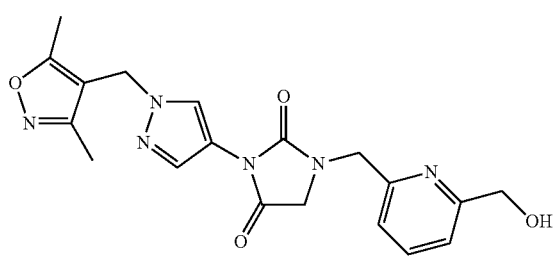 [SMILES: Cc1noc(C)c1Cn1cc(N2C(=O)CN(Cc3cccc(CO)n3)C2=O)cn1]

Prepared as in example 10-5 from 3-(1-((3,5-dimethylisoxazol-4-yl)methyl)-1H-pyrazol-4-yl)imidazolidine-2,4-dione and 6-bromomethyl-2-pyridinemethanol. Yield: 35%.

MS M+H calculated 397.2; found 397.2. The title compound was shown to inhibit hT2R08 bitter receptor and had an IC$_{50}$ of 0.72 μM.

Example 10-72

1-((3,4-dimethoxypyridin-2-yl)methyl)-3-(1-((3,5-dimethylisoxazol-4-yl)methyl)-1H-pyrazol-4-yl)imidazolidine-2,4-dione

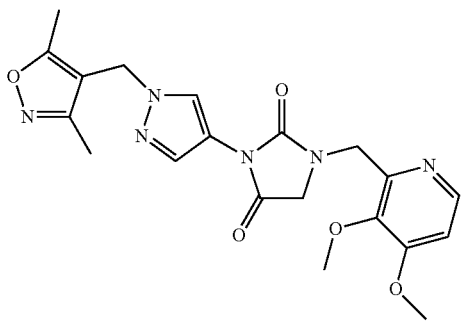 [SMILES: COc1ccnc(CN2CC(=O)N(c3cnn(Cc4c(C)noc4C)c3)C2=O)c1OC]

Prepared as in example 10-5 from 3-(1-((3,5-dimethylisoxazol-4-yl)methyl)-1H-pyrazol-4-yl)imidazolidine-2,4-dione and 3,4-dimethoxy-2-chloromethylpyridine hydrochloride. Yield: 26%. MS M+H calculated 360.2; found 360.2. The title compound was shown to inhibit hT2R08 bitter receptor and had an IC$_{50}$ of 1.0 μM.

Example 10-73

3-(1-((3,5-dimethylisoxazol-4-yl)methyl)-1H-pyrazol-4-yl)-1-((6-(tetrahydrofuran-2-yl)methyl)imidazolidine-2,4-dione

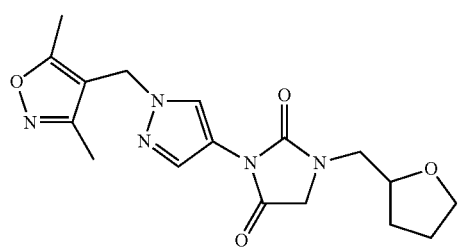 [SMILES: Cc1noc(C)c1Cn1cc(N2C(=O)CN(CC3CCCO3)C2=O)cn1]

Prepared as in example 10-52 from 3-(1-((3,5-dimethylisoxazol-4-yl)methyl)-1H-pyrazol-4-yl)imidazolidine-2,4-dione and tetrahydrofurfuryl bromide. Yield: 28%. MS M+H calculated 427.2; found 427.2. The title compound was shown to inhibit hT2R08 bitter receptor and had an IC$_{50}$ of 1.4 μM.

Example 10-74

1-(cyclohexylmethyl)-3-(1-((3,5-dimethylisoxazol-4-yl)methyl)-1H-pyrazol-4-yl)imidazolidine-2,4-dione

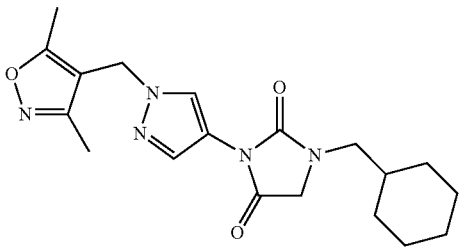 [SMILES: Cc1noc(C)c1Cn1cc(N2C(=O)CN(CC3CCCCC3)C2=O)cn1]

Prepared as in example 10-52 from 3-(1-((3,5-dimethylisoxazol-4-yl)methyl)-1H-pyrazol-4-yl)imidazolidine-2,4-dione (example 10-1) and bromomethylcyclohexane. Yield: 20%. $^1$H NMR (DMSO-d$_6$, 400 MHz): δ0.88 (q, J=10.4 Hz, 2H), 1.09-1.19 (m, 3H), 1.58-1.65 (m, 6H), 2.12 (s, 3H), 2.38 (s, 3H), 3.13 (d, J=7.2 Hz, 2H), 4.06 (s, 2H), 5.17 (s, 2H), 7.75 (s, 1H), 8.14 (s, 1H). MS M+H calculated 372.2; found 372.1. The title compound was shown to inhibit hT2R08 bitter receptor and had an IC$_{50}$ of 0.28 μM.

Example 10-75

3-(1-((3,5-dimethylisoxazol-4-yl)methyl)-1H-pyrazol-4-yl)-1-((6-methoxypyridin-2-yl)methyl)imidazolidine-2,4-dione

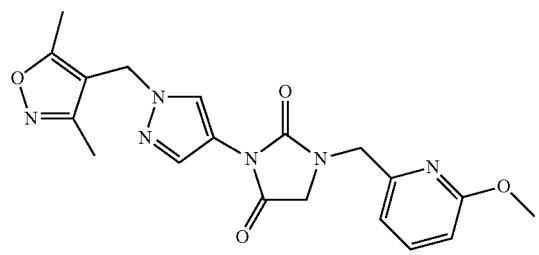 [SMILES: COc1cccc(CN2CC(=O)N(c3cnn(Cc4c(C)noc4C)c3)C2=O)n1]

3-(1-((3,5-dimethylisoxazol-4-yl)methyl)-1H-pyrazol-4-yl)imidazolidine-2,4-dione (100 mg, 0.4 mmol), (6-methoxy-pyridin-2-yl)-methanol (example 10-75a) (101 mg, 0.7 mmol), tributylphosphine (147 mg, 0.7 mmol), and 1,1""-azobis(N,N-dimethylformamide) (125 mg, 0.7 mmol) were dissolved in THF (5 mL) and stirred at room temperature for 15 hours. The reaction was diluted with brine (100 mL) and extracted with ethyl acetate (2×, 100 mL). The combined organic extracts were dried over magnesium sulfate, filtered and concentrated on the rotovap. The residue was taken up in methanol (5 mL) and purified by reversed phase HPLC (5 to 95% acetonitrile in H$_2$O: 25 minute gradient). The pure fractions were combined, concentrated then re-dissolved in ethyl acetate/hexane (1:9). The solution was cooled at 5° C. for 15 hrs, where a white solid formed. The precipitate was collected to afford 3-(1-((3,5-dimethylisoxazol-4-yl)methyl)-1H-pyrazol-4-yl)-1-(6-methoxypyridin-2-yl)methyl)imidazolidine-2,4-dione (5 mg, 4%) as a white solid. $^1$H NMR (DMSO-d$_6$, 400 MHz): δ2.11 (s, 3H), 2.37 (s, 3H), 3.74 (s, 3H), 4.17 (s, 2H), 4.54 (s, 2H), 5.17 (s, 2H), 6.69 (d, J=7.6 Hz, 1H), 6.96 (d, J=6.8 Hz, 1H), 7.67 (d, J=6.8 Hz, 1H), 7.76 (s, 1H), 8.17 (s, 1H). MS M+H calculated 397.2; found 397.2. The title compound was shown to inhibit hT2R08 bitter receptor and had an IC$_{50}$ of 0.23 μM.

Example 10-75a (6-methoxypyridin-2-yl)methanol

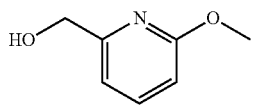

Methyl-6-methoxypyridine-2-carboxylate (2 g, 11.96 mmol) in anhydrous methanol (20 mL) was cooled to 0° C. under nitrogen and sodium borohydride (1.36 g, 35.89 mmol) was slowly added to the solution. The reaction was left stirring at 0° C. for 30 minutes, then allowed to warm up to room temperature for 1 hour. The reaction was quenched with water and concentrated on the rotovap. The reaction was diluted with brine (100 mL) and extracted with dichloromethane/2-propanol solution (2:1) (3×, 150 mL). The combined organic extracts were dried over magnesium sulfate, filtered and concentrated on the rotovap to afford (6-methoxypyridin-2-yl) methanol (500 mg, 30%) as an oil. MS M+H calculated 140.1; found 140.1.

Example 10-76

3-(1-((3,5-dimethylisoxazol-4-yl)methyl)-1H-pyrazol-4-yl)-1-(2-methoxyphenethyl)imidazolidine-2,4-dione

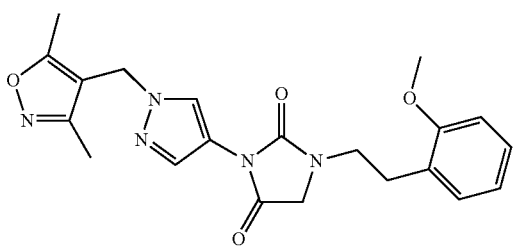 [SMILES: COc1ccccc1CCN1CC(=O)N(c2cnn(Cc3c(C)noc3C)c2)C1=O]

Prepared as in example 10-52 from 3-(1-((3,5-dimethyl-isoxazol-4-yl)methyl)-1H-pyrazol-4-yl)imidazolidine-2,4-dione (example 6) and 2-methoxyphenethyl bromide. Yield: 52%. $^1$H NMR (DMSO-d$_6$, 400 MHz): δ2.11 (s, 3H), 2.38 (s, 3H), 2.80 (t, J=7.2 Hz, 2H), 3.51 (t, J=7.2 Hz, 2H), 3.75 (s, 3H), 4.03 (s, 2H), 5.17 (s, 2H), 6.85 (t, J=7.2 Hz, 1H), 6.95 (d, J=8.4 Hz, 1H), 7.16-7.21 (m, 2H), 7.73 (s, 1H), 8.13 (s, 1H). MS M+H calculated 410.2; found 410.1. Melting point: 97-98° C. The title compound was shown to inhibit hT2R08 bitter receptor and had an IC$_{50}$ of 0.14 μM.

Example 10-77

3-(1-((3,5-dimethylisoxazol-4-yl)methyl)-1H-pyrazol-4-yl)-1-(3-fluorophenethyl)imidazolidine-2,4-dione

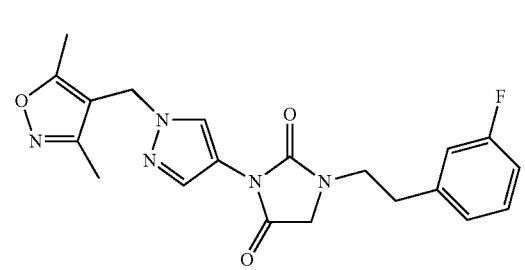 [SMILES: Cc1noc(C)c1Cn1cc(N2C(=O)CN(CCc3cccc(F)c3)C2=O)cn1]

Prepared as in example 10-52 from 3-(1-((3,5-dimethyl-isoxazol-4-yl)methyl)-1H-pyrazol-4-yl)imidazolidine-2,4-dione (example 10-1) and 3-fluorophenethyl bromide. Yield: 22%. $^1$H NMR (DMSO-d$_6$, 400 MHz): δ 2.11 (s, 3H), 2.38 (s, 3H), 2.80 (t, J=7.2 Hz, 2H), 3.57 (t, J=7.2 Hz, 2H), 4.06 (s, 2H), 5.17 (s, 2H), 6.85 (dt, J=8.4, 2.0 Hz, 1H), 7.11 (t, J=8.4 Hz, 2H), 7.32 (q, J=7.8 Hz, 1H), 7.73 (s, 1H), 8.12 (s, 1H). MS M+H calculated 398.2; found 398.1. Melting point: 110-111° C. The title compound was shown to inhibit hT2R08 bitter receptor and had an IC$_{50}$ of 0.06 μM.

Example 10-78

3-(1-((3,5-dimethylisoxazol-4-yl)methyl)-1H-pyrazol-4-yl)-1-phenethylimidazolidine-2,4-dione

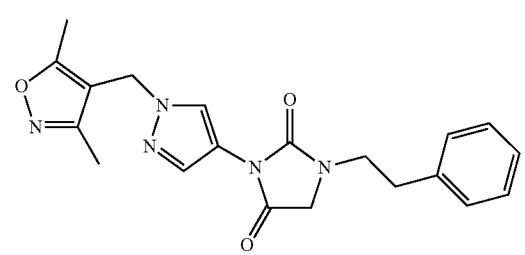 [SMILES: Cc1noc(C)c1Cn1cc(N2C(=O)CN(CCc3ccccc3)C2=O)cn1]

Prepared as in example 10-52 from 3-(1-((3,5-dimethyl-isoxazol-4-yl)methyl)-1H-pyrazol-4-yl)imidazolidine-2,4-dione (example 10-1) and phenethylbromide. Yield: 37%. $^1$H NMR (DMSO-d$_6$, 400 MHz): δ2.11 (s, 3H), 2.38 (s, 3H), 2.83 (t, J=6.4 Hz, 2H), 3.55 (t, J=7.4 Hz, 2H), 4.03 (s, 2H), 5.17 (s, 2H), 7.18-7.30 (m, 5H), 7.73 (s, 1H), 8.13 (s, 1H). MS M+H calculated 380.2; found 380.1. Melting point: 95-96° C. The title compound was shown to inhibit hT2R08 bitter receptor and had an IC$_{50}$ of 0.14 μM.

Example 10-79

3-(1-((3,5-dimethylisoxazol-4-yl)methyl)-1H-pyrazol-4-yl)-1-(4-methoxyphenethyl)imidazolidine-2,4-dione

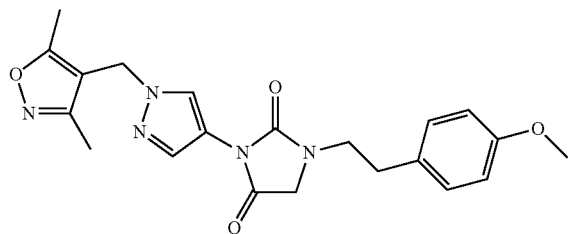 [SMILES: COc1ccc(CCN2CC(=O)N(c3cnn(Cc4c(C)noc4C)c3)C2=O)cc1]

Prepared as in example 10-52 from 3-(1-((3,5-dimethylisoxazol-4-yl)methyl)-1H-pyrazol-4-yl)imidazolidine-2,4-dione (example 10-1) and 4-methoxyphenethyl bromide. Yield: 32%. $^1$H NMR (DMSO-d$_6$, 400 MHz): δ2.11 (s, 3H), 2.38 (s, 3H), 2.78 (t, J=7.4 Hz, 2H), 3.50 (t, J=7.4 Hz, 2H), 3.69 (s, 3H), 4.02 (s, 2H), 5.16 (s, 2H), 6.84 (d, J=8.4 Hz, 2H), 7.15 (d, J=8.4 Hz, 2H), 7.73 (s, 1H), 8.12 (s, 1H). MS M+H calculated 410.18; found 410.2. The title compound was shown to inhibit hT2R08 bitter receptor and had an IC$_{50}$ of 0.04 μM.

Example 10-80

3-(1-((3,5-dimethylisoxazol-4-yl)methyl)-1H-pyrazol-4-yl)-1-(2-naphthalen-1-yl)ethyl)imidazolidine-2,4-dione

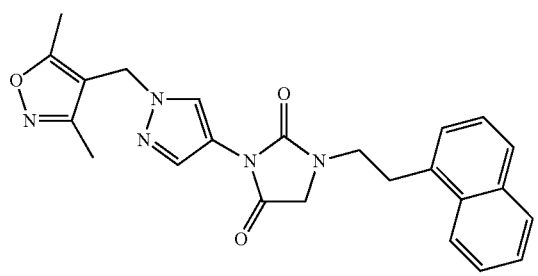 [SMILES: Cc1noc(C)c1Cn1cc(N2C(=O)CN(CCc3cccc4ccccc34)C2=O)cn1]

Prepared as in example 10-52 from 3-(1-((3,5-dimethylisoxazol-4-yl)methyl)-1H-pyrazol-4-yl)imidazolidine-2,4-dione (example 10-1) and 1-(2-bromoethyl)naphthalene.

Yield: 20%. MS M+H calculated 430.18; found 430.2. The title compound was shown to inhibit hT2R08 bitter receptor and had an IC$_{50}$ of 1.27 μM.

Example 10-81

1-(2-chlorophenethyl)-3-(1-((3,5-dimethylisoxazol-4-yl)methyl)-1H-pyrazol-4-yl)imidazolidine-2,4-dione

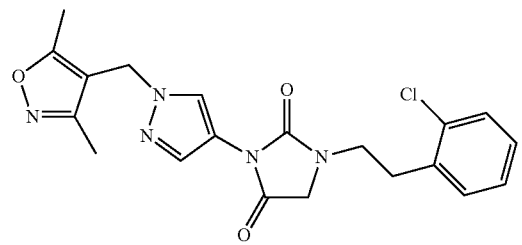 [SMILES: Cc1noc(C)c1Cn1cc(N2C(=O)CN(CCc3ccccc3Cl)C2=O)cn1]

Prepared as in example 10-52 from 3-(1-((3,5-dimethylisoxazol-4-yl)methyl)-1H-pyrazol-4-yl)imidazolidine-2,4-dione (example 10-1) and 2-chlorophenethyl bromide. Yield: 25%. MS M+H calculated 414.13; found 414.2. The title compound was shown to inhibit hT2R08 bitter receptor and had an IC$_{50}$ of 0.25 μM.

Example 10-82

1-(3-chlorophenethyl)-3-(1-((3,5-dimethylisoxazol-4-yl)methyl)-1H-pyrazol-4-yl)imidazolidine-2,4-dione

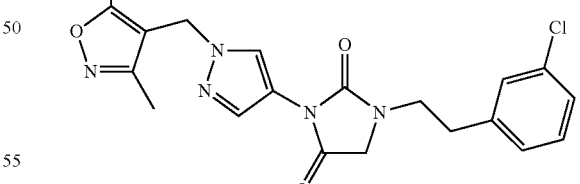

Prepared as in example 10-52 from 3-(1-((3,5-dimethylisoxazol-4-yl)methyl)-1H-pyrazol-4-yl)imidazolidine-2,4-dione (example 10-1) and 3-chlorophenethyl bromide. Yield:

27%. MS M+H calculated 414.13; found 414.2. The title compound was shown to inhibit hT2R08 bitter receptor and had an IC$_{50}$ of 0.20 μM.

Example 10-83

3-(1-((3,5-dimethylisoxazol-4-yl)methyl)-1H-pyrazol-4-yl)-1-(2-fluorophenethyl)imidazolidine-2,4-dione

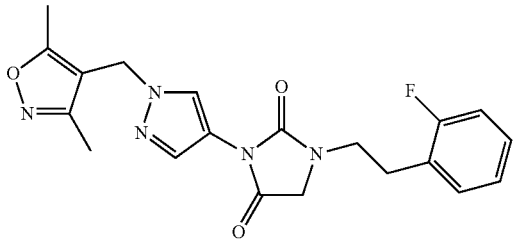 [SMILES: Cc1noc(C)c1Cn1cc(N2C(=O)CN(CCc3ccccc3F)C2=O)cn1]

Prepared as in example 10-52 from 3-(1-((3,5-dimethylisoxazol-4-yl)methyl)-1H-pyrazol-4-yl)imidazolidine-2,4-dione (example 10-1) and 2-fluorophenethyl bromide. Yield: 24%. MS M+H calculated 398.16; found 398.1. The title compound was shown to inhibit hT2R08 bitter receptor and had an IC$_{50}$ of 0.13 μM.

Example 10-84

3-(1-((3,5-dimethylisoxazol-4-yl)methyl)-1H-pyrazol-4-yl)-1-(4-fluorophenethyl)imidazolidine-2,4-dione

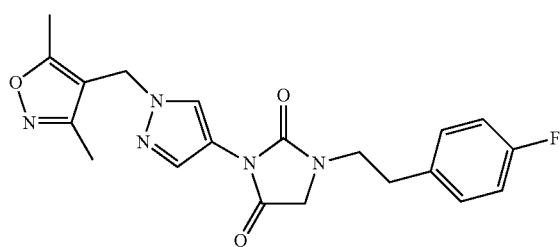 [SMILES: Cc1noc(C)c1Cn1cc(N2C(=O)CN(CCc3ccc(F)cc3)C2=O)cn1]

Prepared as in example 10-52 from 3-(1-((3,5-dimethylisoxazol-4-yl)methyl)-1H-pyrazol-4-yl)imidazolidine-2,4-dione (example 10-1) and 4-fluorophenethyl bromide. Yield:

34%. MS M+H calculated 398.16; found 398.1. The title compound was shown to inhibit hT2R08 bitter receptor and had an IC$_{50}$ of 0.01 μM.

Example 10-85

3-(1-((3,5-dimethylisoxazol-4-yl)methyl)-1H-pyrazol-4-yl)-1-(3-methoxyphenethyl)imidazolidine-2,4-dione

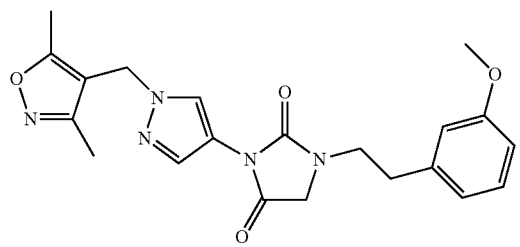 [SMILES: COc1cccc(CCN2CC(=O)N(c3cnn(Cc4c(C)noc4C)c3)C2=O)c1]

Prepared as in example 10-52 from 3-(1-((3,5-dimethylisoxazol-4-yl)methyl)-1H-pyrazol-4-yl)imidazolidine-2,4-dione (example 10-1) and 3-methoxyphenethyl bromide. Yield: 34%. MS M+H calculated 410.18; found 410.1. The title compound was shown to inhibit hT2R08 bitter receptor and had an IC$_{50}$ of 0.16 μM.

Example 10-86

3-(1-((3,5-dimethylisoxazol-4-yl)methyl)-1H-pyrazol-4-yl)-1-(4-hydroxyphenethyl)imidazolidine-2,4-dione

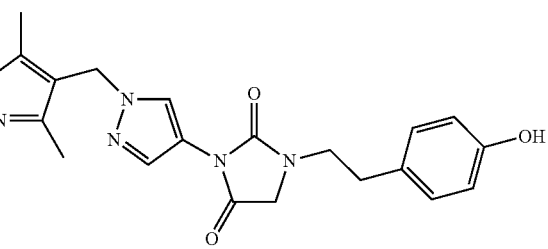

Prepared as in example 10-52 from 3-(1-((3,5-dimethylisoxazol-4-yl)methyl)-1H-pyrazol-4-yl)imidazolidine-2,4-dione (example 10-1) and 4-hydroxyphenethyl bromide.

Yield: 31%. MS M+H calculated 396.16; found 396.1. The title compound was shown to inhibit hT2R08 bitter receptor and had an IC$_{50}$ of 0.41 µM.

Example 10-87

1-(3,4-dimethoxyphenethyl)-3-(1-((3,5-dimethyl-isoxazol-4-yl)methyl)-1H-pyrazol-4-yl)imidazoli-dine-2,4-dione

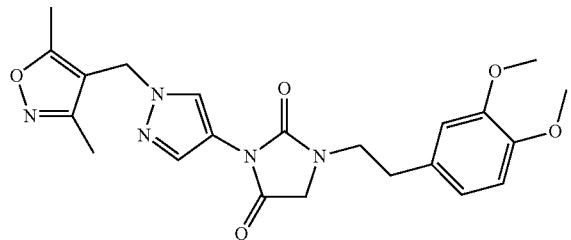 [SMILES: COc1ccc(CCN2CC(=O)N(c3cnn(Cc4c(C)noc4C)c3)C2=O)cc1OC]

Prepared as in example 10-52 from 3-(1-((3,5-dimethyl-isoxazol-4-yl)methyl)-1H-pyrazol-4-yl)imidazolidine-2,4-dione (example 10-1) and 3,4-dimethoxyphenethyl bromide. Yield: 36%. MS M+H calculated 440.19; found 440.2. The title compound was shown to inhibit hT2R08 bitter receptor and had an IC$_{50}$ of 0.26 µM.

Example 10-88

1-benzyl-3-(1-((3,5-dimethylisoxazol-4-yl)methyl)-1H-pyrazol-4-yl)imidazolidin-2-one

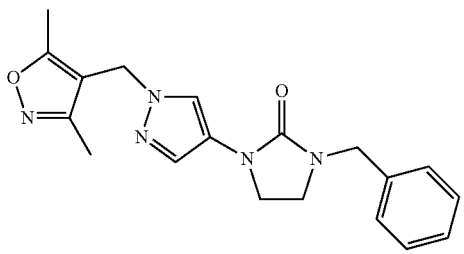 [SMILES: Cc1noc(C)c1Cn1cc(N2CCN(Cc3ccccc3)C2=O)cn1]

1-(1-((3,5-dimethylisoxazol-4-yl)methyl)-1H-pyrazol-4-yl)imidazolidin-2-one (example 10-88a) (50 mg, 0.19 mmol) and 60% sodium hydride (8 mg, 0.21 mmol) in DMF (3 mL) were stirred at room temperature for 15 minutes then cooled to 0° C. Benzyl bromide (33 mg, 0.19 mmol) was added to the mixture and allowed to warm up at room temperature for 2 hours. The reaction was quenched with methanol and concentrated on the rotovap. The reaction was diluted with brine (50 mL) and extracted with dichloromethane (2×, 50 mL). The combined organic extracts were dried over magnesium sulfate, filtered and concentrated on the rotovap. The residue was purified by silica column chromatography (100% to 90% dichloromethane in methanol: 30 minute gradient) to afford 1-benzyl-3-(1-((3,5-dimethylisoxazol-4-yl)methyl)-1H-pyrazol-4-yl)imidazolidin-2-one (21 mg, 31%) as a white solid. MS M+H calculated 352.17; found 352.2. The title compound was shown to inhibit hT2R08 bitter receptor and had an IC$_{50}$ of 0.71 µM.

Example 10-88a 1-(1-((3,5-dimethylisoxazol-4-yl)methyl)-1H-pyra-zol-4-yl)imidazolidin-2-one

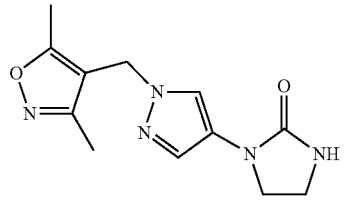 [SMILES: Cc1noc(C)c1Cn1cc(N2CCNC2=O)cn1]

1-(2-chloroethyl)-3-(1-((3,5-dimethylisoxazol-4-yl)me-thyl)1H-pyrazol-4-yl)urea (example 10-88b) (115 mg, 0.39 mmol) and 60% sodium hydride (17 mg, 0.42 mmol) in DMF (2 mL) were stirred at 0° C. for 15 minutes then allowed to warm up to room temperature with stirring for 2 hours. The reaction was quenched with methanol and concentrated on the rotovap. The reaction was diluted with brine (50 mL) and extracted with dichloromethane (2×, 50 mL). The combined organic extracts were dried over magnesium sulfate, filtered and concentrated on the rotovap. The residue was purified by silica column chromatography (100% to 90% dichloromethane in methanol: 30 minute gradient) to afford 1-(1-((3,5-dimethylisoxazol-4-yl)methyl)-1H-pyrazol-4-yl)imi-dazolidin-2-one (98 mg, 97%) as a white solid. $^1$H NMR (DMSO-d$_6$, 400 MHz): δ2.10 (s, 3H), 2.37 (s, 3H), 3.35-3.39 (m, 2H), 3.61 (d, J=8.8 Hz, 1H), 3.63 (d, J=10.4 Hz, 1H), 5.07 (s, 2H), 6.71 (s, 1H), 7.42 (s, 1H), 7.74 (s, 1H). MS M+H calculated 262.12; found 262.1.

Example 10-88b 1-(2-chloroethyl)-3-(1-((3,5-dimethylisoxazol-4-yl)methyl)-1H-pyrazol-4-yl)urea

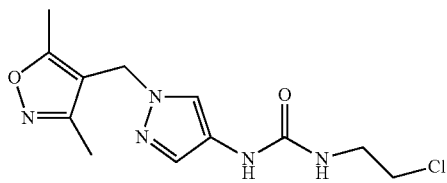 [SMILES: Cc1noc(C)c1Cn1cc(NC(=O)NCCCl)cn1]

1-((3,5-dimethylisoxazol-4-yl)methyl)-1H-pyrazol-4-amine (419 mg, 2.18 mmol) and 2-chloroethyl isocyanate (230 mg, 2.18 mmol) in acetonitrile (5 mL) were heated at 65° C. for 16 hours. The reaction was cooled to room temperature and concentrated on the rotovap. The residue was purified by silica column chromatography (100% to 90% dichloromethane in methanol: 30 minute gradient), dried and tritu-rated with ethyl acetate/hexanes (1/9) to afford (1-(2-chloro-ethyl)-3-(1-((3,5-dimethylisoxazol-4-yl)methyl)1H- pyrazol-4-yl)urea (258 mg, 40%) as a yellow solid. MS M+H calculated 298.10; found 298.1

Example 10-89

1-benzyl-4-(1-((3,5-dimethylisoxazol-4-yl)methyl)-1H-pyrazol-4-yl)-2-(methoxymethyl)-1,2,4-triazolidine-3,5-dione

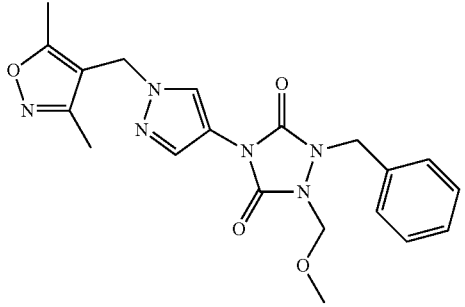 [SMILES: COCn1c(=O)n(-c2cnn(Cc3c(C)noc3C)c2)c(=O)n1Cc1ccccc1]

Prepared as in example 10-91 from 1-benzyl-4-(1-((3,5-dimethylisoxazol-4-yl)methyl)-1H-pyrazol-4-yl)-1,2,4-triazolidine-3,5-dione (example 10-91a) and bromomethyl methyl ether. Yield: 18%. MS M+H calculated 411.17; found 411.2. The title compound was shown to inhibit hT2R08 bitter receptor and had an $IC_{50}$ of 0.02 µM.

Example 10-90

1-((1,3-dimethyl-1H-pyrazol-4-yl)methyl)-3-(1-((3,5-dimethylisoxazol-4-yl)methyl)-1H-pyrazol-4-yl)imidazolidine-2,4-dione

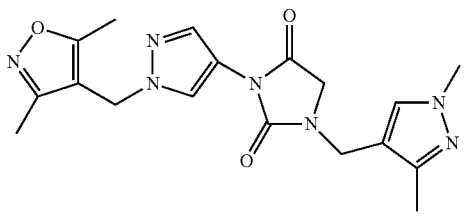 [SMILES: Cc1nn(C)cc1CN1CC(=O)N(c2cnn(Cc3c(C)noc3C)c2)C1=O]

3-(1-((3,5-dimethylisoxazol-4-yl)methyl)-1H-pyrazol-4-yl)imidazolidine-2,4-dione (10a)(200 mg, 0.7 mmol), 4-(chloromethyl)-1,3-dimethyl-1H-pyrazole (144 mg, 1 mmol), and cesium carbonate (325 mg, 1 mmol) were dissolved in 2 mL DMF and irradiated in the microwave reactor at 165° C. for 5 minutes. The reaction was cooled to room temperature, and salt precipitate was removed by filtration. The clear solution containing crude product was obtained and was purified by HPLC (10 to 95% Acetonitrile/water; 25 minutes) to afford 1-((1,3-dimethyl-1H-pyrazol-5-yl)methyl)-3-(1-((3,5-dimethylisoxazol-4-yl)methyl)-1H-pyrazol-4-yl)imidazolidine-2,4-dione (150 mg, 53%) as a light brown solid. [1]2.09H NMR (DMSO, 400 MHz): δ (s, 3H), 2.14 (s, 3H), 2.20 (s, 3H), 3.70 (s, 3H), 3.99 (s, 2H), 4.55 (s, 2H), 5.19 (s, 2H), 6.06 (s, H), 7.77 (s, H), 8.17 (s, H), MS M+H calculated for 384.2. found 384.2; Melting point: 145-146° C.

Example 10-91

1-benzyl-4-(1-((3,5-dimethylisoxazol-4-yl)methyl)-1H-pyrazol-4-yl)-2-ethyl-1,2,4-triazolidine-3,5-dione

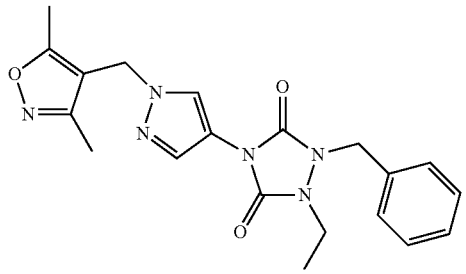 [SMILES: CCn1c(=O)n(-c2cnn(Cc3c(C)noc3C)c2)c(=O)n1Cc1ccccc1]

1-benzyl-4-(1-((3,5-dimethylisoxazol-4-yl)methyl)-1H-pyrazol-4-yl)-1,2,4-triazolidine-3,5-dione (100 mg, 0.27 mmol), bromoethane (149 mg, 1.36 mmol), and cesium carbonate (355 mg, 1.1 mmol) in DMF (5 mL) were heated at 80° C. for 15 hours. The reaction was cooled to room temperature, diluted with brine (50 mL) and extracted with ethyl acetate (2×, 50 mL). The combined organic extracts were dried over magnesium sulfate, filtered and concentrated on the rotovap. The residue was purified by HPLC (5 to 95% acetonitrile in $H_2O$: 25 minute gradient) to afford 1-benzyl-4-(1-((3,5-dimethylisoxazol-4-yl)methyl)-1H-pyrazol-4-yl)-2-ethyl-1,2,4-triazolidine-3,5-dione (40 mg, 37%) as an oil. $^1$H NMR (DMSO-$d_6$, 400 MHz): δ0.97 (t, J=7.2 Hz, 3H), 2.13 (s, 3H), 2.39 (s, 3H), 3.58 (q, J=6.8 Hz, 2H), 4.80 (s, 2H), 5.18 (s, 2H), 7.28-7.36 (m, 5H), 7.77 (s, 1H), 8.19 (s, 1H). MS M+H calculated 395.18; found 395.2. The title compound was shown to inhibit hT2R08 bitter receptor and had an $IC_{50}$ of 0.04 µM.

Example 10-91a 1-benzyl-4-(1-((3,5-dimethylisoxazol-4-yl)methyl)-1H-pyrazol-4-yl)-1,2,4-triazolidine-3,5-dione

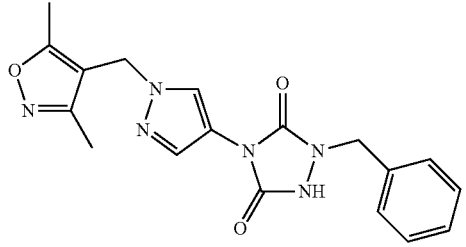 [SMILES: Cc1noc(C)c1Cn1cc(-n2c(=O)[nH]n(Cc3ccccc3)c2=O)cn1]

1-benzyl-N-(1-((3,5-dimethylisoxazol-4-yl)methyl)-1H-pyrazol-4-yl)hydrazinecarboxamide (2.00 g, 5.88 mmol), ethyl chlorformate (6.38 g, 58.77 mmol), and triethylamine (1.78 g, 17.63 mmol) in acetonitrile (50 mL) were heated at 100° C. for 48 hours. The mixture was cooled to 80° C., 1 M NaOH (aq) (5 mL) was added and the reaction mixture was stirred for 1 hour. The reaction was cooled to room temperature and concentrated on the rotpvap. The residue was dissolved in dichloromethane and filtered to remove salts and the solution was concentrated to afford 1-benzyl-4-(1-((3,5-dimethylisoxazol-4-yl)methyl)-1H-pyrazol-4-yl)-1,2,4-triazolidine-3,5-dione (1.28 g, 60%) as a yellow oil. MS M+H calculated 367.14; found 367.2.

Example 10-91b 1-benzyl-N-(1-((3,5-dimethylisoxazol-4-yl)methyl)-1H-pyrazol-4-yl)hydrazinecarboxamide

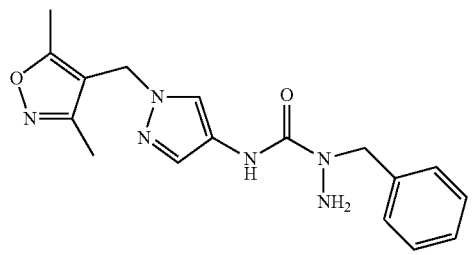 [SMILES: Cc1noc(C)c1Cn1cc(NC(=O)N(N)Cc2ccccc2)cn1]

1-((3,5-dimethylisoxazole-4-yl)methyl-1H-pyrazole-4-carbonyl azide (2.79 g, 11.33 mmol) in toluene (70 mL) was heated at reflux for 4 hours to afford 4-((4-isocyanato-1H-pyrazol-1-yl)methyl)-3,5-dimethylisoxazole in situ. Benzylhydrazine dihydrochloride (2.44 g, 12.45 mmol) and triethylamine (2.29 g, 22.64 mmol) were added to the mixture. The mixture was heated at 100° C. for an additional 4 hours. The reaction was cooled to room temperature, diluted with ethyl acetate (150 mL) and filtered through celite. The mother liquor was then washed with brine (150 mL) and the organic layer were dried over magnesium sulfate, filtered and concentrated. The residue was purified by silica column chromotography (100% to 90% dichloromethane in methanol: 30 minute gradient) to afford 1-benzyl-N-(1-((3,5-dimethylisoxazol-4-yl)methyl)-1H-pyrazol-4-yl)hydrazinecarboxamide (2.00 g, 52%) as an oil. MS M+H calculated 341.16; found 341.2.

Example 10-92

1-benzyl-4-(1-((3,5-dimethylisoxazol-4-yl)methyl)-1H-pyrazol-4-yl)-2-(2-methoxyethyl)-1,2,4-triazolidine-3,5-dione

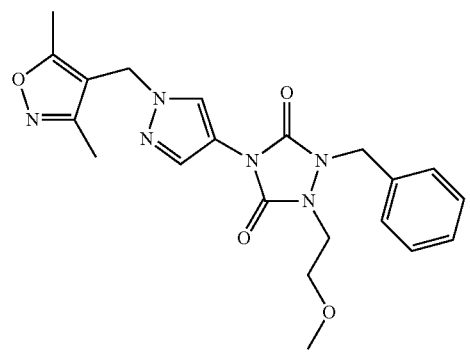 [SMILES: COCCn1c(=O)n(-c2cnn(Cc3c(C)noc3C)c2)c(=O)n1Cc1ccccc1]

Prepared as in example 10-91 from 1-benzyl-4-(1-((3,5-dimethylisoxazol-4-yl)methyl)-1H-pyrazol-4-yl)-1,2,4-triazolidine-3,5-dione (example 10-91a) and 2-bromoethyl methyl ether. Yield: 20%. MS M+H calculated 425.19; found 425.2. The title compound was shown to inhibit hT2R08 bitter receptor and had an $IC_{50}$ of 0.06 µM.

Example 10-93

1-benzyl-4-(1-((3,5-dimethylisoxazol-4-yl)methyl)-1H-pyrazol-4-yl)-2-propyl-1,2,4-triazolidine-3,5-dione

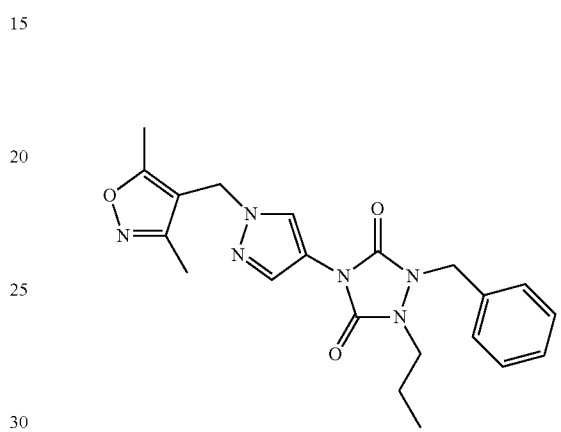

Prepared as in example 10-91 from 1-benzyl-4-(1-((3,5-dimethylisoxazol-4-yl)methyl)-1H-pyrazol-4-yl)-1,2,4-triazolidine-3,5-dione (example 10-91a) and 1-bromopropane. Yield: 38%. MS M+H calculated 409.19; found 409.2. The title compound was shown to inhibit hT2R08 bitter receptor and had an $IC_{50}$ of 0.06 µM.

Example 10-94

3-(1-((3,5-dimethylisoxazol-4-yl)methyl)-1H-pyrazol-4-yl)-1-(3-phenylpropyl)imidazolidine-2,4-dione

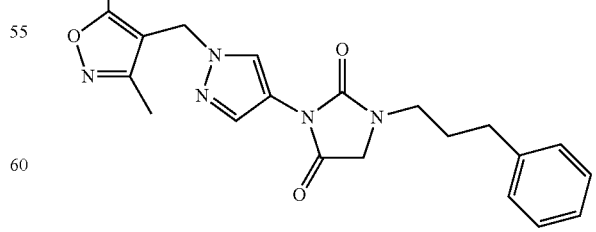

Prepared as in example 10-52 from 3-(1-((3,5-dimethylisoxazol-4-yl)methyl)-1H-pyrazol-4-yl)imidazolidine-2,4-dione (example 10-1) and (3-bromopropyl)benzene. Yield:

36%. MS M+H calculated 394.2; found 394.2. The title compound was shown to inhibit hT2R08 bitter receptor and had an IC$_{50}$ of 0.26 µM.

Example 10-95

1-benzyl-2-butyl-4-(1-((3,5-dimethylisoxazol-4-yl)methyl)-1H-pyrazol-4-yl-1,2,4-triazolidine-3,5-dione

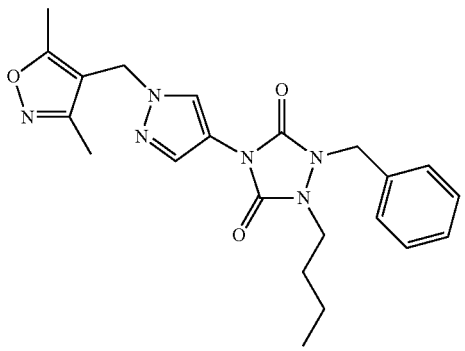

Prepared as in example 10-91 from 1-benzyl-4-(1-((3,5-dimethylisoxazol-4-yl)methyl)-1H-pyrazol-4-yl)-1,2,4-triazolidine-3,5-dione (example 10-91a) and 1-bromobutane. Yield: 22%. MS M+H calculated 423.21; found 423.15. The title compound was shown to inhibit hT2R08 bitter receptor and had an IC$_{50}$ of 0.41 µM.

Example 10-96 tert-butyl 3-((3-(1-((3,5-dimethylisoxazol-4-yl)methyl)-1H-pyrazol-4-yl)-2,4-dioxoimidazolidin-1-yl)methyl)benzylcarbamate

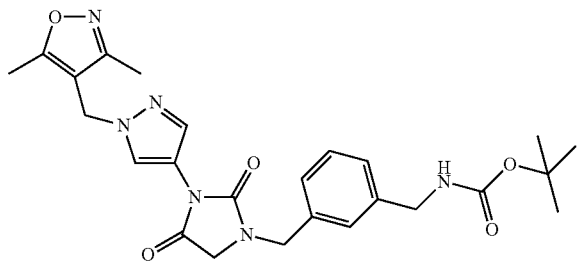 [SMILES: Cc1noc(C)c1Cn1cc(N2C(=O)CN(Cc3cccc(CNC(=O)OC(C)(C)C)c3)C2=O)cn1]

3-(1-((3,5-dimethylisoxazol-4-yl)methyl)-1H-pyrazol-4-yl)imidazolidine-2,4-dione (example 10-1) (070 mg, 0.254 mmol), tert-butyl 3-(hydroxymethyl)benzylcarbamate (0.254 mmol, 60 mg), diethyl azodicarboxylate (0.50 mmol, 86 mg), and P-tBu$_3$ (125 mL, 0.50 mmol) were stirred in THF (1 mL) for 4 hours. The reaction was diluted with ethyl acetate (1.5 mL) and washed with saturated sodium bicarbonate solution (2×, 1.5 mL). The organic phase was collected and the mixture was concentrated under a stream of nitrogen. The crude product was purified by column chromatography on silica gel using ethyl acetate as the eluent. The pure fractions were combined and the solvents were removed on the rotovap to afford tert-butyl 3-((3-(1-((3,5-dimethylisoxazol-4-yl)methyl)-1H-pyrazol-4-yl)-2,4-dioxoimidazolidin-1-yl)methyl)benzylcarbamate as a white solid (112 mg, 90%). $^1$H NMR (CDCl$_3$, 400 MHz): δ 1.44 (s, 9H), 2.19 (s, 3H), 2.42 (s, 3H), 3.48 (bs, 1H), 3.84 (s, 2H), 4.31-4.30 (d, J=6 Hz, 1H), 4.60 (s, 2H), 4.87 (bs, 1H), 5.06 (s, 2H), 7.36-7.16 (m, 4H), 7.92 (s, 1H), 8.08 (s, 1H). The title compound was shown to inhibit hT2R08 bitter receptor and had an IC$_{50}$ of 0.90 µM.

Example 10-97

3-(1-((3,5-dimethylisoxazol-4-yl)methyl)-1H-pyrazol-4-yl)-5-(hydroxymethyl)imidazolidine-2,4-dione

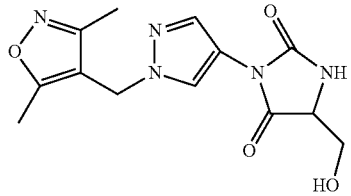 [SMILES: Cc1noc(C)c1Cn1cc(N2C(=O)NC(CO)C2=O)cn1]

4-((4-isocyanato-1H-pyrazol-1-yl)methyl)-3,5-dimethylisoxazole (example 10-1) (784 mg, 3.6 mmol), serine methyl ester hydrochloride (672 mg, 4.32 mmol) and triethylamine (1 mL, 7.2 mmol) were refluxed in toluene (16 mL) for 8 hours. The reaction was allowed to cool to room temperature and then the solution was concentrated on the rotovap. The product was purified by reverse phase HPLC (5 to 95% acetonitrile in H$_2$O: 16 minute gradient) to afford 3-(1-((3,5-dimethylisoxazol-4-yl)methyl)-1H-pyrazol-4-yl)-5-(hydroxymethyl)imidazolidine-2,4-dione as a white solid (60 mg, 25%). $^1$H NMR (CDCl$_3$, 400 MHz): δ (s, 3H), 2.40 (s, 3H), 3.13-3.07 (m, 1H), 3.94-3.93 (d, J=4 Hz, 2H), 4.21-4.19 (t, J=4 Hz, 1H), 5.03 (s, 2H), 6.68 (bs, 1H), 7.87 (s, 1H), 7.99 (s, 1H). The title compound was shown to inhibit hT2R08 bitter receptor and had an IC$_{50}$ of 3 µM.

| Compound No. | Compound | hT2R8 IC$_{50}$ (μM) |
|---|---|---|
| 10-66 | 4-(1-((3,5-dimethylisoxazol-4-yl)methyl)-1H-pyrazol-4-yl)-1-(4-fluorophenethyl)-2-methyl-1,2,4-triazolidine-3,5-dione | 0.012 |
| 10-15 | 3-(1-((3,5-dimethylisoxazol-4-yl)methyl)-1H-pyrazol-4-yl)-1-(2-(methylthio)benzyl)imidazolidine-2,4-dione | 0.016 |
| 10-42 | 5-benzyl-3-(1-((3,5-dimethylisoxazol-4-yl)methyl)-1H-pyrazol-4-yl)-1-methylimidazolidine-2,4-dione | 0.017 |
| 10-26 | 3-(1-((3,5-dimethylisoxazol-4-yl)methyl)-1H-pyrazol-4-yl)-1-(3-methylbenzyl)imidazolidine-2,4-dione | 0.019 |
| 10-43 | 1-benzyl-3-(1-((3,5-dimethylisoxazol-4-yl)methyl)-1H-pyrazol-4-yl)-5-methylimidazolidine-2,4-dione | 0.020 |

-continued

| Compound No. | Compound | hT2R8 IC$_{50}$ (μM) |
|---|---|---|
| 10-89 | 1-benzyl-4-(1-((3,5-dimethylisoxazol-4-yl)methyl)-1H-pyrazol-4-yl)-2-(methoxymethyl)-1,2,4-triazolidine-3,5-dione | 0.024 |
| 10-10 | 3-(1-((3,5-dimethylisoxazol-4-yl)methyl)-1H-pyrazol-4-yl)-1-(3-hydroxybenzyl)imidazolidine-2,4-dione | 0.026 |
| 10-84 | 3-(1-((3,5-dimethylisoxazol-4-yl)methyl)-1H-pyrazol-4-yl)-1-(4-fluorophenethyl)imidazolidine-2,4-dione | 0.027 |
| 10-91 | 1-benzyl-4-(1-((3,5-dimethylisoxazol-4-yl)methyl)-1H-pyrazol-4-yl)-2-ethyl-1,2,4-triazolidine-3,5-dione | 0.041 |
| 10-12 | 3-(1-((3,5-dimethylisoxazol-4-yl)methyl)-1H-pyrazol-4-yl)-1-(4-hydroxybenzyl)imidazolidine-2,4-dione | 0.043 |

-continued

| Compound No. | Compound | hT2R8 IC$_{50}$ (μM) |
|---|---|---|
| 10-79 | 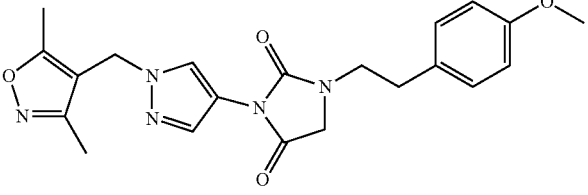<br>3-(1-((3,5-dimethylisoxazol-4-yl)methyl)-1H-pyrazol-4-yl)-1-(4-methoxyphenethyl)imidazolidine-2,4-dione | 0.044 |
| 10-31 | 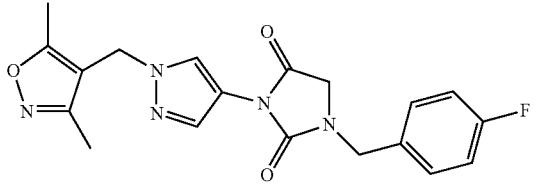 [SMILES: Cc1noc(C)c1Cn1cc(N2C(=O)CN(Cc3ccc(F)cc3)C2=O)cn1]<br>3-(1-((3,5-dimethylisoxazol-4-yl)methyl)-1H-pyrazol-4-yl)-1-(4-fluorobenzyl)imidazolidine-2,4-dione | 0.045 |
| 10-32 | 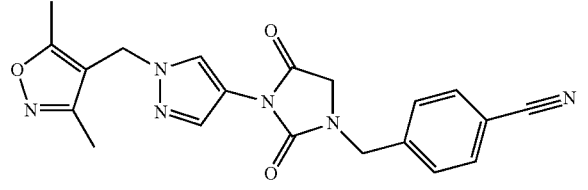 [SMILES: Cc1noc(C)c1Cn1cc(N2C(=O)CN(Cc3ccc(C#N)cc3)C2=O)cn1]<br>4-((3-(1-((3,5-dimethylisoxazol-4-yl)methyl)-1H-pyrazol-4-yl)-2,4-dioxoimidazolidin-1-yl)methyl)benzonitrile | 0.048 |
| 10-35 | 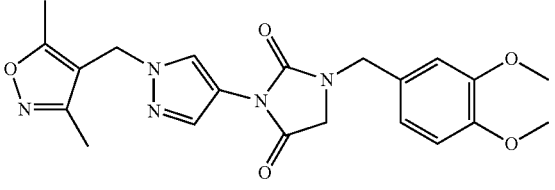 [SMILES: COc1ccc(CN2CC(=O)N(c3cnn(Cc4c(C)noc4C)c3)C2=O)cc1OC]<br>1-(3,4-dimethoxybenzyl)-3-(1-((3,5-dimethylisoxazol-4-yl)methyl)-1H-pyrazol-4-yl)imidazolidine-2,4-dione | 0.051 |
| 10-36 | 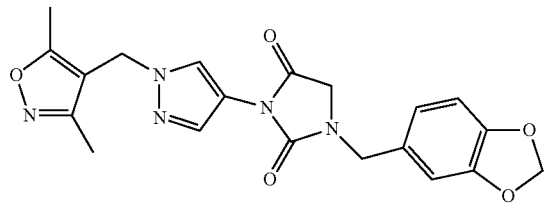 [SMILES: Cc1noc(C)c1Cn1cc(N2C(=O)CN(Cc3ccc4c(c3)OCO4)C2=O)cn1]<br>1-(benzo[d][1,3]dioxol-5-ylmethyl)-3-(1-((3,5-dimethylisoxazol-4-yl)methyl)-1H-pyrazol-4-yl)imidazolidine-2,4-dione | 0.053 |

-continued

| Compound No. | Compound | hT2R8 IC$_{50}$ (μM) |
|---|---|---|
| 10-92 | 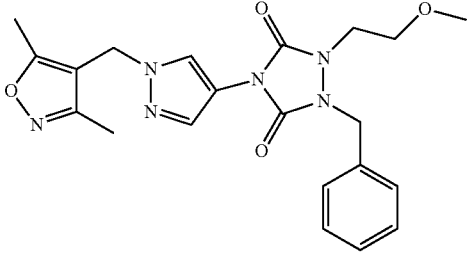 [SMILES: COCCn1c(=O)n(-c2cnn(Cc3c(C)noc3C)c2)c(=O)n1Cc1ccccc1]<br>1-benzyl-4-(1-((3,5-dimethylisoxazol-4-yl)methyl)-1H-pyrazol-4-yl)-2-(2-methoxyethyl)-1,2,4-triazolidine-3,5-dione | 0.057 |
| 10-27 | 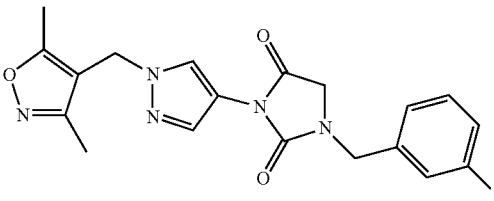<br>3-(1-((3,5-dimethylisoxazol-4-yl)methyl)-1H-pyrazol-4-yl)-1-(3-fluorobenzyl)imidazolidine-2,4-dione | 0.058 |
| 10-18 | 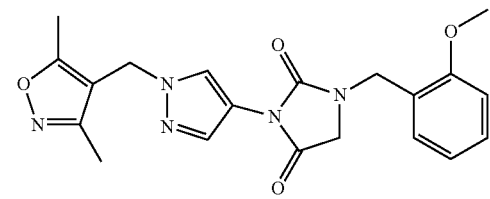 [SMILES: COc1ccccc1CN1CC(=O)N(c2cnn(Cc3c(C)noc3C)c2)C1=O]<br>3-(1-((3,5-dimethylisoxazol-4-yl)methyl)-1H-pyrazol-4-yl)-1-(2-methoxybenzyl)imidazolidine-2,4-dione | 0.060 |
| 10-93 | 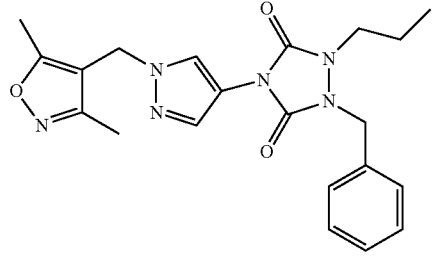 [SMILES: CCCn1c(=O)n(-c2cnn(Cc3c(C)noc3C)c2)c(=O)n1Cc1ccccc1]<br>1-benzyl-4-(1-((3,5-dimethylisoxazol-4-yl)methyl)-1H-pyrazol-4-yl)-2-propyl-1,2,4-triazolidine-3,5-dione | 0.062 |
| 10-5 | 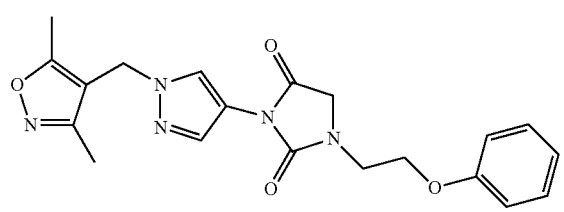<br>3-(1-((3,5-dimethylisoxazol-4-yl)methyl)-1H-pyrazol-4-yl)-1-(2-phenoxyethyl)imidazolidine-2,4-dione | 0.063 |

-continued

| Compound No. | Compound | hT2R8 IC$_{50}$ (μM) |
|---|---|---|
| 10-77 | 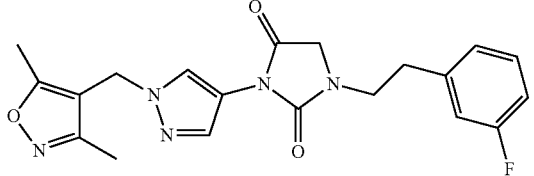 [SMILES: Cc1noc(C)c1Cn1cc(N2C(=O)CN(CCc3cccc(F)c3)C2=O)cn1] 3-(1-((3,5-dimethylisoxazol-4-yl)methyl)-1H-pyrazol-4-yl)-1-(3-fluorophenethyl)imidazolidine-2,4-dione | 0.064 |
| 10-30 | 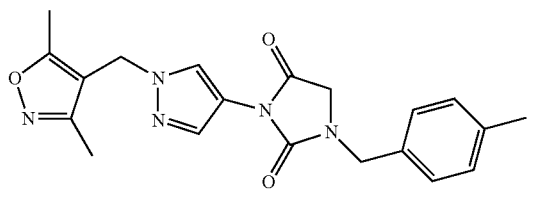 [SMILES: Cc1ccc(CN2CC(=O)N(c3cnn(Cc4c(C)noc4C)c3)C2=O)cc1] 3-(1-((3,5-dimethylisoxazol-4-yl)methyl)-1H-pyrazol-4-yl)-1-(4-methylbenzyl)imidazolidine-2,4-dione | 0.065 |
| 10-94 | 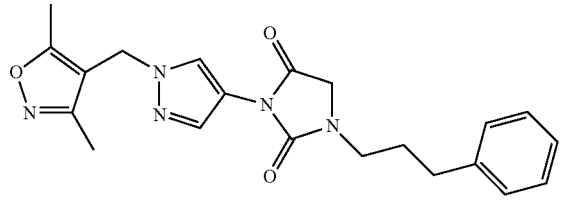 3-(1-((3,5-dimethylisoxazol-4-yl)methyl)-1H-pyrazol-4-yl)-1-(3-phenylpropyl)imidazolidine-2,4-dione | 0.068 |
| 10-11 | 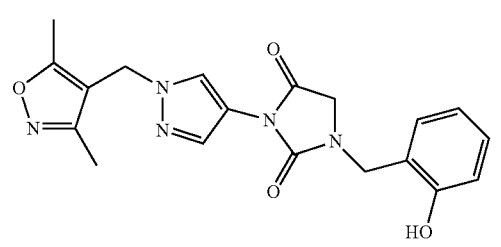 [SMILES: Cc1noc(C)c1Cn1cc(N2C(=O)CN(Cc3ccccc3O)C2=O)cn1] 3-(1-((3,5-dimethylisoxazol-4-yl)methyl)-1H-pyrazol-4-yl)-1-(2-hydroxybenzyl)imidazolidine-2,4-dione | 0.069 |
| 10-6 | 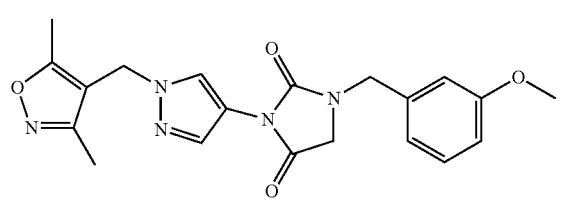 [SMILES: COc1cccc(CN2CC(=O)N(c3cnn(Cc4c(C)noc4C)c3)C2=O)c1] 3-(1-((3,5-dimethylisoxazol-4-yl)methyl)-1H-pyrazol-4-yl)-1-(3-methoxybenzyl)imidazolidine-2,4-dione | 0.073 |

-continued

| Compound No. | Compound | hT2R8 IC$_{50}$ (μM) |
|---|---|---|
| 10-23 | 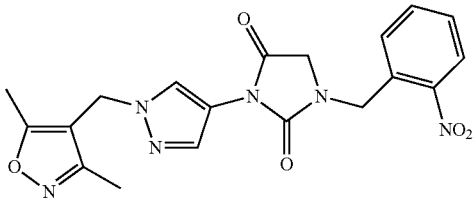 [SMILES: Cc1noc(C)c1Cn1cc(N2C(=O)CN(Cc3ccccc3[N+](=O)[O-])C2=O)cn1]<br>3-(1-((3,5-dimethylisoxazol-4-yl)methyl)-1H-pyrazol-4-yl)-1-(2-nitrobenzyl)imidazolidine-2,4-dione | 0.081 |
| 10-76 | 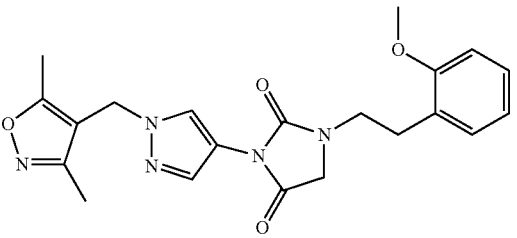 [SMILES: COc1ccccc1CCN1CC(=O)N(c2cnn(Cc3c(C)noc3C)c2)C1=O]<br>3-(1-((3,5-dimethylisoxazol-4-yl)methyl)-1H-pyrazol-4-yl)-1-(2-methoxyphenethyl)imidazolidine-2,4-dione | 0.097 |
| 10-13 | 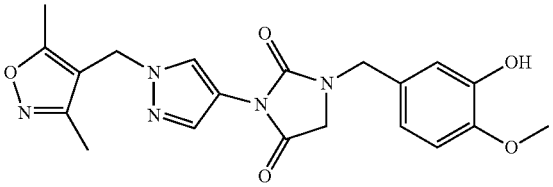 [SMILES: COc1ccc(CN2CC(=O)N(c3cnn(Cc4c(C)noc4C)c3)C2=O)cc1O]<br>3-(1-((3,5-dimethylisoxazol-4-yl)methyl)-1H-pyrazol-4-yl)-1-(3-hydroxy-4-methoxybenzyl)imidazolidine-2,4-dione | 0.087 |
| 10-21 | 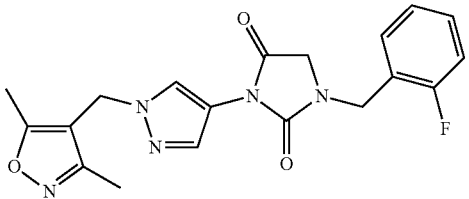<br>3-(1-((3,5-dimethylisoxazol-4-yl)methyl)-1H-pyrazol-4-yl)-1-(2-fluorobenzyl)imidazolidine-2,4-dione | 0.090 |
| 10-7 | 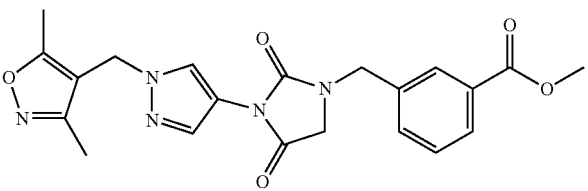 [SMILES: COC(=O)c1cccc(CN2CC(=O)N(c3cnn(Cc4c(C)noc4C)c3)C2=O)c1]<br>methyl 3-((3-(1-((3,5-dimethylisoxazol-4-yl)methyl)-1H-pyrazol-4-yl)-2,4-dioxoimidazolidin-1-yl)methyl)benzoate | 0.102 |

-continued

| Compound No. | Compound | hT2R8 IC$_{50}$ (μM) |
|---|---|---|
| 10-4 | (R)-5-benzyl-3-(1-((3,5-dimethylisoxazol-4-yl)methyl)-1H-pyrazol-4-yl)imidazolidine-2,4-dione | 0.112 |
| 10-3 | (S)-5-benzyl-3-(1-((3,5-dimethylisoxazol-4-yl)methyl)-1H-pyrazol-4-yl)imidazolidine-2,4-dione | 0.113 |
| 10-2 | 5-benzyl-3-(1-((3,5-dimethylisoxazol-4-yl)methyl)-1H-pyrazol-4-yl)imidazolidine-2,4-dione | 0.117 |
| 10-16 | 3-(1-((3,5-dimethylisoxazol-4-yl)methyl)-1H-pyrazol-4-yl)-1-(2-(2-methoxyethoxy)benzyl)imidazolidine-2,4-dione | 0.131 |
| 10-56 | 3-(1-((3,5-dimethylisoxazol-4-yl)methyl)-1H-pyrazol-4-yl)-5-(3-methoxybenzyl)imidazolidine-2,4-dione | 0.131 |

-continued

| Compound No. | Compound | hT2R8 IC$_{50}$ (μM) |
|---|---|---|
| 10-20 | 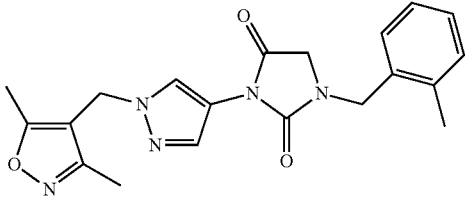<br>3-(1-((3,5-dimethylisoxazol-4-yl)methyl)-1H-pyrazol-4-yl)-1-(2-methylbenzyl)imidazolidine-2,4-dione | 0.133 |
| 10-87 | 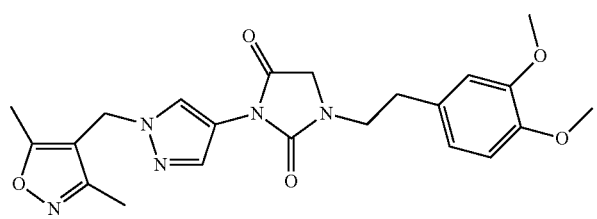<br>1-(3,4-dimethoxyphenethyl)-3-(1-((3,5-dimethylisoxazol-4-yl)methyl)-1H-pyrazol-4-yl)imidazolidine-2,4-dione | 0.137 |
| 10-78 | 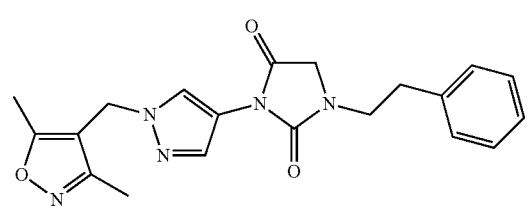 [SMILES: Cc1noc(C)c1Cn1cc(N2C(=O)CN(CCc3ccccc3)C2=O)cn1]<br>3-(1-((3,5-dimethylisoxazol-4-yl)methyl)-1H-pyrazol-4-yl)-1-phenethylimidazolidine-2,4-dione | 0.139 |
| 10-9 | 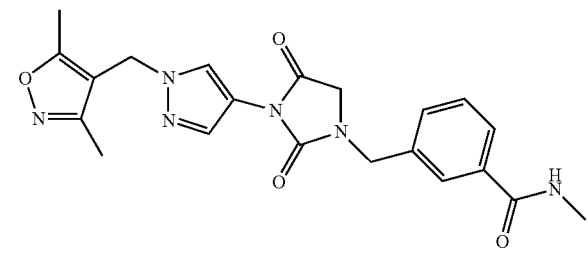 [SMILES: CNC(=O)c1cccc(CN2CC(=O)N(c3cnn(Cc4c(C)noc4C)c3)C2=O)c1]<br>3-((3-(1-((3,5-dimethylisoxazol-4-yl)methyl)-1H-pyrazol-4-yl)-2,4-dioxoimidazolidin-1-yl)methyl)-N-methylbenzamide | 0.141 |
| 10-85 | 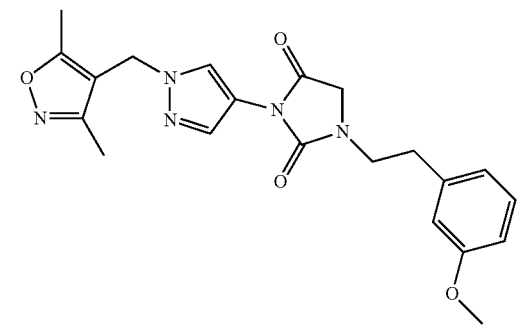 [SMILES: COc1cccc(CCN2CC(=O)N(c3cnn(Cc4c(C)noc4C)c3)C2=O)c1] | 0.158 |

-continued

| Compound No. | Compound | hT2R8 IC$_{50}$ (μM) |
|---|---|---|
|  | 3-(1-((3,5-dimethylisoxazol-4-yl)methyl)-1H-pyrazol-4-yl)-1-(3-methoxyphenethyl)imidazolidine-2,4-dione |  |
| 10-34 |  | 0.163 |
|  | 1-(2-aminobenzyl)-3-(1-((3,5-dimethylisoxazol-4-yl)methyl)-1H-pyrazol-4-yl)imidazolidine-2,4-dione |  |
| 10-24 |  | 0.201 |
|  | 3-((3-(1-((3,5-dimethylisoxazol-4-yl)methyl)-1H-pyrazol-4-yl)-2,4-dioxoimidazolidin-1-yl)methyl)benzaldehyde |  |
| 10-90 |  | 0.215 |
|  | 1-((1,3-dimethyl-1H-pyrazol-5-yl)methyl)-3-(1-((3,5-dimethylisoxazol-4-yl)methyl)-1H-pyrazol-4-yl)imidazolidine-2,4-dione |  |
| 10-22 |  | 0.221 |
|  | 3-(1-((3,5-dimethylisoxazol-4-yl)methyl)-1H-pyrazol-4-yl)-1-(2-(trifluoromethyl)benzyl)imidazolidine-2,4-dione |  |
| 10-75 |  | 0.229 |

-continued

| Compound No. | Compound | hT2R8 IC$_{50}$ (μM) |
|---|---|---|
| | 3-(1-((3,5-dimethylisoxazol-4-yl)methyl)-1H-pyrazol-4-yl)-1-((6-methoxypyridin-2-yl)methyl)imidazolidine-2,4-dione | |
| 10-53 | 1-benzyl-3-(1-((3,5-dimethylisoxazol-4-yl)methyl)-1H-pyrazol-4-yl)imidazolidine-2,4-dione | 0.257 |
| 10-81 | 1-(2-chlorophenethyl)-3-(1-((3,5-dimethylisoxazol-4-yl)methyl)-1H-pyrazol-4-yl)imidazolidine-2,4-dione | 0.248 |
| 10-74 | 1-(cyclohexylmethyl)-3-(1-((3,5-dimethylisoxazol-4-yl)methyl)-1H-pyrazol-4-yl)imidazolidine-2,4-dione | 0.276 |
| 10-58 | 5-(cyclopentylmethyl)-3-(1-((3,5-dimethylisoxazol-4-yl)methyl)-1H-pyrazol-4-yl)imidazolidine-2,4-dione | 0.316 |
| 10-28 | 1-((1,5-dimethyl-1H-pyrazol-3-yl)methyl)-3-(1-((3,5-dimethylisoxazol-4-yl)methyl)-1H-pyrazol-4-yl)imidazolidine-2,4-dione | 0.322 |

-continued

| Compound No. | Compound | hT2R8 IC$_{50}$ (μM) |
|---|---|---|
| 10-33 | 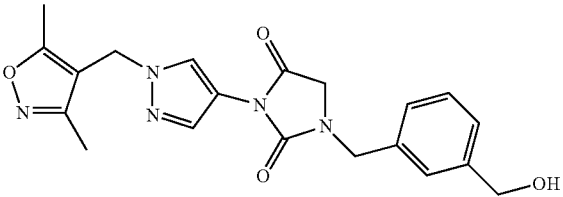 [SMILES: Cc1noc(C)c1Cn1cc(N2C(=O)CN(Cc3cccc(CO)c3)C2=O)cn1]<br>3-(1-((3,5-dimethylisoxazol-4-yl)methyl)-1H-pyrazol-4-yl)-1-(3-(hydroxymethyl)benzyl)imidazolidine-2,4-dione | 0.322 |
| 10-59 | 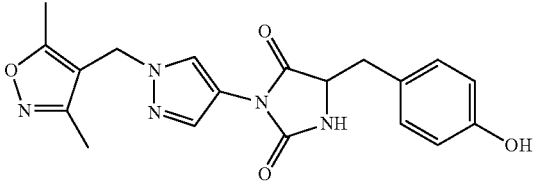 [SMILES: Cc1noc(C)c1Cn1cc(N2C(=O)NC(Cc3ccc(O)cc3)C2=O)cn1]<br>3-(1-((3,5-dimethylisoxazol-4-yl)methyl)-1H-pyrazol-4-yl)-5-(4-hydroxybenzyl)imidazolidine-2,4-dione | 0.327 |
| 10-38 | 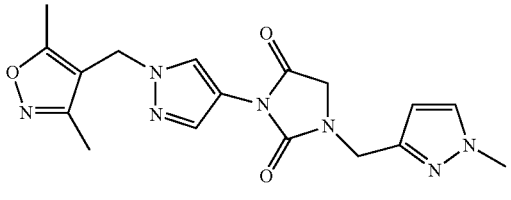 [SMILES: Cc1noc(C)c1Cn1cc(N2C(=O)CN(Cc3ccn(C)n3)C2=O)cn1]<br>3-(1-((3,5-dimethylisoxazol-4-yl)methyl)-1H-pyrazol-4-yl)-1-((1-methyl-1H-pyrazol-3-yl)methyl)imidazolidine-2,4-dione | 0.363 |
| 10-46 | 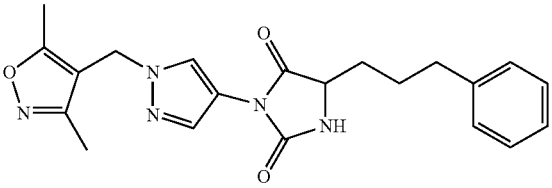 [SMILES: Cc1noc(C)c1Cn1cc(N2C(=O)NC(CCCc3ccccc3)C2=O)cn1]<br>3-(1-((3,5-dimethylisoxazol-4-yl)methyl)-1H-pyrazol-4-yl)-5-(3-phenylpropyl)imidazolidine-2,4-dione | 0.484 |
| 10-95 | 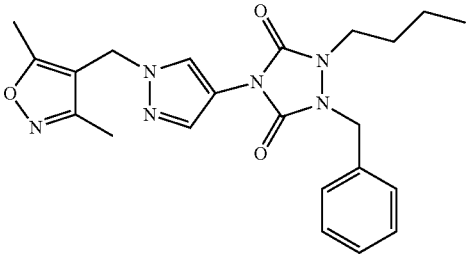 [SMILES: CCCCn1c(=O)n(-c2cnn(Cc3c(C)noc3C)c2)c(=O)n1Cc1ccccc1]<br>1-benzyl-2-butyl-4-(1-((3,5-dimethylisoxazol-4-yl)methyl)-1H-pyrazol-4-yl)-1,2,4-triazolidine-3,5-dione | 0.409 |

| Compound No. | Compound | hT2R8 IC$_{50}$ (μM) |
|---|---|---|
| 10-17 | 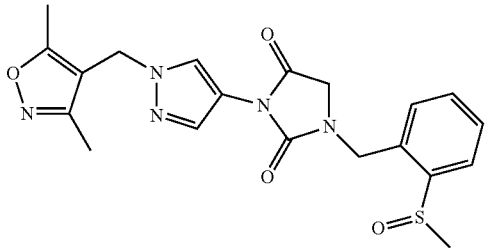 [SMILES: Cc1noc(C)c1Cn1cc(N2C(=O)CN(Cc3ccccc3S(C)=O)C2=O)cn1]<br>3-(1-((3,5-dimethylisoxazol-4-yl)methyl)-1H-pyrazol-4-yl)-1-(2-(methylsulfinyl)benzyl)imidazolidine-2,4-dione | 0.412 |
| 10-86 | 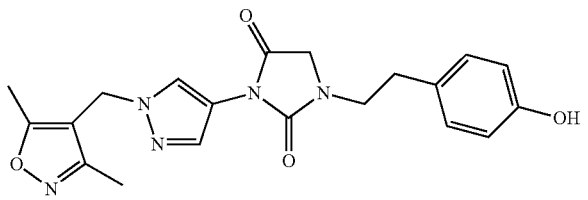 [SMILES: Cc1noc(C)c1Cn1cc(N2C(=O)CN(CCc3ccc(O)cc3)C2=O)cn1]<br>3-(1-((3,5-dimethylisoxazol-4-yl)methyl)-1H-pyrazol-4-yl)-1-(4-hydroxyphenethyl)imidazolidine-2,4-dione | 0.412 |
| 10-83 | 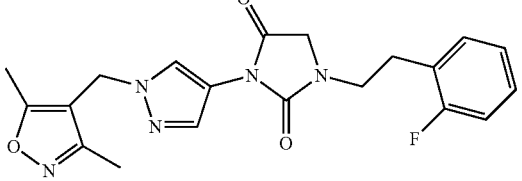<br>3-(1-((3,5-dimethylisoxazol-4-yl)methyl)-1H-pyrazol-4-yl)-1-(2-fluorophenethyl)imidazolidine-2,4-dione | 0.442 |
| 10-55 | 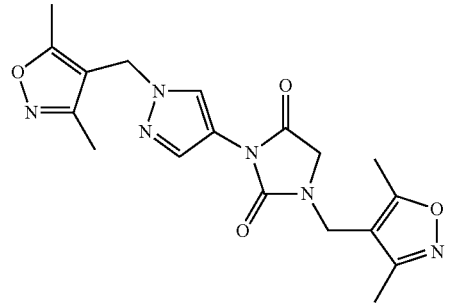 [SMILES: Cc1noc(C)c1CN1CC(=O)N(c2cnn(Cc3c(C)noc3C)c2)C1=O]<br>1-((3,5-dimethylisoxazol-4-yl)methyl)-3-(1-((3,5-dimethylisoxazol-4-yl)methyl)-1H-pyrazol-4-yl)imidazolidine-2,4-dione | 0.479 |
| 10-60 | 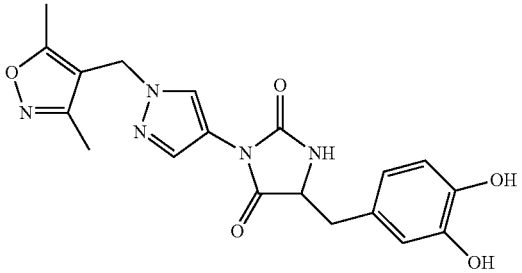 [SMILES: Cc1noc(C)c1Cn1cc(N2C(=O)NC(Cc3ccc(O)c(O)c3)C2=O)cn1] | 0.513 |

-continued

| Compound No. | Compound | hT2R8 IC$_{50}$ (μM) |
|---|---|---|
| | 5-(3,4-dihydroxybenzyl)-3-(1-((3,5-dimethylisoxazol-4-yl)methyl)-1H-pyrazol-4-yl)imidazolidine-2,4-dione | |
| 10-19 | 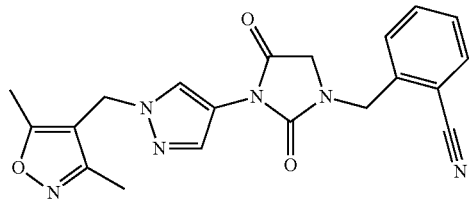 [SMILES: Cc1noc(C)c1Cn1cc(N2C(=O)CN(Cc3ccccc3C#N)C2=O)cn1] 2-((3-(1-((3,5-dimethylisoxazol-4-yl)methyl)-1H-pyrazol-4-yl)-2,4-dioxoimidazolidin-1-yl)methyl)benzonitrile | 0.550 |
| 10-54 | 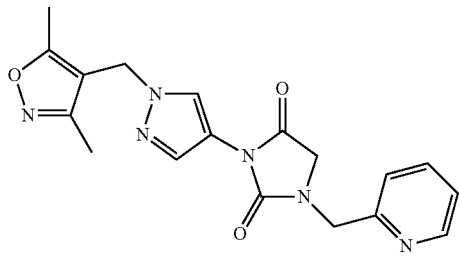 [SMILES: Cc1noc(C)c1Cn1cc(N2C(=O)CN(Cc3ccccn3)C2=O)cn1] 3-(1-((3,5-dimethylisoxazol-4-yl)methyl)-1H-pyrazol-4-yl)-1-(pyridin-2-ylmethyl)imidazolidine-2,4-dione | 0.609 |
| 10-71 | 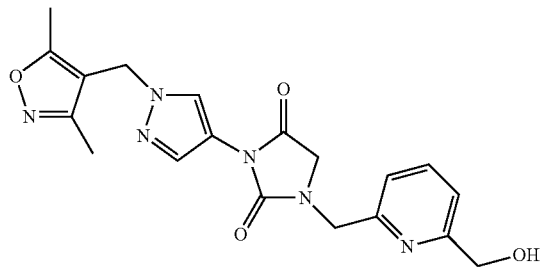 [SMILES: Cc1noc(C)c1Cn1cc(N2C(=O)CN(Cc3cccc(CO)n3)C2=O)cn1] 3-(1-((3,5-dimethylisoxazol-4-yl)methyl)-1H-pyrazol-4-yl)-1-((6-(hydroxymethyl)pyridin-2-yl)methyl)imidazolidine-2,4-dione | 0.721 |
| 10-48 | 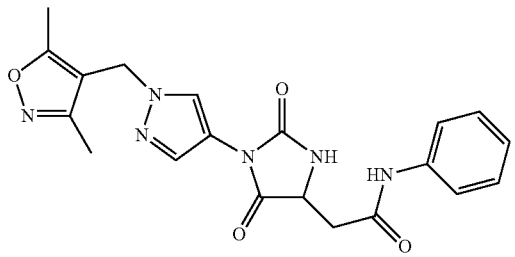 [SMILES: Cc1noc(C)c1Cn1cc(N2C(=O)NC(CC(=O)Nc3ccccc3)C2=O)cn1] 2-(1-(1-((3,5-dimethylisoxazol-4-yl)methyl)-1H-pyrazol-4-yl)-2,5-dioxoimidazolidin-4-yl)-N-phenylacetamide | 0.747 |

-continued

| Compound No. | Compound | hT2R8 IC$_{50}$ (μM) |
|---|---|---|
| 10-47 | 5-(benzyloxymethyl)-3-(1-((3,5-dimethylisoxazol-4-yl)methyl)-1H-pyrazol-4-yl)imidazolidine-2,4-dione | 0.766 |
| 10-96 | tert-butyl 3-((3-(1-((3,5-dimethylisoxazol-4-yl)methyl)-1H-pyrazol-4-yl)-2,4-dioxo-imidazolidin-1-yl)methyl)benzylcarbamate | 0.891 |
| 10-61 | 3-(1-((3,5-dimethylisoxazol-4-yl)methyl)-1H-pyrazol-4-yl)-5-isobutylimidazolidine-2,4-dione | 0.912 |
| 10-80 | 3-(1-((3,5-dimethylisoxazol-4-yl)methyl)-1H-pyrazol-4-yl)-1-(2-(naphthalen-1-yl)ethyl)imidazolidine-2,4-dione | 0.927 |
| 10-57 | 5-(cyclohexylmethyl)-3-(1-((3,5-dimethylisoxazol-4-yl)methyl)-1H-pyrazol-4-yl)imidazolidine-2,4-dione | 0.962 |

-continued

| Compound No. | Compound | hT2R8 IC$_{50}$ (μM) |
|---|---|---|
| 10-51 | 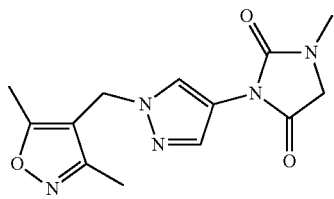<br>3-(1-((3,5-dimethylisoxazol-4-yl)methyl)-1H-pyrazol-4-yl)-1-methylimidazolidine-2,4-dione | 0.966 |
| 10-82 | 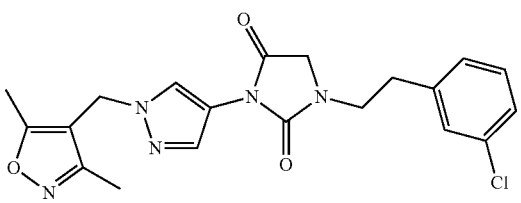 [SMILES: Cc1noc(C)c1Cn1cc(N2C(=O)CN(CCc3cccc(Cl)c3)C2=O)cn1]<br>1-(3-chlorophenethyl)-3-(1-((3,5-dimethylisoxazol-4-yl)methyl)-1H-pyrazol-4-yl)imidazolidine-2,4-dione | 0.982 |
| 10-45 | 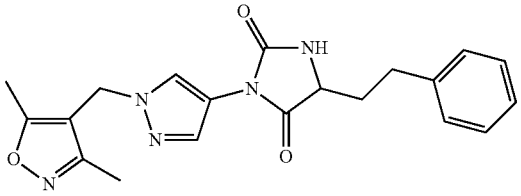 [SMILES: Cc1noc(C)c1Cn1cc(N2C(=O)NC(CCc3ccccc3)C2=O)cn1]<br>3-(1-((3,5-dimethylisoxazol-4-yl)methyl)-1H-pyrazol-4-yl)-5-phenethylimidazolidine-2,4-dione | 0.793 |
| 10-72 | 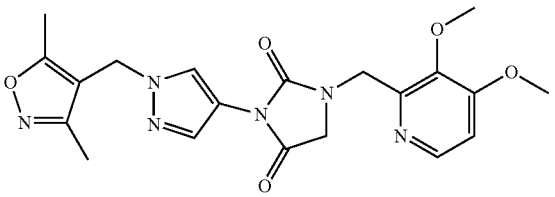 [SMILES: COc1ccnc(CN2CC(=O)N(c3cnn(Cc4c(C)noc4C)c3)C2=O)c1OC]<br>1-((3,4-dimethoxypyridin-2-yl)methyl)-3-(1-((3,5-dimethylisoxazol-4-yl)methyl)-1H-pyrazol-4-yl)imidazolidine-2,4-dione | 0.999 |
| 10-25 | 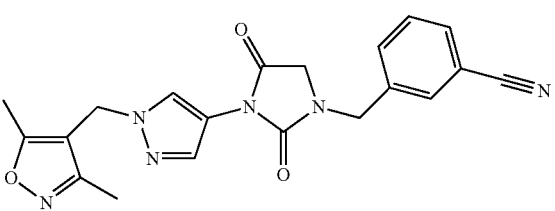 [SMILES: Cc1noc(C)c1Cn1cc(N2C(=O)CN(Cc3cccc(C#N)c3)C2=O)cn1]<br>3-((3-(1-((3,5-dimethylisoxazol-4-yl)methyl)-1H-pyrazol-4-yl)-2,4-dioxoimidazolidin-1-yl)methyl)benzonitrile | 1.003 |

-continued

| Compound No. | Compound | hT2R8 IC$_{50}$ (μM) |
|---|---|---|
| 10-37 | 1-(3-((dimethylamino)methyl)benzyl)-3-(1-((3,5-dimethylisoxazol-4-yl)methyl)-1H-pyrazol-4-yl)imidazolidine-2,4-dione | 1.220 |
| 10-41 | 3-(1-((3,5-dimethylisoxazol-4-yl)methyl)-1H-pyrazol-4-yl)-5-methylimidazolidine-2,4-dione | 1.285 |
| 10-49 | N-benzyl-2-(1-(1-((3,5-dimethylisoxazol-4-yl)methyl)-1H-pyrazol-4-yl)-2,5-dioxoimidazolidin-4-yl)acetamide | 1.329 |
| 10-73 | 3-(1-((3,5-dimethylisoxazol-4-yl)methyl)-1H-pyrazol-4-yl)-1-((tetrahydrofuran-2-yl)methyl)imidazolidine-2,4-dione | 1.362 |
| 10-62 | | 1.440 |

-continued

| Compound No. | Compound | hT2R8 IC$_{50}$ (μM) |
|---|---|---|
| 10-1 | 3-(1-((3,5-dimethylisoxazol-4-yl)methyl)-1H-pyrazol-4-yl)-5-isopropylimidazolidine-2,4-dione | 1.696 |
| 10-50 | 3-(1-((3,5-dimethylisoxazol-4-yl)methyl)-1H-pyrazol-4-yl)imidazolidine-2,4-dione | 1.773 |
| 10-8 | 2-(1-(1-((3,5-dimethylisoxazol-4-yl)methyl)-1H-pyrazol-4-yl)-2,5-dioxoimidazolidin-4-yl)-N-(3-methoxybenzyl)acetamide | 1.798 |
| 9-5 | 3-((3-(1-((3,5-dimethylisoxazol-4-yl)methyl)-1H-pyrazol-4-yl)-2,4-dioxoimidazolidin-1-yl)methyl)benzoic acid | 2.493 |
| 10-29 | 1-benzyl-3-(1-((3,5-dimethylisoxazol-4-yl)methyl)-1H-pyrazol-4-yl)imidazolidine-2,4,5-trione | 3.117 |

| Compound No. | Compound | hT2R8 IC$_{50}$ (μM) |
|---|---|---|
| | 3-(1-((3,5-dimethylisoxazol-4-yl)methyl)-1H-pyrazol-4-yl)-1-(4-methoxybenzyl)imidazolidine-2,4-dione | |
| 10-63 | 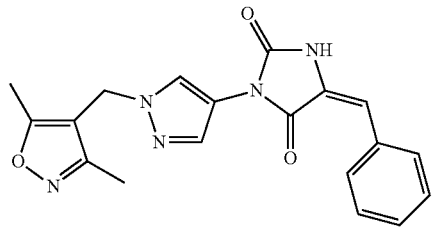 [SMILES: Cc1noc(C)c1Cn1cc(N2C(=O)N/C(=C/c3ccccc3)C2=O)cn1] | |
| | (E)-5-benzylidene-3-(1-((3,5-dimethylisoxazol-4-yl)methyl)-1H-pyrazol-4-yl)imidazolidine-2,4-dione | |
| 10-67 | 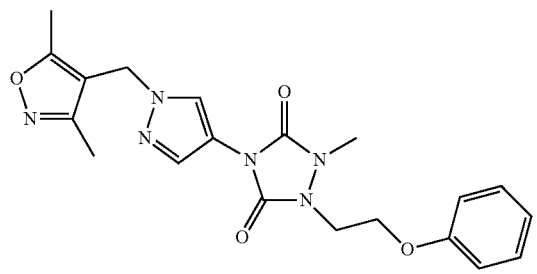 [SMILES: Cc1noc(C)c1Cn1cc(-n2c(=O)n(C)n(CCOc3ccccc3)c2=O)cn1] | |
| | 4-(1-((3,5-dimethylisoxazol-4-yl)methyl)-1H-pyrazol-4-yl)-1-methyl-2-(2-phenoxyethyl)-1,2,4-triazolidine-3,5-dione | |
| 10-97 | 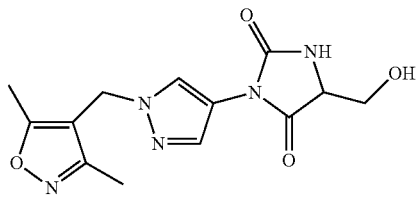 [SMILES: Cc1noc(C)c1Cn1cc(N2C(=O)NC(CO)C2=O)cn1] | |
| | 3-(1-((3,5-dimethylisoxazol-4-yl)methyl)-1H-pyrazol-4-yl)-5-(hydroxymethyl)imidazolidine-2,4-dione | |
| 9-8 | 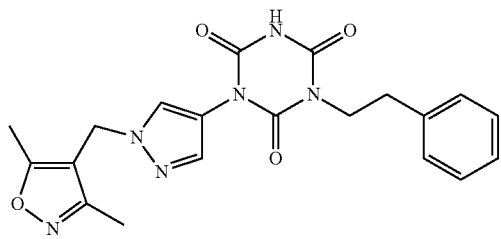 [SMILES: Cc1noc(C)c1Cn1cc(-n2c(=O)[nH]c(=O)n(CCc3ccccc3)c2=O)cn1] | 6.151 |
| | 1-(1-((3,5-dimethylisoxazol-4-yl)methyl)-1H-pyrazol-4-yl)-3-phenethyl-1,3,5-triazinane-2,4,6-trione | |

| Compound No. | Compound | hT2R8 IC$_{50}$ (μM) |
|---|---|---|
| 9-7 | 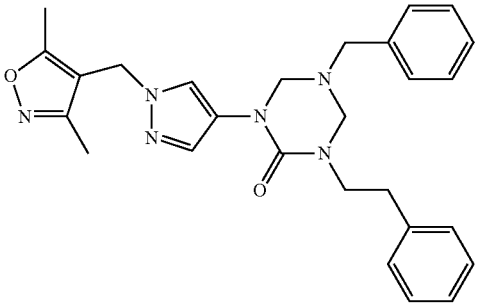 [SMILES: Cc1noc(C)c1Cn1cc(N2CN(Cc3ccccc3)CN(CCc3ccccc3)C2=O)cn1]<br>5-benzyl-1-(1-((3,5-dimethylisoxazol-4-yl)methyl)-1H-pyrazol-4-yl)-3-phenethyl-1,3,5-triazinan-2-one | 6.580 |
| 9-9 | 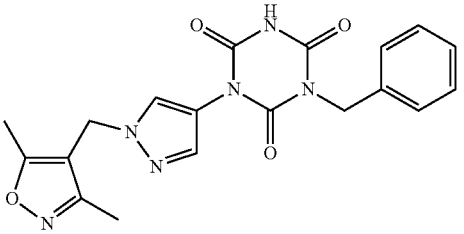 [SMILES: Cc1noc(C)c1Cn1cc(-n2c(=O)[nH]c(=O)n(Cc3ccccc3)c2=O)cn1]<br>1-benzyl-3-(1-((3,5-dimethylisoxazol-4-yl)methyl)-1H-pyrazol-4-yl)-1,3,5-triazinane-2,4,6-trione | 1.562 |
| 10-88 | 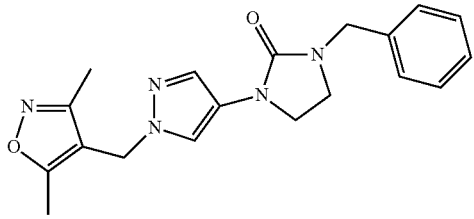 [SMILES: Cc1noc(C)c1Cn1cc(N2CCN(Cc3ccccc3)C2=O)cn1]<br>1-benzyl-3-(1-((3,5-dimethylisoxazol-4-yl)methyl)-1H-pyrazol-4-yl)imidazolidin-2-one | 1.250 |
| 9-5 | 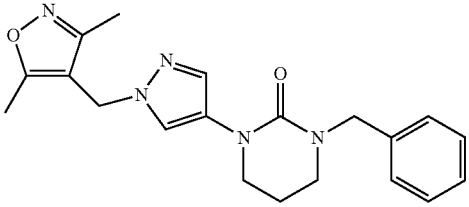 [SMILES: Cc1noc(C)c1Cn1cc(N2CCCN(Cc3ccccc3)C2=O)cn1]<br>1-benzyl-3-(1-((3,5-dimethylisoxazol-4-yl)methyl)-1H-pyrazol-4-yl)tetrahydropyrimidin-2(1H)-one | 3.434 |
| 9-6 | 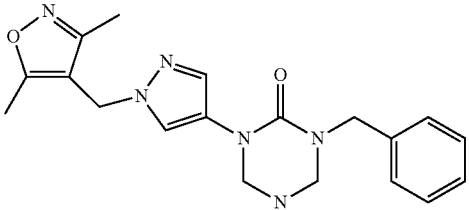 | 6.029 |

| Compound No. | Compound | hT2R8 IC$_{50}$ (μM) |
|---|---|---|
| | 1-benzyl-3-(1-((3,5-dimethylisoxazol-4-yl)methyl)-1H-pyrazol-4-yl)-1,3,5-triazinan-2-one | |
| 10-68 | 4-(1-((3,5-dimethylisoxazol-4-yl)methyl)-1H-pyrazol-4-yl)-1,2,4-triazolidine-3,5-dione | |
| 10-45 | 3-(1-((3,5-dimethylisoxazol-4-yl)methyl)-1H-pyrazol-4-yl)-5-phenethylimidazolidine-2,4-dione | 0.793 |
| 10-44 | 2-(1-(1-((3,5-dimethylisoxazol-4-yl)methyl)-1H-pyrazol-4-yl)-2,5-dioxoimidazolidin-4-yl)acetic acid | |
| 10-65 | 1-benzyl-4-(1-((3,5-dimethylisoxazol-4-yl)methyl)-1H-pyrazol-4-yl)-2-methyl-1,2,4-triazolidine-3,5-dione | 0.019 |
| 10-70 | 1,2-dibenzyl-4-(1-((3,5-dimethylisoxazol-4-yl)methyl)-1H-pyrazol-4-yl)-1,2,4-triazolidine-3,5-dione | 1.799 |

-continued

| Compound No. | Compound | hT2R8 IC$_{50}$ (μM) |
|---|---|---|
| 10-69 | 4-(1-((3,5-dimethylisoxazol-4-yl)methyl)-1H-pyrazol-4-yl)-1,2-dimethyl-1,2,4-triazolidine-3,5-dione | 0.707 |
| 10-52 | 3-(1-((3,5-dimethylisoxazol-4-yl)methyl)-1H-pyrazol-4-yl)-1,5,5-trimethylimidazolidine-2,4-dione | 0.810 |
| 10-14 | 3-(1-((3,5-dimethylisoxazol-4-yl)methyl)-1H-pyrazol-4-yl)-1-(3-(2-methoxyethoxy)benzyl)imidazolidine-2,4-dione | 0.071 |

Example 11 hT2R8 Contributes to the Bitterness of Saccharin for People with the "Non-taster" Versions of the hT2R43 and hT2R44 Genes FIG. 6 shows the dose-response relationships and the effects of saccharin on receptor activities in transfected cells expressing variants of hT2R43, hT2R44 and hT2R8. hT2R8 is less responsive to saccharin in the in vitro assay than the "taster" hT2R43-W35 and hT2R44-W35 alleles, but responds better than the "non-taster" hT2R43-S35 and hT2R44-R35 alleles. Pronin et al., Curr. Biol. 17: 1403-8 (2007). Five individuals with the "taster" alleles (hT2R43-W35 and/or hT2R44-W35) and five with the "non-taster" alleles (hT2R43-S35 and hT2R44-R35) were selected based on genotyping analysis. Each subject was presented with 6 pairs of solutions and asked to determine which of the samples in a pair tasted more bitter. The result shown in Table 8, below, shows that hT2R8 blocker Cpd-D reduces bitter taste of saccharin for people with the "non-taster" alleles of hT2R43 and hT2R44 but has no effect on people with the "taster" alleles of those genes.

TABLE 8

| Taste Test Results | | | | | |
|---|---|---|---|---|---|
| Taste Test | Bitter agonist | Genotype group | Selected as more bitter | | |
| | | | without | +Cpd-D | P value |
| 1 | saccharin | hT2R43-W35 and/or hT2R44-W35 | 13 | 17 | 0.82 |
| 2 | saccharin | hT2R43-S35 and hT2R44-R35 | 27 | 3 | <0.001 |

Example 12

Substituted Hydantoin Analogs (T2R8 Blockers)

Example 12-1

3-(1-((3,5-dimethylisoxazol-4-yl)methyl)-1H-pyrazol-4-yl)-1-(3-hydroxybenzyl)-5,5-dimethylimidazolidine-2,4-dione

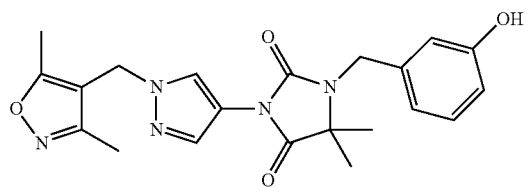 [SMILES: Cc1noc(C)c1Cn1cc(N2C(=O)N(Cc3cccc(O)c3)C(C)(C)C2=O)cn1]

1-(3-(tert-butyldimethylsilyloxy)benzyl)-3-(1-((3,5-dimethylisoxazol-4-yl)methyl)-1H-pyrazol-4-yl)-5,5-dimethylimidazolidine-2,4-dione (Example 12-1a) (2.00 g, 3.82 mmol) was dissolved in methanol (200 mL) and treated with HCl (2.0 M solution in diethyl ether, 10 equivalents). The solution was stirred for 16 hours at 50° C. then allowed to cool down to room temperature and the solvent was removed under reduced pressure. The residue was dissolved in ethanol and recristallized at 4° C. to give 3-(1-((3,5-dimethylisoxazol-4-yl)methyl)-1H-pyrazol-4-yl)-1-(3-hydroxybenzyl)-5,5-dimethylimidazolidine-2,4-dione (1.50 g, 3.67 mmol, 96%) as a white solid. $^1$H NMR (DMSO-d$_6$, 400 MHz): δ 1.31 (s, 6H), 2.16 (s, 3H), 2.42 (s, 3H), 4.47 (s, 2H), 5.20 (s, 2H), 6.65 (ddd, J=0.8, 2.4, 8 Hz, 1H), 6.79 (m, 2H), 7.11 (t, J=8 Hz, 1H), 7.83 (d, J=0.8 Hz, 1H), 8.21 (d, J=0.8 Hz, 1H), 9.36 (s, H). MS 410 (MH$^+$). The title compound was shown to inhibit hT2R08 bitter receptor and had an IC$_{50}$ of 0.05 μM

Example 12-1a 1-(3-(tert-butyldimethylsilyloxy)benzyl)-3-(1-((3,5-dimethylisoxazol-4-yl)methyl)-1H-pyrazol-4-yl)-5,5-dimethylimidazolidine-2,4-dione

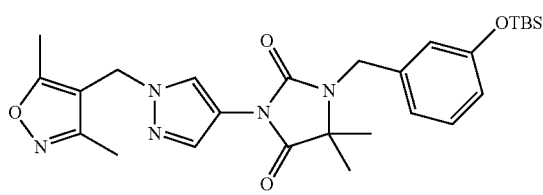 [SMILES: Cc1noc(C)c1Cn1cc(N2C(=O)N(Cc3cccc(O[Si](C)(C)C(C)(C)C)c3)C(C)(C)C2=O)cn1]

1-((3,5-dimethylisoxazol-4-yl)methyl)-1H-pyrazole-4-carbonyl azide (Example 10-1a) (1.26 g, 5.12 mmol) along with molecular sieves are stirred at reflux in dry toluene (100 mL) under nitrogen until no emission of nitrogen was observed, which indicates complete conversion of 1-((3,5-dimethylisoxazol-4-yl)methyl)-1H-pyrazole-4-carbonyl azide into 4-((4-isocyanato-1H-pyrazol-1-yl)methyl)-3,5-dimethylisoxazole. A solution of ethyl 2-(3-(tert-butyldimethylsilyloxy)benzylamino)-2-methylpropanoate (Example 12-1b) (1.50 g, 4.27 mmol) in dry toluene (50 mL) was prepared. To this solution, the mixture obtained above, which contains 4-((4-isocyanato-1H-pyrazol-1-yl)methyl)-3,5-dimethylisoxazole and molecular sieves, was added in one portion at 50° C. and refluxed for 24 h. The mixture was allowed to cool down to room temperature, filtered over a pad of celite and evaporated. The residue was further purified over silica gel using ethyl acetate/hexanes as eluent and the solvents were evaporated to provide a colorless oily material (2.10 g, 94%). MS 524 (MH$^+$).

Example 12-1b

Ethyl 2-(3-(tert-butyldimethylsilyloxy)benzylamino)-2-methylpropanoate

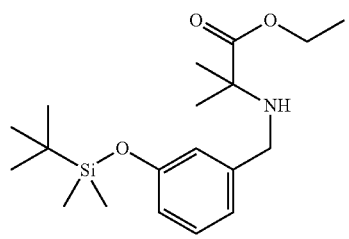 [SMILES: CCOC(=O)C(C)(C)NCc1cccc(O[Si](C)(C)C(C)(C)C)c1]

To 3-(tert-butyldimethylsilyloxy)benzaldehyde (Example 12-1c) (3.00 g, 12.7 mmol) in DCE (100 mL) was added ethyl 2-amino-2-methylpropanoate hydrochloride (25 mmol, ~2 equiv.), molecular sieves 4A (5 g), and Et$_3$N (2 equiv.). The mixture was stirred for 6 hours at room temperature and treated with NaBH(OAc)$_3$ (2 equiv.). After the addition was completed, the reaction mixture was stirred overnight under nitrogen. The mixture was diluted with DMC (200 mL), carefully quenched with saturated aqueous NaHCO$_3$ solution and the layers were separated. The aqueous phase was further extracted with DCM (2×100 mL). The combined organic extract was washed with water (50 mL), brine (100 mL) and dried over Na$_2$SO$_4$. The solvent was removed under vacuum and the residue was purified over silica gel using hexanes/EtOAc (2/8) to give ethyl 2-(3-(tert-butyldimethylsilyloxy)benzylamino)-2-methylpropanoate (4.02 g, 90%). MS 352 (MH$^+$)

Example 12-1c 3-(tert-butyldimethylsilyloxy)benzaldehyde

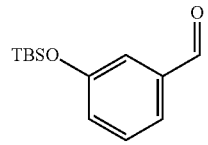 [SMILES: CC(C)(C)[Si](C)(C)Oc1cccc(C=O)c1]

3-Hydroxyldehyde (19.35 g, 81.88 mmol) was dissolved in anhydrous DCM (300 mL) and immidazole (3 equiv.) was added. The mixture was cooled down to 0° C. and a solution of tert-butylchlorodimethylsilane (1.5 equiv.) in DCM (200 mL) was added dropwise. After stirring overnight at room temperature, the reaction mixture was washed with 1M aqueous HCl solution, brine and dried over Na$_2$SO$_4$. After filtration, the solvent was removed under reduced pressure to provide the desired product quantitative yield. MS 237 (MH⁺).

Example 12-2

3-(1-((3,5-dimethylisoxazol-4-yl)methyl)-1H-pyrazol-4-yl)-1-(3-hydroxy-4-methoxybenzyl)-5,5-dimethylimidazolidine-2,4-dione

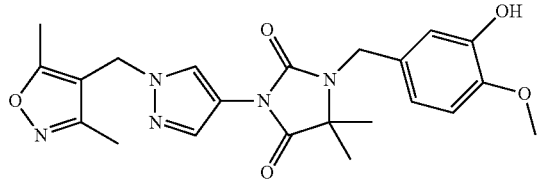 [SMILES: COc1ccc(CN2C(=O)N(c3cnn(Cc4c(C)noc4C)c3)C(=O)C2(C)C)cc1O]

Prepared as in Example 12-1 from 1-(3-(tert-butyldimethylsilyloxy)-4-methoxybenzyl)-3-(1-((3,5-dimethylisoxazol-4-yl)methyl)-1H-pyrazol-4-yl)-5,5-dimethylimidazolidine-2,4-dione (Example 12-2a). Yield 60%, white solid. ¹H NMR (DMSO-d₆, 400 MHz): δ 1.29 (s, 6H), 2.16 (s, 3H), 2.42 (s, 3H), 3.73 (s, 3H), 4.42 (s, 2H), 5.20 (s, 2H), 6.82 (m, 3H) 7.83 (s, 1H), 8.20 (s, 1H), 8.94 (br s, 1H). MS 440 (MH⁺). The title compound was shown to inhibit hT2R08 bitter receptor and had an IC₅₀ of 0.06 μM Example 12-2a 1-(3-(tert-butyldimethylsilyloxy)-4-methoxybenzyl)-3-(1-((3,5-dimethylisoxazol-4-yl)methyl)-1H-pyrazol-4-yl)-5,5-dimethylimidazolidine-2,4-dione

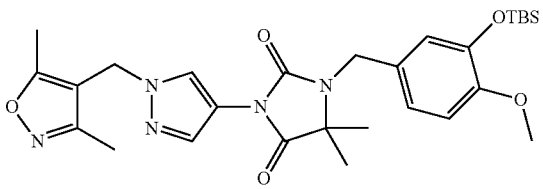 [SMILES: COc1ccc(CN2C(=O)N(c3cnn(Cc4c(C)noc4C)c3)C(=O)C2(C)C)cc1O[Si](C)(C)C(C)(C)C]

Prepared as in Example 12-1a from 2-(3-(tert-butyldimethylsilyloxy)-4-methoxybenzylamino)-2-methylpropanoate (Example 12-2b) and 1-((3,5-dimethylisoxazol-4-yl)methyl)-1H-pyrazole-4-carbonyl azide (Example 10-1a). Yield 85%, white solid. MS 554 (MH⁺).

Example 12-2b

Ethyl 2-(3-(tert-butyldimethylsilyloxy)-4-methoxybenzylamino)-2-methylpropanoate

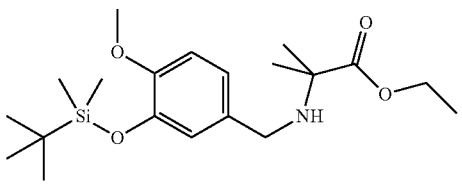 [SMILES: CCOC(=O)C(C)(C)NCc1ccc(OC)c(O[Si](C)(C)C(C)(C)C)c1]

Prepared as in Example 12-1b from 3-(tert-butyldimethylsilyloxy)-4-methoxybenzaldehyde (Example 12-2c) and ethyl 2-amino-2-methylpropanoate hydrochloride. Yield 94%, colorless liquid. MS 382 (MH⁺).

Example 12-2c 3-(tert-butyldimethylsilyloxy)-4-methoxybenzaldehyde

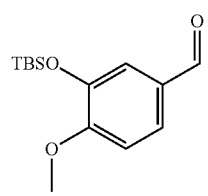 [SMILES: COc1ccc(C=O)cc1O[Si](C)(C)C(C)(C)C]

Prepared as in Example 12-1c from 3-hydroxy-4-methoxybenzaldehyde and tert-butylchlorodimethylsilane. Yield 100%, yellowish liquid. MS 267 (MH⁺).

Example 12-3

1-(3,5-bis(tert-butyldimethylsilyloxy)benzyl)-3-(1-((3,5-dimethylisoxazol-4-yl)methyl)-1H-pyrazol-4-yl)-5,5-dimethylimidazolidine-2,4-dione

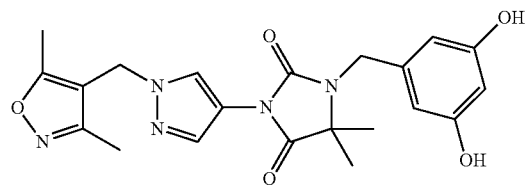 [SMILES: Cc1noc(C)c1Cn1cc(N2C(=O)N(Cc3cc(O)cc(O)c3)C(C)(C)C2=O)cn1]

Prepared as in Example 12-1 from 1-(3,5-bis(tert-butyldimethylsilyloxy)benzyl)-3-(1-((3,5-dimethylisoxazol-4-yl)methyl)-1H-pyrazol-4-yl)-5,5-dimethylimidazolidine-2,4-dione (Example 12-3a). Yield 92%, white solid. ¹H NMR (DMSO-d₆, 400 MHz): δ₁ s, 6H), 2.17 (s, 3H), 2.43 (s, 3H), 4.38 (s, 2H), 5.21 (s, 2H), 6.10 (m, 1H), 6.23 (m, 2H), 7.84 (d, J=0.4 Hz, 1H), 8.22 (d, J=0.4 Hz, 1H), 9.20 (br s, 1H), 9.21

(br, s, 1H). Mp 213-215° C. MS 426 (MH⁺). The title compound was shown to inhibit hT2R08 bitter receptor and had an IC$_{50}$ of 0.01 μM

Example 12-3a 1-(3,5-bis(tert-butyldimethylsilyloxy)benzyl)-3-(1-((3,5-dimethylisoxazol-4-yl)methyl)-1H-pyrazol-4-yl)-5,5-dimethylimidazolidine-2,4-dione

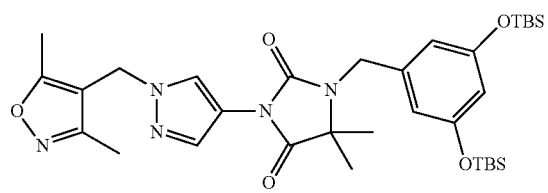 [SMILES: Cc1noc(C)c1Cn1cc(N2C(=O)N(Cc3cc(O[Si](C)(C)C(C)(C)C)cc(O[Si](C)(C)C(C)(C)C)c3)C(C)(C)C2=O)cn1]

Prepared as in Example 12-1a from ethyl 2-(3,5-bis(tert-butyldimethylsilyloxy)benzylamino)-2-methylpropanoate (Example 12-3b) and 1-((3,5-dimethylisoxazol-4-yl)methyl)-1H-pyrazole-4-carbonyl azide (Example 10-1a). Yield 82%, white solid. MS 654 (MH⁺).

Example 12-3b ethyl 2-(3,5-bis(tert-butyldimethylsilyloxy)benzylamino)-2-methylpropanoate

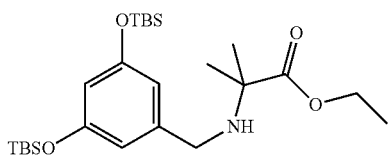 [SMILES: CCOC(=O)C(C)(C)NCc1cc(O[Si](C)(C)C(C)(C)C)cc(O[Si](C)(C)C(C)(C)C)c1]

Prepared as in Example 12-1b from 3,5-bis(tert-butyldimethylsilyloxy)benzaldehyde (Example 12-3c) and ethyl 2-amino-2-methylpropanoate hydrochloride. Yield 88%, colorless liquid. MS 482 (MH⁺).

Example 12-3c 3,5-bis(tert-butyldimethylsilyloxy)benzaldehyde

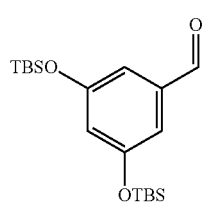 [SMILES: CC(C)(C)[Si](C)(C)Oc1cc(C=O)cc(O[Si](C)(C)C(C)(C)C)c1]

Prepared as in Example 12-1c from 3,5-dihydroxybenzaldehyde and tert-butylchlorodimethylsilane. Yield 100%, yellowish liquid. MS 267 (MH⁺).

Example 12-4

7-(1-((3,5-dimethylisoxazol-4-yl)methyl)-1H-pyrazol-4-yl)-5-(3-hydroxybenzyl)-5,7-diazaspiro[3.4]octane-6,8-dione

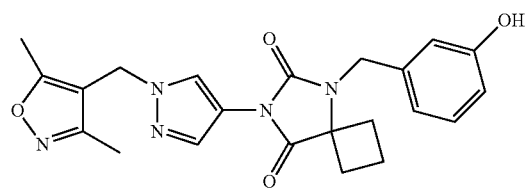 [SMILES: Cc1noc(C)c1Cn1cc(N2C(=O)N(Cc3cccc(O)c3)C3(CCC3)C2=O)cn1]

Prepared as in Example 12-1 from 5-(3-(tert-butyldimethylsilyloxy)benzyl)-7-(1-((3,5-dimethylisoxazol-4-yl)methyl)-1H-pyrazol-4-yl)-5,7-diazaspiro[3.4]octane-6,8-dione (Example 12-4a). Yield 74%, white solid. ¹H NMR (DMSO-d$_6$, 400 MHz): δ 1.73 (m, 1H), 1.98 (m, 1H), 2.15 (s, 3H), 2.27 (m, 2H) 2.42 (s, 3H), 2.45 (m, 2H), 4.65 (s, 2H), 5.20 (s, 2H), 6.65 (m, 1H), 6.73 (m, 1H), 6.76 (m, 1H), 7.13 (t, J=8 Hz, 1H), 7.82 (d, J=0.8 Hz, 1H), 8.20 (d, J=0.8 Hz, 1H), 9.39 (s, H). MS 422 (MH⁺). The title compound was shown to inhibit hT2R08 bitter receptor and had an IC$_{50}$ of 0.03 μM

Example 12-4a 5-(3-(tert-butyldimethylsilyloxy)benzyl)-7-(1-((3,5-dimethylisoxazol-4-yl)methyl)-1H-pyrazol-4-yl)-5,7-diazaspiro[3.4]octane-6,8-dione

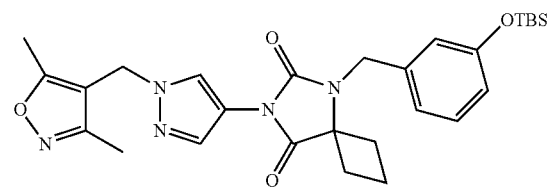 [SMILES: Cc1noc(C)c1Cn1cc(N2C(=O)N(Cc3cccc(O[Si](C)(C)C(C)(C)C)c3)C3(CCC3)C2=O)cn1]

Prepared as in Example 12-1a from ethyl 1-(3-(tert-butyldimethylsilyloxy)benzylamino)cyclobutanecarboxylate (Example 12-4b) and 1-((3,5-dimethylisoxazol-4-yl)methyl)-1H-pyrazole-4-carbonyl azide (Example 10-1a) Yield 89%. MS 536 (MH+).

Example 12-4b ethyl 1-(3-(tert-butyldimethylsilyloxy)benzylamino)cyclobutanecarboxylate

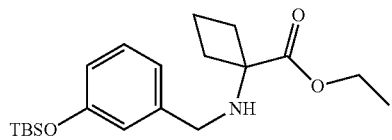 [SMILES: CCOC(=O)C1(NCc2cccc(O[Si](C)(C)C(C)(C)C)c2)CCC1]

Prepared as in Example 12-1b from 3-(tert-butyldimethylsilyloxy)benzaldehyde (Example 12-1c) and ethyl 1-aminocyclobutanecarboxylate hydrochloride. Yield 77%, colorless liquid. MS 364 (MH+).

Example 12-5

3-(1-((3,5-dimethylisoxazol-4-yl)methyl)-1H-pyrazol-4-yl)-1-(3-hydroxybenzyl)-1,3-diazaspiro[4.4]nonane-2,4-dione

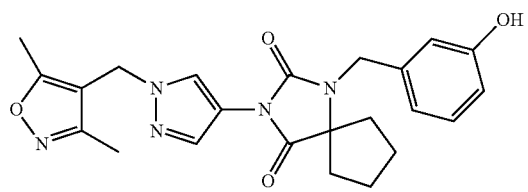 [SMILES: Cc1noc(C)c1Cn1cc(N2C(=O)N(Cc3cccc(O)c3)C3(CCCC3)C2=O)cn1]

Prepared as in Example 12-1 from 1-(3-(tert-butyldimethylsilyloxy)benzyl)-3-(1-((3,5-dimethylisoxazol-4-yl)methyl)-1H-pyrazol-4-yl)-1,3-diazaspiro[4.4]nonane-2,4-dione (Example 12-5a). Yield 81%, white solid. $^1$H NMR (DMSO-$d_6$, 400 MHz): δ 1.72 (m, 4H), 1.89 (m, 4H), 2.16 (s, 3H), 2.42 (s, 3H), 4.49 (s, 2H), 5.20 (s, 2H), 6.65 (m, 1H), 6.76 (m, 2H), 7.12 (t, J=8.0 Hz, 1H), 7.84 (d, J=0.4 Hz, 1H), 8.21 (d, J=0.4 Hz, 1H), 9.38 (s, H). MS 436 (MH+). The title compound was shown to inhibit hT2R08 bitter receptor and had an $IC_{50}$ of 0.07 μM

Example 12-5a 1-(3-(tert-butyldimethylsilyloxy)benzyl)-3-(1-((3,5-dimethylisoxazol-4-yl)methyl)-1H-pyrazol-4-yl)-1,3-diazaspiro[4.4]nonane-2,4-dione

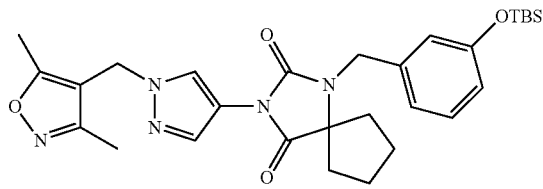 [SMILES: Cc1noc(C)c1Cn1cc(N2C(=O)N(Cc3cccc(O[Si](C)(C)C(C)(C)C)c3)C3(CCCC3)C2=O)cn1]

Prepared as in Example 12-1a from ethyl 1-(3-(tert-butyldimethylsilyloxy)benzylamino)cyclobutanecarboxylate (Example 12-5b) and 1-((3,5-dimethylisoxazol-4-yl)methyl)-1H-pyrazole-4-carbonyl azide (Example 10-1a). Yield 89%. MS 550 (MH+).

Example 12-5b

Ethyl 1-(3-(tert-butyldimethylsilyloxy)benzylamino)-cyclopentanecarboxylate

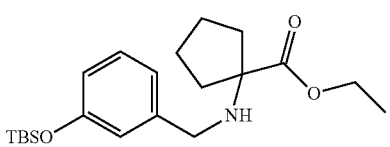 [SMILES: CCOC(=O)C1(NCc2cccc(O[Si](C)(C)C(C)(C)C)c2)CCCC1]

Prepared as in Example 1b-JF from 3-(tert-butyldimethylsilyloxy)benzaldehyde (Example 12-1c) and ethyl 1-aminocyclopentanecarboxylate hydrochloride. Yield 77%, a colorless liquid. MS 378 (MH+).

Example 12-6

(S)-3-(1-((3,5-dimethylisoxazol-4-yl)methyl)-1H-pyrazol-4-yl)-1-(3-hydroxybenzyl)-5-methylimidazolidine-2,4-dione

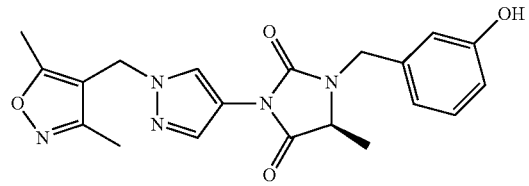 [SMILES: Cc1noc(C)c1Cn1cc(N2C(=O)[C@H](C)N(Cc3cccc(O)c3)C2=O)cn1]

Prepared as in Example 12-1 from (S)-1-(3-(tert-butyldimethylsilyloxy)benzyl)-3-(1-((3,5-dimethylisoxazol-4-yl)methyl)-1H-pyrazol-4-yl)-5-methylimidazolidine-2,4-dione (Example 12-6a). Yield 93%, white solid. $^1$H NMR (DMSO-$d_6$, 400 MHz): $^1$H NMR (DMSO-D6, 400 MHz): δ$_1$˜ (d, J=7.2 Hz, 3H), 2.15 (s, 3H), 2.41 (s, 3H), 4.10 (q, J=7.2 Hz, 1H), 4.34 (d, J=15.6, Hz, 1H), 4.60 (d, J=15.6 Hz, 1H), 5.20 (s, 2H), 6.72 (m, 3H), 7.13 (t, J=8.0 Hz, 1H), 7.81 (d, J=0.4 Hz, 1H), 8.19 (d, J=0.4 Hz, 1H), 9.41 (br s, 1H). MS 396

(MH+). The title compound was shown to inhibit hT2R08 bitter receptor and had an IC$_{50}$ of 0.02 μM

Example 12-6a (S)-1-(3-(tert-butyldimethylsilyloxy)benzyl)-3-(1-((3,5-dimethylisoxazol-4-yl)methyl)-1H-pyrazol-4-yl)-5-methylimidazolidine-2,4-dione

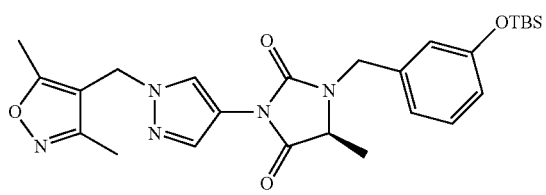 [SMILES: Cc1noc(C)c1Cn1cc(N2C(=O)[C@H](C)N(Cc3cccc(O[Si](C)(C)C(C)(C)C)c3)C2=O)cn1]

Prepared as in Example 12-1a from (S)-ethyl 2-(3-(tert-butyldimethylsilyloxy)benzylamino)propanoate (Example 12-6b) and 1-((3,5-dimethylisoxazol-4-yl)methyl)-1H-pyrazole-4-carbonyl azide (Example 10-1a). Yield 75%. MS 510 (MH+).

Example 12-6b (S)-methyl 2-(3-(tert-butyldimethylsilyloxy)benzylamino)-propanoate

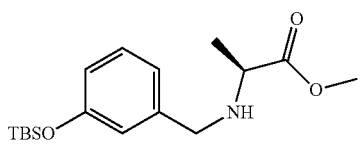 [SMILES: COC(=O)[C@H](C)NCc1cccc(O[Si](C)(C)C(C)(C)C)c1]

Prepared as in Example 12-1b from 3-(tert-butyldimethylsilyloxy)benzaldehyde (Example 12-1c) and (S)-methyl 2-aminopropanoate hydrochloride. Yield 80%, colorless liquid. MS 324 (MH+).

Example 12-7

(R)-3-(1-((3,5-dimethylisoxazol-4-yl)methyl)-1H-pyrazol-4-yl)-1-(3-hydroxybenzyl)-5-methylimidazolidine-2,4-dione

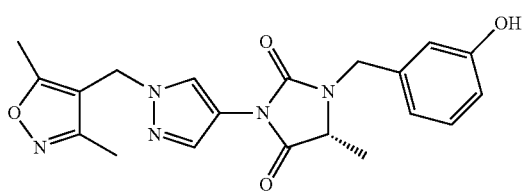 [SMILES: Cc1noc(C)c1Cn1cc(N2C(=O)[C@@H](C)N(Cc3cccc(O)c3)C2=O)cn1]

Prepared as in Example 12-1 from (R)-1-(3-(tert-butyldimethylsilyloxy)benzyl)-3-(1-((3,5-dimethylisoxazol-4-yl)methyl)-1H-pyrazol-4-yl)-5-methylimidazolidine-2,4-dione (Example 12-7a). Yield 96%, white solid. $^1$H NMR (DMSO-d$_6$, 400 MHz): $^1$H NMR (DMSO-D6, 400 MHz): δ$_1$ ~ (d, J=7.2 Hz, 3H), 2.15 (s, 3H), 2.41 (s, 3H), 4.10 (q, J=7.2 Hz, 1H), 4.34 (d, J=15.6, Hz, 1H), 4.60 (d, J=15.6 Hz, 1H), 5.20 (s, 2H), 6.72 (m, 3H), 7.13 (t, J=8.0 Hz, 1H), 7.81 (d, J=0.4 Hz, 1H), 8.19 (d, J=0.4 Hz, 1H), 9.41 (br s, 1H). MS 396 (MH+). The title compound was shown to inhibit hT2R08 bitter receptor and had an IC$_{50}$ of 0.02 μM

Example 12-7a (R)-1-(3-(tert-butyldimethylsilyloxy)benzyl)-3-(1-((3,5-dimethylisoxazol-4-yl)methyl)-1H-pyrazol-4-yl)-5-methylimidazolidine-2,4-dione

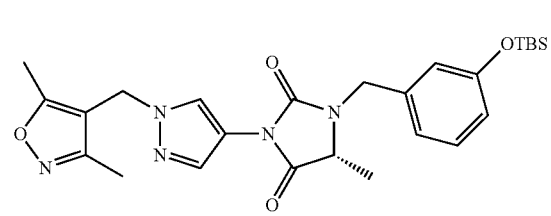 [SMILES: Cc1noc(C)c1Cn1cc(N2C(=O)[C@@H](C)N(Cc3cccc(O[Si](C)(C)C(C)(C)C)c3)C2=O)cn1]

Prepared as in Example 12-1a from (R)-ethyl 2-(3-(tert-butyldimethylsilyloxy)benzylamino)propanoate (Example 12-7b) and 1-((3,5-dimethylisoxazol-4-yl)methyl)-1H-pyrazole-4-carbonyl azide (Example 10-1a). Yield 77%. MS 510 (MH+).

Example 12-7b (R)-methyl 2-(3-(tert-butyldimethylsilyloxy)benzylamino)-propanoate

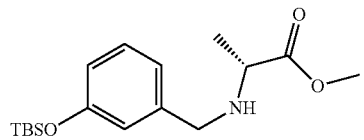 [SMILES: COC(=O)[C@@H](C)NCc1cccc(O[Si](C)(C)C(C)(C)C)c1]

Prepared as in Example 12-1b from 3-(tert-butyldimethylsilyloxy)benzaldehyde (Example 12-1c) and (R)-methyl 2-aminopropanoate hydrochloride. Yield 82%, colorless liquid. MS 324 (MH+).

Example 12-8

(S)-3-(1-((3,5-dimethylisoxazol-4-yl)methyl)-1H-pyrazol-4-yl)-1-(3-hydroxybenzyl)-5-isopropylimidazolidine-2,4-dione

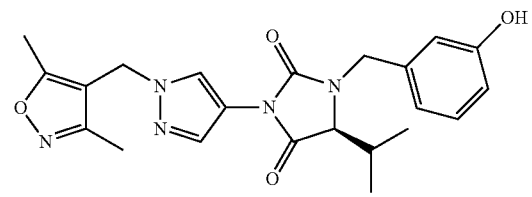 [SMILES: Cc1noc(C)c1Cn1cc(N2C(=O)[C@H](C(C)C)N(Cc3cccc(O)c3)C2=O)cn1]

Prepared as in Example 12-1 from (S)-1-(3-(tert-butyldimethylsilyloxy)benzyl)-3-(1-((3,5-dimethylisoxazol-4-yl)methyl)-1H-pyrazol-4-yl)-5-isopropylimidazolidine-2,4-dione (Example 12-8a). Yield 50%, white solid. MS 423 (MH+).

The title compound was shown to inhibit hT2R08 bitter receptor and had an $IC_{50}$ of 0.65 μM

Example 12-8a (S)-1-(3-(tert-butyldimethylsilyloxy)benzyl)-3-(1-((3,5-dimethylisoxazol-4-yl)methyl)-1H-pyrazol-4-yl)-5-isopropylimidazolidine-2,4-dione

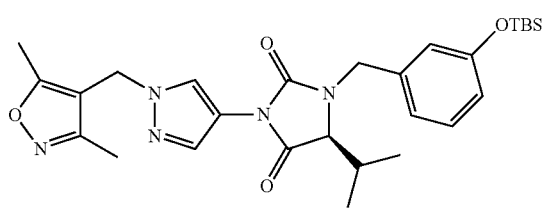 [SMILES: Cc1noc(C)c1Cn1cc(N2C(=O)[C@H](C(C)C)N(Cc3cccc(O[Si](C)(C)C(C)(C)C)c3)C2=O)cn1]

Prepared as in Example 12-1a from (S)-ethyl 2-(3-(tert-butyldimethylsilyloxy)benzylamino)-3-methylbutanoate (Example 12-8b) and 1-((3,5-dimethylisoxazol-4-yl)methyl)-1H-pyrazole-4-carbonyl azide (Example 10-1a). MS 538 $(MH^+)$.

Example 12-8b (S)-ethyl 2-(3-(tert-butyldimethylsilyloxy)benzylamino)-3-methylbutanoate

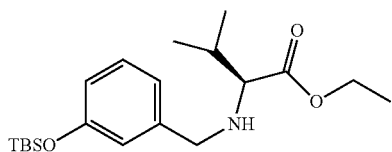 [SMILES: CCOC(=O)[C@@H](NCc1cccc(O[Si](C)(C)C(C)(C)C)c1)C(C)C]

Prepared as in Example 12-1b from 3-(tert-butyldimethylsilyloxy)benzaldehyde (Example 12-1c) and (S)-ethyl 2-amino-3-methylbutanoate hydrochloride. Yield 97%, colorless liquid. MS 352 $(MH^+)$.

Example 12-9

(S)-3-(1-((3,5-dimethylisoxazol-4-yl)methyl)-1H-pyrazol-4-yl)-1-(3-hydroxybenzyl)-5-(hydroxymethyl)imidazolidine-2,4-dione

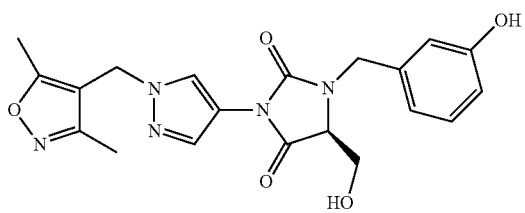 [SMILES: Cc1noc(C)c1Cn1cc(N2C(=O)[C@H](CO)N(Cc3cccc(O)c3)C2=O)cn1]

Prepared as in Example 12-1 from (S)-1-(3-(tert-butyldimethylsilyloxy)benzyl)-5-((tert-butyldimethylsilyloxy)methyl)-3-(1-((3,5-dimethylisoxazol-4-yl)methyl)-1H-pyrazol-4-yl)imidazolidine-2,4-dione (Example 12-9a). Yield 72%, white solid. $^1$H NMR (DMSO-$d_6$, 400 MHz): 2.13 (s, 3H), 2.40 (s, 3H), 3.78 (m, 2H), 4.01 (t, J=2.4 Hz, 1H), 4.80 (d, J=15.6, Hz, 1H), 5.18 (s, 2H), 5.20 (br.t, J=5.6 Hz, 1H), 6.66 (m, 3H), 6.72 (m, 3H), 7.11 (t, J=8.0 Hz, 1H), 7.80 (d, J=0.8 Hz, 1H), 8.18 (d, J=0.8 Hz, 1H), 9.38 (br s, 1H). MS 412 $(MH^+)$. The title compound was shown to inhibit hT2R08 bitter receptor and had an $IC_{50}$ of 0.04 μM

Example 12-9a (S)-1-(3-(tert-butyldimethylsilyloxy)benzyl)-5-((tert-butyldimethylsilyloxy)methyl)-3-(1-((3,5-dimethylisoxazol-4-yl)methyl)-1H-pyrazol-4-yl)imidazolidine-2,4-dione

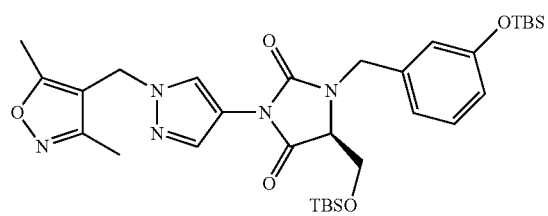 [SMILES: Cc1noc(C)c1Cn1cc(N2C(=O)[C@H](CO[Si](C)(C)C(C)(C)C)N(Cc3cccc(O[Si](C)(C)C(C)(C)C)c3)C2=O)cn1]

Prepared as in Example 12-1a from (S)-methyl 3-(tert-butyldimethylsilyloxy)-2-(3-(tert-butyldimethylsilyloxy)benzylamino)propanoate (Example 12-9b) and 1-((3,5-dimethylisoxazol-4-yl)methyl)-1H-pyrazole-4-carbonyl azide (Example 10-1a). Yield 65%. MS 640 $(MH^+)$.

Example 12-9b (S)-methyl 3-(tert-butyldimethylsilyloxy)-2-(3-(tert-butyldimethylsilyloxy)benzylamino)propanoate

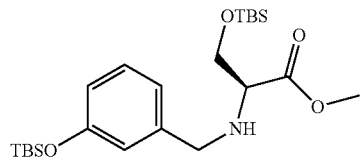 [SMILES: COC(=O)[C@H](CO[Si](C)(C)C(C)(C)C)NCc1cccc(O[Si](C)(C)C(C)(C)C)c1]

Prepared as in Example 12-1c from (S)-methyl 2-(3-(tert-butyldimethylsilyloxy)benzylamino)-3-hydroxypropanoate (Example 12-9c). Yield 85%, colorless liquid. MS 454 $(MH^+)$.

Example 12-9c (S)-methyl 2-(3-(tert-butyldimethylsilyloxy)benzylamino)-3-hydroxypropanoate

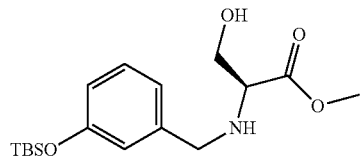 [SMILES: COC(=O)[C@H](CO)NCc1cccc(O[Si](C)(C)C(C)(C)C)c1]

To a solution of 3-(tert-butyldimethylsilyloxy)benzaldehyde (Example 12-1c) 1.52 g (6.43 mmol), triethyl amine (5 mL) and (S)-methyl 2-amino-3-hydroxypropanoate hydrochloride (1.00 g, 6.43 mmol) in DCM (30 mL) was added MgSO$_4$ and the solution was stirred at RT for 36 h. MgSO$_4$ was then filtered off and DCM was removed under vacuum. The residue was dissolved in dry MeOH (40 mL), cooled to 0° C. and treated in small portions with NaBH$_4$ (1.2 equiv.). The mixture was stirred at 0° C. for 3 h, quenched with water (10 mL) and concentrated by removing MeOH. The residue was extracted with Ethyl acetate to provide (S)-methyl 2-(3-(tert-butyldimethylsilyloxy)benzylamino)-3-hydroxypropanoate as yellowish oil (2.10 g, 96%). MS 340 (MH$^+$).

Example 12-10

3-(1-((3,5-dimethylisoxazol-4-yl)methyl)-1H-pyrazol-4-yl)-1-(3-hydroxybenzyl)-5-(hydroxymethyl)-5-methylimidazolidine-2,4-dione

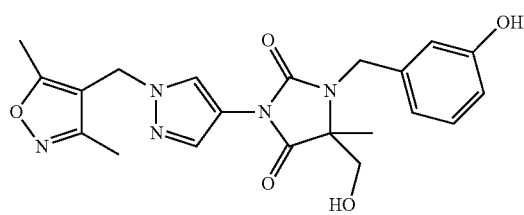 [SMILES: Cc1noc(C)c1Cn1cc(N2C(=O)N(Cc3cccc(O)c3)C(C)(CO)C2=O)cn1]

Prepared as in Example 12-1 from 1-(3-(tert-butyldimethylsilyloxy)benzyl)-5-((tert-butyldimethylsilyloxy)methyl)-3-(1-((3,5-dimethylisoxazol-4-yl)methyl)-1H-pyrazol-4-yl)-5-methylimidazolidine-2,4-dione (Example 12-10a). Yield 62%, white solid. MS 426 (MH$^+$). The title compound was shown to inhibit hT2R08 bitter receptor and had an IC$_{50}$ of 0.13 µM Example 12-10a 1-(3-(tert-butyldimethylsilyloxy)benzyl)-5-((tert-butyldimethylsilyloxy)methyl)-3-(1-((3,5-dimethylisoxazol-4-yl)methyl)-1H-pyrazol-4-yl)-5-methylimidazolidine-2,4-dione

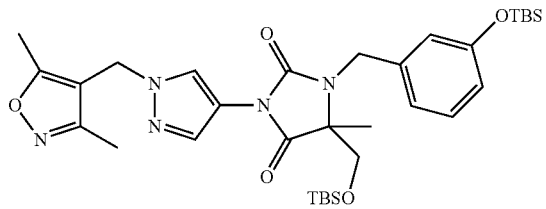 [SMILES: Cc1noc(C)c1Cn1cc(N2C(=O)N(Cc3cccc(O[Si](C)(C)C(C)(C)C)c3)C(C)(CO[Si](C)(C)C(C)(C)C)C2=O)cn1]

Prepared as in Example 12-1a from methyl 3-(tert-butyldimethylsilyloxy)-2-(3-(tert-butyldimethylsilyloxy)benzylamino)-2-methylpropanoate (Example 12-10b) and 1-((3,5-dimethylisoxazol-4-yl)methyl)-1H-pyrazole-4-carbonyl azide (Example 10-1a). Yield 79%. MS 654 (MH$^+$).

Example 12-10b methyl 3-(tert-butyldimethylsilyloxy)-2-(3-(tert-butyldimethylsilyloxy)benzylamino)-2-methylpropanoate

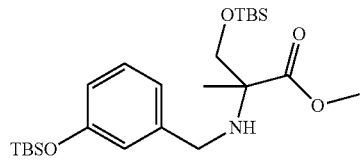 [SMILES: COC(=O)C(C)(CO[Si](C)(C)C(C)(C)C)NCc1cccc(O[Si](C)(C)C(C)(C)C)c1]

Prepared as in Example 12-1c from methyl 2-(3-(tert-butyldimethylsilyloxy)benzylamino)-3-hydroxy-2-methylpropanoate (Example 12-10c). Yield 76%, colorless liquid. MS 468 (MH$^+$).

Example 12-10c methyl 2-(3-(tert-butyldimethylsilyloxy)benzylamino)-3-hydroxy-2-methylpropanoate

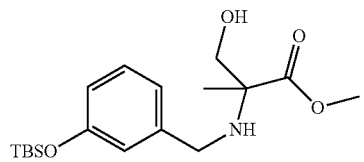 [SMILES: COC(=O)C(C)(CO)NCc1cccc(O[Si](C)(C)C(C)(C)C)c1]

Prepare as in Example 12-9c from 3-(tert-butyldimethylsilyloxy)benzaldehyde (Example 12-1c) and methyl 2-amino-3-hydroxy-2-methylpropanoate hydrochloride. Yield 97%, yellowish oil. MS 354 (MH$^+$).

Example 12-11

(S)-1-benzyl-3-(1-((3,5-dimethylisoxazol-4-yl)methyl)-1H-pyrazol-4-yl)-5-methylimidazolidine-2,4-dione

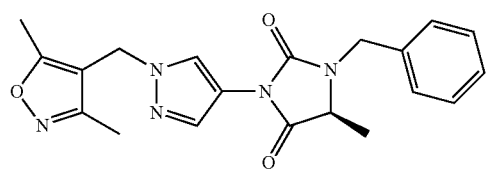 [SMILES: Cc1noc(C)c1Cn1cc(N2C(=O)[C@H](C)N(Cc3ccccc3)C2=O)cn1]

Prepared as in Example 12-1a from (S)-methyl 2-(benzylamino)propanoate (Example 12-11a) and 1-((3,5-dimethylisoxazol-4-yl)methyl)-1H-pyrazole-4-carbonyl azide (Example 10-1a). Yield 89. MS 380 (MH$^+$). The title compound was shown to inhibit hT2R08 bitter receptor and had an IC$_{50}$ of 0.01 μM Example 12-11a (S)-methyl 2-(benzylamino)propanoate

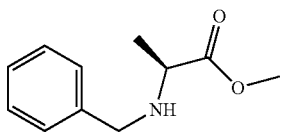

Prepared as in Example 12-1b from benzaldehyde and (R)-methyl 2-aminopropanoate hydrochloride. Yield 95%. MS 194 (MH$^+$).

Example 12-12

6-(1-((3,5-dimethylisoxazol-4-yl)methyl)-1H-pyrazol-4-yl)-4-(3-hydroxy-4-methoxybenzyl)-4,6-diazaspiro[2.4] heptane-5,7-dione

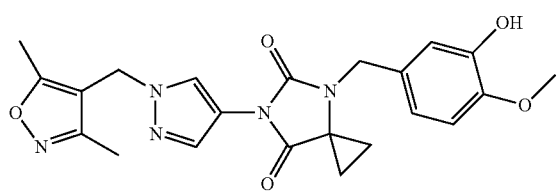 [SMILES: COc1ccc(CN2C(=O)N(c3cnn(Cc4c(C)noc4C)c3)C(=O)C23CC3)cc1O]

Prepared as in Example 12-1 from 4-(3-(tert-butyldimethylsilyloxy)benzyl)-6-(1-((3,5-dimethylisoxazol-4-yl)methyl)-1H-pyrazol-4-yl)-4,6-diazaspiro[2.4] heptane-5,7-dione (Example 12-12a). Yield 90%, white solid. MS 440 (MH$^+$). The title compound was shown to inhibit hT2R08 bitter receptor and had an IC$_{50}$ of 0.02 μM Example 12-12a 4-(3-(tert-butyldimethylsilyloxy)-4-methoxybenzyl)-6-(1-((3,5-dimethylisoxazol-4-yl)methyl)-1H-pyrazol-4-yl)-4,6-diazaspiro[2.4] heptane-5,7-dione

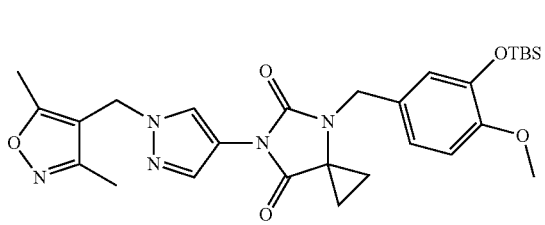 [SMILES: COc1ccc(CN2C(=O)N(c3cnn(Cc4c(C)noc4C)c3)C(=O)C23CC3)cc1O[Si](C)(C)C(C)(C)C]

1-((3,5-dimethylisoxazol-4-yl)methyl)-1H-pyrazole-4-carbonyl azide (Example 10-1a) (650 mg, 2.63 mmol) along with molecular sieves are stirred at reflux in dry toluene (50 mL) under nitrogen gas until no emission of nitrogen was observed. This solution was added to a solution of methyl 1-(3-(tert-butyldimethylsilyloxy)-4-methoxybenzylamino) cyclopropanecarboxylate (Example 12-12b) (800 mg, 2.19 mmol) in dry toluene (25 mL) in one portion at 50° C. and stirred at the same temperature for 24 h. The mixture was directly filtered over a pad of celite. The filtrate was concentrated and the residue was dissolved in dry MeOH (50 mL). Ten drops of NH$_3$ solution in MeOH were added and the mixture stirred at RT for 2 h. Volatiles were then removed under reduce pressure and the residue purified over silica gel using ethyl acetate/hexanes as eluent (3/7) to give the desired product as a colorless oil (856 mg, 75%). MS 522 (MH$^+$).

Example 12-12b methyl 1-(3-(tert-butyldimethylsilyloxy)-4-methoxybenzylamino)cyclopropanecarboxylate

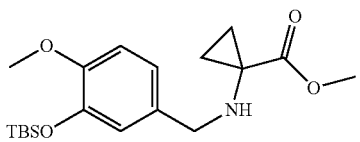

Prepared as in Example 12-1b from 3-(tert-butyldimethylsilyloxy)-4-methoxybenzaldehyde (Example 12-2c) and methyl 1-aminocyclopropanecarboxylate hydrochloride. Yield 79%. MS 366 (MH$^+$).

Example 12-13

4-(3,4-dimethoxybenzyl)-6-(1-((3,5-dimethylisoxazol-4-yl)methyl)-1H-pyrazol-4-yl)-4,6-diazaspiro [2.4]heptane-5,7-dione

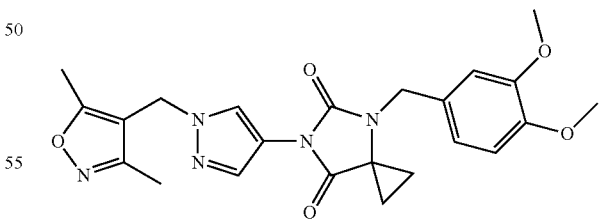

Prepared as in Example 12-12a from methyl 1-(3,4-dimethoxybenzylamino)cyclopropanecarboxylate (Example 12-13a) and 1-((3,5-dimethylisoxazol-4-yl)methyl)-1H-pyrazole-4-carbonyl azide (Example 10-1a). Yield 88%. $^1$H NMR (DMSO-d$_6$, 400 MHz): δ 1.21 (m, 2H), 1.41 (m, 2H), 2.16 (s, 3H), 2.42 (s, 3H), 3.28 (s, 3H), 3.726 (s, 3H), 3.728 (s, 3H), 4.39 (s, 2H), 5.21 (s, 2H), 6.82 (dd, J=2.0 Hz, 8.0 Hz, 1H), 6.90 (m, 2H), 7.83 (d, J=0.4 Hz,1H), 8.22 (d, J=0.4 Hz, 1H). MS 452 (MH+). The title compound was shown to inhibit hT2R08 bitter receptor and had an IC$_{50}$ of 0.02 µM.

Example 12-13a methyl 1-(3,4-dimethoxybenzylamino)cyclopropanecarboxylate

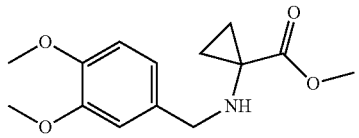

Prepared as in Example 12-1b from 3,4-dimethoxybenzaldehyde and methyl 1-aminocyclopropanecarboxylate hydrochloride. Yield 82%. MS 266 (MH+).

Example 12-14

6-(1-((3,5-dimethylisoxazol-4-yl)methyl)-1H-pyrazol-4-yl)-4-(3-(methoxymethyl)benzyl)-4,6-diazaspiro[2.4]heptane-5,7-dione

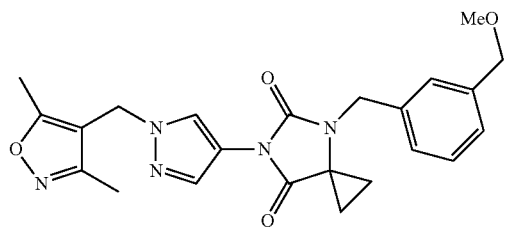 [SMILES: COCc1cccc(CN2C(=O)N(c3cnn(Cc4c(C)noc4C)c3)C(=O)C23CC3)c1]

Prepared as in Example 12-12a from methyl 1-(3-(methoxymethyl)benzylamino)cyclopropanecarboxylate (Example 12-14a) and 1-((3,5-dimethylisoxazol-4-yl)methyl)-1H-pyrazole-4-carbonyl azide (Example 10-1a). Yield 81%. 1H NMR (DMSO-D6, 400 MHz): δ 1.22 (m, 2H), 1.38 (m, 2H), 2.16 (s, 3H), 2.42 (s, 3H), 3.28 (s, 3H), 4.39 (s, 2H), 4.47 (s, 2H), 5.21 (s, 2H), 7.22 (m, 3H), 7.33 (t, J=7.6 Hz, 1H), 7.83 (d, J=0.8 Hz,1H), 8.22 (d, J=0.8 Hz, 1H). MS 436 (MH+). The title compound was shown to inhibit hT2R08 bitter receptor and had an IC50 of 0.03 µM

Example 12-14a methyl 1-(3-(methoxymethyl)benzylamino)cyclopropanecarboxylate

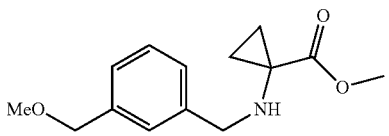 [SMILES: COCc1cccc(CNC2(C(=O)OC)CC2)c1]

Prepared as in Example 12-1b from 3-(methoxymethyl)benzaldehyde (Example 12-14b) and methyl 1-aminocyclopropanecarboxylate hydrochloride. Yield 82%. MS 250 (MH+).

Example 12-14b 3-(methoxymethyl)benzaldehyde

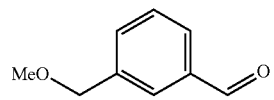

3-(bromomethyl)benzaldehyde (1.00 g, 5.02 mmol) was dissolved in MeOH (100 mL) and treated with 0.5M solution of MeONa (5 equiv.) in MeOH. The mixture was stirred overnight at RT and MeOH was evaporated under reduced pressure. The residue was acidified to pH~6 with 1M aqueous HCl solution. DCM (100 mL) was added and the mixture was vigorously stirred overnight. The organic layer was separated, dried over Na$_2$SO$_4$ and the solvent was removed under reduce pressure to furnish the desired material as yellowish oil (560 mg, 3.75 mmol, 74%). $^1$H NMR (DMSO, 400 MHz): δ 3.33 (s, 3H), 4.51 (s, 1H), 7.62 (m, 2H), 7.85 (m, 2H), 10.02 (s, 1H). MS 151 (MH+).

Example 12-15

6-(1-((3,5-dimethylisoxazol-4-yl)methyl)-1H-pyrazol-4-yl)-4-(3-hydroxybenzyl)-4,6-diazaspiro[2.4]heptane-5,7-dione

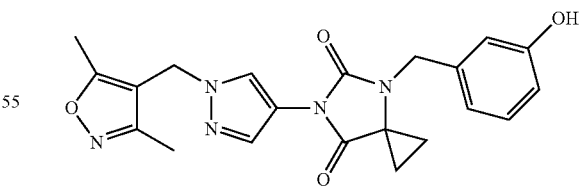

Prepared as in Example 12-1 from 4-(3-(tert-butyldimethylsilyloxy)benzyl)-6-(1-((3,5-dimethylisoxazol-4-yl)methyl)-1H-pyrazol-4-yl)-4,6-diazaspiro[2.4]heptane-5,7-dione (Example 12-15a). Yield 70%, white solid. $^1$H NMR (DMSO-d$_6$, 400 MHz): δ 1.21 (m, 2H), 1.38 (m, 2H), 2.14 (s, 3H), 2.40 (s, 3H), 4.36 (s, 2H), 5.19 (s, 2H), 6.65 (m, 3H), 7.11 (dt, J=1.2, 7.6 Hz, 1H), 7.81 (d, J=0.8 Hz, 1H), 8.21 (d, J=0.8

Hz, 1H), 9.41 (s, H). [MS 408 (MH+). The title compound was shown to inhibit hT2R08 bitter receptor and had an IC$_{50}$ of 0.02 μM

Example 12-15a 4-(3-(tert-butyldimethylsilyloxy)benzyl)-6-(1-((3,5-dimethylisoxazol-4-yl)methyl)-1H-pyrazol-4-yl)-4,6-diazaspiro[2.4]heptane-5,7-dione

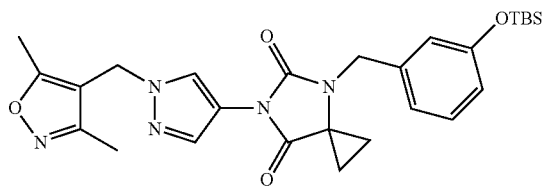 [SMILES: Cc1noc(C)c1Cn1cc(N2C(=O)N(Cc3cccc(O[Si](C)(C)C(C)(C)C)c3)C3(CC3)C2=O)cn1]

Prepared as in Example 12-1a from ethyl 1-(3-(tert-butyldimethylsilyloxy)benzylamino)cyclopropanecarboxylate (Example 12-15b) and 1-((3,5-dimethylisoxazol-4-yl)methyl)-1H-pyrazole-4-carbonyl azide (Example 10-1a). Yield 15%. MS 522 (MH+).

Example 12-15b ethyl 1-(3-(tert-butyldimethylsilyloxy)benzylamino)-cyclopropanecarboxylate

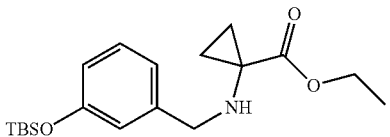 [SMILES: CCOC(=O)C1(NCc2cccc(O[Si](C)(C)C(C)(C)C)c2)CC1]

Prepared as in Example 12-1b from 3-(tert-butyldimethylsilyloxy)benzaldehyde (Example 12-1c) and ethyl 1-aminocyclopropanecarboxylate hydrochloride. Yield 87%, colorless liquid. MS 350 (MH+).

Example 12-16

4-((3-(1-((3,5-dimethylisoxazol-4-yl)methyl)-1H-pyrazol-4-yl)-5,5-dimethyl-2,4-dioxoimidazolidin-1-yl)methyl)benzonitrile

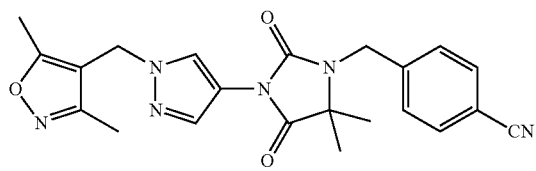 [SMILES: Cc1noc(C)c1Cn1cc(N2C(=O)N(Cc3ccc(C#N)cc3)C(C)(C)C2=O)cn1]

3-(1-((3,5-dimethylisoxazol-4-yl)methyl)-1H-pyrazol-4-yl)-5,5-dimethylimidazolidine-2,4-dione (Example 12-16a) (250 mg, 0.83 mmol), 4-(chloromethyl)benzonitrile (126 mg, 0.83 mmol), and cesium carbonate (536 mg, 1.65 mmol) were stirred in dimethylformamide (4 mL) at 80° C. for 5 hours. The reaction was allowed to cool to room temperature and then filtered. The filtrate was diluted with ethyl acetate (4 mL) and then water (2 mL) was added. The organic phase was collected, dried over anhydrous Na2SO4, and then concentrated under reduced pressure. The residue was purified by reverse phase HPLC (gradient 10% to 100% methanol in water) and further recrystallized from ethanol. Yield 30%. $^1$H NMR (DMSO-d6, 400 MHz): δ$_1$ s, 6H), 2.15 (s, 3H), 2.42 (s, 3H), 4.65 (s, 2H), 5.20 (s, 2H), 7.60 (d, J=8.4 Hz, 2H), 7.81 (m, 3H), 8.20 (d, J=0.8 Hz, 1H). MS 419 (MH+). The title compound was shown to inhibit hT2R08 bitter receptor and had an IC50 of 0.04 μM

Example 12-16a 3-(1-((3,5-dimethylisoxazol-4-yl)methyl)-1H-pyrazol-4-yl)-5,5-dimethylimidazolidine-2,4-dione

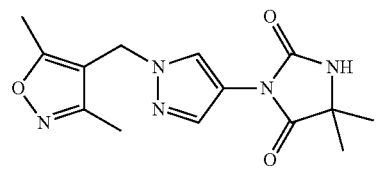 [SMILES: Cc1noc(C)c1Cn1cc(N2C(=O)NC(C)(C)C2=O)cn1]

1-((3,5-dimethylisoxazol-4-yl)methyl)-1H-pyrazole-4-carbonyl azide (Example 10-1a) (10 g, 41.0 mmol) is stirred under nitrogen in dry toluene (150 mL) along with molecular sieves at reflux until no emission of nitrogen was observed, which indicates complete conversion of 1-((3,5-dimethylisoxazol-4-yl)methyl)-1H-pyrazole-4-carbonyl azide into 4-((4-isocyanato-1H-pyrazol-1-yl)methyl)-3,5-dimethylisoxazole. The solution was cooled down to 50° C. and ethyl 2-amino-2-methylpropanoate hydrochloride (5.30 g, 41.0 mmol) was added in one portion. Stirring continued for 3 hours at 50° C. followed by reflux for 12 hours. The mixture was filtered over a pad of celite. The filtrate was concentrated on the rotovap and the residue was purified over silica gel using 25% ethyl acetate in hexanes. Yield 65% (8.00 g), white solid. $^1$H NMR (DMSO-d6, 400 MHz): δ$_1$ s, 6H), 2.15 (s, 3H), 2.41 (s, 3H), 5.18 (s, 2H), 7.78 (d, J=0.4 Hz, 1H), 8.16 (d, J=0.4 Hz, 1H), 8.59 (br s, 1H). MS 304 (MH+). This compound was shown to inhibit hT2R08 bitter receptor and had an IC50 of 2.27 μM.

Example 12-17

3-(1-((3,5-dimethylisoxazol-4-yl)methyl)-1H-pyrazol-4-yl)-1-(3-hydroxy-5-methoxybenzyl)-5,5-dimethylimidazolidine-2,4-dione

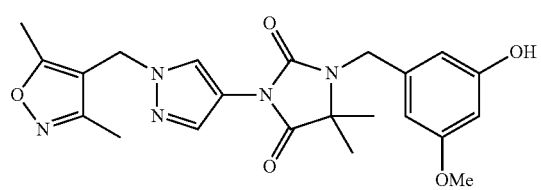 [SMILES: COc1cc(O)cc(CN2C(=O)N(c3cnn(Cc4c(C)noc4C)c3)C(=O)C2(C)C)c1]

1-(3,5-dimethoxybenzyl)-3-(1-((3,5-dimethylisoxazol-4-yl)methyl)-1H-pyrazol-4-yl)-5,5-dimethylimidazolidine-2,4-dione (Example 12-18) (114 mg, 0.252 mmol) was dissolved in dichloromethane (1 mL). The mixture was cooled down to −78° C. and boron tribromide (1.0 M solution in dichloromethane, 1.25 mL) was added dropwise. After complete addition, the mixture was allowed to warm to room temperature and stirring continued for 3 hours. The mixture was quenched with water and the organic phase was separated, dried over anhydrous $Na_2SO_4$, filtered and evaporated under reduced pressure. The residue was suspended in methanol (1 mL) and purified by reverse phase HPLC (25 minute gradient: acetonitrile/water). Yield 47% (45 mg), white solid. $^1$H NMR (DMSO-$d_6$, 400 MHz): $\delta_1$ s, 6H), 2.16 (s, 3H), 2.42 (s, 3H), 3.67 (s, 3H), 4.43 (s, 2H), 5.20 (s, 2H), 6.22 (t, J=2.4 Hz, 1H), 6.39 (m, 2H), 7.83 (d, J=0.4 Hz, 1H), 8.21 (s, 1H), 9.40 (br s, 1H). Mp. 72-74° C. MS 440 (MH$^+$). The title compound was shown to inhibit hT2R08 bitter receptor and had an IC$_{50}$ of 0.02 μM.

Example 12-18

1-(3,5-dimethoxybenzyl)-3-(1-((3,5-dimethylisoxazol-4-yl)methyl)-1H-pyrazol-4-yl)-5,5-dimethylimidazolidine-2,4-dione

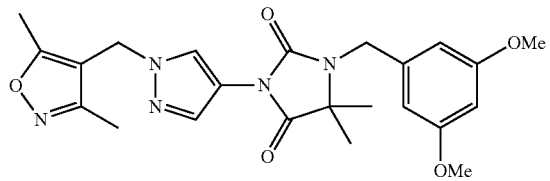 [SMILES: COc1cc(CN2C(=O)N(c3cnn(Cc4c(C)noc4C)c3)C(=O)C2(C)C)cc(OC)c1]

Prepared as in Example 12-16 from 3-(1-((3,5-dimethyl-isoxazol-4-yl)methyl)-1H-pyrazol-4-yl)-5,5-dimethylimidazolidine-2,4-dione (Example 12-16a) and 1-(chloromethyl)-3,5-dimethoxybenzene. MS 454 (MH$^+$). The title compound was shown to inhibit hT2R08 bitter receptor and had an IC$_{50}$ of 0.3 μM.

Example 12-19

3-(1-((3,5-dimethylisoxazol-4-yl)methyl)-1H-pyrazol-4-yl)-1-(4-fluoro-3-hydroxybenzyl)-5,5-dimethylimidazolidine-2,4-dione

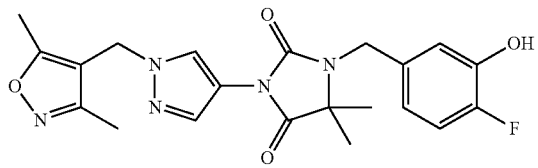 [SMILES: Cc1noc(C)c1Cn1cc(N2C(=O)N(Cc3ccc(F)c(O)c3)C(C)(C)C2=O)cn1]

Prepared as in Example 12-17 from 3-(1-((3,5-dimethyl-isoxazol-4-yl)methyl)-1H-pyrazol-4-yl)-1-(4-fluoro-3-methoxybenzyl)-5,5-dimethylimidazolidine-2,4-dione (Example 12-20). Yield 30%, white solid. MS 428 (MH$^+$). The title compound was shown to inhibit hT2R08 bitter receptor and had an IC$_{50}$ of 0.01 μM.

Example 12-20

3-(1-((3,5-dimethylisoxazol-4-yl)methyl)-1H-pyrazol-4-yl)-1-(4-fluoro-3-methoxybenzyl)-5,5-dimethylimidazolidine-2,4-dione

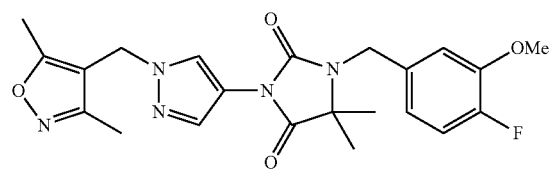 [SMILES: COc1cc(CN2C(=O)N(c3cnn(Cc4c(C)noc4C)c3)C(=O)C2(C)C)ccc1F]

Prepared as in Example 12-16 from 3-(1-((3,5-dimethyl-isoxazol-4-yl)methyl)-1H-pyrazol-4-yl)-5,5-dimethylimidazolidine-2,4-dione (Example 12-16a) and 4-(chloromethyl)-1-fluoro-2-methoxybenzene. MS 442 (MH$^+$). The title compound was shown to inhibit hT2R08 bitter receptor and had an IC$_{50}$ of 0.18 μM.

Example 12-21

1-((3,5-dimethylisoxazol-4-yl)methyl)-3-(1-((3,5-dimethylisoxazol-4-yl)methyl)-1H-pyrazol-4-yl)-5,5-dimethylimidazolidine-2,4-dione

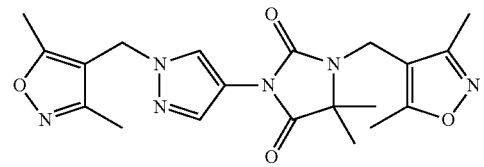 [SMILES: Cc1noc(C)c1CN1C(=O)N(c2cnn(Cc3c(C)noc3C)c2)C(=O)C1(C)C]

Prepared as in Example 12-16 from 3-(1-((3,5-dimethyl-isoxazol-4-yl)methyl)-1H-pyrazol-4-yl)-5,5-dimethylimidazolidine-2,4-dione (Example 12-16a) and 4-(chloromethyl)-3,5-dimethylisoxazole. MS 413 (MH$^+$). The title compound was shown to inhibit hT2R08 bitter receptor and had an IC$_{50}$ of 0.08 μM.

Example 12-22

3-(1-((3,5-dimethylisoxazol-4-yl)methyl)-1H-pyrazol-4-yl)-5,5-dimethyl-1-(2-methylbenzyl)imidazolidine-2,4-dione

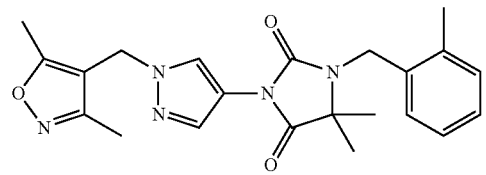 [SMILES: Cc1ccccc1CN1C(=O)N(c2cnn(Cc3c(C)noc3C)c2)C(=O)C1(C)C]

Prepared as in Example 12-16 from 3-(1-((3,5-dimethyl-isoxazol-4-yl)methyl)-1H-pyrazol-4-yl)-5,5-dimethylimidazolidine-2,4-dione (Example 12-16a) and 1-(bromomethyl)-2-methylbenzene. MS 408 (MH+). The title compound was shown to inhibit hT2R08 bitter receptor and had an IC$_{50}$ of 0.1 µM.

Example 12-23

3-(1-((3,5-dimethylisoxazol-4-yl)methyl)-1H-pyrazol-4-yl)-1-(4-methoxyphenethyl)-5,5-dimethylimidazolidine-2,4-dione

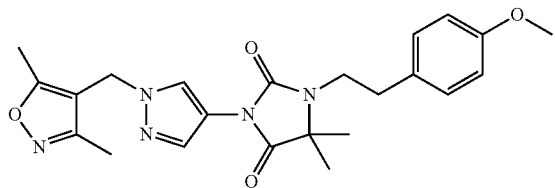 [SMILES: COc1ccc(CCN2C(=O)N(c3cnn(Cc4c(C)noc4C)c3)C(=O)C2(C)C)cc1]

Prepared as in Example 12-16 from 3-(1-((3,5-dimethylisoxazol-4-yl)methyl)-1H-pyrazol-4-yl)-5,5-dimethylimidazolidine-2,4-dione (Example 12-16a) and 1-(2-bromoethyl)-4-methoxybenzene. MS 438 (MH+). The title compound was shown to inhibit hT2R08 bitter receptor and had an IC$_{50}$ of 0.12 µM.

Example 12-24

3-(1-((3,5-dimethylisoxazol-4-yl)methyl)-1H-pyrazol-4-yl)-5,5-dimethyl-1-(1-phenylethyl)imidazolidine-2,4-dione

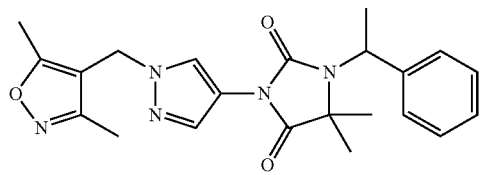 [SMILES: Cc1noc(C)c1Cn1cc(N2C(=O)N(C(C)c3ccccc3)C(C)(C)C2=O)cn1]

Prepared as in Example 16 from 3-(1-((3,5-dimethylisoxazol-4-yl)methyl)-1H-pyrazol-4-yl)-5,5-dimethylimidazolidine-2,4-dione (Example 16a) and (1-bromoethyl)benzene. MS 408 (MH+). The title compound was shown to inhibit hT2R08 bitter receptor and had an IC$_{50}$ of 0.15 µm.

Example 12-25

1-((1,5-dimethyl-1H-pyrazol-3-yl)methyl)-3-(1-((3,5-dimethylisoxazol-4-yl)methyl)-1H-pyrazol-4-yl)-5,5-dimethylimidazolidine-2,4-dione

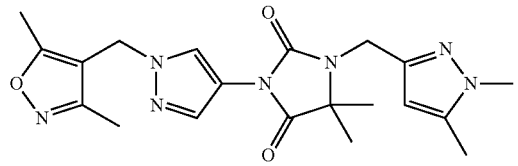 [SMILES: Cc1noc(C)c1Cn1cc(N2C(=O)N(Cc3cc(C)n(C)n3)C(C)(C)C2=O)cn1]

Prepared as in Example 12-16 from 3-(1-((3,5-dimethylisoxazol-4-yl)methyl)-1H-pyrazol-4-yl)-5,5-dimethylimidazolidine-2,4-dione (Example 12-16a) and 3-(chloromethyl)-1,5-dimethyl-1H-pyrazole. MS 412 (MH+). The title compound was shown to inhibit hT2R08 bitter receptor and had an IC$_{50}$ of 0.16 µM.

Example 12-26

1-((1,3-dimethyl-1H-pyrazol-5-yl)methyl)-3-(1-((3,5-dimethylisoxazol-4-yl)methyl)-1H-pyrazol-4-yl)-5,5-dimethylimidazolidine-2,4-dione

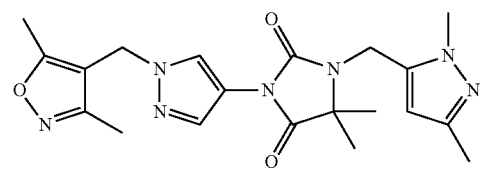 [SMILES: Cc1cc(CN2C(=O)N(c3cnn(Cc4c(C)noc4C)c3)C(=O)C2(C)C)n(C)n1]

Prepared as in Example 12-16 from 3-(1-((3,5-dimethylisoxazol-4-yl)methyl)-1H-pyrazol-4-yl)-5,5-dimethylimidazolidine-2,4-dione (Example 12-16a) and 5-(chloromethyl)-1,3-dimethyl-1H-pyrazole. MS 412 (MH+). The title compound was shown to inhibit hT2R08 bitter receptor and had an IC50 of 0.23 µM.

Example 12-27

3-(1-((3,5-dimethylisoxazol-4-yl)methyl)-1H-pyrazol-4-yl)-5,5-dimethyl-1-(2-phenoxyethyl)imidazolidine-2,4-dione

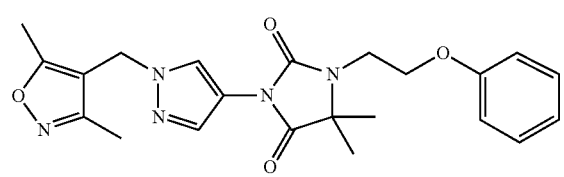 [SMILES: Cc1noc(C)c1Cn1cc(N2C(=O)N(CCOc3ccccc3)C(C)(C)C2=O)cn1]

Prepared as in Example 12-16 from 3-(1-((3,5-dimethylisoxazol-4-yl)methyl)-1H-pyrazol-4-yl)-5,5-dimethylimidazolidine-2,4-dione (Example 12-16a) and (2-bromoethoxy)benzene. MS 424 (MH+). The title compound was shown to inhibit hT2R08 bitter receptor and had an IC$_{50}$ of 0.35 µM.

Example 12-28

3-(1-((3,5-dimethylisoxazol-4-yl)methyl)-1H-pyrazol-4-yl)-1-(2-methoxyethyl)-5,5-dimethylimidazolidine-2,4-dione

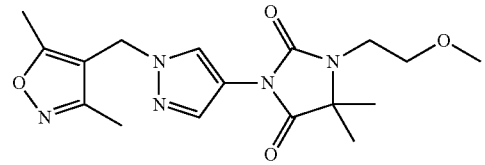 [SMILES: COCCN1C(=O)N(c2cnn(Cc3c(C)noc3C)c2)C(=O)C1(C)C]

Prepared as in Example 12-16 from 3-(1-((3,5-dimethylisoxazol-4-yl)methyl)-1H-pyrazol-4-yl)-5,5-dimethylimidazolidine-2,4-dione (Example 12-16a) and 1-bromo-2-methoxyethane. MS 362 (MH+). The title compound was shown to inhibit hT2R08 bitter receptor and had an IC$_{50}$ of 0.59 μM.

Example 12-29

3-(1-((3,5-dimethylisoxazol-4-yl)methyl)-1H-pyrazol-4-yl)-1-(4-fluorobenzyl)-5,5-dimethylimidazolidine-2,4-dione

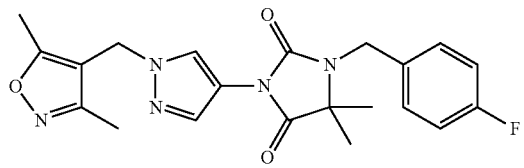 [SMILES: Cc1noc(C)c1Cn1cc(N2C(=O)N(Cc3ccc(F)cc3)C(C)(C)C2=O)cn1]

Prepared as in Example 12-16 from 3-(1-((3,5-dimethylisoxazol-4-yl)methyl)-1H-pyrazol-4-yl)-5,5-dimethylimidazolidine-2,4-dione (Example 12-16a) and 1-(bromomethyl)-4-fluorobenzene. Yield 40%, white solid. $^1$H NMR (DMSO-d$_6$, 400 MHz): δ$_1$ ~ s, 6H), 2.14 (s, 3H), 2.40 (s, 3H), 4.53 (s, 2H), 5.18 (s, 2H), 7.13 (m, 2H) 7.43 (m, 2H), 7.81 (s, H), 8.18 (s, 1H). MS 412 (MH+). The title compound was shown to inhibit hT2R08 bitter receptor and had an IC50 of 0.08 μM.

Example 12-30

1-(3,4-dimethoxybenzyl)-3-(1-((3,5-dimethylisoxazol-4-yl)methyl)-1H-pyrazol-4-yl)-5,5-dimethylimidazolidine-2,4-dione

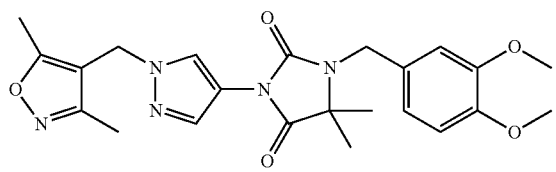 [SMILES: COc1ccc(CN2C(=O)N(c3cnn(Cc4c(C)noc4C)c3)C(=O)C2(C)C)cc1OC]

Prepared as in Example 12-16 from 3-(1-((3,5-dimethylisoxazol-4-yl)methyl)-1H-pyrazol-4-yl)-5,5-dimethylimidazolidine-2,4-dione (Example 12-16a) and 4-(bromomethyl)-1,2-dimethoxybenzene. Yield 67%, white solid. $^1$H NMR (DMSO-d$_6$, 400 MHz): δ$_1$ ~ s, 6H), 2.16 (s, 3H), 2.42 (s, 3H), 3.72 (s, 3H), 3.73 (s, 3H), 4.49 (s, 2H), 5.20 (s, 2H) 6.92 (m, 2H), 7.00 (d, J=2.0 Hz, 1H), 7.83 (d, J=0.4 Hz, 1H), 8.20 (d, J=0.4 Hz, 1H). MS 454 (MH+). The title compound was shown to inhibit hT2R08 bitter receptor and had an IC50 of 0.08 μM.

Example 12-31

3-(1-((3,5-dimethylisoxazol-4-yl)methyl)-1H-pyrazol-4-yl)-1-(2-methoxybenzyl)-5,5-dimethylimidazolidine-2,4-dione

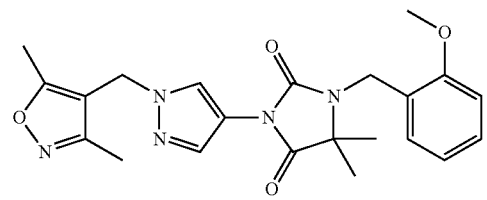 [SMILES: COc1ccccc1CN1C(=O)N(c2cnn(Cc3c(C)noc3C)c2)C(=O)C1(C)C]

Prepared as in Example 12-16 from 3-(1-((3,5-dimethylisoxazol-4-yl)methyl)-1H-pyrazol-4-yl)-5,5-dimethylimidazolidine-2,4-dione (Example 12-16a) and 1-(bromomethyl)-2-methoxybenzene. Yield 53%, white solid. $^1$H NMR (DMSO-d$_6$, 400 MHz): δ$_1$ ~ s, 6H), 2.16 (s, 3H), 2.42 (s, 3H), 3.83 (s, 3H), 4.50 (s, 2H), 5.20 (s, 2H), 6.91 (dt, J=1.2, 7.6 Hz, 1H) 7.00 (dd, J=0.8, 8.0 Hz, 1H), 7.27 (m, 2H), 7.82 (d, J=0.8 Hz, 1H), 8.20 (d, J=0.8 Hz, 1H). MS 424 (MH+). The title compound was shown to inhibit hT2R08 bitter receptor and had an IC50 of 0.08 μM.

Example 12-32

3-(1-((3,5-dimethylisoxazol-4-yl)methyl)-1H-pyrazol-4-yl)-1-(3-methoxybenzyl)-5,5-dimethylimidazolidine-2,4-dione

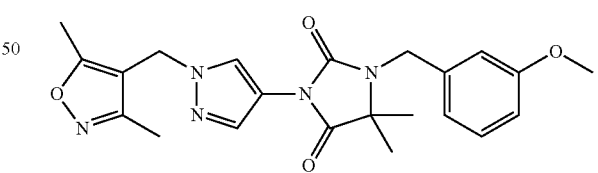

Prepared as in Example 12-16 from 3-(1-((3,5-dimethylisoxazol-4-yl)methyl)-1H-pyrazol-4-yl)-5,5-dimethylimidazolidine-2,4-dione (Example 12-16a) and 1-(bromomethyl)-3-methoxybenzene. Yield 30%, white solid. $^1$H NMR (DMSO-d$_6$, 400 MHz): δ$_1$ ₁ s, 6H), 2.16 (s, 3H), 2.42 (s, 3H), 3.74 (s, 3H), 4.53 (s, 2H), 5.20 (s, 2H), 6.83 (m, 1H) 6.96 (m, 2H), 7.25 (t, J=8.0 Hz, 1H), 7.83 (d, J=0.8 Hz, 1H), 8.21 (d, J=0.8 Hz, 1H). mp 107-108° C. MS 424 (MH⁺). The title compound was shown to inhibit hT2R08 bitter receptor and had an $IC_{50}$ of 0.08 μM.

Example 12-33

3-(1-((3,5-dimethylisoxazol-4-yl)methyl)-1H-pyrazol-4-yl)-1-(4-methoxybenzyl)-5,5-dimethylimidazolidine-2,4-dione

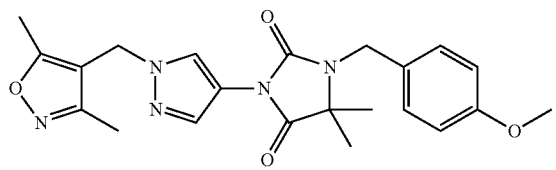 [SMILES: COc1ccc(CN2C(=O)N(c3cnn(Cc4c(C)noc4C)c3)C(=O)C2(C)C)cc1]

Prepared as in Example 12-16 from 3-(1-((3,5-dimethylisoxazol-4-yl)methyl)-1H-pyrazol-4-yl)-5,5-dimethylimidazolidine-2,4-dione (Example 12-16a) and 1-(bromomethyl)-4-methoxybenzene. Yield 35%, colorless gel (195 mg, 35%). ¹H NMR (DMSO-d₆, 400 MHz): δ₁ s, 6H), 2.14 (s, 3H), 2.40 (s, 3H), 3.71 (s, 3H), 4.48 (s, 2H), 5.18 (s, 2H) 6.87 (d, J=8.8 Hz, 2H), 7.31 (d, J=8.4 Hz, 2H), 7.80 (s, 1H), 8.18 (s, 1H). MS 424 (MH+). The title compound was shown to inhibit hT2R08 bitter receptor and had an IC50 of 0.11 μM.

Example 12-34

3-(1-((3,5-dimethylisoxazol-4-yl)methyl)-1H-pyrazol-4-yl)-1-(3-(hydroxymethyl)benzyl)-5,5-dimethylimidazolidine-2,4-dione

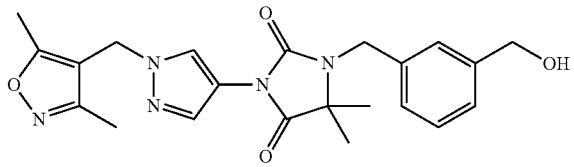 [SMILES: Cc1noc(C)c1Cn1cc(N2C(=O)N(Cc3cccc(CO)c3)C(C)(C)C2=O)cn1]

Prepared as in Example 12-16 from 3-(1-((3,5-dimethylisoxazol-4-yl)methyl)-1H-pyrazol-4-yl)-5,5-dimethylimidazolidine-2,4-dione (Example 12-16a) and (3-(bromomethyl)phenyl)metanol. Yield 70%, white solid. ¹H NMR (DMSO-d₆, 400 MHz): δ1.29 (s, 6H), 2.14 (s, 3H), 2.40 (s, 3H), 4.47 (d, J=6.0 Hz, 2H), 4.54 (s, 2H), 5.15 (t, J=5.6 Hz, 1H) 5.2 (s, 2H), 7.25 (m, 3H), 7.32 (s, 1H), 7.82 (s, 1H) 8.20 (s, 1H). MS 424 (MH⁺). The title compound was shown to inhibit hT2R08 bitter receptor and had an $IC_{50}$ of 0.11 μM.

Example 12-35

3-(1-((3,5-dimethylisoxazol-4-yl)methyl)-1H-pyrazol-4-yl)-1-(3-(methoxymethyl)benzyl)-5,5-dimethylimidazolidine-2,4-dione

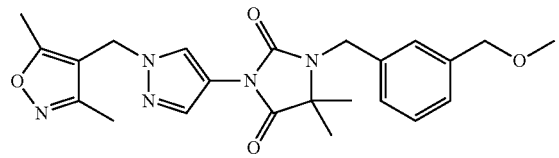 [SMILES: COCc1cccc(CN2C(=O)N(c3cnn(Cc4c(C)noc4C)c3)C(=O)C2(C)C)c1]

To a solution of 3-(1-((3,5-dimethylisoxazol-4-yl)methyl)-1H-pyrazol-4-yl)-1-(3-(hydroxymethyl)benzyl)-5,5-dimethylimidazolidine-2,4-dione (Example 12-34) (559 mg, 1.32 mmol) in anhydrous dimethylformamide (10 mL) at 0° C., was added sodium hydride (53 mg, 1.32 mmol), followed by iodomethane (99 ul, 1.58 mmol). The reaction was allowed to warm to room temperature and stirred for about 4 hours. The resulting mixture was diluted with ethyl acetate (40 mL) and ice water (10 mL), The organic phase was collected, dried over anhydrous MgSO₄, filtered and then concentrated on the rotovap. The residue was purified by reverse phase HPLC (gradient 10% to 100% methanol/water) and further purified by column chromatography (60% EtOAc in hexane). Yield 36%, colorless gel. ¹H NMR (DMSO-d₆, 400 MHz): δ1.29 (s, 6H), 2.14 (s, 3H), 2.40 (s, 3H), 3.25 (s, 3H), 4.37 (s, 2H), 4.55 (s, 2H), 5.18 (s, 2H), 7.19 (t, 1H) 7.30 (d, 2H), 7.32 (s, 1H), 7.82 (s, 1H) 8.20 (s, 1H). MS 438 (MH⁺). The title compound was shown to inhibit hT2R08 bitter receptor and had an $IC_{50}$ of 0.13 μM.

Example 12-36

3-(1-((3,5-dimethylisoxazol-4-yl)methyl)-1H-pyrazol-4-yl)-5,5-dimethyl-1-(pyridin-3-ylmethyl)imidazolidine-2,4-dione

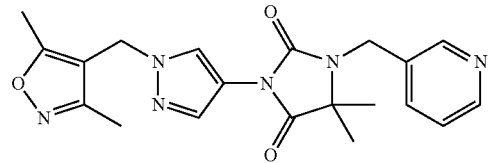 [SMILES: Cc1noc(C)c1Cn1cc(N2C(=O)N(Cc3cccnc3)C(C)(C)C2=O)cn1]

Prepared as in Example 12-1a from ethyl 2-methyl-2-(pyridin-3-ylmethylamino)propanoate (Example 12-36a) and 1-((3,5-dimethylisoxazol-4-yl)methyl)-1H-pyrazole-4-carbonyl azide (Example 10-1a). Yield 47%, white a solid. ¹H NMR (CDCl₃, 400 MHz): δ 1.36 (s, 6H), 2.18 (s, 3H), 2.41 (s, 3H), 4.57 (s, 2H), 5.04 (s, 2H), 7.27 (m, 1H), 7.74 (m, 1H), 7.94 (d, J=0.4 Hz, 1H), 8.09 (d, J=0.4 Hz, 1H), 8.54 (br. d, J=4.0 Hz, 1H), 8.59 (br. S, 1H). MS 395 (MH+). The title compound was shown to inhibit hT2R08 bitter receptor and had an IC$_{50}$ of 0.22 μM.

Example 12-36a ethyl 2-methyl-2-(pyridin-3-ylmethylamino)propanoate

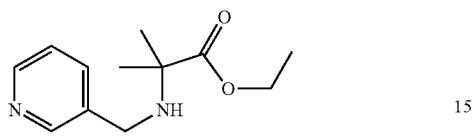

Prepared as in Example 12-1b from nicotinaldehyde and ethyl 1-aminocyclopropanecarboxylate hydrochloride. Yield 95%, a white solid. MS 223 (MH+).

Example 12-37

(R)-1-benzyl-3-(1-((3,5-dimethylisoxazol-4-yl)methyl)-1H-pyrazol-4-yl)-5-methylimidazolidine-2,4-dione

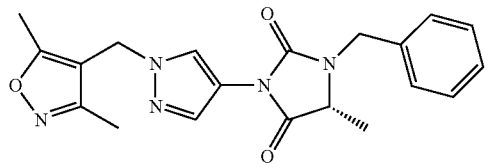 [SMILES: Cc1noc(C)c1Cn1cc(N2C(=O)[C@@H](C)N(Cc3ccccc3)C2=O)cn1]

Prepared as in Example 12-1a from (R)-methyl 2-(benzylamino)propanoate (Example 12-37a) and 1-((3,5-dimethylisoxazol-4-yl)methyl)-1H-pyrazole-4-carbonyl azide (Example 10-1a). Yield 89%. MS 380 (MH+). The title compound was shown to inhibit hT2R08 bitter receptor and had an IC$_{50}$ of 0.01 μM.

Example 12-37a (R)-methyl 2-(benzylamino)propanoate

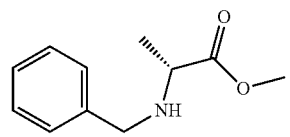

Prepared as in Example 12-1b from benzaldehyde and (R)-methyl 2-aminopropanoate hydrochloride Yield 95%. MS 194 (MH+).

Additional compounds were synthesized according to the above described procedures and experimentally tested and were found to have relatively high effectiveness as inhibitors of hT2R8 bitter receptors. The results of that testing are shown in the table below.

| Compound No. | Compound | hT2R8 IC$_{50}$ (μM) |
| --- | --- | --- |
| 12-38 | 3-(1-((3,5-dimethylisoxazol-4-yl)methyl)-1H-pyrazol-4-yl)-1-(4-hydroxybenzyl)-5,5-dimethylimidazolidine-2,4-dione | 0.07 |
| 12-39 | 3-(1-((3,5-dimethylisoxazol-4-yl)methyl)-1H-pyrazol-4-yl)-1-(2-hydroxybenzyl)-5,5-dimethylimidazolidine-2,4-dione | 0.07 |

-continued

| Compound No. | Compound | hT2R8 IC$_{50}$ (μM) |
|---|---|---|
| 12-40 | 3-(1-((3,5-dimethylisoxazol-4-yl)methyl)-1H-pyrazol-4-yl)-1-((6-methoxypyridin-2-yl)methyl)-5,5-dimethylimidazolidine-2,4-dione | 0.08 |
| 12-41 | 3-(1-((3,5-dimethylisoxazol-4-yl)methyl)-1H-pyrazol-4-yl)-1-((6-methoxypyridin-2-yl)methyl)-5,5-dimethylimidazolidine-2,4-dione | 0.08 |
| 12-42 | 3-((3-(1-((3,5-dimethylisoxazol-4-yl)methyl)-1H-pyrazol-4-yl)-5,5-dimethyl-2,4-dioxoimidazolidin-1-yl)methyl)benzonitrile | 0.09 |
| 12-43 | 1-(2,3-dihydroxybenzyl)-3-(1-((3,5-dimethylisoxazol-4-yl)methyl)-1H-pyrazol-4-yl)-5,5-dimethylimidazolidine-2,4-dione | 0.10 |
| 12-44 | 1-(2,6-difluorobenzyl)-3-(1-((3,5-dimethylisoxazol-4-yl)methyl)-1H-pyrazol-4-yl)-5,5-dimethylimidazolidine-2,4-dione | 0.10 |

-continued

| Compound No. | Compound | hT2R8 IC$_{50}$ (μM) |
|---|---|---|
| 12-45 | 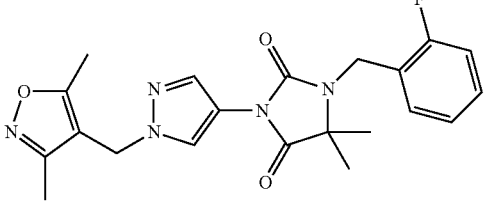<br>3-(1-((3,5-dimethylisoxazol-4-yl)methyl)-1H-pyrazol-4-yl)-1-(2-fluorobenzyl)-5,5-dimethylimidazolidine-2,4-dione | 0.11 |
| 12-46 | 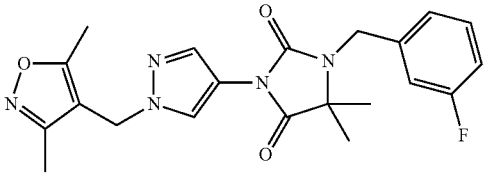<br>3-(1-((3,5-dimethylisoxazol-4-yl)methyl)-1H-pyrazol-4-yl)-1-(2-fluorobenzyl)-5,5-dimethylimidazolidine-2,4-dione | 0.12 |
| 12-47 | 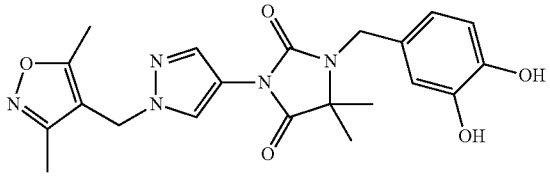<br>3-(1-((3,5-dimethylisoxazol-4-yl)methyl)-1H-pyrazol-4-yl)-1-(2-fluorobenzyl)-5,5-dimethylimidazolidine-2,4-dione | 0.12 |
| 12-48 | 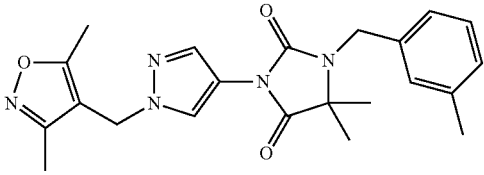<br>3-(1-((3,5-dimethylisoxazol-4-yl)methyl)-1H-pyrazol-4-yl)-5,5-dimethyl-1-(3-methylbenzyl)imidazolidine-2,4-dione | 0.12 |
| 12-49 | 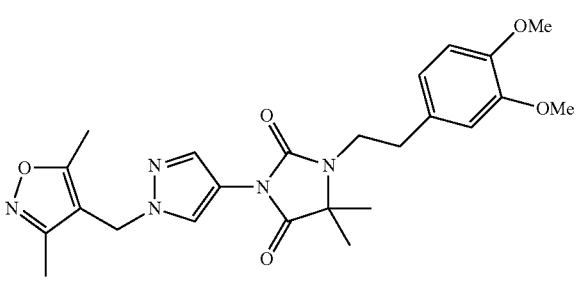<br>1-(3,4-dimethoxyphenethyl)-3-(1-((3,5-dimethylisoxazol-4-yl)methyl)-1H-pyrazol-4-yl)-5,5-dimethylimidazolidine-2,4-dione | 0.13 |

-continued

| Compound No. | Compound | hT2R8 IC$_{50}$ (μM) |
|---|---|---|
| 12-50 | 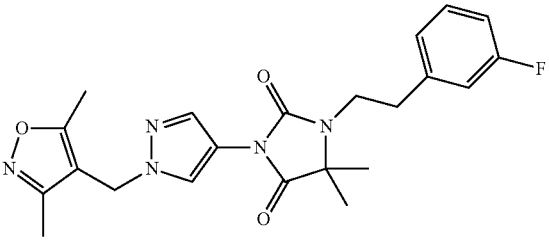<br>3-(1-((3,5-dimethylisoxazol-4-yl)methyl)-1H-pyrazol-4-yl)-1-(3-fluorophenethyl)-5,5-dimethylimidazolidine-2,4-dione | 0.15 |
| 12-51 | 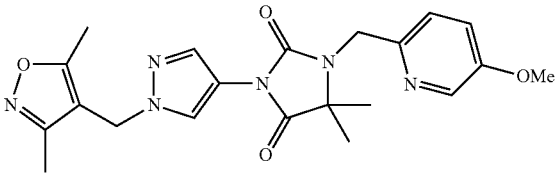<br>3-(1-((3,5-dimethylisoxazol-4-yl)methyl)-1H-pyrazol-4-yl)-1-(5-methoxypyridin-2-yl)methyl)-5,5-dimethylimidazolidine-2,4-dione | 0.19 |
| 12-52 | 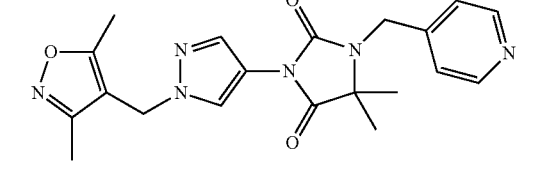<br>3-(1-((3,5-dimethylisoxazol-4-yl)methyl)-1H-pyrazol-4-yl)-5,5-dimethyl-1-(pyridin-4-ylmethyl)imidazolidine-2,4-dione | 0.19 |
| 12-53 | 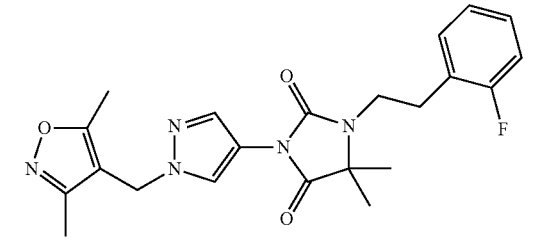<br>3-(1-((3,5-dimethylisoxazol-4-yl)methyl)-1H-pyrazol-4-yl)-1-(2-fluorophenethyl)-5,5-dimethylimidazolidine-2,4-dione | 0.20 |
| 12-54 | 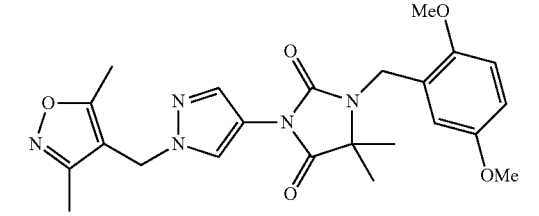<br>1-(2,5-dimethoxybenzyl)-3-(1-((3,5-dimethylisoxazol-4-yl)methyl)-1H-pyrazol-4-yl)-5,5-dimethylimidazolidine-2,4-dione | 0.20 |

| Compound No. | Compound | hT2R8 IC$_{50}$ (μM) |
|---|---|---|
| 12-55 | 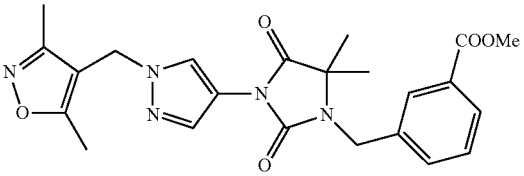<br>methyl 3-((3-(1-((3,5-dimethylisoxazol-4-yl)methyl)-1H-pyrazol-4-yl)-5,5-dimethyl-2,4-dioxoimidazolidin-1-yl)methyl)benzolate | 0.22 |
| 12-56 | 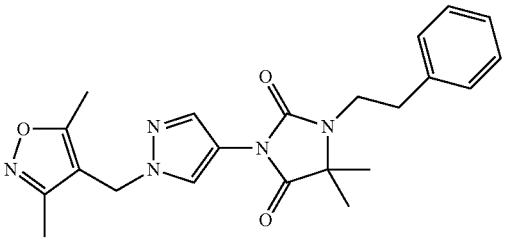<br>3-(1-((3,5-dimethylisoxazol-4-yl)methyl)-1H-pyrazol-4-yl)-5,5-dimethyl-1-phenethylimidazolidine-2,4-dione | 0.23 |
| 12-57 | 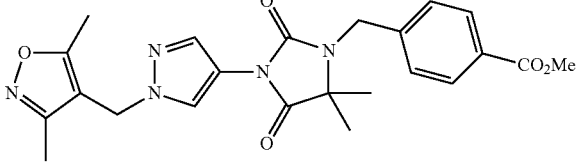<br>methyl 4-((3-(1-((3,5-dimethylisoxazol-4-yl)methyl)-1H-pyrazol-4-yl)-5,5-dimethyl-2,4-dioxoimidazolidin-1-yl)methyl)benzoate | 0.23 |
| 12-58 | 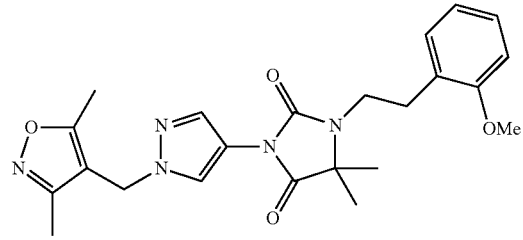<br>3-(1-((3,5-dimethylisoxazol-4-yl)methyl)-1H-pyrazol-4-yl)-1-(2-methoxyphenethyl)-5,5-dimethylimidazolidine-2,4-dione | 0.24 |
| 12-59 | 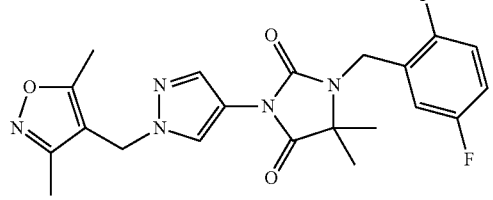<br>1-(2,5-difluorobenzyl)-3-(1-((3,5-dimethylisoxazol-4-yl)methyl)-1H-pyrazol-4-yl)-5,5-dimethylimidazolidine-2,4-dione | 0.24 |

| Compound No. | Compound | hT2R8 IC$_{50}$ (μM) |
|---|---|---|
| 12-60 | 3-(1-((3,5-dimethylisoxazol-4-yl)methyl)-1H-pyrazol-4-yl)-1-(3-methoxyphenethyl)-5,5-dimethylimidazolidine-2,4-dione | 0.25 |
| 12-61 | 3-(1-((3,5-dimethylisoxazol-4-yl)methyl)-1H-pyrazol-4-yl)-5,5-dimethyl-1-(pyridin-2-ylmethyl)imidazolidine-2,4-dione | 0.26 |
| 12-62 | 1-((2,3-dihydrobenzo[b][1,4]dioxin-6-yl)methyl)-3-(1-((3,5-dimethylisoxazol-4-yl)methyl)-1H-pyrazol-4-yl)-5,5-dimethylimidazolidine-2,4-dione | 0.27 |
| 12-63 | 3-(1-((3,5-dimethylisoxazol-4-yl)methyl)-1H-pyrazol-4-yl)-1-(3-(2-hydroxyethoxy)benzyl)-5,5-dimethylimidazolidine-2,4-dione | 0.28 |
| 12-64 | 1-(2,3-dimethoxybenzyl)-3-(1-((3,5-dimethylisoxazol-4-yl)methyl)-1H-pyrazol-4-yl)-5,5-dimethylimidazolidine-2,4-dione | 0.30 |

-continued

| Compound No. | Compound | hT2R8 IC$_{50}$ (μM) |
|---|---|---|
| 12-65 | 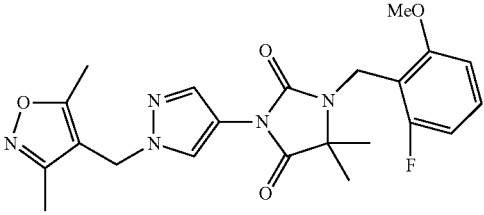<br>3-(1-((3,5-dimethylisoxazol-4-yl)methyl)-1H-pyrazol-4-yl)-1-(2-fluoro-6-methoxybenzyl)-5,5-dimethylimidazolidine-2,4-dione | 0.31 |
| 12-66 | 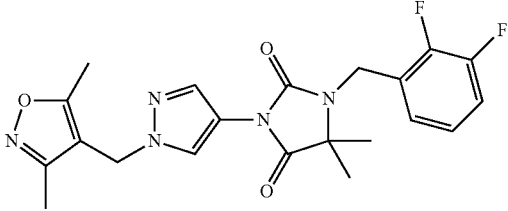<br>1-(2,3-difluorobenzyl)-3-(1-((3,5-dimethylisoxazol-4-yl)methyl)-1H-pyrazol-4-yl)-5,5-dimethylimidazolidine-2,4-dione | 0.31 |
| 12-67 | 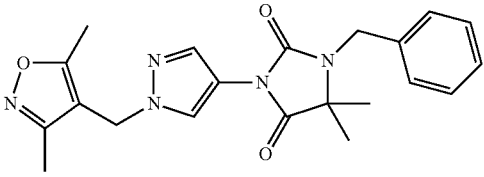<br>1-benzyl-3-(1-((3,5-dimethylisoxazol-4-yl)methyl)-1H-pyrazol-4-yl)-5,5-dimethylimidazolidine-2,4-dione | 0.32 |
| 12-68 | 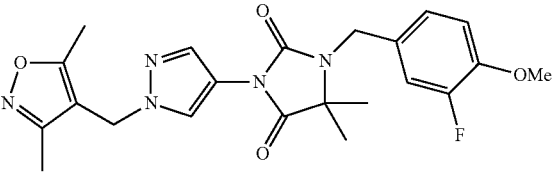<br>1-benzyl-3-(1-((3,5-dimethylisoxazol-4-yl)methyl)-1H-pyrazol-4-yl)-5,5-dimethylimidazolidine-2,4-dione | 0.33 |
| 12-69 | 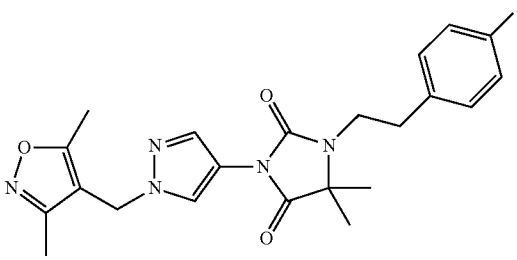<br>3-(1-((3,5-dimethylisoxazol-4-yl)methyl)-1H-pyrazol-4-yl)-1-(4-fluorophenethyl)-5,5-dimethylimidazolidine-2,4-dione | 0.33 |

-continued

| Compound No. | Compound | hT2R8 IC$_{50}$ (μM) |
|---|---|---|
| 12-70 | 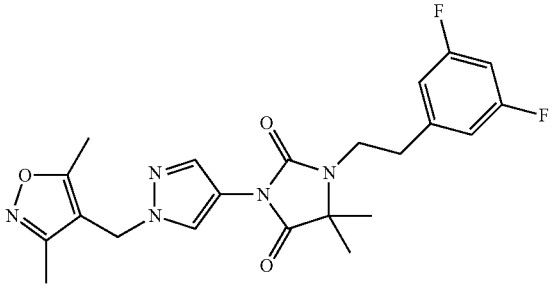  1-(3,5-difluorophenethyl)-3-(1-((3,5-dimethylisoxazol-4-yl)methyl)-1H-pyrazol-4-yl)-5,5-dimethylimidazolidine-2,4-dione | 0.40 |
| 12-71 | 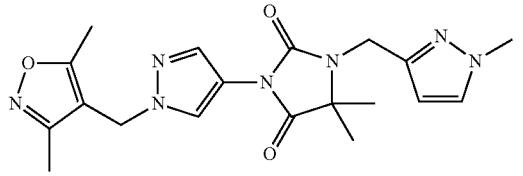  3-(1-((3,5-dimethylisoxazol-4-yl)methyl)-1H-pyrazol-4-yl)-5,5-dimethyl-1-((1-methyl-1H-pyrazol-3-yl)methyl)imidazolidine-2,4-dione | 0.42 |
| 12-72 | 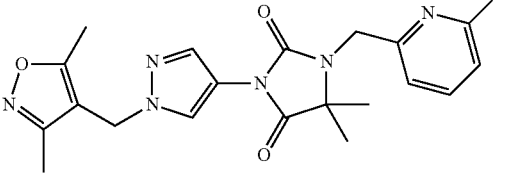  3-(1-((3,5-dimethylisoxazol-4-yl)methyl)-1H-pyrazol-4-yl)-1-((6-hydroxypyridin-2-yl)methyl)-5,5-dimethylimidazolidine-2,4-dione | 0.44 |
| 12-73 | 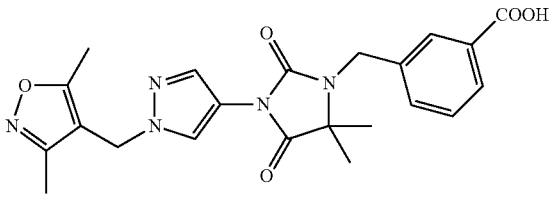  3-((3-(1-((3,5-dimethylisoxazol-4-yl)methyl)-1H-pyrazol-4-yl)-5,5-dimethyl-2,4-dioxoimidazolidin-1yl)methyl)benzoic acid | 0.46 |
| 12-74 | 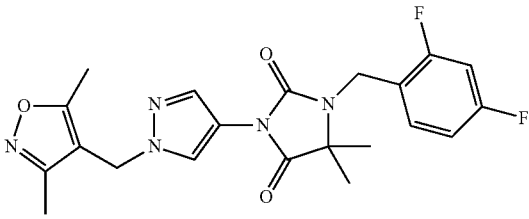  1-(2,4-difluorobenzyl)-3-(1-((3,5-dimethylisoxazol-4-yl)methyl)-1H-pyrazol-4-yl)-5,5-dimethylimidazolidine-2,4-dione | 0.53 |

-continued

| Compound No. | Compound | hT2R8 IC$_{50}$ (μM) |
|---|---|---|
| 12-75 | 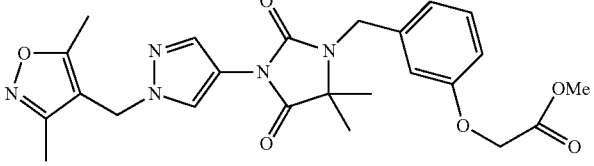<br>methyl 2-(3-((3-(1-((3,5-dimethylisoxazol-4-yl)methyl)-1H-pyrazol-4-yl)-5,5-dimethyl-2,4-dioxoimidazolidin-1-yl)methyl)phenoxy)acetate | 0.53 |
| 12-76 | 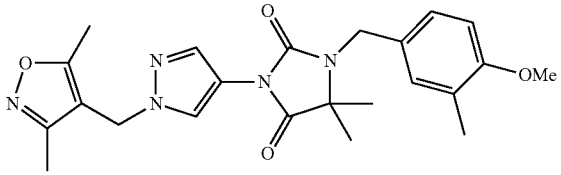<br>3-(1-((3,5-dimethylisoxazol-4-yl)methyl)-1H-pyrazol-4-yl)-1-(4-methoxy-3-methylbenzyl)-5,5-dimethylimidazolidine-2,4-dione | 0.54 |
| 12-77 | 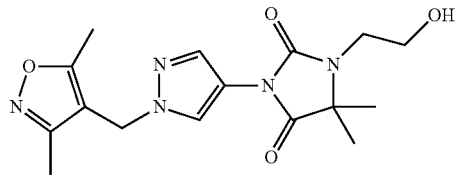<br>3-(1-((3,5-dimethylisoxazol-4-yl)methyl)-1H-pyrazol-4-yl)-1-(2-hydroxyethyl)-5,5-dimethylimidazolidine-2,4-dione | 0.56 |
| 12-78 | 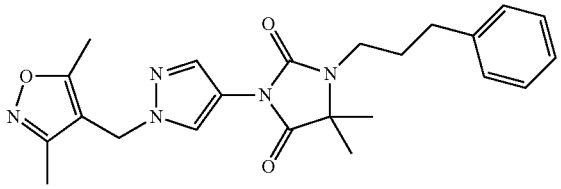<br>3-(1-((3,5-dimethylisoxazol-4-yl)methyl)-1H-pyrazol-4-yl)-5,5-dimethyl-1-(3-phenylpropyl)imidazolidine-2,4-dione | 0.58 |
| 12-79 | 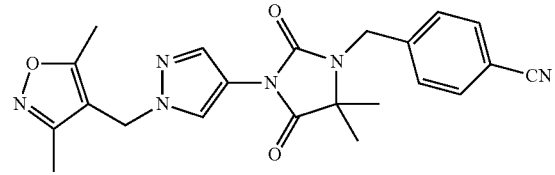<br>4-((3-(1-((3,5-dimethylisoxazol-4-yl)methyl)-1H-pyrazol-4-yl)-5,5-dimethyl-2,4-dioxoimidazolidine-1-yl)methyl)benzonitrile | 0.05 |
| 12-80 | 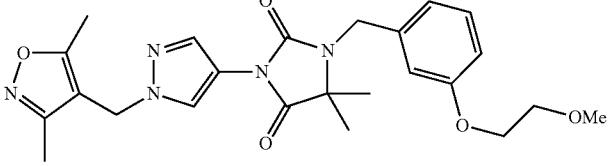<br>3-(1-((3,5-dimethylisoxazol-4-yl)methyl)-1H-pyrazol-4-yl)-1-(3-(2-methoxyethoxy)benzyl)-5,5-dimethylimidazolidin-2,4-dione | 0.71 |

-continued

| Compound No. | Compound | hT2R8 IC$_{50}$ (μM) |
|---|---|---|
| 12-81 | 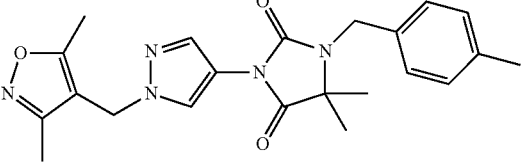<br>3-(1-((3,5-dimethylisoxazol-4-yl)methyl)-1H-pyrazol-4-yl)-5,5-dimethyl-1-(4-methylbenzyl)imidazolidine-2,4-dione | 0.74 |
| 12-82 | 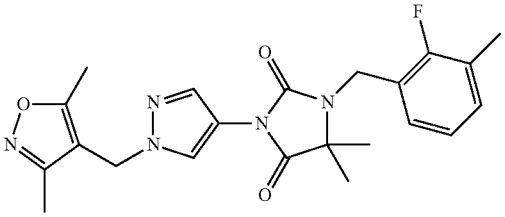<br>3-(1-((3,5-dimethylisoxazol-4-yl)methyl)-1H-pyrazol-4-yl)-1-(2-fluoro-3-methylbenzyl)-5,5-dimethylimidazolidine-2,4-dione | 0.81 |
| 12-83 | 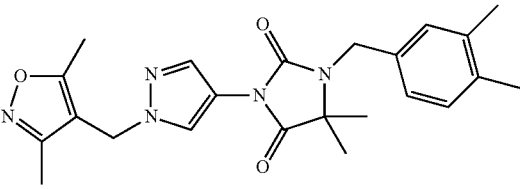<br>1-(3,4-dimethylbenzyl)-3-(1-((3,5-dimethylisoxazol-4-yl)methyl)-1H-pyrazol-4-yl)-5,5-dimethylimidazolidine-2,4-dione | 1.22 |
| 12-84 | 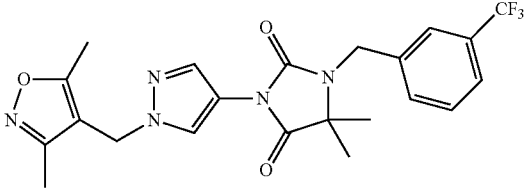<br>3-(1-((3,5-dimethylisoxazol-4-yl)methyl)-1H-pyrazol-4-yl)-5,5-dimethyl-1-(3-(trifluoromethyl)benzyl)imidazolidine-2,4-dione | 1.54 |
| 12-85 | 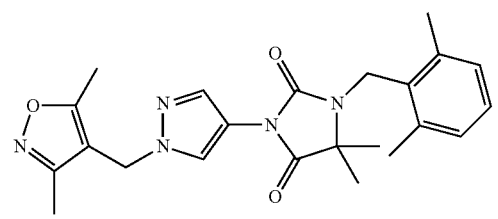<br>1-(2,6-dimethylbenzyl)-3-(1-((3,5-dimethylisoxazol-4-yl)methyl)-1H-pyrazol-4-yl)-5,5-dimethylimidazolidine-2,4-dione | 1.58 |

-continued

| Compound No. | Compound | hT2R8 IC$_{50}$ (µM) |
|---|---|---|
| 12-86 | 1-(2,4-dimethylbenzyl)-3-(1-((3,5-dimethylisoxazol-4-yl)methyl)-1H-pyrazol-4-yl)-5,5-dimethylimidazolidine-2,4-dione | 1.89 |
| 12-87 | 1-(3-(2-dimethylamino)ethoxy)benzyl)-3-(1-((3,5-dimethylisoxazol-4-yl)methyl)-1H-pyrazol-4-yl)-5,5-dimethylimidazolidin-2,4-dione | 2.08 |
| 12-88 | 3-(1-((3,5-dimethylisoxazol-4-yl)methyl)-1H-pyrazol-4-yl)-1-(4-(hydroxymethyl)benzyl)-5,5-dimethylimidazolidine-2,4-dione | 0.36 |
| 12-89 | 4-((3-(1-((3,5-dimethylisoxazol-4-yl)methyl)-1H-pyrazol-4-yl)-5,5-dimethyl-2,4-dioxoimidazolidin-1-yl)methyl)benzoic acid | 2.31 |
| 12-90 | 2-(3-((3-(1-((3,5-dimethylisoxazol-4-yl)methyl)-1H-pyrazol-4-yl)-5,5-dimethyl-2,4-dioxoimidazolidin-1-yl)methyl)phenoxy)acetic acid | 2.85 |
| 12-91 | 2-((3-(1-((3,5-dimethylisoxazol-4-yl)methyl)-1H-pyrazol-4-yl)-5,5-dimethyl-2,4-dioxoimidazolidin-1-yl)methyl)benzoic acid | 4.23 |

| Compound No. | Compound | hT2R8 IC$_{50}$ (μM) |
|---|---|---|
| 12-92 | 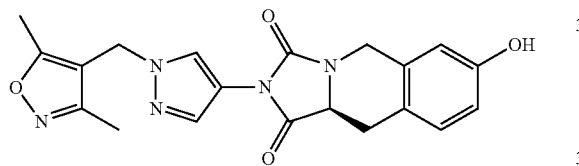 3-(1-((3,5-dimethylisoxazol-4-yl)methyl)-1H-pyrazol-4-yl)-1-(4-(methoxymethyl)benzyl)-5,5-dimethylimidazolidine-2,4-dione | 0.28 |

Example 13

Constrained Hydantoin Analogs (T2R8 Blockers)

Example 13-1

(S)-2-(1-((3,5-dimethylisoxazol-4-yl)methyl)-1H-pyrazol-4-yl)-7-hydroxy-10,10a-dihydroimidazo[1,5-b]isoquinoline-1,3(2H,5H)-dione

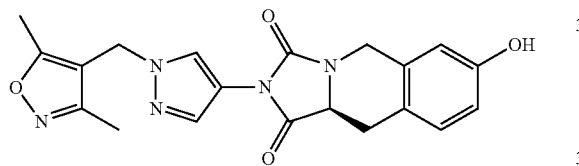

Prepared as in Example 12-1 from (S)-7-(tert-butyldimethylsilyloxy)-2-(1-((3,5-dimethylisoxazol-4-yl)methyl)-1H-pyrazol-4-yl)-10,10a-dihydroimidazo[1,5-b]isoquinoline-1,3(2H,5H)-dione (Example 13-1a). Yield 98%, white solid. $^1$H NMR (DMSO-d$_6$, 400 MHz): δ 2.15 (s, 3H), 2.41 (s, 3H), 2.85 (dd, J=8.0, 15.2 Hz, 1H), 3.07 (dd, J=4.8, 15.2 Hz, 1H), 4.33 (m, 2H), 4.79 (d, J=16.8 Hz, 1H), 5.21 (s, 2H), 6.64 (m, 2H), 7.06 (d, J=78.0 Hz, 1H), 7.81 (d, J=0.8 Hz, 1H), 8.20 (d, J=0.8 Hz, 1H), 9.39 (s, H). [MS 394 (MH$^+$). The title compound was shown to inhibit hT2R08 bitter receptor and had an IC$_{50}$ of 0.02 μM.

Example 13-1a (S)-7-(tert-butyldimethylsilyloxy)-2-(1-((3,5-dimethylisoxazol-4-yl)methyl)-1H-pyrazol-4-yl)-10,10a-dihydroimidazo[1,5-b]isoquinoline-1,3(2H,5H)-dione

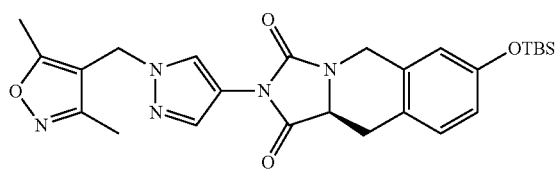 [SMILES: Cc1noc(C)c1Cn1cc(N2C(=O)[C@@H]3Cc4ccc(O[Si](C)(C)C(C)(C)C)cc4CN3C2=O)cn1]

Prepared as in Example 12-1a from (S)-methyl 7-(tert-butyldimethylsilyloxy)-1,2,3,4-tetrahydroisoquinoline-3-carboxylate (Example 13-1b) and 1-((3,5-dimethylisoxazol-4-yl)methyl)-1H-pyrazole-4-carbonyl azide (Example 10-1a). Yield 92%, yellow solid. MS 508 (MH$^+$).

Example 13-1b (S)-methyl 7-(tert-butyldimethylsilyloxy)-1,2,3,4-tetrahydroisoquinoline-3-carboxylate

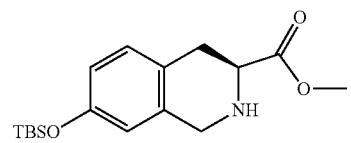 [SMILES: COC(=O)[C@@H]1Cc2ccc(O[Si](C)(C)C(C)(C)C)cc2CN1]

Prepared as in Example 12-1c from (S)-methyl 7-hydroxy-1,2,3,4-tetrahydroisoquinoline-3-carboxylate hydrochloride (Example 13-1c) and tert-butylchlorodimethylsilane. Yield 87%, yellow oil. MS 322 (MH$^+$).

Example 13-1c (S)-methyl 7-hydroxy-1,2,3,4-tetrahydroisoquinoline-3-carboxylate hydrochloride

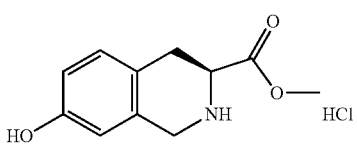

Prepared by refluxing (S)-7-hydroxy-1,2,3,4-tetrahydroisoquinoline-3-carboxylic acid in a concentrated methanolic solution of HCl. Yield 100%, Beige powder. MS 208 (MH⁺ —Cl⁻).

Example 13-2

(R)-2-(1-((3,5-dimethylisoxazol-4-yl)methyl)-1H-pyrazol-4-yl)-7-hydroxy-10,10a-dihydroimidazo[1,5-b]isoquinoline-1,3(2H,5H)-dione

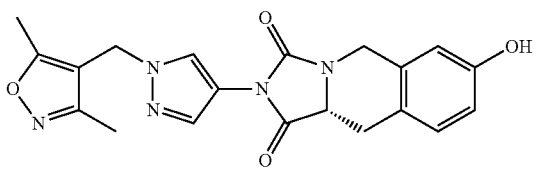 [SMILES: Cc1noc(C)c1Cn1cc(N2C(=O)[C@H]3Cc4ccc(O)cc4CN3C2=O)cn1]

Prepared as in Example 12-1 from (R)-7-(tert-butyldimethylsilyloxy)-2-(1-((3,5-dimethylisoxazol-4-yl)methyl)-1H-pyrazol-4-yl)-10,10a-dihydroimidazo[1,5-b]isoquinoline-1,3(2H,5H)-dione (Example 13-2a). Yield 85%, white solid. [MS 394 (MH⁺). The title compound was shown to inhibit hT2R08 bitter receptor and had an $IC_{50}$ of 0.03 μM Example 13-2a (R)-7-(tert-butyldimethylsilyloxy)-2-(1-((3,5-dimethylisoxazol-4-yl)methyl)-1H-pyrazol-4-yl)-10,10a-dihydroimidazo[1,5-b]isoquinoline-1,3(2H,5H)-dione

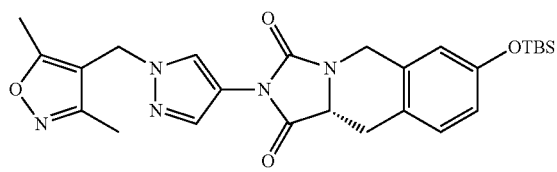 [SMILES: Cc1noc(C)c1Cn1cc(N2C(=O)[C@H]3Cc4ccc(O[Si](C)(C)C(C)(C)C)cc4CN3C2=O)cn1]

Prepared as in Example 12-1a from (R)-methyl 7-(tert-butyldimethylsilyloxy)-1,2,3,4-tetrahydroisoquinoline-3-carboxylate (Example 13-2b) and 1-((3,5-dimethylisoxazol-4-yl)methyl)-1H-pyrazole-4-carbonyl azide (Example 10-1a). Yield 84%, yellowish solid. MS 508 (MH⁺).

Example 13-2b (R)-methyl 7-(tert-butyldimethylsilyloxy)-1,2,3,4-tetrahydroisoquinoline-3-carboxylate

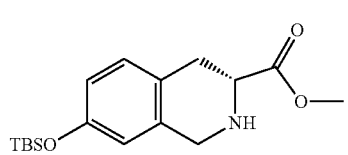 [SMILES: COC(=O)[C@H]1Cc2ccc(O[Si](C)(C)C(C)(C)C)cc2CN1]

Prepared as in Example 1c-JF from (R)-methyl 7-hydroxy-1,2,3,4-tetrahydroisoquinoline-3-carboxylate hydrochloride (Example 13-2c) and tert-butylchlorodimethylsilane. Yield 79%, yellow oil (1.15 g, 79%). MS 322 (MH⁺).

Example 13-2c (R)-methyl 7-hydroxy-1,2,3,4-tetrahydroisoquinoline-3-carboxylate hydrochloride

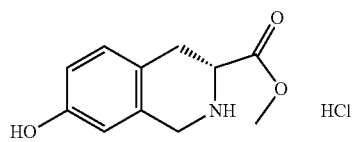

Prepared by refluxing (R)-7-hydroxy-1,2,3,4-tetrahydroisoquinoline-3-carboxylic acid in a concentrated methanolic solution of HCl. Yield 100%, beige powder. MS 208 (MH⁺ —Cl⁻).

Example 13-3

2-(1-((3,5-dimethylisoxazol-4-yl)methyl)-1H-pyrazol-4-yl)-8-hydroxy-10,10a-dihydroimidazo[1,5-b]isoquinoline-1,3(2H,5H)-dione

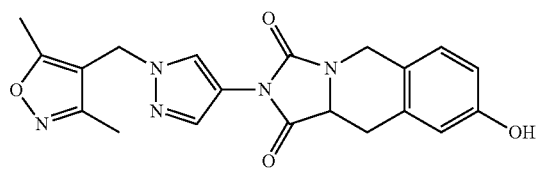 [SMILES: Cc1noc(C)c1Cn1cc(N2C(=O)C3Cc4cc(O)ccc4CN3C2=O)cn1]

Prepared as in Example 12-1 from 8-(tert-butyldimethylsilyloxy)-2-(1-((3,5-dimethylisoxazol-4-yl)methyl)-1H-pyrazol-4-yl)-10,10a-dihydroimidazo[1, 5-1)]isoquinoline-1,3(2H,5H)-dione (Example 13-3a). Yield 96%, a white solid. MS 394 (MH⁺). The title compound was shown to inhibit hT2R⁰⁸ bitter receptor and had an $IC_{50}$ of 0.03 μM Example 13-3a 8-(tert-butyldimethylsilyloxy)-2-(1-((3,5-dimethylisoxazol-4-yl)methyl)-1H-pyrazol-4-yl)-10,10a-dihydroimidazo[1,5-b]isoquinoline-1,3(2H,5H)-dione

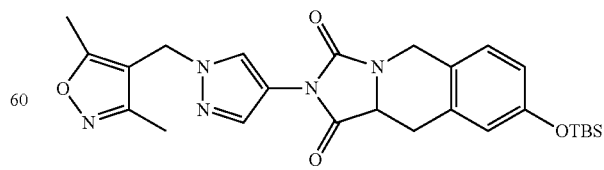

Prepared as in Example 12-1a from methyl 6-(tert-butyldimethylsilyloxy)-1,2,3,4-tetrahydroisoquinoline-3-carboxylate (Example 13-3b) and 1-((3,5-dimethylisoxazol-4- yl)methyl)-1H-pyrazole-4-carbonyl azide (Example 10-1a). Yield 90%, yellowish solid. MS 508 (MH⁺).

Example 13-3b methyl 6-(tert-butyldimethylsilyloxy)-1,2,3,4-tetrahydroisoquinoline-3-carboxylate

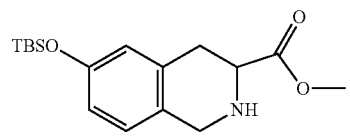 [SMILES: COC(=O)C1Cc2cc(O[Si](C)(C)C(C)(C)C)ccc2CN1]

Prepared as in Example 12-1c from methyl 6-hydroxy-1,2,3,4-tetrahydroisoquinoline-3-carboxylate hydrochloride (Example 13-3c) and tert-butylchlorodimethylsilane. Yield 83%, yellowish. MS 322 (MH⁺).

Example 13-3c methyl 6-hydroxy-1,2,3,4-tetrahydroisoquinoline-3-carboxylate hydrochloride

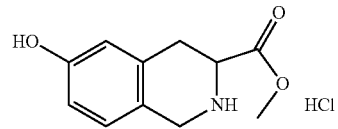

Prepared by refluxing 6-hydroxy-1,2,3,4-tetrahydroisoquinoline-3-carboxylic acid in a concentrated methanolic solution of HCl. Yield 100%, beige powder. MS 208 (MH⁺ —Cl⁻).

Example 14 hT2R⁸ Antagonists Reduce Bitter Taste of Instant Coffee

Taste tests were performed with hT2R⁸ antagonists in instant coffee using a 2-alternative forced choice method with a taste panel of 15-20 panelists. Coffee samples with the antagonists were given to the taste panelists together with the same sample without antagonists, the panelists were asked to identify the bitterer sample within the pair. As shown in Table 9, the panelists consistently identified the coffee fraction samples without antagonists as being bitterer than the ones with antagonists, indicating that the antagonists reduced the bitter taste of instant coffee.

TABLE 9

Taste test results with Instant Coffee and T2R8 antagonists

| T2R8 Antagonist | Concentration (µM) | Selected as bitterer | | P value |
| --- | --- | --- | --- | --- |
| | | Without antagonists | With antagonists | |
| Example 10-10 | 5 | 14 | 2 | 0.004 |
| Example 12-1 | 5 | 14 | 2 | 0.004 |
| Example 12-34 | 5 | 13 | 3 | 0.021 |

TABLE 9-continued

Taste test results with Instant Coffee and T2R8 antagonists

| T2R8 Antagonist | Concentration (µM) | Selected as bitterer | | P value |
| --- | --- | --- | --- | --- |
| | | Without antagonists | With antagonists | |
| Example 12-17 | 5 | 17 | 3 | 0.003 |
| Example 12-2 | 5 | 14 | 2 | 0.004 |

Other exemplary compounds provided by the present invention and/or suitable to be used for methods of the present invention include compounds of the following formulae.

In a first aspect, a compound of structural Formula (I) is provided:

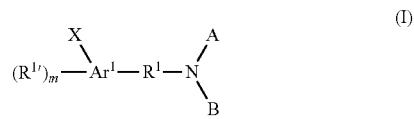

or a salt, hydrate, solvate or N-oxide thereof wherein:

$Ar^1$ a five or six membered aryl, heteroaryl or cycloalkyl ring;

m is 0, 1, 2 or 3;

$R^1$ is $SO_2$; C=O; C=S; or C=NOR⁴;

X is selected from the group consisting of hydrogen, halogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, CN, $NO_2$, $OR^6$, $S(O)_bR^6$, $NR^6R^7$, $CONR^6R^7$, $CO_2R^6$, $NR^6CO_2R^7$, $NR^6CONR^7R^8$, $NR^6CSNR^7R^8$, $NR^6C(=NH)NR^7R^8$, $SO_2NR^5R^6$, $NR^5SO_2R^6$, $NR^5SO_2NR^6R^7$, $B(OR^5)(OR^6)$, $P(O)(OR^5)(OR^6)$, and $P(O)(R^5)(OR^6)$;

each $R^{1'}$ is independently selected from the group consisting of hydrogen, halogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, CN, $NO_2$, $OR^6$, $S(O)_bR^6$, $NR^6R^7$, $CONR^6R^7$, $CO_2R^6$, $NR^6CO_2R^7$, $NR^6CONR^7R^8$, $NR^6CSNR^7R^8$, $NR^6C(=NH)NR^7R^8$, $SO_2NR^5R^6$, $NR^5SO_2R^6$, $NR^5SO_2NR^6R^7$, $B(OR^5)(OR^6)$, $P(O)(OR^5)(OR^6)$, and $P(O)(R^5)(OR^6)$;

or alternatively, X and/or at least one $R^{1'}$ together with the atoms to which they are bonded form an aryl, substituted aryl, heteroaryl, substituted heteroaryl, cycloalkyl, substituted cycloalkyl, cycloheteroalkyl or substituted cycloheteroalkyl ring where the ring is optionally fused to another aryl, substituted aryl, heteroaryl, substituted heteroaryl, cycloalkyl, substituted cycloalkyl, cycloheteroalkyl or substituted cycloheteroalkyl ring;

$R^4$-$R^8$ are independently selected from the group consisting of hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl and substituted heteroarylalkyl or alternatively, $R^5$ and $R^6$, $R^6$ and $R^7$, $R^7$ and $R^8$, together with the atoms to which they are bonded form a cycloheteroalkyl or substituted cycloheteroalkyl ring;

A and B are independently selected from the group consisting of hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl; and
b is 0, 1, or 2;

In a second aspect the invention provides compounds of structural Formula (II) shown below:

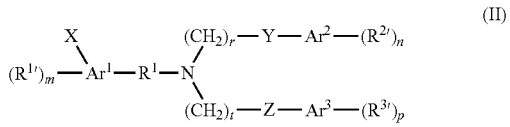

or a salt, hydrate, solvate or N-oxide thereof wherein:

$Ar^1$, $Ar^2$ and $Ar^3$ are independently a five or six membered aryl, heteroaryl, or cycloalkyl ring;

m is 0, 1, 2 or 3;

n and p are independently 0, 1, 2, 3 or 4;

r and t are independently 0, 1 or 2;

Y and Z are independently selected from the group consisting of $CR^6R^7$, C=O, C=S, $C=NOR^6$, O, $NR^6$, and $S(O)_b$;

$R^1$ is selected from the group consisting of $SO_2$, C=O, C=S, and $C=NOR^4$;

X may be selected from the group consisting of hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, CN, $NO_2$, —$OR^6$, $S(O)_bR^6$, $NR^6R^7$, $CONR^6R^7$, $CO_2R^6$, $NR^6CO_2R^7$, $NR^6CONR^7R^8$, $NR^6CSNR^7R^8$, $NR^6C(=NH)NR^7R^8$, $SO_2NR^5R^6$, $NR^5SO_2R^6$, $NR^5SO_2NR^6R^7$, $B(OR^5)(OR^6)$, $P(O)(OR^5)(OR^6)$, and $P(O)(R^5)(OR^6)$;

X is preferably selected from the group consisting of hydrogen, heteroalkyl, substituted heteroalkyl, heteroaryl, substituted heteroaryl, heteroarylalkyl, substituted heteroarylalkyl, CN, $S(O)_bR^6$, $CONR^6R^7$, —$CO_2R^6$, $SO_2NR^5R^6$, $NR^5SO_2R^6$, $NR^5SO_2NR^6R^7$, $B(OR^5)(OR^6)$, $P(O)(OR^5)(OR^6)$, and $P(O)(R^5)(OR^6)$.

each $R^{1'}$ is independently selected from the group consisting of hydrogen, halogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, CN, $NO_2$, $OR^6$, $S(O)_bR^6$, $NR^6R^7$, $CONR^6R^7$, $CO_2R^6$, $NR^6CO_2R^7$, $NR^6CONR^7R^8$, $NR^6CSNR^7R^8$, $NR^6C(=NH)NR^7R^8$, $SO_2NR^5R^6$, $NR^5SO_2R^6$, $NR^5SO_2NR^6R^7$, $B(OR^5)(OR^6)$, $P(O)(OR^5)(OR^6)$, and $P(O)(R^5)(OR^6)$;

each $R^{2'}$ is independently selected from the group consisting of hydrogen, halogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, CN, $NO_2$, $OR^6$, $S(O)_bR^6$, $NR^6R^7$, $CONR^6R^7$, $CO_2R^6$, $NR^6CO_2R^7$, $NR^6CONR^7R^8$, $NR^6CSNR^7R^8$, $NR^6C(=NH)NR^7R^8$, $SO_2NR^5R^6$, $NR^5SO_2R^6$, $NR^5SO_2NR^6R^7$, $B(OR^5)(OR^6)$, and $P(O)(OR^5)(OR^6)$;

each $R^{3'}$ is independently selected from the group consisting of hydrogen, halogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, CN, $NO_2$, $OR^6$, $S(O)_bR^6$, $NR^6R^7$, $CONR^6R^7$, $CO_2R^6$, $NR^6CO_2R^7$, $NR^6CONR^7R^8$, $NR^6CSNR^7R^8$, $NR^6C(=NH)NR^7R^8$, $SO_2NR^5R^6$, $NR^5SO_2R^6$, $NR^5SO_2NR^6R^7$, $B(OR^5)(OR^6)$, $P(O)(OR^5)(OR^6)$, and $P(O)(R^5)(OR^6)$;

or alternatively, X and/or at least one of $R^{1'}$ together with the atoms to which they are bonded form an aryl, substituted aryl, heteroaryl, substituted heteroaryl, cycloalkyl, substituted cycloalkyl, cycloheteroalkyl or substituted cycloheteroalkyl ring where the ring is optionally fused to another aryl, substituted aryl, heteroaryl, substituted heteroaryl, cycloalkyl, substituted cycloalkyl, cycloheteroalkyl or substituted cycloheteroalkyl ring;

$R^4$-$R^8$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl or alternatively, $R^5$ and $R^6$, $R^6$ and $R^7$, $R^7$ and $R^8$, together with the atoms to which they are bonded form a cycloheteroalkyl or substituted cycloheteroalkyl ring;

b is 0, 1, or 2.

In another aspect the invention provides compounds having structural Formula (III) shown below:

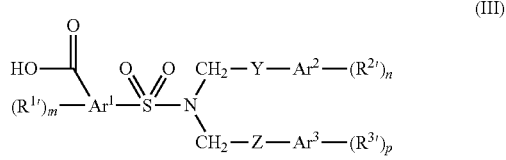

or a salt, hydrate, solvate or N-oxide thereof wherein:

$Ar^1$, $Ar^2$ and $Ar^3$ are independently a five or six membered aryl, heteroaryl, or cycloalkyl ring, and $Ar^2$ and $Ar^3$ may optionally be omitted;

m is 0, 1, 2 or 3;

n and p are independently 0, 1, 2, 3 or 4;

each $R^{1'}$ is independently selected from the group consisting of hydrogen, halogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, CN, $NO_2$, $OR^6$, $S(O)_bR^6$, $NR^6R^7$, $CONR^6R^7$, $CO_2R^6$, $NR^6CO_2R^7$, $NR^6CONR^7R^8$, $NR^6CSNR^7R^8$, $NR^6C(=NH)NR^7R^8$, $SO_2NR^5R^6$, $NR^5SO_2R^6$, $NR^5SO_2NR^6R^7$, $B(OR^5)(OR^6)$, $P(O)(OR^5)(OR^6)$, and $P(O)(R^5)(OR^6)$;

each $R^{2'}$ is independently selected from the group consisting of hydrogen, halogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, CN, $NO_2$, $OR^6$, $S(O)_bR^6$, $NR^6R^7$, $CONR^6R^7$, $CO_2R^6$, $NR^6CO_2R^7$, $NR^6CONR^7R^8$, $NR^6CSNR^7R^8$, $NR^6C(=NH)NR^7R^8$, $SO_2NR^5R^6$, $NR^5SO_2R^6$, $NR^5SO_2NR^6R^7$, $B(OR^5)(OR^6)$, $P(O)(OR^5)(OR^6)$, and $P(O)(R^5)(OR^6)$;

each $R^{3'}$ is independently selected from the group consisting of hydrogen, halogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, CN, $NO_2$, $OR^6$, $S(O)_bR^6$, $NR^6R^7$, $CONR^6R^7$, $CO_2R^6$, $NR^6CO_2R^7$, $NR^6CONR^7R^8$, $NR^6CSNR^7R^8$, $NR^6C(=NH)NR^7R^8$, $SO_2NR^5R^6$, $NR^5SO_2R^6$, $NR^5SO_2NR^6R^7$, $B(OR^5)(OR^6)$, $P(O)(OR^5)(OR^6)$, and $P(O)(R^5)(OR^6)$;

$R^5$-$R^8$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl or alternatively, $R^5$ and $R^6$, $R^6$ and $R^7$, $R^7$ and $R^8$, together with the atoms to which they are bonded form a cycloheteroalkyl or substituted cycloheteroalkyl ring;

b is 0, 1, or 2.

In yet another aspect the invention provides a compound having the structure below:

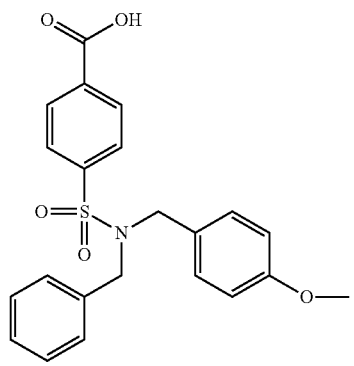 [SMILES: COc1ccc(CN(Cc2ccccc2)S(=O)(=O)c2ccc(C(=O)O)cc2)cc1]

or a salt, hydrate, solvate or N-oxide thereof.

In yet another aspect the invention provides compounds having the structure below:

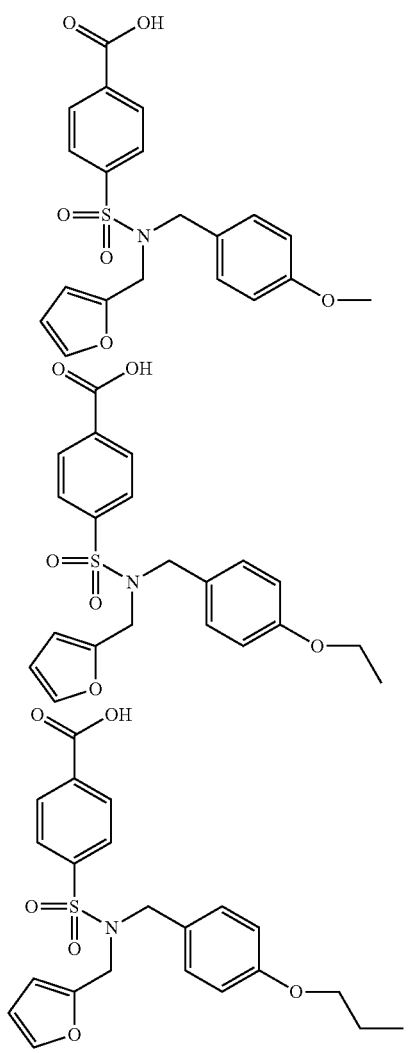

-continued

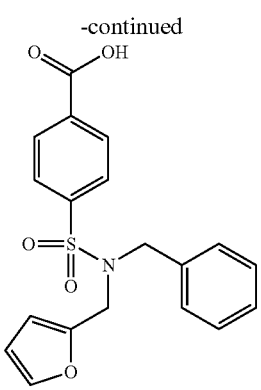

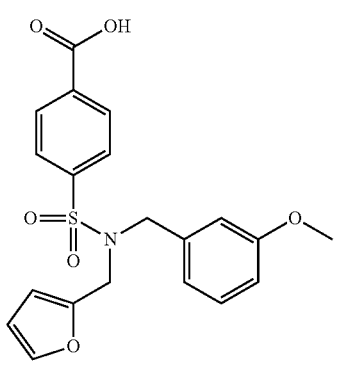

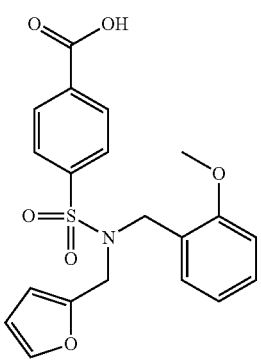 [SMILES: COc1ccccc1CN(Cc1ccco1)S(=O)(=O)c1ccc(C(=O)O)cc1]

or a salt, hydrate, solvate or N-oxide thereof.

In still other embodiments, the invention provides compounds having the structure below:

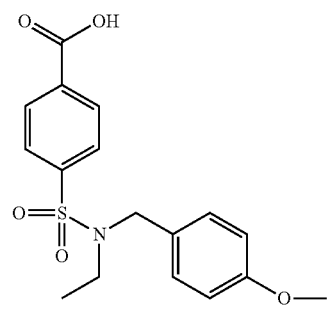

-continued

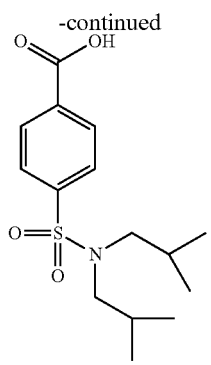

or a salt, hydrate, solvate or N-oxide thereof.

In a related aspect, a compound of structural Formula (IV) is provided:

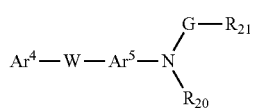 (IV)

or a salt, hydrate, solvate or N-oxide thereof wherein:

$Ar^4$ and $Ar^5$ are independently a five or six membered aryl or heteroaryl ring;

W is selected from the group consisting of $CR^6R^7$, C=O, C=S; C=$NOR^6$; O, $NR^6$, S, SO, $SO_2$, and $(CH_2)_n$;

n is 0, 1, 2, or 3;

G is selected from the group consisting of $CR^6R^7$, C=O, C=S, C=$NOR^6$, and $S(O)_b$;

$R^{20}$ is selected from the group consisting of hydrogen, arylalkenyl, heteroarylalkenyl, arylalkyl, heteroarylalkyl, aryl, heteroaryl, alkyl, alkoxy-alkyl, alkenyl, cycloalkyl, cycloalkenyl, and substituted derivatives;

$R^{21}$ is selected from the group consisting of an arylalkenyl, heteroarylalkenyl, arylalkyl, heteroarylalkyl, aryl, heteroaryl, alkyl, alkoxy-alkyl, alkenyl, cycloalkyl, cycloalkenyl, and substituted derivatives;

$R^6$ and $R^7$ are independently selected from the group consisting of hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl or alternatively, $R^6$ and $R^7$, together with the atoms to which they are bonded form a cycloheteroalkyl or substituted cycloheteroalkyl ring; and b is 0, 1, or 2.

In another related aspect a compound of structural Formula (V) is provided:

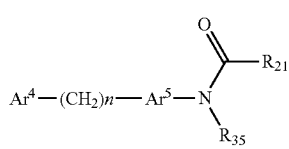 (V)

or a salt, hydrate, solvate or N-oxide thereof wherein:

$Ar^4$ and $Ar^5$ are independently a five or six membered aryl or heteroaryl ring;

n is 0, 1, 2, or 3;

$R^{21}$ is selected from the group consisting of an arylalkenyl, heteroarylalkenyl, arylalkyl, hereoarylalky, aryl, heteroaryl, alkyl, alkoxy-alkyl, alkenyl, cycloalkyl, cycloalkenyl, and substituted derivatives;

$R^{35}$ is selected from the group consisting of hydrogen, alkyl, and substituted alkyl.

In still additional embodiments the invention a compound of structural Formula (VI) is provided

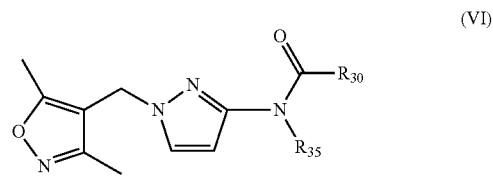 (VI)

or a salt, hydrate, solvate or N-oxide thereof wherein:

$R^{30}$ is selected from the group consisting of an arylalkenyl, heteroarylalkenyl, arylalkyl, hereoarylalky, aryl, heteroaryl, alkyl, alkoxy-alkyl, alkenyl, cycloalkyl, cycloalkenyl, and substituted derivatives;

$R^{35}$ is selected from the group consisting of hydrogen, alkyl, and substituted alkyl.

In still additional embodiments the invention provides compounds having the structure below:

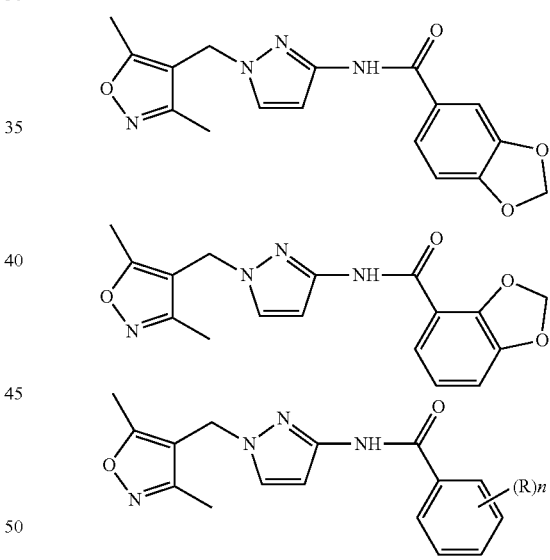

or a salt, hydrate, solvate or N-oxide thereof, wherein each R is independently Cl, MeO, CN, EtO, OH, Me, —$SO_2$Me, F, or H, and n is 0, 1, 2, 3 or 4.

In still other embodiments, the invention provides compounds having the structure below:

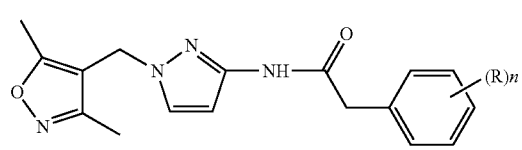

or a salt, hydrate, solvate or N-oxide thereof,
wherein each R is independently MeO or OH, and
n is 0, 1, 2, 3 or 4.
In still other embodiments, the invention provides compounds having the structure below:
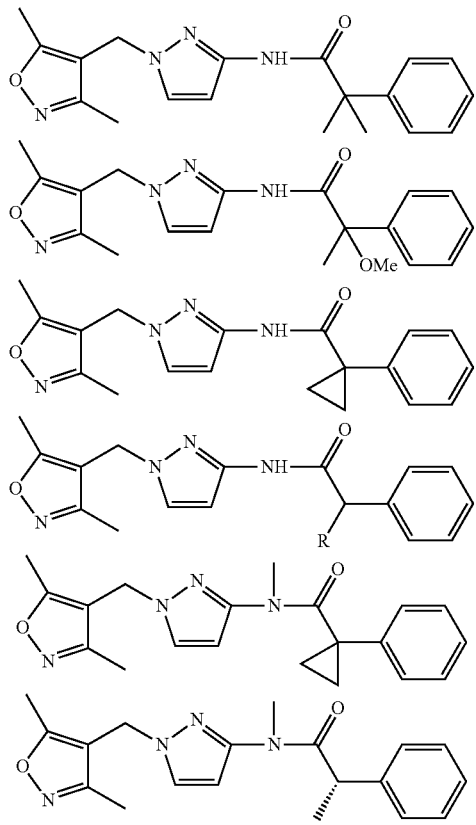
or a salt, hydrate, solvate or N-oxide thereof,
wherein R is H, Me, Et, OCOMe, CH₂OH, OMe, or Ph.
In still other embodiments, the invention provides compounds having the structure below:
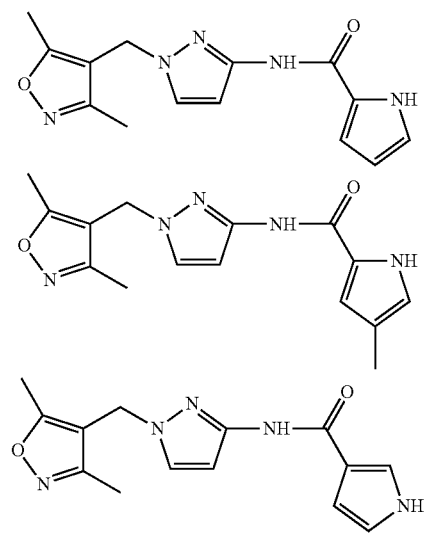
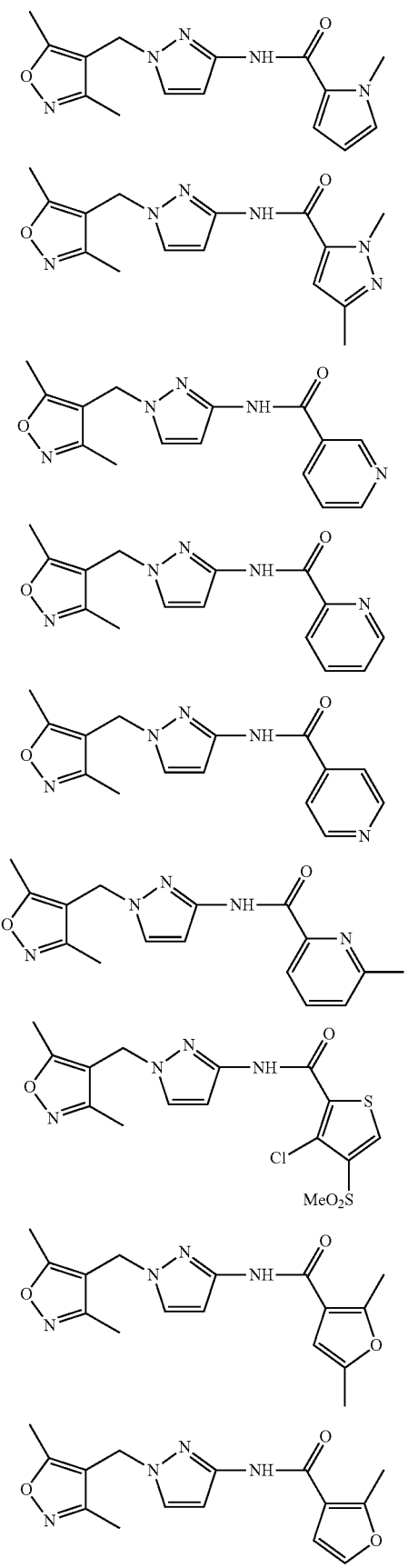

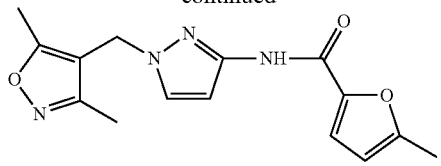

or a salt, hydrate, solvate or N-oxide thereof.

In still other embodiments, the invention provides compounds having the structure below:

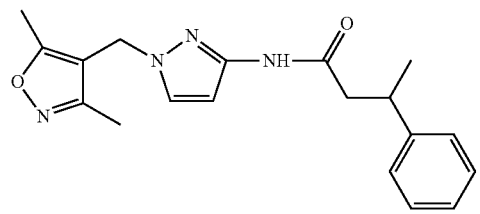

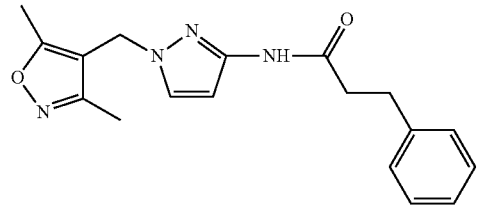

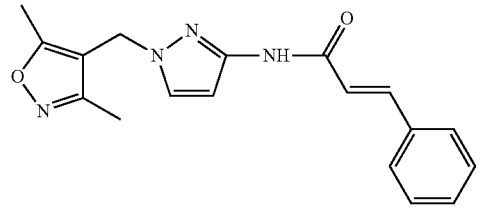

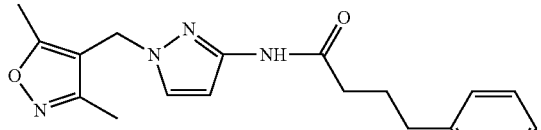

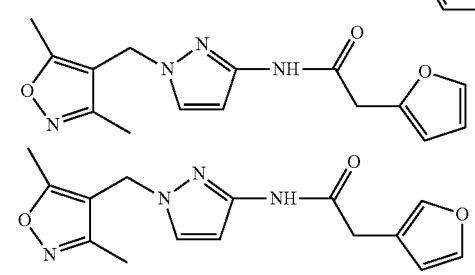

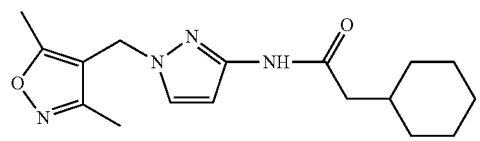

or a salt, hydrate, solvate or N-oxide thereof.

In still other embodiments, the invention provides compounds having the structure below:

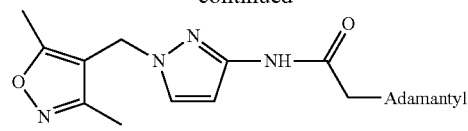

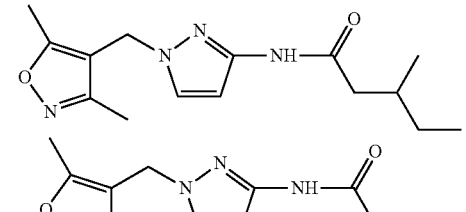

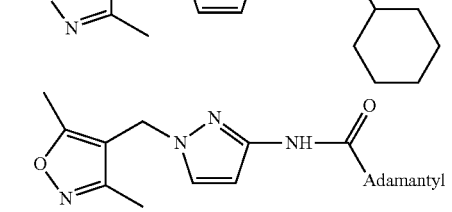

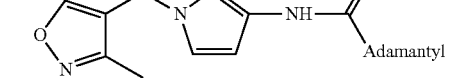

or a salt, hydrate, solvate or N-oxide thereof.

In still other embodiments, the invention provides compounds having the structure below:

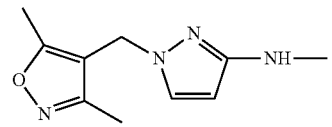

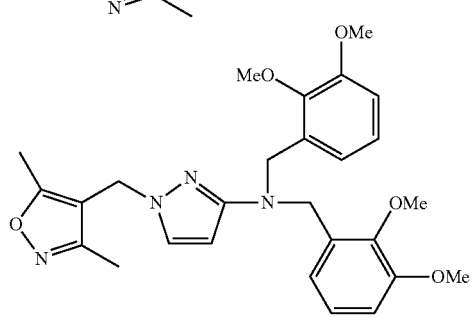

In one aspect, the invention relates to a compound of the formula:

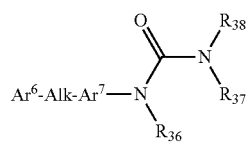

or a salt, hydrate, solvate, N-oxide or prodrug thereof, wherein $Ar^6$ and $Ar^7$ are, the same or different independently one from the other, a five- or six-membered aryl group or a five- or six-membered heteroaryl group;

Alk is an alkyl group, optionally interrupted by a heteroatom;

$R_{36}$ and $R_{37}$ are, the same or different independently one from the other, H, alkyl, or, $R_{36}$ and $R_{37}$, together with the atoms to which they are attached, form an optionally substituted five- or six-membered heterocycle; and $R_{38}$ is H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted heteroarylamidoalkyl, substituted or unsubstituted arylalkyl, substituted or unsubstituted arylalkoxy, substituted or unsubstituted heteroaryl, substituted or unsubstituted heteroarylalkyl, or haloalkyl.

In one aspect the compounds of the invention contain a five-membered heterocycle. In one embodiment, the five-membered heterocycle is a hydantoin or a substituted or unsubstituted cyclic urea.

In one embodiment, the hydantoin is a hydantoin of the formula:

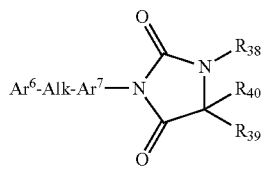

or a salt, hydrate, solvate, N-oxide or prodrug thereof, wherein $Ar^6$ and $Ar^7$ are, the same or different independently one from the other, a five- or six-membered aryl group or a five- or six-membered heteroaryl group;

Alk is an alkyl group, optionally interrupted by a heteroatom;

$R_{38}$ is H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted heteroarylamidoalkyl, substituted or unsubstituted arylalkyl, substituted or unsubstituted arylalkoxy, substituted or unsubstituted heteroaryl, substituted or unsubstituted heteroarylalkyl, or haloalkyl; and $R_{39}$ and $R_{40}$ are, the same or different independently one from the other, H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted arylalkylamidoalkyl, substituted or unsubstituted heteroarylamidoalkyl, substituted or unsubstituted heteroarylalkylamidoalkyl, substituted or unsubstituted arylalkyl, substituted or unsubstituted arylalkoxy, substituted or unsubstituted heteroaryl, substituted or unsubstituted heteroarylalkyl, haloalkyl, or $R_{39}$ and $R_{40}$, together with the carbon atom to which they are attached, form a C=O group or a substituted or unsubstituted alkenyl group.

In another aspect the compounds of the invention contain a five-membered heterocycle which is a urazole. In one embodiment, the urazole is a urazole of the formula:

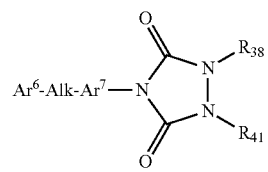

or a salt, hydrate, solvate, N-oxide or prodrug thereof, wherein $Ar^6$ and $Ar^7$ are, the same or different independently one from the other, a five- or six-membered aryl group or a five- or six-membered heteroaryl group;

Alk is an alkyl group, optionally interrupted by a heteroatom;

$R_{38}$ is H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted heteroarylamidoalkyl, substituted or unsubstituted arylalkyl, substituted or unsubstituted arylalkoxy, substituted or unsubstituted heteroaryl, substituted or unsubstituted heteroarylalkyl, or haloalkyl; and $R_{41}$ is H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted arylalkylamidoalkyl, substituted or unsubstituted heteroarylamidoalkyl, substituted or unsubstituted heteroarylalkylamidoalkyl, substituted or unsubstituted arylalkyl, substituted or unsubstituted arylalkoxy, substituted or unsubstituted heteroaryl, substituted or unsubstituted heteroarylalkyl, or haloalkyl.

In another aspect the compounds of the invention contain a six-membered heterocycle. In one embodiment, the six-membered heterocycle is a six-membered heterocycle of the formula:

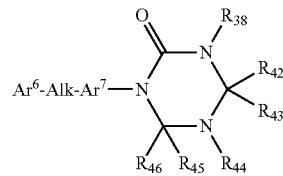

or a salt, hydrate, solvate, N-oxide or prodrug thereof, wherein $R_{38}$ is H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted heteroarylamidoalkyl, substituted or unsubstituted arylalkyl, substituted or unsubstituted arylalkoxy, substituted or unsubstituted heteroaryl, substituted or unsubstituted heteroarylalkyl, or haloalkyl; and $R_{42}$, $R_{43}$, $R_{44}$, $R_{45}$, and $R_{46}$ are, the same or different independently one from the other, H, substituted or unsubstituted alkyl, substituted or unsubstituted cycloalkyl alkyl, substituted or unsubstituted arylalkyl, substituted or unsubstituted arylalkoxy, substituted or unsubstituted heteroaryl, substituted or unsubstituted heteroarylalkyl, or $R_{42}$ and $R_{43}$, or $R_{45}$ and $R_{46}$, together with the carbon atoms to which each are attached, form a C=O group.

In still another aspect, the invention relates to a compound of the formula:

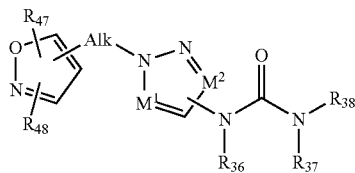

or a salt, hydrate, solvate, N-oxide or prodrug thereof,
wherein Alk is an alkyl group, optionally interrupted by a heteroatom;

$M^1$ is N or $CR_{49}$, wherein $R_{49}$ is H or substituted or unsubstituted alkyl;

$M^2$ is N or $CR_{50}$, wherein $R_{50}$ is H or substituted or unsubstituted alkyl;

$R_{36}$ and $R_{37}$ are, the same or different independently one from the other, H, alkyl, or, $R_{36}$ and $R_{37}$, together with the atoms to which they are attached, form an optionally substituted five- or six-membered heterocycle; and $R_{38}$ is H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted heteroarylamidoalkyl, substituted or unsubstituted arylalkyl, substituted or unsubstituted arylalkoxy, substituted or unsubstituted heteroaryl, substituted or unsubstituted heteroarylalkyl, or haloalkyl;

$R_{47}$ is H, substituted or unsubstituted alkyl, substituted or unsubstituted alkoxy, substituted or unsubstituted aryl, substituted or unsubstituted arylalkyl, or halo; and $R_{48}$ is H, substituted or unsubstituted alkyl, substituted or unsubstituted alkoxy, substituted or unsubstituted aryl, substituted or unsubstituted arylalkyl, or halo.

In still another aspect, the invention relates to a compound of the formula:

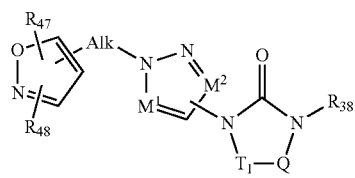

or a salt, hydrate, solvate, N-oxide or prodrug thereof,
wherein Alk is an alkyl group, optionally interrupted by a heteroatom;

$T_1$ is C=O and Q is $CR_{51}R_{52}$ or $NR_{51}$, wherein $R_{51}$ and $R_{52}$ are, the same or different independently one from the other, H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted arylalkylamidoalkyl, substituted or unsubstituted heteroarylamidoalkyl, substituted or unsubstituted heteroarylalkylamidoalkyl, substituted or unsubstituted arylalkyl, substituted or unsubstituted arylalkoxy, substituted or unsubstituted heteroaryl, substituted or unsubstituted heteroarylalkyl, haloalkyl, or $R_{51}$ and $R_{52}$, together with the carbon atom to which they are attached, form a C=O group or a substituted or unsubstituted alkenyl group;

$M^1$ is N or $CR_{49}$, wherein $R_{49}$ is H or substituted or unsubstituted alkyl;

$M^2$ is N or $CR_{50}$, wherein $R_{50}$ is H or substituted or unsubstituted alkyl;

$R_{38}$ is H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted heteroarylamidoalkyl, substituted or unsubstituted arylalkyl, substituted or unsubstituted arylalkoxy, substituted or unsubstituted heteroaryl, substituted or unsubstituted heteroarylalkyl, or haloalkyl;

$R_{47}$ is H, substituted or unsubstituted alkyl, substituted or unsubstituted alkoxy, substituted or unsubstituted aryl, substituted or unsubstituted arylalkyl, or halo; and $R_{48}$ is H, substituted or unsubstituted alkyl, substituted or unsubstituted alkoxy, substituted or unsubstituted aryl, substituted or unsubstituted arylalkyl, or halo.

In still another aspect, the invention relates to a compound of the formula:

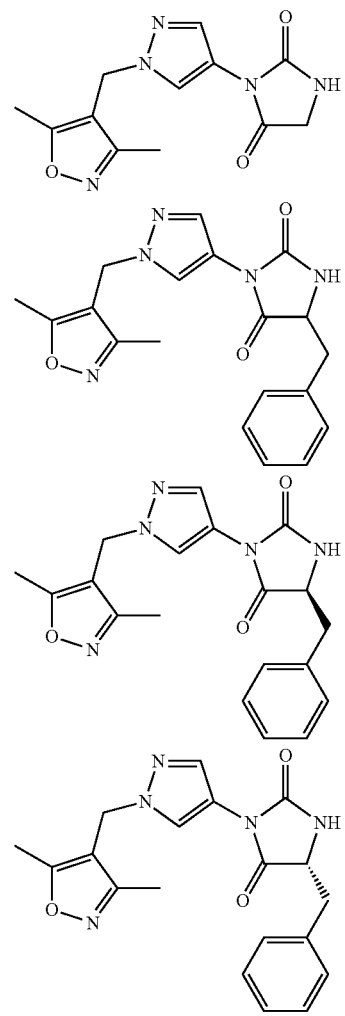

431
-continued
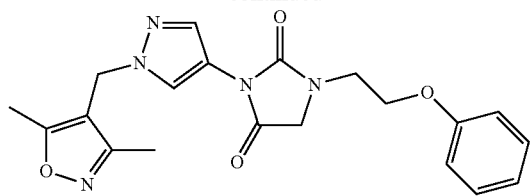
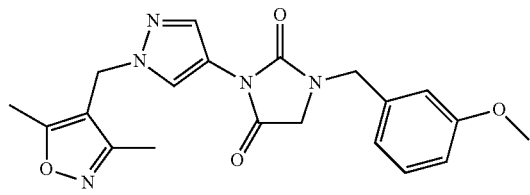
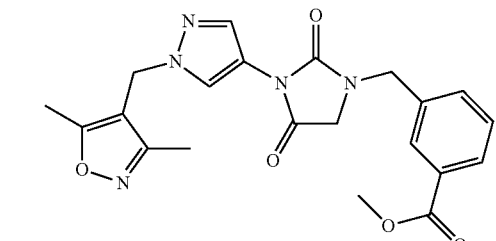
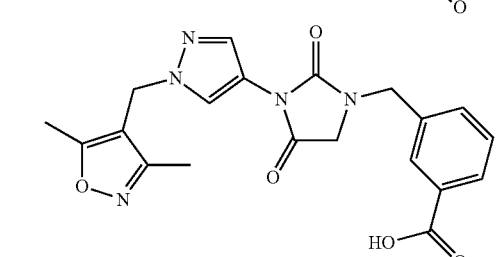
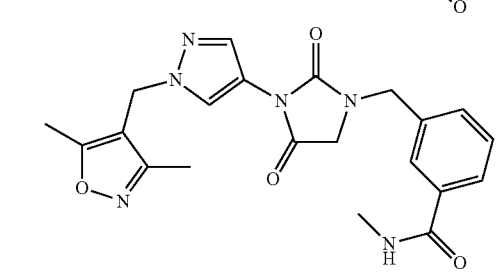
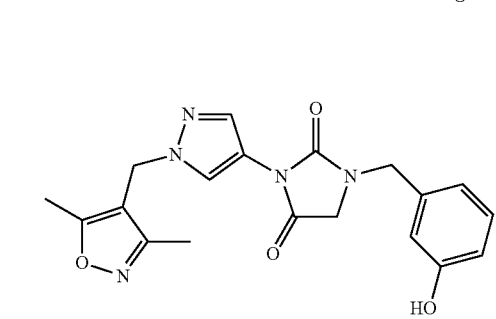
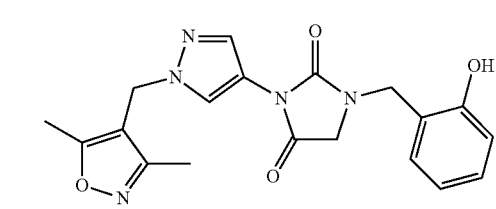
432
-continued
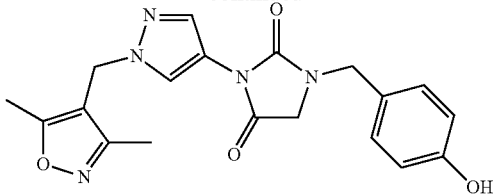
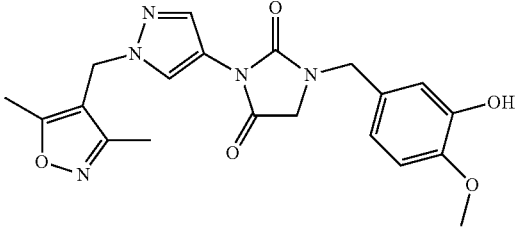
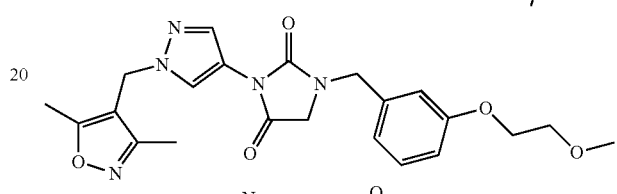
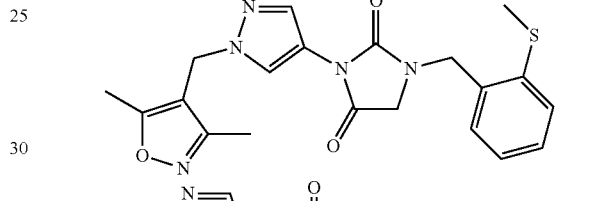
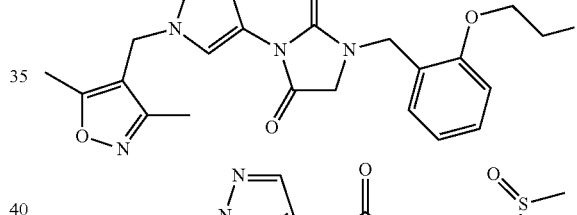
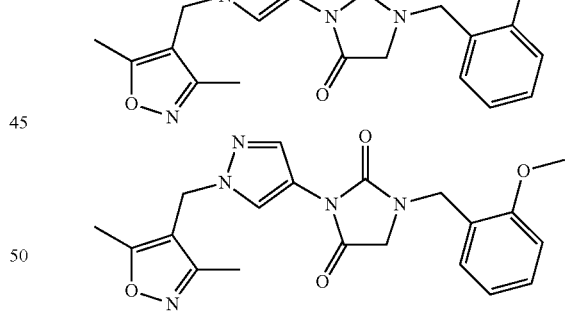
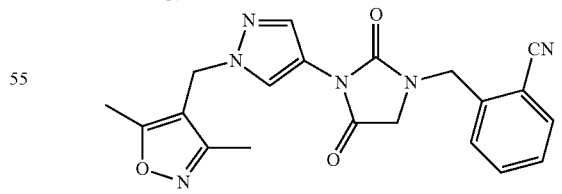
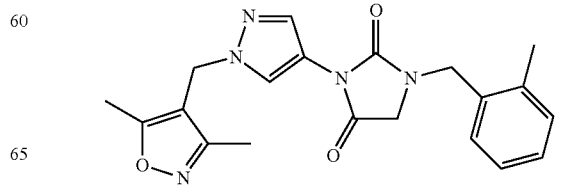

433
-continued
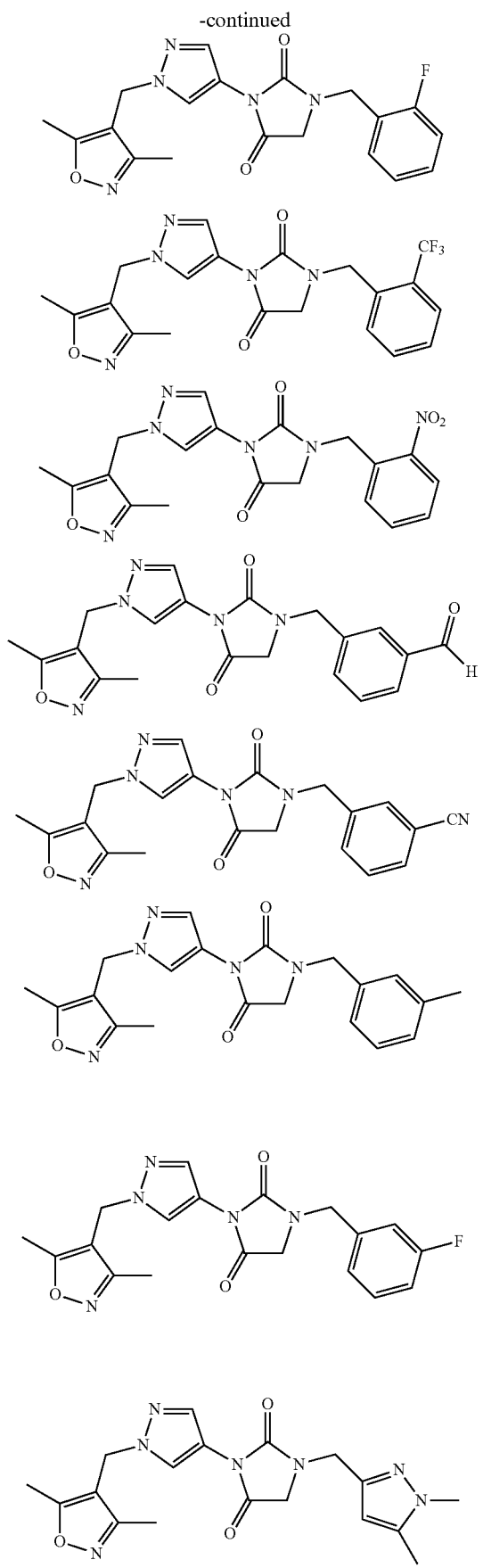
434
-continued
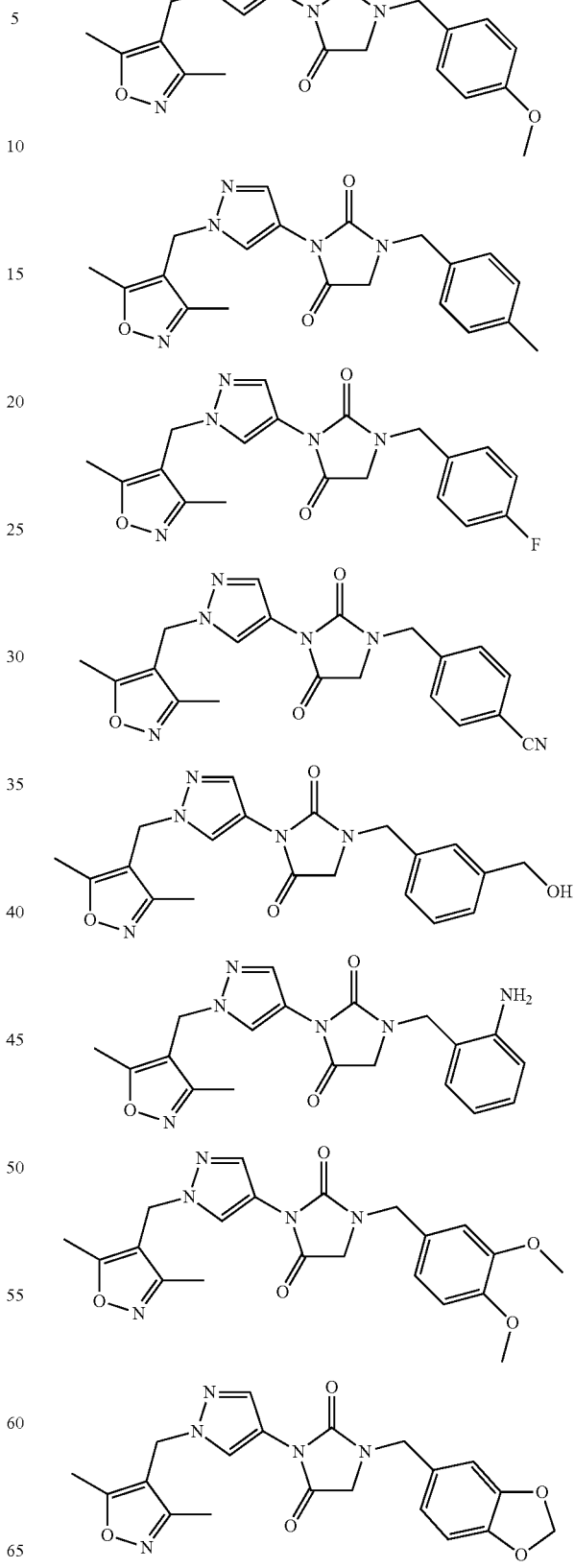

435
-continued
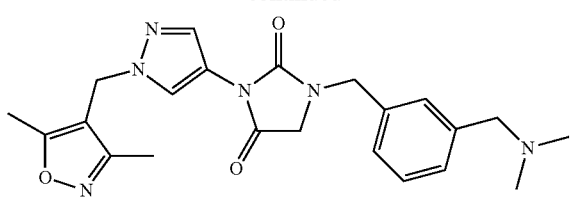
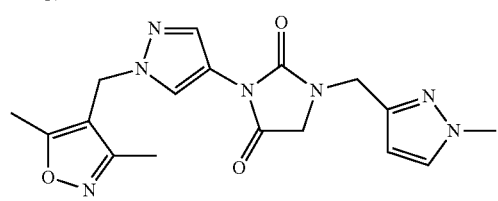
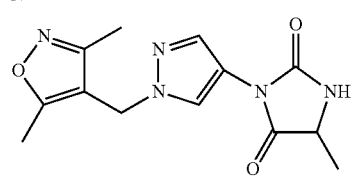
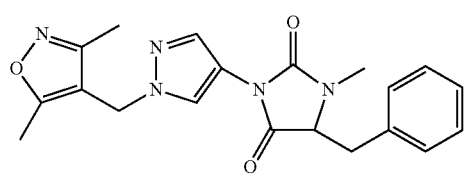
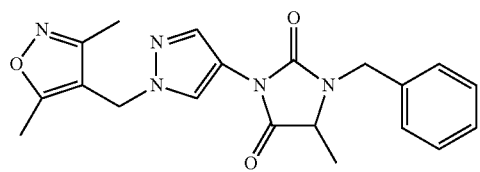
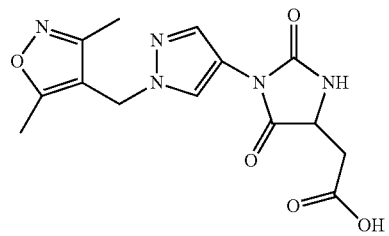
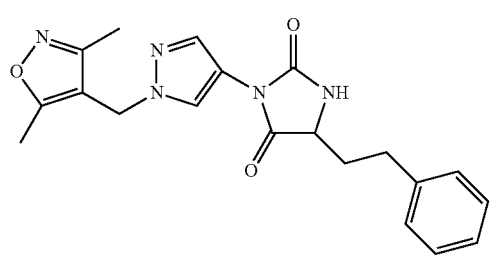
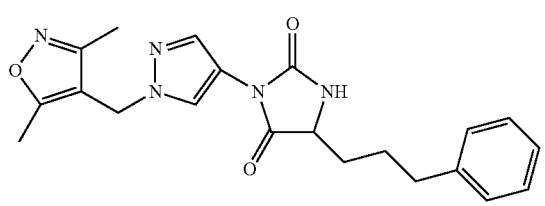
436
-continued
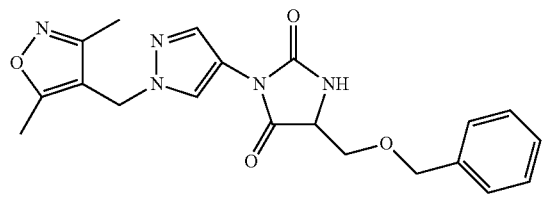
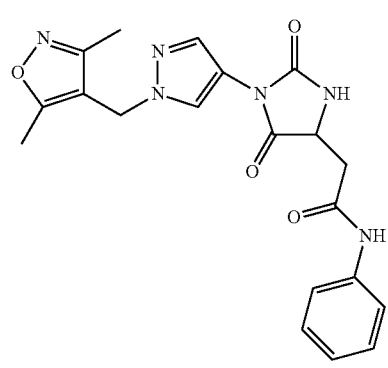
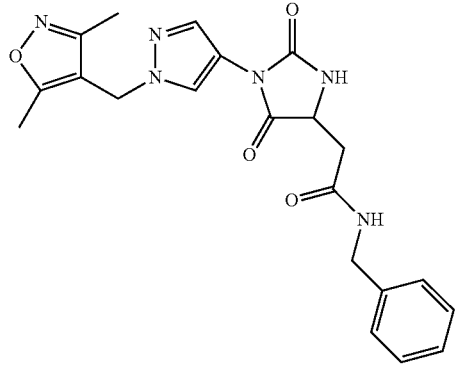
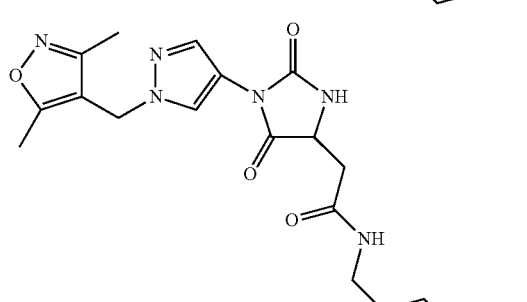
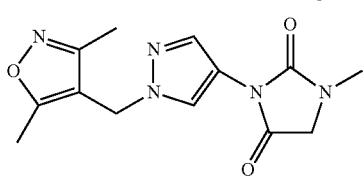
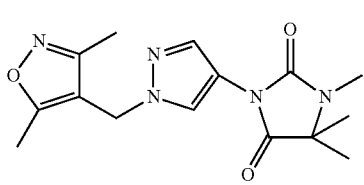

437
-continued
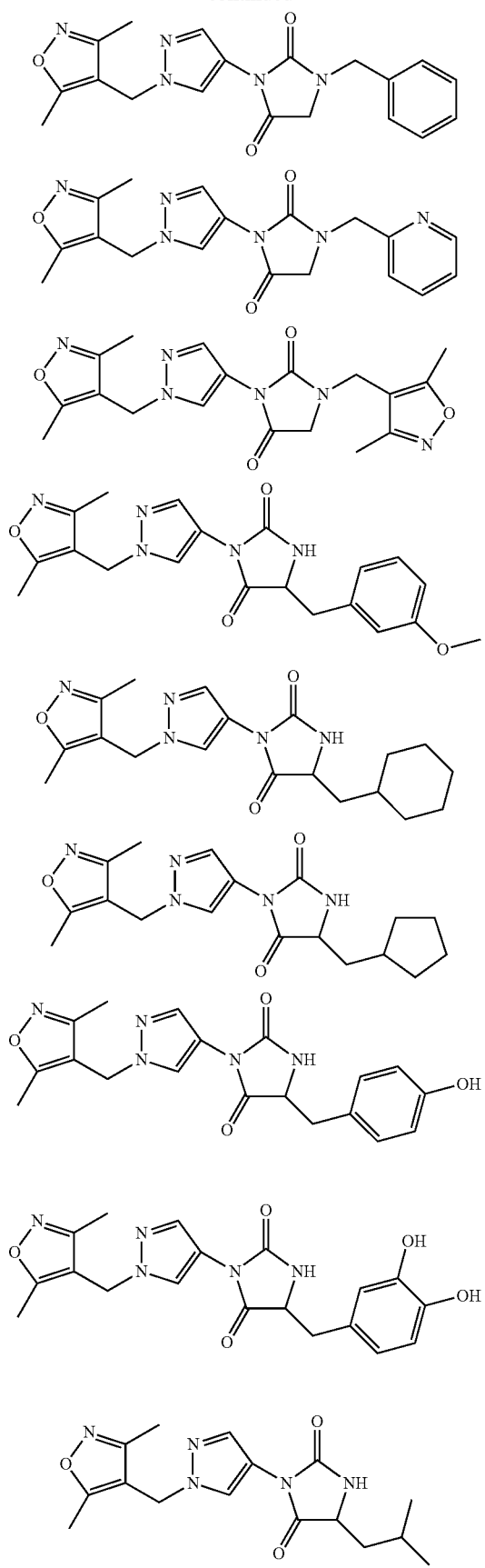
438
-continued
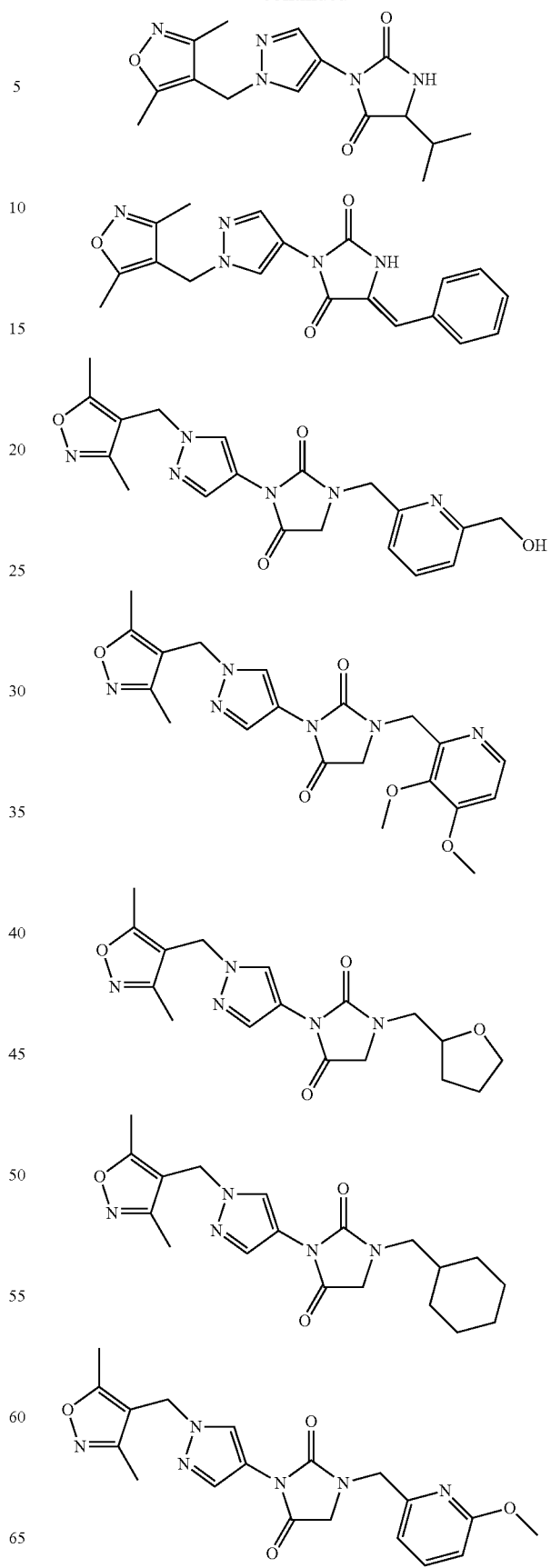

439
-continued
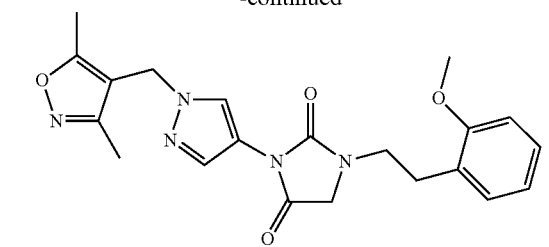
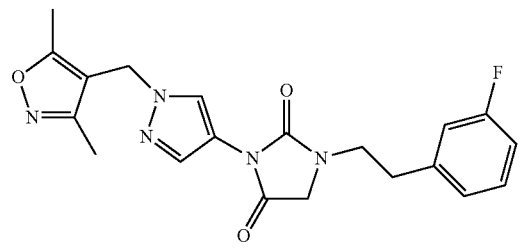
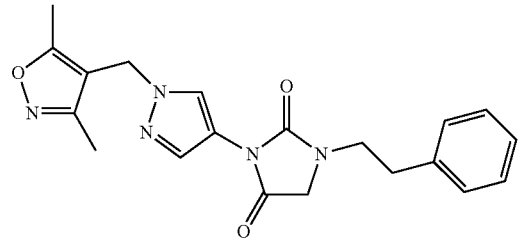
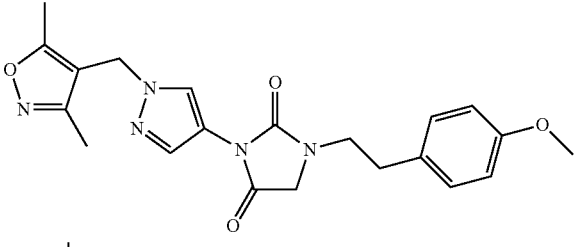
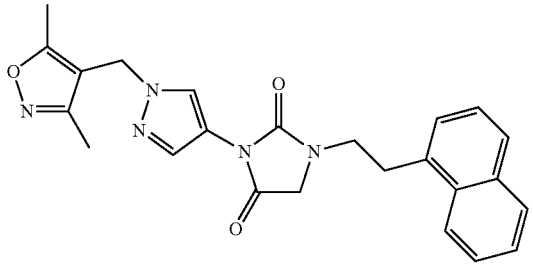
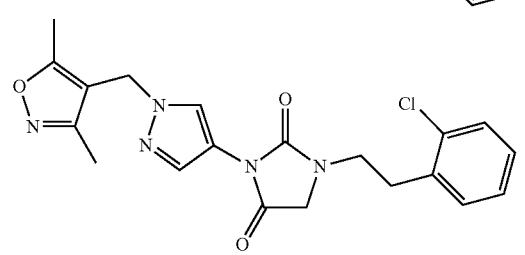
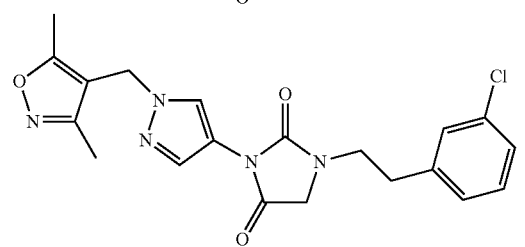
440
-continued
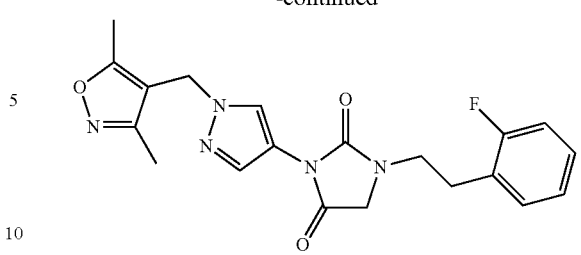
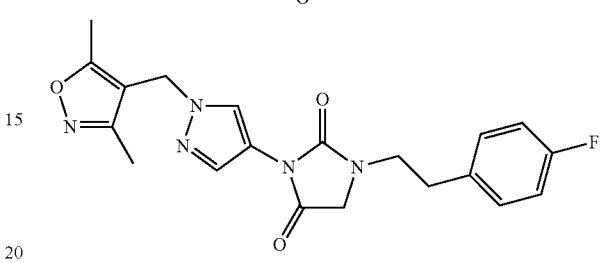
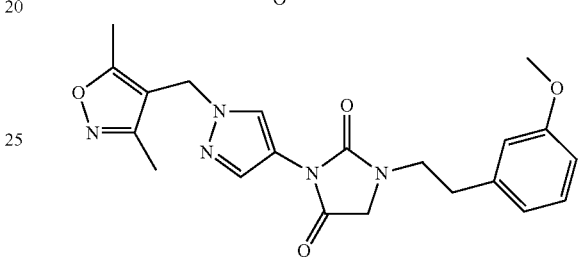
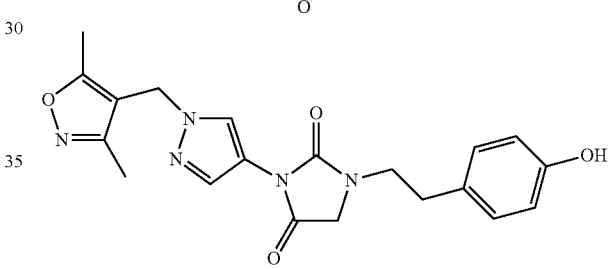
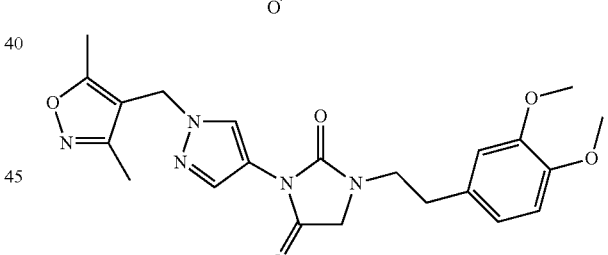
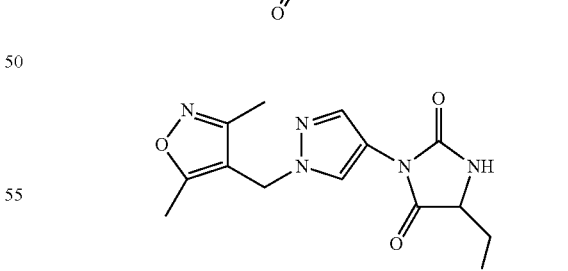
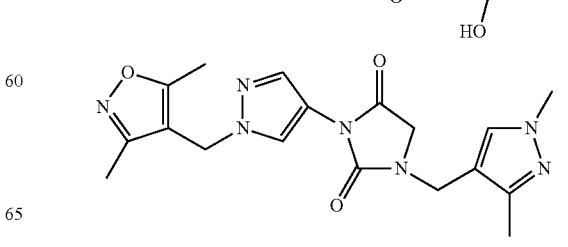

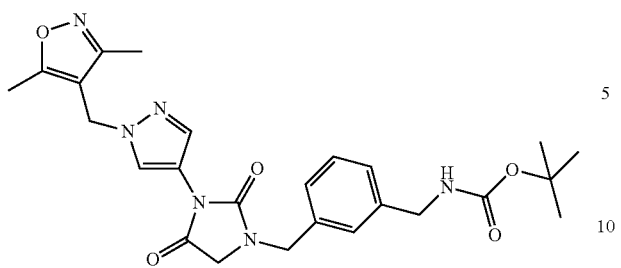
or a salt, hydrate, solvate, N-oxide or prodrug thereof.
In still another aspect, the invention relates to a compound of the formula:
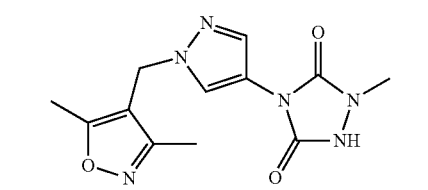
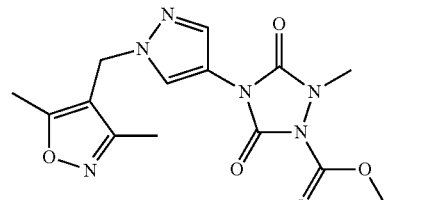
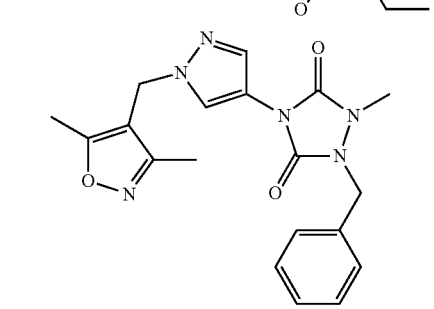
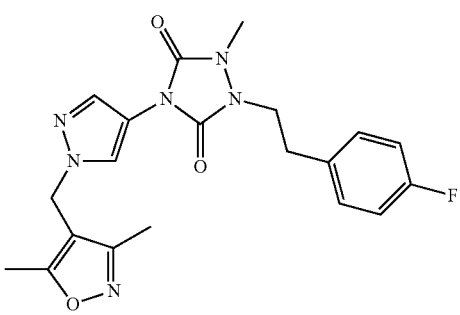
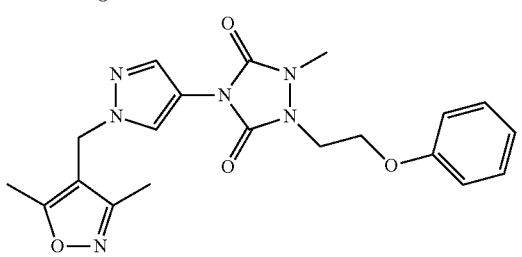
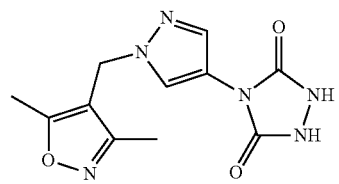
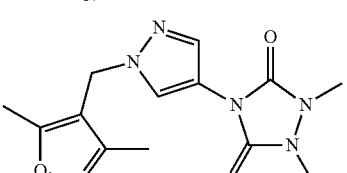
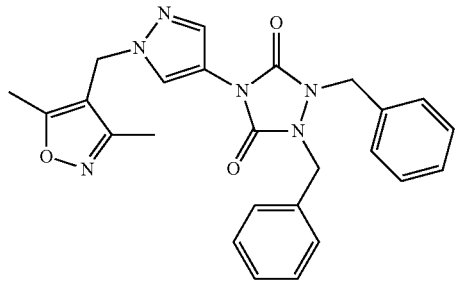
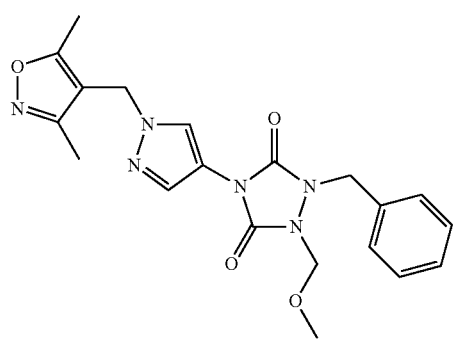
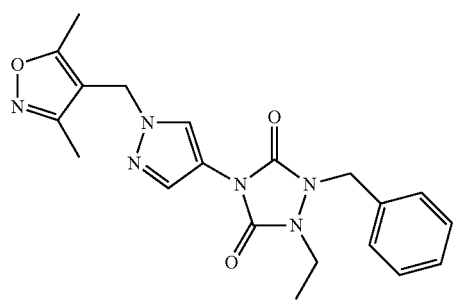
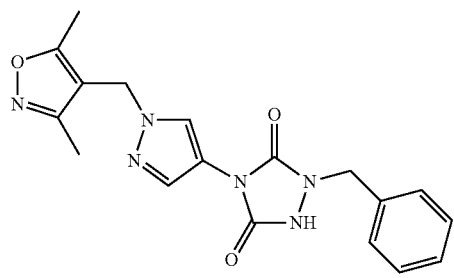

-continued

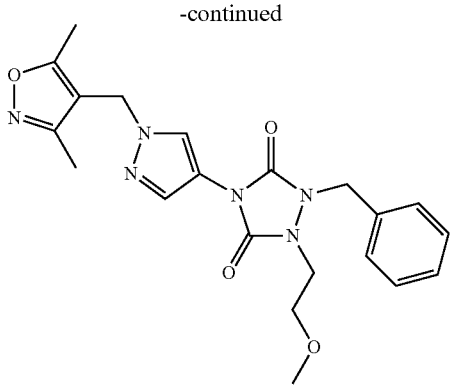

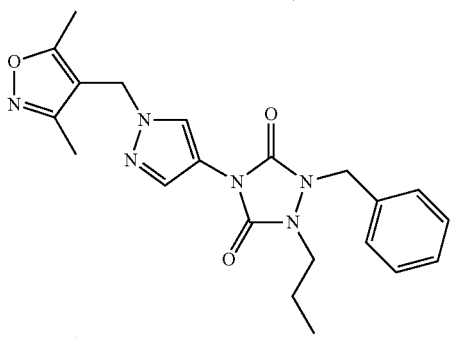

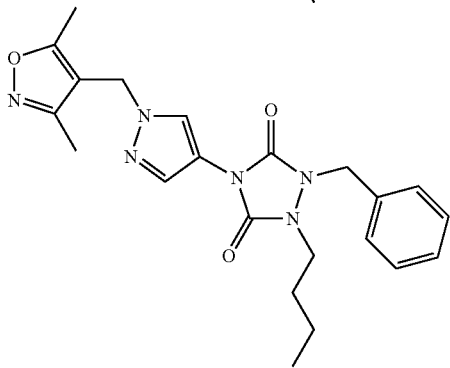

or a salt, hydrate, solvate, N-oxide or prodrug thereof.

In still another aspect, the invention relates to a method of making a compound of the formula:

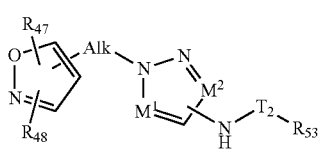

or a salt, hydrate, solvate, N-oxide or prodrug thereof, wherein Alk is an alkyl group, optionally interrupted by a heteroatom;

$T_2$ is C=S, C=O, or $S(O)_2$;

$R_{53}$ is substituted or unsubstituted alkyl, substituted or unsubstituted cycloalkyl, substituted or unsubstituted heteroaryl, substituted or unsubstituted aryl, or substituted or unsubstituted arylalkyl;

$M^1$ is N or $CR_{54}$, wherein $R_{54}$ is H or substituted or unsubstituted alkyl;

$M^2$ is N or $CR_{55}$, wherein $R_{55}$ is H or substituted or unsubstituted alkyl;

$R_{56}$ is H, substituted or unsubstituted alkyl, substituted or unsubstituted alkoxy, substituted or unsubstituted aryl, substituted or unsubstituted arylalkyl, or halo; and $R_{57}$ is H, substituted or unsubstituted alkyl, substituted or unsubstituted alkoxy, substituted or unsubstituted aryl, substituted or unsubstituted arylalkyl, or halo;

wherein the method comprises reacting a compound of the formula:

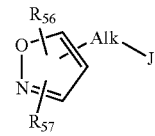

wherein $R_{56}$, $R_{57}$, and Alk are defined above and J is a leaving group;

with a compound of the formula:

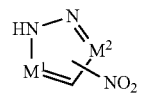

wherein $M^1$ and $M^2$ are defined above to give a compound of the formula

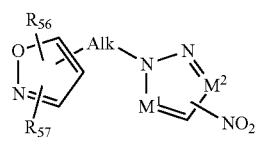

having an $NO_2$ group;

reducing the $NO_2$ group to give a compound having an $NH_2$ group; and reacting the compound having an $NH_2$ group with a compound of the formula

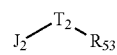

wherein $J_2$ is a leaving group and $T_2$ and $R_{53}$ are defined above.

In still another aspect, the invention relates to a method of making a compound of the formula:

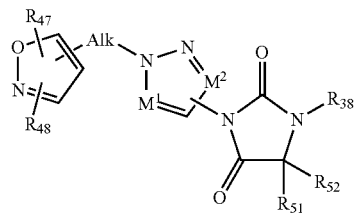

or a salt, hydrate, solvate, N-oxide or prodrug thereof, wherein Alk is an alkyl group, optionally interrupted by a heteroatom;

$R_{51}$ and $R_{52}$ are, the same or different independently one from the other, H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted arylalkylamidoalkyl, substituted or unsubstituted heteroarylamidoalkyl, substituted or unsubstituted heteroarylalkylamidoalkyl, substituted or unsubstituted arylalkyl, substituted or unsubstituted arylalkoxy, substituted or unsubstituted heteroaryl, substituted or unsubstituted heteroarylalkyl, haloalkyl, or $R_{51}$ and $R_{52}$, together with the carbon atom to which they are attached, form a substituted or unsubstituted alkenyl group;

$M^1$ is N or $CR_{49}$, wherein $R_{49}$ is H or substituted or unsubstituted alkyl;

$M^2$ is N or $CR_{50}$, wherein $R_{50}$ is H or substituted or unsubstituted alkyl;

$R_{38}$ is H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted heteroarylamidoalkyl, substituted or unsubstituted arylalkyl, substituted or unsubstituted arylalkoxy, substituted or unsubstituted heteroaryl, substituted or unsubstituted heteroarylalkyl, or haloalkyl;

$R_{47}$ is H, substituted or unsubstituted alkyl, substituted or unsubstituted alkoxy, substituted or unsubstituted aryl, substituted or unsubstituted arylalkyl, or halo; and $R_{48}$ is H, substituted or unsubstituted alkyl, substituted or unsubstituted alkoxy, substituted or unsubstituted aryl, substituted or unsubstituted arylalkyl, or halo;

wherein the method comprises heating a compound of the formula:

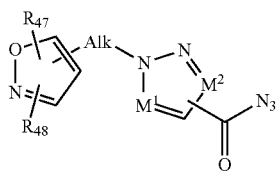

wherein $R_{47}$, $R_{48}$, Alk, $M^1$, and $M^2$ are defined above;
to convert the —$CON_3$ group to a —N=C=O group, and then reacting with a compound of the formula:

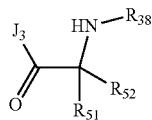

wherein $J_3$ is a leaving group and $R_{38}$, $R_{51}$, and $R_{52}$ are defined above.

In still another aspect, the invention relates to a method of making a compound of the formula:

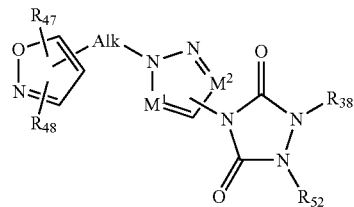

or a salt, hydrate, solvate, N-oxide or prodrug thereof,
wherein Alk is an alkyl group, optionally interrupted by a heteroatom;

$R_{52}$ is H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted arylalkylamidoalkyl, substituted or unsubstituted heteroarylamidoalkyl, substituted or unsubstituted heteroarylalkylamidoalkyl, substituted or unsubstituted arylalkyl, substituted or unsubstituted arylalkoxy, substituted or unsubstituted heteroaryl, substituted or unsubstituted heteroarylalkyl, haloalkyl;

$M^1$ is N or $CR_{49}$, wherein $R_{49}$ is H or substituted or unsubstituted alkyl;

$M^2$ is N or $CR_{50}$, wherein $R_{50}$ is H or substituted or unsubstituted alkyl;

$R_{38}$ is H, substituted or unsubstituted alkyl, substituted or unsubstituted cycloalkyl alkyl, substituted or unsubstituted heterocycloalkylalkyl, substituted or unsubstituted aryl, substituted or unsubstituted arylamidoalkyl, substituted or unsubstituted heteroarylamidoalkyl, substituted or unsubstituted arylalkyl, substituted or unsubstituted arylalkoxy, substituted or unsubstituted heteroaryl, substituted or unsubstituted heteroarylalkyl, or haloalkyl;

$R_{47}$ is H, substituted or unsubstituted alkyl, substituted or unsubstituted alkoxy, substituted or unsubstituted aryl, substituted or unsubstituted arylalkyl, or halo; and $R_{48}$ is H, substituted or unsubstituted alkyl, substituted or unsubstituted alkoxy, substituted or unsubstituted aryl, substituted or unsubstituted arylalkyl, or halo;

wherein the method comprises heating a compound of the formula:

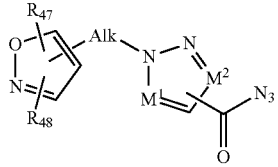

wherein $R_{47}$, $R_{48}$, Alk, $M^1$, and $M^2$ are defined above;
to covert the —$CON_S$ group to a —N=C=O group, and then reacting with a hydrazine of the formula:

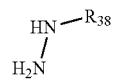

wherein $R_{38}$ is defined above.

In still another aspect, the invention relates to a method of making a compound of the formula:

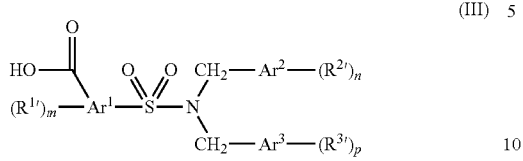
(III)

or a salt, hydrate, solvate or N-oxide thereof wherein:
$Ar^1$, $Ar^2$ and $Ar^3$ are independently a five or six membered aryl, heteroaryl, or cycloalkyl ring, and $Ar^2$ and $Ar^3$ may optionally be omitted;
m is 0, 1, 2 or 3;
n and p are independently 0, 1, 2, 3 or 4;
each $R^{1\prime}$ is independently selected from the group consisting of hydrogen, halogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, CN, $NO_2$, $OR^6$, $S(O)_bR^6$, $NR^6R^7$, $CONR^6R^7$, $CO_2R^6$, $NR^6CO_2R^7$, $NR^6CONR^7R^8$, $NR^6CSNR^7R^8$, $NR^6C(=NH)NR^7R^8$, $SO_2NR^5R^6$, $NR^5SO_2R^6$, $NR^5SO_2NR^6R^7$, $B(OR^5)(OR^6)$, $P(O)(OR^5)(OR^6)$, and $P(O)(R^5)(OR^6)$;
each $R^{2\prime}$ is independently selected from the group consisting of hydrogen, halogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, CN, $NO_2$, $OR^6$, $S(O)_bR^6$, $NR^6R^7$, $CONR^6R^7$, $CO_2R^6$, $NR^6CO_2R^7$, $NR^6CONR^7R^8$, $NR^6CSNR^7R^8$, $NR^6C(=NH)NR^7R^8$, $SO_2NR^5R^6$, $NR^5SO_2R^6$, $NR^5SO_2NR^6R^7$, $B(OR^5)(OR^6)$, $P(O)(OR^5)(OR^6)$, and $P(O)(R^5)(OR^6)$;
each $R^{3\prime}$ is independently selected from the group consisting of hydrogen, halogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, CN, $NO_2$, $OR^6$, $S(O)_bR^6$, $NR^6R^7$, $CONR^6R^7$, $CO_2R^6$, $NR^6CO_2R^7$, $NR^6CONR^7R^8$, $NR^6CSNR^7R^8$, $NR^6C(=NH)NR^7R^8$, $SO_2NR^5R^6$, $NR^5SO_2R^6$, $NR^5SO_2NR^6R^7$, $B(OR^5)(OR^6)$, $P(O)(OR^5)(OR^6)$, and $P(O)(R^5)(OR^6)$;
$R^5$-$R^8$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl or alternatively, $R^6$ and $R^7$, $R^7$ and $R^8$, together with the atoms to which they are bonded form a cycloheteroalkyl or substituted cycloheteroalkyl ring;
b is 0, 1, or 2;
wherein the method comprises reacting a compound of the formula:

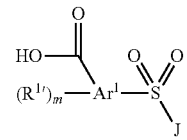

wherein J is a leaving group;
with a compound of the formula:

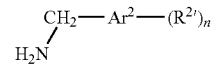

to give a product; and
reacting the product with a compound of the formula:

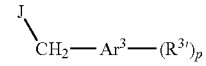

wherein J is a leaving group.

Sequences of Chimeric G Protein and hT2R Genes and Polypeptides

Protein Sequence of the Rhodopsin tag: (SEQ ID NO:1)

```
MNGTEGPNFYVPFSNKTGVVRSPFEAPQYYLAEPW
```

Protein Sequence of G16gust44: (SEQ ID NO:2)

```
MARSLTWRCCPWCLTEDEKAAARVDQEINRILLEQKKQDRGELKLLLLGPGESGKSTFI
KQMRIIHGAGYSEEERKGFRPLVYQNIFVSMRAMIEAMERLQIPFSRPESKHHASLVMSQ
DPYKVTTFEKRYAAAMQWLWRDAGIRACYERRREFHLLDSAVYYLSHLERITEEGYVP
TAQDVLRSRMPTTGINEYCFSVQKTNLRIVDVGGQKSERKKWIHCFENVIALIYLASLSE
YDQCLEENNQENRMKESLALFGTILELPWFKSTSVILFLNKTDILEEKIPTSHLATYFPSFQ
GPKQDAEAAKRFILDMYTRMYTGCVDGPEGSNLKKEDKEIYSHMTCATDTQNVKFVFD
AVTDIIIKENLKDCGLF
``` hT2R8 sequences:
DNA-(SEQ ID NO:3)

```
ATGTTCAGTCCTGCAGATAACATCTTTATAATCCTAATAACTGGAGAATTCATACTAGGA
ATATTGGGGAATGGATACAT
TGCACTAGTCAACTGGATTGACTGGATTAAGAAGAAAAAGATTTCCACAGTTGACTACAT
```

-continued

```
CCTTACCAATTTAGTTATCG

CCAGAATTTGTTTGATCAGTGTAATGGTTGTAAATGGCATTGTAATAGTACTGAACCCAG

ATGTTTATACAAAAAATAAA

CAACAGATAGTCATTTTTACCTTCTGGACATTTGCCAACTACTTAAATATGTGGATTACC

ACCTGCCTTAATGTCTTCTA

TTTTCTGAAGATAGCCAGTTCCTCTCATCCACTTTTTCTCTGGCTGAAGTGGAAAATTGA

TATGGTGGTGCACTGGATCC

TGCTGGGATGCTTTGCCATTTCCTTGTTGGTCAGCCTTATAGCAGCAATAGTACTGAGTT

GTGATTATAGGTTTCATGCA

ATTGCCAAACATAAAAGAAACATTACTGAAATGTTCCATGTGAGTAAAATACCATACTTT

GAACCCTTaACTCTCTTTAA

CCTGTTTGCAATTGTCCCATTTATTGTGTCACTGATATCATTTTTCCTTTTAGTAAGATC

TTTATGGAGACATACCAAGC

AAATAAAACTCTATGCTACCGGCAGTAGAGACCCCAGCACAGAAGTTCATGTGAGAGCCA

TTAAAACTATGACTTCATTT

ATCTTCTTTTTTTTCCTATACTATATTTCTTCTATTTTGATGACCTTTAGCTATCTTATG

ACAAAATACAAGTTAGCTGT

GGAGTTTGGAGAGATTGCAGCAATTCTCTACCCCTTGGGTCACTCACTTATTTTAATTGT

TTTAAATAATAAACTGAGGC

AGACATTTGTCAGAATGCTGACATGTAGAAAAATTGCCTGCATGATATGA
```

Protein-(SEQ ID NO:4)

```
MFSPADNIFIILITGEFILGILGNGYIALVNWIDWIKKKKISTVDYILTNLVIARICLISVMVV

NGIVIVLNPDVYTKNK

QQIVIFTFWTFANYLNMWITTCLNVFYFLKIASSSHPLFLWLKWKIDMVVHWILLGCFAI

SLLVSLIAAIVLSCDYRFHA

IAKHKRNITEMFHVSKIPYFEPLTLFNLFAIVPFIVSLISFFLLVRSLWRHTKQIKLYATGSR

DPSTEVHVRAIKTMTSF

IFFFFLYYISSILMTFSYLMTKYKLAVEFGEIAAILYPLGHSLILIVLNNKLRQTFVRMLTCR

KIACMI
``` hT2R14 sequences:
DNA-(SEQ ID NO:5)

```
ATGGGTGGTGTCATAAAGAGCATATTTACATTCGTTTTAATTGTGGAATTTATAATTGGA

AATTTAGGAAATAGTTTCAT

AGCACTGGTGAACTGTATTGACTGGGTCAAGGGAAGAAAGATCTCTTCGGTTGATCGGAT

CCTCACTGCTTTGGCAATCT

CTCGAATTAGCCTGGTTTGGTTAATATTCGGAAGCTGGTGTGTGTCTGTGTTTTCCCAG

CTTTATTTGCCACTGAAAAA

ATGTTCAGAATGCTTACTAATATCTGGACAGTGATCAATCATTTTAGTGTCTGGTTAGCT
```

-continued

ACAGGCCTCGGTACTTTTTA

TTTTCTCAAGATAGCCAATTTTTCTAACTCTATTTTTCTCTACCTAAAGTGGAGaGTTAA

AAAGGTGGTTTTGGTGCTGC

TTCTTGTGACTTCGGTCTTCTTGTTTTTAAATATTGCACTGATAAACATCCATATAAATG

CCAGTATCAATGGATACAGA

AGAAACAAGACTTGCAGTTCTGATTCAAGTAACTTTACACGATTTTCCAGTCTTATTGTA

TTAACCAGCACTGTGTTCAT

TTTCATACCCTTTACTTTGTCCCTGGCAATGTTTCTTCTCCTCATCTTCTCCATGTGGAA

ACATCGCAAGAAGATGCAGC

ACACTGTCAAAATATCCGGAGACGCCAGCACCAAAGCCCACAGAGGAGTTAAAAGTGTGA

TCACTTTCTTCCTACTCTAT

GCCATTTTCTCTCTGTCTTTTTTCATATCAGTTTGGACCTCTGAAAGGTTGGAGGAAAAT

CTAATTATTCTTTCCCAGGT

GATGGGAATGGCTTATCCTTCATGTCACTCATGTGTTCTGATTCTTGGAAACAAGAAGCT

GAGACAGGCCTCTCTGTCAG

TGCTACTGTGGCTGAGGTACATGTTCAAAGATGGGGAGCCCTCAGGTCACAAAGAATTTA

GAGAATCATCTTGA

Protein-(SEQ ID NO:6)

MGGVIKSIFTFVLIVEFIIGNLGNSFIALVNCIDWVKGRKISSVDRILTALAISRISLVWLIFG

SWCVSVFFPALFATEK

MFRMLTNIWTVINHFSVWLATGLGTFYFLKIANFSNSIFLYLKWRVKKVVLVLLLVTSVF

LFLNIALINIHINASINGYR

RNKTCSSDSSNFTRFSSLIVLTSTVFIFIPFTLSLAMFLLLIFSMWKHRKKMQHTVKISGDA

STKAHRGVKSVITFFLLY

AIFSLSFFISVWTSERLEENLIILSQVMGMAYPSCHSCVLILGNKKLRQASLSVLLWLRYM

FKDGEPSGHKEFRESS

While the foregoing detailed description has described several embodiments of the present invention, it is to be understood that the above description is illustrative only and not limiting of the disclosed invention. The invention is to be limited only by the claims which follow.

The invention claimed is:
1. A method of reducing or alleviating bitter taste comprising adding at least one compound to a composition for ingestion by humans or animals at a concentration effective to alleviate or reduce the bitter taste associated with the composition, the at least one compound having the formula:

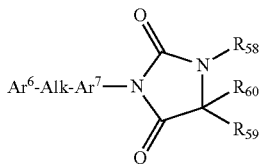

or a salt, hydrate, solvate or N-oxide thereof,
wherein $Ar^6$ and $Ar^7$ are, the same or different independently one from the other, a five-membered aryl, six-membered aryl, or a five-membered heteroaryl;
Alk is alkyl;
$R_{58}$ is H, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl;
$R_{59}$ and $R_{60}$ are, the same or different independently one from the other, H, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl, with the proviso that when one of $R_{59}$ or $R_{60}$ is H, then the other of $R_{59}$ or $R_{60}$ is not H; or
$R_{59}$ and $R_{60}$, together with the atom to which the are attached, form a cycloalkyl, a substituted cycloalkyl, a cycloheteroalkyl, or substituted cycloheteroalkyl ring; or
$R_{58}$ and $R_{60}$, together with the atoms to which the are attached, form a five-membered cycloheteroalkyl, six-membered cycloheteroalkyl, or substituted cycloheteroalkyl ring; or

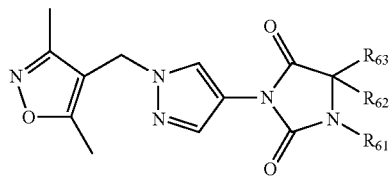

or a salt, hydrate, solvate or N-oxide thereof,
wherein:
$R_{61}$ is H, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl;
$R_{62}$ and $R_{63}$ are, the same or different independently one from the other, H, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl, with the proviso that when one of $R_{62}$ or $R_{63}$ is H, then the other of $R_{62}$ or $R_{63}$ is not H, or $R_{62}$ and $R_{63}$, together with the atoms to which the are attached, form a cycloalkyl, a substituted cycloalkyl, a cycloheteroalkyl, or substituted cycloheteroalkyl ring; or
$R_{61}$ and $R_{62}$, together with the atoms to which the are attached, form a five-membered cycloheteroalkyl, six-membered cycloheteroalkyl, or substituted cycloheteroalkyl ring; or

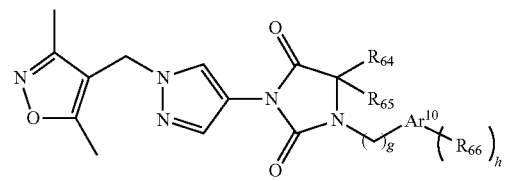

or a salt, hydrate, solvateor N-oxide thereof,
wherein:
$R_{64}$ and $R_{65}$ are the same or different independently one from the other, H, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl, with the proviso that when one of $R_{64}$ or $R_{65}$ is H, then the other of $R_{64}$ or $R_{65}$ is not H,
or $R_{64}$ and $R_{65}$, together with the atoms to which the are attached, form a cycloalkyl, a substituted cycloalkyl, a cycloheteroalkyl, or substituted cycloheteroalkyl ring;
each $R_{66}$ is independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —F, —Cl, —CN, —$NO_2$, —$OR_{67}$, —$S(O)_iR_{67}$, —$NR_{67}R_{68}$, —$CONR_{67}R_{68}$, —$CO_2R_{67}$, —$NR_{67}CO_2R_{68}$, —$NR_{67}CONR_{68}R_{69}$, —$NR_{67}CSNR_{68}R_{69}$ or —$NR_{67}C(=NH)NR_{68}R_{69}$, —$SO_2NR_{67}R_{68}$, —$NR_{67}SO_2R_{68}$, —$NR_{67}SO_2NR_{68}R_{69}$, —$B(OR_{67})(OR_{68})$, —$P(O)(OR_{67})(OR_{68})$, or —$P(O)(R_{67})(OR_{68})$, wherein $R_{67}$, $R_{68}$, and $R_{69}$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, or substituted heteroarylalkyl or alternatively, $R_{67}$ and $R_{68}$ or $R_{68}$ and $R_{69}$, together with the atoms to which they are attached, form a cycloheteroalkyl or substituted cycloheteroalkyl ring;
$Ar^{10}$ is an aryl or heteroaryl ring;
g is 0, 1, 2, 3, or 4;
h is 0, 1, 2, 3, or 4; and
i is 0, 1, or 2; or

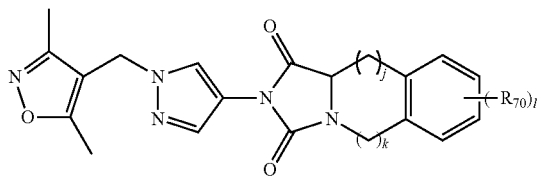

or a salt, hydrate, solvate or N-oxide thereof, wherein:

each $R_{70}$ is independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —F, —Cl, —CN, —$NO_2$, —$OR_{67}$, —$S(O)_jR_{67}$, —$NR_{67}R_{68}$, —$CONR_{67}R_{68}$, —$CO_2R_{67}$, —$NR_{67}CO_2R_{68}$, —$NR_{67}CONR_{68}R_{69}$, —$NR_{67}CSNR_{68}R_{69}$ or —$NR_{67}C(=NH)NR_{68}R_{69}$, —$SO_2NR_{67}R_{68}$, —$NR_{67}SO_2R_{68}$, —$NR_{67}SO_2NR_{68}R_{69}$, —$B(OR_{67})(OR_{68})$, —$P(O)(OR_{67})(OR_{68})$, or —$P(O)(R_{67})(OR_{68})$, wherein $R_{67}$, $R_{68}$, and $R_{69}$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl or, alternatively, $R_{67}$ and $R_{68}$ or $R_{68}$ and $R_{69}$, together with the atoms to which they are attached, form a cycloheteroalkyl or substituted cycloheteroalkyl ring;

j is 0, 1, or 2;

k is 0, 1, or 2; and l is 0, 1, or 2;

with the proviso that j and k are not simultaneously both 0; or

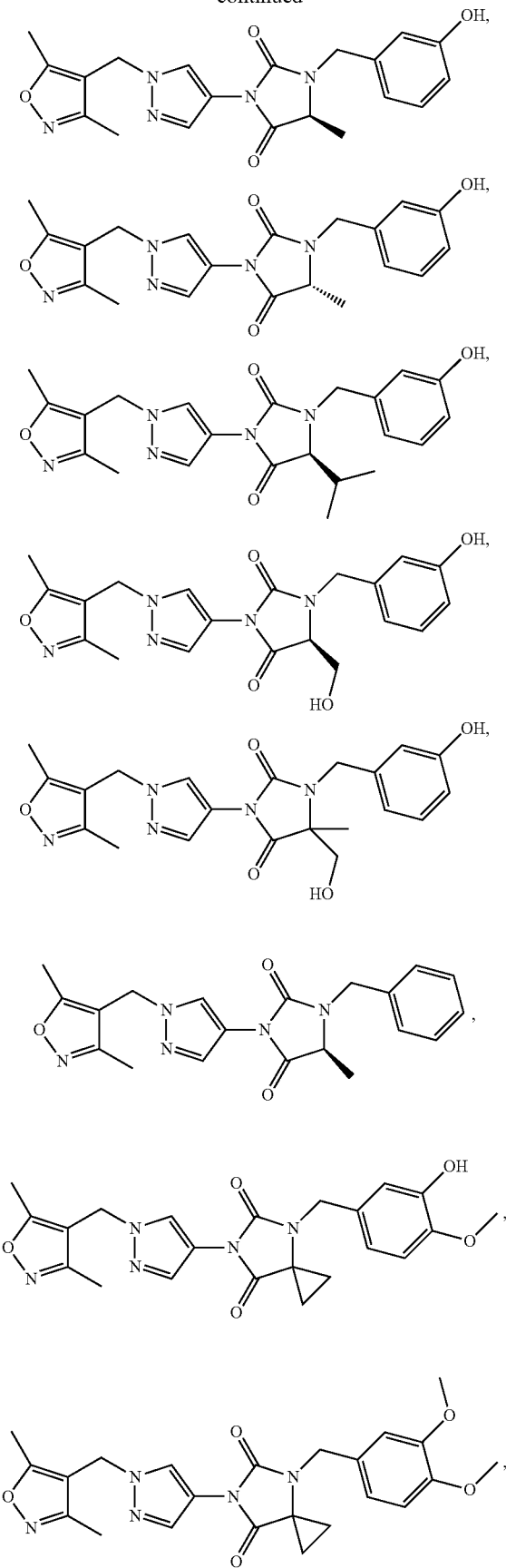

465
-continued
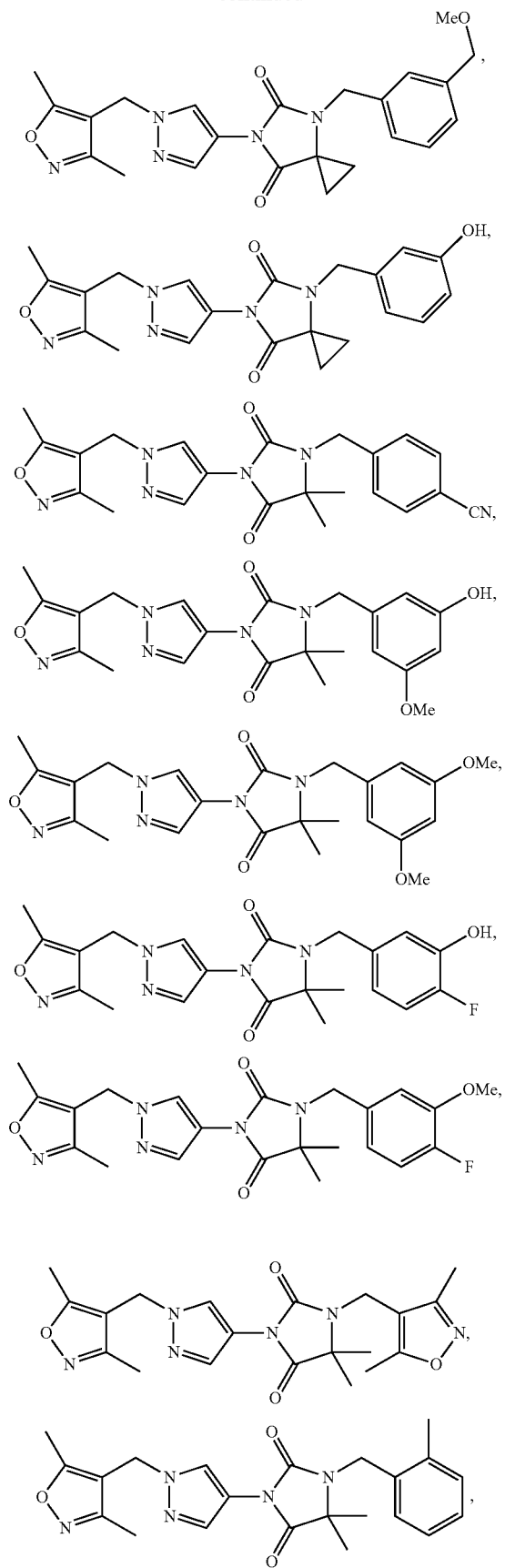
466
-continued
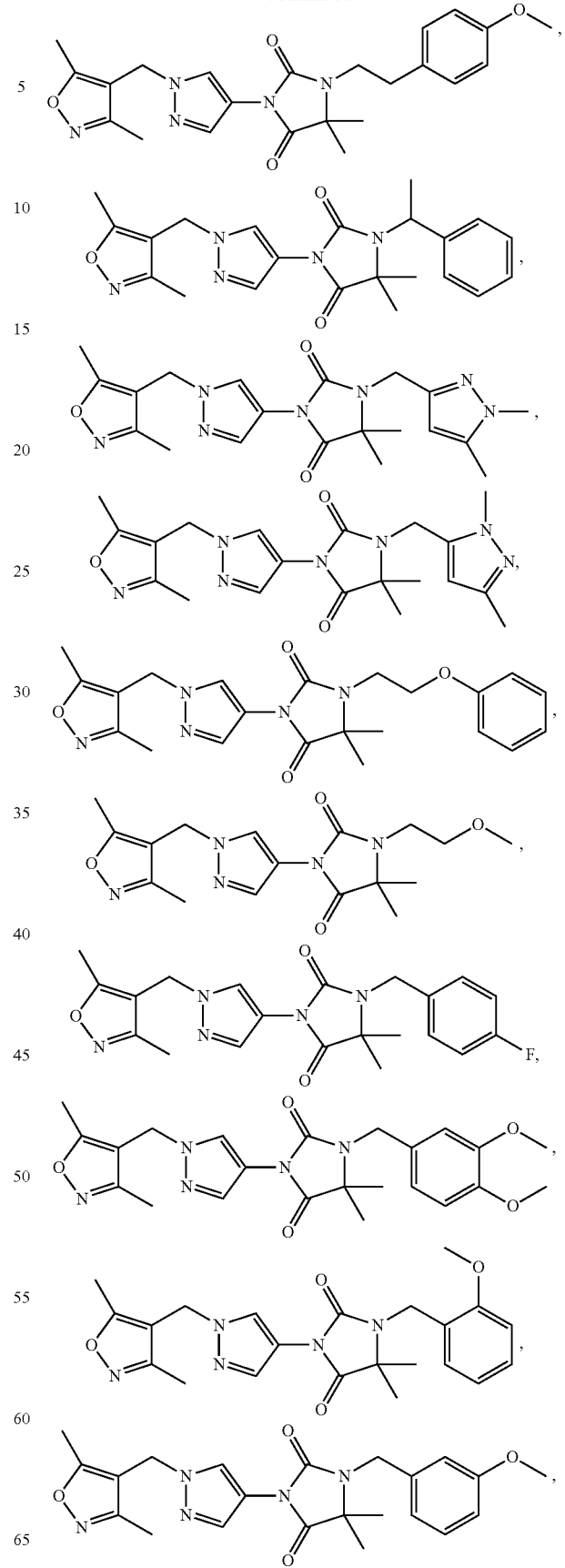

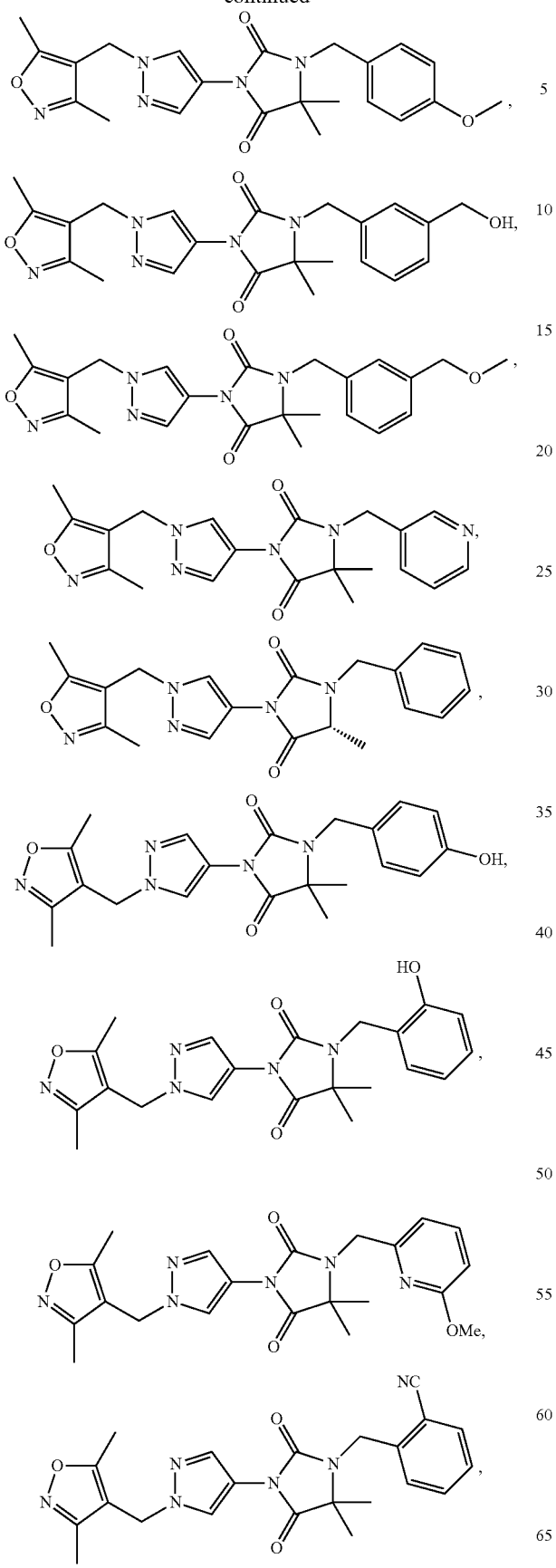
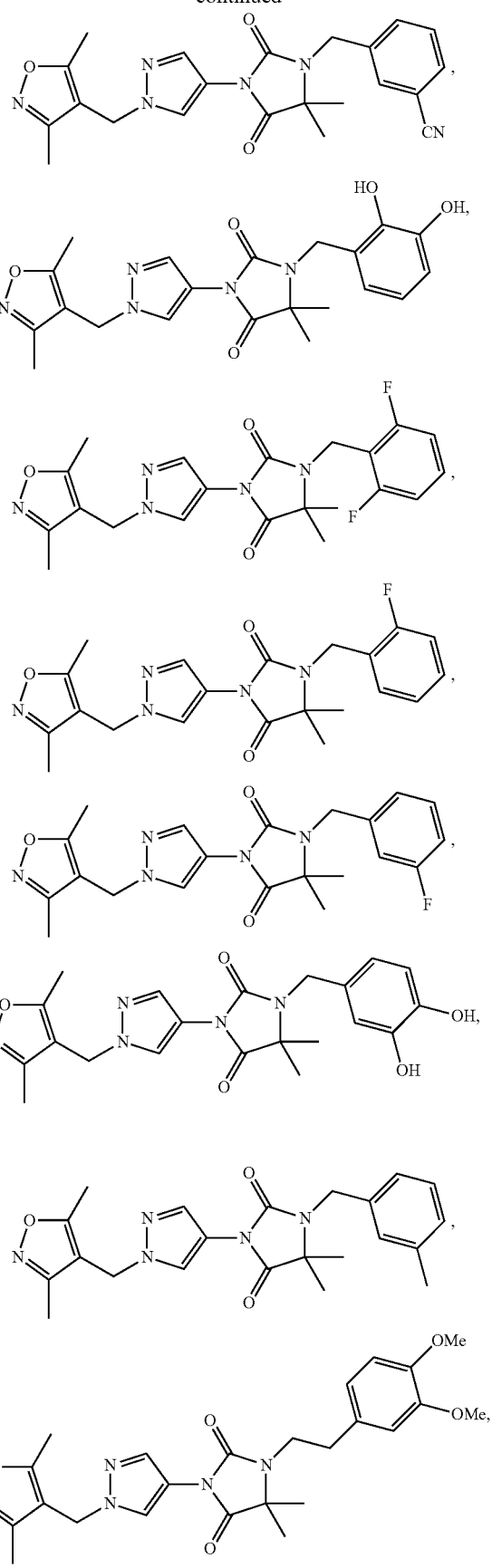

469
-continued
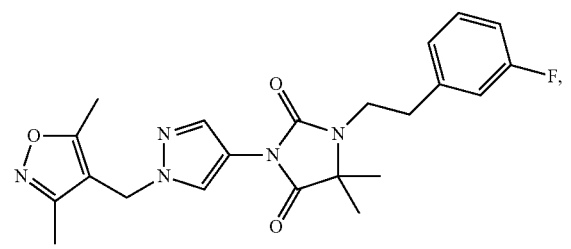
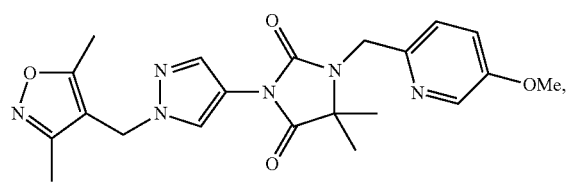
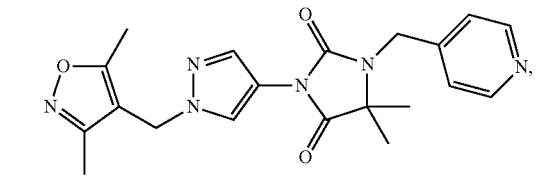
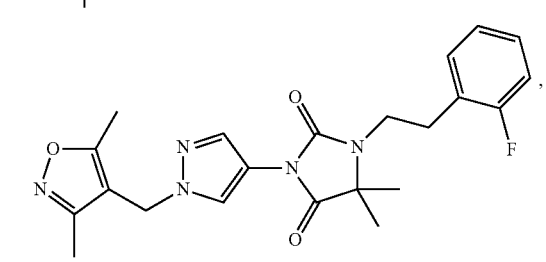
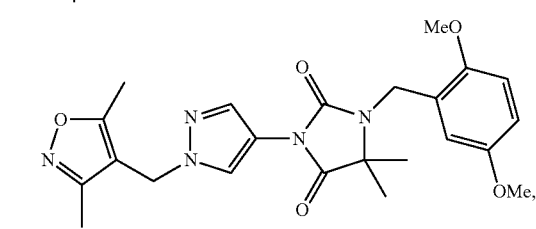
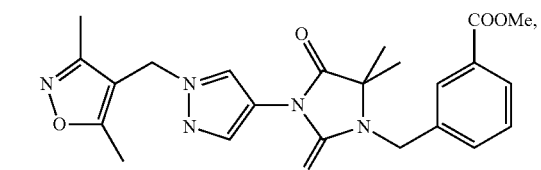
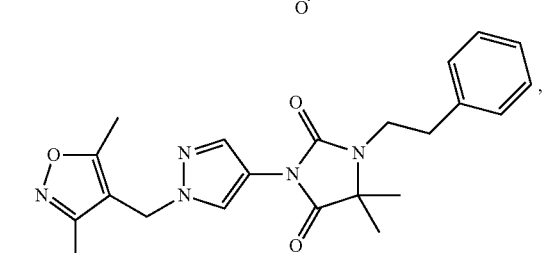
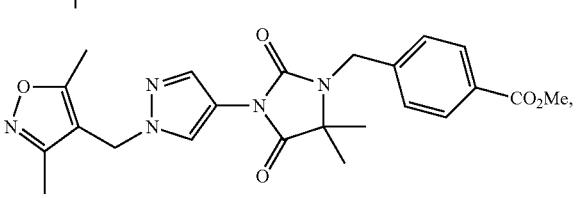
470
-continued
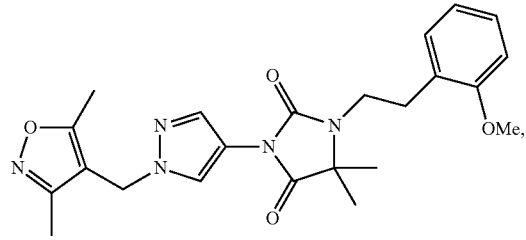
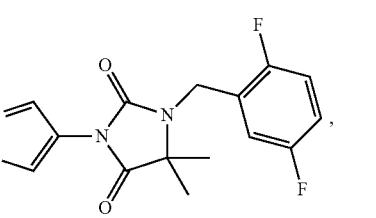
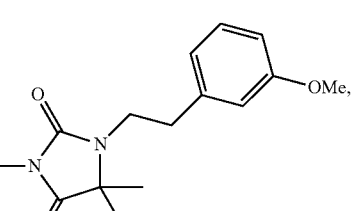
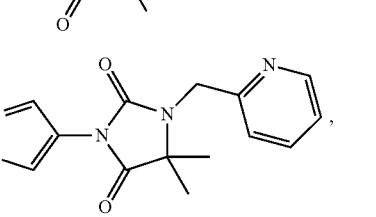
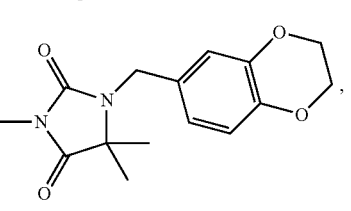
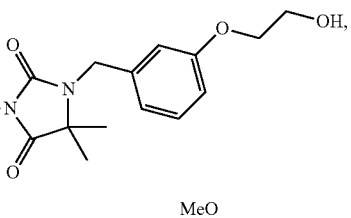
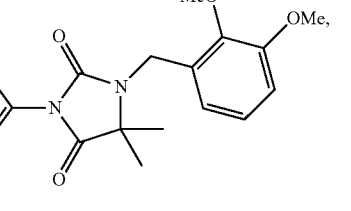
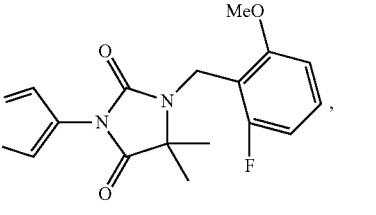

471
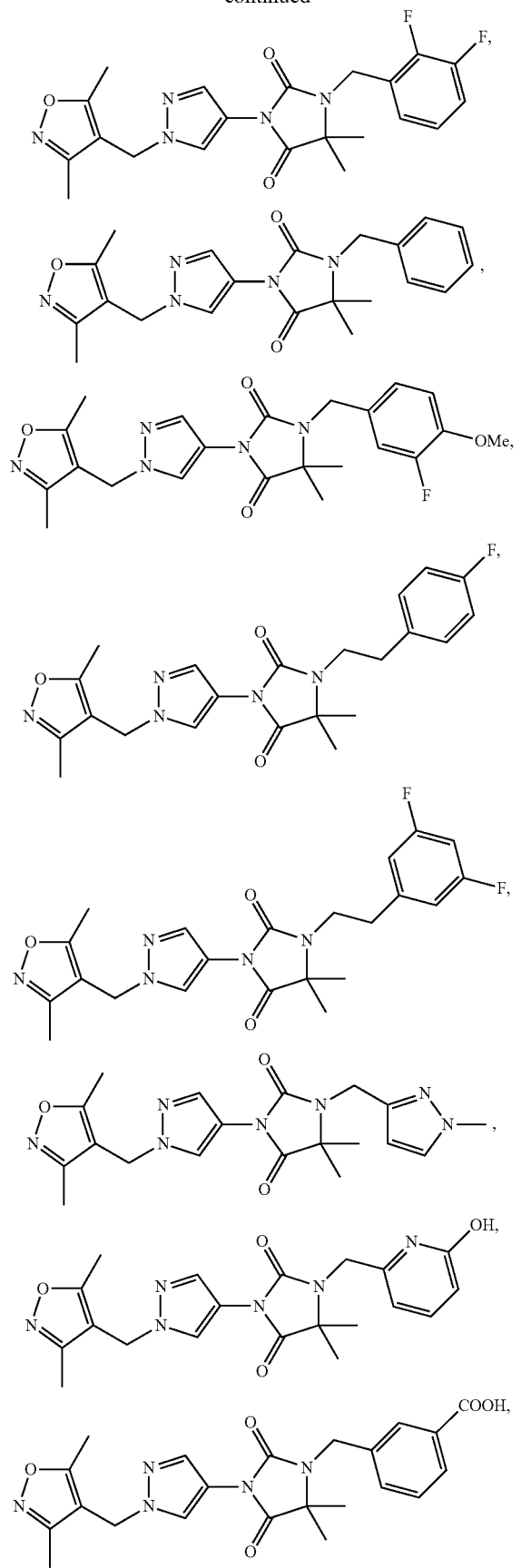
472
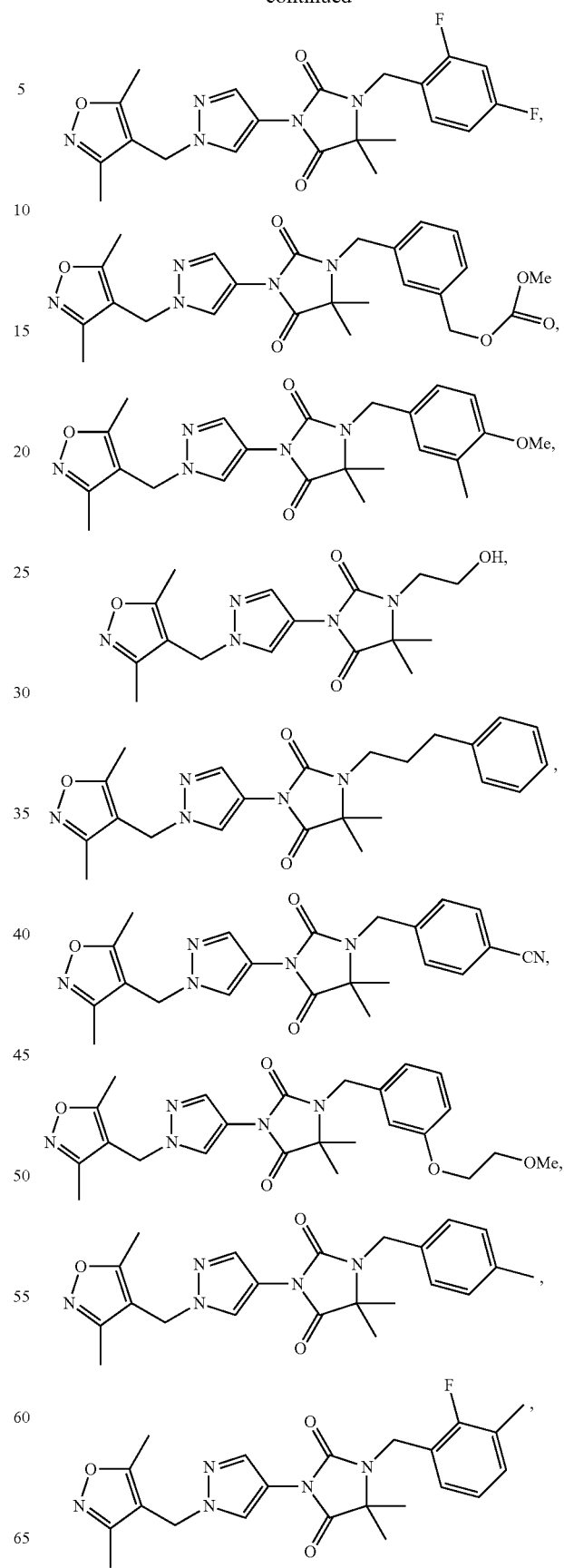

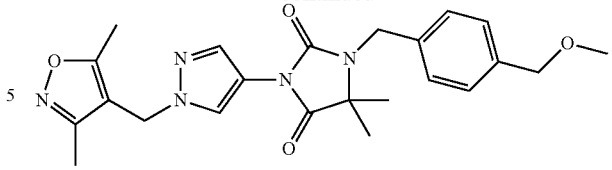

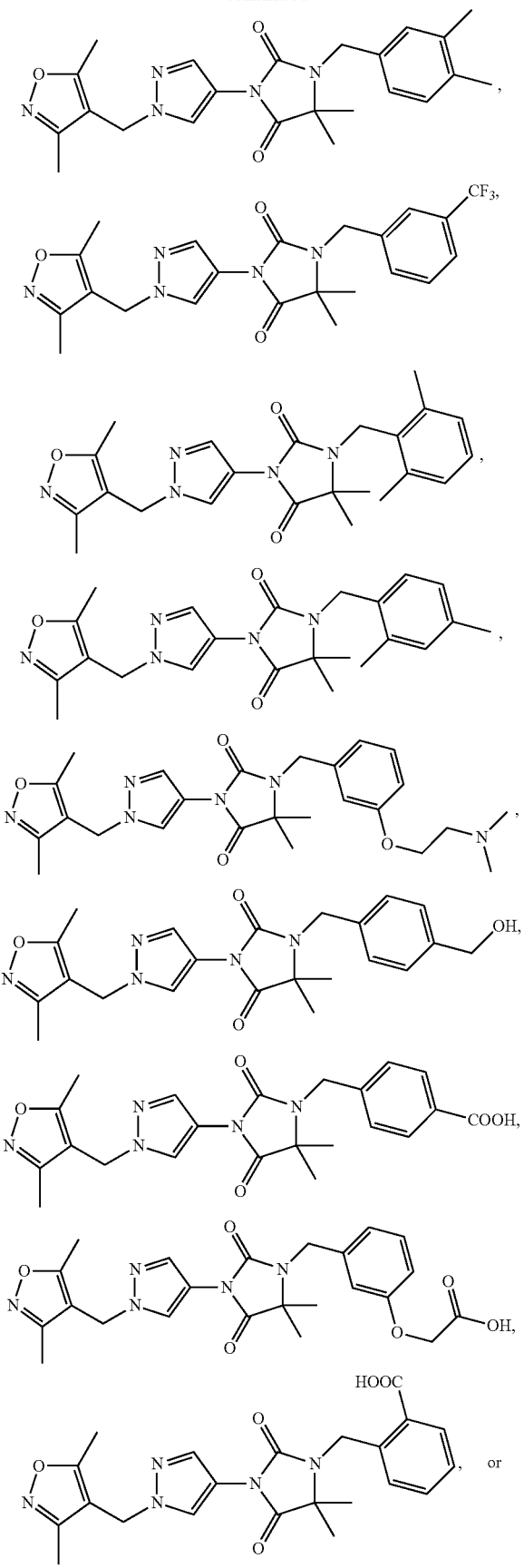

or a salt, hydrate, solvate or N-oxide thereof.

2. The method of claim 1, wherein the concentration of the at least one compound is from about 0.1 ppm to about 100 ppm.

3. The method of claim 1, wherein the concentration of the at least one compound is from about 1 ppm to about 25 ppm.

4. The method of claim 1, wherein the composition is a food, beverage, or medicament.

5. The method of claim 1, wherein the composition contains bitter compounds that activate one or more of hT2R3, 7, 10, 14, 16, 44, 51, 55, 61, 63, 65, 71 and/or hT2R5, 9, 13, 54, 67, and 75.

6. The method of claim 1, wherein the composition contains at least one bitter compound that activates multiple bitter receptors or which has an undetermined bitter receptor specificity.

7. The method of claim 1, wherein the composition is a coffee or coffee flavored composition.

8. The method of claim 7, wherein the composition comprises at least 2 compounds at least one of which is an hT2R8 antagonist and at least one of which is an hT2R14 antagonist.

9. The method of claim 7, wherein the coffee or coffee flavored composition is an instant coffee or brewed coffee.

10. A method of identifying a conserved binding motif present in different human T2Rs comprising exposing the cell membrane of a cell to a compound having the formula:

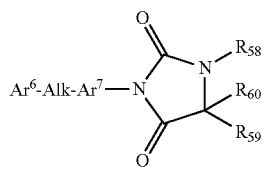

or a salt, hydrate, solvate or N-oxide thereof, wherein $Ar^6$ and $Ar^7$ are, the same or different independently one from the other, a five-membered aryl, six-membered aryl, or a five-membered heteroaryl;

Alk is alkyl;

$R_{58}$ is H, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl;

$R_{59}$ and $R_{60}$ are, the same or different independently one from the other, H, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl, with the proviso that when one of $R_{59}$ or $R_{60}$ is H, then the other of $R_{59}$ or $R_{60}$ is not H; or $R_{59}$ and $R_{60}$, together with the atom to which the are attached, form a cycloalkyl, a substituted cycloalkyl, a cycloheteroalkyl, or substituted cycloheteroalkyl ring; or $R_{58}$ and $R_{60}$, together with the atoms to which the are attached, form a five-membered cycloheteroalkyl, six-membered cycloheteroalkyl, or substituted cycloheteroalkyl ring; or

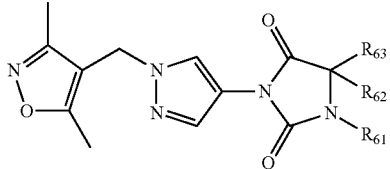

or a salt, hydrate, solvate or N-oxide thereof,
wherein:
$R_{61}$ is H, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl;
$R_{62}$ and $R_{63}$ are the same or different independently one from the other, H, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, or substituted heteroarylalkyl, with the proviso that when one of $R_{62}$ or $R_{63}$ is H, then the other of $R_{62}$ or $R_{63}$ is not H,
or $R_{62}$ and $R_{63}$, together with the atoms to which the are attached, form a cycloalkyl, a substituted cycloalkyl, a cycloheteroalkyl or substituted cycloheteroalkyl ring; or
$R_{61}$ and $R_{62}$, together with the atoms to which the are attached, form a five-membered cycloheteroalkyl, six-membered cycloheteroalkyl, or substituted cycloheteroalkyl ring; or

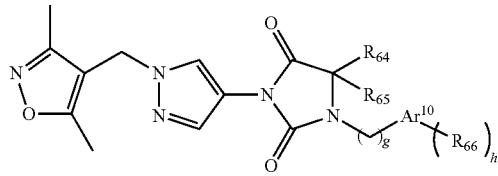

or a salt, hydrate, solvate or N-oxide thereof,
wherein:
$R_{64}$ and $R_{65}$ are the same or different independently one from the other, H, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl, with the proviso that when one of $R_{64}$ or $R_{65}$ is H, then the other of $R_{64}$ or $R_{65}$ is not H,
or $R_{64}$ and $R_{65}$, together with the atoms to which the are attached, form a cycloalkyl, a substituted cycloalkyl, a cycloheteroalkyl, or substituted cycloheteroalkyl ring;
each $R_{66}$ is independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —F, —Cl, —CN, —NO$_2$, —OR$_{67}$, —S(O)$_t$R$_{67}$, —NR$_{67}$R$_{68}$, —CONR$_{67}$R$_{68}$, —CO$_2$R$_{67}$, —NR$_{67}$CO$_2$R$_{68}$, —NR$_{67}$CONR$_{68}$R$_{69}$, —NR$_{67}$CSNR$_{68}$R$_{69}$ or —NR$_{67}$C (=NH)NR$_{68}$R$_{69}$, —SO$_2$NR$_{67}$R$_{68}$, —NR$_{67}$SO$_2$R$_{68}$, —NR$_{67}$SO$_2$NR$_{68}$R$_{69}$, —B(OR$_{67}$)(OR$_{68}$), —P(O) (OR$_{67}$)(OR$_{68}$), or —P(O)(R$_{67}$)(OR$_{68}$), wherein R$_{67}$, R$_{68}$, and R$_{69}$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, or substituted heteroarylalkyl or, alternatively, R$_{67}$ and R$_{68}$ or R$_{68}$ and R$_{69}$, together with the atoms to which they are attached, form a cycloheteroalkyl or substituted cycloheteroalkyl ring;

Ar$^{10}$ is an aryl or heteroaryl ring;
g is 0, 1, 2, 3, or 4;
h is 0, 1, 2, 3, or 4; and
i is 0, 1, or 2; or

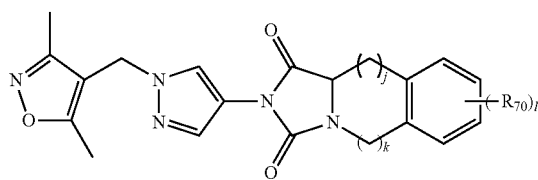

or a salt, hydrate, solvate or N-oxide thereof,
wherein:
each $R_{70}$ is independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —F, —Cl, —CN, —NO$_2$, —OR$_{67}$, —S(O)$_t$R$_{67}$, —NR$_{67}$R$_{68}$, —CONR$_{67}$R$_{68}$, —CO$_2$R$_{67}$, —NR$_{67}$CO$_2$R$_{68}$, —NR$_{67}$CONR$_{68}$R$_{69}$, —NR$_{67}$CSNR$_{68}$R$_{69}$ or —NR$_{67}$C (=NH)NR$_{68}$R$_{69}$, —SO$_2$NR$_{67}$R$_{68}$, —NR$_{67}$SO$_2$R$_{68}$, —NR$_{67}$SO$_2$NR$_{68}$R$_{69}$, —B(OR$_{67}$)(OR$_{68}$), —P(O) (OR$_{67}$)(OR$_{68}$), or —P(O)(R$_{67}$)(OR$_{68}$), wherein R$_{67}$, R$_{68}$, and R$_{69}$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl or, alternatively, R$_{67}$ and R$_{68}$ or R$_{68}$ and R$_{69}$, together with the atoms to which they are attached, form a cycloheteroalkyl or substituted cycloheteroalkyl ring;

j is 0, 1, or 2;
k is 0, 1, or 2; and
l is 0, 1, or 2;
with the proviso that j and k are not simultaneously both 0; or

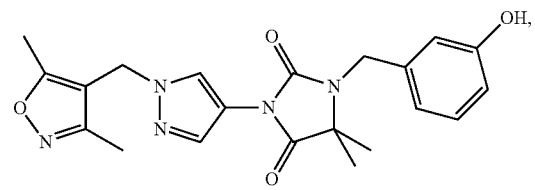

477
-continued
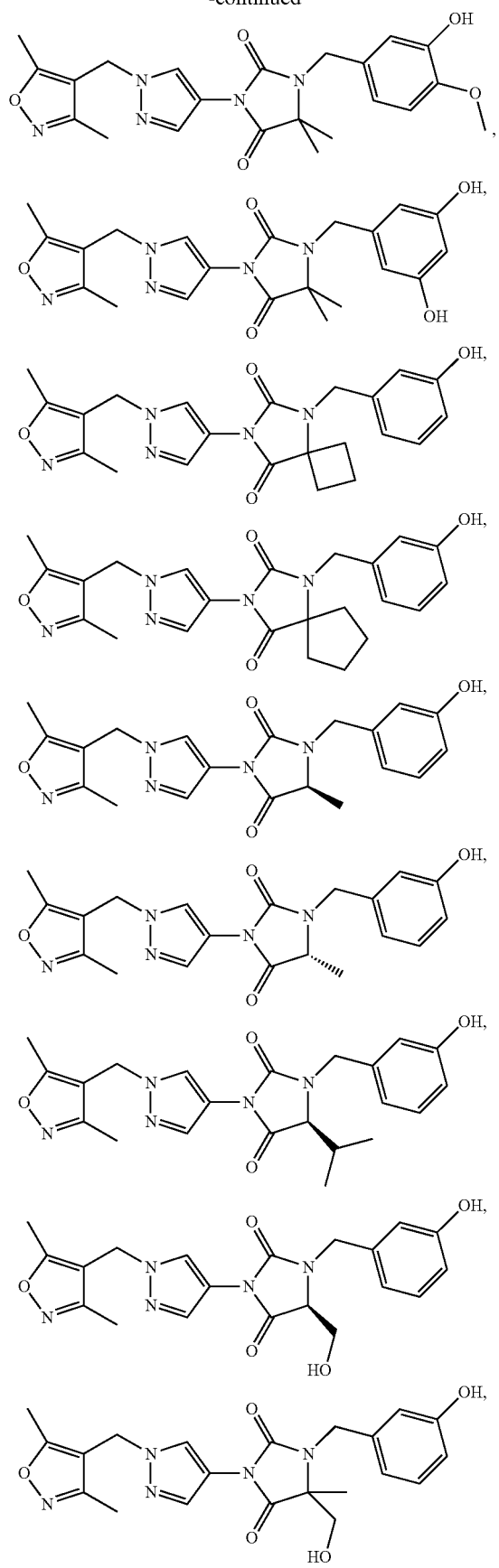
478
-continued
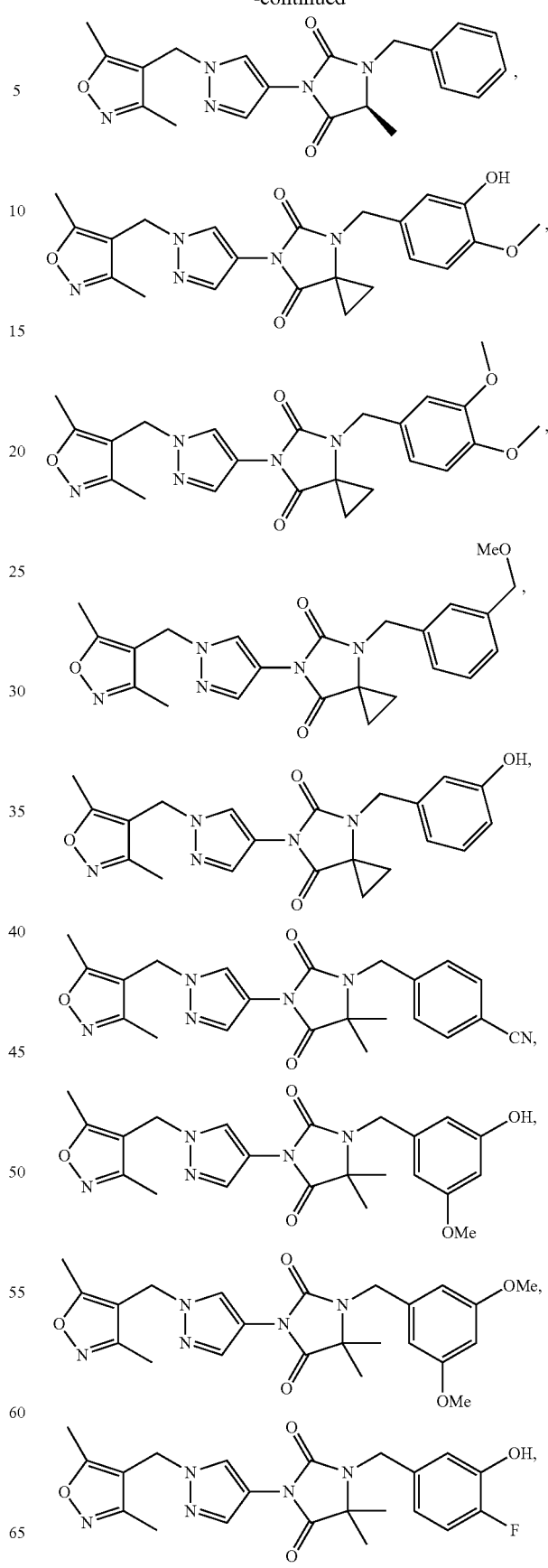

479
-continued
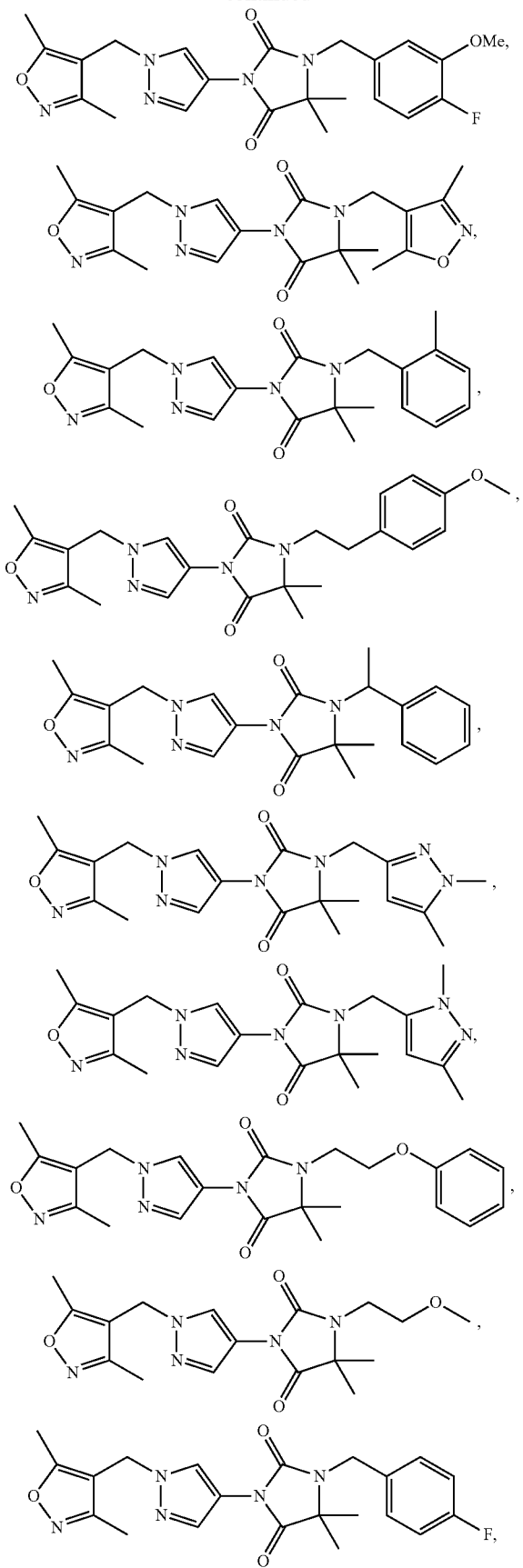
480
-continued
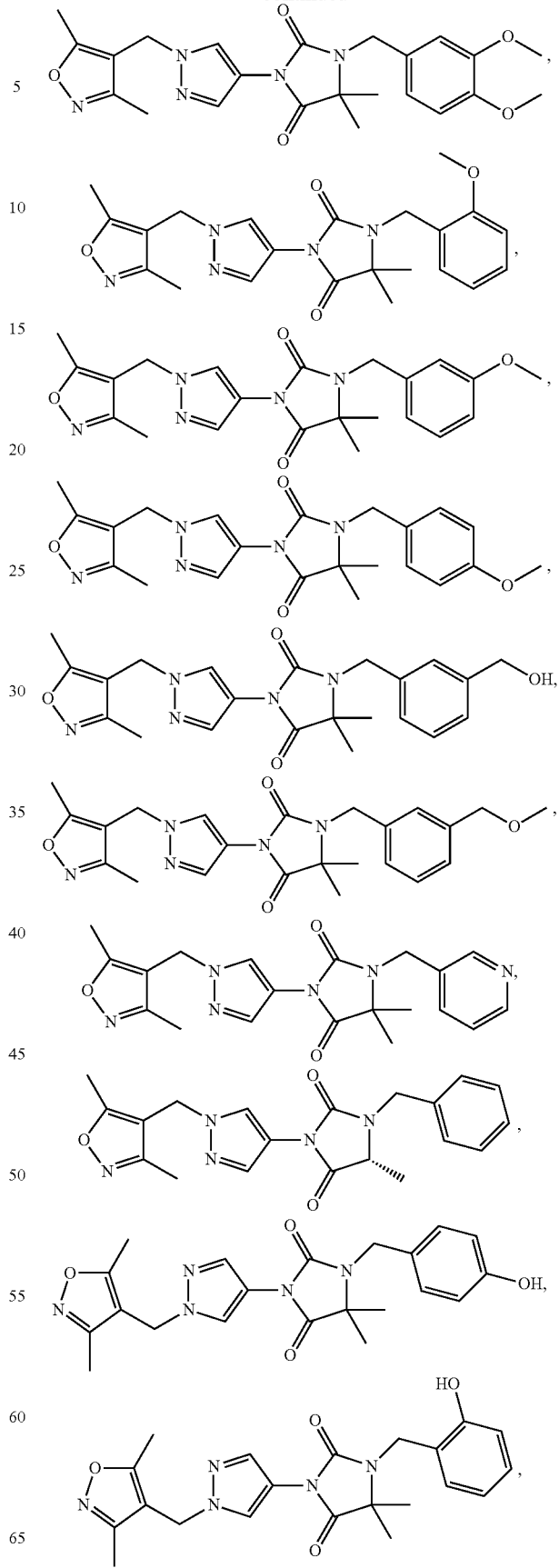

481
-continued
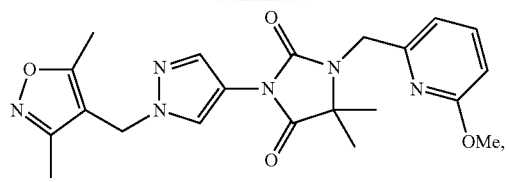
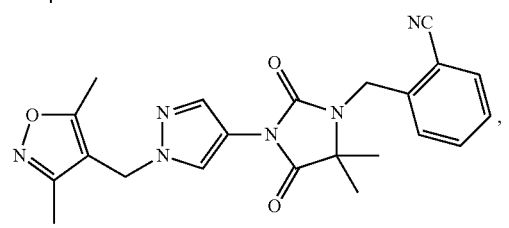
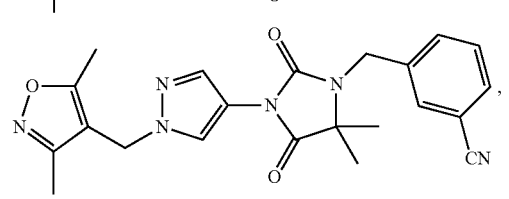
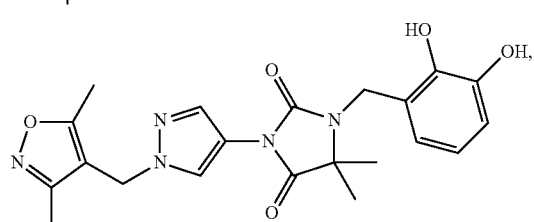
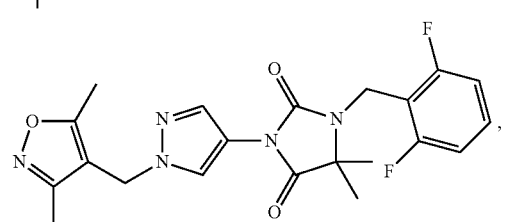
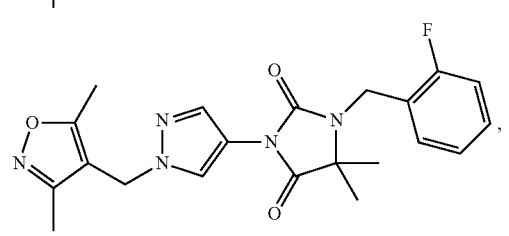
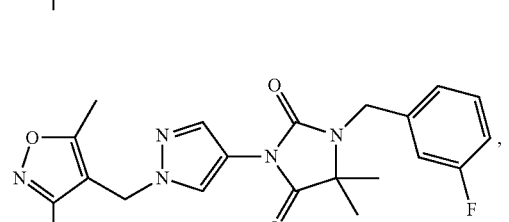
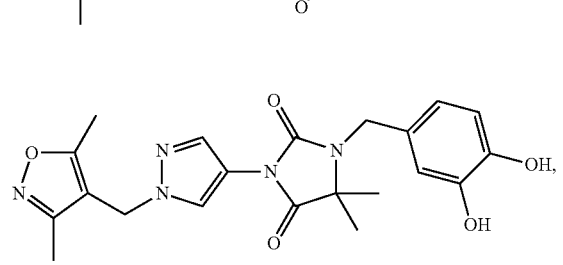
482
-continued
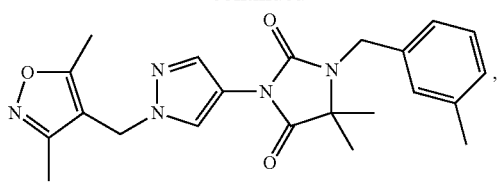
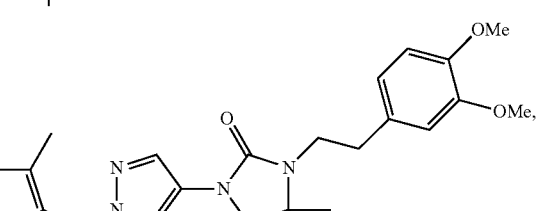
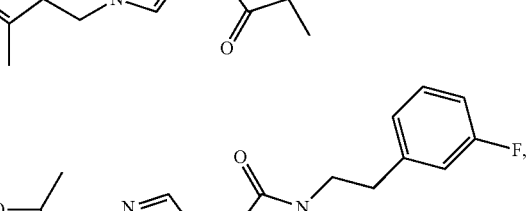
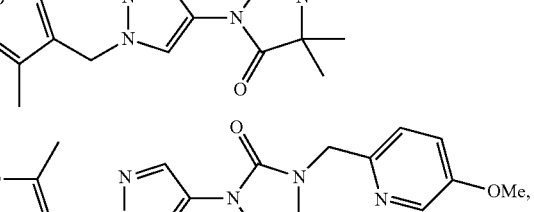
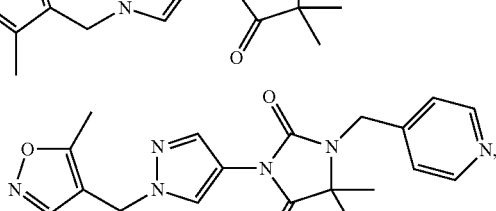
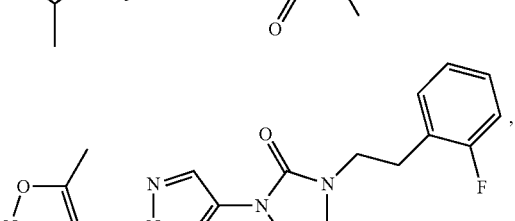
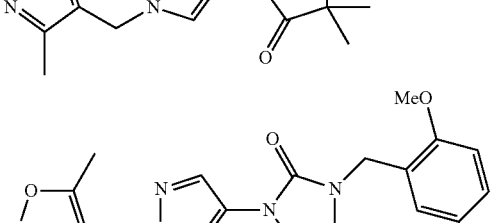
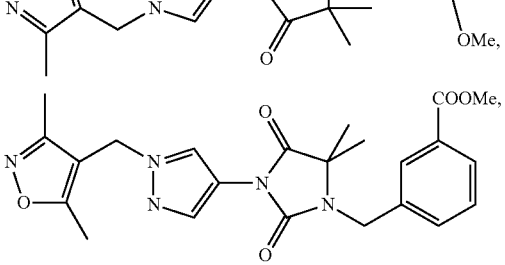

483
-continued
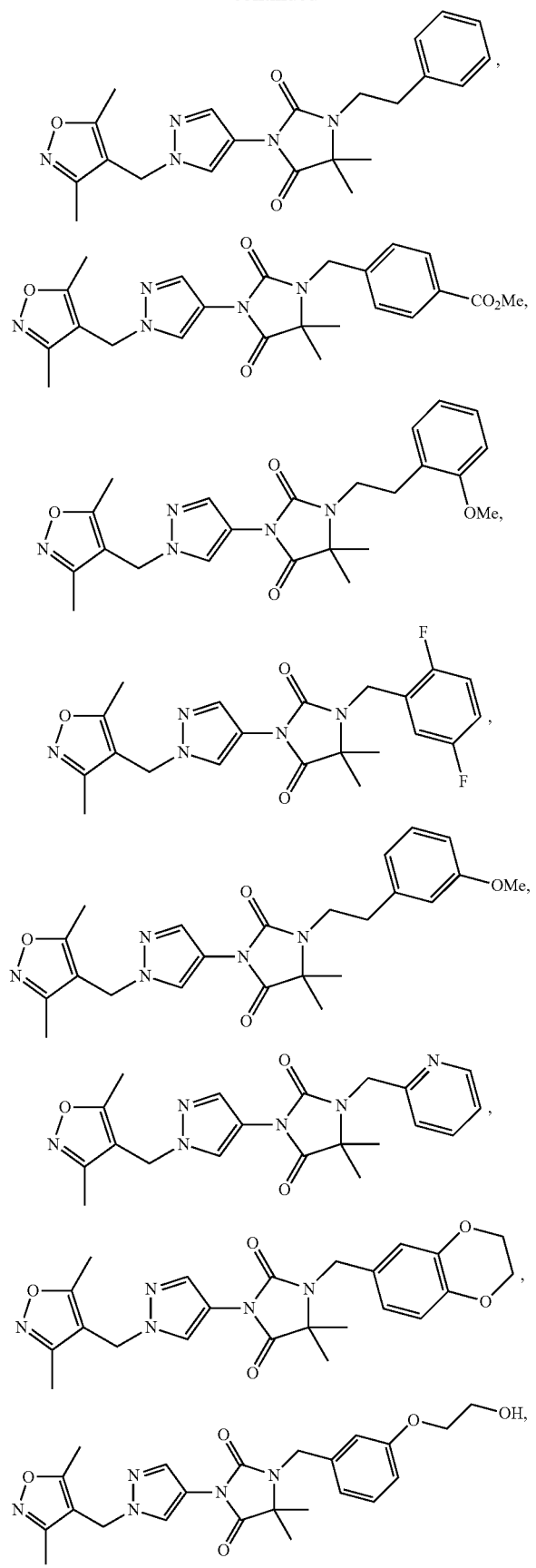
484
-continued
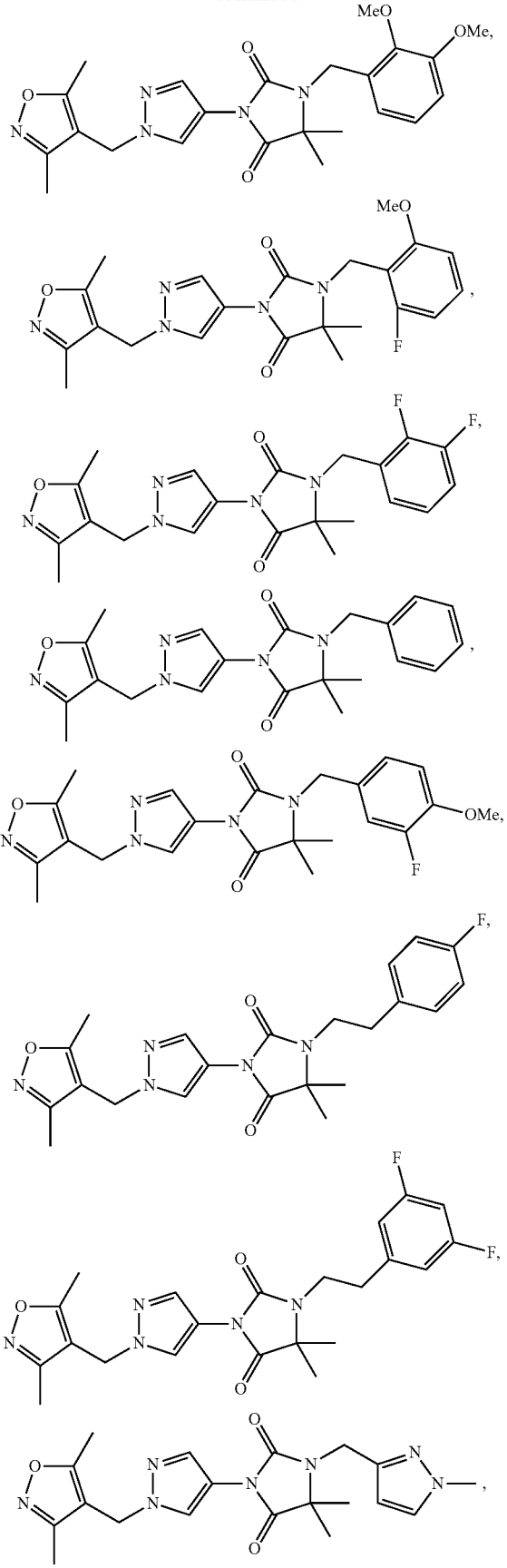

485
-continued
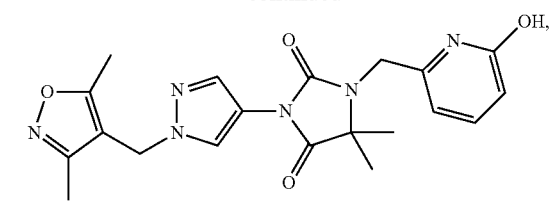
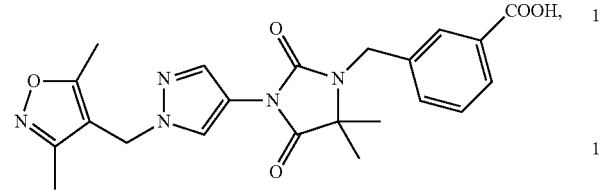
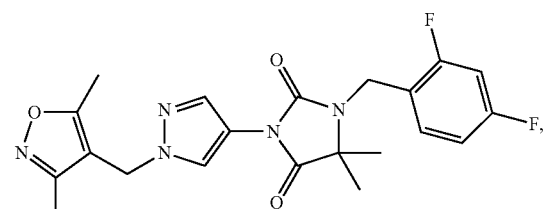
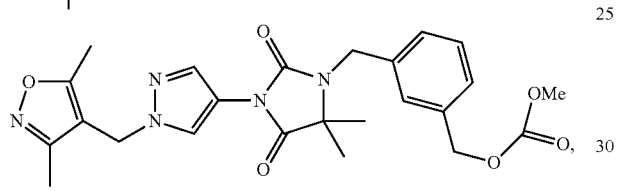
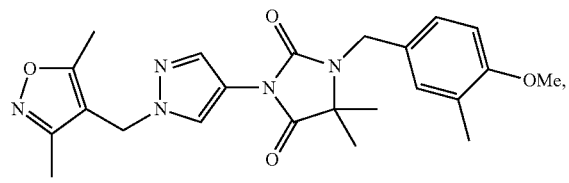
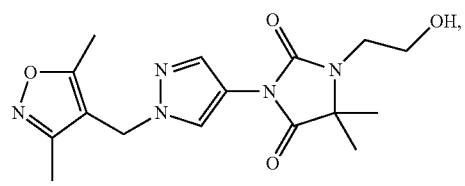
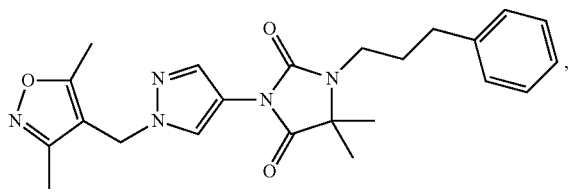
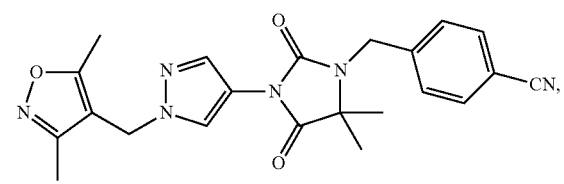
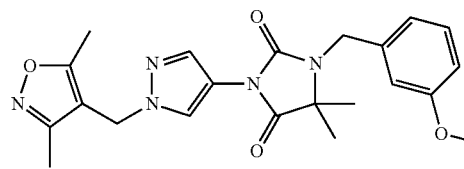
486
-continued
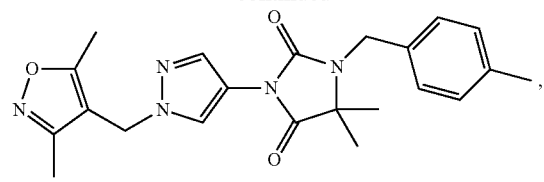
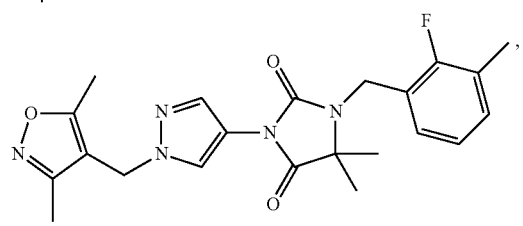
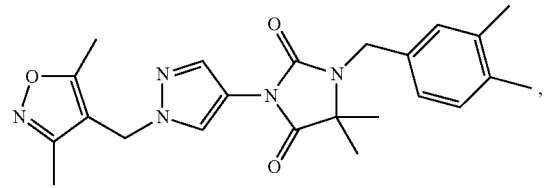
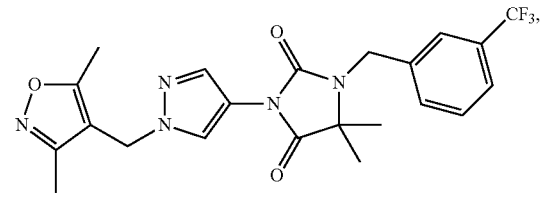
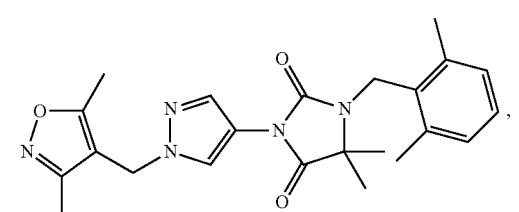
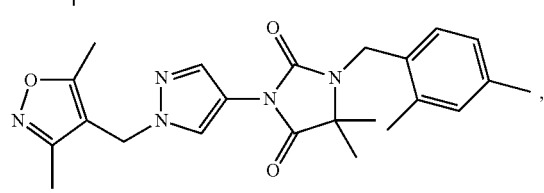
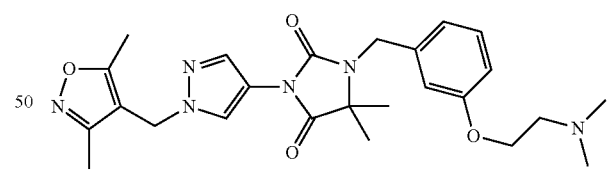
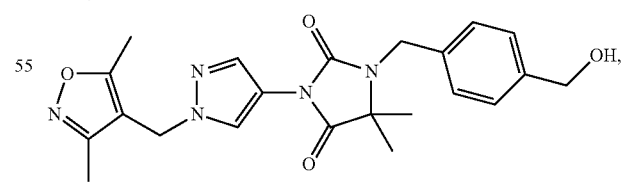
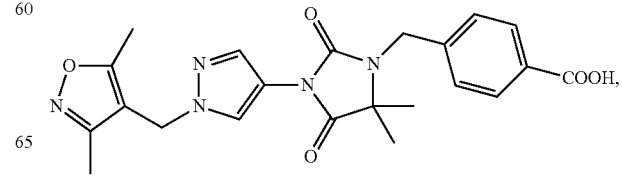

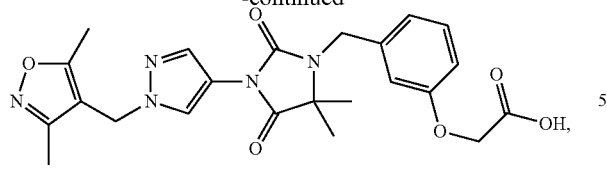
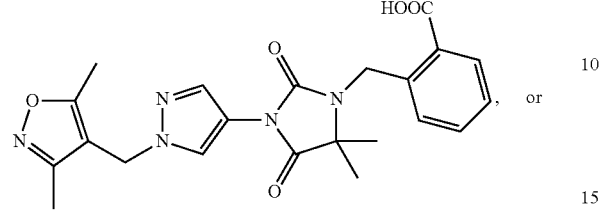
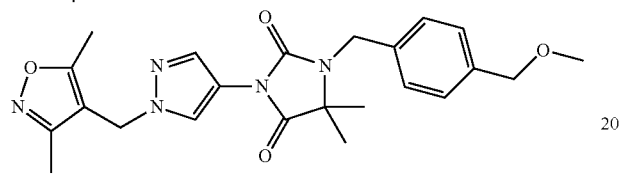
or a salt, hydrate, solvate or N-oxide thereof.
* * * * *

SEQUENCE LISTING

<160> NUMBER OF SEQ ID NOS: 6

<210> SEQ ID NO 1
<211> LENGTH: 35
<212> TYPE: PRT
<213> ORGANISM: Artificial Sequence
<220> FEATURE:
<223> OTHER INFORMATION: Synthetic Peptide

<400> SEQUENCE: 1

Met Asn Gly Thr Glu Gly Pro Asn Phe Tyr Val Pro Phe Ser Asn Lys
1               5                   10                  15

```
Thr Gly Val Val Arg Ser Pro Phe Glu Ala Pro Gln Tyr Tyr Leu Ala
            20                  25                  30

Glu Pro Trp
        35

<210> SEQ ID NO 2
<211> LENGTH: 374
<212> TYPE: PRT
<213> ORGANISM: artificial sequence
<220> FEATURE:
<223> OTHER INFORMATION: Synthetic chimeric protein

<400> SEQUENCE: 2

Met Ala Arg Ser Leu Thr Trp Arg Cys Cys Pro Trp Cys Leu Thr Glu
1               5                   10                  15

Asp Glu Lys Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu
        35                  40                  45

Gly Pro Gly Glu Ser Gly Lys Ser Thr Phe Ile Lys Gln Met Arg Ile
    50                  55                  60

Ile His Gly Ala Gly Tyr Ser Glu Glu Arg Lys Gly Phe Arg Pro
65                  70                  75                  80

Leu Val Tyr Gln Asn Ile Phe Val Ser Met Arg Ala Met Ile Glu Ala
            85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
    130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
            165                 170                 175

Pro Thr Ala Gln Asp Val Leu Arg Ser Arg Met Pro Thr Thr Gly Ile
        180                 185                 190

Asn Glu Tyr Cys Phe Ser Val Gln Lys Thr Asn Leu Arg Ile Val Asp
    195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
            245                 250                 255

Leu Phe Gly Thr Ile Leu Glu Leu Pro Trp Phe Lys Ser Thr Ser Val
        260                 265                 270

Ile Leu Phe Leu Asn Lys Thr Asp Ile Leu Glu Glu Lys Ile Pro Thr
    275                 280                 285

Ser His Leu Ala Thr Tyr Phe Pro Ser Phe Gln Gly Pro Lys Gln Asp
    290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Asn Leu Lys Lys Glu Asp
            325                 330                 335

Lys Glu Ile Tyr Ser His Met Thr Cys Ala Thr Asp Thr Gln Asn Val
```

```
                340             345             350
Lys Phe Val Phe Asp Ala Val Thr Asp Ile Ile Ile Lys Glu Asn Leu
            355             360             365

Lys Asp Cys Gly Leu Phe
        370

<210> SEQ ID NO 3
<211> LENGTH: 930
<212> TYPE: DNA
<213> ORGANISM: Homo sapiens

<400> SEQUENCE: 3
atgttcagtc ctgcagataa catctttata atcctaataa ctggagaatt catactagga      60
atattgggga atggatacat tgcactagtc aactggattg actggattaa gaagaaaaag     120
atttccacag ttgactacat ccttaccaat ttagttatcg ccagaatttg tttgatcagt     180
gtaatggttg taaatggcat tgtaatagta ctgaacccag atgtttatac aaaaaataaa     240
caacagatag tcattttttac cttctggaca tttgccaact acttaaatat gtggattacc     300
acctgcctta atgtcttcta ttttctgaag atagccagtt cctctcatcc acttttttctc    360 tggctgaagt ggaaaattga tatggtggtg cactggatcc tgctgggatg ctttgccatt     420
tccttgttgg tcagccttat agcagcaata gtactgagtt gtgattatag gtttcatgca     480
attgccaaac ataaaagaaa cattactgaa atgttccatg tgagtaaaat accatacttt     540
gaacccttaa ctctctttaa cctgtttgca attgtcccat ttattgtgtc actgatatca     600 ttttccttt tagtaagatc tttatggaga cataccaagc aaataaaact ctatgctacc     660
ggcagtagag accccagcac agaagttcat gtgagagcca ttaaaactat gacttcattt     720
atcttctttt ttttcctata ctatatttct tctattttga tgacctttag ctatcttatg     780
acaaaataca agttagctgt ggagtttgga gagattgcag caattctcta cccttgggt      840 cactcactta ttttaattgt tttaaataat aaactgaggc agacatttgt cagaatgctg     900
acatgtagaa aaattgcctg catgatatga                                      930

<210> SEQ ID NO 4
<211> LENGTH: 309
<212> TYPE: PRT
<213> ORGANISM: Homo sapiens

<400> SEQUENCE: 4

Met Phe Ser Pro Ala Asp Asn Ile Phe Ile Leu Ile Thr Gly Glu
1               5                   10                  15

Phe Ile Leu Gly Ile Leu Gly Asn Gly Tyr Ile Ala Leu Val Asn Trp
            20                  25                  30

Ile Asp Trp Ile Lys Lys Lys Ile Ser Thr Val Asp Tyr Ile Leu
        35                  40                  45

Thr Asn Leu Val Ile Ala Arg Ile Cys Leu Ile Ser Val Met Val Val
        50                  55                  60

Asn Gly Ile Val Ile Val Leu Asn Pro Asp Val Tyr Thr Lys Asn Lys
65                  70                  75                  80

Gln Gln Ile Val Ile Phe Thr Phe Trp Thr Phe Ala Asn Tyr Leu Asn
                85                  90                  95

Met Trp Ile Thr Thr Cys Leu Asn Val Phe Tyr Phe Leu Lys Ile Ala
            100                 105                 110

Ser Ser Ser His Pro Leu Phe Leu Trp Leu Lys Trp Lys Ile Asp Met
            115                 120                 125
```

```
Val Val His Trp Ile Leu Leu Gly Cys Phe Ala Ile Ser Leu Leu Val
    130                 135                 140

Ser Leu Ile Ala Ala Ile Val Leu Ser Cys Asp Tyr Arg Phe His Ala
145                 150                 155                 160

Ile Ala Lys His Lys Arg Asn Ile Thr Glu Met Phe His Val Ser Lys
                165                 170                 175

Ile Pro Tyr Phe Glu Pro Leu Thr Leu Phe Asn Leu Phe Ala Ile Val
            180                 185                 190

Pro Phe Ile Val Ser Leu Ile Ser Phe Phe Leu Leu Val Arg Ser Leu
        195                 200                 205

Trp Arg His Thr Lys Gln Ile Lys Leu Tyr Ala Thr Gly Ser Arg Asp
    210                 215                 220

Pro Ser Thr Glu Val His Val Arg Ala Ile Lys Thr Met Thr Ser Phe
225                 230                 235                 240

Ile Phe Phe Phe Phe Leu Tyr Tyr Ile Ser Ser Ile Leu Met Thr Phe
                245                 250                 255

Ser Tyr Leu Met Thr Lys Tyr Lys Leu Ala Val Glu Phe Gly Glu Ile
            260                 265                 270

Ala Ala Ile Leu Tyr Pro Leu Gly His Ser Leu Ile Leu Ile Val Leu
        275                 280                 285

Asn Asn Lys Leu Arg Gln Thr Phe Val Arg Met Leu Thr Cys Arg Lys
    290                 295                 300

Ile Ala Cys Met Ile
305

<210> SEQ ID NO 5
<211> LENGTH: 954
<212> TYPE: DNA
<213> ORGANISM: Homo sapiens

<400> SEQUENCE: 5
atgggtggtg tcataaagag catatttaca ttcgttttaa ttgtggaatt tataattgga      60
aatttaggaa atagtttcat agcactggtg aactgtattg actgggtcaa gggaagaaag     120
atctcttcgg ttgatcggat cctcactgct ttggcaatct ctcgaattag cctggtttgg     180
ttaatattcg gaagctggtg tgtgtctgtg ttttcccag ctttatttgc cactgaaaaa      240
atgttcagaa tgcttactaa tatctggaca gtgatcaatc atttagtgt ctggttagct      300 acaggcctcg gtacttttta ttttctcaag atagccaatt tttctaactc tatttttctc     360
tacctaaagt ggagagttaa aaaggtggtt ttggtgctgc ttcttgtgac ttcggtcttc     420
ttgtttttaa atattgcact gataaacatc catataaatg ccagtatcaa tggatacaga     480
agaaacaaga cttgcagttc tgattcaagt aactttacac gattttccag tcttattgta     540
ttaaccagca ctgtgttcat tttcataccc tttactttgt ccctggcaat gtttcttctc     600
ctcatcttct ccatgtggaa acatcgcaag aagatgcagc acactgtcaa atatccgga     660 gacgccagca ccaaagccca cagaggagtt aaaagtgtga tcactttctt cctactctat     720
gccattttct ctctgtcttt tttcatatca gtttggacct ctgaaaggtt ggaggaaaat     780
ctaattattc tttcccaggt gatgggaatg gcttatcctt catgtcactc atgtgttctg     840
attcttggaa acaagaagct gagacaggcc tctctgtcag tgctactgtg gctgaggtac     900
atgttcaaag atggggagcc ctcaggtcac aaagaattta gagaatcatc ttga           954

<210> SEQ ID NO 6
<211> LENGTH: 317
<212> TYPE: PRT
```

<213> ORGANISM: Homo sapiens

<400> SEQUENCE: 6

| | | | | | | | | | | | | | | |
|---|---|---|---|---|---|---|---|---|---|---|---|---|---|---|
| Met | Gly | Gly | Val | Ile | Lys | Ser | Ile | Phe | Thr | Phe | Val | Leu | Ile | Val | Glu |
| 1 | | | | 5 | | | | | 10 | | | | | 15 | |

Met Gly Gly Val Ile Lys Ser Ile Phe Thr Phe Val Leu Ile Val Glu
1               5                   10                  15

Phe Ile Ile Gly Asn Leu Gly Asn Ser Phe Ile Ala Leu Val Asn Cys
                20                  25                  30

Ile Asp Trp Val Lys Gly Arg Lys Ile Ser Ser Val Asp Arg Ile Leu
            35                  40                  45

Thr Ala Leu Ala Ile Ser Arg Ile Ser Leu Val Trp Leu Ile Phe Gly
        50                  55                  60

Ser Trp Cys Val Ser Val Phe Phe Pro Ala Leu Phe Ala Thr Glu Lys
65                  70                  75                  80

Met Phe Arg Met Leu Thr Asn Ile Trp Thr Val Ile Asn His Phe Ser
                85                  90                  95

Val Trp Leu Ala Thr Gly Leu Gly Thr Phe Tyr Phe Leu Lys Ile Ala
                100                 105                 110

Asn Phe Ser Asn Ser Ile Phe Leu Tyr Leu Lys Trp Arg Val Lys Lys
            115                 120                 125

Val Val Leu Val Leu Leu Val Thr Ser Val Phe Leu Phe Leu Asn
        130                 135                 140

Ile Ala Leu Ile Asn Ile His Ile Asn Ala Ser Ile Asn Gly Tyr Arg
145                 150                 155                 160

Arg Asn Lys Thr Cys Ser Ser Asp Ser Ser Asn Phe Thr Arg Phe Ser
                165                 170                 175

Ser Leu Ile Val Leu Thr Ser Thr Val Phe Ile Phe Ile Pro Phe Thr
            180                 185                 190

Leu Ser Leu Ala Met Phe Leu Leu Ile Phe Ser Met Trp Lys His
        195                 200                 205

Arg Lys Lys Met Gln His Thr Val Lys Ile Ser Gly Asp Ala Ser Thr
210                 215                 220

Lys Ala His Arg Gly Val Lys Ser Val Ile Thr Phe Phe Leu Leu Tyr
225                 230                 235                 240

Ala Ile Phe Ser Leu Ser Phe Phe Ile Ser Val Trp Thr Ser Glu Arg
                245                 250                 255

Leu Glu Glu Asn Leu Ile Ile Leu Ser Gln Val Met Gly Met Ala Tyr
                260                 265                 270

Pro Ser Cys His Ser Cys Val Leu Ile Leu Gly Asn Lys Lys Leu Arg
            275                 280                 285

Gln Ala Ser Leu Ser Val Leu Leu Trp Leu Arg Tyr Met Phe Lys Asp
        290                 295                 300

Gly Glu Pro Ser Gly His Lys Glu Phe Arg Glu Ser Ser
305                 310                 315